(12) United States Patent
Potdar et al.

(10) Patent No.: US 12,264,368 B2
(45) Date of Patent: Apr. 1, 2025

(54) METHODS OF TREATING REFRACTORY INFLAMMATORY DISEASE USING TRANSCRIPTOMIC AND GENETIC RISK SIGNATURES

(71) Applicant: CEDARS-SINAI MEDICAL CENTER, Los Angeles, CA (US)

(72) Inventors: Alka Potdar, Cumming, GA (US); Dermot P. McGovern, Los Angeles, CA (US); Janine Bilsborough, Simi Valley, CA (US); Stephan Targan, Santa Monica, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 1036 days.

(21) Appl. No.: 17/258,133

(22) PCT Filed: Jul. 2, 2019

(86) PCT No.: PCT/US2019/040394
§ 371 (c)(1),
(2) Date: Jan. 5, 2021

(87) PCT Pub. No.: WO2020/010139
PCT Pub. Date: Jan. 9, 2020

(65) Prior Publication Data
US 2021/0277477 A1 Sep. 9, 2021

Related U.S. Application Data

(60) Provisional application No. 62/786,207, filed on Dec. 28, 2018, provisional application No. 62/694,935, filed on Jul. 6, 2018.

(51) Int. Cl.
*C12Q 1/6883* (2018.01)
(52) U.S. Cl.
CPC ..... *C12Q 1/6883* (2013.01); *C12Q 2600/106* (2013.01); *C12Q 2600/112* (2013.01); *C12Q 2600/156* (2013.01); *C12Q 2600/158* (2013.01)
(58) Field of Classification Search
CPC .................................................. C12Q 2600/156
See application file for complete search history.

(56) References Cited

U.S. PATENT DOCUMENTS

| | | | |
|---|---|---|---|
| 4,229,447 A | 10/1980 | Porter | |
| 4,476,116 A | 10/1984 | Anik | |
| 4,596,795 A | 6/1986 | Pitha | |
| 4,755,386 A | 7/1988 | Hsiao et al. | |
| 5,011,692 A | 4/1991 | Fujioka et al. | |
| 5,017,381 A | 5/1991 | Maruyama et al. | |
| 5,116,817 A | 5/1992 | Anik | |
| 5,229,135 A | 7/1993 | Philippon et al. | |
| 5,739,136 A | 4/1998 | Ellinwood, Jr. et al. | |
| 5,837,284 A | 11/1998 | Mehta et al. | |
| 5,840,329 A | 11/1998 | Bai | |
| 5,858,401 A | 1/1999 | Bhalani et al. | |
| 6,391,452 B1 | 5/2002 | Antonsen et al. | |
| 6,667,048 B1 | 12/2003 | Lambert et al. | |
| 6,960,563 B2 | 11/2005 | Egbaria et al. | |
| 10,626,180 B2 | 4/2020 | McGovern et al. | |

FOREIGN PATENT DOCUMENTS

WO  WO-2018035330 A1  2/2018

OTHER PUBLICATIONS

Nuij et al. Genetic polymorphism in ATG16L1 gene is associated with adalimumab use in inflammatory bowel disease. J Transl Med 15, 248 (2017). doi.org/10.1186/s12967-017-1355-9 (Year: 2017).*
Benno et al., P-257 Apremilast Prevents Intestinal Inflammation in Colitis Models via Influencing Epithelial Barrier, Inflammatory Bowel Diseases, vol. 23, Issue suppl_1, Feb. 2017, p. S84. (Year: 2017).*
Denny et al., Systematic comparison of phenome-wide association study of electronic medical record data and genome-wide association study data. Nat Biotechnol. Dec. 2013;31(12):1102-10. doi: 10.1038/nbt.2749. PMID: 24270849; PMCID: PMC3969265 (Year: 2013).*
Spadaccini M, D'Alessio S, Peyrin-Biroulet L, Danese S. PDE4 Inhibition and Inflammatory Bowel Disease: A Novel Therapeutic Avenue. Int J Mol Sci. Jun. 15, 2017;18(6):1276. doi: 10.3390/ijms18061276. PMID: 28617319; PMCID: PMC5486098. (Year: 2017).*
Sherry, S T,et al., dbSNP-Database for Single Nucleotide Polymorphisms and Other Classes of Minor Genetic Variation. Genome Res 9:677-679 (1999).
Altschul et al.: Basic local alignment search tool. Journal of Molecular Biology. 1990, vol. 215, No. 3, pp. 403-410. Oct. 5, 1990.
Altschul et al.: Gapped BLAST and PSI-BLAST: a new generation of protein database search programs. Nucleic Acids Res. 25:3389-3402 (1997).
Ansel et al.: Pharmaceutical Dosage Forms and Drug Delivery Systems 213, 6th ed., (1995).
Danese et al.: Journal of Crohn's and Colitis, 12(1):S004-S005 (2018) Abstract OP006.
Database of Single Nucleotide Polymorphism, Reference SNP (refSNP) Cluster Report: rs7958372; Mar. 2018 [online]. Retrieved Nov. 11, 2019 https://www.ncbi.nlm.nih.gov/projects/SNP/snp_ref.cgi?do_not_redirect&rs=rs7958372.

(Continued)

*Primary Examiner* — Aaron A Priest
*Assistant Examiner* — Tian Yu
(74) *Attorney, Agent, or Firm* — Wilson Sonsini Goodrich & Rosati

(57) ABSTRACT

Disclosed herein are methods, kits and compositions for treating an inflammatory disease. These methods. kits and compositions may be particularly useful for subjects carrying a risk genotype and/or expressing a transcriptomic risk signature that is indicative of severe inflammatory disease phenotypes for which existing treatment options are limited.

10 Claims, 13 Drawing Sheets
Specification includes a Sequence Listing.

(56) References Cited

OTHER PUBLICATIONS

GenBank: HY128075.1 RIKEN full-length enriched human cDNA library, brain *Homosapiens* cDNA clone H06D085E04, mRNA sequence 2014 (retrieved Dec. 10, 2019) from Internet: URL: https://www.ncbi.nlm.nih.gov/nuccore/HY128075.1/.
Huang et al.: Using an Uncertainty-Coding Matrix in Bayesian Regression Models for Haplotype-Specific Risk Detection in Family Association Studies. PLoS One: 6(7):e21890 (2011).
International Application No. PCT/US2019/040394 International Preliminary Report on Patentability dated Jan. 21, 2021.
International Application No. PCT/US2019/040394 International Search Report and Written Opinion dated Nov. 27, 2019.
International Application No. PCT/US2019/040394 Invitation to Pay Additional Fees dated Sep. 30, 2019.
Jia et al.: Polymorphisms of PTPN11 gene could influence serum lipid levels in a sex-specific patters. Lipids Health Dis.: vol. 12; p. 72; Abstract (2013).
Jin et al.: Phosphodiesterase 4 and Its Inhibitors in Inflammatory Diseases; Department of Life Sciences, National Central University; p. 197-210 (2011).
Marigorta et al.: Transcriptional risk scores link GWAS to eQTLs and predict complications in Crohn's disease. Nat Genet. Oct. 2017 ; 49(10): 1517-1521.
Prometheus Biosciences, Inc. Form S-1 Registration Statement as filed with the Securities and Exchange Commission on Feb. 19, 2021 (246 pages).
Remington: The Science and Practice of Pharmacy. 21st Edition, Lippincott Williams & Wilkins (2005).
Singh et al.: Encyclopedia of Pharmaceutical Technology 2nd Ed., pp. 754-757 (2002).
Vandussen et al.: Genetic variants synthesize to produce paneth cell phenotypes that define subtypes of Crohn's disease. Gastroenterology. 146(1):200-209 (2014).
Yoon et al.: Colonic Phenotypes are Associated with Poorer Response to Anti-TNF Therapies in Patients with IBD. Inflammatory Bowel Diseases. 23(8):1382-1393 (2017).
Zhuo et al.: Chemotherapy Effectiveness and Prognosis of Gastric Cancer Influenced by PTPN11 Polymorphisms. Cell Physiol Biochem: 39(4):1537-1552 (2016).

* cited by examiner

FIG. 4A

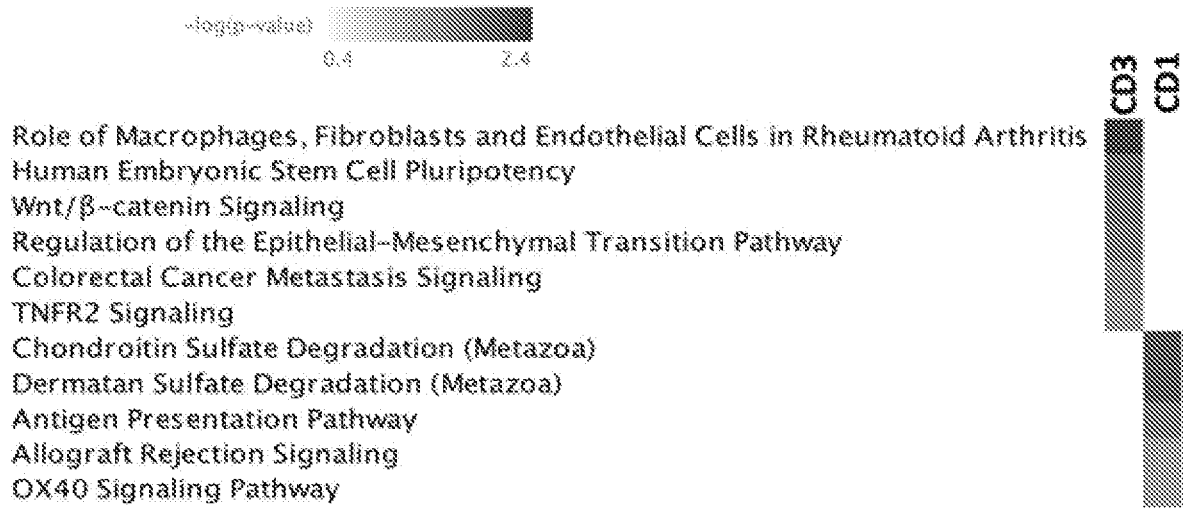

Role of Macrophages, Fibroblasts and Endothelial Cells in Rheumatoid Arthritis
Human Embryonic Stem Cell Pluripotency
Wnt/β-catenin Signaling
Regulation of the Epithelial-Mesenchymal Transition Pathway
Colorectal Cancer Metastasis Signaling
TNFR2 Signaling
Chondroitin Sulfate Degradation (Metazoa)
Dermatan Sulfate Degradation (Metazoa)
Antigen Presentation Pathway
Allograft Rejection Signaling
OX40 Signaling Pathway

FIG. 4B

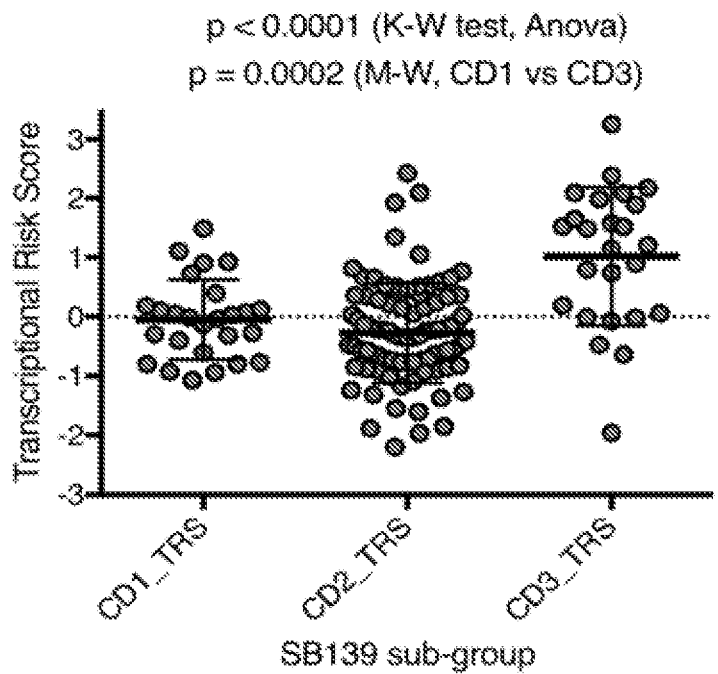

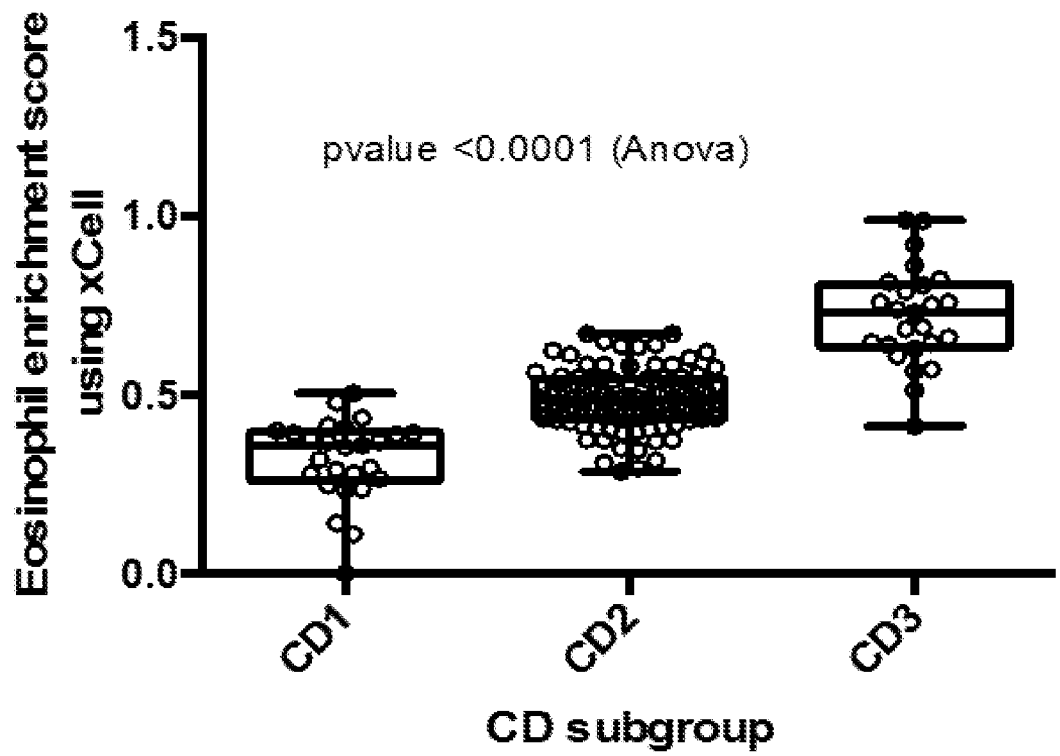

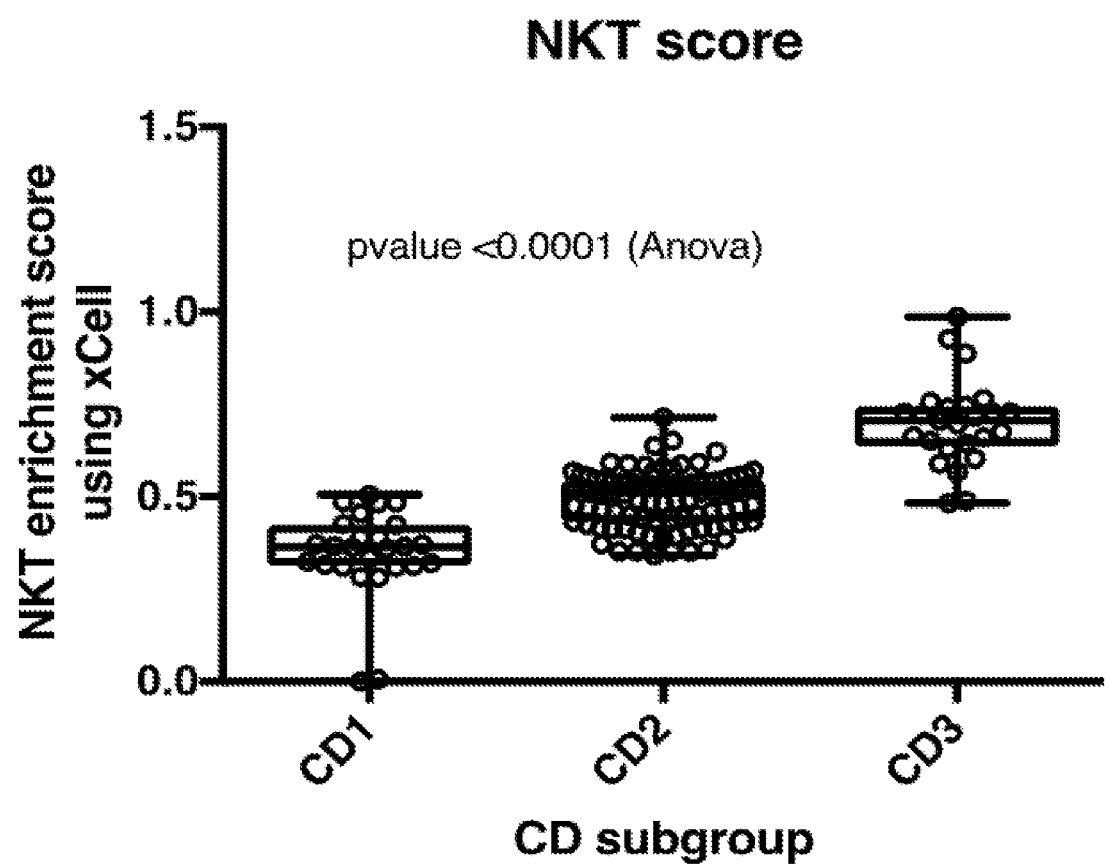

METHODS OF TREATING REFRACTORY INFLAMMATORY DISEASE USING TRANSCRIPTOMIC AND GENETIC RISK SIGNATURES

CROSS-REFERENCE

This application is a national phase entry of International Application No. PCT/US2019/040394 filed Jul. 2, 2019, which claims the benefit of U.S. provisional application Ser. No. 62/694,935 filed Jul. 6, 2018, and U.S. provisional application Ser. No. 62/786,207 filed Dec. 28, 2018, each of which are incorporated herein by reference in their entirety.

SEQUENCE LISTING

The instant application contains a Sequence Listing which has been submitted electronically in ASCII format and is hereby incorporated by reference in its entirety. Said ASCII copy created Jun. 26, 2019, is named 52388-742_601_SL.txt and is 1,087,608 bytes in size.

BACKGROUND

Inflammatory bowel disease (IBD) comprises a variety of disorders associated with chronic inflammation of gastrointestinal tract. Classically, IBD has been assigned as either ulcerative colitis (UC) or Crohn's disease (CD). CD most commonly affects the small bowel (SB) and exhibits a diversity of clinical and subclinical phenotypes including stricturing, internal penetrating and perianal CD (pCD). By contrast, UC predominantly affects the large intestine or colon, and likewise exhibits many clinical and subclinical phenotypes, including medically refractory UC (mrUC). IBD is further characterized based on disease location, which in some cases, can serve as a predictor of disease severity. For example, CD predominantly affecting the ileum is associated with worse patient outcomes, as compared to colonic disease. This heterogeneity provides a challenge for the development of effective therapies and may be one of the reasons behind drug development failures and limited efficacy with existing therapies.

Existing IBD therapies, such as steroids and tumor necrosis factor (TNF) inhibitors are typically used as a first line treatment for treating IBD. Unfortunately, a significant number of patients experience a lack of response, or a loss-of-response over time, to the IBD therapy. While a patient is treated with an IBD therapy that is ineffective, the disease worsens. Surgery, in the form of strictureplasty (reshaping of the intestine) or resection (removal of the intestine), is the only treatment option for patients that do not respond to first line therapies. Surgical treatments for IBD are invasive, causing post-operative risks for an estimated third of patients undergoing surgery, such as anastomotic leak, infection, and bleeding.

The heterogeneity of disease pathogenesis and clinical course, combined with the variable response to treatment and its associated side effects, suggests a personalized medicine approach to treating these diseases is best treatment strategy. A unique genetic or transcriptomic signature is needed to identify homogenous CD patient subgroups with shared disease pathology, to aid in the development and the selection of effective therapeutic strategies for these patients.

SUMMARY

Provided herein are methods of classifying Crohn's disease (CD) subtypes using transcriptomic and genetic signatures associated with clinically distinct forms of CD. Colon-like (e.g., disease affecting the colon) or ileum-like (e.g., disease affecting the ileum) gene expression profiles are used herein to classify adult and pediatric CD patients by clinically distinct subgroups. Disease course was classified using transcriptional profiling of T cells from patients. Transcriptional risk scores (TRS) calculated in a CD cohort were used to connect genetic variants, such as single nucleotide polymorphisms (SNPs), to expression quantitative trait loci (eQTL), that can be used to identify CD patients that have an increased likelihood of progressing to complicated forms of CD over time.

A cohort of refractory CD patients with varying disease course who underwent small bowel (SB) resection as part of treatment were analyzed to stratify the CD patients based on the pathogenic homogeneity. Clinically relevant subgroups were identified using both messenger RNA (mRNA) expression and genetic data from uninvolved ileal tissue taken from SB resections. Within this heterogeneous, refractory CD population, clinically distinct patient subgroups with varying disease severity were identified. The genetic- and transcriptomics-based signals from the same patients were overlapped to define molecular signatures, disclosed herein, that aid in the development of therapeutic strategies for these patient subgroups.

Refractory CD can be stratified into three patient subgroups disclosed herein, including CD 1 subgroup (CD1), CD 2 subgroup (CD2) and CD 3 subgroup (CD3). CD3 is characterized by a more severe, refractory, disease course, as compared to CD1 and CD2. Compared to CD1, CD3 is enriched for subjects with increased disease recurrence after a first surgery (OR=6.78, P=0.04), and are more likely to undergo a second surgery (OR=5.07, P=0.016). CD3 is also enriched for a presence of perianal CD (OR=3.61, P=0.036), which includes inflammation at or near the anus, and in many cases includes fissures, abscesses or stenosis. In addition, there are fewer patients in CD3 that show recurrence-free survival, as compared to CD1 (p=0.02, median survival time (months), CD1=10 and CD3=6). CD3 patients represent a severe, refractory CD patient subgroup that would benefit from an earlier and more aggressive therapeutic intervention, as compared to CD1.

Provided herein are 174 genes that were identified representing both genetic and biological differences between the CD subgroups, by overlaying differential gene expression between CD1 and CD3 with CD subgroup-associated genetic polymorphisms or genotypes.

In addition, CD3 was associated with higher transcriptional risk score and enriched with eosinophil and natural killer T (NKT) cell gene signatures. Pathway analyses using this unique gene signature indicated eukaryotic initiation factor 2 (EIF2) and cyclic adenosine monophosphate (cAMP) signaling as dominant pathways associated with CD3, suggesting that modulators of these pathways may provide a promising therapeutic strategy for CD3 patients.

Therapeutic targets for the treatment of IBD were identified by analysis of the genetic contribution to the susceptibility of a patient developing CD. Among the targets identified are Adenylate cyclase 7 (ADCY7) and phosphodiesterase 4C (PDE4C). ADCY7 and members of the PDE4 family modulate innate immune responses through G-protein coupled receptor (GPCR) signaling. ADCY7 catalyzes the formation of cAMP in response to GPCR activation, which serves to control the innate immune response. The PDE4 family, composed of four subfamilies encoded by four paralog genes (e.g., PDE4A, PDE4B, PDE4C, and PDE4D), are cAMP-degrading isozymes in most, if not all, inflammatory cells.

The genetic polymorphisms or genotypes described herein, and the transcriptomic risk profiles provided herein, are associated with, and therefore predictive of, severe and refractory forms of inflammatory diseases and conditions, such as IBD. The genotypes and transcriptomic risk profiles may be detected in a sample containing genetic material obtained from the subject (e.g., whole blood, tissue, saliva). The detection of the risk genotypes or transcriptomic risk profiles may be detected at the point of need or at a medical healthcare facility. The genetic polymorphisms or genotypes are useful for identifying a subject who may be at risk for developing a severe or refractory form of IBD (e.g., "risk genotype"). In some cases, a transcriptomic profile may be used to identify a subject at risk for developing the severe or refractory disease (e.g., "transcriptomic risk profile). In addition, these risk genotypes and transcriptomic risk profiles described herein, can be used to select a patient for treatment with a therapeutic agent disclosed herein (e.g., agonist of ADCY7 and/or inhibitor of PDE4C).

Aspects disclosed here provide methods of treating an inflammatory bowel disease, the method comprising: (a) identifying a presence of a transcriptomic risk signature predictive of a severe or refractory form of inflammatory bowel disease (IBD) in a subject by assaying a sample obtained from the subject to detect a presence of a risk genotype comprising a single nucleotide polymorphism (SNP) selected from the group consisting of an "A" at rs7958372, a "C" at rs2877453, an "A" at rs71327010, a "C" at rs1169302C, a "G" at rs1169303, an "A" at rs6519183, a "C" at rs685548, an "A" at rs11998187, an "A" at rs531819A, a "G" at rs1041968, a "G" at rs693, an "A" at rs512535, a "G" at rs550619G, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547, an "A" at rs10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs10821830, an "A" at rs975262, an "A" at rs973067, a "G" at rs10509139, an "A" at rs1442539, an "A" at rs2197155, a "G" at rs7919914, a "G" at rs10994476, an "A" at rs35471473, a "G" at rs12785023, a "G" at rs12783716, a "G" at rs10821821, a "G" at rs10994441, a "C" at rs10994442, a "T" at rs10821814, an "A" at rs10994465, a "T" at rs12218617, a "C" at rs10509138, an "A" at rs61854518, a "G" at rs10821699, a "G" at rs7919274, an "A" at rs10761552, a "G" at rs17037425, an "A" at rs2893861, a "C" at rs1993939, a "G" at rs10821833, a "G" at rs1904418, a "G" rs16915196, an "A" at rs61853514, an "A" at rs10994430, an "A" at rs16915231, a "G" at rs2028564, a "G" at rs13196552, an "A" at rs17587597, an "A" at rs17587226, an "A" at rs2276917, an "A" at rs10013653, an "A" at rs11582799, an "A" at rs111692854, and an "A" at rs72632053; and (b) administering to the subject a therapeutically effective amount of a therapeutic agent, the therapeutic agent comprising at least one of an inhibitor of PDE4C activity or expression inhibitor and an agonist of ADCY7, provided the transcriptomic risk signature is detected in (a). In some embodiments, the IBD is Crohn's disease (CD). In some embodiments, the IBD is ileal CD. In some embodiments, the subject is, or is suspected to be, non-responsive to a standard therapy selected from the group consisting of anti-tumor necrosis factor (TNF) alpha therapy, anti-a4-b7 therapy (vedolizumab), anti-IL12p40 therapy (ustekinumab), Thalidomide, Cytoxin, and a combination thereof. In some embodiments, the risk genotype further comprises at least two SNPs selected from the group consisting of the "A" at rs7958372, the "C" at rs2877453, the "A" at rs71327010, the "C" at rs1169302C, the "G" at rs1169303, the "A" at rs6519183, the "C" at rs685548, the "A" at rs11998187, the "A" at rs531819A, the "G" at rs1041968, the "G" at rs693, the "A" at rs512535, the "G" at rs550619G, the "A" at rs570877, the "G" at rs12713956, the "A" at rs2301723, the "A" at rs2499714, the "A" at rs6583176, the "A" at rs369880, the "G" at rs57884093, the "A" at rs989690, the "A" at rs7704116, the "A" at rs12984273, the "G" at rs16891235, the "C" at rs7296651, the "A" at is rs516535, the "A" at rs9276427, the "A" at rs296564, the "A" at rs296569, the "A" at rs296568, the "G" at rs296567, the "G" at rs296561, the "G" at rs72749142, the "A" at rs9291547, the "A" at rs10761532, the "A" at rs10821813, the "C" at rs1561852, the "A" at rs10994464, the "G" at rs993402, the "A" at rs10994467, the "A" at rs10821822, the "G" at rs1837949, the "C" at rs35597961, the "G" at rs10821830, the "A" at rs975262, the "A" at rs973067, the "G" at rs10509139, the "A" at rs1442539, the "A" at rs2197155, the "G" at rs7919914, the "G" at rs10994476, the "A" at rs35471473, the "G" at rs12785023, the "G" at rs12783716, the "G" at rs10821821, the "G" at rs10994441, the "C" at rs10994442, the "T" at rs10821814, the "A" at rs10994465, the "T" at rs12218617, the "C" at rs10509138, the "A" at rs61854518, the "G" at rs10821699, the "G" at rs7919274, the "A" at rs10761552, the "G" at rs17037425, the "A" at rs2893861, the "C" at rs 1993939, the "G" at rs10821833, the "G" at rs 1904418, the "G" rs16915196, the "A" at rs61853514, the "A" at rs10994430, the "A" at rs16915231, the "G" at rs2028564, the "G" at rs13196552, the "A" at rs17587597, the "A" at rs17587226, the "A" at rs2276917, the "A" at rs10013653, the "A" at rs11582799, the "A" at rs111692854, and the "A" at rs72632053. In some embodiments, methods further comprise assaying a sample obtained from the subject to detect a transcriptomic risk signature, the transcriptomic risk signature comprising:

(a) a high level of expression of at least one of X-C motif chemokine receptor 1 (XCR1), HNF1 homeobox A (HNF1A), metabotropic receptor 4 (GRM4), cholinergic receptor muscarinic 3(CHRM3), phosphodiesterase 4C (PDE4C), protein kinase C alpha (PRKCA), phosphatidylinositol-4-phosphate 5-kinase type 1 gamma (PIP5K1C), histone cluster 1 H1 family member A (HIST1H1A), and kinesin family member 21B (KIF21B), as compared to a reference level; and (b) a low level of expression of at least one of ribosomal protein L3 (RPL3), protein tyrosine phosphatase, non-receptor type 11 (PTPN11), ribosomal protein (RL30), cholinergic receptor muscarinic 3 (CHRM3), DLC1 Rho GTPase activating protein (DLC1), apolipoprotein B (APOB), ribosomal protein L6 (RPL6), p21 (RAC1) activated kinase 2 (PAK2), ribosomal protein L18 (RPL18), protein phosphatase 2 catalytic subunit alpha (PPP2CA), Aldehyde Dehydrogenase 2 Family Member (ALDH2), bromodomain containing 2 (BRD2), major histocompatibility complex, class II, DQ alpha 2 (HLA-DQA2), Protocadherin 7 (PCDH7), Ankyrin 3 (ANK3), Tripartite Motif Containing 38 (TRIM38), and Cytochrome P450 Family 4 Subfamily V Member 2 (CYP4V2), Vesicle Associated Membrane Protein 3 (VAMP3), as compared to a reference level. In some embodiments, the presence of the risk genotype is indicative of a presence of the transcriptomic risk signature, the transcriptomic risk signature comprising:
(a) a high level of expression of at least one of XCR1, HNF1A, GRM4, CHRM3, PDE4C, PRKCA, PIP5K1C, HIST1H1A, and KIF21B, as compared to a reference level; and (b) a low level of expression of at least one of RPL3, PTPN11, RPL30, DLC1, APOB, RPL6, PAK2, RPL18, PPP2CA, ALDH2, BRD2, HLA-DQA2, PCDH7, ANK3, TRIM38, CYP4V2, and VAMP3, as compared to a reference level. In some embodiments, the reference value is derived from a level of expression in a non-diseased individual. In some embodiments, the subject is human.

Aspects disclosed here provide methods of treating an inflammatory bowel disease (IBD), the method comprising: (a) identifying a presence of a transcriptomic risk signature predictive of a severe or refractory form of the IBD in a subject by assaying a sample obtained from the subject to detect a presence of transcriptomic risk signature comprising:
(i) a high level of expression of at least one XCR1, HNF1A, GRM4, CHRM3, PDE4C, PRKCA, PIP5K1C, HIST1H1A, and KIF21B, as compared to a reference level; and
(ii) a low level of expression of at least one of RPL3, PTPN11, RPL30, DLC1, APOB, RPL6,PAK2, RPL18, PPP2CA, ALDH2, BRD2, HLA-DQA2, PCDH7, ANK3, TRIM38, CYP4V2, and VAMP3, as compared to a reference level; and (b) administering to the subject a therapeutically effective amount of a therapeutic agent. the therapeutic agent comprising at least one of an inhibitor of PDE4C activity or expression inhibitor and an agonist of ADCY7, provided the presence of the transcriptomic risk signature is detected in (a). In some embodiments, the IBD is CD. In some embodiments, the CD is perianal CD. In some embodiments, the CD is ileal CD. In some embodiments, the reference value is derived from a level of expression in a non-diseased individual. In some embodiments, the subject is human. In some embodiments, the level of expression is a level of mRNA expression. In some embodiments, the level of expression is a level of protein expression.

Aspects disclosed here provide methods of treating a CD in a subject comprising administering a therapeutically effective amount of at least one of an inhibitor of PDE4C activity or expression inhibitor and an agonist of ADCY7 to the subject, provided a risk genotype comprising a SNP selected from the group consisting of an "A" at rs7958372, a "C" at rs2877453, an "A" at rs71327010, a "C" at rs1169302C, a "G" at rs1169303, an "A" at rs6519183, a "C" at rs685548, an "A" at rs11998187, an "A" at rs531819A, a "G" at rs 1041968, a "G" at rs693, an "A" at rs512535, a "G" at rs550619G, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547,an "A" at rs10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs10821830, an "A" at rs975262, an "A" at rs973067, a "G" at rs10509139, an "A" at rs1442539, an "A" at rs2197155, a "G" at rs7919914, a "G" at rs10994476, an "A" at rs35471473, a "G" at rs12785023, a "G" at rs12783716, a "G" at rs10821821, a "G" at rs10994441, a "C" at rs10994442, a "T" at rs10821814, an "A" at rs10994465, a "T" at rs12218617, a "C" at rs10509138, an "A" at rs61854518, a "G" at rs10821699, a "G" at rs7919274, an "A" at rs 10761552, a "G" at rs 17037425, an "A" at rs2893861, a "C" at rs1993939, a "G" at rs10821833, a "G" at rs1904418, a "G" rs16915196, an "A" at rs61853514, an "A" at rs10994430, an "A" at rs16915231, a "G" at rs2028564, a "G" at rs13196552, an "A" at rs17587597, an "A" at rs17587226, an "A" at rs2276917, an "A" at rs10013653, an "A" at rs11582799, an "A" at rs111692854, and an "A" at rs72632053, is detected in a sample obtained from the subject. In some embodiments, the risk genotype further comprises at least two SNPs selected from the group consisting of the "A" at rs7958372, the "C" at rs2877453, the "A" at rs71327010, the "C" at rs1169302C, the "G" at rs1169303, the "A" at rs6519183, the "C" at rs685548, the "A" at rs11998187, the "A" at rs531819A, the "G" at rs1041968, the "G" at rs693, the "A" at rs512535, the "G" at rs550619G, the "A" at rs570877, the "G" at rs12713956, the "A" at rs2301723, the "A" at rs2499714, the "A" at rs6583176, the "A" at rs369880, the "G" at rs57884093, the "A" at rs989690, the "A" at rs7704116, the "A" at rs12984273, and the "G" at rs16891235, the "C" at rs7296651, the "A" at is rs516535, the "A" at rs9276427, the "A" at rs296564, the "A" at rs296569, the "A" at rs296568, the "G" at rs296567, the "G" at rs296561, the "G" at rs72749142, the "A" at rs9291547, the "A" at rs10761532, the "A" at rs10821813, the "C" at rs1561852, the "A" at rs10994464, the "G" at rs993402, the "A" at rs10994467, the "A" at rs10821822, the "G" at rs1837949, the "C" at rs35597961, the "G" at rs10821830, the "A" at rs975262, the "A" at rs973067, the "G" at rs10509139, the "A" at rs1442539, the "A" at rs2197155, the "G" at rs7919914, the "G" at rs 10994476, the "A" at rs35471473, the "G" at rs12785023, the "G" at rs12783716, the "G" at rs10821821, the "G" at rs10994441, the "C" at rs10994442, the "T" at rs10821814, the "A" at rs10994465, the "T" at rs12218617, the "C" at rs10509138. the "A" at rs61854518, the "G" at rs10821699, the "G" at rs7919274, the "A" at rs10761552, the "G" at rs17037425, the "A" at rs2893861, the "C" at rs1993939, the "G" at rs10821833, the "G" at rs1904418, the "G" rs16915196, the "A" at rs61853514, the "A" at rs10994430, the "A" at rs16915231, the "G" at rs2028564, the "G" at rs13196552, the "A" at rs17587597, the "A" at rs17587226, the "A" at rs2276917, the "A" at rs10013653, the "A" at rs11582799, the "A" at rs111692854, and the "A" at rs72632053, is detected in a sample obtained from the subject. In some embodiments, a transcriptomic risk signature is detected in a sample obtained from the subject, the transcriptomic risk signature comprising:
(a) a high level of expression of at least one of XCR1, HNF1A, GRM4, CHRM3, PDE4C, PRKCA, PIP5K1C, HIST1H1A, and KIF21B, as compared to a reference level; and
(b) a low level of expression of at least one of RPL3, PTPN11, RPL30, DLC1, APOB, RPL6,PAK2, RPL18, PPP2CA, ALDH2, BRD2, HLA-DQA2, PCDH7, ANK3, TRIM38, CYP4V2, and VAMP3, as compared to a reference level. A In some embodiments, the CD is ileal CD. In some embodiments, the CD is refractory CD. In some embodiments, the CD is perianal CD. In some embodiments, the subject is selected for treatment because the subject is, or is suspected to be, non-responsive to a standard therapy selected from the group consisting of anti-tumor necrosis factor (TNF) alpha therapy, anti-a4-b∂(vedolizumab), anti-IL12p40 therapy (ustekinumab), Thalidomide, Cytoxin, and a combination thereof. In some embodiments, the subject is human. In some embodiments, the level of expression is a level of mRNA expression. In some embodiments, the level of expression is a level of protein expression.

Aspects disclosed here provide methods of characterizing an inflammatory bowel disease, the method comprising: (a) obtaining a sample comprising genetic material from a subject having an inflammatory bowel disease; (b) providing a nucleic acid molecule comprising a detectable moiety, the nucleic acid molecule comprising a nucleic acid sequence that is capable of hybridizing to a risk genotype comprising a SNP selected from the group consisting of an "A" at rs7958372, a "C" at rs2877453, an "A" at rs71327010, a "C" at rs1169302C. a "G" at rs1169303, an "A" at rs6519183, a "C" at rs685548, an "A" at rs11998187, an "A" at rs531819A, a "G" at rs 1041968, a "G" at rs693, an "A" at rs512535, a "G" at rs550619G, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547,an "A" at rs10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs10821830, an "A" at rs975262, an "A" at rs973067, a "G" at rs10509139, an "A" at rs1442539, an "A" at rs2197155, a "G" at rs7919914, a "G" at rs10994476, an "A" at rs35471473, a "G" at rs12785023, a "G" at rs12783716, a "G" at rs 10821821, a "G" at rs10994441, a "C" at rs10994442, a "T" at rs10821814, an "A" at rs10994465, a "T" at rs12218617, a "C" at rs10509138, an "A" at rs61854518, a "G" at rs 10821699, a "G" at rs7919274, an "A" at rs10761552, a "G" at rs17037425, an "A" at rs2893861, a "C" at rs1993939, a "G" at rs10821833, a "G" at rs1904418, a "G" rs16915196, an "A" at rs61853514, an "A" at rs10994430, an "A" at rs16915231, a "G" at rs2028564, a "G" at rs13196552, an "A" at rs17587597, an "A" at rs17587226, an "A" at rs2276917, an "A" at rs 10013653, an "A" at rs11582799, an "A" at rs111692854, and an "A" at rs72632053: (c) contacting the nucleic acid molecule to the sample obtained from the subject; (d) detecting a hybridization complex between the nucleic acid molecule and the risk genotype; and (e) characterizing the inflammatory bowel disease as a severe form of Crohn's disease (CD). In some embodiments, the risk genotype further comprises at least two SNPs selected from the group consisting of the "A" at rs7958372, the "C" at rs2877453, the "A" at rs71327010, the "C" at rs1169302C, the "G" at rs1169303, the "A" at rs6519183, the "C" at rs685548, the "A" at rs11998187, the "A" at rs531819A, the "G" at rs1041968, the "G" at rs693, the "A" at rs512535, the "G" at rs550619G, the "A" at rs570877, the "G" at rs12713956, the "A" at rs2301723, the "A" at rs2499714, the "A" at rs6583176, the "A" at rs369880, the "G" at rs57884093, the "A" at rs989690, the "A" at rs7704116, the "A" at rs12984273, and the "G" at rs16891235, the "C" at rs7296651, the "A" at is rs516535, the "A" at rs9276427, the "A" at rs296564, the "A" at rs296569, the "A" at rs296568, the "G" at rs296567, the "G" at rs296561, the "G" at rs72749142, the "A" at rs9291547, the "A" at rs10761532, the "A" at rs10821813, the "C" at rs1561852, the "A" at rs10994464, the "G" at rs993402, the "A" at rs10994467, the "A" at rs10821822, the "G" at rs1837949, the "C" at rs35597961, the "G" at rs 10821830, the "A" at rs975262, the "A" at rs973067, the "G" at rs 10509139, the "A" at rs1442539, the "A" at rs2197155, the "G" at rs7919914, the "G" at rs10994476, the "A" at rs35471473, the "G" at rs12785023, the "G" at rs12783716, the "G" at rs10821821, the "G" at rs10994441, the "C" at rs10994442, the "T" at rs10821814, the "A" at rs10994465, the "T" at rs12218617, the "C" at rs10509138, the "A" at rs61854518, the "G" at rs10821699, the "G" at rs7919274, the "A" at rs10761552, the "G" at rs17037425, the "A" at rs2893861, the "C" at rs1993939, the "G" at rs10821833, the "G" at rs1904418, the "G" rs16915196, the "A" at rs61853514, the "A" at rs10994430, the "A" at rs16915231, the "G" at rs2028564, the "G" at rs13196552, the "A" at rs17587597, the "A" at rs17587226, the "A" at rs2276917, the "A" at rs10013653, the "A" at rs11582799, the "A" at rs111692854, and the "A" at rs72632053. In some embodiments, the presence of the risk genotype is indicative of a presence of the transcriptomic risk signature, the transcriptomic risk signature comprising: (a) a high level of expression of at least one of XCR1, HNF1A, GRM4, CHRM3, PDE4C, PRKCA, PIP5K1C, HIST1H1A, and KIF21B, as compared to a reference level; and (b) a low level of expression of at least one of RPL3, PTPN11,RPL30, DLC1, APOB, RPL6, PAK2, RPL18, PPP2CA, ALDH2, BRD2, HLA-DQA2, PCDH7,ANK3, TRIM38, CYP4V2, and VAMP3, as compared to a reference level. In some embodiments, the CD is refractory CD. In some embodiments, the CD is perianal CD. In some embodiments, the detectable moiety is a fluorophore, and wherein the nucleic acid optionally comprises a quencher molecule. In some embodiments, methods further comprise selecting the subject for treatment with a therapeutic agent comprising at least one of an inhibitor of PDE4C activity or expression inhibitor and an agonist of ADCY7. In some embodiments, the subject is human.

Aspects disclosed here provide methods of characterizing an inflammatory bowel disease, the method comprising: (a) obtaining a sample comprising genetic material from a subject having an inflammatory bowel disease; (b) detecting a transcriptomic risk signature comprising:
(a) a high level of expression of at least one XCR1, HNF1A, GRM4, CHRM3, PDE4C, PRKCA, PIP5K1C, HIST1H1A, and KIF21B, as compared to a reference level; and
(b) a low level of expression of at least one of RPL3, PTPN11, RPL30, DLC1, APOB, RPL6, PAK2, RPL18, PPP2CA, ALDH2, BRD2, HLA-DQA2, PCDH7, ANK3, TRIM38, CYP4V2, and VAMP3, as compared to a reference level; (c) contacting the nucleic acid molecule to the sample obtained from the subject; (d) detecting a hybridization complex between the nucleic acid molecule and the one or more genes; and (e) characterizing the inflammatory bowel disease as a severe form of Crohn's disease (CD). In some embodiments, the CD is perianal CD. In some embodiments, the CD is ileal CD. In some embodiments, the detectable moiety is a fluorophore, and wherein the nucleic acid optionally comprises a quencher molecule. In some embodiments, methods further comprise selecting the subject for treatment with a therapeutic agent comprising at least one of an inhibitor of PDE4C activity or expression inhibitor and an agonist of ADCY7. In some embodiments, the subject is human. In some embodiments, the level of expression is a level of mRNA expression.

Aspects disclosed herein provide systems comprising: (a) a computer processing device, optionally connected to a computer network; and (b) a software module executed by the computer processing device to detect a transcriptomic risk signature by analyzing a sample for a presence and/or a level of expression of a gene or gene expression product, the gene selected from the group consisting of PTPN11, RPL30, XCR1, HNF1A, RPL3, CHRM3, DLC1, APOB, RPL6, GRM4, PAK2, RPL18, PDE4C, PRKCA, PPP2CA, PIP5K1C, HIST1H1A, ALDH2, BRD2, HLA-DQA2, KIF21B, PCDH7, ANK3, TRIM38, CYP4V2, VAMP3. In some embodiments, the transcriptomic risk signature comprises: (a) a high level of expression of at least one of XCR1, HNF1A, GRM4, CHRM3, PDE4C, PRKCA, PIP5K1C, HIST1H1A, and KIF21B, as compared to a reference level; and (b) a low level of expression of at least one of RPL3, PTPN11, RPL30, DLC1, APOB, RPL6, PAK2, RPL18, PPP2CA, ALDH2, BRD2, HLA-DQA2, PCDH7, ANK3, TRIM38, CYP4V2, and VAMP3, as compared to a reference level. In some embodiments, the reference level is a level of expression of the gene or gene expression product in a non-diseased individual. In some embodiments, a SNP at the gene is analyzed, the SNP selected from Table 2. In some embodiments, the SNP is selected from the group consisting of an "A" at rs7958372, a "C" at rs2877453, an "A" at rs71327010, a "C" at rs1169302C. a "G" at rs1169303, an "A" at rs6519183, a "C" at rs685548, an "A" at rs11998187, an "A" at rs531819A, a "G" at rs 1041968, a "G" at rs693, an "A" at rs512535, a "G" at rs550619G, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547,an "A" at rs10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs10821830, an "A" at rs975262, an "A" at rs973067, a "G" at rs10509139, an "A" at rs1442539, an "A" at rs2197155, an "A" at rs2197155, a "G" at rs7919914, a "G" at rs 10994476, an "A" at rs10994441, a "C" at rs10994442, a "T" at rs10821814, an "A" at rs10994465, an "A" at rs10994465, a "T" at rs12218617, a "C" at rs10509138, an "A" at rs61854518, a "G" at rs10821699, a "G" at rs7919274, an "A" at rs10761552, a "G" at rs17037425, an "A" at rs2893861, a "C" at rs1993939, a "G" at rs10821833, a "G" at rs1904418, a "G" rs16915196, an "A" at rs61853514, an "A" at rs10994430, an "A" at rs16915231, a "G" at rs2028564, a "G" at rs13196552, an "A" at rs17587597, an "A" at rs17587226, an "A" at rs2276917, an "A" at rs10013653, an "A" at rs11582799, an "A" at rs111692854, and an "A" at rs72632053. In some embodiments, the SNP predictive of an upregulation or a downregulation of the gene, which is associated with a severe form of CD characteristic of CD3.

Aspects disclosed here provide kits: comprising a nucleic acid molecule comprising a detectable moiety and a nucleic acid sequence capable of hybridizing to a risk genotype or a gene in a transcriptomic risk signature. In some embodiments, the gene is selected from the group consisting of PTPN11, RPL30, XCR1, HNF1A, RPL3, CHRM3, DLC1, APOB, RPL6, GRM4, PAK2, RPL18, PDE4C, PRKCA, PPP2CA, PIP5K1C, HIST1H1A, ALDH2, BRD2, HLA-DQA2, KIF21B, PCDH7, ANK3, TRIM38, CYP4V2, VAMP3. In some embodiments, the risk genotype is selected from the group consisting of an "A" at rs7958372, a "C" at rs2877453, an "A" at rs71327010, a "C" at rs1169302C. a "G" at rs1169303, an "A" at rs6519183, a "C" at rs685548, an "A" at rs11998187, an "A" at rs531819A, a "G" at rs1041968, a "G" at rs693, an "A" at rs512535, a "G" at rs550619G, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547, an "A" at rs 10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs10821830, an "A" at rs975262, an "A" at rs973067, a "G" at rs10509139, an "A" at rs1442539, an "A" at rs2197155, a "G" at rs7919914, a "G" at rs 10994476, an "A" at rs35471473, a "G" at rs12785023, a "G" at rs12783716, a "G" at rs10821821, a "G" at rs10994441, a "C" at rs10994442, a "T" at rs10821814, an "A" at rs10994465, a "T" at rs 12218617, a "C" at rs10509138, an "A" at rs61854518, a "G" at rs10821699, a "G" at rs7919274, an "A" at rs10761552, a "G" at rs17037425, an "A" at rs2893861, a "C" at rs1993939, a "G" at rs10821833, a "G" at rs1904418, a "G" rs16915196, an "A" at rs61853514, an "A" at rs10994430, an "A" at rs16915231, a "G" at rs2028564, a "G" at rs13196552, an "A" at rs17587597, an "A" at rs17587226, an "A" at rs2276917, an "A" at rs10013653, an "A" at rs11582799, an "A" at rs111692854, and an "A" at rs72632053. In some embodiments, the detectable moiety is a fluorophore, and wherein the nucleic acid optionally comprises a quencher molecule.

Aspects disclosed herein provide methods of detecting a presence of a transcriptomic risk signature, the methods comprising: (a) contacting the nucleic acid molecule of the kits provided herein to a sample obtained from a subject: and (b) detecting a hybridization complex between the nucleic acid molecule and the risk genotype or a gene. In some embodiments, methods further comprise selecting the subject for treatment with a therapeutic agent comprising at least one of an inhibitor of PDE4C activity or expression inhibitor and an agonist of ADCY7.

BRIEF DESCRIPTION OF THE DRAWINGS

FIG. 1A shows a heatmap showing Pearson correlation coefficient between samples using normalized probe gene expression in SB85 cohort. FIG. 1B shows three sample clusters in the principle component analysis (PCA) plot using top three PCs in expression data in SB85 cohort. The sample clusters, CD1, CD2 and CD3 were detected using hierarchical and k-means clustering. FIG. 1C shows batch effect present in the two cohorts (left) was removed (right) while merged the cohorts to have better power in genetic and clinical phenotype associations. FIG. 1D shows the presence of the three CD patient subgroups confirmed in an expanded cohort (SB139) using k-means/hierarchical clustering. FIG. 1E shows a Gaussian model-based clustering method.

FIG. 2A shows that survival analysis (Gehan-Breslow-Wilcoxon test) using time from first surgery to recurrence or last follow-up of CD1, CD2, and CD3 clusters indicated proportion of recurrence free survival in CD3 cluster was smaller than CD1 in SB85 cohort (p=0.02, median survival time (months), CD1=10, CD2 (8) and CD3=6. FIG. 2B shows the survival analysis using time from first to second surgery or last follow-up within five (5) years. which indicates greater proportion without a second surgery in CD1 compared to CD3 (marginally significant. p=0.08) in combined cohort of SB139.

FIGS. 4A-4B shows cis-cQTL based pathway analysis and Transcriptional risk scores (TRS) underline transition to increasing disease risk from CD1 to CD3. FIG. 4A shows a comparison pathway analysis using eGenes from cis-eQTLs unique to either CD1 and CD3 (p<1e-08 for eQTL and p<0.05 for Fisher's exact test based pathway analysis) revealed that the CD3 sub-group is enriched in Wnt/beta-catenin signaling and regulation of EMT. This possibly indicates that the underlying pathobiology for recurring and complicated disease in CD3 could be changes in epithelial architecture. FIG. 4B shows association of TRS with the three subgroups (p<0.0001, Kruskal-Wallis (K-W) test). CD3 sub-group was associated with higher TRS compared to CD1 sub-group confirming CD3 as being more complicated and severe subgroup (p=0.0002, Mann-Whitney (M-W) test)

FIGS. 5A-5C shows cell-type specific signatures associated with the three sub-groups. FIG. 5A shows a statistical analysis of eosinophil (EOS) enrichment scores from xCell (ANOVA, p<0.0001) indicated significantly higher scores in CD3 sub-group while CD1 had the lowest score. Similar trend was obtained in NKT cells. The presence of EOS in the small bowel (SB) resected tissue were manually counted using H&E staining of FFPE slides for 67 out of the 139 patients (CD1=18, CD2=27 and CD3=22). FIG. 5B shows that a statistically significant difference in the eosinophil (EOS) counts across the three subgroups was not observed. FIG. 5C shows enrichment of NKT cells in CD3 subgroup. Statistical analysis of NKT enrichment scores from xCell (ANOVA, p<0.0001) indicated significantly higher scores in CD3 sub-group while CD1 had the lowest score.

FIG. 7A optimal model (VVV) and number of clusters (three) determined using Bayesian information criterion (BIC). Best model is one with highest BIC score (VVV in this case). FIG. 7B shows classification of samples in the combined SB139 cohort using BIC-scatter plot with samples colored based on classification in a sub-group.

FIG. 8A shows a Manhattan plot for genetic associations with CD1 sub-group in SB139 samples. FIG. 8B shows a Manhattan plot for genetic associations with CD3 sub-groups in SB139 samples. The gene locus of top SNP on each chromosome with p<0.001 is shown in the Manhattan plots. FIG. 8C shows that the CD3 sub-group is associated with SNPs in DAPK1 gene, a previously reported pCD phenotype locus.

DETAILED DESCRIPTION

Figure 1B:
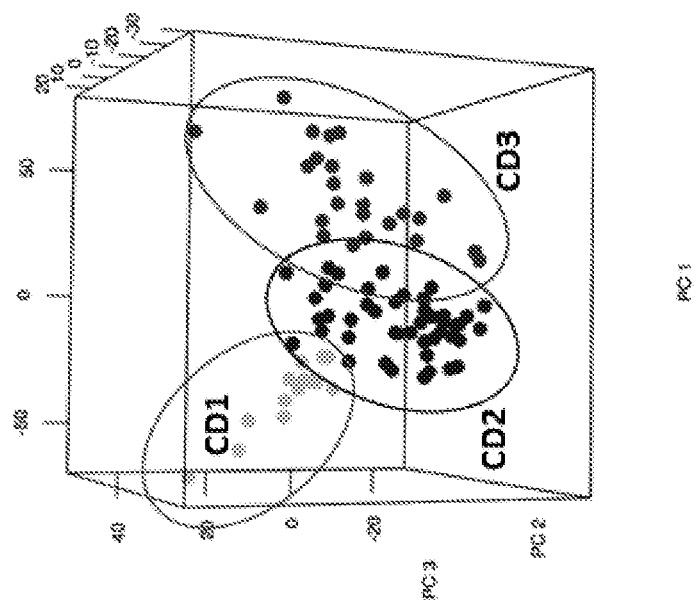
FIGS. 1A-1E shows the presence of three patient subgroups in small bowel resection mRNA expression.

Personalized therapeutic strategies are a promising solution to the unmet challenges of treating complex genetically and clinically heterogeneous disease, such as inflammatory diseases. The methods. systems. kits and compositions described herein practically apply the associations between a presence of the risk genotypes and/or transcriptomic risk profiles described herein and incidences of severe and refractory forms of inflammatory diseases and disorders, such as inflammatory bowel disease (IBD), in an effort to meet these unmet challenges. The risk genotypes and/or transcriptomic risk profiles of the present disclosure can be used to identify a subject as being at a high risk of developing an inflammatory disease or condition as compared to an individual who does not carry the risk genotype or transcriptomic risk signature. The genotypes are also useful to identify a patient previously diagnosed with some form of an inflammatory disease or condition who may be at a high risk for developing a severe or refractory form of the disease, as compared to an individual with the disease or condition who does not carry the risk genotype or transcriptomic risk profile. The early identification of patients who are at a high risk for developing severe or refractory forms of disease, may be prescribed earlier and more aggressive treatment regimens. In addition, or alternatively, these patients may be prescribed a second-line therapies. such as those described herein (e.g., anti-PDE4therapy, agonist of ADCY7), rather than a first line therapy, such as an anti-TNF therapy.

The risk genotypes and/or transcriptomic risk profiles disclosed herein are enriched for genes involved in the innate immune response, and in some cases, are associated with a variation in an expression of genes in these pathways. For example, the risk genotypes or transcriptomic risk profiles provided herein may be indicative of a variation in expression or an activity of ADCY7 and/or PDE4. In some cases, the risk genotypes and/or transcriptomic risk profiles can be used to identify a patient who may be suitable for treatment with a targeted ADCY7 and/or PDE4 therapy (e.g., a patient carrying a risk genotype associated with an increase in PDE4C may be suitable for a treatment with an ADCY7 agonist or anti-PDE4 therapy). Exemplary conditions include UC and CD. In some cases, a subject is administered a therapeutic agent (e.g., ADCY7 agonist, anti-PDE4 inhibitor) provided the risk genotype and/or transcriptomic risk profile disclosed herein is detected in a sample obtained from the subject.

Compositions and kits for detecting the risk genotypes and transcriptomic risk profiles described herein are provided as further exemplary practical applications. Suitable methods of using the compositions and kits described herein quantitative PCR (qPCR), sequencing methodologies, and microarray methodologies. The compositions disclosed herein may include, for example, primers suitable for amplifying a region of DNA of interest (e.g., a polymorphism), and/or detectable nucleic acid probes capable of hybridizing the DNA of interest, such that it may be visualized.

I. METHODS

Methods are provided herein comprising selecting a subject for treatment of an inflammatory disease or condition with a modulator of phosphodiesterase 4 (PDE4) and/or an agonist of adenylate cyclase 7 (ADCY7) based on a presence of a risk genotype or transcriptomic risk profile. The risk genotype and transcriptomic risk profile are predictive of severe forms of the inflammatory disease or condition. In some cases, the inflammatory disease or disorder is treated by administering a therapeutically effective amount of the modulator of PDE4 and/or ADCY7 to the subject. An exemplary inflammatory disease or disorder is inflammatory bowel disease (IBD), such as Crohn's disease (CD) or ulcerative colitis (UC).

Further provided are methods of characterizing an inflammatory disease or condition in a subject based on the presence of the risk genotype and/or transcriptomic risk signature detected in a sample obtained from the subject. Suitable methods of detecting the risk genotype and transcriptomic risk profile are provided herein, which include quantitative polymerase chain reaction (qPCR). In some case, the subject is treated with a modulator of PDE4 and/or an agonist of ADCY7, provided that the inflammatory disease or condition is characterized as severe or refractory.

A. Subject

The subject disclosed herein can be a mammal, such as for example a mouse, rat, guinea pig, rabbit, non-human primate, or farm animal. In some instances, the subject is human. In some instances, the subject is a patient who is diagnosed with the disease or condition disclosed herein. In some instances, the subject is not diagnosed with the disease or condition. In some instances, the subject is suffering from a symptom related to a disease or condition disclosed herein (e.g., abdominal pain, cramping, diarrhea, rectal bleeding, fever, weight loss, fatigue, loss of appetite, dehydration, and malnutrition, anemia, or ulcers).

In some embodiments, the subject is susceptible to, or is inflicted with, thiopurine toxicity, or a disease caused by thiopurine toxicity (such as pancreatitis or leukopenia). The subject may experience, or is suspected of experiencing, non-response or loss-of-response to a standard treatment (e.g., anti-TNF alpha therapy, anti-a4-b7 therapy (vedolizumab), anti-IL 12p40 therapy (ustekinumab), Thalidomide, or Cytoxin). In alternative embodiments, the subject is determined to be responsive to a standard treatment.

B. Disease or Condition

The disease or condition disclosed herein is at least one of an inflammatory disease. a fibrostenotic disease, and a fibrotic disease. Non-limiting examples of inflammatory diseases include diseases of the gastrointestinal (GI) tract, liver, gallbladder, and joints. In some cases, the inflammatory disease inflammatory bowel disease (IBD), Crohn's disease (CD), or ulcerative colitis, systemic lupus erythematosus (SLE), or rheumatoid arthritis. A subject may suffer from fibrosis, fibrostenosis, or a fibrotic disease, either isolated or in combination with an inflammatory disease. In some cases, the CD is obstructive CD. The obstructive CD may result from inflammation that has led to the formation of scar tissue in the intestinal wall (fibrostenosis) and/or swelling. In some cases, the CD is characterized by the presence of fibrotic and/or inflammatory strictures. The strictures may be determined by computed tomography enterography (CTE), and magnetic resonance imaging enterography (MRE). In some embodiments, the disease is primary sclerosing cholangitis (PSC). Exemplary methods of diagnosing PSC include magnetic resonance cholangiopancreatography (MRCP), liver function tests, and histology. Liver function tests are valuable in the laboratory workup, and may include measurement of levels of serum alkaline phosphatase, serum aminotransferase, gamma glutamyl transpeptidase, and the presence of hypergammaglobulinemia. The disease or condition may comprise thiopurine toxicity, or a disease caused by thiopurine toxicity (such as pancreatitis or leukopenia). In further embodiments provided, the subject experiences non-response to an induction of a therapy, or a loss-of-response to the therapy after a successful induction of the therapy. Non-limiting examples of standard treatment include glucocorticosteriods, anti-TNF therapy, anti-a4-b7 therapy (vedolizumab), anti-IL12p40 therapy (ustekinumab), Thalidomide, and Cytoxin.

C. Risk Genotypes

Disclosed herein, in some embodiments are genotypes that are detected in a sample obtained from a subject by analyzing the genetic material in the sample. In some instances, the subject may be human. In some embodiments, the genetic material is obtained from a subject having a disease or condition disclosed herein. In some cases, the genetic material is obtained from blood, serum, plasma, sweat, hair, tears, urine, and other techniques known by one of skill in the art. In some cases, the genetic material is obtained for a biopsy, e.g., from the intestinal track of the subject.

The genotypes of the present disclosure comprise genetic material that is deoxyribonucleic acid (DNA). In some instances, the genotype comprises a denatured DNA molecule or fragment thereof. In some instances, the genotype comprises DNA selected from: genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. The circular DNA may be cleaved or fragmented.

The genotypes disclosed herein comprise at least one polymorphisms at a gene or genetic locus described herein. In some instances, the gene or genetic locus comprises phosphodiesterase 4C (PDE4C). In some instances, the genotype comprises a particular polymorphism, a polymorphism in linkage disequilibrium (LD) therewith, or a combination thereof. In some cases, LD is defined by an $r^2$ of at least or about 0.70, 0.75, 0.80, 0.85, 0.90, or 0.1. The genotypes disclosed herein can comprise at least or about 1, 2, 3, 4, 5, 6, 7, 8, 9, 10, 11, 12, 13, 14, 15, 16, 17, 18, 19, 20, 21, 22, 23, 24, 25, 26,27, 28, 29, 30, or more polymorphisms.

The polymorphisms described herein can be a single nucleotide polymorphism, or an indel (insertion/deletion). In some instances, the polymorphism is an insertion or a deletion of at least one nucleobase (e.g., an indel). In some instances, the genotype may comprise a copy number variation (CNV), which is a variation in a number of a nucleic acid sequence between individuals in a given population. In some instances, the CNV comprises at least or about two, three, four, five, six, seven, eight, nine, ten, twenty, thirty, forty or fifty nucleic acid molecules. In some instances, the genotype is heterozygous. In some instances, the genotype is homozygous.

In an aspect, provided herein, a risk genotype comprising one or more polymorphisms detected in a sample obtained from the subject is located at a gene locus involved in the mammalian innate and adaptive immune responses. In some embodiments, the gene locus is involved in the pathogenesis of inflammatory disease, such as IBD. In further embodiments. the gene locus is involved in autophagy, innate immunity, adaptive immunity, Wnt/beta-catenin signaling, the regulation of epithelial-mesenchymal transition, antigen presentation, or OX40 signaling. In some embodiments, the gene locus is involved in PDE4 mediated pathways, including EIF2 and cAMP signaling pathways. The gene locus may comprise a gene from Table 3 or Table 4.

In some embodiments, the polymorphisms within the risk genotypes are uniquely associated with an inflammatory disease clinical subgroup. In some embodiments, the polymorphism is at a gene locus of a gene that is differentially expressed in inflammatory disease clinical subgroups. In some embodiments, the clinical subgroup comprises subjects with inflammatory disease that is characterized by a less severe form of disease (CD1). Table 1 lists risk genotypes comprising polymorphisms that are associated with the CD1 subgroup. In some embodiments, the clinical subgroup comprises subjects with inflammatory disease that is characterized by a more severe form of disease (CD3). Table 2 lists risk genotypes comprising polymorphisms that are associated with the CD3 subgroup. In some embodiments the CD3 subgroup is characterized by a faster time between first surgery, and second surgery or last follow-up.

In some embodiments, the CD3 subgroup is characterized as having more female patients than male patients. The CD3 subgroup, in some cases, is characterized by refractory disease.

As used herein, in Table 1 and Table 2, the term "gene" refers to the gene expression product that is up or down regulated in the CD1 cohort (Table 1) or CD3 cohort (Table 2). The abbreviation "CHR" refers to the human chromosome on which the polymorphism is located. The term "polymorphism" may be a single nucleotide polymorphism or an indel (e.g., insertion/deletion) located at a genetic locus associated with inflammatory bowel disease. The minor allele is indicated with "A1" and the major allele is indicated with "A2." The allele indicated with "Risk" is the allele, the presence of which is associated with the phenotype of interest (e.g., fold change in expression of the gene). The term, "OR" stands for "Odds Ratio," which represents the odds that an outcome (e.g., fold change in expression of the gene) will occur given a particular exposure (e.g., presence of the polymorphism) in a logistic regression analysis. If OR<1, the minor allele correlates to a reduced risk of a patient exhibiting the listed phenotype. If OR>1, the minor allele correlates to an increased risk of a patient exhibiting the listed phenotype. The "P" indicates P value, which represents the association of a presence of the polymorphism with the occurrence of a phenotype (e.g., fold change in expression of the gene).

In some embodiments, the polymorphisms provided in Table 1 or Table 2 are associated with a differential expression (e.g., a fold change in messenger RNA (mRNA)) of a gene between the CD3 and CD1 subgroups, listed in Table 1 or Table 2, respectively. In some cases, the mRNA level of expression is a level measured in a tissue sample obtained from the small bowel of a subject in the CD1 and CD3 subgroups, respectively. A negative fold change value indicates that the presence of the "risk" allele is associated with a downregulation of the "gene" in the CD1 (Table 1) or CD3 (Table 2) subgroup. A positive fold change value indicates that the presence of the "risk" allele is associated with an upregulation of the "gene" in the CD1 (Table 1) or CD3 (Table 2) subgroup.

A presence of a polymorphism provided herein that is detected in a sample (e.g., blood) obtained from a subject is predictive of a corresponding differential expression of the gene in the subject. In a non-limiting example, detection of an "A" allele at rs470119 is predictive of an upregulation of thymidine phosphorylase (TYMP) (P=4.73E-4), and a likelihood that the subject has less severe form of Crohn's disease (CD), as compared to an individual who does not carry the "A" allele at rs470119.

TABLE 1

Polymorphisms Unique to Inflammatory Disease CD1 Subgroup

| Gene | FoldChange_CD3vsCD1 | CHR | Polymorphism | A1 | A2 | Risk | OR | P |
|---|---|---|---|---|---|---|---|---|
| TYMP | 3.019 | 22 | rs470119 | A | G | A | 3.338 | 4.73E−04 |
| PACS1 | −2.613 | 11 | rs559298 | G | A | G | 5.834 | 9.24E−04 |
| CNNM2 | 2.008 | 10 | rs12764154 | C | A | C | 2.906 | 2.17E−03 |
| COL5A1 | −2.532 | 9 | rs4842139 | A | G | A | 3.929 | 3.29E−03 |
| CNNM2 | 2.008 | 10 | rs2297786 | A | G | A | 2.437 | 3.65E−03 |
| SLC9A3 | −1.548 | 5 | rs9764991 | G | A | G | 2.823 | 4.09E−03 |
| CNNM2 | 2.008 | 10 | rs10509757 | A | G | A | 2.375 | 4.37E−03 |
| CNNM2 | 2.008 | 10 | rs10748836 | A | G | A | 2.375 | 4.37E−03 |
| CNNM2 | 2.008 | 10 | rs10883824 | G | A | G | 2.375 | 4.37E−03 |
| CNNM2 | 2.008 | 10 | rs10883826 | G | A | G | 2.375 | 4.37E−03 |
| CNNM2 | 2.008 | 10 | rs1926034 | A | G | A | 2.375 | 4.37E−03 |
| CNNM2 | 2.008 | 10 | rs2275271 | G | A | G | 2.375 | 4.37E−03 |

TABLE 1-continued

Polymorphisms Unique to Inflammatory Disease CD1 Subgroup

| Gene | FoldChange_CD3vsCD1 | CHR | Polymorphism | A1 | A2 | Risk | OR | P |
|---|---|---|---|---|---|---|---|---|
| CNNM2 | 2.008 | 10 | rs4917994 | A | G | A | 2.375 | 4.37E-03 |
| CNNM2 | 2.008 | 10 | rs7914558 | A | G | A | 2.375 | 4.37E-03 |
| CNNM2 | 2.008 | 10 | rs943035 | G | A | G | 2.375 | 4.37E-03 |
| CNNM2 | 2.008 | 10 | rs943036 | G | A | G | 2.375 | 4.37E-03 |
| MAGI3 | -2.654 | 1 | rs6704188 | A | G | A | 2.952 | 5.35E-03 |
| MAGI3 | -2.654 | 1 | rs11102651 | G | A | G | 2.865 | 6.76E-03 |
| MAGI3 | -2.654 | 1 | rs12144505 | G | A | G | 7.08 | 6.91E-03 |
| MAGI3 | -2.654 | 1 | rs12117465 | A | G | A | 7.08 | 6.91E-03 |
| MAGI3 | -2.654 | 1 | rs17448063 | G | A | G | 7.08 | 6.91E-03 |
| MAGI3 | -2.654 | 1 | rs11102629 | C | A | C | 7.08 | 6.91E-03 |
| MAGI3 | -2.654 | 1 | rs12130729 | A | G | A | 7.08 | 6.91E-03 |
| MAGI3 | -2.654 | 1 | rs12145834 | A | C | A | 7.08 | 6.91E-03 |
| MAGI3 | -2.654 | 1 | rs17461007 | G | A | G | 7.08 | 6.91E-03 |
| MAGI3 | -2.654 | 1 | rs75402723 | G | A | G | 7.08 | 6.91E-03 |
| MAGI3 | -2.654 | 1 | rs75372342 | G | A | G | 7.08 | 6.91E-03 |
| MAGI3 | -2.654 | 1 | rs12131115 | A | G | A | 7.08 | 6.91E-03 |
| FYB | 1.898 | 5 | rs6896856 | A | G | A | 2.441 | 6.98E-03 |
| FYB | -2.353 | 5 | rs6896856 | A | G | A | 2.441 | 6.98E-03 |
| CFL1P1 | -2.819 | 10 | rs12775504 | C | A | A | 0.2285 | 7.00E-03 |
| PPARGC1B | -2.383 | 5 | rs10515638 | A | C | A | 3.912 | 7.06E-03 |
| MAGI3 | -2.654 | 1 | rs17507884 | G | A | G | 6.419 | 7.44E-03 |
| DTX3 | -3.054 | 12 | rs1806652 | A | G | A | 2.519 | 7.81E-03 |
| BAK1 | 2.131 | 6 | rs5745582 | A | G | A | 2.479 | 7.97E-03 |
| MAGI3 | -2.654 | 1 | rs2153977 | A | G | A | 2.663 | 8.49E-03 |
| MAGI3 | -2.654 | 1 | rs11102658 | G | C | G | 2.663 | 8.49E-03 |
| SSC5D | 2.498 | 19 | rs542186 | C | A | A | 0.4067 | 9.11E-03 |
| DAAM2 | 1.816 | 6 | rs2504803 | G | A | G | 2.532 | 9.47E-03 |
| DOCK10 | -2.615 | 2 | rs10933073 | G | A | A | 0.431 | 1.03E-02 |
| MTR | -1.944 | 1 | rs10158822 | C | A | A | 0.1463 | 1.04E-02 |
| MTR | -1.944 | 1 | rs1805087 | G | A | A | 0.1463 | 1.04E-02 |
| MAGI3 | -2.654 | 1 | rs10858002 | G | A | G | 2.591 | 1.06E-02 |
| MAGI3 | -2.654 | 1 | rs10858008 | A | G | A | 2.704 | 1.06E-02 |
| COL4A2 | -2.222 | 13 | rs2025906 | G | G | G | 0.4005 | 1.07E-02 |
| TNR | 4.657 | 1 | rs12082376 | A | C | A | 3.222 | 1.07E-02 |
| PECAM1 | -1.889 | 17 | rs2070783 | A | G | A | 2.272 | 1.16E-02 |
| SLAIN2 | -1.87 | 4 | rs7438704 | A | G | G | 0.3589 | 1.35E-02 |
| SLAIN2 | -2.333 | 4 | rs7438704 | A | G | G | 0.3589 | 1.35E-02 |
| KLHDC7B | 3.419 | 22 | rs131779 | A | G | A | 2.276 | 1.39E-02 |
| MAGI3 | -2.654 | 1 | rs12125741 | G | A | G | 5.336 | 1.43E-02 |
| MAGI3 | -2.654 | 1 | rs12130763 | C | A | C | 5.336 | 1.43E-02 |
| MAGI3 | -2.654 | 1 | rs17461231 | C | A | C | 5.336 | 1.43E-02 |
| GIT2 | -2.131 | 12 | rs2292354 | A | G | G | 0.3335 | 1.52E-02 |
| SMAD3 | -2.289 | 15 | rs1470002 | A | G | A | 2.193 | 1.62E-02 |
| SMAD3 | -2.332 | 15 | rs1470002 | A | G | A | 2.193 | 1.62E-02 |
| SMAD3 | -2.37 | 15 | rs1470002 | A | G | A | 2.193 | 1.62E-02 |
| SMAD3 | -2.389 | 15 | rs1470002 | A | G | A | 2.193 | 1.62E-02 |
| SMAD3 | -2.422 | 15 | rs1470002 | A | G | A | 2.193 | 1.62E-02 |
| SMAD3 | -2.428 | 15 | rs1470002 | A | G | A | 2.193 | 1.62E-02 |
| SMAD3 | -2.459 | 15 | rs1470002 | A | G | A | 2.193 | 1.62E-02 |
| SMAD3 | -2.499 | 15 | rs1470002 | A | G | A | 2.193 | 1.62E-02 |
| SMAD3 | -2.53 | 15 | rs1470002 | A | G | A | 2.193 | 1.62E-02 |
| SMAD3 | -2.556 | 15 | rs1470002 | A | G | A | 2.193 | 1.62E-02 |
| ST6GALNAC5 | 2.614 | 1 | rs199720 | G | A | A | 0.3603 | 1.70E-02 |
| SLC9A3 | -1.548 | 5 | rs11748410 | A | G | A | 3.113 | 1.72E-02 |
| MYO16 | 1.73 | 13 | rs9587731 | A | G | A | 2.768 | 1.77E-02 |
| TBX19 | 1.937 | 1 | rs1000533 | G | A | G | 2.333 | 1.79E-02 |
| PHLDB2 | 1.685 | 3 | rs1443078 | C | A | C | 3.455 | 1.80E-02 |
| LRRC4C | 2.118 | 11 | rs1158362 | A | C | C | 0.376 | 1.85E-02 |
| ULK1 | -2.038 | 12 | rs11615995 | G | A | A | 0.2769 | 1.88E-02 |
| COL4A2 | -2.222 | 13 | rs7317733 | A | C | A | 2.31 | 1.98E-02 |
| PCGF3 | -1.688 | 4 | rs4076064 | G | A | A | 0.2432 | 1.99E-02 |
| PCGF3 | -2.03 | 4 | rs4076064 | G | A | A | 0.2432 | 1.99E-02 |
| MTSS1 | 1.947 | 8 | rs3901290 | G | A | A | 0.1725 | 2.01E-02 |
| LCE1C | 3 | 1 | rs35436039 | A | G | G | 0.4249 | 2.02E-02 |
| LCE1C | 3 | 1 | rs17624493 | A | G | G | 0.4047 | 2.10E-02 |
| MSRA | -2.27 | 8 | rs4448276 | A | C | A | 2.206 | 2.27E-02 |
| GGNBP2 | 3.205 | 17 | rs9906189 | G | A | G | 1.974 | 2.27E-02 |
| ST8SIA2 | 3.756 | 15 | rs2168351 | G | A | G | 2.101 | 2.28E-02 |
| MAGI3 | -2.654 | 1 | rs1113523 | A | G | A | 2.401 | 2.33E-02 |
| S1PR2 | 2.402 | 19 | rs2288937 | G | A | A | 0.3789 | 2.41E-02 |
| MAGI3 | -2.654 | 1 | rs1343630 | G | A | A | 0.3789 | 2.53E-02 |
| FMO1 | -2.768 | 1 | rs10912694 | G | A | A | 0.3679 | 2.56E-02 |
| MAGI3 | -2.654 | 1 | rs1343629 | C | G | G | 0.4664 | 2.59E-02 |
| VARS2 | 3.442 | 6 | rs7766094 | A | G | A | 3.558 | 2.60E-02 |
| MAGI3 | -2.654 | 1 | rs66602772 | G | A | A | 0.468 | 2.61E-02 |

TABLE 1-continued

Polymorphisms Unique to Inflammatory Disease CD1 Subgroup

| Gene | FoldChange_CD3vsCD1 | CHR | Polymorphism | A1 | A2 | Risk | OR | P |
|---|---|---|---|---|---|---|---|---|
| MAPK11 | 2.201 | 22 | rs2076139 | A | G | A | 2.248 | 2.63E-02 |
| BEST3 | 2.333 | 12 | rs4761251 | G | A | A | 0.4507 | 2.71E-02 |
| FAM71B | 2.615 | 5 | rs31220 | G | A | A | 0.2515 | 2.84E-02 |
| DOCK10 | -2.615 | 2 | rs1565073 | A | C | C | 0.4889 | 2.85E-02 |
| MAST2 | -1.506 | 1 | rs2236560 | A | G | A | 2.124 | 2.89E-02 |
| TNS3 | 1.902 | 7 | rs2692541 | A | C | C | 0.4691 | 2.94E-02 |
| MME | -2.42 | 3 | rs1836917 | G | A | G | 1.954 | 3.00E-02 |
| GPX4 | -2.286 | 19 | rs4807543 | A | C | A | 3.567 | 3.03E-02 |
| PSMA6 | -1.98 | 14 | rs12878391 | G | A | A | 0.3538 | 3.11E-02 |
| MTMR9LP | 2.681 | 1 | rs747020 | A | G | A | 2.738 | 3.12E-02 |
| MTMR9LP | -2.266 | 1 | rs747020 | A | G | A | 2.738 | 3.12E-02 |
| MAGI3 | -2.654 | 1 | rs4259646 | A | G | G | 0.4817 | 3.15E-02 |
| MAGI3 | -2.654 | 1 | rs6537790 | A | C | C | 0.4817 | 3.15E-02 |
| HLA-DOA | 2.801 | 6 | rs592625 | G | A | A | 0.3491 | 3.15E-02 |
| SLC9A3 | -1.548 | 5 | rs13181243 | A | C | A | 2.067 | 3.17E-02 |
| FKBP5 | -1.813 | 6 | rs4713899 | A | G | A | 2.242 | 3.23E-02 |
| FKBP5 | -2.153 | 6 | rs4713899 | A | G | A | 2.242 | 3.23E-02 |
| TCEA3 | -1.785 | 1 | rs4648892 | G | A | A | 0.344 | 3.29E-02 |
| LRRC4C | 2.118 | 11 | rs896617 | A | G | G | 0.4383 | 3.30E-02 |
| LRRC4C | 2.118 | 11 | rs896618 | A | G | A | 0.4383 | 3.30E-02 |
| MME | -2.42 | 3 | rs2016848 | A | G | A | 1.933 | 3.33E-02 |
| LOC728175 | 2.484 | 4 | rs76450153 | A | C | A | 2.693 | 3.34E-02 |
| MAGI3 | -2.654 | 1 | rs35390985 | A | G | G | 0.4843 | 3.38E-02 |
| MAGI3 | -2.654 | 1 | rs7554019 | A | G | G | 0.4843 | 3.38E-02 |
| CEP72 | 2.59 | 5 | rs74553530 | T | A | T | 2.414 | 3.42E-02 |
| TCF4 | -2.386 | 18 | rs1660241 | A | G | G | 0.437 | 3.43E-02 |
| VNN1 | -1.99 | 6 | rs3798792 | G | A | A | 0.442 | 3.45E-02 |
| PCGF3 | -1.688 | 4 | rs6838241 | C | A | A | 0.4193 | 3.50E-02 |
| PCGF3 | -2.03 | 4 | rs6838241 | C | A | A | 0.4193 | 3.50E-02 |
| PSMA6 | -1.98 | 14 | rs11621075 | G | A | A | 0.3636 | 3.56E-02 |
| NFIA | -2.008 | 1 | rs2474358 | A | G | G | 0.3387 | 3.57E-02 |
| NFIA | -2.244 | 1 | rs2474358 | A | G | G | 0.3387 | 3.57E-02 |
| HHAT | -1.744 | 1 | rs7548180 | G | A | G | 1.992 | 3.59E-02 |
| DKFZP434K028 | 2.118 | 11 | rs2238003 | A | G | A | 2.193 | 3.62E-02 |
| LCE1F | 3.218 | 1 | rs12239774 | A | G | G | 0.4629 | 3.65E-02 |
| WNK1 | -2.073 | 12 | rs12828016 | A | C | A | 1.903 | 3.67E-02 |
| HLA-DPA1 | -3.667 | 6 | rs7905 | A | G | A | 0.2691 | 3.68E-02 |
| SNAPC4 | -2.11 | 9 | rs10747031 | G | C | G | 1.977 | 3.69E-02 |
| TBX19 | 1.937 | 1 | rs17502484 | A | G | A | 2.018 | 3.74E-02 |
| NMD3 | -1.987 | 3 | rs4350933 | C | A | A | 0.4996 | 3.84E-02 |
| NMD3 | -1.987 | 3 | rs6794601 | G | A | A | 0.4996 | 3.84E-02 |
| LTB4R | 2.868 | 14 | rs1046587 | A | G | A | 1.962 | 3.85E-02 |
| MAGI3 | -2.654 | 1 | rs10858000 | A | G | A | 2.258 | 3.96E-02 |
| MAGI3 | -2.654 | 1 | rs11102648 | A | C | A | 2.258 | 3.96E-02 |
| MAGI3 | -2.654 | 1 | rs4456089 | A | G | A | 2.258 | 3.96E-02 |
| MAGI3 | -2.654 | 1 | rs10745339 | G | A | G | 2.258 | 3.96E-02 |
| MAGI3 | -2.654 | 1 | rs17013326 | A | G | A | 2.258 | 3.96E-02 |
| MAGI3 | -2.654 | 1 | rs12037873 | T | A | T | 2.258 | 3.96E-02 |
| MAGI3 | -2.654 | 1 | rs11102652 | A | G | A | 2.258 | 3.96E-02 |
| MAGI3 | -2.654 | 1 | rs12077419 | A | T | A | 2.258 | 3.96E-02 |
| MAGI3 | -2.654 | 1 | rs1343128 | A | G | A | 2.258 | 3.96E-02 |
| P4HA2 | -3.126 | 5 | rs156025 | A | G | G | 0.3995 | 3.96E-02 |
| LAT | 2.138 | 16 | rs1131543 | A | G | A | 2.133 | 3.98E-02 |
| IGFBP4 | -2.236 | 17 | rs584828 | A | G | A | 1.91 | 4.01E-02 |
| CNNM2 | 2.008 | 10 | rs12248123 | G | A | G | 1.894 | 4.03E-02 |
| ITPKB | -1.559 | 1 | rs3768414 | G | A | G | 2.075 | 4.03E-02 |
| ITPKB | -1.597 | 1 | rs3768414 | G | A | G | 2.075 | 4.03E-02 |
| IFNGR1 | -1.802 | 6 | rs11754268 | A | G | G | 0.4053 | 4.05E-02 |
| MAGI3 | -2.654 | 1 | rs2027536 | A | G | A | 2.18 | 4.15E-02 |
| MAGI3 | -2.654 | 1 | rs1343630 | A | T | A | 2.18 | 4.15E-02 |
| MAGI3 | -2.654 | 1 | rs11102627 | A | G | A | 2.18 | 4.15E-02 |
| MAGI3 | -2.654 | 1 | rs11102628 | A | G | A | 2.18 | 4.15E-02 |
| MAGI3 | -2.654 | 1 | rs11102647 | G | A | G | 2.18 | 4.15E-02 |
| SYMPK | 3.38 | 19 | rs10500292 | A | G | G | 0.4896 | 4.17E-02 |
| GPR17 | 1.739 | 2 | rs13021001 | G | A | G | 2.169 | 4.20E-02 |
| MBNL1 | -2.508 | 3 | rs17371539 | A | G | G | 0.1231 | 4.22E-02 |
| NMD3 | -1.987 | 3 | rs4273380 | A | G | G | 0.5048 | 4.24E-02 |
| NMD3 | -1.987 | 3 | rs4370045 | A | G | G | 0.5048 | 4.24E-02 |
| NMD3 | -1.987 | 3 | rs4597724 | A | G | G | 0.5048 | 4.24E-02 |
| SEMA3F | 1.881 | 3 | rs2859580 | G | A | A | 0.1213 | 4.25E-02 |
| CEP72 | 2.59 | 5 | rs3805416 | A | G | A | 2.315 | 4.32E-02 |
| MAGI3 | -2.654 | 1 | rs11579386 | G | C | G | 4.304 | 4.32E-02 |
| MAGI3 | -2.654 | 1 | rs56092022 | G | A | G | 4.304 | 4.32E-02 |
| MAGI3 | -2.654 | 1 | rs76658509 | A | G | A | 4.304 | 4.32E-02 |
| MAGI3 | -2.654 | 1 | rs17031640 | G | A | G | 4.304 | 4.32E-02 |

TABLE 1-continued

Polymorphisms Unique to Inflammatory Disease CD1 Subgroup

| Gene | FoldChange_CD3vsCD1 | CHR | Polymorphism | A1 | A2 | Risk | OR | P |
|---|---|---|---|---|---|---|---|---|
| MAGI3 | −2.654 | 1 | rs17031645 | G | A | G | 4.304 | 4.32E−02 |
| MAGI3 | −2.654 | 1 | rs17031648 | T | A | T | 4.304 | 4.32E−02 |
| MAGI3 | −2.654 | 1 | rs78838491 | A | G | A | 4.304 | 4.32E−02 |
| MAGI3 | −2.654 | 1 | rs7528311 | G | A | G | 4.304 | 4.32E−02 |
| MAGI3 | −2.654 | 1 | rs75016316 | G | A | G | 4.304 | 4.32E−02 |
| MAGI3 | −2.654 | 1 | rs6671518 | A | G | A | 4.304 | 4.32E−02 |
| MAGI3 | −2.654 | 1 | rs7553181 | A | C | A | 4.304 | 4.32E−02 |
| MAGI3 | −2.654 | 1 | rs7555259 | G | A | G | 4.304 | 4.32E−02 |
| SEMA3F | 1.881 | 3 | rs2624842 | C | A | A | 0.2138 | 4.34E−02 |
| IFT172 | −2.249 | 2 | rs1260345 | G | A | G | 1.802 | 4.39E−02 |
| SORCS3 | 4.436 | 10 | rs1565419 | G | C | G | 1.996 | 4.44E−02 |
| IL37 | 2.497 | 2 | rs3811047 | A | G | G | 0.4182 | 4.50E−02 |
| SLC9A3 | −1.548 | 5 | rs4957044 | C | A | C | 2.625 | 4.52E−02 |
| ARSB | 2.73 | 5 | rs13178105 | A | G | A | 2.233 | 4.57E−02 |
| ZNF609 | −2.576 | 15 | rs11631564 | A | G | A | 2.053 | 4.57E−02 |
| MAGI3 | −2.654 | 1 | rs11102649 | G | A | G | 2.203 | 4.60E−02 |
| VAV3 | −2.043 | 1 | rs2504469 | A | G | A | 1.926 | 4.62E−02 |
| MAGI3 | −2.654 | 1 | rs1217204 | C | G | C | 2.202 | 4.62E−02 |
| MAGI3 | −2.654 | 1 | rs1217237 | A | C | A | 2.202 | 4.62E−02 |
| MAGI3 | −2.654 | 1 | rs80218678 | G | A | G | 2.202 | 4.62E−02 |
| MAGI3 | −2.654 | 1 | rs10858011 | A | G | A | 2.202 | 4.62E−02 |
| MAGI3 | −2.654 | 1 | rs11102661 | A | G | A | 2.202 | 4.62E−02 |
| PPARGC1B | −2.383 | 5 | rs2010994 | A | G | G | 0.429 | 4.66E−02 |
| PPARGC1B | −2.383 | 5 | rs2012547 | A | G | G | 0.5251 | 4.70E−02 |
| FAM178B | 3.451 | 2 | rs7589232 | A | G | A | 1.998 | 4.70E−02 |
| BAK1 | 2.131 | 6 | rs210139 | C | A | C | 1.875 | 4.70E−02 |
| G6PC2 | 2.783 | 2 | rs560887 | A | G | A | 1.974 | 4.85E−02 |
| SMPD3 | −3.131 | 16 | rs12444619 | C | A | C | 2.059 | 4.96E−02 |

TABLE 2

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| RPL3 | −2.361 | 22 | rs6519183 | A | G | A | 3.82 | 8.10E−04 |
| PSMD5 | 1.81 | 9 | rs12343516 | A | C | C | 0.2774 | 1.72E−03 |
| POU5F1 | −1.53 | 6 | rs2106074 | G | A | G | 3.068 | 1.88E−03 |
| TNXB | −1.643 | 6 | rs17421624 | G | A | A | 0.2593 | 2.13E−03 |
| TNXB | −1.643 | 6 | rs2071293 | A | G | G | 0.2593 | 2.13E−03 |
| CLPTM1L | 2.624 | 5 | rs401681 | A | G | G | 0.3243 | 2.23E−03 |
| MTTP | −2.052 | 4 | rs982424 | G | A | G | 8.54 | 2.28E−03 |
| GRM4 | 2.625 | 6 | rs2499714 | A | G | A | 4.365 | 2.84E−03 |
| CLPTM1L | 2.624 | 5 | rs31489 | A | C | C | 0.2979 | 2.91E−03 |
| PSMD5 | 1.81 | 9 | rs3793638 | C | A | A | 0.3035 | 2.94E−03 |
| PSMD5 | 1.81 | 9 | rs1060817 | A | G | G | 0.3035 | 2.94E−03 |
| PSMD5 | 1.81 | 9 | rs10760117 | A | C | C | 0.3035 | 2.94E−03 |
| PSMD5 | 1.81 | 9 | rs12684934 | G | A | A | 0.3035 | 2.94E−03 |
| TNXB | −1.643 | 6 | rs2857009 | C | G | G | 0.2924 | 2.98E−03 |
| OPCML | 3.91 | 11 | rs476840 | C | A | C | 3.888 | 3.39E−03 |
| GLB1 | −2.833 | 3 | rs9828592 | A | G | A | 2.815 | 3.42E−03 |
| TNXB | −1.643 | 6 | rs2071295 | A | G | G | 0.2995 | 3.43E−03 |
| TNXB | −1.643 | 6 | rs2239689 | A | G | G | 0.2995 | 3.43E−03 |
| TNXB | −1.643 | 6 | rs6902493 | A | G | G | 0.2995 | 3.43E−03 |
| TNXB | −1.643 | 6 | rs7766862 | A | G | G | 0.2995 | 3.43E−03 |
| ANK3 | −1.906 | 10 | rs10761532 | A | G | A | 3.056 | 3.58E−03 |
| ANK3 | −1.906 | 10 | rs10821813 | A | G | A | 3.056 | 3.58E−03 |
| ANK3 | −1.906 | 10 | rs1561852 | C | A | C | 3.056 | 3.58E−03 |
| ANK3 | −2.062 | 10 | rs10761532 | A | G | A | 3.056 | 3.58E−03 |
| ANK3 | −2.062 | 10 | rs10821813 | A | G | A | 3.056 | 3.58E−03 |
| ANK3 | −2.062 | 10 | rs1561852 | C | A | C | 3.056 | 3.58E−03 |
| CTSH | −1.638 | 15 | rs12441725 | A | G | A | 7.282 | 3.60E−03 |
| GLB1 | −2.833 | 3 | rs35570272 | A | C | C | 0.3291 | 3.62E−03 |
| GLB1 | −2.833 | 3 | rs7650543 | G | A | G | 2.759 | 3.76E−03 |
| CYP4V2 | −2.02 | 4 | rs2276917 | G | A | A | 0.3232 | 4.40E−03 |
| ATF6B | 2.094 | 6 | rs8111 | A | G | G | 0.2947 | 4.86E−03 |
| DNMT3A | 2.471 | 2 | rs72810046 | C | G | C | 3.738 | 4.97E−03 |
| AFF3 | 3.218 | 2 | rs7340465 | A | G | A | 2.806 | 7.14E−03 |
| ANK3 | −1.906 | 10 | rs10994464 | A | C | A | 2.763 | 7.31E−03 |
| ANK3 | −1.906 | 10 | rs993402 | G | A | G | 2.763 | 7.31E−03 |
| ANK3 | −1.906 | 10 | rs10994467 | A | G | A | 2.763 | 7.31E−03 |

TABLE 2-continued

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| ANK3 | −1.906 | 10 | rs10821822 | A | G | A | 2.763 | 7.31E−03 |
| ANK3 | −1.906 | 10 | rs1837949 | G | A | G | 2.763 | 7.31E−03 |
| ANK3 | −1.906 | 10 | rs35597961 | C | A | C | 2.763 | 7.31E−03 |
| ANK3 | −1.906 | 10 | rs10821830 | G | A | G | 2.763 | 7.31E−03 |
| ANK3 | −1.906 | 10 | rs975262 | A | G | A | 2.763 | 7.31E−03 |
| ANK3 | −1.906 | 10 | rs973067 | A | G | A | 2.763 | 7.31E−03 |
| ANK3 | −1.906 | 10 | rs10509139 | G | A | G | 2.763 | 7.31E−03 |
| ANK3 | −1.906 | 10 | rs1442539 | A | C | A | 2.763 | 7.31E−03 |
| ANK3 | −1.906 | 10 | rs2197155 | A | G | A | 2.763 | 7.31E−03 |
| ANK3 | −1.906 | 10 | rs7919914 | G | C | G | 2.763 | 7.31E−03 |
| ANK3 | −2.062 | 10 | rs10994464 | A | C | A | 2.763 | 7.31E−03 |
| ANK3 | −2.062 | 10 | rs993402 | G | A | G | 2.763 | 7.31E−03 |
| ANK3 | −2.062 | 10 | rs10994467 | A | G | A | 2.763 | 7.31E−03 |
| ANK3 | −2.062 | 10 | rs10821822 | A | G | A | 2.763 | 7.31E−03 |
| ANK3 | −2.062 | 10 | rs1837949 | G | A | G | 2.763 | 7.31E−03 |
| ANK3 | −2.062 | 10 | rs35597961 | C | A | C | 2.763 | 7.31E−03 |
| ANK3 | −2.062 | 10 | rs10821830 | G | A | G | 2.763 | 7.31E−03 |
| ANK3 | −2.062 | 10 | rs975262 | A | G | A | 2.763 | 7.31E−03 |
| ANK3 | −2.062 | 10 | rs973067 | A | G | A | 2.763 | 7.31E−03 |
| ANK3 | −2.062 | 10 | rs10509139 | G | A | G | 2.763 | 7.31E−03 |
| ANK3 | −2.062 | 10 | rs1442539 | A | C | A | 2.763 | 7.31E−03 |
| ANK3 | −2.062 | 10 | rs2197155 | A | G | A | 2.763 | 7.31E−03 |
| ANK3 | −2.062 | 10 | rs7919914 | G | C | G | 2.763 | 7.31E−03 |
| ATF6B | 2.094 | 6 | rs2228628 | G | C | C | 0.3386 | 7.64E−03 |
| DNMT3A | 2.471 | 2 | rs2276598 | A | G | A | 3.321 | 7.89E−03 |
| SMG7 | −2.353 | 1 | rs10797885 | A | C | A | 3.861 | 8.39E−03 |
| SMG7 | −2.353 | 1 | rs72637285 | G | A | G | 3.861 | 8.39E−03 |
| PLBD1 | −3.224 | 12 | rs1862013 | G | A | G | 2.422 | 8.75E−03 |
| VAMP3 | −1.738 | 1 | rs11582799 | A | G | A | 3.974 | 8.84E−03 |
| VAMP3 | −1.738 | 1 | rs111692854 | A | G | A | 3.974 | 8.84E−03 |
| VAMP3 | −1.738 | 1 | rs72632053 | A | C | A | 3.974 | 8.84E−03 |
| POU5F1 | −1.53 | 6 | rs3130501 | A | G | A | 2.586 | 8.88E−03 |
| CTSH | −1.638 | 15 | rs7161986 | C | A | C | 5.263 | 8.98E−03 |
| CTSH | −1.638 | 15 | rs12440862 | G | A | G | 5.263 | 8.98E−03 |
| CTSH | −1.638 | 15 | rs3784537 | A | G | A | 5.263 | 8.98E−03 |
| CTSH | −1.638 | 15 | rs3784538 | A | G | A | 5.263 | 8.98E−03 |
| CTSH | −1.638 | 15 | rs3784540 | A | G | A | 5.263 | 8.98E−03 |
| CTSH | −1.638 | 15 | rs3825931 | A | G | A | 5.263 | 8.98E−03 |
| CTSH | −1.638 | 15 | rs8039683 | C | G | C | 5.263 | 8.98E−03 |
| CTSH | −1.638 | 15 | rs7163828 | C | G | C | 5.263 | 8.98E−03 |
| CTSH | −1.638 | 15 | rs2289697 | G | A | G | 5.263 | 8.98E−03 |
| CTSH | −1.638 | 15 | rs9302286 | G | A | G | 5.263 | 8.98E−03 |
| HIST1H1A | 2.77 | 6 | rs16891235 | G | A | G | 3.504 | 9.35E−03 |
| TRIM38 | −2.16 | 6 | rs13196552 | G | A | G | 3.504 | 9.35E−03 |
| THRB | 2.234 | 3 | rs7632903 | A | G | A | 2.523 | 9.71E−03 |
| GLB1 | −2.833 | 3 | rs34064757 | A | G | G | 0.3903 | 1.12E−02 |
| NELFE | −2.702 | 6 | rs760070 | G | A | G | 2.935 | 1.18E−02 |
| FOXO1 | 2.033 | 13 | rs2701865 | G | A | G | 3.054 | 1.27E−02 |
| FOXO1 | 2.033 | 13 | rs2701880 | C | A | C | 3.054 | 1.27E−02 |
| ANK3 | −1.906 | 10 | rs35471473 | A | G | A | 2.559 | 1.28E−02 |
| ANK3 | −1.906 | 10 | rs12785023 | G | A | G | 2.559 | 1.28E−02 |
| ANK3 | −1.906 | 10 | rs12783716 | G | A | G | 2.559 | 1.28E−02 |
| ANK3 | −1.906 | 10 | rs10821821 | G | A | G | 2.559 | 1.28E−02 |
| ANK3 | −2.062 | 10 | rs35471473 | A | G | A | 2.559 | 1.28E−02 |
| ANK3 | −2.062 | 10 | rs12785023 | G | A | G | 2.559 | 1.28E−02 |
| ANK3 | −2.062 | 10 | rs12783716 | G | A | G | 2.559 | 1.28E−02 |
| ANK3 | −2.062 | 10 | rs10821821 | G | A | G | 2.559 | 1.28E−02 |
| C19orf60 | 2.362 | 19 | rs10409392 | A | C | A | 2.425 | 1.32E−02 |
| SMG7-AS1 | 1.969 | 1 | rs16861076 | G | A | G | 3.475 | 1.34E−02 |
| SMG7 | −2.353 | 1 | rs72637284 | A | C | A | 3.475 | 1.34E−02 |
| SMG7 | −2.353 | 1 | rs12144253 | A | G | A | 3.475 | 1.34E−02 |
| SMG7 | −2.353 | 1 | rs3754519 | G | A | G | 3.475 | 1.34E−02 |
| POU5F1 | −1.53 | 6 | rs3130502 | A | G | A | 2.447 | 1.36E−02 |
| PDE4C | 2.673 | 19 | rs11670370 | A | G | A | 2.396 | 1.38E−02 |
| PDE4C | 2.673 | 19 | rs55887216 | G | C | G | 2.396 | 1.38E−02 |
| PDE4C | 2.259 | 19 | rs11670370 | A | G | A | 2.396 | 1.38E−02 |
| PDE4C | 2.259 | 19 | rs55887216 | G | C | G | 2.396 | 1.38E−02 |
| PDE4C | 2.223 | 19 | rs11670370 | A | G | A | 2.396 | 1.38E−02 |
| PDE4C | 2.223 | 19 | rs55887216 | G | C | G | 2.396 | 1.38E−02 |
| PDE4C | 2.146 | 19 | rs11670370 | A | G | A | 2.396 | 1.38E−02 |
| PDE4C | 2.146 | 19 | rs55887216 | G | C | G | 2.396 | 1.38E−02 |
| PDE4C | 2.128 | 19 | rs11670370 | A | G | A | 2.396 | 1.38E−02 |
| PDE4C | 2.128 | 19 | rs55887216 | G | C | G | 2.396 | 1.38E−02 |
| PDE4C | 2.107 | 19 | rs11670370 | A | G | A | 2.396 | 1.38E−02 |
| PDE4C | 2.107 | 19 | rs55887216 | G | C | G | 2.396 | 1.38E−02 |

TABLE 2-continued

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| PDE4C | 2.046 | 19 | rs11670370 | A | G | A | 2.396 | 1.38E−02 |
| PDE4C | 2.046 | 19 | rs55887216 | G | C | G | 2.396 | 1.38E−02 |
| PDE4C | 2.015 | 19 | rs11670370 | A | G | A | 2.396 | 1.38E−02 |
| PDE4C | 2.015 | 19 | rs55887216 | G | C | G | 2.396 | 1.38E−02 |
| PDE4C | 1.993 | 19 | rs11670370 | A | G | A | 2.396 | 1.38E−02 |
| PDE4C | 1.993 | 19 | rs55887216 | G | C | G | 2.396 | 1.38E−02 |
| PDE4C | 1.908 | 19 | rs11670370 | A | G | A | 2.396 | 1.38E−02 |
| PDE4C | 1.908 | 19 | rs55887216 | G | C | G | 2.396 | 1.38E−02 |
| PDE4C | 1.892 | 19 | rs11670370 | A | G | A | 2.396 | 1.38E−02 |
| PDE4C | 1.892 | 19 | rs55887216 | G | C | G | 2.396 | 1.38E−02 |
| PCDH7 | −2.222 | 4 | rs9291547 | A | G | A | 2.511 | 1.40E−02 |
| ACKR2 | 2.64 | 3 | rs4396867 | A | G | A | 2.384 | 1.45E−02 |
| CTSH | −1.638 | 15 | rs7182836 | A | G | A | 4.546 | 1.47E−02 |
| APOB | −2.511 | 2 | rs531819 | A | C | A | 2.465 | 1.48E−02 |
| APOB | −2.514 | 2 | rs531819 | A | C | A | 2.465 | 1.48E−02 |
| APOB | −2.534 | 2 | rs531819 | A | C | A | 2.465 | 1.48E−02 |
| APOB | −2.555 | 2 | rs531819 | A | C | A | 2.465 | 1.48E−02 |
| APOB | −2.863 | 2 | rs531819 | A | C | A | 2.465 | 1.48E−02 |
| APOB | −2.882 | 2 | rs531819 | A | C | A | 2.465 | 1.48E−02 |
| APOB | −2.898 | 2 | rs531819 | A | C | A | 2.465 | 1.48E−02 |
| APOB | −2.923 | 2 | rs531819 | A | C | A | 2.465 | 1.48E−02 |
| APOB | −2.982 | 2 | rs531819 | A | C | A | 2.465 | 1.48E−02 |
| APOB | −3.014 | 2 | rs531819 | A | C | A | 2.465 | 1.48E−02 |
| TNXB | −1.643 | 6 | rs2269426 | A | G | G | 0.4419 | 1.50E−02 |
| PSMD5 | 1.81 | 9 | rs62581708 | C | A | A | 0.2814 | 1.52E−02 |
| CTU2 | 1.933 | 16 | rs3826076 | A | G | A | 3.703 | 1.55E−02 |
| POU5F1 | −1.53 | 6 | rs3130931 | A | G | A | 2.224 | 1.64E−02 |
| GLB1 | −2.833 | 3 | rs6781531 | A | G | A | 2.366 | 1.64E−02 |
| AFF3 | 3.218 | 2 | rs7423759 | G | A | G | 2.455 | 1.65E−02 |
| CTSH | −1.638 | 15 | rs3784539 | A | G | A | 2.856 | 1.68E−02 |
| CTSH | −1.638 | 15 | rs10400902 | A | G | A | 2.482 | 1.68E−02 |
| CTSH | −1.638 | 15 | rs11072817 | G | A | G | 2.428 | 1.70E−02 |
| CTSH | −1.638 | 15 | rs11072818 | A | G | A | 2.428 | 1.70E−02 |
| CTSH | −1.638 | 15 | rs1036937 | C | A | C | 2.428 | 1.70E−02 |
| GLB1 | −2.833 | 3 | rs28752078 | A | G | G | 0.4189 | 1.71E−02 |
| GLB1 | −2.833 | 3 | rs9310998 | A | C | A | 2.633 | 1.73E−02 |
| GLB1 | −2.833 | 3 | rs9310999 | A | C | A | 2.633 | 1.73E−02 |
| C5orf56 | −1.636 | 5 | rs6868372 | G | A | G | 2.211 | 1.76E−02 |
| C5orf56 | −2.192 | 5 | rs6868372 | G | A | G | 2.211 | 1.76E−02 |
| PCSK5 | −2.042 | 9 | rs7045212 | G | A | A | 0.2337 | 1.78E−02 |
| ANK3 | −1.906 | 10 | rs10994476 | G | A | G | 2.401 | 1.82E−02 |
| ANK3 | −2.062 | 10 | rs10994476 | G | A | G | 2.401 | 1.82E−02 |
| LSP1 | −2.084 | 11 | rs11041476 | A | G | A | 2.213 | 1.92E−02 |
| PDE4C | 2.673 | 19 | rs4808120 | A | G | A | 2.284 | 1.96E−02 |
| PDE4C | 2.673 | 19 | rs4808770 | A | G | A | 2.284 | 1.96E−02 |
| PDE4C | 2.259 | 19 | rs4808120 | A | G | A | 2.284 | 1.96E−02 |
| PDE4C | 2.259 | 19 | rs4808770 | A | G | A | 2.284 | 1.96E−02 |
| PDE4C | 2.223 | 19 | rs4808120 | A | G | A | 2.284 | 1.96E−02 |
| PDE4C | 2.223 | 19 | rs4808770 | A | G | A | 2.284 | 1.96E−02 |
| PDE4C | 2.146 | 19 | rs4808120 | A | G | A | 2.284 | 1.96E−02 |
| PDE4C | 2.146 | 19 | rs4808770 | A | G | A | 2.284 | 1.96E−02 |
| PDE4C | 2.128 | 19 | rs4808120 | A | G | A | 2.284 | 1.96E−02 |
| PDE4C | 2.128 | 19 | rs4808770 | A | G | A | 2.284 | 1.96E−02 |
| PDE4C | 2.107 | 19 | rs4808120 | A | G | A | 2.284 | 1.96E−02 |
| PDE4C | 2.107 | 19 | rs4808770 | A | G | A | 2.284 | 1.96E−02 |
| PDE4C | 2.046 | 19 | rs4808120 | A | G | A | 2.284 | 1.96E−02 |
| PDE4C | 2.046 | 19 | rs4808770 | A | G | A | 2.284 | 1.96E−02 |
| PDE4C | 2.015 | 19 | rs4808120 | A | G | A | 2.284 | 1.96E−02 |
| PDE4C | 2.015 | 19 | rs4808770 | A | G | A | 2.284 | 1.96E−02 |
| PDE4C | 1.993 | 19 | rs4808120 | A | G | A | 2.284 | 1.96E−02 |
| PDE4C | 1.993 | 19 | rs4808770 | A | G | A | 2.284 | 1.96E−02 |
| PDE4C | 1.908 | 19 | rs4808120 | A | G | A | 2.284 | 1.96E−02 |
| PDE4C | 1.908 | 19 | rs4808770 | A | G | A | 2.284 | 1.96E−02 |
| PDE4C | 1.892 | 19 | rs4808120 | A | G | A | 2.284 | 1.96E−02 |
| PDE4C | 1.892 | 19 | rs4808770 | A | G | A | 2.284 | 1.96E−02 |
| MIR210HG | −1.866 | 11 | rs7936401 | G | A | A | 0.4255 | 1.97E−02 |
| TRIM15 | −2.457 | 6 | rs1029239 | C | G | C | 2.122 | 1.98E−02 |
| TRIM15 | −2.457 | 6 | rs1029239 | C | G | C | 2.122 | 1.98E−02 |
| TNS1 | −1.848 | 2 | rs2288169 | C | G | G | 0.1703 | 2.05E−02 |
| TNS1 | −2.874 | 2 | rs2288169 | C | G | G | 0.1703 | 2.05E−02 |
| TRIM38 | −2.16 | 6 | rs17587597 | A | G | A | 3.446 | 2.07E−02 |
| PDE4C | 2.673 | 19 | rs62120395 | G | A | G | 2.271 | 2.10E−02 |
| PDE4C | 2.259 | 19 | rs62120395 | G | A | G | 2.271 | 2.10E−02 |
| PDE4C | 2.223 | 19 | rs62120395 | G | A | G | 2.271 | 2.10E−02 |
| PDE4C | 2.146 | 19 | rs62120395 | G | A | G | 2.271 | 2.10E−02 |

TABLE 2-continued

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| PDE4C | 2.128 | 19 | rs62120395 | G | A | G | 2.271 | 2.10E-02 |
| PDE4C | 2.107 | 19 | rs62120395 | G | A | G | 2.271 | 2.10E-02 |
| PDE4C | 2.046 | 19 | rs62120395 | G | A | G | 2.271 | 2.10E-02 |
| PDE4C | 2.015 | 19 | rs62120395 | G | A | G | 2.271 | 2.10E-02 |
| PDE4C | 1.993 | 19 | rs62120395 | G | A | G | 2.271 | 2.10E-02 |
| PDE4C | 1.908 | 19 | rs62120395 | G | A | G | 2.271 | 2.10E-02 |
| PDE4C | 1.892 | 19 | rs62120395 | G | A | G | 2.271 | 2.10E-02 |
| ANK3 | -1.906 | 10 | rs10994441 | G | A | G | 2.841 | 2.11E-02 |
| ANK3 | -1.906 | 10 | rs10994442 | C | G | C | 2.841 | 2.11E-02 |
| ANK3 | -1.906 | 10 | rs10821814 | T | A | T | 2.841 | 2.11E-02 |
| ANK3 | -1.906 | 10 | rs10994465 | A | G | A | 2.841 | 2.11E-02 |
| ANK3 | -1.906 | 10 | rs12218617 | T | A | T | 2.841 | 2.11E-02 |
| ANK3 | -1.906 | 10 | rs10509138 | C | A | C | 2.841 | 2.11E-02 |
| ANK3 | -1.906 | 10 | rs61854518 | A | G | A | 2.841 | 2.11E-02 |
| ANK3 | -2.062 | 10 | rs10994441 | G | A | G | 2.841 | 2.11E-02 |
| ANK3 | -2.062 | 10 | rs10994442 | C | G | C | 2.841 | 2.11E-02 |
| ANK3 | -2.062 | 10 | rs10821814 | T | A | T | 2.841 | 2.11E-02 |
| ANK3 | -2.062 | 10 | rs10994465 | A | G | A | 2.841 | 2.11E-02 |
| ANK3 | -2.062 | 10 | rs12218617 | T | A | T | 2.841 | 2.11E-02 |
| ANK3 | -2.062 | 10 | rs10509138 | C | A | C | 2.841 | 2.11E-02 |
| ANK3 | -2.062 | 10 | rs61854518 | A | G | A | 2.841 | 2.11E-02 |
| CTSH | -1.638 | 15 | rs58119858 | A | G | A | 4.039 | 2.16E-02 |
| CTSH | -1.638 | 15 | rs2289700 | A | G | A | 4.039 | 2.16E-02 |
| CTSH | -1.638 | 15 | rs7496812 | G | A | G | 2.355 | 2.18E-02 |
| CTSH | -1.638 | 15 | rs2289699 | A | G | A | 2.355 | 2.18E-02 |
| OSBP | -2.137 | 11 | rs12289921 | A | C | A | 3.614 | 2.22E-02 |
| FBXL5 | -2.003 | 4 | rs10017222 | T | A | A | 0.4565 | 2.25E-02 |
| FBXL5 | -2.003 | 4 | rs10433813 | A | G | G | 0.4565 | 2.25E-02 |
| FBXL5 | -2.003 | 4 | rs6827406 | G | A | A | 0.4565 | 2.25E-02 |
| AFF3 | 3.218 | 2 | rs11123807 | G | A | G | 2.343 | 2.30E-02 |
| GATA4 | 2.909 | 8 | rs13273672 | G | A | G | 2.216 | 2.33E-02 |
| TRIM38 | -2.16 | 6 | rs17587226 | A | G | A | 3.685 | 2.37E-02 |
| AFF3 | 3.218 | 2 | rs1370355 | A | G | A | 2.317 | 2.38E-02 |
| ARHGEF10L | 2.853 | 1 | rs1408953 | G | A | G | 2.267 | 2.42E-02 |
| CTSH | -1.638 | 15 | rs10400877 | A | T | A | 2.296 | 2.45E-02 |
| CTSH | -1.638 | 15 | rs10400881 | C | G | C | 2.296 | 2.45E-02 |
| CTSH | -1.638 | 15 | rs11855406 | A | G | A | 2.296 | 2.45E-02 |
| CTSH | -1.638 | 15 | rs3825932 | A | G | A | 2.296 | 2.45E-02 |
| BCR | 2.54 | 22 | rs5751621 | A | G | A | 3.516 | 2.49E-02 |
| FER1L4 | -1.507 | 20 | rs1886695 | G | A | G | 2.393 | 2.52E-02 |
| CTSH | -1.638 | 15 | rs12148472 | A | G | A | 2.691 | 2.54E-02 |
| MIR210HG | -1.866 | 11 | rs7927267 | A | G | G | 0.4472 | 2.55E-02 |
| CYP4V2 | -2.02 | 4 | rs10013653 | A | C | A | 2.249 | 2.55E-02 |
| LEMD2 | -2.598 | 6 | rs2296748 | A | G | G | 0.4162 | 2.61E-02 |
| MPPED1 | 3.836 | 22 | rs6519378 | C | A | C | 2.751 | 2.62E-02 |
| FRMD4A | -1.861 | 10 | rs1000962 | G | A | G | 2.07 | 2.72E-02 |
| UBE2E3 | -2.544 | 2 | rs1949453 | A | T | A | 2.028 | 2.72E-02 |
| CFAP69 | 1.822 | 7 | rs10226014 | A | G | G | 0.4494 | 2.73E-02 |
| AP1G1 | -2.455 | 16 | rs11645475 | G | A | A | 3.251 | 2.74E-02 |
| OSBPL5 | -2.052 | 11 | rs4758538 | A | G | G | 0.3724 | 2.79E-02 |
| BRD2 | -5.369 | 6 | rs516535 | G | A | A | 0.4688 | 2.81E-02 |
| PRKCA | 1.976 | 17 | rs9896905 | A | G | A | 3.175 | 2.83E-02 |
| PRKCA | 1.931 | 17 | rs9896905 | A | G | A | 3.175 | 2.83E-02 |
| PRKCA | 1.92 | 17 | rs9896905 | A | G | A | 3.175 | 2.83E-02 |
| PRKCA | 1.886 | 17 | rs9896905 | A | G | A | 3.175 | 2.83E-02 |
| PRKCA | 1.867 | 17 | rs9896905 | A | G | A | 3.175 | 2.83E-02 |
| PRKCA | 1.865 | 17 | rs9896905 | A | G | A | 3.175 | 2.83E-02 |
| PRKCA | 1.859 | 17 | rs9896905 | A | G | A | 3.175 | 2.83E-02 |
| PRKCA | 1.851 | 17 | rs9896905 | A | G | A | 3.175 | 2.83E-02 |
| PRKCA | 1.766 | 17 | rs9896905 | A | G | A | 3.175 | 2.83E-02 |
| PRKCA | 1.754 | 17 | rs9896905 | A | G | A | 3.175 | 2.83E-02 |
| PRKCA | -2.506 | 17 | rs9896905 | A | G | A | 3.175 | 2.83E-02 |
| XPO1 | -2.383 | 2 | rs17009924 | G | A | G | 3.18 | 2.87E-02 |
| KIF21B | 1.983 | 1 | rs296564 | A | G | A | 2.291 | 2.89E-02 |
| MACROD2 | 2.336 | 20 | rs204609 | A | G | A | 3.762 | 2.90E-02 |
| CD209 | 2.135 | 19 | rs735239 | G | A | G | 2.022 | 2.93E-02 |
| MPZL3 | -2.879 | 11 | rs12419365 | A | C | C | 0.1044 | 2.93E-02 |
| CTSH | -1.638 | 15 | rs34593439 | A | G | A | 2.877 | 2.94E-02 |
| SLC17A4 | -2.641 | 6 | rs4712969 | A | G | A | 3.457 | 2.98E-02 |
| PIGT | -3.62 | 20 | rs2741585 | A | G | G | 2.304 | 2.99E-02 |
| PIGT | -3.62 | 20 | rs2251230 | A | G | A | 2.304 | 2.99E-02 |
| KIF21B | 1.983 | 1 | rs296569 | A | G | A | 2.396 | 3.04E-02 |
| KIF21B | 1.983 | 1 | rs296568 | A | C | A | 2.396 | 3.04E-02 |
| KIF21B | 1.983 | 1 | rs296567 | G | A | G | 2.396 | 3.04E-02 |
| KIF21B | 1.983 | 1 | rs296561 | G | C | G | 2.396 | 3.04E-02 |

TABLE 2-continued

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| MRVI1 | −1.588 | 11 | rs11042902 | A | G | A | 2.044 | 3.05E−02 |
| HNF1A | 4.423 | 12 | rs1169302 | C | A | C | 2.227 | 3.07E−02 |
| POU5F1 | −1.53 | 6 | rs3130503 | A | G | A | 2.601 | 3.08E−02 |
| ALPL | 2.754 | 1 | rs869179 | A | G | A | 2.001 | 3.11E−02 |
| PTPN11 | −1.575 | 12 | rs2301756 | G | A | G | 3.38 | 3.11E−02 |
| RPL6 | −1.995 | 12 | rs2301723 | A | G | A | 3.38 | 3.11E−02 |
| PAK2 | −2.675 | 3 | rs6583176 | A | G | A | 2.054 | 3.12E−02 |
| HNF1A | 4.423 | 12 | rs1169303 | A | C | C | 0.4555 | 3.14E−02 |
| MACROD2 | 2.336 | 20 | rs1890564 | A | G | A | 2.931 | 3.18E−02 |
| SLC17A4 | −2.641 | 6 | rs6910549 | A | G | A | 2.742 | 3.21E−02 |
| ANK3 | −1.906 | 10 | rs10821699 | A | G | G | 0.4789 | 3.24E−02 |
| ANK3 | −2.062 | 10 | rs10821699 | A | G | G | 0.4789 | 3.24E−02 |
| SAR1B | −1.58 | 5 | rs11948613 | G | A | G | 2.624 | 3.25E−02 |
| SAR1B | −2.72 | 5 | rs11948613 | G | A | G | 2.624 | 3.25E−02 |
| TCF7 | −1.54 | 5 | rs6876997 | G | A | G | 3.137 | 3.26E−02 |
| TCF7 | −1.544 | 5 | rs6876997 | G | A | G | 3.137 | 3.26E−02 |
| TCF7 | −1.552 | 5 | rs6876997 | G | A | G | 3.137 | 3.26E−02 |
| TCF7 | −1.559 | 5 | rs6876997 | G | A | G | 3.137 | 3.26E−02 |
| TCF7 | −1.572 | 5 | rs6876997 | G | A | G | 3.137 | 3.26E−02 |
| TCF7 | −1.58 | 5 | rs6876997 | G | A | G | 3.137 | 3.26E−02 |
| TCF7 | −1.6 | 5 | rs6876997 | G | A | G | 3.137 | 3.26E−02 |
| TCF7 | −1.612 | 5 | rs6876997 | G | A | G | 3.137 | 3.26E−02 |
| TCF7 | −1.613 | 5 | rs6876997 | G | A | G | 3.137 | 3.26E−02 |
| PPP2CA | −2.033 | 5 | rs7704116 | A | G | A | 3.137 | 3.26E−02 |
| DDC | −3.01 | 7 | rs3807563 | A | G | G | 0.4565 | 3.26E−02 |
| C3orf20 | 2.403 | 3 | rs11128719 | A | G | G | 0.4002 | 3.34E−02 |
| HLA-DQA2 | 1.541 | 6 | rs9276427 | A | G | A | 1.999 | 3.36E−02 |
| HLA-DQA2 | −1.56 | 6 | rs9276427 | A | G | A | 1.999 | 3.36E−02 |
| ANK3 | −1.906 | 10 | rs7919274 | G | A | G | 2.571 | 3.38E−02 |
| ANK3 | −2.062 | 10 | rs7919274 | G | A | G | 2.571 | 3.38E−02 |
| RPL30 | −1.895 | 8 | rs2877453 | A | C | C | 0.4584 | 3.43E−02 |
| RPL30 | −1.936 | 8 | rs2877453 | A | C | C | 0.4584 | 3.43E−02 |
| APOB | −2.511 | 2 | rs1041968 | A | G | G | 0.459 | 3.43E−02 |
| APOB | −2.514 | 2 | rs1041968 | A | G | G | 0.459 | 3.43E−02 |
| APOB | −2.534 | 2 | rs1041968 | A | G | G | 0.459 | 3.43E−02 |
| APOB | −2.555 | 2 | rs1041968 | A | G | G | 0.459 | 3.43E−02 |
| APOB | −2.863 | 2 | rs1041968 | A | G | G | 0.459 | 3.43E−02 |
| APOB | −2.882 | 2 | rs1041968 | A | G | G | 0.459 | 3.43E−02 |
| APOB | −2.898 | 2 | rs1041968 | A | G | G | 0.459 | 3.43E−02 |
| APOB | −2.923 | 2 | rs1041968 | A | G | G | 0.459 | 3.43E−02 |
| APOB | −2.982 | 2 | rs1041968 | A | G | G | 0.459 | 3.43E−02 |
| APOB | −3.014 | 2 | rs1041968 | A | G | G | 0.459 | 3.43E−02 |
| DDC | −3.01 | 7 | rs2329340 | A | G | A | 1.984 | 3.50E−02 |
| DDC | −3.01 | 7 | rs2329341 | C | A | C | 1.984 | 3.50E−02 |
| DDC | −3.01 | 7 | rs10247443 | A | G | A | 1.984 | 3.50E−02 |
| DDC | −3.01 | 7 | rs10250513 | C | A | C | 1.984 | 3.50E−02 |
| DDC | −3.01 | 7 | rs6949897 | A | G | A | 1.984 | 3.50E−02 |
| DDC | −3.01 | 7 | rs1451373 | G | A | G | 1.984 | 3.50E−02 |
| DDC | −3.01 | 7 | rs1451374 | A | G | A | 1.984 | 3.50E−02 |
| DDC | −3.01 | 7 | rs1451375 | A | C | A | 1.984 | 3.50E−02 |
| DDC | −3.01 | 7 | rs9214514 | G | A | G | 1.984 | 3.50E−02 |
| DDC | −3.01 | 7 | rs2329342 | A | G | A | 1.984 | 3.50E−02 |
| DDC | −3.01 | 7 | rs4452748 | A | C | A | 1.984 | 3.50E−02 |
| DDC | −3.01 | 7 | rs1966839 | G | A | G | 1.984 | 3.50E−02 |
| HLA-DMB | −1.711 | 6 | rs151719 | G | A | G | 2.358 | 3.50E−02 |
| HLA-DMB | −1.812 | 6 | rs151719 | G | A | G | 2.358 | 3.50E−02 |
| ANK3 | −1.906 | 10 | rs10761552 | A | C | A | 2.22 | 3.51E−02 |
| ANK3 | −2.062 | 10 | rs10761552 | A | C | A | 2.22 | 3.51E−02 |
| CLCN6 | −2.964 | 1 | rs17037425 | A | G | G | 0.2621 | 3.52E−02 |
| ANK3 | −1.906 | 10 | rs2893861 |   | G | A | 2.205 | 3.55E−02 |
| ANK3 | −1.906 | 10 | rs1993939 | C | A | C | 2.205 | 3.55E−02 |
| ANK3 | −1.906 | 10 | rs10821833 | G | C | G | 2.205 | 3.55E−02 |
| ANK3 | −1.906 | 10 | rs1904418 | G | A | G | 2.205 | 3.55E−02 |
| ANK3 | −2.062 | 10 | rs2893861 | A | G | A | 2.205 | 3.55E−02 |
| ANK3 | −2.062 | 10 | rs1993939 | C | A | C | 2.205 | 3.55E−02 |
| ANK3 | −2.062 | 10 | rs10821833 | G | C | G | 2.205 | 3.55E−02 |
| ANK3 | −2.062 | 10 | rs1904418 | G | A | G | 2.205 | 3.55E−02 |
| SNAP47 | 2.803 | 1 | rs7533588 | A | G | G | 0.4483 | 3.56E−02 |
| LRRC56 | −1.987 | 11 | rs12277611 | A | G | G | 0.4553 | 3.56E−02 |
| LZTFL1 | 2.29 | 3 | rs34068335 | A | G | A | 2.572 | 3.56E−02 |
| DDC | −3.01 | 7 | rs11238134 | A | C | A | 2.038 | 3.56E−02 |
| XCR1 | 3.186 | 3 | rs36040135 | G | A | G | 2.563 | 3.57E−02 |
| XCR1 | 3.186 | 3 | rs13074382 | G | A | G | 2.563 | 3.57E−02 |
| XCR1 | 3.186 | 3 | rs13097556 | G | A | G | 2.563 | 3.57E−02 |
| XCR1 | 3.186 | 3 | rs2230322 | G | A | G | 2.563 | 3.57E−02 |

TABLE 2-continued

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| XCR1 | 3.186 | 3 | rs71327010 | A | C | A | 2.563 | 3.57E−02 |
| TRIM15 | −2.457 | 6 | rs1008403 | G | A | G | 2.513 | 3.59E−02 |
| TRIM15 | −2.457 | 6 | rs9368624 | A | G | A | 2.513 | 3.59E−02 |
| TRIM15 | −2.457 | 6 | rs1008403 | G | A | G | 2.513 | 3.59E−02 |
| TRIM15 | −2.457 | 6 | rs9368624 | A | G | A | 2.513 | 3.59E−02 |
| CTSH | −1.638 | 15 | rs16970287 | G | A | G | 3.966 | 3.59E−02 |
| CTSH | −1.638 | 15 | rs8034542 | G | A | G | 3.966 | 3.59E−02 |
| XPO1 | −2.383 | 2 | rs1050567 | A | G | A | 2.595 | 3.60E−02 |
| APOB | −2.511 | 2 | rs693 | A | G | G | 0.4602 | 3.61E−02 |
| APOB | −2.514 | 2 | rs693 | A | G | G | 0.4602 | 3.61E−02 |
| APOB | −2.534 | 2 | rs693 | A | G | G | 0.4602 | 3.61E−02 |
| APOB | −2.555 | 2 | rs693 | A | G | G | 0.4602 | 3.61E−02 |
| APOB | −2.863 | 2 | rs693 | A | G | G | 0.4602 | 3.61E−02 |
| APOB | −2.882 | 2 | rs693 | A | G | G | 0.4602 | 3.61E−02 |
| APOB | −2.898 | 2 | rs693 | A | G | G | 0.4602 | 3.61E−02 |
| APOB | −2.923 | 2 | rs693 | A | G | G | 0.4602 | 3.61E−02 |
| APOB | −2.982 | 2 | rs693 | A | G | G | 0.4602 | 3.61E−02 |
| APOB | −3.014 | 2 | rs693 | A | G | G | 0.4602 | 3.61E−02 |
| KIF21B | 1.983 | 1 | rs72749142 | A | G | G | 0.2179 | 3.61E−02 |
| AVIL | −2.063 | 12 | rs12582311 | G | A | G | 2.179 | 3.61E−02 |
| HLA-DMA | −1.596 | 6 | rs6899309 | G | A | G | 3.951 | 3.66E−02 |
| HLA-DMA | −2.28 | 6 | rs6899309 | G | A | G | 3.951 | 3.66E−02 |
| DDC | −3.01 | 7 | rs1470750 | G | C | C | 0.4737 | 3.69E−02 |
| AGAP2 | −1.67 | 12 | rs12368653 | A | G | G | 2.041 | 3.69E−02 |
| IGFBP7 | −2.231 | 4 | rs11573051 | A | G | A | 2.344 | 3.77E−02 |
| RPL18 | −1.79 | 19 | rs369880 | A | G | A | 2.348 | 3.79E−02 |
| PDE4C | 2.673 | 19 | rs57884093 | A | G | G | 0.4433 | 3.88E−02 |
| PDE4C | 2.259 | 19 | rs57884093 | A | G | G | 0.4433 | 3.88E−02 |
| PDE4C | 2.223 | 19 | rs57884093 | A | G | G | 0.4433 | 3.88E−02 |
| PDE4C | 2.146 | 19 | rs57884093 | A | G | G | 0.4433 | 3.88E−02 |
| PDE4C | 2.128 | 19 | rs57884093 | A | G | G | 0.4433 | 3.88E−02 |
| PDE4C | 2.107 | 19 | rs57884093 | A | G | G | 0.4433 | 3.88E−02 |
| PDE4C | 2.046 | 19 | rs57884093 | A | G | G | 0.4433 | 3.88E−02 |
| PDE4C | 2.015 | 19 | rs57884093 | A | G | G | 0.4433 | 3.88E−02 |
| PDE4C | 1.993 | 19 | rs57884093 | A | G | G | 0.4433 | 3.88E−02 |
| PDE4C | 1.908 | 19 | rs57884093 | A | G | G | 0.4433 | 3.88E−02 |
| PDE4C | 1.892 | 19 | rs57884093 | A | G | G | 0.4433 | 3.88E−02 |
| DGKD | −2.251 | 2 | rs60137910 | G | A | A | 0.3211 | 3.93E−02 |
| MACROD2 | 2.336 | 20 | rs1998105 | A | G | G | 0.4126 | 3.97E−02 |
| AFF3 | 3.218 | 2 | rs1814009 | A | G | G | 0.3738 | 4.14E−02 |
| APOB | −2.511 | 2 | rs512535 | A | G | A | 1.984 | 4.22E−02 |
| APOB | −2.514 | 2 | rs512535 | A | G | A | 1.984 | 4.22E−02 |
| APOB | −2.534 | 2 | rs512535 | A | G | A | 1.984 | 4.22E−02 |
| APOB | −2.555 | 2 | rs512535 | A | G | A | 1.984 | 4.22E−02 |
| APOB | −2.863 | 2 | rs512535 | A | G | A | 1.984 | 4.22E−02 |
| APOB | −2.882 | 2 | rs512535 | A | G | A | 1.984 | 4.22E−02 |
| APOB | −2.898 | 2 | rs512535 | A | G | A | 1.984 | 4.22E−02 |
| APOB | −2.923 | 2 | rs512535 | A | G | A | 1.984 | 4.22E−02 |
| APOB | −2.982 | 2 | rs512535 | A | G | A | 1.984 | 4.22E−02 |
| APOB | −3.014 | 2 | rs512535 | A | G | A | 1.984 | 4.22E−02 |
| MIR210HG | −1.866 | 11 | rs3740651 | G | A | A | 0.4255 | 4.27E−02 |
| SMARCA4 | −2.783 | 19 | rs1122608 | A | C | C | 0.3678 | 4.35E−02 |
| SMARCA4 | −2.783 | 19 | rs12052058 | A | C | C | 0.3678 | 4.35E−02 |
| DLC1 | −1.868 | 8 | rs11998187 | G | A | A | 0.3688 | 4.40E−02 |
| PIP5K1C | 2.257 | 19 | rs12984273 | G | A | A | 0.4936 | 4.42E−02 |
| PIP5K1C | −1.825 | 19 | rs12984273 | G | A | A | 0.4936 | 4.42E−02 |
| APOB | −2.511 | 2 | rs550619 | G | A | G | 2.183 | 4.44E−02 |
| APOB | −2.511 | 2 | rs570877 | A | C | A | 2.183 | 4.44E−02 |
| APOB | −2.514 | 2 | rs550619 | G | A | G | 2.183 | 4.44E−02 |
| APOB | −2.514 | 2 | rs570877 | A | C | A | 2.183 | 4.44E−02 |
| APOB | −2.534 | 2 | rs550619 | G | A | G | 2.183 | 4.44E−02 |
| APOB | −2.534 | 2 | rs570877 | A | C | A | 2.183 | 4.44E−02 |
| APOB | −2.555 | 2 | rs550619 | G | A | G | 2.183 | 4.44E−02 |
| APOB | −2.555 | 2 | rs570877 | A | C | A | 2.183 | 4.44E−02 |
| APOB | −2.863 | 2 | rs550619 | G | A | G | 2.183 | 4.44E−02 |
| APOB | −2.863 | 2 | rs570877 | A | C | A | 2.183 | 4.44E−02 |
| APOB | −2.882 | 2 | rs550619 | G | A | G | 2.183 | 4.44E−02 |
| APOB | −2.882 | 2 | rs570877 | A | C | A | 2.183 | 4.44E−02 |
| APOB | −2.898 | 2 | rs550619 | G | A | G | 2.183 | 4.44E−02 |
| APOB | −2.898 | 2 | rs570877 | A | C | A | 2.183 | 4.44E−02 |
| APOB | −2.923 | 2 | rs550619 | G | A | G | 2.183 | 4.44E−02 |
| APOB | −2.923 | 2 | rs570877 | A | C | A | 2.183 | 4.44E−02 |
| APOB | −2.982 | 2 | rs550619 | G | A | G | 2.183 | 4.44E−02 |
| APOB | −2.982 | 2 | rs570877 | A | C | A | 2.183 | 4.44E−02 |
| APOB | −3.014 | 2 | rs550619 | G | A | G | 2.183 | 4.44E−02 |

TABLE 2-continued

Polymorphisms Unique to Inflammatory Disease CD3 Subgroup

| Gene | FoldChange_CD3vsCD1 | CHR | Polymorphism | A1 | A2 | Risk | OR | P |
|---|---|---|---|---|---|---|---|---|
| APOB | -3.014 | 2 | rs570877 | A | C | A | 2.183 | 4.44E-02 |
| PTPN11 | -1.575 | 12 | rs7958372 | A | G | A | 3.097 | 4.46E-02 |
| HNF4A | 2.051 | 20 | rs6130615 | A | G | G | 0.2157 | 4.48E-02 |
| DNMT3A | 2.471 | 2 | rs58552784 | C | G | G | 0.3441 | 4.49E-02 |
| MIR210HG | -1.866 | 11 | rs1062099 | C | G | G | 0.3488 | 4.49E-02 |
| ALDH2 | -2.899 | 12 | rs7296651 | C | G | C | 2.369 | 4.52E-02 |
| UQCR10 | -2.73 | 22 | rs16988025 | A | G | A | 3.007 | 4.59E-02 |
| LZTFL1 | 2.29 | 3 | rs12493471 | A | G | A | 1.868 | 4.59E-02 |
| MIR210HG | -1.866 | 11 | rs12792868 | T | A | A | 0.4276 | 4.63E-02 |
| DDC | -3.01 | 7 | rs2329365 | G | A | G | 1.956 | 4.64E-02 |
| DDC | -3.01 | 7 | rs12718527 | A | G | A | 1.956 | 4.64E-02 |
| DDC | -3.01 | 7 | rs11238138 | G | A | G | 1.956 | 4.64E-02 |
| DDC | -3.01 | 7 | rs4579483 | G | A | G | 1.956 | 4.64E-02 |
| DDC | -3.01 | 7 | rs4580999 | G | A | G | 1.956 | 4.64E-02 |
| DDC | -3.01 | 7 | rs4436083 | G | A | G | 1.956 | 4.64E-02 |
| SAR1B | -1.58 | 5 | rs2305049 | A | C | A | 2.421 | 4.65E-02 |
| SAR1B | -2.72 | 5 | rs2305049 | A | C | A | 2.421 | 4.65E-02 |
| CHRM3 | 2.562 | 1 | rs685548 | A | C | C | 0.4816 | 4.73E-02 |
| HNF1A | 4.423 | 12 | rs2244608 | G | A | G | 2.114 | 4.77E-02 |
| CDK13 | 2.087 | 7 | rs773386 | G | A | A | 0.5228 | 4.79E-02 |
| DDC | -3.01 | 7 | rs6593010 | G | A | G | 1.897 | 4.79E-02 |
| DDC | -3.01 | 7 | rs10278338 | A | G | A | 1.897 | 4.79E-02 |
| DDC | -3.01 | 7 | rs56233242 | A | C | A | 1.929 | 4.81E-02 |
| MACROD2 | 2.336 | 20 | rs1225888 | G | A | G | 1.953 | 4.84E-02 |
| RASSF7 | -2.144 | 11 | rs11246189 | A | G | G | 0.3533 | 4.84E-02 |
| CEP85L | -1.803 | 6 | rs17348534 | A | G | G | 0.4018 | 4.85E-02 |
| ANK3 | -1.906 | 10 | rs16915196 | G | A | G | 2.257 | 4.88E-02 |
| ANK3 | -1.906 | 10 | rs61853514 | A | C | A | 2.257 | 4.88E-02 |
| ANK3 | -1.906 | 10 | rs10994430 | A | C | A | 2.257 | 4.88E-02 |
| ANK3 | -1.906 | 10 | rs16915231 | A | G | A | 2.257 | 4.88E-02 |
| ANK3 | -1.906 | 10 | rs2028564 | G | A | G | 2.257 | 4.88E-02 |
| ANK3 | -2.062 | 10 | rs16915196 | G | A | G | 2.257 | 4.88E-02 |
| ANK3 | -2.062 | 10 | rs61853514 | A | C | A | 2.257 | 4.88E-02 |
| ANK3 | -2.062 | 10 | rs10994430 | A | C | A | 2.257 | 4.88E-02 |
| ANK3 | -2.062 | 10 | rs16915231 | A | G | A | 2.257 | 4.88E-02 |
| ANK3 | -2.062 | 10 | rs2028564 | G | A | G | 2.257 | 4.88E-02 |
| APOB | -2.511 | 2 | rs12713956 | G | A | G | 2.14 | 4.89E-02 |
| APOB | -2.514 | 2 | rs12713956 | G | A | G | 2.14 | 4.89E-02 |
| APOB | -2.534 | 2 | rs12713956 | G | A | G | 2.14 | 4.89E-02 |
| APOB | -2.555 | 2 | rs12713956 | G | A | G | 2.14 | 4.89E-02 |
| APOB | -2.863 | 2 | rs12713956 | G | A | G | 2.14 | 4.89E-02 |
| APOB | -2.882 | 2 | rs12713956 | G | A | G | 2.14 | 4.89E-02 |
| APOB | -2.898 | 2 | rs12713956 | G | A | G | 2.14 | 4.89E-02 |
| APOB | -2.923 | 2 | rs12713956 | G | A | G | 2.14 | 4.89E-02 |
| APOB | -2.982 | 2 | rs12713956 | G | A | G | 2.14 | 4.89E-02 |
| APOB | -3.014 | 2 | rs12713956 | G | A | G | 2.14 | 4.89E-02 |
| RORA | -1.764 | 15 | rs922778 | G | A | G | 2.171 | 4.91E-02 |
| PCSK5 | -2.042 | 9 | rs1006280 | G | A | A | 0.4936 | 4.92E-02 |

One polymorphism from Table 1 or Table 2, or any combination of polymorphisms from Table 1 or Table 2, may be detected in a sample obtained from the subject for purposes of characterizing and/or treating an inflammatory disease using the methods disclosed herein. In some embodiments, two copies of the polymorphism are detected in the sample obtained from the subject. A subject carrying one copy of the polymorphism has a heterozygous risk genotype. In some embodiments, one copy of the polymorphism is detected in the sample obtained from the subject. A subject carrying two copies of the polymorphism has a homozygous risk genotype. The method of obtaining the sample may include acquisition of the sample from the subject directly, or indirectly. In some embodiments provided are methods of assaying to detect in the sample a presence of a polymorphism located at the gene locus.

In some cases, the genotype is indicative of a downregulation of PTPN11, which is predictive of a risk of developing a severe form of CD characteristic of CD3. In some cases, the genotype comprise is rs2301756G, which is provided in SEQ ID NO: 339. In some cases, the genotype is rs7958372A, which is provided in SEQ ID NO: 408.

In some cases, the genotype is indicative of a downregulation of RPL30, which is predictive of a risk of developing a severe form of CD characteristic of CD3. In some cases, the genotype is rs2877453C, which is provided in SEQ ID NO: 353.

In some cases, the genotype is indicative of an upregulation of XCR1, which is predictive of a risk of developing a severe form of CD characteristic of CD3. In some cases, the genotype is rs36040135G, which is provided in SEQ ID NO: 378. In some cases, the genotype is rs13074382G, which is provided in SEQ ID NO: 379. In some cases, the genotype is rs13097556G, which is provided in SEQ ID NO: 380. In some cases, the genotype is rs2230322G, which is provided in SEQ ID NO: 381. In some cases, the genotype is rs71327010A, which is provided in SE ID NO: 382.

In some cases, the genotype is indicative of an upregulation of HNF1A, which is predictive of a risk of developing a severe form of CD characteristic of CD3. In some cases, the genotype is rs2244608G, which is provided in SEQ ID NO: 424. In some cases, the genotype is rs1169302C, which is provided in SEQ ID NO: 336. In some cases, the genotype is rs1169303G, which is provided in SEQ ID NO: 337.

In some cases, the genotype is indicative of a downregulation of RPL3, which is predictive of a risk of developing a severe form of CD characteristic of CD3. In some cases, the genotype is rs6519183A, which is provided in SEQ ID NO: 174.

In some cases, the genotype is indicative of a upregulation of CHRM3, which is predictive of a risk of developing a severe form of CD characteristic of CD3. In some cases, the genotype is rs685548C, which is provided in SEQ ID NO: 423.

In some cases, the genotype is indicative of a downregulation of DLC1, which is predictive of a risk of developing a severe form of CD characteristic of CD3. In some cases, the genotype is rs11998187A, which is provided in SEQ ID NO: 404.

In some cases, the genotype is indicative of a downregulation of APOB, which is predictive of a risk of developing a severe form of CD characteristic of CD3. In some cases, the genotype is rs531819A, which is provided in SEQ ID NO: 258. In some cases, the genotype is rs1041968G, which is provided in SEQ ID NO: 354. In some cases, the genotype is rs693G, which is provided in SEQ ID NO: 388. In some cases, the genotype is rs512535A, which is provided in SEQ ID NO: 400. In some cases, the genotype is rs550619G. which is provided in SEQ ID NO: 406. In some cases, the genotype is rs570877A, which is provided in SEQ ID NO: 407. In some cases, the genotype is rs 12713956G, which is provided in SEQ ID NO: 437.

In some cases, the genotype is indicative of a downregulation of RPL6, which is predictive of a risk of developing a severe form of CD characteristic of CD3. In some cases, the genotype is rs2301723A, which is provided in SEQ ID NO: 340.

In some cases, the genotype is indicative of an upregulation of GRM4, which is predictive of a risk of developing a severe form of CD characteristic of CD3. In some cases, the genotype is rs2499714A, which is provided in SEQ ID NO: 181.

In some cases, the genotype is indicative of a downregulation of PAK2, which is predictive of a risk of developing a severe form of CD characteristic of CD3. In some cases, the genotype is rs6583176A, which is provided in SEQ ID NO: 341.

In some cases, the genotype is indicative of a downregulation of RPL18, which is predictive of a risk of developing a severe form of CD characteristic of CD3. In some cases, the genotype is rs369880A, which is provided in SEQ ID NO: 395.

In some cases, the genotype is indicative of an upregulation of PDE4C, which is predictive of a risk of developing a severe form of CD characteristic of CD3. In some cases, the genotype is rs57884093G, which is provided in SEQ ID NO: 396.

In some cases, the genotype is indicative of an upregulation or downregulation of PRKCA, which is predictive of a risk of developing a severe form of CD characteristic of CD3. In some cases, the genotype is rs9896905A, which is provided in SEQ ID NO: 321.

In some cases, the genotype is indicative of a downregulation of PPP2CA, which is predictive of a risk of developing a severe form of CD characteristic of CD3. In some cases, the genotype is rs7704116A, which is provided in SEQ ID NO: 348.

In some cases, the genotype is indicative of a downregulation of RIP5K1C, which is predictive of a risk of developing a severe form of CD characteristic of CD3. In some cases, the genotype is rs 12984273A, which is provided in SEQ ID NO: 405.

In some cases, the genotype is indicative of an upregulation of HIST1H1A, which is predictive of a risk of developing a severe form of CD characteristic of CD3. In some cases, the genotype is rs16891235G, which is provided in SEQ ID NO: 236.

In some cases, the genotype is indicative of a downregulation of BRD2, which is predictive of a risk of developing a severe form of CD characteristic of CD3. In some cases, the genotype is rs516535A, which is provided in SEQ ID NO: 320.

In some cases, the genotype is indicative of an upregulation or a downregulation of HLA-DQA2, which is predictive of a risk of developing a severe form of CD characteristic of CD3. In some cases, the genotype is rs9276427A, which is provided in SEQ ID NO: 351.

In some cases, the genotype is indicative of an upregulation of KIF21B, which is predictive of a risk of developing a severe form of CD characteristic of CD3. In some cases, the genotype is rs296564A, rs296569A, which is provided in SEQ ID NO: 331. In some cases, the genotype is rs296568A, which is provided in SEQ ID NO: 332. In some cases, the genotype is rs296567G, which is provided in SEQ ID NO: 333. In some cases, the genotype is rs296561G, which is provided in SEQ ID NO: 334. In some cases, the genotype is rs72749142G, which is provided in SEQ ID NO: 389.

In some cases, the genotype is indicative of a downregulation of PCDH7, which is predictive of a risk of developing a severe form of CD characteristic of CD3. In some cases, the genotype is rs9291547A, which is provided in SEQ ID NO: 255.

In some cases, the genotype is indicative of a downregulation of ANK3, which is predictive of a risk of developing a severe form of CD characteristic of CD3. In some cases, the genotype is rs10761532A, which is provided in SEQ ID NO: 194. In some cases, the genotype is rs10821813A, which is provided in SEQ ID NO: 195. In some cases, the genotype is rs1561852C, which is provided in SEQ ID NO: 196. In some cases, the genotype is rs10994464A, which is provided in SEQ ID NO: 204. In some cases, the genotype is rs993402G, which is provided in SEQ ID NO: 205. In some cases, the genotype is rs10994467A, which is provided in SEQ ID NO: 206. In some cases, the genotype is rs10821822A, which is provided in SEQ ID NO: 207. In some cases, the genotype is rs1837949G, which is provided in SEQ ID NO: 208. In some cases, the genotype is rs35597961C, which is provided in SEQ ID NO: 209. In some cases, the genotype is rs10821830G, which is provided in SEQ ID NO: 210. In some cases, the genotype is rs975262A, which is provided in SEQ ID NO: 211. In some cases, the genotype is rs973067A, which is provided in SEQ ID NO: 212. In some cases, the genotype is rs10509139G, which is provided in SEQ ID NO: 213. In some cases, the genotype is rs1442539A, which is provided in SEQ ID NO: 214. In some cases, the genotype is rs2197155A, which is provided in SEQ ID NO: 215. In some cases, the genotype is rs7919914G, which is provided in SEQ ID NO: 216. In some cases, the genotype is rs10994476G, which is provided in SEQ ID NO: 275. In some cases, the genotype is rs35471473A, which is provided in SEQ ID NO: 243. In some cases, the genotype is rs12785023G, which is provided in SEQ ID NO: 244. In some cases, the genotype is rs12783716G, which is provided in SEQ ID NO: 245. In some cases, the genotype is rs10821821G, which is provided in SEQ ID NO: 246. In some cases, the genotype is rs10994441G, which is provided in SEQ ID NO: 284. In some cases, the genotype is rs10994442C, which is provided in SEQ ID NO: 285. In some cases, the genotype is rs10821814T, which is provided in SEQ ID NO: 286. In some cases, the genotype is rs10994465A, which is provided in SEQ ID NO: 287. In some cases, the genotype is rs12218617T, which is provided in SEQ ID NO: 288. In some cases, the genotype is rs10509138C, which is provided in SEQ ID NO: 289. In some cases, the genotype is rs61854518A, which is provided in SEQ ID NO: 290. In some cases, the genotype is rs10821699G, which is provided in SEQ ID NO: 345. In some cases, the genotype is rs7919274G, which is provided in SEQ ID NO: 352. In some cases, the genotype is rs10761552A, which is provided in SEQ ID NO: 368. In some cases, the genotype is rs17037425G, which is provided in SEQ ID NO: 369. In some cases, the genotype is rs2893861A, which is provided in SEQ ID NO: 370. In some cases, the genotype is rs1993939C, which is provided in SEQ ID NO: 371. In some cases, the genotype is rs10821833G, which is provided in SEQ ID NO: 372. In some cases, the genotype is rs1904418G, which is provided in SEQ ID NO: 373. In some cases, the genotype is rs16915196G, which is provided in SEQ ID NO: 432. In some cases, the genotype is rs61853514A, which is provided in SEQ ID NO: 433. In some cases, the genotype is rs10994430A, which is provided in SEQ ID NO: 434. In some cases, the genotype is rs16915231A, which is provided in SEQ ID NO: 435. In some cases, the genotype is rs2028564G, which is provided in SEQ ID NO: 436.

In some cases, the genotype is indicative of a downregulation of TRIM38, which is predictive of a risk of developing a severe form of CD characteristic of CD3. In some cases. the genotype is rs13196552G, which is provided in SEQ ID NO: 237. In some cases, the genotype is rs17587597A, which is provided in SEQ ID NO: 282. In some cases, the genotype is rs17587226A, which is provided in SEQ ID NO: 301.

In some cases, the genotype is indicative of a downregulation of CYP4V2, which is predictive of a risk of developing a severe form of CD characteristic of CD3. In some cases, the genotype is rs2276917A, which is provided in SEQ ID NO: 200. In some cases, the genotype is rs10013653A, which is provided in SEQ ID NO: 312.

In some cases, the genotype is indicative of a downregulation of VAMP3, which is predictive of a risk of developing a severe form of CD characteristic of CD3. In some cases, the genotype is rs11582799A, which is provided in SEQ ID NO: 222. In some cases, the genotype is rs111692854A, which is provided in SEQ ID NO: 223. In some cases, the genotype is rs72632053A, which is provided in SEQ ID NO: 224.

In some embodiments, the risk genotype is associated with a clinical subgroup of patients with the inflammatory disease or subclinical phenotype. A subclinical phenotype may include specific diagnosable diseases or conditions, in addition to disease progression that is characteristic of severe or unusual forms of inflammatory disease. Non-limiting examples of inflammatory disease subclinical phenotypes include, but are not limited to, non-stricturing, stricturing, stricturing and penetrating, and isolated internal penetrating, disease, and perianal Crohn's disease (pCD). Stricturing is the progressive narrowing of the intestine. Internal penetrating disease creates abnormal passageways (fistulae) between the bowel and other structures. pCD is a form of Crohn's disease that causes inflammation around the anus. Further, patients with disease that is stricturing, penetrating and stricturing, or isolated internal penetrating, and patients with pCD are more likely to require surgery in a shorter timespan than a patient who has an inflammatory disease, such as IBD, but who does not exhibit these subclinical phenotypes. In some embodiments, the polymorphism is associated with a time to first surgery, or a time to second surgery (defined as time between first surgery and either of a second surgery or last follow-up), or a combination thereof. The time to first surgery may be from about 2 to 8 years. The time to first surgery may be from about 4 to 10 years. The time to first surgery may be from about 6 to 12 years. The time to first surgery may be from about 8 to 14 years. The time to first surgery may be from about 10 to 16 years. The time to second surgery may be about 2-10 months. The time to second surgery may be about 20 to 120 months. The time to second surgery may be about 30 to 140 months. The time to second surgery may be about 50 to 160 months. The time to second surgery may be about 70 to 180 months. Subclinical phenotypes of IBD may manifest in specific disease locations. Non-limiting examples of disease location include the ileum, colon, region spanning the ileum and colon (ilealcolonic region), and small bowel. In some embodiments, the risk genotype is associated with stricturing disease in the ileum, colon, ilealcolonic region, or small bowel. In some embodiments, the risk genotype is associated with stricturing and penetrating disease in the ileum, colon, ilealcolonic region, or small bowel. In some embodiments, the risk genotype is associated with isolated penetrating disease in the ileum, colon, ilealcolonic region, or small bowel. Subclinical phenotypes of inflammatory disease may also include non-response to current inflammatory disease therapies. In some embodiments, the risk genotype is associated with non-response to anti-TNF-alpha therapy, anti-a4-b7 therapy (vedolizumab), anti-IL12p40 therapy (ustekinumab), Thalidomide, or Cytoxin. In some embodiments, the risk genotype is associated with thiopurine toxicity, or a disease or condition caused by thiopurine toxicity (such as pancreatitis or leukopenia). A subject may exhibit only one, or any combination of, the subclinical phenotypes disclosed herein, as well as others that would be readily apparent to a person of ordinary skill in the art.

In some embodiments the presence of the polymorphism is associated with an increase or decrease in expression of the genes listed in the first column of Table 1 or Table 2. A decrease in gene expression is represented by a negative "fold change" value (see column 2 in Table 1 and Table 2). An increase in gene expression is represented by a positive "fold change" value. In further embodiments provided, are methods of obtaining the sample from a subject with an inflammatory disease. As disclosed herein, gene expression may comprise expression of the DNA or RNA molecule, or protein molecule. Gene expression may be detected in a particular disease location. In some embodiments, the risk genotype is associated with an increase in gene expression in a region of the intestine comprising the ileum, colon, ileocolonic region, small bowel, or anus, or a combination thereof. In some embodiments, increased or decreased gene expression fold-change is observed. The increase or decrease in expression may be an increase or decrease of 1.1-fold, 1.2-fold, 1.3-fold, 1.4-fold, 1.5 fold, 1.6-fold. 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.0-fold, 3.0-fold, 3.1-fold, 3.2-fold, 3.3-fold, 3.4-fold, 3.5-fold, 4-fold, 5-fold, 10-fold, 20-fold, 30-fold, 40-fold, 50-fold, or more between the sample obtained from the subject and an expression of the gene in an individual who does not express the risk genotype. In some embodiments, the expression of the gene in an individual who does not express the polymorphism is a control or standard. In some embodiments, detection of only one or any combination of the polymorphisms of Table 1 and/or Table 2 is associated with an increase or decrease in expression of gene expression.

D. Transcriptomic Risk Signature

In an aspect, provided herein, a transcriptomic risk signature is detected in a sample obtained from the subject for purposes of characterizing and/or treating an inflammatory disease using the methods disclosed herein. In some embodiments, transcriptomic risk signature comprises one or more genes. In some embodiments, a presence, absence, or level of expression of the one or more genes is detected for purposes of characterizing and/or treating an inflammatory disease using the methods disclosed herein. The genes may be involved in the mammalian innate and adaptive immune responses. In some embodiments, the gene locus is involved in the pathogenesis of inflammatory disease, such as IBD. In further embodiments, the gene locus is involved in autophagy, innate immunity, adaptive immunity, Wnt/beta-catenin signaling, the regulation of epithelial-mesenchymal transition, antigen presentation, or OX40 signaling. In some embodiments, the gene locus is involved in PDE4 mediated pathways, including EIF2 and cAMP signaling pathways.

The transcriptomic risk signature may comprise one or more genes from Table 3 and/or Table 4. In some embodiments, the transcriptomic risk signature comprises two, three, four, five, six, seven, eight, nine, or ten, genes from Table 3 and/or Table 4. In some embodiments, the transcriptomic risk signature comprises 10, 20, 20, 30, 40, 50, 60, 70, 80, 90, or 100 genes from Table 3 and/or Table 4. In some embodiments, the transcriptomic risk signature comprises genes that are uniquely associated with an inflammatory disease clinical subgroup. In some embodiments, the clinical subgroup comprises subjects with inflammatory disease that is characterized by a less severe form of disease (CD1). In some embodiments, the clinical subgroup comprises subjects with inflammatory disease that is characterized by a more severe form of disease (CD3). In some embodiments, the transcriptomic risk signature associated with the CD3 subgroup comprises genes from Table 3 and/or Table 4.

Table 4 lists genes differentially expressed between the CD1 and CD3 subgroups, and uniquely associated with CD1 or CD3.

The transcriptomic risk signature may comprise: (a) a high level of expression of at least one of phosphodiesterase 4C (PDE4C), intercellular adhesion molecule 3 (ICAM3), interleukin 18binding protein (IL18BP), and oncostatin-M-specific receptor subunit (OSMR), as compared to a reference level; and (b) a low level of expression of SMAD Family Member 3 (SMAD3), as compared to a reference level. In some embodiments, the transcriptomic risk signature comprises: (a) a high level of expression of at least two, three, or all four of PDE4C, ICAM3, IL18BP, and OSMR, as compared to a reference level; and (b) a low level of expression SMAD3, as compared to a reference level. In some cases, a transcriptomic risk profile is detected, which comprises a level of expression of a biomarkers described above. The level of expression for a transcriptomic risk profile is, in some cases, relative to a level of the reference level. In some embodiments, a "reference level" is a level of expression in an individual that does not have the disease or the condition (e.g., IBD). In some embodiments, the reference level is a level of expression in a patient who has a mild and non-refractory form of the disease or the condition.

The genes provided in Table 3 were identified as cis genes to the known IBD loci cis-eQTL in small bowel tissues obtained from CD patients. TRS was calculated using the methods in work by Marigorta, U. M., et al., *Nature Genetics* volume 49, pages 1517-1521 (2017), which is incorporated by reference herein in its entirety. Cis expression quantitative trait loci (eQTL), which explains the genetic variance at a particular genetic locus that is associated with an up-or down-regulation of a cis gene in small bowel tissues obtained from CD patients. Thus, the genes in Table 3 represent a unique transcriptomic signature with biological and genetic significance.

The genes provided in Table 3 are useful biomarkers for selecting a patient for treatment of, or identifying a patient to be at risk for developing, a severe form of CD characteristic of CD3.

TABLE 3

Genes Used to Calculate the Transcriptomic Risk Score (TRS)

| AKAP11 | CPEB4 | GNPDA1 | LIME1 | PLCL1 | SDHC | TEF |
|---|---|---|---|---|---|---|
| ALDH2 | CTSW | GPR35 | LNPEP | PMM1 | SERINC3 | THEM4 |
| ANKRD55 | DAP | GSDMB | LY9 | PNKD | SF3A1 | TIMP2 |
| APEH | DAP3 | HHEX | MANBA | POP7 | SH2B3 | TM9SF4 |
| ASXL1 | DNAJC27 | ICAM3 | MAP3K8 | PTGER4 | SKAP2 | TMEM180 |
| ATG16L1 | DUSP16 | ICAM4 | MEI1 | PTGIR | SLC11A1 | TMEM50B |
| BACH2 | EDEM2 | IFNG | MRPL20 | PTGS2 | SLC15A3 | TNFRSF14 |
| BANF1 | EEF1A2 | IKZF3 | MUS81 | PTK2B | SLC22A4 | TNFRSF18 |
| CALM3 | EIF2B4 | IL18R1 | NCKIPSD | PTPN22 | SLC22A5 | TNFRSF4 |
| CARD9 | EP300 | IL18RAP | NDFIP1 | PTPRC | SLC7A6 | TNFSF8 |
| CCDC101 | EPHB4 | IL1R2 | NFATC1 | RAB24 | SMAD3 | TNPO3 |
| CD226 | FADS1 | INPP5E | NFKB1 | RGS14 | SNAPC4 | TRIM8 |
| CD244 | FADS2 | IRF1 | NRBP1 | RNASET2 | SOCS1 | TRPT1 |
| CD28 | FCAR | IRF5 | ORMDL3 | RNF145 | SP110 | TYK2 |
| CD40 | FCGR2B | ITIH4 | PARK7 | RORC | SP140 | USF1 |
| CDC42SE2 | FCGR3B | KEAP1 | PDGFB | RPS6KA4 | SPHK2 | USP4 |
| CDKN2D | FIBP | KIR2DL4 | PF4V1 | RSPH3 | SSU72 | WSB1 |
| CEBPB | GALC | KIR2DS4 | PFKFB4 | SBK1 | STAT3 | ZFP90 |
| CISD1 | GNA12 | KIR3DL1 | PLA2R1 | SDCCAG3 | SYNGR1 | ZGPAT |
| COMMD7 | GNG8 | LGALS9 | PLCH2 | SDF4 | SYT11 | |

The genes provided in Table 4 are consolidated from Table 2, and represent the genes up-or-down-regulated in CD3 as compared to CD1. The genes provided in Table 4 are useful biomarkers for selecting a patient for treatment of, or identifying a patient to be at risk for developing, a severe form of CD characteristic of CD3. The directionality of expression of the genes in Table 4 can be determined by the fold change value corresponding to the gene in Table 2. A positive fold change value indicates an upregulation of the gene, and a negative fold change value indicates a downregulation of the gene.

In some cases, the genes provided in Table 4 correspond to cis eQTL of the gene in small bowel tissue obtained from CD patients. The genes additionally corresponding to cis eQTL include, bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2(CYP4V2), Vesicle Associated Membrane Protein 3 (VAMP3). This subset of genes is useful biomarkers, with both biological and genetic significance, constitute a transcriptomic risk signature that may be detected either by detecting a level of the gene expression products (mRNA, protein) or detecting a presence of a corresponding polymorphism in Table 2.

TABLE 4

Gene Loci (Genes) differentially expressed between CD1 and CD3 and uniquely associated with CD1 or CD3 genotype

| | | | | |
|---|---|---|---|---|
| TYMP | S1PR2 | GPR17 | FOXO1 | SLC17A4 |
| PACS1 | FMO1 | MBNL1 | C19orf60 | PIGT |
| CNNM2 | VARS2 | SEMA3F | SMG7-AS1 | MRVI1 |
| COL5A1 | MAPK11 | IFT172 | PDE4C | HNF1A |
| SLC9A3 | BEST3 | SORCS3 | PCDH7 | ALPL |
| MAGI3 | FAM71B | IL37 | ACKR2 | PTPN11 |
| FYB | MAST2 | ARSB | APOB | RPL6 |
| CFL1P1 | TNS3 | ZNF609 | CTU2 | PAK2 |
| PPARGC1B | MME | VAV3 | C5orf56 | SAR1B |
| DTX3 | GPX4 | FAM178B | PCSK5 | TCF7 |
| BAK1 | PSMA6 | G6PC2 | LSP1 | PPP2CA |
| SSC5D | MTMR9LP | SMPD3 | MIR210HG | DDC |
| DAAM2 | HLA-DOA | RPL3 | TRIM15 | C3orf20 |
| DOCK10 | FKBP5 | PSMD5 | TNS1 | HLA-DQA2 |
| MTR | TCEA3 | POU5F1 | OSBP | RPL30 |
| COL4A2 | LOC728175 | TNXB | FBXL5 | HLA-DMB |
| TNR | CEP72 | CLPTM1L | GATA4 | CLCN6 |
| PECAM1 | TCF4 | MTTP | ARHGEF10L | SNAP47 |
| SLAIN2 | VNN1 | GRM4 | BCR | LRRC56 |
| KLHDC7B | NFIA | OPCML | FER1L4 | LZTFL1 |
| GIT2 | HHAT | GLB1 | LEMD2 | XCR1 |
| SMAD3 | DKFZP434K028 | ANK3 | MPPED1 | AVIL |
| ST6GALNAC5 | LCEIF | CTSH | FRMD4A | HLA-DMA |
| MYO16 | WNK1 | CYP4V2 | UBE2E3 | AGAP2 |
| TBX19 | HLA-DPA1 | ATF6B | CFAP69 | IGFBP7 |
| PHLDB2 | SNAPC4 | DNMT3A | APIG1 | RPL18 |
| LRRC4C | NMD3 | AFF3 | OSBPL5 | DGKD |
| ULK1 | LTB4R | SMG7 | BRD2 | SMARCA4 |
| PCGF3 | P4HA2 | PLBD1 | PRKCA | DLC1 |
| MTSS1 | LAT | VAMP3 | XPO1 | PIP5K1C |
| LCE1C | IGFBP4 | HISTIH1A | KIF21B | HNF4A |
| MSRA | ITPKB | TRIM38 | MACROD2 | ALDH2 |
| GGNBP2 | IFNGR1 | THRB | CD209 | UQCR10 |
| ST8SIA2 | SYMPK | NELFE | MPZL3 | CHRM3 |
| CDK13 | RASSF7 | CEP85L | RORA | |

Genes provided in Table 4 were narrowed to a set of 17 genes listed in Table 13 that have been determined to drive specific gene pathways (e.g., cAMP, or RhoGDI) based on the overlap observed of genetics and expression between CD1 and CD3 subgroups. This subset of genes is useful biomarkers, with both biological and genetic significance, constitute a transcriptomic risk signature that may be detected either by detecting a level of the gene expression products (mRNA, protein) or detecting a presence of a corresponding polymorphism provided in Table 2.

The genes provided in Table 4 and Table 3 were overlapped to identify genes with both biological and genetic significance. Aldehyde Dehydrogenase 2 Family Member (ALDH2) was identified. ALDH2 is downregulated in CD3, as indicated by the negative fold change value corresponding to rs7296651, provided in Table 2.

The transcriptional risk signature (TRSig) disclosed herein may include one or more genes provided in Table 3 or Table 4. In preferred embodiments, genes with biological and genetic significance that have the highest predictive value for a severe CD phenotype (e.g., CD3) constitute the TRSig.

Genes provided in Table 2 that had cis eQTL in the small bowel expression data (p<0.01), were identified as a subset of biomarkers with both biological an genetic significance that may be useful as biomarkers highly predictive of severe CD phenotype. The genes include bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2 (CYP4V2), Vesicle Associated Membrane Protein 3 (VAMP3).

Provided herein are transcriptomic risk signatures involving protein tyrosine phosphatase, non-receptor type 11 (PTPN11) that are useful for the diagnosis and treatment of inflammatory bowel disease (IBD), such as Crohn's disease (CD) and ulcerative colitis (UC). In some cases, the transcriptomic risk signature is a downregulation of PTPN11, as compared to a normal (e.g., non-diseased individual), or an individual with a less severe form of CD, such as CD1. In some cases, the transcriptomic risk signature is detected by detecting a level of gene expression product expressed from PTPN11. In some cases, the transcriptomic risk signature is detected by detecting a presence of a single nucleotide polymorphism (SNP) associated with the downregulation of PTPN11. In some cases, the SNP is at rs2301756 and comprises a "G" allele, which is provided in SEQ ID NO: 339. In some cases, the SNP is rs7958372 and comprises an "A" allele, which is provided in SEQ ID NO: 408.

Also provided are transcriptomic risk signatures involving ribosomal protein (RL30) are useful for the diagnosis and treatment of IBD, such as CD and UC. In some cases, the transcriptomic risk signature is a downregulation of RPL30, as compared to a normal (e.g., non-diseased individual), or an individual with a less severe form of CD, such as CD1. In some cases, the transcriptomic risk signature is detected by detecting a level of gene expression product expressed from RPL30. In some cases, the transcriptomic risk signature is detected by detecting a presence of a SNP associated with the downregulation of RPL30. In some cases, the SNP is at rs2877453 and comprises a "C" allele, which is provided in SEQ ID NO: 353.

Disclosed herein are transcriptomic risk signatures involving X-C motif chemokine receptor 1 (XCR1) are useful for the diagnosis and treatment of IBD, such as CD and UC. In some cases, the transcriptomic risk signature is an upregulation of XCR1, as compared to a normal (e.g., non-diseased individual), or an individual with a less severe form of CD, such as CD1. In some cases, the transcriptomic risk signature is detected by detecting a level of gene expression product expressed from XCR1. In some cases, the transcriptomic risk signature is detected by detecting a presence of a SNP associated with the upregulation of XCR1. In some cases, the SNP is selected from the group consisting of a G at rs36040135 (SEQ ID NO: 378), a "G" at rs13074382 (SEQ ID NO: 379), a "G" at rs13097556 (SEQ ID NO: 380), a "G" at rs2230322 (SEQ ID NO: 381), and an "A" at rs71327010 (SE ID NO: 382).

Also disclosed herein are transcriptomic risk signatures involving HNF1 homeobox A (HNF1A) are useful for the diagnosis and treatment of IBD, such as CD and UC. In some cases, the transcriptomic risk signature is an upregulation of HNF1A, as compared to a normal (e.g., non-diseased individual), or an individual with a less severe form of CD, such as CD1. In some cases, the transcriptomic risk signature is detected by detecting a level of gene expression product expressed from HNF1. In some cases, the transcriptomic risk signature is detected by detecting a presence of a SNP associated with the upregulation of HNF1A. In some cases, the SNP is selected from the group consisting of a "G" at rs2244608 (SEQ ID NO: 424), a "C" at rs1169302 (SEQ ID NO: 336), and a "G" at rs1169303G (SEQ ID NO: 337).

Provided herein are transcriptomic risk signatures involving ribosomal protein L3 (RPL3) are useful for the diagnosis and treatment of IBD, such as CD and UC. In some cases, the transcriptomic risk signature is a downregulation of RPL3, as compared to a normal (e.g., non-diseased individual), or an individual with a less severe form of CD, such as CD1. In some cases, the transcriptomic risk signature is detected by detecting a level of gene expression product expressed from RPL3 In some cases, the transcriptomic risk signature is detected by detecting a presence of a SNP associated with the downregulation of RPL3. In some cases, the SNP is an "A" at rs6519183,which is provided in SEQ ID NO: 174.

Also provided herein are transcriptomic risk signatures involving cholinergic receptor muscarinic 3 (CHRM3) are useful for the diagnosis and treatment of IBD, such as CD and UC. In some cases, the transcriptomic risk signature is a upregulation of CHRM3, as compared to a normal (e.g., non-diseased individual), or an individual with a less severe form of CD, such as CD1. In some cases, the transcriptomic risk signature is detected by detecting a level of gene expression product expressed from CHRM3. In some cases, the transcriptomic risk signature is detected by detecting a presence of a SNP associated with the upregulation of CHRM3. In some cases, the SNP is a "C" at rs685548, which is provided in SEQ ID NO: 423.

Disclosed herein are transcriptomic risk signatures involving DLC1 Rho GTPase activating protein (DLC1) are useful for the diagnosis and treatment of IBD, such as CD and UC. In some cases, the transcriptomic risk signature is a downregulation of DLC1, as compared to a normal (e.g., non-diseased individual), or an individual with a less severe form of CD, such as CD1. In some cases, the transcriptomic risk signature is detected by detecting a level of gene expression product expressed from DLC1. In some cases, the transcriptomic risk signature is detected by detecting a presence of a SNP associated with the downregulation of DLC1. In some cases, the SNP is an "A" at rs11998187A, which is provided in SEQ ID NO: 404.

Also disclosed herein are transcriptomic risk signatures involving apolipoprotein B (APOB) are useful for the diagnosis and treatment of IBD, such as CD and UC. In some cases, the transcriptomic risk signature is a downregulation of APOB, as compared to a normal (e.g., non-diseased individual), or an individual with a less severe form of CD, such as CD1. In some cases, the transcriptomic risk signature is detected by detecting a level of gene expression product expressed from APOB. In some cases, the transcriptomic risk signature is detected by detecting a presence of a SNP associated with the downregulation of APOB. In some cases, the SNP is selected from the group consisting of an "A" at rs531819 (SEQ ID NO: 258), a "G" at rs1041968 (SEQ ID NO: 354), a "G" at rs693 (SEQ ID NO: 388), an "A" at rs512535 (SEQ ID NO: 400), a "G" at rs550619 (SEQ ID NO: 406), an "A" at rs570877 (SEQ ID NO: 407), and a "G" at rs12713956 (SEQ ID NO: 437)

Provided herein are transcriptomic risk signatures involving ribosomal protein L6 (RPL6) are useful for the diagnosis and treatment of IBD, such as CD and UC. In some cases, the transcriptomic risk signature is a downregulation of RPL6, as compared to a normal (e.g., non-diseased individual), or an individual with a less severe form of CD, such as CD1. In some cases, the transcriptomic risk signature is detected by detecting a level of gene expression product expressed from RPL6. In some cases, the transcriptomic risk signature is detected by detecting a presence of a SNP associated with the downregulation of RPL6. In some cases, the SNP is an "A" at rs2301723A, which is provided in SEQ ID NO: 340.

Also provided herein are transcriptomic risk signatures involving glutamate metabotropic receptor 4 (GRM4) are useful for the diagnosis and treatment of IBD, such as CD and UC. In some cases, the transcriptomic risk signature is an upregulation of GRM4, as compared to a normal (e.g., non-diseased individual), or an individual with a less severe form of CD, such as CD1. In some cases, the transcriptomic risk signature is detected by detecting a level of gene expression product expressed from GRM4. In some cases, the transcriptomic risk signature is detected by detecting a presence of a SNP associated with the upregulation of GRM4. In some cases, the SNP is an "A" at rs2499714A, which is provided in SEQ ID NO: 181.

Disclosed herein are transcriptomic risk signatures involving p21 (RAC1) activated kinase 2 (PAK2) are useful for the diagnosis and treatment of IBD, such as CD and UC. In some cases, the transcriptomic risk signature is a downregulation of PAK2, as compared to a normal (e.g., non-diseased individual), or an individual with a less severe form of CD, such as CD1. In some cases, the transcriptomic risk signature is detected by detecting a level of gene expression product expressed from PAK2. In some cases, the transcriptomic risk signature is detected by detecting a presence of a SNP associated with the downregulation of PAK2. In some cases, the SNP is an "A" at rs6583176, which is provided in SEQ ID NO: 341.

Also disclosed herein are transcriptomic risk signatures involving ribosomal protein L18(RPL18) are useful for the diagnosis and treatment of IBD, such as CD and UC. In some cases, the transcriptomic risk signature is a downregulation of RPL18, as compared to a normal (e.g., non-diseased individual), or an individual with a less severe form of CD, such as CD1. In some cases, the transcriptomic risk signature is detected by detecting a level of gene expression product expressed from RPL18. In some cases, the transcriptomic risk signature is detected by detecting a presence of a SNP associated with the downregulation of RPL18. In some cases, the SNP is an "A" at rs369880, which is provided in SEQ ID NO: 395.

Provided herein are transcriptomic risk signatures involving phosphodiesterase 4C (PDE4C) are useful for the diagnosis and treatment of IBD, such as CD and UC. In some cases, the transcriptomic risk signature is an upregulation of PDE4C, as compared to a normal (e.g., non-diseased individual), or an individual with a less severe form of CD, such as CD1. In some cases, the transcriptomic risk signature is detected by detecting a level of gene expression product expressed from PDE4C. In some cases, the transcriptomic risk signature is detected by detecting a presence of a SNP associated with the upregulation of PDE4C. In some cases, the SNP is a "G" at rs57884093G, which is provided in SEQ ID NO: 396.

Also provided herein are transcriptomic risk signatures involving protein kinase C alpha (PRKCA) are useful for the diagnosis and treatment of IBD, such as CD and UC. In some cases, the transcriptomic risk signature is an upregulation or downregulation of PRKCA, as compared to a normal (e.g., non-diseased individual), or an individual with a less severe form of CD, such as CD1. In some cases, the transcriptomic risk signature is detected by detecting a level of gene expression product expressed from PRKCA. In some cases, the transcriptomic risk signature is detected by detecting a presence of a SNP associated with the upregulation or downregulation of PRKCA. In some cases, the SNP is an "A" at rs9896905, which is provided in SEQ ID NO: 321.

Disclosed herein are transcriptomic risk signatures involving protein phosphatase 2catalytic subunit alpha (PPP2CA) are useful for the diagnosis and treatment of IBD, such as CD and UC. In some cases, the transcriptomic risk signature is a downregulation of PPP2CA, as compared to a normal (e.g., non-diseased individual), or an individual with a less severe form of CD, such as CD1. In some cases, the transcriptomic risk signature is detected by detecting a level of gene expression product expressed from PPP2CA. In some cases, the transcriptomic risk signature is detected by detecting a presence of a SNP associated with the downregulation of PPP2CA. In some cases, the SNP is an "A" at rs7704116, which is provided in SEQ ID NO: 348.

Also disclosed herein are transcriptomic risk signatures involving phosphatidylinositol-4-phosphate 5-kinase type 1 gamma (PIP5K1C) are useful for the diagnosis and treatment of IBD, such as CD and UC. In some cases, the transcriptomic risk signature is an upregulation or a downregulation of PIP5K1C, as compared to a normal (e.g., non-diseased individual), or an individual with a less severe form of CD, such as CD1. In some cases, the transcriptomic risk signature is detected by detecting a level of gene expression product expressed from PIP5K1C. In some cases, the transcriptomic risk signature is detected by detecting a presence of a SNP associated with the downregulation of PIP5K1C. In some cases, the SNP is an "A" at rs12984273, which is provided in SEQ ID NO: 405.

Provided herein are transcriptomic risk signatures involving histone cluster 1 H1 family member A (HIST1H1A) are useful for the diagnosis and treatment of IBD, such as CD and UC. In some cases, the transcriptomic risk signature is a downregulation of HIST1H1A, as compared to a normal (e.g., non-diseased individual), or an individual with a less severe form of CD, such as CD1. In some cases, the transcriptomic risk signature is detected by detecting a level of gene expression product expressed from HIST1H1A. In some cases, the transcriptomic risk signature is detected by detecting a presence of a SNP associated with the downregulation of HIST1H1A In some cases, the SNP is a "G" at rs16891235, which is provided in SEQ ID NO: 236.

Provided herein are transcriptomic risk signatures involving Aldehyde Dehydrogenase 2 Family Member (ALDH2) that are useful for the diagnosis and treatment of inflammatory bowel disease (IBD), such as Crohn's disease (CD) and ulcerative colitis (UC). In some cases, the transcriptomic risk signature is a downregulation of ALDH2, as compared to a normal (e.g., non-diseased individual), or an individual with a less severe form of CD, such as CD1. In some cases, the transcriptomic risk signature is detected by detecting a level of gene expression product expressed from ALDH2. In some cases, the transcriptomic risk signature is detected by detecting a presence of a single nucleotide polymorphism (SNP) associated with the downregulation of ALDH2. In some cases, the SNP is at rs7296651 and comprises a "C" allele, which is provided in SEQ ID NO: 412.

Also disclosed herein are transcriptomic risk signatures involving BRD2, which is predictive of a risk of developing a severe form of CD characteristic of CD3. In some cases, the transcriptomic risk signature is a downregulation of BRD2, as compared to a normal (e.g., non-diseased individual), or an individual with a less severe form of CD, such as CD1. In some cases, the transcriptomic risk signature is detected by detecting a level of gene expression product expressed from BRD2. In some cases, the transcriptomic risk signature is detected by detecting a presence of a SNP associated with the downregulation of BRD2. In some cases, the SNP is at is rs516535 and comprises an "A" allele, which is provided in SEQ ID NO: 320.

Provided herein are transcriptomic risk signatures involving HLA-DQA2, which is predictive of a risk of developing a severe form of CD characteristic of CD3. In some cases, the transcriptomic risk signature is a downregulation or upregulation of HLA-DQA2, as compared to a normal (e.g., non-diseased individual), or an individual with a less severe form of CD, such as CD1. In some cases, the transcriptomic risk signature is detected by detecting a level of gene expression product expressed from HLA-DQA2. In some cases, the transcriptomic risk signature is detected by detecting a presence of a SNP associated with the downregulation or the upregulation of AHLA-DQA2. In some cases, the SNP is at rs9276427 and comprises an "A' allele, which is provided in SEQ ID NO: 351.

Also provided herein are transcriptomic risk signatures involving KIF21B, which is predictive of a risk of developing a severe form of CD characteristic of CD3. In some cases, the transcriptomic risk signature is an upregulation of KIF21B, as compared to a normal (e.g., non-diseased individual), or an individual with a less severe form of CD, such as CD1. In some cases, the transcriptomic risk signature is detected by detecting a level of gene expression product expressed from KIF21B. In some cases, the transcriptomic risk signature is detected by detecting a presence of a SNP associated with the upregulation of KIF21B. In some cases, the SNP is at rs296564 and comprises an "A" allele, which is provided in SEQ ID NO: 323. In some cases, the SNP is at rs296569 and comprises a "A" allele, which is provided in SEQ ID NO: 331. In some cases, the SNP is and comprises an "A" allele, which is provided in SEQ ID NO: 332. In some cases, the SNP is at rs296567 and comprises a "G' allele, which is provided in SEQ ID NO: 333. In some cases, the SNP is at rs296561 and comprises a "G" allele, which is provided in SEQ ID NO: 334. In some cases, the SNP is at rs72749142 and comprises a "G" allele, which is provided in SEQ ID NO: 389.

Disclosed herein are transcriptomic risk signatures involving PCDH7, which is predictive of a risk of developing a severe form of CD characteristic of CD3. In some cases, the transcriptomic risk signature is a downregulation of PCDH7, as compared to a normal (e.g., non-diseased individual), or an individual with a less severe form of CD, such as CD1. In some cases, the transcriptomic risk signature is detected by detecting a level of gene expression product expressed from PCDH7. In some cases, the transcriptomic risk signature is detected by detecting a presence of a SNP associated with the downregulation of PCDH7. In some cases, the SNP is at rs9291547 and comprises an "A" allele, which is provided in SEQ ID NO: 255.

Also disclosed herein are transcriptomic risk signatures involving ANK3, which is predictive of a risk of developing a severe form of CD characteristic of CD3. In some cases, the transcriptomic risk signature is a downregulation of ANK3, as compared to a normal (e.g., non-diseased individual), or an individual with a less severe form of CD, such as CD1. In some cases, the transcriptomic risk signature is detected by detecting a level of gene expression product expressed from ANK3. In some cases, the transcriptomic risk signature is detected by detecting a presence of a SNP associated with the downregulation of ANK. In some cases, the SNP is at rs10761532 and comprises an "A" allele, which is provided in SEQ ID NO: 194. In some cases, the SNP is at rs10821813 and comprises an "A" allele, which is provided in SEQ ID NO: 195. In some cases, the SNP is at rs1561852 and comprises a "C" allele, which is provided in SEQ ID NO: 196. In some cases, the SNP is at rs10994464 and comprises an "A" allele, which is provided in SEQ ID NO: 204. In some cases, the SNP is at rs993402 and comprises a "G" allele, which is provided in SEQ ID NO: 205. In some cases, the SNP is at rs10994467 and comprises an "A" allele, which is provided in SEQ ID NO: 206. In some cases, the SNP is at rs10821822 and comprises an "A" allele, which is provided in SEQ ID NO: 207. In some cases, the SNP is at rs1837949 and comprises a "G" allele, which is provided in SEQ ID NO: 208. In some cases, the SNP is at rs35597961 and comprises a "C" allele, which is provided in SEQ ID NO: 209. In some cases, the SNP is at rs10821830 and comprises a "G" allele, which is provided in SEQ ID NO: 210. In some cases, the SNP is at rs975262 and comprises an "A" allele, which is provided in SEQ ID NO: 211. In some cases, the SNP is at rs973067 and comprises an "A" allele, which is provided in SEQ ID NO: 212. In some cases, the SNP is at rs10509139 and comprises a "G" allele, which is provided in SEQ ID NO: 213. In some cases, the SNP is at rs1442539 and comprises an "A" allele, which is provided in SEQ ID NO: 214. In some cases, the SNP is at rs2197155 and comprises an "A" allele, which is provided in SEQ ID NO: 215. In some cases, the SNP is at rs7919914 and comprises a "G" allele, which is provided in SEQ ID NO: 216. In some cases, the SNP is at rs10994476 and comprises a "G" allele, which is provided in SEQ ID NO: 275. In some cases, the SNP is at rs35471473 and comprises an "A" allele, which is provided in SEQ ID NO: 243. In some cases, the SNP is at rs12785023 and comprises a "G" allele, which is provided in SEQ ID NO: 244. In some cases, the SNP is at rs12783716 and comprises a "G" allele, which is provided in SEQ ID NO: 245. In some cases, the SNP is at rs10821821 and comprises a "G" allele, which is provided in SEQ ID NO: 246. In some cases, the SNP is at rs10994441 and comprises a "G" allele, which is provided in SEQ ID NO: 284. In some cases, the SNP is at rs10994442 and comprises a "C" allele, which is provided in SEQ ID NO: 285. In some cases, the SNP is at rs10821814 and comprises a "T" allele, which is provided in SEQ ID NO: 286. In some cases, the SNP is at rs10994465 and comprises an "A" allele, which is provided in SEQ ID NO: 287. In some cases, the SNP is at rs12218617 and comprises a "T" allele, which is provided in SEQ ID NO: 288. In some cases, the SNP is at rs10509138 and comprises a "C" allele, which is provided in SEQ ID NO: 289. In some cases, the SNP is at rs61854518 and comprises an "A" allele, which is provided in SEQ ID NO: 290. In some cases, the SNP is at rs10821699 and comprises a "G" allele, which is provided in SEQ ID NO: 345. In some cases, the SNP is at rs7919274 and comprises a "G" allele, which is provided in SEQ ID NO: 352. In some cases, the SNP is at rs10761552 and comprises an "A" allele, which is provided in SEQ ID NO: 368. In some cases, the SNP is at rs17037425 and comprises a "G" allele, which is provided in SEQ ID NO: 369. In some cases, the SNP is at rs2893861 and comprises an "A" allele, which is provided in SEQ ID NO: 370. In some cases, the SNP is at rs1993939 and comprises a "C" allele, which is provided in SEQ ID NO: 371. In some cases, the SNP is at rs10821833 and comprises a "G" allele, which is provided in SEQ ID NO: 372. In some cases, the SNP is at rs1904418 and comprises a "G" allele, which is provided in SEQ ID NO: 373. In some cases, the SNP is at rs16915196 and comprises a "G" allele, which is provided in SEQ ID NO: 432. In some cases, the SNP is at rs61853514 and comprises an "A" allele, which is provided in SEQ ID NO: 433. In some cases. the SNP is at rs10994430 and comprises an "A" allele, which is provided in SEQ ID NO: 434. In some cases, the SNP is at rs16915231 and comprises an "A" allele, which is provided in SEQ ID NO: 435. In some cases, the SNP is at rs2028564 and comprises a "G" allele, which is provided in SEQ ID NO: 436.

Provided herein are transcriptomic risk signatures involving TRIM38, which is predictive of a risk of developing a severe form of CD characteristic of CD3. In some cases, the transcriptomic risk signature is a downregulation of TRIM38, as compared to a normal (e.g., non-diseased individual), or an individual with a less severe form of CD, such as CD1. In some cases, the transcriptomic risk signature is detected by detecting a level of gene expression product expressed from TRIM38. In some cases, the transcriptomic risk signature is detected by detecting a presence of a SNP associated with the downregulation of TRIM38. In some cases, the SNP is at rs13196552 and comprises a "G" allele, which is provided in SEQ ID NO: 237. In some cases, the SNP is at rs17587597 and comprises an "A" allele, which is provided in SEQ ID NO: 282. In some cases, the SNP is at rs17587226 and comprises an "A" allele, which is provided in SEQ ID NO: 301.

Also provided herein are transcriptomic risk signatures involving CYP4V2, which is predictive of a risk of developing a severe form of CD characteristic of CD3. In some cases, the transcriptomic risk signature is a downregulation of CYP4V2, as compared to a normal (e.g., non-diseased individual), or an individual with a less severe form of CD, such as CD1. In some cases, the transcriptomic risk signature is detected by detecting a level of gene expression product expressed from CYP4V2. In some cases, the transcriptomic risk signature is detected by detecting a presence of a SNP associated with the downregulation of CYP4V2. In some cases, the SNP is at rs2276917 and comprises an "A" allele, which is provided in SEQ ID NO: 200. In some cases, the SNP is at rs10013653 and comprises an "A" allele, which is provided in SEQ ID NO: 312.

Provided herein are transcriptomic risk signatures involving VAMP3, which is predictive of a risk of developing a severe form of CD characteristic of CD3. In some cases, the transcriptomic risk signature is a downregulation of VAMP3, as compared to a normal (e.g., non-diseased individual), or an individual with a less severe form of CD, such as CD1. In some cases, the transcriptomic risk signature is detected by detecting a level of gene expression product expressed from VAMP3. In some cases, the transcriptomic risk signature is detected by detecting a presence of a SNP associated with the downregulation of VAMP3. In some cases, the SNP is at rs11582799 and comprises an "A" allele, which is provided in SEQ ID NO: 222. In some cases, the SNP is at rs111692854 and comprises an "A" allele, which is provided in SEQ ID NO: 223. In some cases, the SNP is at rs72632053 and comprises an "A" allele, which is provided in SEQ ID NO: 224.

E. Methods of Treatment

Disclosed herein are methods of treating an inflammatory disease in a subject, by administering a therapeutically effective amount of a therapeutic agent to the subject, provided a risk genotype or a transcriptomic risk signature is detected in a sample obtained from the subject. In some embodiments, methods comprise diagnosing the inflammatory disease in the subject. In some cases, a presence of the risk genotype or transcriptomic risk signature is used to diagnose the inflammatory disease. Alternatively, in some embodiments, the subject has been previously diagnosed with the inflammatory disease, and methods comprise characterizing the inflammatory disease as inflammatory bowel disease (IBD), or a subtype thereof. In some embodiments, methods comprise diagnosing the subject with Crohn's disease (UC) or ulcerative colitis (UC). In some embodiments, methods comprise diagnosing the subject with a severe or refractory form of the IBD, such as medically refractory CD.

In some cases, the risk genotype detected comprises a polymorphism provided in Table 2. The genotype may comprise two or more polymorphisms from Table 2. The genotype may comprise at least or about three, four, five, six, seven, eight, nine, 10, 11, 12, 13, 14, 15, 16, 17,18, 19, 20, 21,22, 23, 24, 25, 26, 27, 28, 29, 30, 31, 32, 33, 34, 35, 36, 37, 38, 39, 40 or more polymorphisms from Table 2. In some cases, the genotype is heterozygous for the "risk allele" provided in Table 2(column seven). In some cases, the genotype is homozygous for the risk allele provided in Table 2. If two or more polymorphisms make up the genotype, then in some embodiments, the genotype for each polymorphism will be heterozygous or homozygous, for the risk allele. In this example, one genotype may be homozygous, and the other heterozygous, for the risk allele. In some cases, detecting a presence of the risk genotype in a sample obtained from a subject is indicative that the subject has, or will develop, the associated clinical or subclinical phenotype (e.g., severe and refractory Crohn's disease).

In some cases, the transcriptomic risk profile comprises two or more genes provided in Table 3 and/or Table 4. The transcriptomic risk profile comprises, in some embodiments, at least three, four, five, six, seven, eight, nine, 10, 11, 12, 13, 14, 15, 16, 17,18, 19, 20, 21, 22, 23, 24, 25, 26, 27,28, 29, 30, 31, 32, 33, 34, 35, 36, 37, 38, 39, 40 genes provided in Table 3 and/or Table 4. The transcriptomic risk profile may require all 139 genes provided in Table 3 and/or Table 4. In some cases, an expression of the gene is high as compared to an individual who does not have a severe or refractory form of the inflammatory disease. In some cases, an expression of the gene is low as compared to an individual who does not have a severe or refractory form of the inflammatory disease.

Provided herein are methods of selecting a subject for treatment, at least in part, because the subject is, or as been, identified as being at risk for developing a toxicity, a non-response, or a loss-of-response, to a standard therapy. In some cases, the subject is selected for treatment if the subject is, or is at risk for developing, thiopurine toxicity, or a disease caused by thiopurine toxicity (such as pancreatitis or leukopenia). In some cases, the subject is selected for treatment if the subject is, or is at risk for developing non-response or loss-of-response to a standard therapy. In some cases, the standard therapy is selected from the group consisting of anti-TNF alpha therapy, anti-a4-b7 therapy (vedolizumab), anti-IL12p40 therapy (ustekinumab), thiopurine, Thalidomide, Cytoxin, and a combination thereof.

Methods of treatment provided herein comprise administering to the subject at least one of an inhibitor of phosphodiesterase 4 (PDE4) and an agonist of adenylate cyclase 7 (ADCY7). In some embodiments, the inhibitor of PDE4 and the agonist of ADCY7 are administered separately. In some embodiments, the inhibitor of PDE4 is administered before the agonist of ADCY7. In some embodiments, the inhibitor of PDE4 is administered after the agonist of ADCY7. In some instances, an additional therapeutic agent is administered to the subject either alone, or in combination with at least one of the inhibitor of PDE4 and agonist of ADCY7.

Provided herein are methods of treating inflammatory bowel disease (IBD), such as Crohn's disease (CD) and ulcerative colitis (UC) in a subject, provided that a presence of a transcriptomic risk signature is detected in the subject. Once the transcriptomic risk signature is detected in the subject, in some cases, the subject is administered a therapeutically effective amount of an agonist of ADCY7 or an inhibitor of PDE4. The transcriptomic risk signature may involve one gene. Alternatively, the transcriptomic risk signature involves multiple genes, for e.g., 2, 3, 4, 5, 6, 7,8, 9, 10, 11, 12, 13, 14, 15, 16, or 17 genes described herein.

Methods disclosed herein comprise detecting a transcriptomic risk signature in a subject, which in some cases involves detecting a level of protein tyrosine phosphatase, non-receptor type 11(PTPN11). In some cases, the transcriptomic risk signature is a downregulation of PTPN11, as compared to a normal (e.g., non-diseased individual), or an individual with a less severe form of CD, such as CD1. In some cases, the transcriptomic risk signature is detected by detecting a level of gene expression product expressed from PTPN11. In some cases, the transcriptomic risk signature is detected by detecting a presence of a single nucleotide polymorphism (SNP) associated with the downregulation of PTPN11. In some cases, the SNP is at rs2301756 and comprises a "G" allele. which is provided in SEQ ID NO: 339. In some cases, the SNP is rs7958372 and comprises an "A" allele, which is provided in SEQ ID NO: 408.The transcriptomic signature may be detected with a single SNP. Alternatively, the transcriptomic risk signature may be detected with multiple SNPs described herein, for e.g., both rs2301756 and rs7958372. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of ribosomal protein (RPL30). In some cases, the transcriptomic risk signature is a downregulation of RPL30, as compared to a normal (e.g., non-diseased individual), or an individual with a less severe form of CD, such as CD1. In some cases, the transcriptomic risk signature is detected by detecting a level of gene expression product expressed from RPL30. In some cases, the transcriptomic risk signature is detected by detecting a presence of a SNP associated with the downregulation of RPL30. In some cases, the SNP is at rs2877453 and comprises a "C" allele, which is provided in SEQ ID NO: 353. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of X-C motif chemokine receptor 1 (XCR1) In some cases, the transcriptomic risk signature is an upregulation of XCR1, as compared to a normal (e.g., non-diseased individual), or an individual with a less severe form of CD, such as CD1. In some cases, the transcriptomic risk signature is detected by detecting a level of gene expression product expressed from XCR1. In some cases, the transcriptomic risk signature is detected by detecting a presence of a SNP associated with the upregulation of XCR1. In some cases, the SNP is selected from the group consisting of a G at rs36040135 (SEQ ID NO: 378), a "G" at rs13074382 (SEQ ID NO: 379), a "G" at rs13097556 (SEQ ID NO: 380), a "G" at rs2230322 (SEQ ID NO: 381), and an "A" at rs71327010(SE ID NO: 382). The transcriptomic signature may be detected with a single SNP. Alternatively, the transcriptomic risk signature may be detected with multiple SNPs described herein, for e.g., two or more of rs36040135, rs13074382, rs13097556, rs2230322, and rs71327010. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of HNF1 homeobox A (HNF1A). In some cases, the transcriptomic risk signature is an upregulation of HNF1A, as compared to a normal (e.g., non-diseased individual), or an individual with a less severe form of CD, such as CD1. In some cases, the transcriptomic risk signature is detected by detecting a level of gene expression product expressed from HNF1A. In some cases, the transcriptomic risk signature is detected by detecting a presence of a SNP associated with the upregulation of HNF1A. In some cases, the SNP is selected from the group consisting of a "G" at rs2244608 (SEQ ID NO: 424), a "C" at rs1169302 (SEQ ID NO: 336), and a "G" at rs1169303 (SEQ ID NO: 337). The transcriptomic signature may be detected with a single SNP. Alternatively, the transcriptomic risk signature may be detected with multiple SNPs described herein, e.g., two or more of rs2244608, rs1169302, and rs1169303. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of ribosomal protein L3 (RPL3). In some cases, the transcriptomic risk signature is a downregulation of RPL3, as compared to a normal (e.g., non-diseased individual), or an individual with a less severe form of CD, such as CD1. In some cases, the transcriptomic risk signature is detected by detecting a level of gene expression product expressed from RPL3 In some cases, the transcriptomic risk signature is detected by detecting a presence of a SNP associated with the downregulation of RPL3. In some cases, the SNP is an "A" at rs6519183, which is provided in SEQ ID NO: 174. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of cholinergic receptor muscarinic 3 (CHRM3). In some cases, the transcriptomic risk signature is a upregulation of CHRM3, as compared to a normal (e.g., non-diseased individual), or an individual with a less severe form of CD, such as CD1. In some cases, the transcriptomic risk signature is detected by detecting a level of gene expression product expressed from CHRM3. In some cases, the transcriptomic risk signature is detected by detecting a presence of a SNP associated with the upregulation of CHRM3. In some cases, the SNP is a "C" at rs685548, which is provided in SEQ ID NO: 423. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of DLC1 Rho GTPase activating protein (DLC1). In some cases, the transcriptomic risk signature is a downregulation of DLC1, as compared to a normal (e.g., non-diseased individual), or an individual with a less severe form of CD, such as CD1. In some cases, the transcriptomic risk signature is detected by detecting a level of gene expression product expressed from DLC1. In some cases, the transcriptomic risk signature is detected by detecting a presence of a SNP associated with the downregulation of DLC1. In some cases, the SNP is an "A" at rs11998187A, which is provided in SEQ ID NO: 404. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of apolipoprotein B (APOB). In some cases, the transcriptomic risk signature is a downregulation of APOB, as compared to a normal (e.g., non-diseased individual), or an individual with a less severe form of CD, such as CD1. In some cases, the transcriptomic risk signature is detected by detecting a level of gene expression product expressed from APOB. In some cases, the transcriptomic risk signature is detected by detecting a presence of a SNP associated with the downregulation of APOB. In some cases, the SNP is selected from the group consisting of an "A" at rs531819 (SEQ ID NO: 258), a "G" at rs1041968 (SEQ ID NO: 354), a "G" at rs693 (SEQ ID NO: 388), an "A" at rs512535 (SEQ ID NO: 400), a "G" at rs550619 (SEQ ID NO: 406), an "A" at rs570877 (SEQ ID NO: 407), and a "G" at rs12713956 (SEQ ID NO: 437). The transcriptomic signature may be detected with a single SNP. Alternatively, the transcriptomic risk signature may be detected with multiple SNPs described herein, e.g., two or more of rs531819,rs1041968, rs693, rs512535, rs550619, rs570877, and rs12713956. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject. which in some cases involves detecting a level of ribosomal protein L6 (RPL6). In some cases, the transcriptomic risk signature is a downregulation of RPL6, as compared to a normal (e.g., non-diseased individual), or an individual with a less severe form of CD, such as CD1. In some cases, the transcriptomic risk signature is detected by detecting a level of gene expression product expressed from RPL6. In some cases, the transcriptomic risk signature is detected by detecting a presence of a SNP associated with the downregulation of RPL6. In some cases, the SNP is an "A" at rs2301723A, which is provided in SEQ ID NO: 340. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of glutamate metabotropic receptor 4 (GRM4). In some cases, the transcriptomic risk signature is an upregulation of GRM4, as compared to a normal (e.g., non-diseased individual), or an individual with a less severe form of CD, such as CD1. In some cases, the transcriptomic risk signature is detected by detecting a level of gene expression product expressed from GRM4. In some cases, the transcriptomic risk signature is detected by detecting a presence of a SNP associated with the upregulation of GRM4. In some cases, the SNP is an "A" at rs2499714A, which is provided in SEQ ID NO: 181. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of p21 (RAC1) activated kinase 2 (PAK2). In some cases, the transcriptomic risk signature is a downregulation of PAK2, as compared to a normal (e.g., non-diseased individual), or an individual with a less severe form of CD, such as CD1. In some cases, the transcriptomic risk signature is detected by detecting a level of gene expression product expressed from PAK2. In some cases, the transcriptomic risk signature is detected by detecting a presence of a SNP associated with the downregulation of PAK2. In some cases, the SNP is an "A" at rs6583176, which is provided in SEQ ID NO: 341. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of ribosomal protein L18 (RPL18). In some cases, the transcriptomic risk signature is a downregulation of RPL18, as compared to a normal (e.g., non-diseased individual), or an individual with a less severe form of CD, such as CD1. In some cases, the transcriptomic risk signature is detected by detecting a level of gene expression product expressed from RPL18. In some cases, the transcriptomic risk signature is detected by detecting a presence of a SNP associated with the downregulation of RPL18. In some cases, the SNP is an "A" at rs369880, which is provided in SEQ ID NO: 395. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of phosphodiesterase 4C (PDE4C). In some cases, the transcriptomic risk signature is an upregulation of PDE4C, as compared to a normal (e.g., non-diseased individual), or an individual with a less severe form of CD, such as CD1. In some cases, the transcriptomic risk signature is detected by detecting a level of gene expression product expressed from PDE4C. In some cases, the transcriptomic risk signature is detected by detecting a presence of a SNP associated with the upregulation of PDE4C. In some cases, the SNP is a "G" at rs57884093G, which is provided in SEQ ID NO: 396. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of protein kinase C alpha (PRKCA). In some cases, the transcriptomic risk signature is an upregulation or downregulation of PRKCA, as compared to a normal (e.g., non-diseased individual), or an individual with a less severe form of CD, such as CD1. In some cases, the transcriptomic risk signature is detected by detecting a level of gene expression product expressed from PRKCA. In some cases, the transcriptomic risk signature is detected by detecting a presence of a SNP associated with the upregulation or downregulation of PRKCA. In some cases, the SNP is an "A" at rs9896905, which is provided in SEQ ID NO: 321. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of protein phosphatase 2 catalytic subunit alpha (PPP2CA). In some cases, the transcriptomic risk signature is a downregulation of PPP2CA, as compared to a normal (e.g., non-diseased individual), or an individual with a less severe form of CD, such as CD1. In some cases, the transcriptomic risk signature is detected by detecting a level of gene expression product expressed from PPP2CA. In some cases, the transcriptomic risk signature is detected by detecting a presence of a SNP associated with the downregulation of PPP2CA. In some cases, the SNP is an "A" at rs7704116, which is provided in SEQ ID NO: 348. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject,. which in some cases involves detecting a level of phosphatidylinositol-4-phosphate 5-kinase type 1gamma (PIP5K1C). In some cases, the transcriptomic risk signature is an upregulation or a downregulation of PIP5K1C, as compared to a normal (e.g., non-diseased individual), or an individual with a less severe form of CD, such as CD1. In some cases, the transcriptomic risk signature is detected by detecting a level of gene expression product expressed from PIP5K1C. In some cases, the transcriptomic risk signature is detected by detecting a presence of a SNP associated with the downregulation of PIP5K1C. In some cases, the SNP is an "A" at rs12984273, which is provided in SEQ ID NO: 405. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of histone cluster 1 H1 family member A (HIST1H1A). In some cases, the transcriptomic risk signature is an upregulation of HIST1H1A, as compared to a normal (e.g., non-diseased individual), or an individual with a less severe form of CD, such as CD1. In some cases, the transcriptomic risk signature is detected by detecting a level of gene expression product expressed from HIST1H1A. In some cases, the transcriptomic risk signature is detected by detecting a presence of a SNP associated with the upregulation of XCR10. In some cases, the SNP is a "G" at rs16891235, which is provided in SEQ ID NO: 236. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of Aldehyde Dehydrogenase 2 Family Member (ALDH2). In some cases, the transcriptomic risk signature is a downregulation of ALDH2, as compared to a normal (e.g., non-diseased individual), or an individual with a less severe form of CD, such as CD1. In some cases, the transcriptomic risk signature is detected by detecting a level of gene expression product expressed from ALDH2. In some cases, the transcriptomic risk signature is detected by detecting a presence of a SNP associated with the downregulation of ALDH2. In some cases, the SNP is at rs729665 land comprises a "C" allele, which is provided in SEQ ID NO: 412. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of BRD2, which is predictive of a risk of developing a severe form of CD characteristic of CD3. In some cases, the transcriptomic risk signature is a downregulation of BRD2, as compared to a normal (e.g., non-diseased individual), or an individual with a less severe form of CD, such as CD1. In some cases, the transcriptomic risk signature is detected by detecting a level of gene expression product expressed from BRD2. In some cases, the transcriptomic risk signature is detected by detecting a presence of a SNP associated with the downregulation of BRD2. In some cases, the SNP is at rs516535 and comprises an "A" allele. which is provided in SEQ ID NO: 320. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of HLA-DQA2, which is predictive of a risk of developing a severe form of CD characteristic of CD3. In some cases, the transcriptomic risk signature is a downregulation or upregulation of HLA-DQA2, as compared to a normal (e.g., non-diseased individual), or an individual with a less severe form of CD, such as CD1. In some cases, the transcriptomic risk signature is detected by detecting a level of gene expression product expressed from HLA-DQA2. In some cases, the transcriptomic risk signature is detected by detecting a presence of a SNP associated with the downregulation or the upregulation of AHLA-DQA2. In some cases, the SNP is at rs9276427 and comprises an "A' allele, which is provided in SEQ ID NO: 351. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject. which in some cases involves detecting a level of KIF21B, which is predictive of a risk of developing a severe form of CD characteristic of CD3. In some cases, the transcriptomic risk signature is an upregulation of KIF21B, as compared to a normal (e.g., non-diseased individual), or an individual with a less severe form of CD, such as CD1. In some cases, the transcriptomic risk signature is detected by detecting a level of gene expression product expressed from KIF21B. In some cases, the transcriptomic risk signature is detected by detecting a presence of a SNP associated with the upregulation of KIF21B. In some cases, the SNP is at rs296564 and comprises an "A" allele, which is provided in SEQ ID NO: 323. In some cases, the SNP is at rs296569 and comprises a "A" allele, which is provided in SEQ ID NO: 331. In some cases, the SNP is and comprises an "A" allele, which is provided in SEQ ID NO: 332. In some cases, the SNP is at rs296567 and comprises a "G' allele, which is provided in SEQ ID NO: 333. In some cases, the SNP is at rs296561 and comprises a "G" allele, which is provided in SEQ ID NO: 334. In some cases, the SNP is at rs72749142 and comprises a "G" allele, which is provided in SEQ ID NO: 389. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of PCDH7, which is predictive of a risk of developing a severe form of CD characteristic of CD3. In some cases, the transcriptomic risk signature is a downregulation of PCDH7, as compared to a normal (e.g., non-diseased individual), or an individual with a less severe form of CD, such as CD1. In some cases, the transcriptomic risk signature is detected by detecting a level of gene expression product expressed from PCDH7. In some cases, the transcriptomic risk signature is detected by detecting a presence of a SNP associated with the downregulation of PCDH7. In some cases, the SNP is at rs9291547 and comprises an "A" allele, which is provided in SEQ ID NO:

255. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of ANK3, which is predictive of a risk of developing a severe form of CD characteristic of CD3. In some cases, the transcriptomic risk signature is a downregulation of ANK3, as compared to a normal (e.g., non-diseased individual), or an individual with a less severe form of CD, such as CD1. In some cases, the transcriptomic risk signature is detected by detecting a level of gene expression product expressed from ANK3. In some cases, the transcriptomic risk signature is detected by detecting a presence of a SNP associated with the downregulation of ANK. In some cases, the SNP is at rs10761532 and comprises an "A" allele, which is provided in SEQ ID NO: 194. In some cases, the SNP is at rs10821813 and comprises an "A" allele, which is provided in SEQ ID NO: 195. In some cases, the SNP is at rs1561852 and comprises a "C" allele, which is provided in SEQ ID NO: 196. In some cases, the SNP is at rs10994464 and comprises an "A" allele, which is provided in SEQ ID NO: 204. In some cases, the SNP is at rs993402 and comprises a "G" allele, which is provided in SEQ ID NO: 205. In some cases, the SNP is at rs10994467 and comprises an "A" allele, which is provided in SEQ ID NO: 206. In some cases, the SNP is at rs10821822 and comprises an "A" allele, which is provided in SEQ ID NO: 207. In some cases, the SNP is at rs1837949 and comprises a "G" allele, which is provided in SEQ ID NO: 208. In some cases, the SNP is at rs35597961 and comprises a "C" allele, which is provided in SEQ ID NO: 209. In some cases, the SNP is at rs10821830 and comprises a "G" allele, which is provided in SEQ ID NO: 210. In some cases, the SNP is at rs975262 and comprises an "A" allele, which is provided in SEQ ID NO: 211. In some cases, the SNP is at rs973067 and comprises an "A" allele, which is provided in SEQ ID NO: 212. In some cases, the SNP is at rs10509139 and comprises a "G" allele, which is provided in SEQ ID NO: 213. In some cases, the SNP is at rs1442539 and comprises an "A" allele, which is provided in SEQ ID NO: 214. In some cases, the SNP is at rs2197155 and comprises an "A" allele, which is provided in SEQ ID NO: 215. In some cases, the SNP is at rs7919914 and comprises a "G" allele, which is provided in SEQ ID NO: 216. In some cases, the SNP is at rs10994476 and comprises a "G" allele, which is provided in SEQ ID NO: 275. In some cases, the SNP is at rs35471473 and comprises an "A" allele, which is provided in SEQ ID NO: 243. In some cases, the SNP is at rs12785023 and comprises a "G" allele, which is provided in SEQ ID NO: 244. In some cases, the SNP is at rs12783716 and comprises a "G" allele, which is provided in SEQ ID NO: 245. In some cases, the SNP is at rs10821821 and comprises a "G" allele, which is provided in SEQ ID NO: 246. In some cases, the SNP is at rs10994441 and comprises a "G" allele, which is provided in SEQ ID NO: 284. In some cases, the SNP is at rs10994442 and comprises a "C" allele, which is provided in SEQ ID NO: 285. In some cases, the SNP is at rs10821814 and comprises a "T" allele, which is provided in SEQ ID NO: 286. In some cases, the SNP is at rs10994465 and comprises an "A" allele, which is provided in SEQ ID NO: 287. In some cases, the SNP is at rs12218617 and comprises a "T" allele, which is provided in SEQ ID NO: 288. In some cases, the SNP is at rs10509138 and comprises a "C" allele, which is provided in SEQ ID NO: 289. In some cases, the SNP is at rs61854518 and comprises an "A" allele, which is provided in SEQ ID NO: 290. In some cases, the SNP is at rs10821699 and comprises a "G" allele, which is provided in SEQ ID NO: 345. In some cases, the SNP is at rs7919274 and comprises a "G" allele, which is provided in SEQ ID NO: 352. In some cases, the SNP is at rs10761552 and comprises an "A" allele, which is provided in SEQ ID NO: 368. In some cases, the SNP is at rs17037425 and comprises a "G" allele, which is provided in SEQ ID NO: 369. In some cases, the SNP is at rs2893861 and comprises an "A" allele, which is provided in SEQ ID NO: 370. In some cases, the SNP is at rs1993939 and comprises a "C" allele, which is provided in SEQ ID NO: 371. In some cases, the SNP is at rs10821833 and comprises a "G" allele, which is provided in SEQ ID NO: 372. In some cases, the SNP is at rs1904418 and comprises a "G" allele, which is provided in SEQ ID NO: 373. In some cases, the SNP is at rs16915196 and comprises a "G" allele, which is provided in SEQ ID NO: 432. In some cases, the SNP is at rs61853514 and comprises an "A" allele, which is provided in SEQ ID NO: 433. In some cases, the SNP is at rs10994430 and comprises an "A" allele, which is provided in SEQ ID NO: 434. In some cases, the SNP is at rs16915231 and comprises an "A" allele, which is provided in SEQ ID NO: 435. In some cases, the SNP is at rs2028564 and comprises a "G" allele, which is provided in SEQ ID NO: 436. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of TRIM38, which is predictive of a risk of developing a severe form of CD characteristic of CD3. In some cases, the transcriptomic risk signature is a downregulation of TRIM38, as compared to a normal (e.g., non-diseased individual), or an individual with a less severe form of CD, such as CD1. In some cases, the transcriptomic risk signature is detected by detecting a level of gene expression product expressed from TRIM38. In some cases, the transcriptomic risk signature is detected by detecting a presence of a SNP associated with the downregulation of TRIM38. In some cases, the SNP is at rs13196552 and comprises a "G" allele, which is provided in SEQ ID NO: 237. In some cases, the SNP is at rs17587597 and comprises an "A" allele, which is provided in SEQ ID NO: 282. In some cases, the SNP is at rs17587226 and comprises an "A" allele, which is provided in SEQ ID NO: 301. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of CYP4V2, which is predictive of a risk of developing a severe form of CD characteristic of CD3. In some cases, the transcriptomic risk signature is a downregulation of CYP4V2, as compared to a normal (e.g., non-diseased individual), or an individual with a less severe form of CD, such as CD1. In some cases, the transcriptomic risk signature is detected by detecting a level of gene expression product expressed from CYP4V2. In some cases, the transcriptomic risk signature is detected by detecting a presence of a SNP associated with the downregulation of CYP4V2. In some cases, the SNP is at rs2276917 and comprises an "A" allele, which is provided in SEQ ID NO: 200. In some cases, the SNP is at rs10013653 and comprises an "A" allele, which is provided in SEQ ID NO: 312. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise detecting a transcriptomic risk signature in a subject, which in some cases involves detecting a level of VAMP3, which is predictive of a risk of developing a severe form of CD characteristic of CD3. In some cases, the transcriptomic risk signature is a downregulation of VAMP3, as compared to a normal (e.g., non-diseased individual), or an individual with a less severe form of CD, such as CD1. In some cases, the transcriptomic risk signature is detected by detecting a level of gene expression product expressed from VAMP3. In some cases, the transcriptomic risk signature is detected by detecting a presence of a SNP associated with the downregulation of VAMP3. In some cases, the SNP is at rs11582799 and comprises an "A" allele, which is provided in SEQ ID NO: 222. In some cases, the SNP is at rs111692854 and comprises an "A" allele, which is provided in SEQ ID NO: 223. In some cases, the SNP is at rs72632053 and comprises an "A" allele, which is provided in SEQ ID NO: 224. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

G. Therapeutic Agents

Compositions, kits and methods disclosed herein may comprise a therapeutic agent or use thereof. Thetherapeutic agents disclosed herein are useful for the treatment of the inflammatory diseases or conditions. or symptoms of the inflammatory diseases or conditions disclosed herein. Non-limiting examples of classes of therapeutic agents used to treat the inflammatory diseases or conditions disclosed herein include anti-inflammatory mediators (e.g., small molecule and large molecule), steroids, and tumor necrosis factor (TNF) inhibitors. Non-limiting examples of therapeutic agents used to treat inflammatory bowel disease (IBD) include azathioprine, methotrexate, 6-mercaptopurine, prednisone, mesalazine, and budesonide. Targeted therapies, disclosed herein, are particular useful for the treatment of subjects selected on the basis of a presence of a risk genotype or transcriptomic risk signature provided herein. For example, in some embodiments, a subject is identified as a responder for a particular therapeutic agent disclosed herein, and subsequently treated with that therapeutic agent.

Inhibitors of PDE4

Disclosed herein are therapeutic agents that are modulators of Phosphodiesterase 4(PDE4) that are useful for the treatment of a disease or condition, or symptom of the disease or the condition, disclosed herein. There are roughly 20 PDE4 variants present in mammalian cells due to alternative splicing or the use of different transcriptional units. Each PDE4 member shares a highly conservative catalytic domain of about 320-350 amino acids with more than 80% sequence identity between the members of the four isotypes, PDE4A, PDE4B, PDE4C, and PDE4D. In some embodiments, the modulators of PDE4 disclosed herein are inhibitors of PDE4 expression or activity. An inhibitor of PDE4 expression or activity may be an antagonist, a partial antagonist, or an inverse agonist. The inhibitor of PDE4 may be a non-specific inhibitor of PDE4 isotypes, or a specific inhibitor to one of the four isotypes disclosed herein (e.g., PDE4A, PDE4B, PDE4C, and PDE4D). An "inhibitor of PDE4 expression or activity" as used herein means a inhibitor of the expression or the activity of one or more of the isotypes described herein.

In some cases, the inhibitor of PDE4 expression or activity disclosed herein is effective to target a region of the PDE4C protein or mRNA. PDE4C is encoded on Chromosome 19(NG_029629.1). The messenger RNA (mRNA) sequence for PDE4C isoform 1 is provided in NM_000923.5, which encodes PDE4C protein isoform 1 provided in NP_000914.2, SEQ ID NO: 440.The mRNA sequence for PDE4C isoform 2 is provided in NM_001098819.3, which encodes PDE4C protein isoform 2 provided in NP_001092289.1, which differs in the 5' UTR, lacks a portion of the 5' coding region, and initiates translation at a downstream start codon, compared to isoform 1. The encoded isoform 2 has a shorter N-terminus compared to isoform 1. The mRNA for PDE4C isoform 3 is provided in NM_001098818.4, which encodes PDE4C protein isoform 3 provided in NP_001092288.1, which 0differs in the 5' UTR. lacks a portion of the 5' coding region. and initiates translation at an alternate start codon, compared to isoform 1. The encoded isoform has a shorter, distinct N-terminus compared to isoform 1.

In some embodiments, the inhibitor of PDE4 expression or activity comprises an allosteric modulator of PDE4. An allosteric modulator of PDE4 may indirectly influence the effects PDE4 and binding partners of PDE4. The inhibitor of PDE4 expression or activity may be a direct inhibitor or indirect inhibitor. Non-limiting examples of an inhibitor of PDE4 expression include RNA to protein translation inhibitors, antisense oligonucleotides targeting the PDE4A, PDE4B, PDE4C, and PDE4D, or homolog thereof, mRNA (such as miRNAs, or siRNA), epigenetic editing (such as post-translational modifications of histone tails and/or DNA molecules). Non-limiting examples of an inhibitor of PDE4 activity include antagonists to the PDE4 antigen, and antagonists to gene expression products involved in PDE4 mediated disease. Inhibitors of PDE4 disclosed herein, may include, but are not limited to, a small molecule. The small molecule may be a small molecule that binds to PDE4 or binding partners to PDE4. The small molecule may be a selective inhibitor of an isoform of PDE4. Non-limiting examples of PDE4 inhibitors include theophylline, rolipram, prostacyclin, Apremilast (Otexla®), Cilomilast, Roflumilast (Daliresp®), HT-0712, BPN14770, Crisaborole, MK0952, CHF6001, ASP9831 (ASTER), GSK356278, OPA15406, CC-10004, RPL554, Hemay500, GSK256006, CC-11050, GW842470X, and BLX-028914. In some cases, the small molecule inhibitor of PDE4 is an inhibitor of PDE4C specifically.

Inhibitors of PDE4 disclosed herein, may include, but are not limited to, an anti-PDE4antibody, an antigen-binding fragment thereof. The anti-PDE4 antibody may be monoclonal or polyclonal. The anti-PDE4 antibody may be humanized or chimeric. The anti-PDE4 antibody may be a fusion protein. The anti-PDE4 antibody may be a blocking anti-PDE4 antibody. A blocking antibody blocks binding between two proteins, e.g., a ligand and its receptor. In a non-limiting example, the PDE4 blocking antibody binds to a binding partner of PDE4. In another example, the PDE4 blocking antibody prevents PDE4 from hydrolyzing cyclic adenosine monophosphate (cAMP). In some cases, the PDE4 antibody is an anti-PDE4C antibody that specifically binds to PDE4C.

Non-limiting methods for determining whether an anti-PDE4 antibody binds to the same region of a reference antibody are known in the art. An exemplary method comprises a competition assay. For instance, the method comprises determining whether a reference antibody can compete with binding between the reference antibody and the PDE4 protein or portion thereof, or determining whether the reference antibody can compete with binding between the reference antibody and the PDE4 protein or portion thereof. Exemplary methods include use of surface plasmon resonance to evaluate whether an anti-PDE4 antibody can compete with the binding between PDE4 and another anti-PDE4 antibody. In some cases, surface plasmon resonance is utilized in the competition assay.

Agonists of ADCY7

Disclosed herein are therapeutic agents that are modulators of Adenylate Cyclase 7(ADCY7) that are useful for the treatment of a disease or condition, or symptom of the disease or the condition. disclosed herein. The modulator of ADCY7, in some cases, is an agonist, partial agonist. The inhibitor of ADCY7 may be a non-specific inhibitor of ADCY7, or a specific inhibitor to ADCY7.

In some cases, the agonists of ADCY7 are effective to specifically target a region of the ADCY7 protein or mRNA. ADCY7, and nucleic acids encoding ADCY7 (Entrez ID 113), is located on human chromosome 16 at 16q12.1. The amino acid sequence for ADCY7 isoform 1(NP_001105.1) is provided in SEQ ID NO: 452, which is encoded by mRNA transcript variant 1(NM_001114.4). An additional ADCY7 protein isoform is provided in SEQ ID NOS: 453, which is encoded by transcript variant 2 (NM_001286057.1).

Agonists of ADCY7 disclosed herein are effective to increase the expression or activity of ADCY7 in a subject. In some embodiments, the agonist of ADCY7 comprises an allosteric modulator of ADCY7. An allosteric modulator of ADCY7 may indirectly influence the effects ADCY7 and binding partners of ADCY7. Non-limiting examples of an agonist of ADCY7 expression include RNA to protein ADCY7 translation agonists, antisense oligonucleotides targeting the ADCY7, or homolog thereof, mRNA (such as miRNAs, or siRNA), epigenetic editing (such as post-translational modifications of histone tails and/or DNA molecules). Non-limiting examples of an agonist of ADCY7 activity include antagonists to the ADCY7 antigen, and antagonists to gene expression products involved in ADCY7 mediated disease. Agonists as disclosed herein, may include, but are not limited to, an ADCY7 antibody, an ADCY7-binding antibody fragment, recombinant polypeptide, or a small molecule. The small molecule may be a small molecule that binds to ADCY7or binding partners to ADCY7. The ADCY7 antibody may be monoclonal or polyclonal. The ADCY7antibody may be humanized or chimeric. The ADCY7 antibody may be a fusion protein. The ADCY7antibody may be a blocking ADCY7 antibody. A blocking antibody blocks binding between two proteins. e.g., a ligand and its receptor. In a non-limiting example, the ADCY7 blocking antibody binds to a binding partner of ADCY7. In some cases, the ADCY7 antibody is an ADCY7 antibody that specifically binds to ADCY7. In some cases the ADCY7 is naturally occurring. In some embodiments, the ADCY7 agonists comprise one or more small molecule compounds that are pan-activators of adenylyl cyclases (ACs). Non-limiting examples of ADCY7 agonists that are pan-activators of ACs include forskolin, colforsin daropate, and analogs thereof.

Disclosed herein, in some embodiments are methods of treating a disease or condition in a subject by administering a therapeutically effective amount of an allosteric modulator of ADCY7activity or expression to the subject, thereby decreasing or increasing ADCY7 expression or activity. In some embodiments, the allosteric modulator of ADCY7 is a positive allosteric modulator (PAM) effective to enhance or potentiate a ligand of ADCY7. In some embodiments, the allosteric modulator of ADCY7 is a negative allosteric modulator (NAM) effective to reduce the effect of a primary ligand of ADCY7. In some embodiments, the allosteric modulator binds to a non-orthosteric binding site of ADCY7. In some embodiments, the modulator of ADCY7 affects a conformation of the orthosteric binding site of ADCY7 effective decrease or increase activity of ADCY7. In some embodiments, the modulator of ADCY7 is effective to increase or decrease a rate of catalysis of cyclic adenosine monophosphate (cAMP) from adenosine triphosphate (ATP) by ADCY7. In some embodiments, the modulator of ADCY7 is effective to reduce or enhance the inhibition of ADCY7 activity by calcium. Non-limiting examples of ligands that activate ADCY7 include G protein alpha subunit, G protein beta and gamma subunit complex, G Protein Subunit Alpha 13 (GNA13), G Protein Subunit Alpha 12(GNA12), and ethanol. A non-limiting example of a ligand that inhibits ADCY7 includes lithium.

RIPK2 Modulators

Disclosed herein, in some embodiments, are therapeutic agents useful for the treatment of a disease or condition. or symptom of the disease or condition, disclosed herein. Disclosed herein, in some embodiments, are modulators of Receptor Interacting Serine/Threonine Kinase 2 (RIPK2) activity or expression. In some embodiments, a modulator of RIPK2 activity or expression comprises an antagonist or a partial antagonist of RIPK2. In some embodiments, the RIPK2 antagonist or partial antagonist comprises an antibody or antigen-binding fragment, or a small molecule.

In some embodiments, the RIPK2 antagonist or partial antagonist comprises a type I RIPK2 inhibitor effective to bind to the ATP binding pocket of an active conformation of the RIPK2 kinase domain. In some embodiments, the RIPK2 antagonist or partial antagonist comprises a type I½ RIPK2 inhibitor effective to bind to the ATP binding pocket of an inactive conformation of the RIPK2 kinase domain without displacing the RIPK2 kinase activation segment. In some embodiments, the RIPK2 antagonist or partial antagonist comprises a type II RIPK2 inhibitor effective to displace a RIPK2 kinase activation segment. In some embodiments, the RIPK2 antagonist or partial antagonist comprises a type III RIPK2 inhibitor effective to bind an allosteric site of RIPK2located in the cleft between the small and large lobes adjacent to the ATP binding pocket. In some embodiments, the RIPK2 antagonist or partial antagonist comprises a type IV RIPK2 inhibitor effective to bind an allosteric site of RIPK2 located outside of the cleft and the phosphoacceptor region. In some embodiments, the RIPK2 antagonist or partial antagonist comprises a type V RIPK2inhibitor effective to span two regions of the RIPK2 kinase domain. In some embodiments, the RIPK2antagonist or partial antagonist comprises a type VI RIPK2 inhibitor effective to form a covalent adduct with RIPK2. In some embodiments, the RIPK2 antagonist or partial antagonist comprises a RIPK2 inhibitor effective to inhibit RIPK2 ubiquitination. In some embodiments, the RIPK2antagonist or partial antagonist comprises a RIPK2 inhibitor effective to inhibit RIPK2autophosphorylation. In some embodiments, the RIPK2 antagonist or partial antagonist comprises a RIPK2 inhibitor effective to block NOD-dependent tumor necrosis factor production without affecting lipopolysaccharide-dependent pathways. In some embodiments, the RIPK2 antagonist or partial antagonist comprises ponatinib, sorafenib, regorafenib, gefitinib, or erlotinib. In some embodiments, the RIPK2 antagonist or parital antagonist comprises GSK2983559, GSK583, Inhibitor 7, Biaryl Urea, CSR35, CSLP37, CSLP43, RIPK2 inhibitor 1, CS6, PP2, WEHI-345, SB203580, OD36,OD38, RIPK2-IN-8, RIPK2-IN-1, or RIPK2-IN-2, or any combination thereof.

Disclosed herein, in some embodiments, are antagonists or partial antagonists of RIPK2 having a structure of Formula (I) or a pharmaceutically acceptable salt or isotopic variant thereof:

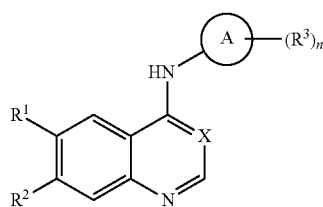

Formula (I)

wherein
Ring A is $C_{3-8}$cycloalkyl, $C_{2-9}$heterocycloalkyl, $C_{2-9}$heteroaryl, or 6- to 10-membered aryl;
X is N or $CR^4$;
$R^1$ and $R^2$ are independently —H, halogen, —OH, —$OR^5$, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$;
each $R^3$ is independently —H, halogen, —$NO_2$, —CN, —OH, —$OR^5$, —$SR^5$, —$N(R^6)_2$, —$S(O)R^5$, —$S(=O)_2$ $R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O-$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;
$R^4$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;
each $R^5$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;
each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ substituents are taken together with the nitrogen atom to which they are attached to form a 5- or 6-membered heterocycle; and
$R^7$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl; and
n is 0, 1, 2, 3, 4, or 5.

In some embodiments of a compound of Formula (I), Ring A is $C_{3-8}$cycloalkyl, $C_{2-9}$-heterocycloalkyl, $C_{2-9}$heteroaryl, or 6- to 10-membered aryl. In some embodiments of a compound of Formula (I), Ring A is $C_{3-7}$heteroaryl or 6-membered aryl. In some embodiments of a compound of Formula (I), Ring A is pyrrazolyl. In some embodiments of a compound of Formula (I), Ring A is C-heteroaryl. In some embodiments of a compound of Formula (I), Ring A is phenyl.

In some embodiments, for a compound of Formula (I), X is N or $CR^4$. In some embodiments, for a compound of Formula (I), X is N or CH. In some embodiments, for a compound of Formula (I), X is N. In some embodiments, for a compound of Formula (I), X is CH.

In some embodiments, for a compound of Formula (I), $R^1$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl—OH, —O—$C_{1-6}$alkyl-$OR^5$, —O—$C_{1-6}$alkyl-$N(R^6)_2$, or —$S(=O)_2R^5$. In some embodiments, for a compound of Formula (I), $R^1$ is $C_{1-6}$alkyl, $C_{2-6}$alkenyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (I), $R^1$ is —O—$C_{1-6}$alkyl, —O—$C_{1-6}$alkyl-$OR^5$, —O—$C_{1-6}$alkyl-$N(R^6)_2$, or —$S(=O)_2R^5$. In some embodiments, for a compound of Formula (I), $R^1$ is —O—$C_{1-6}$alkyl. In some embodiments, for a compound of Formula (I), $R^1$ is —$OCH_3$. In some embodiments, for a compound of Formula (I), $R^1$ is —O—$C_{1-6}$alkyl-$OR^5$. In some embodiments, for a compound of Formula (I), $R^1$ is —$OCH_2CH_2OCH_3$. In some embodiments, for a compound of Formula (I), $R^1$ is —O—$C_{1-6}$alkyl- $N(R^6)_2$. In some embodiments, for a compound of Formula (I), $R^1$ is —O $CH_2CH_2CH_2$morpholine. In some embodiments, for a compound of Formula (I), $R^1$ is —$S(=O)_2R^5$. In some embodiments, for a compound of Formula (I), $R^1$ is —S $(=O)_2$tert-butyl.

In some embodiments, for a compound of Formula (I), $R^2$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$allkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (I), $R^2$ is —H, —O—$C_{1-6}$alkyl, —O—$C_{1-6}$alkyl-$OR^5$, or —O—$C_{1-6}$alkyl-OH. In some embodiments, for a compound of Formula (I), $R^2$ is —H. In some embodiments, for a compound of Formula (I), $R^2$ is —O—$C_{1-6}$alkyl. In some embodiments, for a compound of Formula (I), $R^2$ is —$OCH_3$. In some embodiments, for a compound of Formula (I), $R^2$ is —O—$C_{1-6}$alkyl-$OR^5$. In some embodiments, for a compound of Formula (I), $R^2$ is —$OCH_2CH_2OCH_3$. In some embodiments, for a compound of Formula (I), $R^2$ is —O—$C_{1-6}$alkyl-OH. In some embodiments, for a compound of Formula (I), $R^2$ is —$OCH_2CH_2OH$.

In some embodiments, for a compound of Formula (I), $R^3$ is —H, halogen, —$NO_2$, —CN, —OH, —$OR^5$, —$SR^5$, —N(R⁶)₂, —S(O)R⁵, —S(=O)₂R⁵, —NR⁶S(=O)₂R⁵, —S(=O)₂N(R⁶)₂, —C(O)R⁵, —C(O)OR⁵, —OC(O)R⁵, —C(O)N(R⁶)₂, —OC(O)N(R⁶)₂, —NR⁶C(O)N(R⁶)₂, —NR⁶C(O)R⁵, —NR⁶C(O)OR⁵, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or -O-phenyl, wherein each alkyl, haloalkyl, heteroalkyl, cycloalkyl, heterocycloalkyl, aryl, and heteroaryl is optionally substituted with one or more R⁷. In some embodiments, for a compound of Formula (I), R³ is —H, halogen, $C_{1-6}$alkyl, $C_{2-6}$alkynyl, or —O-phenyl. In some embodiments, for a compound of Formula (I), R³ is —H. In some embodiments, for a compound of Formula (I), R³ is —Cl. In some embodiments, for a compound of Formula (I), R³ is —F. In some embodiments, for a compound of Formula (I), R³ is —CH₃. In some embodiments, for a compound of Formula (I), R³ is —CCH. In some embodiments, for a compound of Formula (I), R³ is —O-phenyl.

In some embodiments, for a compound of Formula (I), n is 0, 1, 2, or 3. In some embodiments, for a compound of Formula (I), n is 1, 2, or 3. In some embodiments, for a compound of Formula (I), n is 1 or 2. In some embodiments, for a compound of Formula (I), n is 0. In some embodiments, for a compound of Formula (I), n is 1. In some embodiments, for a compound of Formula (I), n is 2. In some embodiments, for a compound of Formula (I), n is 3.

Disclosed herein, in some embodiments, are antagonists or partial antagonists of RIPK2 having a structure of Formula (Ia) or a pharmaceutically acceptable salt or isotopic variant thereof:

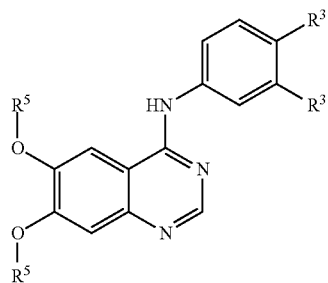

Formula (Ia)

wherein:
each R³ is independently —H, halogen, —C≡CH, or —O-aryl; and
each R⁵ is independently $C_{1-6}$alkyl, —$C_{1-6}$alkyl-O—$C_{1-6}$alkyl, or —$C_{1-6}$alkyl-heterocycloalkyl.

Disclosed herein, in some embodiments, are antagonists or partial antagonists of RIPK2 having a structure of Formula (Ia) or a pharmaceutically acceptable salt or isotopic variant thereof:

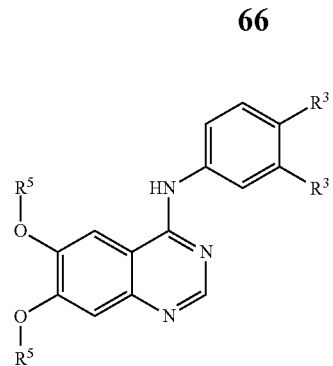

Formula (Ia)

wherein;
each R³ is independently —H, —Cl, —F, —C≡CH, or —O-phenyl; and
each R⁵ is independently —CH₃, —CH₂CH₂OCH₃, or —CH₂CH₂CH₂morpholine.

Disclosed herein, in some embodiments, are antagonists or partial antagonists of RIPK2 having a structure of Formula (Ib) or a pharmaceutically acceptable salt or isotopic variant thereof:

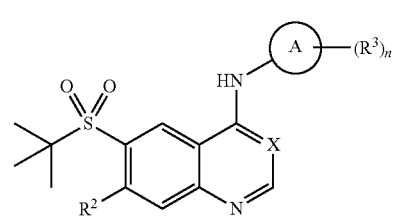

Formula (Ib)

wherein;
Ring A is $C_{3-7}$heteroaryl;
X is N or CH;
R² is —H, —OC$_{1-6}$alkyl, or —O—C$_{1-6}$alkyl-OH;
each R³ is independently —H, —C$_{1-6}$alkyl, or halogen; and
n is 0, 1, or 2.

Disclosed herein, in some embodiments, are antagonists or partial antagonists of RIPK2 having a structure of Formula (Ib) or a pharmaceutically acceptable salt or isotopic variant thereof:

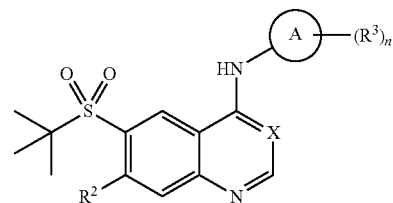

Formula (Ib)

wherein;
Ring A is $C_{3-7}$heteroaryl;
X is N or CH;
R² is —H, —OCH₃, or —OCH₂CH₂OH;
each R³ is independently —H, —CH₃, or —F; and
n is 0, 1, or 2.

In some embodiments a compound of Formula (I) or a pharmaceutically acceptable salt or isotopic variant thereof has the structure of:

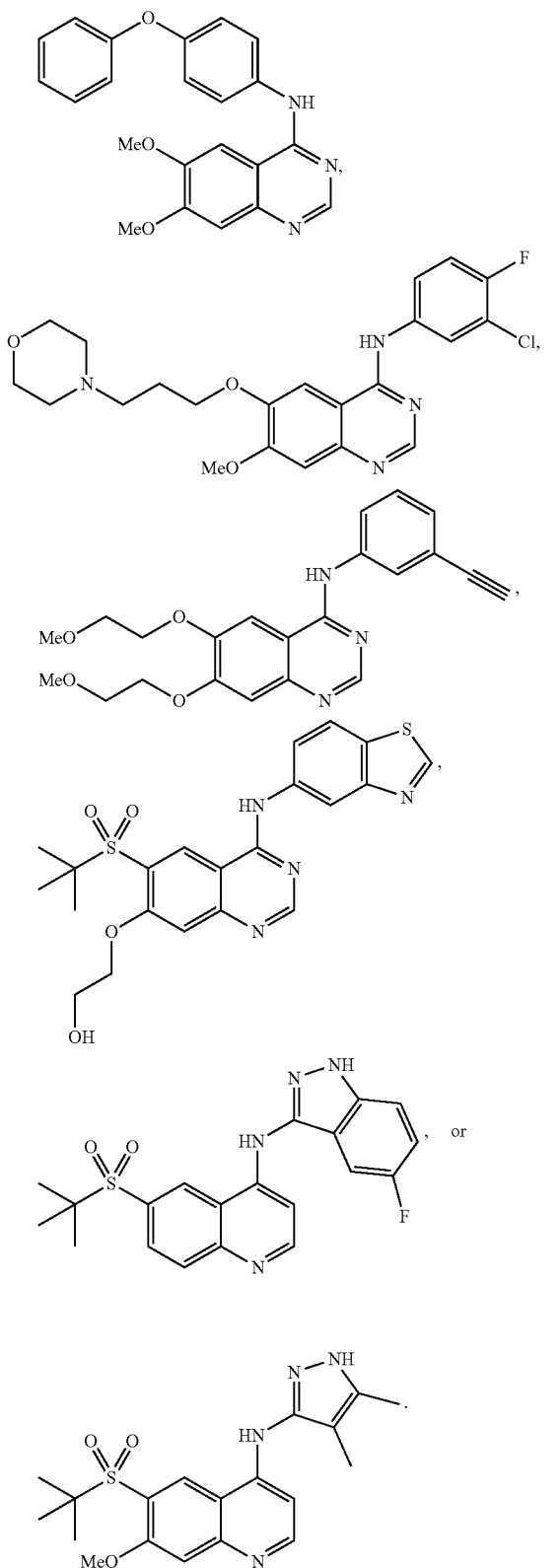

Disclosed herein, in some embodiments, are antagonists or partial antagonists of RIPK2 having a structure of Formula (II) or a pharmaceutically acceptable salt or isotopic variant thereof:

Formula (II)

wherein
Rings A and B are independently $C_{3-8}$cycloalkyl, $C_{2-9}$heterocycloalkyl, $C_{2-9}$heteroaryl, or 6- to 10-membered aryl;
$X^1$, $X^2$, and $X^3$ are independently N or $CR^4$;
$Y^1$ and $Y^2$ are independently a bond, —O—, —S—, —C$(R^5)_2$, —$NR^6$-, —$NR^6C(O)$—, —$C(O)NR^6$-, or —$NR^6C(O)NR^6$-;
each $R^1$ and $R^2$ is independently —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$SCH_2C(O)OR^5$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;
each $R^4$ is independently —H, halogen, —$N(R^6)_2$, —$NO_2$, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;
each $R^5$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;
each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or
two $R^6$ are taken together with the nitrogen atom to which they are attached to form a 5- or 6-membered heterocycle; and
$R^7$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl; and
m and n are each independently 0, 1, 2, 3, 4, or 5.
In some embodiments, for a compound of Formula (II), Rings A and B are independently $C_{3-8}$cycloalkyl, $C_{2-9}$heterocycloalkyl, $C_{2-9}$heteroaryl, or 6- to 10-membered aryl. In some embodiments, for a compound of Formula (II), Rings A and B are independently $C_{2-9}$heteroaryl or 6- to 10-membered aryl. In some embodiments, for a compound of Formula (II), Ring A is phenyl. In some embodiments, for a compound of Formula (II), Ring A is pyridyl. In some embodiments, for a compound of Formula (II), Ring A is furanyl. In some embodiments, for a compound of Formula (II), Ring B is phenyl. In some embodiments, for a compound of Formula (II), Ring B is pyrrazolyl. In some embodiments, for a compound of Formula (II), Ring B is pyridyl. In some embodiments, for a compound of Formula (II), Ring B is isoxazolyl. In some embodiments, for a compound of Formula (II), Ring A is phenyl and Ring B is pyrrazolyl. In some embodiments, for a compound of Formula (II), Ring A is phenyl and Ring B is phenyl. In some embodiments, for a compound of Formula (II), Ring A is phenyl and Ring B is pyridyl. In some embodiments, for a compound of Formula (II), Ring A is pyridyl and Ring B is phenyl. In some embodiments, for a compound of Formula (II), Ring A is pyridyl and Ring B is isoxazolyl. In some embodiments, for a compound of Formula (II), Ring A is isoxazoylyl and Ring B is pyridyl. In some embodiments, for a compound of Formula (II), Ring A is furanyl and Ring B is phenyl.

In some embodiments, for a compound of Formula (II), $X^1$, $X^2$, and $X^3$ are independently N or $CR^4$. In some embodiments, for a compound of Formula (II), $X^1$ is CH. In some embodiments, for a compound of Formula (II), $X^1$ is CF. In some embodiments, for a compound of Formula (II), $X^1$ is $CCH_3$. In some embodiments, for a compound of Formula (II), $X^1$ is $CNH_2$. In some embodiments, for a compound of Formula (II), $X^1$ is N. In some embodiments, for a compound of Formula (II), $X^2$ is CH. In some embodiments, for a compound of Formula (II), $X^2$ is CF. In some embodiments, for a compound of Formula (II), $X^2$ is N. In some embodiments, for a compound of Formula (II), $X^2$ is C—N-methylpyrazinc. In some embodiments, for a compound of Formula (II), $X^3$ is CH. In some embodiments, for a compound of Formula (II), $X^3$ is N. In some embodiments, for a compound of Formula (II), $X^1$ is CF and $X^2$ and $X^3$ are CH. In some embodiments, for a compound of Formula (II), $X^2$ is CF and $X^1$ and $X^3$ are CH. In some embodiments, for a compound of Formula (II), $X^1$, $X^2$, and $X^3$ are CH. In some embodiments, for a compound of Formula (II), $X^1$ is $CCH_3$; and $X^2$ and $X^3$ are CH. In some embodiments, for a compound of Formula (II), $X^1$ is $CNH_2$, $X^2$ is N, and $X^3$ is CH. In some embodiments, for a compound of Formula (II), $X^2$ is C—N-methylpyrazine and $X^1$ and $X^3$ are N.

In some embodiments, for a compound of Formula (II), $Y^1$ and $Y^2$ are independently a bond, —O—, —S—, —C($R^5$)$_2$, —$NR^6$-, —$NR^6$(O)—, —C(O)$NR^6$-, —NRC(O)(O)$NR^6$-. In some embodiments, for a compound of Formula (II). $Y^1$ is —$NR^6$C(O)—. In some embodiments, for a compound of Formula (II), $Y^1$ is —O—. In some embodiments, for a compound of Formula (II), $Y^1$ is —$NR^6$C(O)$NR^6$-. In some embodiments, for a compound of Formula (II), $Y^1$ is a bond. In some embodiments, for a compound of Formula (II), $Y^1$ is —$NR^6$-. In some embodiments, for a compound of Formula (II), $Y^2$ is —$NR^6$C(O)—. In some embodiments, for a compound of Formula (II), $Y^2$ is —O—. In some embodiments, for a compound of Formula (II), $Y^2$ is —$NR^6$C(O)$NR^6$-. In some embodiments, for a compound of Formula (II), $Y^2$ is a bond. In some embodiments, for a compound of Formula (II), $Y^1$ is —S—. In some embodiments, for a compound of Formula (II), $Y^1$ and $Y^2$ are —NHC(O)—. In some embodiments, for a compound of Formula (II), $Y^1$ is —O— and $Y^2$ is —NHC(O)NH—. In some embodiments, for a compound of Formula (II), $Y^1$ is —NHC(O)NH— and $Y^2$ is —O—. In some embodiments, for a compound of Formula (II), $Y^1$ and $Y^2$ are bonds. In some embodiments, for a compound of Formula (II), $Y^1$ is —NH— and $Y^2$ is —S—.

In some embodiments, for a compound of Formula (II), $R^1$ is —H, halogen, —$NO_2$, —CN, —OH, —$OR^5$, —$SR^5$, —N($R^6$)$_2$, —S(O)$R^5$, —S(=O)$_2R^5$, —$NR^6$S(=O)$_2R^5$, —S(=O)$_2$N($R^6$)$_2$, —C(O)$R^5$, —C(O)O$R^5$, —OC(O)$R^5$, —C(O)N($R^6$)$_2$, —OC(O)N($R^6$)$_2$, —$NR^6$C(O)N($R^6$)$_2$, —$NR^6$C(O)$R^5$, —$NR^6$C(O)O$R^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (II), $R^1$ is —Cl. In some embodiments, for a compound of Formula (II), $R^1$ is —F. In some embodiments, for a compound of Formula (II), $R^1$ is —C(O)NHCH$_3$. In some embodiments, for a compound of Formula (II), $R^1$ is 2-methylpyrrazolyl. In some embodiments, for a compound of Formula (II), $R^1$ is N-methylimidazolyl. In some embodiments, for a compound of Formula (II), $R^1$ is tert-butyl. In some embodiments, for a compound of Formula (II), $R^1$ is —NHC(O)cyclopropyl. In some embodiments, for a compound of Formula (II), $R^1$ is —SCH$_2$C(O)OH. In some embodiments, for a compound of Formula (II), $R^1$ is —OCH$_3$. In some embodiments, for a compound of Formula (II), $R^1$ is —NHS(=O)$_2$CH$_2$CH$_2$CH$_3$.

In some embodiments, for a compound of Formula (II), $R^2$ is —H, halogen, —$NO_2$, —CN, —OH, —$OR^5$, —$SR^5$, —N($R^6$)$_2$, —S(O)$R^5$, —S(=O)$_2R^5$, —$NR^6$S(=O)$_2R^5$, —S(=O)$_2$N($R^6$)$_2$, —C(O)$R^5$, —C(O)O$R^5$, —OC(O)$R^5$, —C(O)N($R^6$)$_2$, —OC(O)N($R^6$)$_2$, —$NR^6$C(O)N($R^6$)$_2$, —$NR^6$C(O)$R^5$, —$NR^6$C(O)O$R^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (II), $R^2$ is —Cl. In some embodiments, for a compound of Formula (II), $R^2$ is —F. In some embodiments, for a compound of Formula (II), $R^2$ is —C(O)NHCH$_3$. In some embodiments, for a compound of Formula (II), $R^1$ is 2-methylpyrrazolyl. In some embodiments, for a compound of Formula (II), $R^1$ is N-methylimidazolyl. In some embodiments, for a compound of Formula (II), $R^2$ is —CH$_2$-(2-iso-propylimidazole). In some embodiments, for a compound of Formula (II), $R^2$ is tert-butyl. In some embodiments, for a compound of Formula (II), $R^2$ is —CH$_3$. In some embodiments, for a compound of Formula (II), $R^2$ is —C(O)NHCH$_3$. In some embodiments, for a compound of Formula (II), $R^2$ is pyrazinyl.

In some embodiments, for a compound of Formula (II), m is 1 or 2. In some embodiments, for a compound of Formula (II), m is 1. In some embodiments, for a compound of Formula (II), m is 2. In some embodiments, for a compound of Formula (II), n is 1 or 2. In some embodiments, for a compound of Formula (II), n is 1. In some embodiments, for a compound of Formula (II), n is 2.

Disclosed herein, in some embodiments, are antagonists or partial antagonists of RIPK2 having a structure of Formula (IIa) or a pharmaceutically acceptable salt or isotopic variant thereof:

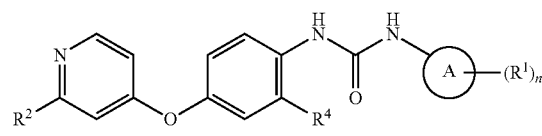

Formula (IIa)

wherein

Ring A is phenyl or isoxazolyl:

each $R^1$ is independently $C_{1-6}$alkyl, halogen, —$C_{1-6}$fluoroalkyl, or —S—$C_{1-6}$alkyl-C(O)OH:

$R^2$ is —H or —C(O)NHCH$_3$;

$R^4$ is —H or halogen; and m is 1 or 2.

Disclosed herein, in some embodiments, are antagonists or partial antagonists of RIPK2 having a structure of Formula (IIa) or a pharmaceutically acceptable salt or isotopic variant thereof:

Formula (IIa)

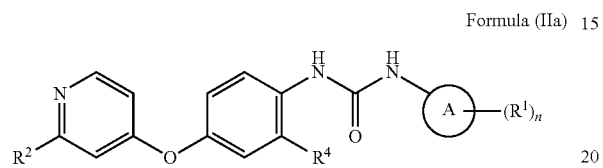

wherein

Ring A is phenyl or isoxazolyl;

each $R^1$ is independently tert-butyl, —Cl, —F, —CF$_3$, or —SCH$_2$C(O)OH;

$R^2$ is —H or —C(O)NHCH$_3$;

$R^4$ is —H or halogen; and m is 1 or 2.

Disclosed herein, in some embodiments, are antagonists or partial antagonists of RIPK2 having a structure of Formula (IIb) or a pharmaceutically acceptable salt or isotopic variant thereof:

Formula (IIb)

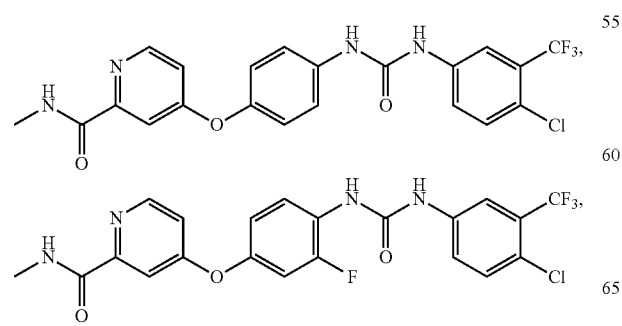

wherein $R^1$ is halogen or —OR$^5$.

In some embodiments a compound of Formula (II) or a pharmaceutically acceptable salt or isotopic variant thereof has the structure of:

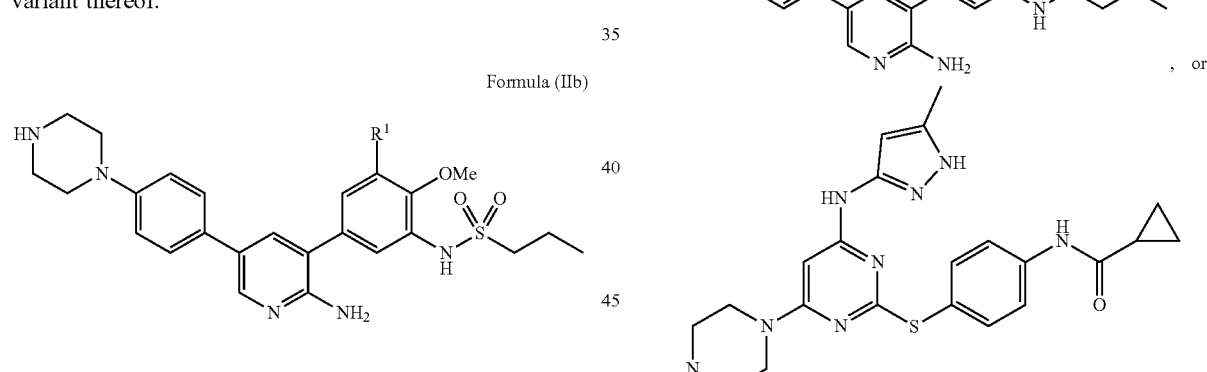

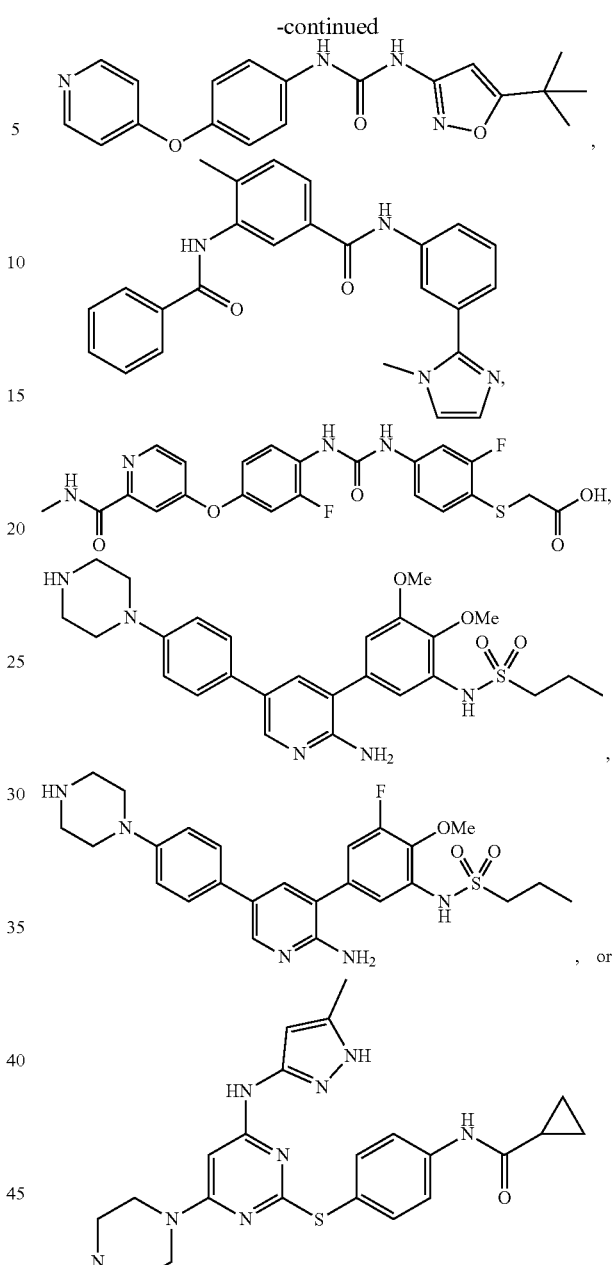

Disclosed herein, in some embodiments, are antagonists or partial antagonists of RIPK2 having a structure of Formula (III) or a pharmaceutically acceptable salt or isotopic variant thereof:

Formula (III)

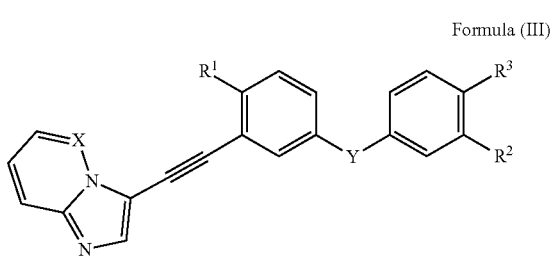

wherein

X is N or CR$^4$;

Y is a bond, —O—, —S—, —C(R$^5$)$_2$, —NR$^6$—, —NR$^6$C(O)—, —C(O)NR$^6$-, or —NR$^6$C(O)NR$^6$-;

R$^1$ is —H, halogen, —OH, —CN, —N(R$^6$)$_2$, —NR$^6$C(O) R$^5$, —C(O)OR$^5$, —C(O)N(R$^6$)$_2$, C$_{1-6}$alkyl, C$_{2-6}$alkenyl, C$_{2-6}$alkynyl, C$_{3-8}$cycloalkyl, —C$_{1-6}$alkyl-OH, —C$_{1-6}$alkyl-OR$^5$, —C$_{1-6}$alkyl-N(R$^6$)$_2$, —O—C$_{1-6}$alkyl, —O—C$_{1-6}$alkyl-OH, —O—C$_{1-6}$alkyl-OR$^5$, —O—C$_{1-6}$alkyl-N (R$^6$)$_2$, or —S(=O)$_2$R$^5$;

R$^2$ and R$^3$ are independently —H, halogen, —NO$_2$, —CN, —OH, —OR$^5$, —SR$^5$, —N(R$^6$)$_2$, —S(O)R$^5$, —S(=O)$_2$R$^5$, —NR$^6$S(=O)$_2$R$^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, C$_{1-6}$alkyl, C$_{2-6}$alkenyl, C$_{2-6}$alkynyl, C$_{1-6}$haloalkyl, C$_{1-6}$heteroalkyl, —O—C$_{1-6}$alkyl, C$_{3-8}$cycloalkyl, C$_{2-9}$heterocycloalkyl, C$_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R$^7$; or R$^2$ and R$^3$ are taken together with the atoms to which they are attached to form an optionally substituted C$_{3-8}$cycloalkyl; and R$^4$ is hydrogen, halogen, —N(R$^6$)$_2$, —NO$_2$, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, or —C$_{1-6}$alkyl-C$_{2-9}$heteroaryl, wherein the alkyl, haloalkyl, cycloalkyl, phenyl, heteroaryl, and heterocycloalkyl are optionally substituted;

R$^5$ is —H, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, or —C$_{1-6}$alkyl-C$_{2-9}$heteroaryl;

each R$^6$ is independently —H, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, or C$_{2-9}$heteroaryl; or two R$^6$ substituents are taken together with the nitrogen atom to which they are attached to form a 5- or 6-membered heterocycle; and R$^7$ is —H, halogen, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, or —C$_{1-6}$alkyl-C$_{2-9}$heteroaryl.

In some embodiments, for a compound of Formula (III), X is N or CR$^4$. In some embodiments, for a compound of Formula (III), X is N and CH. In some embodiments, for a compound of Formula (III), X is N. In some embodiments, for a compound of Formula (III), X is CH.

In some embodiments, for a compound of Formula (III), Y is a bond, —O—, —S—, —C(R$^5$)$_2$, —NR$^6$-, —NR$^6$C(O)—, —C(O)NR$^6$-, or —NR$^6$C(O)NR$^6$-. In some embodiments, for a compound of Formula (III), Y is —NR$^6$C(O)— or —C(O)NR$^6$-. In some embodiments, for a compound of Formula (III), Y is —NHC(O)—. In some embodiments, for a compound of Formula (III), Y is —C(O)NH—.

In some embodiments, for a compound of Formula (III), R$^1$ is —H, halogen, —OH, —CN, —N(R$^6$)$_2$, —NR$^6$C(O) R$^5$, —C(O)OR$^5$, —C(O)N(R$^6$)$_2$, C$_{1-6}$alkyl, C$_{2-6}$alkenyl, C$_{2-6}$alkynyl, C$_{3-8}$cycloalkyl, —C$_{1-6}$alkyl-OH, —C$_{1-6}$alkyl-OR$^5$, —C$_{1-6}$alkyl-N(R$^6$)$_2$, —O—C$_{1-6}$alkyl, —O—C$_{1-6}$alkyl-OH, —O—C$_{1-6}$alkyl-OR$^5$, —O—C$_{1-6}$alkyl-N(R$^6$)$_2$, or —S(=O)$_2$R$^5$. In some embodiments, for a compound of Formula (III), R$^1$ is —H, halogen, —OH, —CN, —N(R$^6$)$_2$, C$_{1-6}$alkyl, C$_{2-6}$alkynyl, or C$_{3-8}$cycloalkyl. In some embodiments, for a compound of Formula (III), R$^1$ is C$_{1-6}$alkyl. In some embodiments, for a compound of Formula (III), R$^1$ is —CH$_3$. In some embodiments, for a compound of Formula (III), R$^1$ is tert-butyl.

In some embodiments, for a compound of Formula (III), R$^2$ is —H, halogen, —NO$_2$, —CN, —OH, —OR$^5$, —SR$^5$, —N(R$^6$)$_2$, —S(O)R$^5$, —S(=O)$_2$R$^5$, —NR$^6$S(=O)$_2$R$^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, C$_{1-6}$alkyl, C$_{2-6}$alkenyl, C$_{2-6}$alkynyl, C$_{1-6}$haloalkyl, C$_{1-6}$heteroalkyl, —O—C$_{1-6}$alkyl, C$_{3-8}$cycloalkyl, C$_{2-9}$heterocycloalkyl, C$_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R$^7$, or R$^2$ and R$^3$ are taken together with the atoms to which they are attached to form an optionally substituted C$_{3-8}$cycloalkyl. In some embodiments, for a compound of Formula (III), R$^2$ is —H, halogen, —NO$_2$, —CN, —OH, —OR$^5$, C$_{1-6}$alkyl, C$_{1-6}$haloalkyl, C$_{1-6}$heteroalkyl, C$_{3-8}$cycloalkyl, C$_{2-9}$heterocycloalkyl, C$_{2-9}$heteroaryl, or 6- to 10-membered aryl, or R$^2$ and R$^3$ are taken together with the atoms to which they are attached to form an optionally substituted C$_{3-8}$cycloalkyl. In some embodiments, for a compound of Formula (III), R$^2$ is C$_{1-6}$alkyl, C$_{1-6}$haloalkyl, or C$_{3-8}$cycloalkyl, or R$^2$ and R$^3$ are taken together with the atoms to which they are attached to form an optionally substituted C$_{3-8}$cycloalkyl. In some embodiments, for a compound of Formula (III), R$^2$ is —CH$_3$, —CF$_3$, or cyclopropyl, or R$^2$ and R$^3$ are taken together with the atoms to which they are attached to form an optionally substituted C$_{3-8}$cycloalkyl. In some embodiments, for a compound of Formula (III), R$^2$ is —CH$_3$, —CF$_3$, or cyclopropyl. In some embodiments, for a compound of Formula (III), R$^2$ is —CH$_3$. In some embodiments, for a compound of Formula (III), R$^2$ is —CF$_3$. In some embodiments, for a compound of Formula (III), R$^2$ is cyclopropyl. In some embodiments, for a compound of Formula (III), R$^2$ and R$^3$ are taken together with the atoms to which they are attached to form a C$_5$ cycloalkyl. In some embodiments, for a compound of Formula (III), R$^2$ and R$^3$ are taken together with the atoms to which they are attached to form a C$_5$ cycloalkyl substituted with an N-methylpiperazine.

In some embodiments, for a compound of Formula (III), R$^3$ is —H, halogen, —NO$_2$, —CN, —OH, —OR$^5$, —SR$^5$, —N(R$^6$)$_2$, —S(O)R$^5$, —S(=O)$_2$R$^5$, —NR$^6$S(=O)$_2$R$^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$(O)R$^5$, —NR$^6$C(O)OR$^5$, C$_{1-6}$alkyl, C$_{2-6}$alkenyl, C$_{2-6}$alkynyl, C$_{1-6}$haloalkyl, C$_{1-6}$heteroalkyl, —O—C$_{1-6}$alkyl, C$_{3-8}$cycloalkyl, C$_{2-9}$heterocycloalkyl, C$_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R$^7$, or R$^2$ and R$^3$ are taken together with the atoms to which they are attached to form an optionally substituted C$_{3-8}$cycloalkyl. In some embodiments, for a compound of Formula (III), R$^3$ is —H, halogen, —CN, —OR$^5$, —N(R$^6$)$_2$, —S(=O)$_2$R$^5$, —C(O)R$^5$, —C(O)OR$^5$, —NR$^6$C(O)N(R$^6$)$_2$, —NR$^6$C(O) R$^5$, —NR$^6$C(O)OR$^5$, C$_{1-6}$alkyl, C$_{1-6}$heteroalkyl, C$_{2-9}$heterocycloalkyl, or C$_{2-9}$heteroaryl, wherein each alkyl, heteroalkyl, heterocycloalkyl, and heteroaryl is optionally substituted with one or more R$^7$, or R$^2$ and R$^3$ are taken together with the atoms to which they are attached to form an optionally substituted C$_{3-8}$cycloalkyl. In some embodiments, for a compound of Formula (III), R³ is C₁₋₆alkyl substituted with C₂₋₉heterocycloalkyl. In some embodiments, for a compound of Formula (III), R³ is CH₂—N—methylpiperazine. In some embodiments, for a compound of Formula (III), R² and R³ are taken together with the atoms to which they are attached to form a C₅ cycloalkyl. In some embodiments, for a compound of Formula (III), R² and R³ are taken together with the atoms to which they are attached to form a C₅ cycloalkyl substituted with an N-methylpiperazine.

Disclosed herein, in some embodiments, are antagonists or partial antagonists of RIPK2 having a structure of Formula (III) or a pharmaceutically acceptable salt or isotopic variant thereof:

Formula (III)

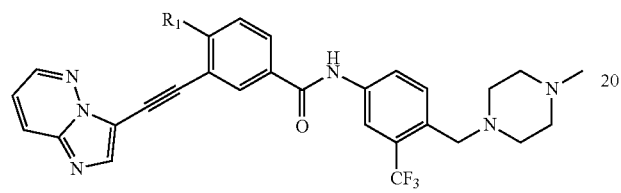

wherein
R¹ is C₁₋₆alkyl.

In some embodiments a compound of Formula (III) or a pharmaceutically acceptable salt or isotopic variant thereof has the structure of:

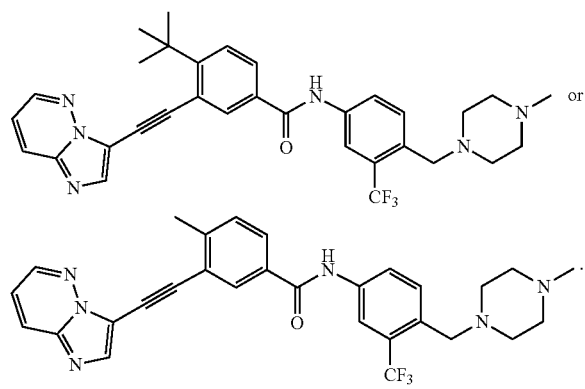

Disclosed herein, in some embodiments, are antagonists or partial antagonists of RIPK2 having a structure of Formula (IV) or a pharmaceutically acceptable salt or isotopic variant thereof:

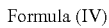

Formula (IV)

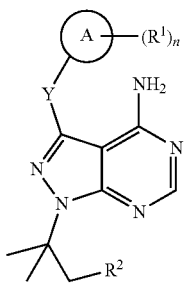

wherein
Ring A is C₃₋₈cycloalkyl, C₂₋₉heterocycloalkyl, C₂₋₉heteroaryl, or 6- to 10-membered aryl;
Y is a bond, —O—, —S—, —C(R⁵)₂-, —NR⁶-, —NR⁶C(O)—, —C(O)NR⁶-, or —NR⁶C(O)NR⁶-;
R¹ is —H, halogen, —OH, —CN, —N(R⁶)₂, —NR⁶C(O)R⁵, —C(O)OR⁵, —C(O)N(R⁶)₂, C₁₋₆alkyl, C₂₋₆alkenyl, C₂₋₆alkynyl, C₃₋₈cycloalkyl, —C₁₋₆alkyl-OH, —C₁₋₆alkyl-OR⁵, —C₁₋₆alkyl-N(R⁶)₂, —O—C₁₋₆alkyl, —O—C₁₋₆alkyl-OH, —O—C₁₋₆alkyl-OR⁵, —O—C₁₋₆alkyl-N(R⁶)₂, or —S(=O)₂R⁵;
R² is —H, halogen, —NO₂, —CN, —OH, —OR⁵, —SR⁵, —N(R⁶)₂, —S(O)R⁵, —S(=O)₂R⁵, —NR⁶S(=O)₂R⁵, —S(=O)₂N(R⁶)₂, —C(O)R⁵, —C(O)OR⁵, —OC(O)R⁵, —C(O)N(R⁶)₂, —OC(O)N(R⁶)₂, —NR⁶C(O)N(R⁶)₂, —NR⁶C(O)R⁵, —NR⁶C(O)OR⁵, C₁₋₆alkyl, C₂₋₆alkenyl, C₂₋₆alkynyl, C₁₋₆haloalkyl, C₁₋₆heteroalkyl, —O—C₁₋₆alkyl, C₃₋₈cycloalkyl, C₂₋₉heterocycloalkyl, C₂₋₉heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R⁷;
R⁵ is —H, C₁₋₆alkyl, C₂₋₆alkenyl, C₂₋₆alkynyl, C₁₋₆haloalkyl, C₃₋₈cycloalkyl, —C₁₋₆alkyl-C₃₋₈cycloalkyl, phenyl, —C₁₋₆alkyl-phenyl, C₂₋₉heterocycloalkyl, —C₁₋₆alkyl-C₂₋₉heterocycloalkyl, C₂₋₉heteroaryl, or —C₁₋₆alkyl-C₂₋₉heteroaryl;
each R⁶ is independently —H, C₁₋₆alkyl, C₂₋₆alkenyl, C₂₋₆alkynyl, C₁₋₆haloalkyl, C₃₋₈cycloalkyl, —C₁₋₆alkyl-C₃₋₈cycloalkyl, phenyl, —C₁₋₆alkyl-phenyl, or C₂₋₉heteroaryl; or
two R⁶ substituents are taken together with the nitrogen atom to which they are attached to form a 5- or 6-membered heterocycle;
R⁷ is —H, halogen, C₁₋₆alkyl, C₂₋₆alkenyl, C₂₋₆alkynyl, C₁₋₆haloalkyl, C₃₋₈cycloalkyl, —C₁₋₆alkyl-C₃₋₈cycloalkyl, phenyl, —C₁₋₆alkyl-phenyl, C₂₋₉heterocycloalkyl, —C₁₋₆alkyl-C₂₋₉heterocycloalkyl, C₂₋₉heteroaryl, or —C₁₋₆alkyl-C₂₋₉heteroaryl; and
n is 0, 1, 2, 3, 4, or 5.

In some embodiments, for a compound of Formula (IV), Ring A is C₃₋₈cycloalkyl, C₂₋₉heterocycloalkyl, C₂₋₉heteroaryl, or 6- to 10-membered aryl. In some embodiments, for a compound of Formula (IV), Ring A is 6- to 10-membered aryl. In some embodiments, for a compound of Formula (IV), Ring A is phenyl. In some embodiments, for a compound of Formula (IV), Ring A is naphthyl.

In some embodiments, for a compound of Formula (IV), Y is a bond, —O—, —S—, —C(R⁵)₂-, —NR⁶-, —NR⁶C(O)—, —C(O)NR⁶-, or —NR⁶C(O)NR⁶-. In some embodiments, for a compound of Formula (IV), Y is a bond or —C(R⁵)₂-. In some embodiments, for a compound of Formula (IV), Y is a bond. In some embodiments, for a compound of Formula (IV), Y is —CH₂-.

In some embodiments, for a compound of Formula (IV), R¹ is —H, halogen, —OH, —CN, —N(R⁶)₂, —NR⁶C(O)R⁵, —C(O)OR⁵, —C(O)N(R⁶)₂, C₁₋₆alkyl, C₂₋₆alkenyl, C₂₋₆alkynyl, C₃₋₈cycloalkyl, —C₁₋₆alkyl-OH, —C₁₋₆alkyl-OR⁵, —C₁₋₆alkyl-N(R⁶)₂, —O—C₁₋₆alkyl, —O—C₁₋₆alkyl-OH, —O—C₁₋₆alkyl-OR⁵, —O—C₁₋₆alkyl-N(R⁶)₂, or —S(=O)₂R⁵. In some embodiments, for a compound of Formula (IV), R¹ is —H, halogen, or C₁₋₆alkyl. In some embodiments, for a compound of Formula (IV), R¹ is —H, —Cl, or CH₃. In some embodiments, for a compound of Formula (IV), R¹ is —H. In some embodiments, for a compound of Formula (IV), R¹ is —Cl. In some embodiments, for a compound of Formula (IV), R¹ is —CH₃.

In some embodiments, for a compound of Formula (IV), $R^2$ is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (IV), $R^2$ is —H or —$NR^6C(O)R^5$. In some embodiments, for a compound of Formula (IV), $R^2$ is —H or —$NR^6C(O)C_{2-9}$heteroaryl. In some embodiments, for a compound of Formula (IV), $R^2$ is —H. In some embodiments, for a compound of Formula (IV), $R^2$ is —NHC(O)pyridyl.

In some embodiments, for a compound of Formula (IV), n is 1, 2, or 3. In some embodiments, for a compound of Formula (IV), n is 1 or 2. In some embodiments, for a compound of Formula (IV), n is 1. In some embodiments, for a compound of Formula (IV), n is 2. In some embodiments, for a compound of Formula (IV), n is 3.

Disclosed herein, in some embodiments, are antagonists or partial antagonists of RIPK2 having a structure of Formula (IVa) or a pharmaceutically acceptable salt or isotopic variant thereof:

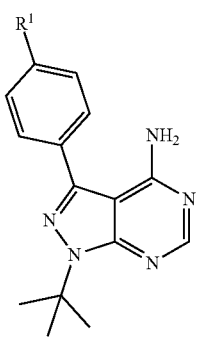

Formula (IVa)

wherein
$R^1$ is halogen or $C_{1-6}$alkyl.

Disclosed herein, in some embodiments, are antagonists or partial antagonists of RIPK2 having a structure of Formula (IVb) or a pharmaceutically acceptable salt or isotopic variant thereof:

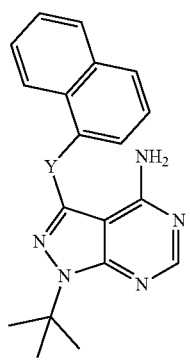

Formula (IVb)

wherein Y is a bond or —$C_{1-3}$alkyl-.

Disclosed herein, in some embodiments, are antagonists or partial antagonists of RIPK2 having a structure of Formula (IVb) or a pharmaceutically acceptable salt or isotopic variant thereof:

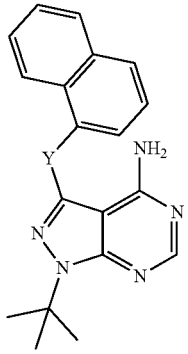

Formula (IVb)

wherein
Y is a bond or —$CH_2$—.

In some embodiments a compound of Formula (IV) or a pharmaceutically acceptable salt or isotopic variant thereof has the structure of:

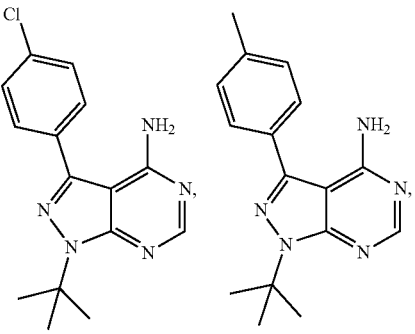

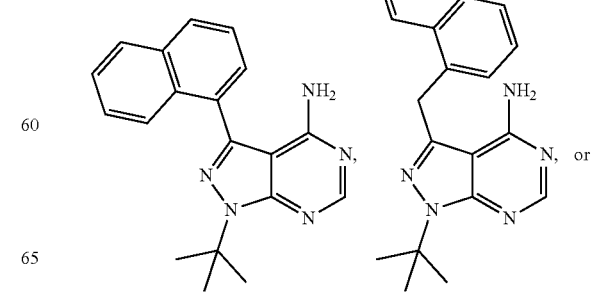

-continued

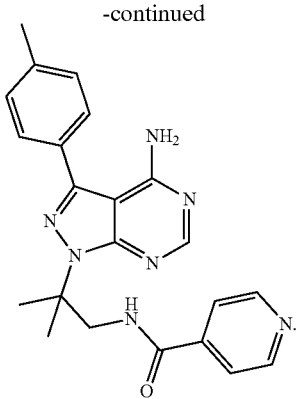

Disclosed herein, in some embodiments, are antagonists or partial antagonists of RIPK2 having a structure of Formula (V) or a pharmaceutically acceptable salt or isotopic variant thereof:

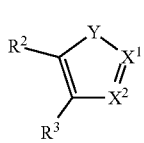

Formula (V)

wherein
$X^1$ and $X^2$ are independently N or $CR^4$;
Y is S, O, or $NR^1$;
$R^1$ is —H, —S(=O)$_2R^5$, —S(=O)$_2N(R^6)_2$, —C(O)$R^5$, —C(O)O$R^5$, —C(O)N(R^6)_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, $C_{2-9}$heterocycloalkyl, $C_{2-9}$heteroaryl, or 6- to 10-membered aryl, wherein each alkyl, haloalkyl, heteroalkyl, cycloalkyl, heterocycloalkyl, aryl, and heteroaryl is optionally substituted with one or more $R^7$;
$R^2$ is —H, halogen, —NO$_2$, —CN, —OH, —OR$^5$, —SR$^5$, —N(R$^6$)$_2$, —S(O)R$^5$, —S(=O)$_2R^5$, —NR$^6$S(=O)$_2R^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$; or
$R^1$ and $R^2$ are taken together with the atoms to which they are attached to form an optionally substituted $C_{3-8}$heterocycloalkyl; and
$R^3$ and $R^4$ are independently —H, halogen, —NO$_2$, —CN, —OH, —OR$^5$, —SR$^5$, —N(R$^6$)$_2$, —S(O)R$^5$, —S(=O)$_2R^5$, —NR$^6$S(=O)$_2R^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$:

$R^5$ is —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;
each $R^6$ is independently –H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or
two $R^6$ substituents are taken together with the nitrogen atom to which they are attached to form a 5- or 6-membered heterocycle; and
$R^7$ is —H, halogen, —S(=O)CH$_3$, —N(R$^6$)$_2$, —C(O)N(R$^6$)$_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl.

In some embodiments, for a compound of Formula (V), $X^1$ and $X^2$ are independently N or $CR^4$. In some embodiments, for a compound of Formula (V), $X^1$ is N. In some embodiments, for a compound of Formula (V), $X^1$ is $CR^4$. In some embodiments, for a compound of Formula (V), $X^2$ is N. In some embodiments, for a compound of Formula (V), $X^2$ is $CR^4$. In some embodiments, for a compound of Formula (V), $X^1$ is N and $X^2$ is $CR^4$. In some embodiments, for a compound of Formula (V), $X^1$ is $CR^4$ and $X^2$ is N.

In some embodiments, for a compound of Formula (V), Y is S, O, or $NR^1$. In some embodiments, for a compound of Formula (V), Y is S. In some embodiments, for a compound of Formula (V), Y is NH. In some embodiments, for a compound of Formula (V), Y is $NR^1$.

In some embodiments, for a compound of Formula (V), $R^1$ is —H, —S(=O)$_2R^5$, —S(=O)$_2N(R^6)_2$, —C(O)$R^5$, —C(O)O$R^5$, —C(O)N(R^6)_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, $C_{2-9}$heterocycloalkyl, $C_{2-9}$heteroaryl, or 6- to 10-membered aryl, wherein each alkyl, haloalkyl, heteroalkyl, cycloalkyl, heterocycloalkyl, aryl, and heteroaryl is optionally substituted with one or more $R^7$. In some embodiments, for a compound of Formula (V), $R^1$ is —H, $C_{1-6}$alkyl, $C_{3-8}$cycloalkyl, $C_{2-9}$heterocycloalkyl, $C_{2-9}$heteroaryl, or 6- to 10-membered aryl, wherein each cycloalkyl, heterocycloalkyl, aryl, and heteroaryl is optionally substituted with one or more $R^7$. In some embodiments, for a compound of Formula (V), $R^1$ is aryl optionally substituted with one or more $R^7$. In some embodiments, for a compound of Formula (V), $R^1$ is 2,4-dichlorophenyl.

In some embodiments, for a compound of Formula (V), $R^2$ is —H, halogen, —NO$_2$, —CN, —OH, —OR$^5$, —SR$^5$, —N(R$^6$)$_2$, —S(O)R$^5$, —S(=O)$_2R^5$, —NR$^6$S(=O)$_2R^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$, or $R^1$ and $R^2$ are taken together with the atoms to which they are attached to form an optionally substituted $C_{3-8}$heterocycloalkyl. In some embodiments, for a compound of Formula (V), $R^2$ is —H, halogen, —S(=O)$_2R^5$, —NR$^6$S(=O)$_2R^5$, —S(=O)$_2$N(R$^6$)$_2$, —C(O)R$^5$, —C(O)N(R$^6$)$_2$, $C_{1-6}$alkyl, $C_{2-6}$alkenyl, $C_{2-6}$alkynyl, $C_{3-8}$cycloalkyl, $C_{2-9}$heterocycloalkyl, $C_{2-9}$heteroaryl, 6- to 10-membered aryl, or —O-phenyl, wherein each alkyl, cycloalkyl, heterocycloalkyl, aryl, and heteroaryl is optionally substituted with one or more R⁷, or R¹ and R² are taken together with the atoms to which they are attached to form an optionally substituted C₃₋₈heterocycloalkyl. In some embodiments, for a compound of Formula (V), R² is —C(O)N(R⁶)₂ or 6-membered aryl optionally substituted with one or more R⁷. In some embodiments, for a compound of Formula (V), R² is 4-fluorophenyl. In some embodiments, for a compound of Formula (V), R² is 4-chlorophenyl. In some embodiments, for a compound of Formula (V), R² is 2-methylpyridinyl. In some embodiments, for a compound of Formula (V), R² is —C(O)NH—(2-methyl-6-chlorophenyl). In some embodiments, for a compound of Formula (V), R¹ and R² are taken together with the atoms to which they are attached to form an optionally substituted C₃₋₈heterocycloalkyl. In some embodiments, for a compound of Formula (V), R¹ and R² are taken together with the atoms to which they are attached to form a C₅ heterocycloalkyl.

In some embodiments, for a compound of Formula (V), R³ is —H, halogen, —NO₂, —CN, —OH, —OR⁵, —SR⁵, —N(R⁶)₂, —S(O)R⁵, —S(=O)₂R⁵, —NR⁶S(=O)₂R⁵, —S(=O)₂N(R⁶)₂, —C(O)R⁵, —C(O)OR⁵, OC(O)R⁵, —C(O)N(R⁶)₂, —OC(O)N(R⁶)₂—NR⁶C(O)N(R⁶)₂, —NR⁶C(O)R⁵, —NR⁶C(O)OR⁵, C₁₋₆alkyl, C₂₋₆alkenyl, C₂₋₆alkynyl, C₁₋₆haloalkyl, C₁₋₆heteroalkyl, —O—C₁₋₆alkyl, C₃₋₈cycloalkyl, C₂₋₉heterocycloalkyl, C₂₋₉heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R⁷. In some embodiments, for a compound of Formula (V), R³ is —H, C₁₋₆alkyl, C₂₋₆alkenyl, C₂₋₆alkynyl, C₁₋₆haloalkyl, C₁₋₆heteroalkyl, —O—C₁₋₆alkyl, C₃₋₈cycloalkyl, C₂₋₉heterocycloalkyl, C₂₋₉heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R⁷. In some embodiments, for a compound of Formula (V), R³ is —H or C₂₋₉heteroaryl optionally substituted with one or more R⁷. In some embodiments, for a compound of Formula (V), R³ is H. In some embodiments, for a compound of Formula (V), R³ is C₂₋₉heteroaryl optionally substituted with one or more R⁷. In some embodiments, for a compound of Formula (V), R³ is optionally substituted pyridinyl. In some embodiments, for a compound of Formula (V), R³ is optionally substituted quinolinyl. In some embodiments, for a compound of Formula (V), R³ is optionally substituted [1,2,4] triazolopyridinyl.

In some embodiments, for a compound of Formula (V), R⁴ is —H, halogen, —NO₂, —CN, —OH, —OR⁵, —SR⁵, —N(R⁶)₂, —S(O)R⁵, —S(=O)₂R⁵, —NR⁶S(=O)₂R⁵, —S(=O)₂N(R⁶)₂, —C(O)R⁵, —C(O)OR⁵, —OC(O)R⁵, —C(O)N(R⁶)₂, —OC(O)N(R⁶)₂, —NR⁶C(O)N(R⁶)₂, —NR⁶C(O)R⁵, —NR⁶C(O)OR⁵, C₁₋₆alkyl, C₂₋₆alkenyl, C₂₋₆alkynyl, C₁₋₆haloalkyl, C₁₋₆heteroalkyl, —O-C₁₋₆alkyl, C₃₋₈cycloalkyl, C₂₋₉heterocycloalkyl, C₂₋₉heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R⁷. In some embodiments, for a compound of Formula (V), R⁴ is —H, —N(R⁶)₂, —C(O)R⁵, —C(O)OR⁵, —OC(O)R⁵, —C(O)N(R⁶)₂, —OC(O)N(R⁶)₂, C₁₋₆alkyl, C₂₋₆alkenyl, C₂₋₆alkynyl, C₁₋₆haloalkyl, C₁₋₆heteroalkyl, —O-C₁₋₆alkyl, C₃₋₈cycloalkyl, C₂₋₉heterocycloalkyl, C₂₋₉heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R⁷. In some embodiments, for a compound of Formula (V), R⁴ is —N(R⁶)₂, C₁₋₆alkyl, C₂₋₉heteroaryl, or 6- to 10-membered aryl, wherein each aryl and heteroaryl is optionally substituted with one or more R⁷. In some embodiments, for a compound of Formula (V), R⁴ is optionally substituted phenyl. In some embodiments, for a compound of Formula (V), R⁴ is optionally substituted pyridyl. In some embodiments, for a compound of Formula (V), R⁴ is —NHpyrimidine. In some embodiments, for a compound of Formula (V), R⁴ is —CH₂phenyl. In some embodiments, for a compound of Formula (V), R⁴ is CH₂NHphenyl.

In some embodiments a compound of Formula (V) or a pharmaceutically acceptable salt or isotopic variant thereof has the structure of:

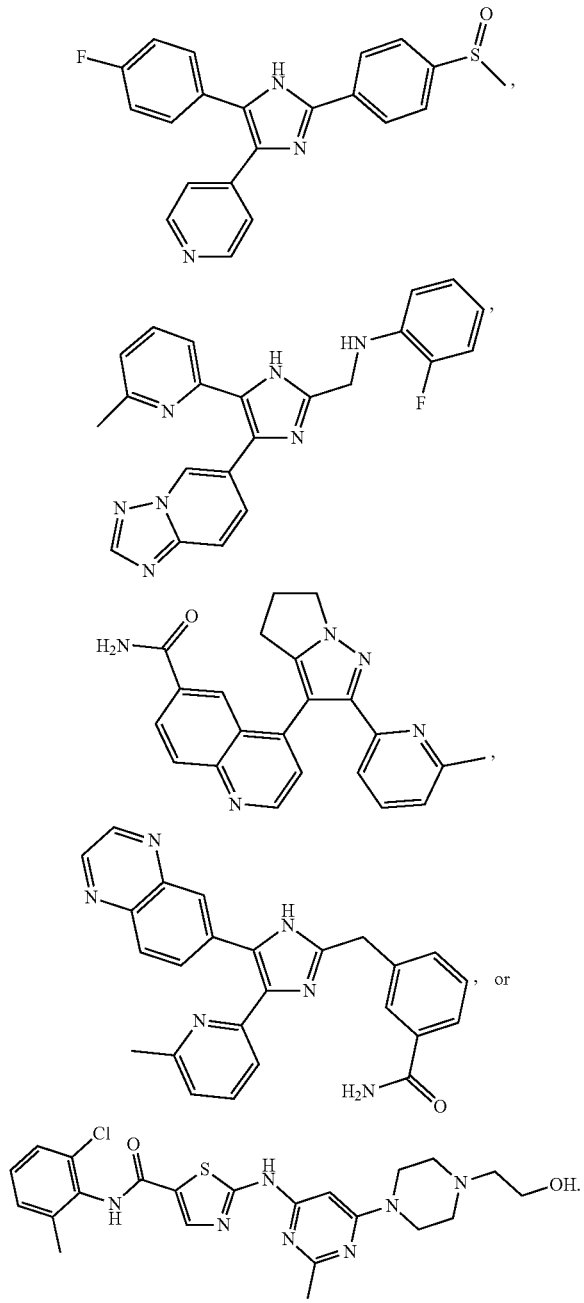

Disclosed herein, in some embodiments, are antagonists or partial antagonists of RIPK2 having a structure of Formula (VI) or a pharmaceutically acceptable salt or isotopic variant thereof:

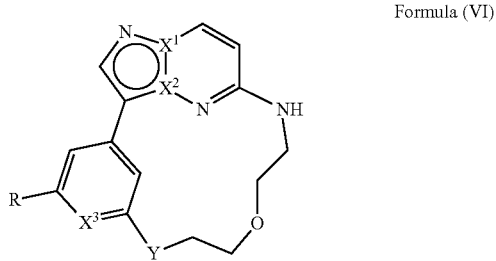

Formula (VI)

wherein
$X^1$ and $X^2$ are independently N or C:
$X^3$ is N or $CR^4$;
Y is a bond, —O—, —S—, —C($R^5$)$_2$, —$NR^6$—, —$NR^6$C(O)—, —C(O)$NR^6$—, or —$NR^6$C(O)$NR^6$—;
R is —H, halogen, —NO$_2$, —CN, —OH, —OR$^5$, —SR$^5$, —N(R$^6$)$_2$, —S(O)R$^5$, —S(=O)$_2$R$^5$, —NR$^6$S(=O)$_2$R$^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, C$_{1-6}$alkyl, C$_{2-6}$alkenyl, C$_{2-6}$alkynyl, C$_{1-6}$haloalkyl, C$_{1-6}$heteroalkyl, —O—C$_{1-6}$alkyl, C$_{3-8}$cycloalkyl, C$_{2-9}$heterocycloalkyl, C$_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R$^7$;
R$^4$ is —H, halogen, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, or —C$_{1-6}$alkyl-C$_{2-9}$heteroaryl, wherein the alkyl, haloalkyl, cycloalkyl, phenyl, heteroaryl, and heterocycloalkyl are optionally substituted;
R$^5$ is —H, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, or —C$_{1-6}$alkyl-C$_{2-9}$heteroaryl;
each R$^6$ is independently —H, C$_{1-6}$alkyl, C$_{2-6}$alkenyl, C$_{2-6}$alkynyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, orC$_{2-9}$heteroaryl; or
two R$^6$ are taken together with the nitrogen atom to which they are attached to form a 5- or 6-membered heterocycle; and
R$^7$ is —H, halogen, —S(=O)CH$_3$, —N(R$^6$)$_2$, —C(O)N(R$^6$)$_2$, C$_{1-6}$alkyl, C$_{2-6}$alkenyl, C$_{2-6}$alkynyl, C$_{1-6}$haloalkyl, C$_{1-6}$heteroalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, or —C$_{1-6}$alkyl-C$_{2-9}$heteroaryl.

In some embodiments, for a compound of Formula (VII), $X^1$ and $X^2$ are independently N or C. In some embodiments, for a compound of Formula (VII), $X^1$ is N. In some embodiments, for a compound of Formula (VII), $X^1$ is C. In some embodiments, for a compound of Formula (VII), $X^2$ is N. In some embodiments, for a compound of Formula (VII), $X^2$ is C. In some embodiments, for a compound of Formula (VII), $X^1$ is N and $X^2$ is C. In some embodiments, for a compound of Formula (VII), $X^1$ is C and $X^2$ is N.

In some embodiments, for a compound of Formula (VII), $X^3$ is N or $CR^4$. In some embodiments, for a compound of Formula (VII), $X^3$ is N or CH. In some embodiments, for a compound of Formula (VII), $X^3$ is N. In some embodiments, for a compound of Formula (VII), $X^3$ is CH.

In some embodiments, for a compound of Formula (VI), Y is a bond, —O—, —S—, —C(R$^5$)$_2$, —NR$^6$—, —NR$^6$C(O)—, —C(O)NR$^6$—, or —NR$^6$C(O)NR$^6$—. In some embodiments, for a compound of Formula (VI), Y is —O— or —NR$^6$—. In some embodiments, for a compound of Formula (VI), Y is —O— or —NH—. In some embodiments, for a compound of Formula (VI), Y is —O—. In some embodiments, for a compound of Formula (VI), Y is —NH—.

In some embodiments, for a compound of Formula (VI), R is —H, halogen, —NO$_2$, —CN, —OH, —OR$^5$, —SR$^5$, —N(R$^6$)$_2$, —S(O)R$^5$, —S(=O)$_2$R$^5$, —NR$^6$S(=O)$_2$R$^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, —NR$^6$C(O)N(R$^6$)$_2$, —NR$^6$C(O)R$^5$, —NR$^6$C(O)OR$^5$, C$_{1-6}$alkyl, C$_{2-6}$alkenyl, C$_{2-6}$alkynyl, C$_{1-6}$haloalkyl, C$_{1-6}$heteroalkyl, —O—C$_{1-6}$alkyl, C$_{3-8}$cycloalkyl, C$_{2-9}$heterocycloalkyl, C$_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more R$^7$. In some embodiments, for a compound of Formula (VI), R is —H, halogen, —S(=O)$_2$R$^5$, —NR$^6$S(=O)$_2$R$^5$, —S(=O)$_2$N(R$^6$)$_2$, —C(O)R$^5$, —C(O)OR$^5$, —OC(O)R$^5$, —C(O)N(R$^6$)$_2$, —OC(O)N(R$^6$)$_2$, C$_{1-6}$alkyl, C$_{2-6}$alkenyl, C$_{1-6}$heteroalkyl, C$_{3-8}$cycloalkyl, C$_{2-9}$heterocycloalkyl, C$_{2-9}$heteroaryl, 6- to 10-membered aryl, or —O-phenyl, wherein each alkyl, heteroalkyl, cycloalkyl, heterocycloalkyl, aryl, and heteroaryl is optionally substituted with one or more R$^7$. In some embodiments, for a compound of Formula (VI), R is —H or halogen. In some embodiments, for a compound of Formula (VI), R is —H. In some embodiments, for a compound of Formula (VI), R is —Cl.

In some embodiments a compound of Formula (VI) or a pharmaceutically acceptable salt or isotopic variant thereof has the structure of:

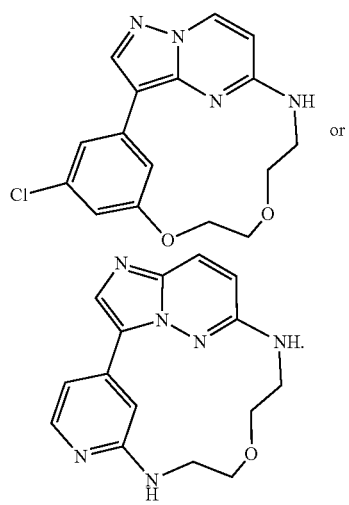

or

Disclosed herein, in some embodiments, are antagonists or partial antagonists of RIPK2 having a structure of Formula (VII) or a pharmaceutically acceptable salt or isotopic variant thereof:

Formula (VII)

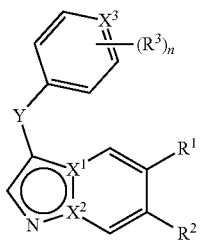

wherein
$X^1$ and $X^2$ are independently N or C;
$X^3$ is N or $CR^4$;
Y is a bond, —O—, —S—, —C($R^5$)$_2$, —$NR^6$—, —$NR^6$C(O)—, —C(O)$NR^6$-, or —$NR^6$C(O)$NR^6$-;
$R^1$ and $R^2$ are independently —H, halogen, —OH, —CN, —N($R^6$)$_2$, —$_{NR}{}^6$C(O)$R^5$, —C(O)O$R^5$, —C(O)N($R^6$)$_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-O$R^5$, —$C_{1-6}$alkyl-N($R^6$)$_2$, —O—$C_{1-6}$alkyl, —O—$C_{1-6}$alkyl-OH, —O—$C_{1-6}$alkyl-O$R^5$, —O—$C_{1-6}$alkyl-N($R^6$)$_2$, or —S(=O)$_2R^5$;
$R^3$ is —H, halogen, —NO$_2$, —CN, —OH, —O$R^5$, —S$R^5$, —N($R^6$)$_2$, —S(O)$R^5$, —S(=O)$_2R^5$, —$NR^6$S(=O)$_2R^5$, —S(=O)$_2$N($R^6$)$_2$, —C(O)$R^5$, —C(O)O$R^5$, —OC(O)$R^5$, —C(O)N($R^6$)$_2$, —OC(O)N($R^6$)$_2$, —$NR^6$C(O)N($R^6$)$_2$, —$NR^6$C(O)$R^5$, —$NR^6$C(O)O$R^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;
$R^4$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl -$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;
$R^5$ is —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;
each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or
two $R^6$ substituents are taken together with the nitrogen atom to which they are attached to form a 5- or 6-membered heterocycle;
$R^7$ is —H, halogen, —S(=O)CH$_3$, —N($R^6$)$_2$, —C(O)N($R^6$)$_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, —$C_{1-6}$alkyl-$C_{3-8}$cycloalkyl, phenyl, —$C_{1-6}$alkyl phenyl, $C_{2-9}$heterocycloalkyl, —$C_{1-6}$alkyl-$C_{2-9}$heterocycloalkyl, $C_{2-9}$heteroaryl, or —$C_{1-6}$alkyl -$C_{2-9}$heteroaryl; and
n is 0, 1, 2, 3, 4, or 5.

In some embodiments, for a compound of Formula (VII), $X^1$ and $X^2$ are independently N or C. In some embodiments, for a compound of Formula (VII), $X^1$ is N. In some embodiments, for a compound of Formula (VII), $X^1$ is C. In some embodiments, for a compound of Formula (VII), $X^2$ is N. In some embodiments, for a compound of Formula (VII), $X^2$ is C. In some embodiments, for a compound of Formula (VII), $X^1$ is N and $X^2$ is C. In some embodiments, for a compound of Formula (VII), $X^1$ is C and $X^2$ is N.

In some embodiments, for a compound of Formula (VII), $X^3$ is N or $CR^4$. In some embodiments, for a compound of Formula (VII), $X^3$ is N or CH. In some embodiments, for a compound of Formula (VII), $X^3$ is N. In some embodiments, for a compound of Formula (VII), $X^3$ is CH.

In some embodiments, for a compound of Formula (VII), Y is a bond, —O—, —S—, —C($R^5$)$_2$, —$NR^6$—, —$NR^6$C(O)—, —C(O)$NR^6$-, or —$NR^6$C(O)$NR^6$-. In some embodiments, for a compound of Formula (VII), Y is a bond, —$NR^6$C(O)—, or —C(O)$NR^6$-. In some embodiments, for a compound of Formula (VII), Y is a bond, —NHC(O)—, or —C(O)NH—. In some embodiments, for a compound of Formula (VII), Y is a bond. In some embodiments, for a compound of Formula (VII), Y is —NHC(O)—. In some embodiments, for a compound of Formula (VII), Y is —C(O)NH—.

In some embodiments, for a compound of Formula (VII), $R^1$ is —H, halogen, —OH, —CN, —N($R^6$)$_2$, —$NR^6$C(O)$R^5$, —C(O)O$R^5$, —C(O)N($R^6$)$_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-O$R^5$, —$C_{1-6}$alkyl-N($R^6$)$_2$, —O—$C_{1-6}$alkyl, —O—$C_{1-6}$alkyl-OH, —O—$C_{1-6}$alkyl-O$R^5$, —O—$C_{1-6}$alkyl-N($R^6$)$_2$, or —S(=O)$_2R^5$. In some embodiments, for a compound of Formula (VII), $R^1$ is —H, halogen, —N($R^6$)$_2$, —$NR^6$C(O)$R^5$, $C_{1-6}$alkyl, $C_{3-8}$cycloalkyl, —$C_{1-6}$alkyl-OH, —$C_{1-6}$alkyl-O$R^5$, —$C_{1-6}$alkyl -N($R^6$)$_2$, —O—$C_{1-6}$alkyl-N($R^6$)$_2$, or —S(=O)$_2R^5$. In some embodiments, for a compound of Formula (VII), $R^1$ is —H or —S(=O)$_2R^5$. In some embodiments, for a compound of Formula (VII), $R^1$ is —H. In some embodiments, for a compound of Formula (VII), $R^1$ is —S(=O)$_2$iso-propyl. In some embodiments, for a compound of Formula (VII), $R^1$ is —S(=O)$_2$tert-butyl.

In some embodiments, for a compound of Formula (VII), $R^2$ is —H, halogen, —OH, —CN, —N($R^6$)$_2$, —$NR^6$C(O)$R^5$, —C(O)O$R^5$, —C(O)N($R^6$)$_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-O$R^5$, —$C_{1-6}$alkyl-N($R^6$)$_2$, —O—$C_{1-6}$alkyl, —O—$C_{1-6}$alkyl-OH, —O—$C_{1-6}$alkyl-O$R^5$, —O—$C_{1-6}$alkyl-N($R^6$)$_2$, or —S(=O)$_2R^5$. In some embodiments, for a compound of Formula (VII), $R^2$ is —H, $C_{1-6}$alkyl, $C_{2-6}$alkenyl, $C_{2-6}$alkynyl, $C_{3-8}$cycloalkyl, —O—$C_{1-6}$alkyl, —O—$C_{1-6}$alkyl-OH, or —O—$C_{1-6}$alkyl-O$R^5$. In some embodiments, for a compound of Formula (VII), $R^2$ is —H or —O—$C_{1-6}$alkyl. In some embodiments, for a compound of Formula (VII), $R^2$ is —H. In some embodiments, for a compound of Formula (VII), $R^2$ is —OCH$_3$. In some embodiments, for a compound of Formula (VII), $R^2$ is —OCH$_2$CH$_3$.

In some embodiments, for a compound of Formula (VII), $R^3$ is —H, halogen, —NO$_2$, —CN, —OH, —O$R^5$, —S$R^5$, —N($R^6$)$_2$, —S(O)$R^5$, —S(=O)$_2R^5$, —$NR^6$S(=O)$_2R^5$, —S(=O)$_2$N($R^6$)$_2$, —C(O)$R^5$, —C(O)O$R^5$, 13 OC(O)$R^5$, —C(O)N($R^6$)$_2$, —OC(O)N($R^6$)$_2$, —$NR^6$C(O)N($R^6$)$_2$, —$NR^6$C(O)$R^5$, —$NR^6$C(O)O$R^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (VII), $R^3$ is —H, halogen, —N($R^6$)$_2$, —S(=O)$_2R^5$, —$NR^6$S(=O)$_2R^5$, —S(=O)$_2$N($R^6$)$_2$, —$NR^6$C(O)N($R^6$)$_2$, —$NR^6$C(O)$R^5$, —$NR^6$C(O)O$R^5$, $C_{1-6}$alkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, or 6- to 10-membered aryl, wherein each alkyl, heteroalkyl, cycloalkyl, heterocycloalkyl, aryl, and heteroaryl is optionally substituted with one or more $R^7$. In some embodiments, for a compound of Formula (VII), $R^3$ is —H, halogen, —N($R^6$)$_2$, or $C_{1-6}$alkyl. In some embodiments, for a compound of Formula (VII), $R^3$ is —H. In some embodiments, for a compound of Formula (VII), $R^3$ is —Cl. In some embodiments, for a compound of Formula (VII), $R^3$ is —F. In some embodiments, for a compound of Formula (VII), $R^3$ is —CH$_3$.

In some embodiments a compound of Formula (VII) or a pharmaceutically acceptable salt or isotopic variant thereof has the structure of:

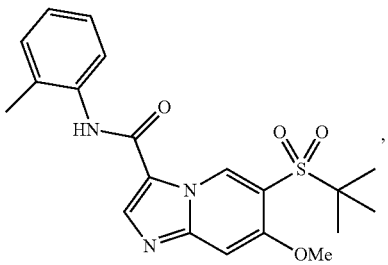
,

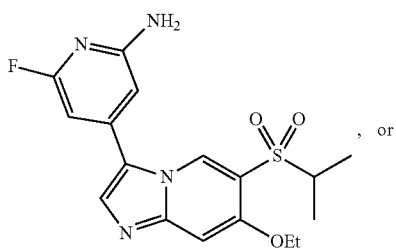
, or

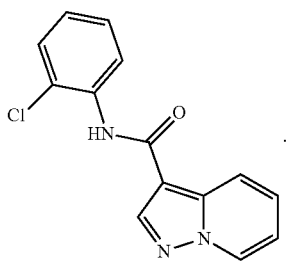
.

Disclosed herein, in some embodiments, are antagonists or partial antagonists of RIPK2 having a structure of Formula (VIII) or a pharmaceutically acceptable salt or isotopic variant thereof:

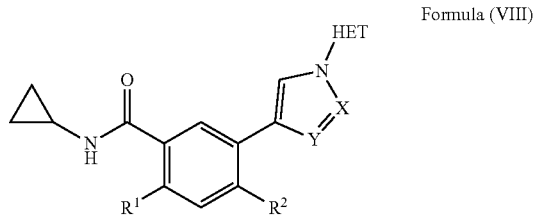

Formula (VIII)

wherein:
HET is

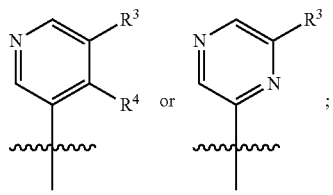
;

X is N and Y is CH; or
X is CH and Y is N;
$R^1$ is —H, or —F;
$R^2$ is $C_{1-3}$alkyl, —Cl, or —F;
$R^3$ and $R^4$ are each independently —H; —OR$^5$; —O—$C_{1-6}$ alkyl-O—$C_{1-3}$alkyl; —O—$C_{3-6}$cycloalkyl; —C(O)R$^5$, $C_{1-6}$alkyl optionally substituted with one to three —OH, —F, $C_{3-8}$heterocycloalkyl optionally substituted with oxo, $C_{3-6}$cycloalkyl, —C(O)OR$^5$, —O—$C_{1-6}$alkyl, aryl, —N(R$^5$)(R$^6$), —CN, or —C(O)N(R$^5$)(R$^6$); $C_{3-6}$cycloalkyl optionally substituted with one to three —OH, one to three —F, $C_{1-6}$alkyl, —O—$C_{1-6}$alkyl, $C_{1-6}$alkyl-O$C_{1-6}$alkyl, $C_{1-6}$alkyl-OH, —CF$_3$, —CN, —OC$_{3-6}$cycloalkyl, —C(O)OH, —C(O)OR$^5$, $C_{3-6}$cycloalkyl, 5-6 membered heteroaryl, $C_{3-6}$heterocycloalkyl, N(R$^5$)(R$^6$), or —C(O)N(R$^5$)(R$^6$); —C(O)OR$^5$; —C(O)N(R$^5$)(R$^6$); —S(=O)$_2$N(R$^5$)(R$^6$); —S(O)$_n$—R$^5$; a 4-10 membered monocyclic, bicyclic, or spirocyclyl heterocyclyl group containing nitrogen, sulfur, or oxygen and optionally substituted with one to three —N(R$^5$)(R$^6$), halogen, —$C_{1-6}$alkyl, —O—$C_{1-6}$alkyl, or —$C_{1-6}$haloalkyl; aryl; —N(R$^5$)(R$^6$); or halogen;

$R^5$ and $R^6$ are each independently —H; —$C_{1-6}$alkyl-$C_{3-8}$heterocycloalkyl; a 4-6 membered heterocycloalkyl wherein the heterocycloalkyl ring is optionally substituted with one to three $C_{1-6}$alkyl, —OC$_{1-6}$alkyl, —$C_{1-6}$haloalkyl, $C_{1-6}$cycloalkyl, halogen, acyl, heterocycloalkyl, heterocycloalkyl-$C_{1-6}$alkyl, heterocycloalkyl-O—$C_{1-6}$alkyl, heterocycloalkyl-OH, heterocycloalkyl-C(O)CH$_3$, heterocycloalkyl-C(O)OC$_{1-3}$alkyl, —$C_{1-6}$alkyl-heterocycloalkyl, —$C_{1-6}$alkyl-heterocycloalkyl-$C_{1-6}$alkyl, —$C_{1-6}$alkyl-OH, —$C_{1-6}$alkyl-O—$C_{1-6}$alkyl, $C_{3-6}$cycloalkyl, —$C_{1-6}$alkyl-cycloalkyl, $C_{3-6}$cycloalkyl-$C_{1-6}$alkyl, $C_{3-6}$cycloalkyl-O—$C_{1-6}$alkyl, or $C_{3-6}$cycloalkyl-O—$C_{1-6}$alkyl-OH; acyl; $C_{3-6}$cycloalkyl-C(O)—$C_{1-3}$alkyl; —C(O)—$C_{1-3}$alkyl-O—CH$_3$; —C(O)—$C_{1-3}$alkyl; —C(O)—$C_{3-6}$cycloalkyl; —C(O)—NH—$C_{1-3}$alkyl; —C(O)—NH—$C_{1-3}$alkyl; —C(O)—NH—$C_{3-6}$cycloalkyl optionally monosubstituted or disubstituted with —$C_{1-3}$alkyl-OH, —C(O)—NH—$C_{3-6}$heterocyclyl, —C(O)-aryl, —C(O)-heteroaryl, or —S(O)$_n$—$C_{1-3}$alkyl; and $C_{1-6}$alkyl optionally substituted with —OH, O—$C_{1-3}$alkyl, $C_{3-6}$cycloalkyl, heterocyclyl, aryl, —NH—$C_{1-3}$alkyl, or —N—($C_{1-3}$alkyl)$_2$; or $R^5$ and $R^6$ together with the nitrogen atom to which they are attached form a 5-6 membered heterocyclic ring optionally substituted with methyl; and n is 0, 1, or 2.

In some embodiments, for a compound of Formula (VIII), HET is

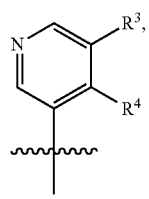

X is N, Y is CH, and n is 1 or 2. In some embodiments, for a compound of Formula (VIII), HET is

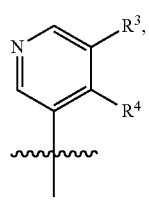

X is N, Y is CH, R² is —CH₃ or —Cl, R⁴ is H, and n is 2. In some embodiments, for a compound of Formula (VIII), HET is

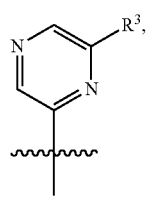

X is N, Y is CH, R² is —CH₃ or —Cl, and n is 2. In some embodiments, for a compound of Formula (VIII), HET is

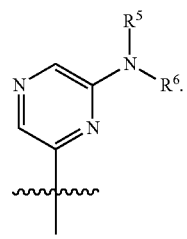

In some embodiments, for a compound of Formula (VIII), HET is

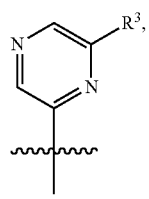

X is CH, Y is N, R² is —CH₃ or —Cl, and n is 2. In some embodiments, for a compound of Formula (VIII), HET is

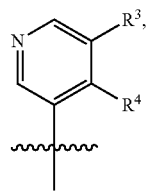

X is CH, Y is N, R² is —CH₃ or —Cl, R⁴ is —H, and n is 2. In some embodiments, for a compound of Formula (VIII), HET is

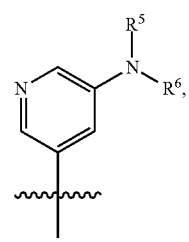

X is CH, Y is N, R² is —CH₃ or —Cl, R⁴ is —H, and n is 2.

In some embodiments, for a compound of Formula (VIII), HET is

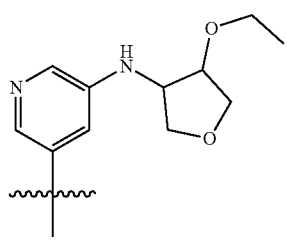

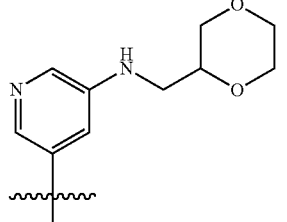

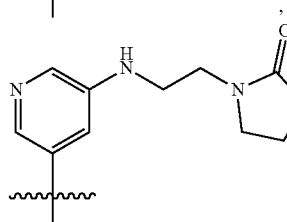

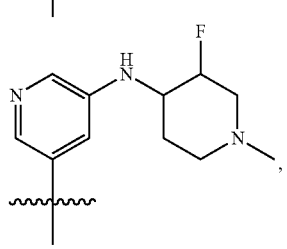

91
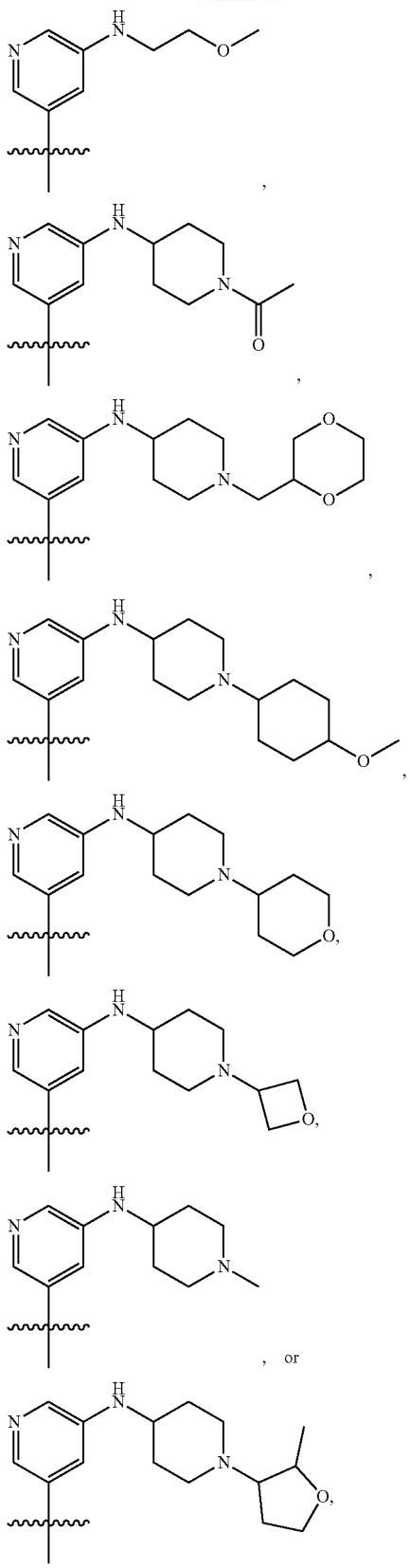
, or
X is N, Y is CH, R¹ is —F, and R² is —CH₃. In some embodiments, for a compound of Formula (VIII), HET is
92
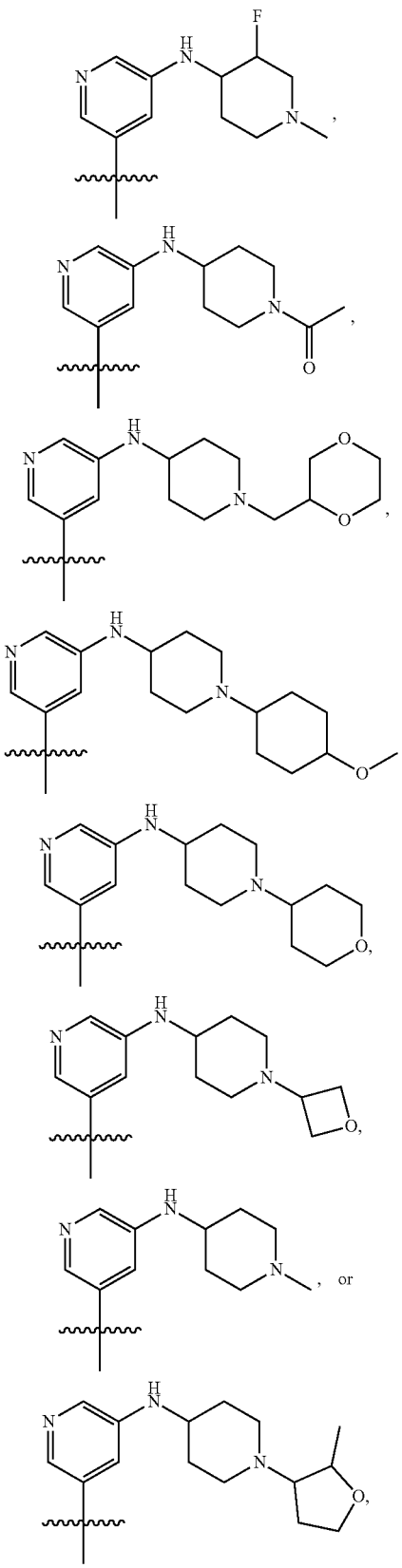
X is N, Y is CH, R¹ is —F, and R² is —CH₃. In some embodiments, for a compound of Formula (VIII), HET is

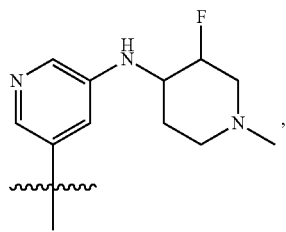

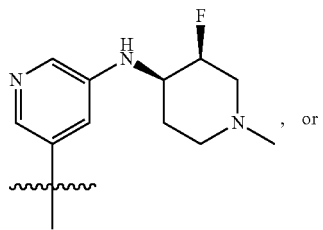, or

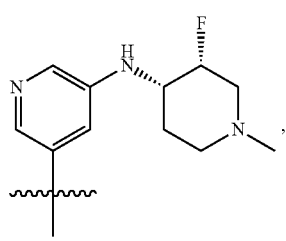,

X is N, Y is CH, R¹ is —F, and R² is —CH₃.

In some embodiments, for a compound of Formula (VIII), HET is

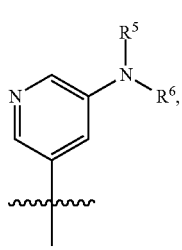

X is N, Y is CH, R² is —CH₃ or —Cl, R⁴ is H, and n is 2. In some embodiments, for a compound of Formula (VIII), HET is

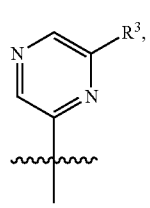

X is N, and Y is CH. In some embodiments, for a compound of Formula (VIII), HET is

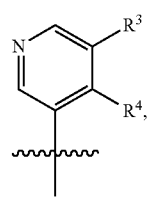

X is CH, and Y is N. In some embodiments, for a compound of Formula (VIII), HET is

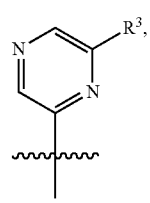

X is CH, and Y is N.

In some embodiments, for a compound of Formula (VIII), HET is

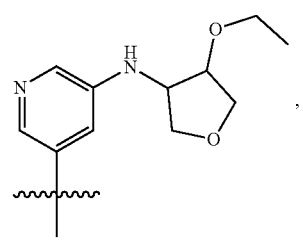,

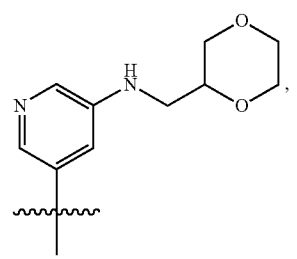,

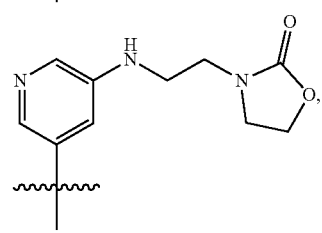,

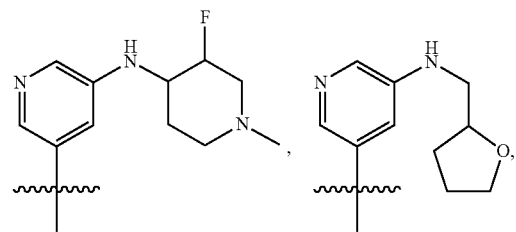

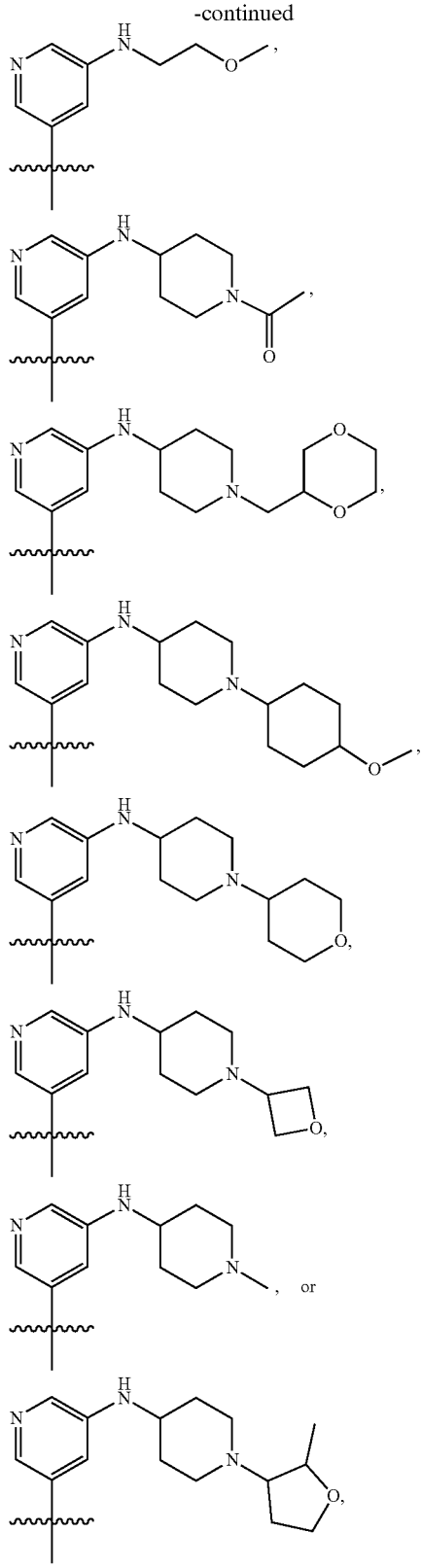
X is N, Y is CH, R² is —CH₃ or —Cl, R⁴ is H, and n is 2.
In some embodiments, a compound of Formula (VIII), or a pharmaceutically acceptable salt or isotopic variant thereof, has the structure of:

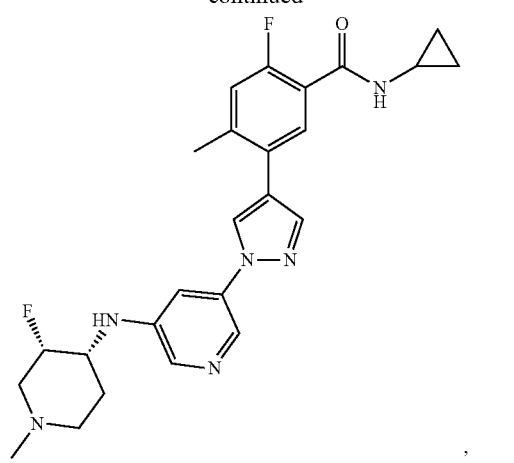
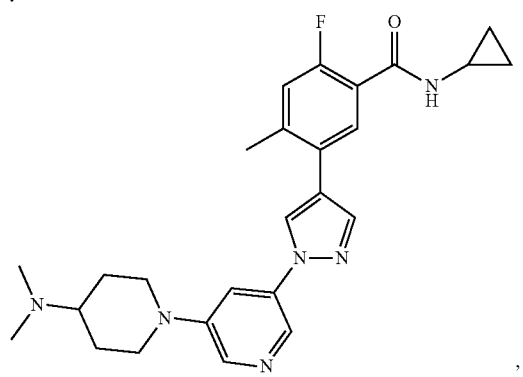
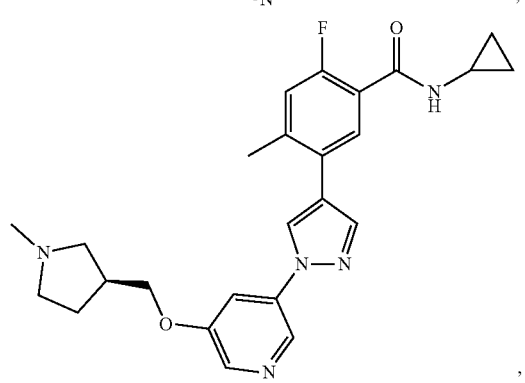
,
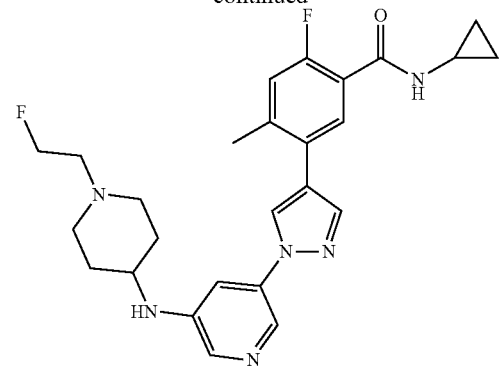
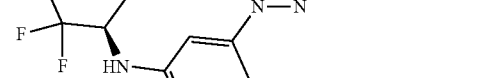
, or
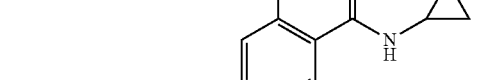
.
Disclosed herein, in some embodiments, are antagonists or partial antagonists of RIPK2 having a structure of Formula (IX), or a pharmaceutically acceptable salt or isotopic variant thereof:
Formula (IX)
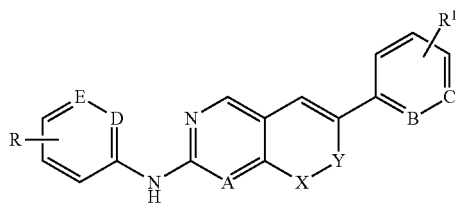

wherein
R is —H; or
R is

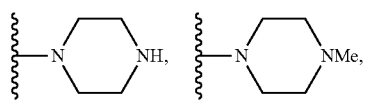

S(=O)₂CH₃,

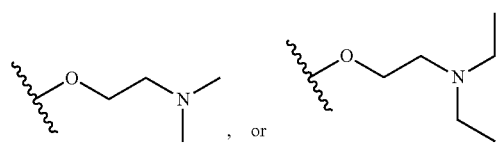

, or at one available ring position;
A and D are independently N or CH;
E is N, CH, or CR;
B and C are independently N, CH, or C—Cl;
R¹ is H; or
R¹ is C—Cl, C—F, C—OCH₃, C—C(CH₃)₃, or C—OH at one available ring position; and
X-Y are C=C or

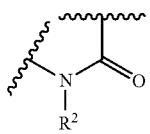

wherein R² is —H, $C_{1-6}$alkyl, $C_{1-6}$alkyl-OH, $C_{1-6}$alkyl-OC$_{1-6}$ alkyl, or $C_{1-6}$alkyl-aryl.

In some embodiments, for a compound of Formula (IX), R² is methyl, ethyl, isobutyl, 2-hydroxyethyl, 2-methoxyethyl, benzyl, or phenethyl. In some embodiments, for a compound of Formula (IX), R² is methyl. In some embodiments, for a compound of Formula (IX), R² is ethyl. In some embodiments, for a compound of Formula (IX), R² is isobutyl. In some embodiments, for a compound of Formula (IX), R² is 2-hydroxyethyl. In some embodiments, for a compound of Formula (IX), R² is 2-methoxyethyl. In some embodiments, for a compound of Formula (IX), R² is benzyl. In some embodiments, for a compound of Formula (IX), R² is phenethyl.

In some embodiments, a compound of Formula (IX), or a pharmaceutically acceptable salt and isotopic variant thereof, has the structure of:

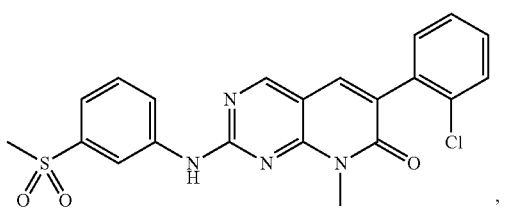

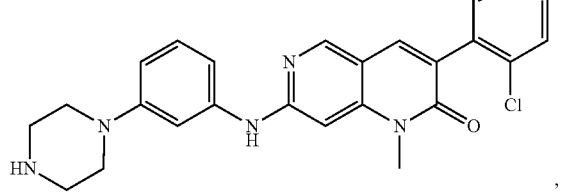

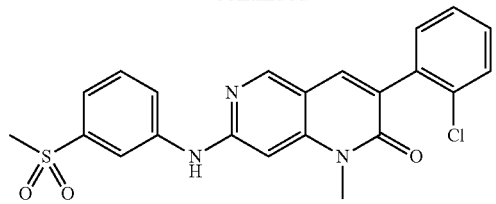

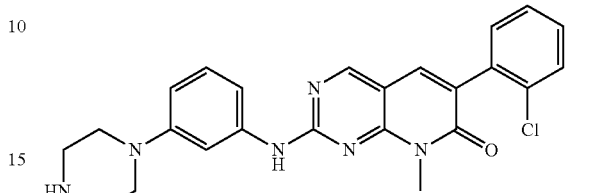

, or

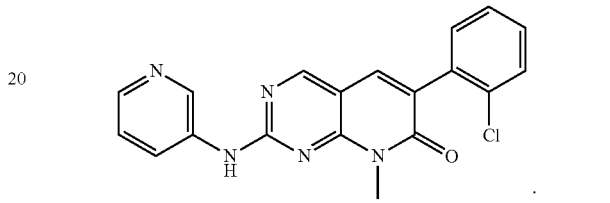

.

Disclosed herein, in some embodiments, are antagonists or partial antagonists of RIPK2 having a structure of Formula (IXa) or a pharmaceutically acceptable salt and isotopic variant thereof:

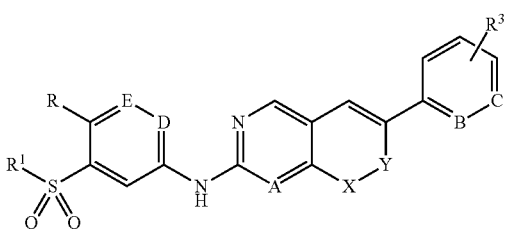

wherein
R is —H,

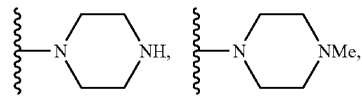

S(=O)₂CH₃,

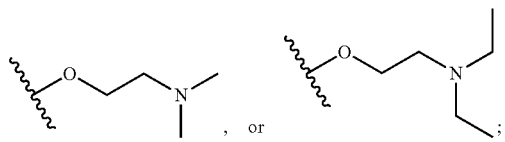

, or

;

R¹ is $C_{1-6}$alkyl or 6- to 10-membered aryl;
A and D are independently N or CH;
E is N, CH, or CR;
B and C are independently N, CH, or C—Cl;
R³ is H; or R$^3$ is C—Cl, C—F, C—OCH$_3$, C—C(CH$_3$)$_3$, or C—OH at one available ring position; and X-Y are C=C or

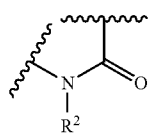

wherein R$^2$ is —H, C$_{1-6}$alkyl, C$_{1-6}$alkyl-OH, C$_{1-6}$alkyl-OC$_{1-6}$ alkyl, or C$_{1-6}$alkyl-aryl.

In some embodiments, for a compound of Formula (IXa), R$^1$ is methyl, ethyl, or propyl. In some embodiments, for a compound of Formula (IXa), R$^1$ is methyl. In some embodiments, for a compound of Formula (IXa), R$^1$ is ethyl. In some embodiments, for a compound of Formula (IXa), R$^1$ is propyl.

In some embodiments, for a compound of Formula (IXa), R$^2$ is methyl, ethyl, isobutyl, 2-hydroxyethyl, 2-methoxyethyl, benzyl, or phenethyl. In some embodiments, for a compound of Formula (IXa), R$^2$ is methyl. In some embodiments, for a compound of Formula (IXa), R$^2$ is ethyl. In some embodiments, for a compound of Formula (IXa), R$^2$ is isobutyl. In some embodiments, for a compound of Formula (IXa), R$^2$ is 2-hydroxyethyl. In some embodiments, for a compound of Formula (IXa), R$^2$ is 2-methoxyethyl. In some embodiments, for a compound of Formula (IXa), R$^2$ is benzyl. In some embodiments, for a compound of Formula (IXa), R$^2$ is phenethyl.

Disclosed herein, in some embodiments, are antagonists or partial antagonists of RIPK2 having a structure of Formula (X), or a pharmaceutically acceptable salt or isotopic variant thereof:

Formula (X)

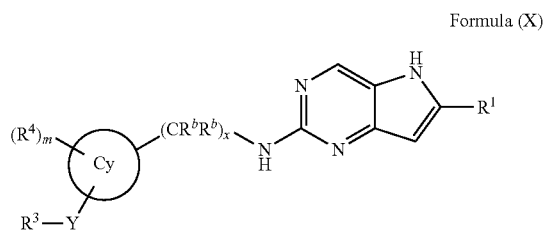

wherein

Cy is C$_{3-8}$cycloalkyl, C$_{2-9}$heterocycloalkyl, 6- to 10-membered aryl, or C$_{2-9}$heteroaryl;

Y is absent, —CR$^b$R$^b$—, —O—, —NR$^b$—, or —S(O)$_n$—;

R$^1$ is C$_{3-8}$cycloalkyl, C$_{2-9}$heterocycloalkyl, 6- to 10-membered aryl, or C$_{2-9}$heteroaryl, each of which is optionally substituted with one to three R$^a$;

R$^3$ is —H, C$_{2-9}$heterocycloalkyl, or C$_{2-9}$heteroaryl, wherein the heterocycloalkyl and heteroaryl are optionally substituted with one to three —F, —Cl, —Br, I, —CN, —NO$_2$, —OR$^b$, C$_{1-4}$alkyl, —C$_{1-3}$alkyl-OR$^b$, —C$_{1-3}$alkyl-NR$^b$R$^b$, C$_{1-4}$haloalkyl, C$_{1-4}$haloalkoxy, C$_{3-8}$cycloalkyl, —NR$^b$R$^b$, —C(O)NR$^b$R$^b$, —NR$^b$C(O)NR$^b$R$^b$, —S(O)$_n$NR$^b$R$^b$, C(O)OR$^b$, —OC(O)OR$^b$, —S(O)$_n$R$^b$, —NR$^b$S(O)$_n$R$^b$, —C(S)OR$^b$, —OC(S)R$^b$, —NR$^b$C(O)R$^b$, —C(S)NR$^b$R$^b$, —NR$^b$C(S)R$^b$, —NR$^b$C(O)OR$^b$, —OC(O)NR$^b$R$^b$, —NR$^b$C(S)OR$^b$, —OC(S)NR$^b$R$^b$, —NRC(S)NR$^b$R$^b$, —C(S)R$^b$, or —C(O)R$^b$;

each R$^4$ is independently halogen, —CN, —NR$^b$R$^b$, —OR$^b$, C$_{1-4}$alkyl, —C$_{1-3}$alkyl-OR$^b$, —C$_{1-3}$alkyl-NR$^b$R$^b$, C$_{1-4}$haloalkyl, or C$_{1-4}$haloalkoxy;

each R$^a$ is independently —F, —Cl, —Br, I, —CN, OR$^b$, C$_{1-4}$alkyl, C$_{2-6}$alkenyl, C$_{2-6}$alkynyl, C$_{1-4}$haloalkyl, C$_{1-4}$haloalkoxy, —C$_{1-3}$alkyl-OR$^b$, or —C$_{1-3}$alkyl-NR$^b$R$^b$;

each R$^b$ is independently —H or C$_{1-4}$alkyl;

x is 0, 1, 2, 3, or 4;

each m is independently 0, 1, 2, or 3; and each n is independently 0, 1, or 2.

Disclosed herein, in some embodiments, are antagonists or partial antagonists of RIPK2 having a structure of Formula (Xa) or a pharmaceutically acceptable salt or isotopic variant thereof:

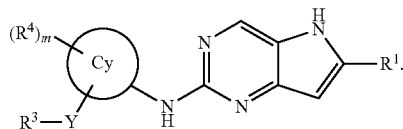

Disclosed herein, in some embodiments, are antagonists or partial antagonists of RIPK2 having a structure of Formula (Xb) or a pharmaceutically acceptable salt or isotopic variant thereof:

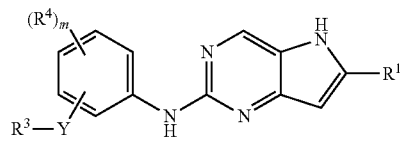

In some embodiments, for a compound of Formula (X), R$^1$ is optionally substituted phenyl, optionally substituted cyclopentyl, optionally substituted cyclohexyl, optionally substituted thienyl, optionally substituted pyridinyl, optionally substituted thiazolyl, optionally substituted pyrrolyl, optionally substituted imidazolyl, optionally substituted furanyl, optionally substituted oxazolyl, optionally substituted isoxazolyl, optionally substituted pyrazolyl, optionally substituted isothiazolyl, optionally substituted pyrmidinyl, optionally substituted pyrazinyl, optionally substituted pyridazinyl, optionally substituted oxadiazolyl, optionally substituted tetrahydropyranyl, optionally substituted triazolyl, or optionally substituted thiadiazolyl. In some embodiments, for a compound of Formula (X), R$^1$ is optionally substituted phenyl, optionally substituted cyclopentyl, optionally substiuted thienyl, or optionally substituted tetrahydropyranyl. In some embodiments, for a compound of Formula (X), R$^1$ is optionally substituted phenyl. In some embodiments, for a compound of Formula (X), R$^1$ is optionally substituted cyclopentyl. In some embodiments, for a compound of Formula (X), R$^1$ is optionally substituted thienyl. In some embodiments, for a compound of Formula (X), R$^1$ is optionally substituted tetrahydropyranyl.

In some embodiments, for a compound of Formula (X), R$^3$ is optionally substituted monocyclic heterocycloalkyl or optionally substituted monocyclic heteroaryl. In some embodiments, for a compound of Formula (X), R$^3$ is optionally substituted monocyclic heterocycloalkyl. In some embodiments, for a compound of Formula (X), R$^3$ is optionally substituted monocyclic heterocyloaryl.

In some embodiments, for a compound of Formula (X), m is 0 to 3. In some embodiments, for a compound of Formula (X), m is 0. In some embodiments, for a compound of Formula (X), m is 1. In some embodiments, for a compound of Formula (X), m is 2. In some embodiments, for a compound of Formula (X), m is 3.

In some embodiments, for a compound of Formula (X), $R^3$ is optionally substituted azetidinyl, optionally substituted morpholinyl, optionally substituted piperazinyl, optionally substituted piperidinyl, optionally substituted tetrahydropyranyl, optionally substituted pyrrolidinyl, optionally substituted thiomorpholinyl, optionally substituted tetrahydrofuryanyl, optionally substituted homomorpholinyl, optionally substituted homopiperazinyl, optionally substituted thiomorpholine dioxide, or optionally substituted thienomorpholine oxide. In some embodiments, for a compound of Formula (X), $R^3$ is optionally substituted morpholinyl, optionally substituted piperazinyl, optionally substituted piperidinyl, or optionally substituted thiomorpholinyl. In some embodiments, for a compound of Formula (X), $R^3$ is optionally substituted morpholinyl. In some embodiments, for a compound of Formula (X), $R^3$ is optionally substituted piperazinyl. In some embodiments, for a compound of Formula (X), $R^3$ is optionally substituted piperidinyl. In some embodiments, for a compound of Formula (X), $R^3$ is optionally substituted thiomorpholinyl.

Disclosed herein, in some embodiments, are antagonists or partial antagonists of RIPK2 having a structure of Formula (Xc) or a pharmaceutically acceptable salt or isotopic variant thereof:

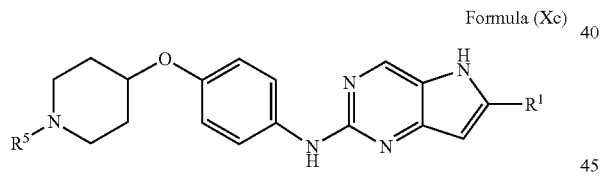

Formula (Xc)

wherein
$R^5$ is $C_{1-4}$alkyl or —$C_{1-3}$alkyl-$OR^b$.

Disclosed herein, in some embodiments, are antagonists or partial antagonists of RIPK2 having a structure of Formula (Xd) or a pharmaceutically acceptable salt or isotopic variant thereof:

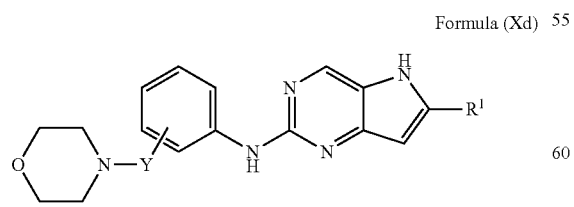

Formula (Xd)

wherein:
Y is absent or —$CH_2$—; and
Y is attached to the meta or para position of the phenyl ring.

Disclosed herein, in some embodiments, are antagonists or partial antagonists of RIPK2 having a structure of Formula (Xe) or a pharmaceutically acceptable salt or isotopic variant thereof:

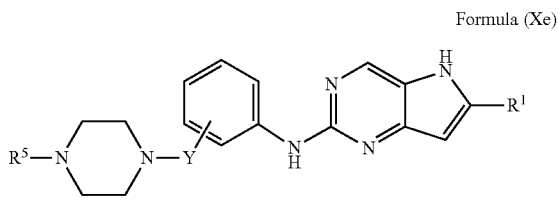

Formula (Xe)

wherein
$R^5$ is —H, $C_{1-4}$alkyl, or —$C_{1-3}$alkyl-$OR^b$;
Y is absent or —$CH_2$-; and
Y is attached to the meta or para position of the phenyl ring.

In some embodiments, for a compound of Formula (X), $R^1$ is

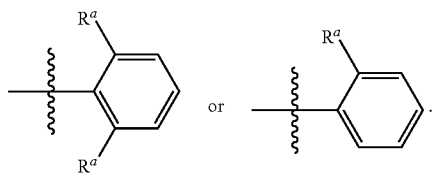

In some embodiments, for a compound of Formula (X), $R^1$ is

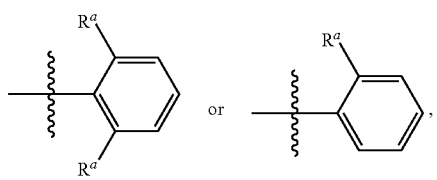

wherein each $R^a$ is independently —F, —Cl, or —$CH_3$.

GPR35 Modulators

Disclosed herein are therapeutic agents that modulate G-Protein Coupled Receptor 35 (GPR35) ("GPR35 modulator"). In some instances, the GPR35 modulator is an agonist or partial agonist. In some instances, the GPR35 modulator is an antagonist, partial antagonist, or inverse agonist. The GPR35 modulator may be a small molecule. In some instances, the therapeutic agent is a small molecule that binds GPR35. In some instances, the small molecule that binds GPR35 is a GPR35 agonist. In some instances, the small molecule that binds GPR35 is a GPR35 partial agonist. In some instances, the small molecule that binds GPR35 is a GPR35 antagonist. In some instances, the small molecule that binds GPR35 is a GPR35 partial agonist.

In some instances, the small molecule that binds GPR35 is a compound of Formula (I):

Formula (I)

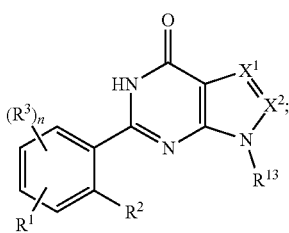

wherein:
X¹ and X² are independently selected from N and $CR^{14}$;
$R^1$ is —$CH_2R^4$, —CN, —$B(OH)_2$, —$N(R^{10})_2$, —$NR^{10}C(O)R^9$, —$CH_2C(O)OH$, —$C(O)N(R^{10})_2$, —$C(O)NHS(O)_2N(R^{10})_2$, —$C_{1-6}$alkyl-OH, $C_{3-8}$cycloalkyl,

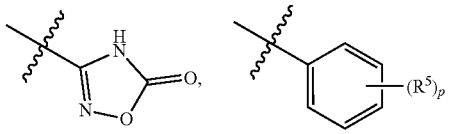

or a 5- or 6-membered heteroaryl optionally substituted with one, two, or three $R^8$ groups;
$R^2$ is H, —OH, —$N(R^{10})_2$, —$NHS(O)_2R^9$, —$S(O)_2N(R^{10})_2$, —$C(O)N(R^{10})_2$, $OC(O)N(R^{10})_2$, —O—$C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl;
each $R^3$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^4$ is

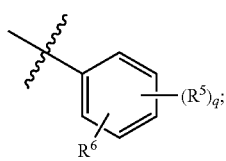

each $R^5$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{2-6}$alkenyl, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;
$R^6$ is —$C(O)OR^7$, —$C(O)NHS(O)_2N(R^{10})_2$,

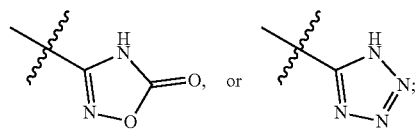 [SMILES: *c1noc(=O)[nH]1 ; *c1nnn[nH]1]

each $R^7$ is independently selected from H and $C_{1-6}$alkyl;
each $R^8$ is independently selected from halogen, —OH, —$OR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R_{10})_2$, —$C_{1-6}$alkyl-$C(O)OR^{10}$, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;
each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$C(O)R^{12}$, and —$C(O)OR^{12}$;
each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —$N(R^{11})_2$, and —$C(O)OR^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —$C(O)OH$;
each $R^{11}$ is independently selected from H and $C_{1-6}$alkyl;
$R^{12}$ is independently selected from H and $C_{1-6}$alkyl;
$R^{13}$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;
each $R^{14}$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl;
n is 0, 1, 2, or 3;

p is 0, 1, 2, 3, 4, or 5; and
q is 0, 1, 2, 3, or 4:
or a pharmaceutically acceptable salt or solvate thereof.
In some instances, the small molecule that binds GPR35 is a compound of Formula (II):

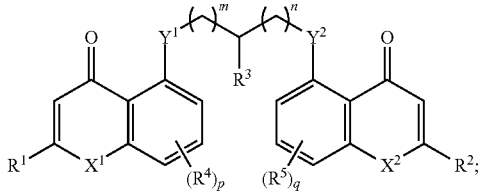

Formula (II)

wherein:
- $X^1$, $X^2$, $Y^1$, and $Y^2$ are independently selected from O, $NR^{13}$, and $C(R^{14})_2$;
- $R^1$ and $R^2$ are independently selected from —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —$NR^{10}$C(O)N($R^{10}$)$_2$, —$NR^{10}$C(O)$R^9$, —$NR^{10}$C(O)O$R^9$, $C_{1-6}$alkyl, —$C_{1-6}$alkyl-OH, —$C_{1-6}$alkyl-O$R^9$, and —$C_{1-6}$alkyl-N($R^{10}$)$_2$;
- $R^3$ is selected from —OH, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —$NR^{10}$C(O)N($R^{10}$)$_2$, —$NR^{10}$C(O)$R^9$, —$NR^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
- each $R^4$ and $R^5$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —$NR^{10}$C(O)N($R^{10}$)$_2$, —$NR^{10}$C(O)$R^9$, —$NR^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
- each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C_{1-6}$alkyl, $C_{3-8}$cycloalkyl, —C(O)$R^{12}$, and —C(O)O$R^{12}$;
- each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —N($R^{11}$)$_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;
- each $R^{11}$ is independently selected from H and $C_{1-6}$alkyl;
- each $R^{12}$ is independently selected from H and $C_{1-6}$alkyl;
- each $R^{13}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;
- each $R^{14}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl;
- m is 1, 2, 3, 4, or 5;
- n is 1, 2, 3, 4, or 5;
- p is 0, 1, 2, or 3; and
- q is 0, 1, 2, or 3;

or a pharmaceutically acceptable salt or solvate thereof.
In some instances, the small molecule that binds GPR35 is a compound of Formula (III):

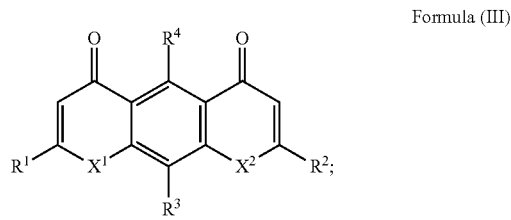

Formula (III)

wherein:
- $X^1$ and $X^2$ are independently selected from O, $NR^{13}$, and $C(R^{14})_2$;
- $R^1$ and $R^2$ are independently selected from —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —$NR^{10}$C(O)N($R^{10}$)$_2$, —$NR^{10}$C(O)$R^9$, —$NR^{10}$C(O)O$R^9$, $C_{1-6}$alkyl, —$C_{1-6}$alkyl-OH, —$C_{1-6}$alkyl-O$R^9$, and —$C_{1-6}$alkyl-N($R^{10}$)$_2$;
- $R^3$ and $R^4$ are independently selected from H, halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)$R^9$, —C(O)O$R^{10}$, —OC(O)$R_9$, —C(O)N($R^{10}$)$_2$, —OC(O)N($R^{10}$)$_2$, —$NR^{10}$C(O)N($R^{10}$)$_2$, —$NR^{10}$C(O)$R_9$, —$NR^{10}$C(O)O$R_9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
- each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C^{1-6}$alkyl, $C_{3-8}$cycloalkyl, —C(O)$R^{12}$, and —C(O)O$R^{12}$;
- each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —N($R^{11}$)$_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
each $R^{12}$ is independently selected from H and $C_{1-6}$alkyl;
each $R^{13}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl; and
each $R^{14}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl;

or a pharmaceutically acceptable salt or solvate thereof.

In some instances, the small molecule that binds GPR35 is a compound of Formula (IV):

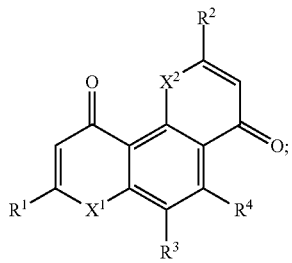

Formula (IV)

wherein:

$X^1$ and $X^2$ are independently selected from O, $NR^{13}$, and $C(R^{14})_2$;

$R^1$ and $R^2$ are independently selected from —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, and —$C_{1-6}$alkyl-N($R^{10}$)$_2$;

$R^3$ and $R^4$ are independently selected from H, halogen, —CN, —OH, —O$R^9$, —S$R^9$, —N($R^{10}$)$_2$, —S(O)$R^9$, —S(O)$_2R^9$, NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C_{1-6}$alkyl, $C_{3-8}$cycloalkyl, —C(O)$R^{12}$, and —C(O)O$R^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
each $R^{12}$ is independently selected from H and $C_{1-6}$alkyl;
each $R^{13}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl; and
each $R^{14}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl;

or a pharmaceutically acceptable salt or solvate thereof.

In some instances, the small molecule that binds GPR35 is a compound of Formula (V):

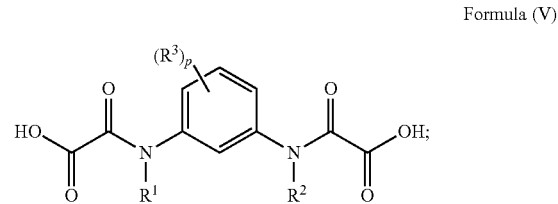

Formula (V)

wherein:

$R^1$ and $R^2$ are independently selected from H, $C_{1-6}$alkyl, $C_{1-6}$haloalkyl, $C_{3-8}$cycloalkyl, —$C_{1-6}$alkyl -$C_{3-8}$cycloalkyl, phenyl, —$C_{1-6}$alkyl-phenyl, and $C_{2-9}$heteroaryl;

each $R^3$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C_{1-6}$alkyl, $C_{3-8}$cycloalkyl, —C(O)$R^{12}$, and —C(O)O$R^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;

each $R^{12}$ is independently selected from H and $C_{1-6}$alkyl; and p is 0, 1, 2, 3, or 4;

or a pharmaceutically acceptable salt or solvate thereof.

In some instances, the small molecule that binds GPR35 is a compound of Formula (VI):

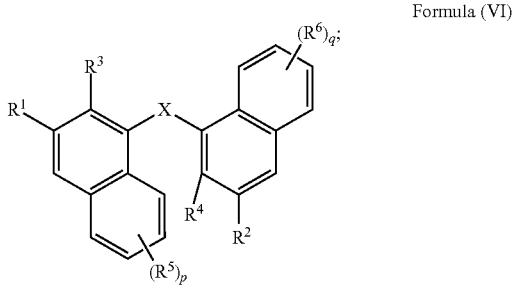

Formula (VI)

wherein:

X is selected from O, $NR^{13}$, and $C(R^{14})_2$;

$R^1$ and $R^2$ are independently selected from —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, and-$C_{1-6}$alkyl-N($R^{10}$)$_2$;

$R^3$ and $R^4$ are independently selected from H, halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^5$ and each $R^6$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C_{1-6}$alkyl, $C_{3-8}$cycloalkyl, —C(O)$R^{12}$, and —C(O)O$R^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —N($R^{11}$)$_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;

each $R^{12}$ is independently selected from H and $C_{1-6}$alkyl;

$R^{13}$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;

each $R^{14}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and-$C_{1-6}$alkyl-$C_{2-9}$heteroaryl;

p is 0, 1, 2, 3, or 4; and q is 0, 1, 2, 3, or 4;

or a pharmaceutically acceptable salt or solvate thereof.

In some instances, the small molecule that binds GPR35 is a compound of Formula (VII):

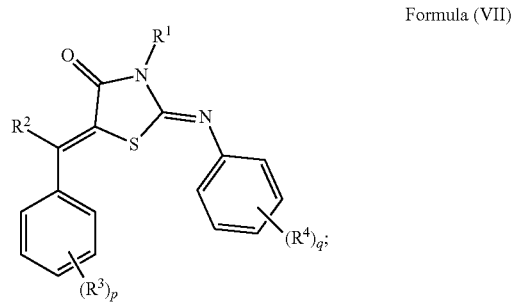

Formula (VII)

$R^1$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;

$R^2$ is selected from H, halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^3$ and each $R^4$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2N(R^{10})_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$C(O)R^{12}$, and —$C(O)OR^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —$C(O)OH$;

each $R^{11}$ is independently selected from H and $C_{1-6}$alkyl;
each $R^{12}$ is independently selected from H and $C_{1-6}$alkyl;
is 0, 1, 2, 3, or 4; and
q is 0, 1, 2, 3, or 4;

or a pharmaceutically acceptable salt or solvate thereof.

In some instances, the small molecule that binds GPR35 is a compound of Formula (VIII):

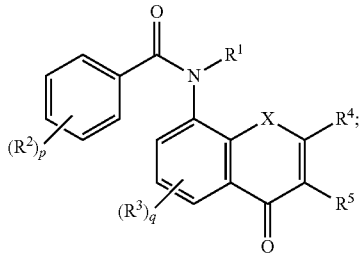

Formula (VIII)

wherein:
X is selected from —O—, —S—, and —$SO_2$—;
$R^1$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;
each $R^2$ and each $R^3$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^4$ is selected from —$C(O)OH$, —$C(O)OR^{10}$,

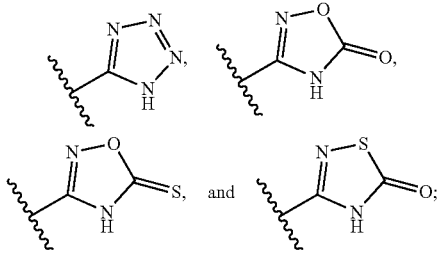

$R^5$ is selected from H, halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R_9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$C(O)R^{12}$, and —$C(O)OR^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —$C(O)OH$;

each $R^{11}$ is independently selected from H and $C_{1-6}$alkyl;
each $R^{12}$ is independently selected from H and $C_{1-6}$alkyl;
p is 0, 1, 2, 3, or 4; and
q is 0, 1, 2, or 3;

or a pharmaceutically acceptable salt or solvate thereof.

In some instances, the small molecule that binds GPR35 is a compound of Formula (IX):

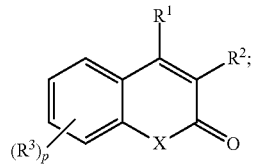

Formula (IX)

wherein:
X is selected from —O— and —S—;
$R^1$ is selected from H, halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, $C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^2$ is selected from —$C(O)OH$, —$C(O)OR^{10}$,

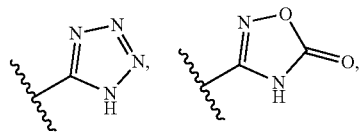

-continued

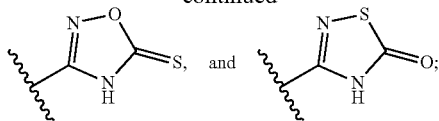

each R³ is independently selected from halogen, —CN, —OH, NO₂, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each R⁹ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl,-$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR¹¹, —N(R¹¹)₂, $C_{1-6}$alkyl, $C_{3-8}$cycloalkyl, —C(O)R¹², and —C(O)OR¹²;

each R¹⁰ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —N(R¹¹)₂; or two R¹⁰ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each R¹¹ is independently selected from H and $C_{1-6}$alkyl;
each R¹² is independently selected from H and $C_{1-6}$alkyl; and p is 0, 1, 2, 3, or 4;

or a pharmaceutically acceptable salt or solvate thereof.

In some instances, the small molecule that binds GPR35 is a compound of Formula (X):

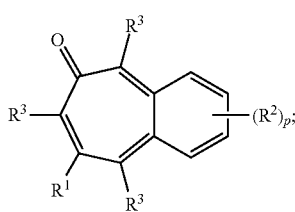

Formula (X)

wherein:
R¹ is selected from —C(O)OH, —C(O)OR¹⁰,

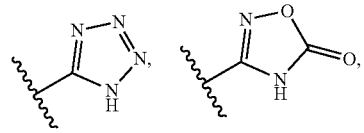

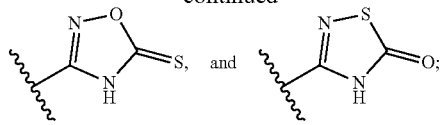

each R² is independently selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each R³ is independently selected from H, halogen, —CN, —OH, NO₂, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each R⁹ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR¹¹, —N(R¹¹)₂, $C_{1-6}$alkyl, $C_{3-8}$cycloalkyl, —C(O)R¹², and —C(O)OR¹²;

each R¹⁰ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —N(R¹¹)₂; or two R¹⁰ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each R¹¹ is independently selected from H and $C_{1-6}$alkyl:
each R¹² is independently selected from H and $C_{1-6}$alkyl; and p is 0, 1, 2, 3, or 4;

or a pharmaceutically acceptable salt or solvate thereof.

In some instances, the small molecule that binds GPR35 is a compound of Formula (XI):

Formula (XI)

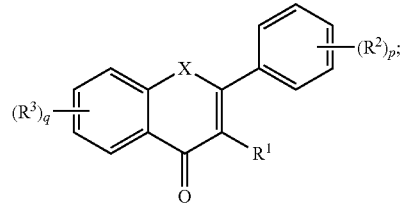

wherein:

X is selected from —O—, —S—, and —SO$_2$—;

R$^1$ is selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^2$ and each R$^3$ is independently selected from halogen, —CN, —OH, —OR$^9$, —SR$^9$, —N(R$^{10}$), —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and -C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$.

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;
each R$^{12}$ is independently selected from H and C$_{1-6}$alkyl;
p is 0, 1, 2, 3, or 4; and
q is 0, 1, 2, 3, or 4;

or a pharmaceutically acceptable salt or solvate thereof.

In some instances, the small molecule that binds GPR35 is a compound of Formula (XII):

Formula (XII)

wherein:

X is selected from —O—, —S—, —NR$^{13}$-, and —C(R$^{14}$)$_2$-;

each R$^1$ is independently selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

R$^2$ is selected from H and C$_{1-6}$alkyl;

each R$^3$ and each R$^4$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;

each R$^{12}$ is independently selected from H and C$_{1-6}$alkyl;

R$^{13}$ is selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl;

R$^{14}$ is selected from H, C$_{1-6}$alkyl, C$_{1-6}$haloalkyl, C$_{3-8}$cycloalkyl, C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl;

p is 0, 1, 2, 3, or 4; and q is 0, 1, 2, 3, or 4;

or a pharmaceutically acceptable salt or solvate thereof.

In some instances, the small molecule that binds GPR35 is a compound of Formula (XIII):

Formula (XIII)

wherein:

X$^1$ and X$^2$ are independently —O—, —S—, or —NR$^{13}$-;

R$^1$ is selected from —C(O)OH, —C(O)OR$^{10}$,

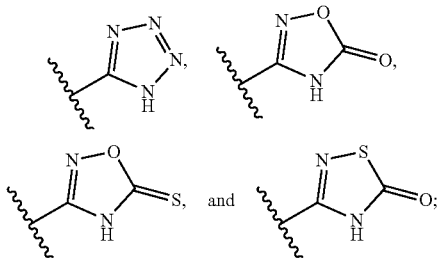

$R^2$ is selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^3$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and -C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;

each R$^{12}$ is independently selected from H and C$_{1-6}$alkyl;

R$^{13}$ is selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl; and p is 0, 1 or 2, or a pharmaceutically acceptable salt or solvate thereof.

In some instances, the small molecule that binds GPR35 is a compound of Formula (XIV):

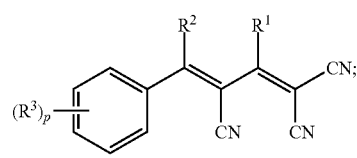

Formula (XIV)

wherein:

R$^1$ and R$^2$ are independently selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^3$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and-C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;

each R$^{12}$ is independently selected from H and C$_{1-6}$alkyl; and p is 0, 1, 2, 3, or 4;

or a pharmaceutically acceptable salt or solvate thereof.

In some instances, the small molecule that binds GPR35 is a compound of Formula (XV):

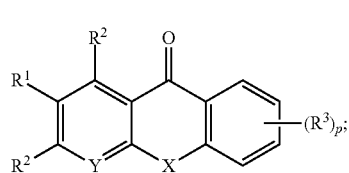

Formula (XV)

wherein:
X is selected from —O—, —S—, and —SO$_2$-;
Y is N or CR$^2$;
R$^1$ is —C(O)OH, —C(O)OR$^{10}$,

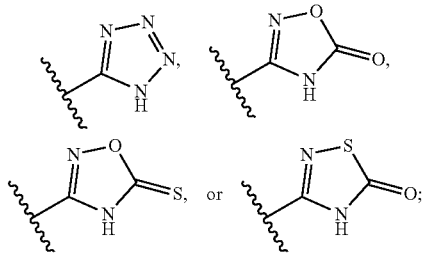

each R$^2$ is independently selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^3$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;
each R$^{12}$ is independently selected from H and C$_{1-6}$alkyl; and
p is 0, 1, 2, 3, or 4;
or a pharmaceutically acceptable salt or solvate thereof.

In some instances, the small molecule that binds GPR35 is a compound of Formula (XVI):

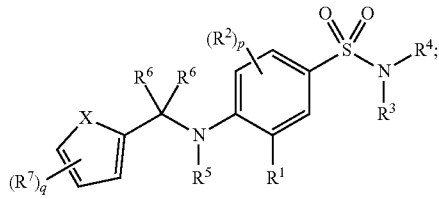

Formula (XVI)

wherein:
X is selected from —O—, —S—, and —NR$^{13}$-;
R$^1$ is selected from —C(O)OH, —C(O)OR$^{10}$,

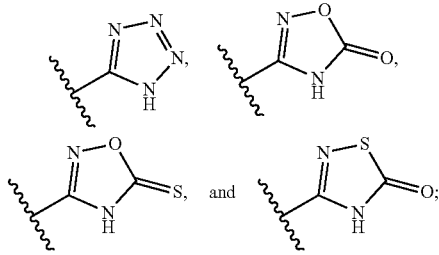

each R$^2$ and each R$^7$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{2-9}$heteroaryl;

R$^3$ and R$^4$ are independently selected from H and C$_{1-6}$alkyl;

R$^5$ is selected from H, C$_{1-6}$alkyl, C$_{1-6}$haloalkyl, C$_{1-6}$cycloalkyl, —C$_{1-6}$alkyl-C$_{3-8}$cycloalkyl, phenyl, —C$_{1-6}$alkyl-phenyl, and C$_{2-9}$heteroaryl;

R$^6$ is independently H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, $C_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;
each R$^{11}$ is independently selected from H and $C_{1-6}$alkyl;
each R$^{12}$ is independently selected from H and $C_{1-6}$alkyl;
R$^{13}$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;
p is 0, 1, 2, or 3; and
q is 0, 1, 2, or 3;
or a pharmaceutically acceptable salt or solvate thereof.

In some instances, the small molecule that binds GPR35 is a compound of Formula (XVII):

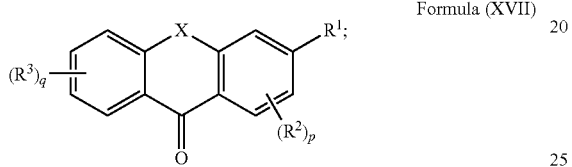

Formula (XVII)

wherein:
X is selected from —O—, —S—, and —SO$_2$—;
R$^1$ is selected from —C(O)OH, —C(O)OR$^{10}$,

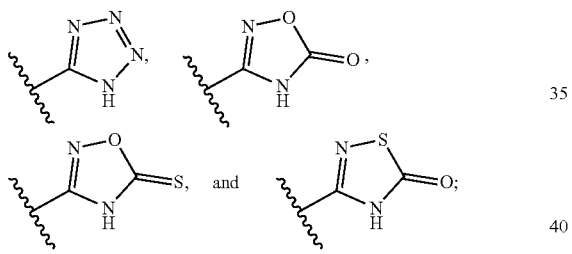

each R$^2$ and each R$^3$ is independently selected from halogen, —CN, —OH, —OR$^9$, —SR$^3$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each R$^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR$^{11}$, —N(R$^{11}$)$_2$, $C_{1-6}$alkyl, $C_{3-8}$cycloalkyl, —C(O)R$^{12}$, and —C(O)OR$^{12}$;
each R$^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;
each R$^{11}$ is independently selected from H and $C_{1-6}$alkyl;
each R$^{12}$ is independently selected from H and $C_{1-6}$alkyl;
p is 0, 1, 2, or 3; and
q is 0, 1, 2, 3, or 4;
or a pharmaceutically acceptable salt or solvate thereof.

In some instances, the small molecule that binds GPR35 is a compound of Formula (XVIII):

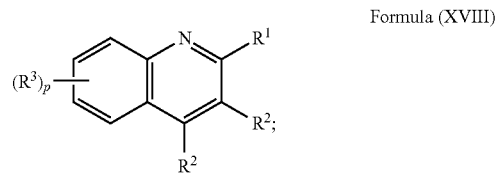

Formula (XVIII)

wherein:
R$^1$ is selected from —C(O)OH, —C(O)OR$^{10}$,

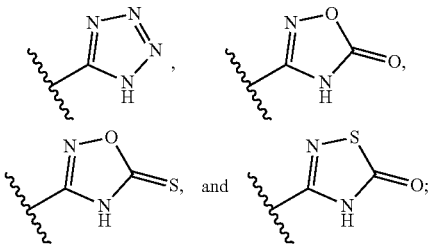

R$^2$ is independently selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each R$^3$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each R$^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR$^{11}$, —N(R$^{11}$)$_2$, $C_{1-6}$alkyl, $C_{3-8}$cycloalkyl, —C(O)R$^{12}$, and —C(O)OR$^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
each $R^{12}$ is independently selected from H and $C_{1-6}$alkyl; and
p is 0, 1, 2, 3, or 4;
or a pharmaceutically acceptable salt or solvate thereof.

In some instances, the small molecule that binds GPR35 is a compound of Formula (XIX):

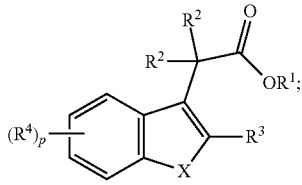

Formula (XIX)

wherein:
X is selected from —O—, —S—, and —$NR^{13}$-;
$R^1$ is selected from H and $C^{1-6}$alkyl;
$R^2$ is independently selected from H, halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^3$ is selected from H, halogen, —CN, —OH, —$OR^9$, —$SR^9$—$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and-$C_{1-6}$alkyl-$C_{3-8}$cycloalkyl;
each $R^4$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$C(O)R^{12}$, and —$(O)OR^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
each $R^{12}$ is independently selected from H and $C_{1-6}$alkyl;
$R^{13}$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl; and
p is 0, 1, 2, 3, or 4;
or a pharmaceutically acceptable salt or solvate thereof.

In some instances, the small molecule that binds GPR35 is a compound of Formula (XX):

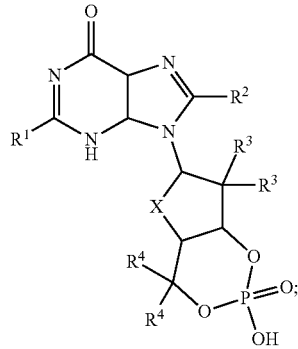

Formula (XX)

wherein:
X is selected from —O— and —$C(R^{14})_2$-;
$R^1$ is selected from H, halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^2$ is selected from H, halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each $R^3$ and each $R^4$ is selected from H, halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$ alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;
each R$^{12}$ is independently selected from H and C$_{1-6}$alkyl;
each R$^{14}$ is independently selected from H, halogen, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl; and or a pharmaceutically acceptable salt or solvate thereof.

In some instances, the small molecule that binds GPR35 is a compound of Formula (XXI):

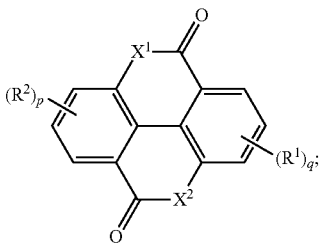

Formula (XXI)

wherein:
X$^1$ and X$^2$ are independently selected from —O— and —S—;
each R$^1$ and each R$^2$ are independently selected from halogen, —CN, OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, and —N(R$^{11}$)$_2$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;
each R$^{12}$ is independently selected from H and C$_{1-6}$alkyl;
R$^{13}$ is selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl;
p is 0, 1, 2, or 3;
q is 0, 1, 2, or 3; and
or a pharmaceutically acceptable salt or solvate thereof.

In some instances, the small molecule that binds GPR35 is a compound of Formula (XXII):

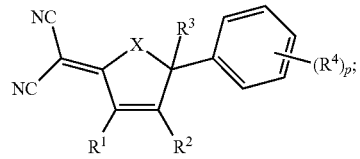

Formula (XXII)

wherein:
X is selected from —O— and —S—;
R$^1$, R$^2$, and R$^3$ are independently selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^4$ is selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$_{12}$, and —C(O)OR$^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
each $R^{12}$ is independently selected from H and $C_{1-6}$alkyl; and
p is 0, 1, 2, 3, or 4;
or a pharmaceutically acceptable salt or solvate thereof.

In some instances, the small molecule that binds GPR35 is a compound of Formula (XXIII):

Formula (XXIII)

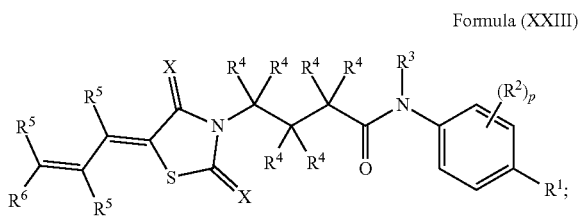

wherein:
each X is independently selected from —O— and —S—;
$R^1$ is selected from —C(O)OH, —C(O)OR$^{10}$,

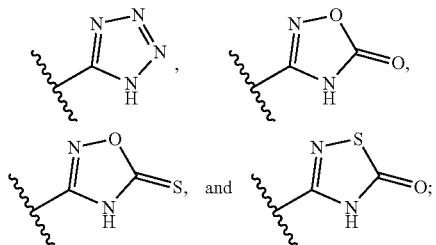

each $R^2$ is selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^3$ is selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl;
each $R^4$ and each $R^5$ are independently selected from H, halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$_9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

$R^6$ is selected from $C_{3-8}$cycloalkyl, $C_{2-9}$heterocycloalkyl, $C_{2-9}$heteroaryl, and phenyl, wherein $C_{3-8}$cycloalkyl, $C_{2-9}$heterocycloalkyl, $C_{2-9}$heteroaryl, and phenyl are optionally substituted with one or two groups independently selected from $C_{1-6}$alkyl, —OR$^{11}$, —N(R$^{11}$)$_2$, $C_{1-6}$alkyl, $C_{3-8}$cycloalkyl, —C(O)R$^{12}$, and —C(O)OR$^{12}$;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and-$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and-$C_{1-6}$alkyl-$C_{2-9}$heteroaryl are optionally substituted with one or two groups independently selected from $C_{1-6}$alkyl, —OR$^{11}$, —N(R$^{11}$)$_2$, $C_{1-6}$alkyl, $C_{3-8}$cycloalkyl, —C(O)R$^{12}$, and —C(O)OR$^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, and —$N(R^{11})_2$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
each $R^{12}$ is independently selected from H and $C_{1-6}$alkyl;
and p1 p is 0, 1, 2, 3, or 4;
or a pharmaceutically acceptable salt or solvate thereof.

In some instances, the small molecule that binds GPR35 is a compound of Formula (XXIV):

Formula (XXIV)

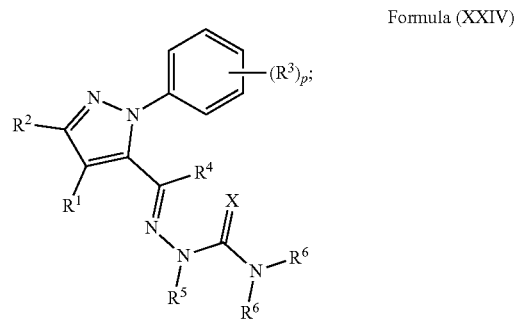

wherein:
X is selected from —O— and —S—;
$R^1$ is selected from —C(O)OH, —C (O)OR$^{10}$,

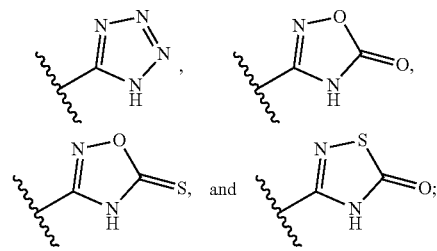

each R² is selected from H, halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, C₁₋₆alkyl, —C₁₋₆alkyl-OH, —C₁₋₆alkyl-OR⁹, —C₁₋₆alkyl-N(R¹⁰)₂, C₂₋₆alkenyl, C₂₋₆alkynyl, C₁₋₆haloalkyl, C₃₋₈cycloalkyl, and —C₁₋₆alkyl-C₃₋₈cycloalkyl;

each R³ is selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R₉, —NR¹⁰C(O)OR⁹, C₁₋₆alkyl, —C₁₋₆alkyl-OH, —C₁₋₆alkyl-OR⁹, —C₁₋₆ alkyl-N(R¹⁰)₂, C₂₋₆alkenyl, C₂₋₆alkynyl, C₁₋₆haloalkyl, C₃₋₈cycloalkyl, and -C₁₋₆alkyl-C₃₋₈cycloalkyl;

R⁴ is selected from H, C₁₋₆alkyl, C₁₋₆haloalkyl, and C₃₋₈cycloalkyl;

R⁵ is selected from H, C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, and C₂₋₉heteroaryl;

R⁶ is independently selected from H, C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, and C₂₋₉heteroaryl;

each R⁹ is independently selected from C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, C₂₋₉heterocycloalkyl, —C₁₋₆alkyl-C₂₋₉heterocycloalkyl, —C₁₋₆alkyl-C₂₋₉heterocycloalkyl, C₂₋₉heteroaryl, and —C₁₋₆alkyl-C₂₋₉heteroaryl, wherein C₁₋₆alkyl, phenyl, —C₁₋₆alkyl-phenyl, —C₁₋₆alkyl-C₂₋₉heterocycloalkyl, C₂₋₉heteroaryl, and —C₁₋₆alkyl-C₂₋₉heteroaryl are optionally substituted with one or two groups independently selected from C₁₋₆alkyl, —OR¹¹, —N(R¹¹)₂, C₁₋₆alkyl, C₃₋₈cycloalkyl, —C(O)R¹², and —C(O)OR¹²;

each R¹⁰ is independently selected from H, C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, and C₂₋₉heteroaryl, wherein C₁₋₆alkyl, phenyl, —C₁₋₆alkyl-phenyl, and C₂₋₉heteroaryl are optionally substituted with one or two groups independently selected from halogen, C₁₋₆alkyl, and —N(R¹¹)₂; or two R¹⁰ and the nitrogen atom to which they are attached are combined to form a 5- or 6-membered heterocycloalkyl ring optionally substituted with one, two, or three groups independently selected from C₁₋₆alkyl, oxo, and —C(O)OH, each R¹¹ is independently selected from H and C₁₋₆alkyl;

each R¹² is independently selected from H and C₁₋₆alkyl; and p is 0, 1, 2, 3, or 4;

or a pharmaceutically acceptable salt or solvate thereof.

In some instances, the small molecule that binds GPR35 is a compound of Formula (XXV):

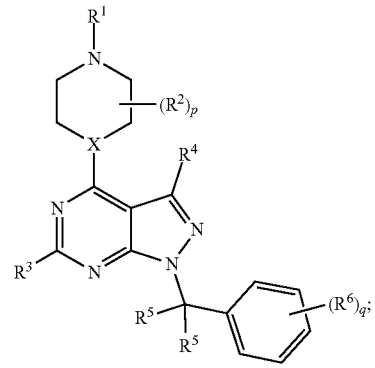

Formula (XXV)

wherein:

X is selected from CR² or N;

R¹ is selected from C₃₋₈cycloalkyl, C₂₋₉heterocycloalkyl, C₂₋₉heteroaryl, and phenyl, wherein C₃₋₈cycloalkyl, C₂₋₉heterocycloalkyl, C₂₋₉heteroaryl, and phenyl are optionally substituted with one or two groups independently selected from C₁₋₆alkyl, —OR¹¹, —N(R¹¹)₂, C₁₋₆alkyl, C₃₋₈cycloalkyl, —C(O)R¹², and —C(O)OR¹²;

each R² and each R⁶ is selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, C₁₋₆alkyl, —C₁₋₆alkyl-OH, —C₁₋₆alkyl-OR⁹, —C₁₋₆alkyl-N(R¹⁰)₂, C₂₋₆alkenyl, C₂₋₆alkynyl, C₁₋₆haloalkyl, C₃₋₈cycloalkyl, and —C₁₋₆alkyl-C₃₋₈cycloalkyl;

R³ and R⁴ are independently selected from H, halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, C₁₋₆alkyl, —C₁₋₆alkyl-OH, —C₁₋₆alkyl-OR⁹, —C₁₋₆alkyl-N(R¹⁰)₂, C₂₋₆alkenyl, C₂₋₆alkynyl, C₁₋₆haloalkyl, C₃₋₈cycloalkyl, and —C₁₋₆alkyl-C₃₋₈cycloalkyl;

each R⁵ are independently selected from H, halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, C₁₋₆alkyl, —C₁₋₆alkyl-OH, —C₁₋₆alkyl-OR⁹, —C₁₋₆alkyl-N(R¹⁰)₂, C₂₋₆alkenyl, C₂₋₆alkynyl, C₁₋₆haloalkyl, C₃₋₈cycloalkyl, and —C₁₋₆alkyl-C₃₋₈cycloalkyl;

each R⁹ is independently selected from C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, C₂₋₉heterocycloalkyl, —C₁₋₆alkyl-C₂₋₉heterocycloalkyl, C₂₋₉heteroaryl, and —C₁₋₆alkyl-C₂₋₉heteroaryl, wherein C₁₋₆alkyl, phenyl, —C₁₋₆alkyl-phenyl, —C₁₋₆alkyl-C₂₋₉heterocycloalkyl, C₂₋₉heteroaryl, and —C₁₋₆alkyl-C₂₋₉heteroaryl are optionally substituted with one or two groups independently selected from C₁₋₆alkyl, —OR¹¹, —N(R¹¹)₂, C₁₋₆alkyl, C₃₋₈cycloalkyl, —C(O)R¹², and —C(O)OR¹²;

each R¹⁰ is independently selected from H, C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, and C₂₋₉heteroaryl, wherein C₁₋₆alkyl, phenyl, —C₁₋₆alkyl-phenyl, and C₂₋₉heteroaryl are optionally substituted with one or two groups independently selected from halogen, C₁₋₆alkyl, and —N(R¹¹)₂; or two R¹⁰ and the nitrogen atom to which they are attached are combined to form a 5- or 6-membered heterocycloalkyl ring optionally substituted with one, two, or three groups independently selected from C₁₋₆alkyl, oxo, and —C(O)OH;

each R¹¹ is independently selected from H and C₁₋₆alkyl;
each R¹² is independently selected from H and C₁₋₆alkyl;
p is 0, 1, 2, 3, 4, 5, or 6; and
q is 0, 1, 2, 3, or 4;

or a pharmaceutically acceptable salt or solvate thereof.

In some instances, the small molecule that binds GPR35 is a compound of Formula (XXVI):

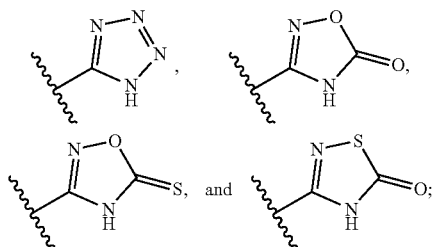

Formula (XXVI)

wherein:

R¹ is selected from —C(O)OH, —C(O)OR¹⁰,

[structures shown]

each R² is selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, C₁₋₆alkyl, —C₁₋₆alkyl-OH, —C₁₋₆alkyl-OR⁹, —C₁₋₆ alkyl-N(R¹⁰)₂, C₂₋₆alkenyl, C₂₋₆alkynyl, C₁₋₆haloalkyl, C₃₋₈cycloalkyl, and —C₁₋₆alkyl-C₃₋₈cycloalkyl;

each R⁹ is independently selected from C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, C₂₋₉heterocycloalkyl, —C₁₋₆alkyl-C₂₋₉heterocycloalkyl, C₂₋₉heteroaryl, and —C₁₋₆alkyl-C₂₋₉heteroaryl, wherein C₁₋₆alkyl, phenyl, —C₁₋₆alkyl-phenyl, —C₁₋₆alkyl-C₂₋₉heterocycloalkyl, C₂₋₉heteroaryl, and —C₁₋₆alkyl-C₂₋₉heteroaryl are optionally substituted with one or two groups independently selected from C₁₋₆alkyl, —OR¹¹, —N(R¹¹)₂, C₁₋₆alkyl, C₃₋₈cycloalkyl, —C(O)R¹², and —C(O)OR¹²;

each R¹⁰ is independently selected from H, C₁₋₆alkyl, C₁₋₆haloalkyl, C₃₋₈cycloalkyl, —C₁₋₆alkyl-C₃₋₈cycloalkyl, phenyl, —C₁₋₆alkyl-phenyl, and C₂₋₉heteroaryl, wherein C₁₋₆alkyl, phenyl, —C₁₋₆alkyl-phenyl, and C₂₋₉heteroaryl are optionally substituted with one or two groups independently selected from halogen, C₁₋₆alkyl, and —N(R¹¹)₂; or two R¹⁰ and the nitrogen atom to which they are attached are combined to form a 5- or 6-membered heterocycloalkyl ring optionally substituted with one, two, or three groups independently selected from C₁₋₆alkyl, oxo, and —C(O)OH;

each R¹¹ is independently selected from H and C₁₋₆alkyl;
each R¹² is independently selected from H and C₁₋₆alkyl;
p is 0, 1, 2, 3, or 4; and or a pharmaceutically acceptable salt or solvate thereof.

In some instances, the small molecule that binds GPR35 is selected from zaprinast, lodoxamide, bufrolin, TC-G 1001, nedocromil, PSB-13253, 6-bromo-7-hydroxy-8-nitro-3-(1H-tetrazol-5-yl)-2H-chromen-2-one, 6-bromo-7-hydroxy-8-nitro-2-oxo-2H-chromene-3-carboxylic acid, 7-deshydroxypyrogallin-4-carboxylic acid (DCA), morin, cromolyn, T₃, reverse T₃, YE-210, cromoglicic acid, nedocromil, pamoic acid, and tyrphostin-51.

In some instances, the small molecule that binds GPR35 is selected from pamoic acid, amlexanox, furosemide, doxantrazole, kynurenic acid, DHICA, cyclic guanosine monophosphate (cGMP), 2,3,5-THB, ellagic acid,, LPA species, and YE120.

In some instances, the small molecule that binds GPR35 is selected from ML-145, ML-194, and ML-144.

In some instances, the small molecule that binds GPR35 is selected from:

[chemical structures]

-continued
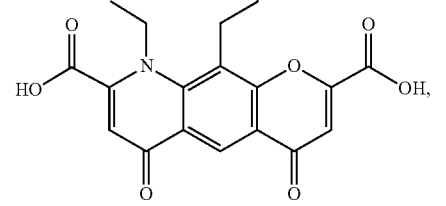
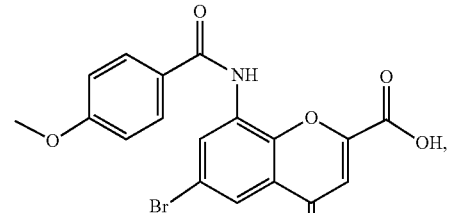
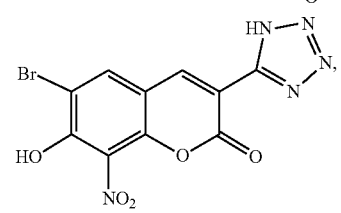
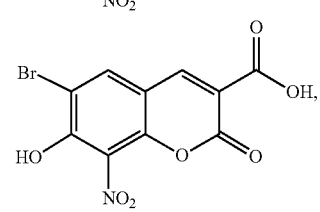
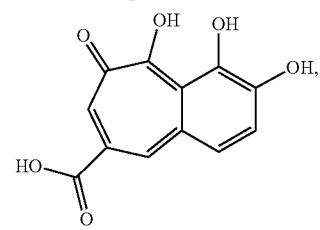
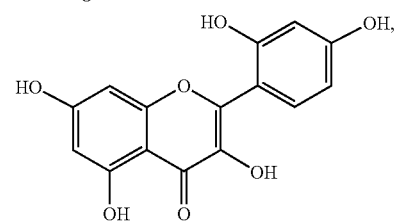
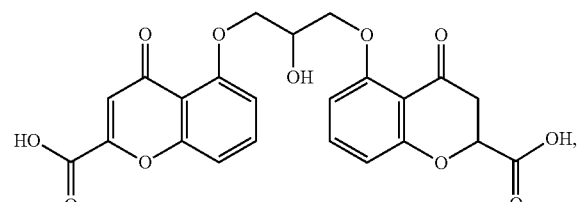
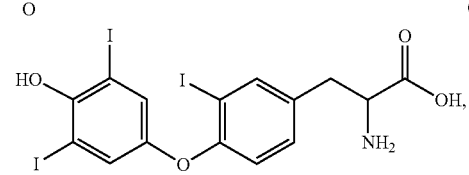
-continued
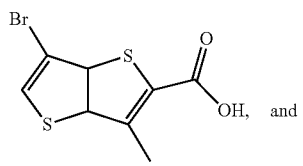
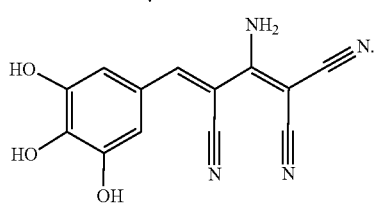
In some instances, the small molecule that binds GPR35 is selected from:
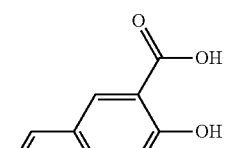
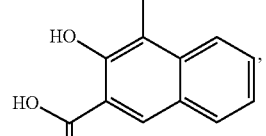
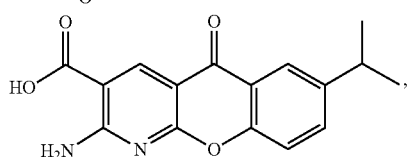
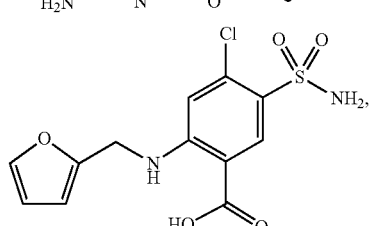
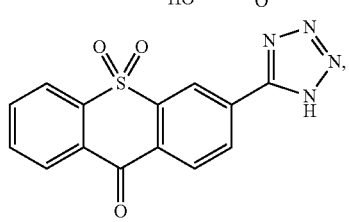
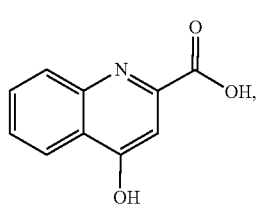

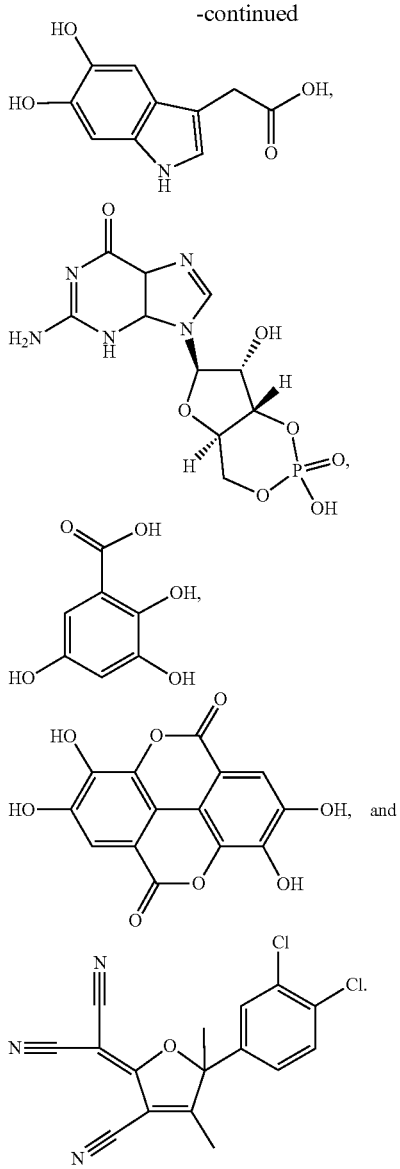

In some instances, the small molecule that binds GPR35 is selected from:

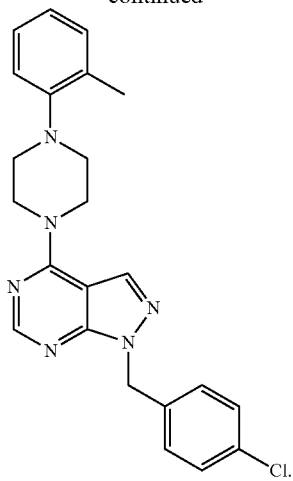

TL1A Modulators

In some embodiments, the therapeutic agent comprises a modulator of Tumor Necrosis Factor Ligand 1A (TL1A) (UniProtKB: 095150). In some embodiments, the modulator of TL1A is an antagonist of TL1A. In some embodiments the therapeutic agent comprises an inhibitor of TL1A expression or activity. In some cases, the inhibitor of TL1A expression or activity is effective to inhibit TL1A-DR3 binding. In some embodiments, the inhibitor of TL1A expression or activity comprises an allosteric modulator of TL1A. An allosteric modulator of TL1A may indirectly influence the effects TL1A on DR3, or TR6/DcR3 on TL1A or DR3. The inhibitor of TL1A expression or activity may be a direct inhibitor or indirect inhibitor. Non-limiting examples of an inhibitor of TL1A expression include RNA to protein TL1A translation inhibitors, antisense oligonucleotides targeting the TNFSF15 mRNA (such as miRNAs, or siRNA), epigenetic editing (such as targeting the DNA-binding domain of TNFSF15, or post-translational modifications of histone tails and/or DNA molecules). Non-limiting examples of an inhibitor of TL1A activity include antagonists to the TL1A receptors, (DR3 and TR6/DcR3), antagonists to TL1A antigen, and antagonists to gene expression products involved in TL1A mediated disease. Antagonists as disclosed herein, may include, but are not limited to, an anti-TL1A antibody, an anti-TL1A-binding antibody fragment, or a small molecule. The small molecule may be a small molecule that binds to TL1A or DR3. The anti-TL1A antibody may be monoclonal or polyclonal. The anti-TL1A antibody may be humanized or chimeric. The anti-TL1A antibody may be a fusion protein. The anti-TL1A antibody may be a blocking anti-TL1A antibody. A blocking antibody blocks binding between two proteins, e.g., a ligand and its receptor. Therefore, a TL1A blocking antibody includes an antibody that prevents binding of TL1A to DR3 or TR6/DcR3 receptors. In a non-limiting example, the TL1A blocking antibody binds to DR3. In another example. the TL1A blocking antibody binds to DcR3. In some cases. the TL1A antibody is an anti-TL1A antibody that specifically binds to TL1A.

The anti-TL1A antibody. in some embodiments. specifically targets part of amino acid sequence provided in SEQ ID NO: 450, which is the human isoform VEGI-192 (NP_001191273.1). In some instances, the anti-TL1A antibody. specifically targets part of amino acid sequence provided in SEQ ID ID NO: 45, which is the human isoform VEGI0251 (NP_005109.2).

The anti-TL1A antibody may comprise one or more of the antibody sequences of Table 5. The anti-DR3 antibody may comprise an amino acid sequence that is at least 85% identical to any one of SEQ ID NOS: 10358-10370 and an amino acid sequence that is at least 85% identical to any one of SEQ ID NOS: 10371-10375. The anti-DR3 antibody may comprise an amino acid sequence comprising the HCDR1, HCDR2, HCDR3 domains of any one of SEQ ID NOS: 10358-10370 and the LCDR1, LCDR2, and LCDR3 domains of any one of SEQ ID NOS: 10371-10375.

In some embodiments, an anti-TL1A antibody comprises a heavy chain comprising three complementarity-determining regions: HCDR1, HCDR2, and HCDR3; and a light chain comprising three complementarity-determining regions: LCDR1, LCDR2, and LCDR3. In some embodiments, the anti-TL1A antibody comprises a HCDR1 comprising SEQ ID NO: 10209, a HCDR2 comprising SEQ ID NO: 10210, a HCDR3 comprising SEQ ID NO: 10211, a LCDR1 comprising SEQ ID NO: 10212, a LCDR2 comprising SEQ ID NO: 10213, and a LCDR3 comprising SEQ ID NO: 10214. In some cases, the anti-TL1A antibody comprises a heavy chain (HC) variable domain comprising SEQ ID NO: 10215 and a light chain (LC) variable domain comprising SEQ ID NO: 10216.

In some embodiments, the anti-TL1A antibody comprises a HCDR1 comprising SEQ ID NO: 10217, a HCDR2 comprising SEQ ID NO: 10218, a HCDR3 comprising SEQ ID NO: 10219, a LCDR1 comprising SEQ ID NO: 10220, a LCDR2 comprising SEQ ID NO: 10221, and a LCDR3 comprising SEQ ID NO: 10222. In some cases, the anti-TL1A antibody comprises a heavy chain (HC) variable domain comprising SEQ ID NO: 10223 and a light chain (LC) variable domain comprising SEQ ID NO: 10224.

In some embodiments, the anti-TL1A antibody comprises a HCDR1 comprising SEQ ID NO: 10225, a HCDR2 comprising SEQ ID NO: 10226, a HCDR3 comprising SEQ ID NO: 10227, a LCDR1 comprising SEQ ID NO: 10228, a LCDR2 comprising SEQ ID NO: 10229, and a LCDR3 comprising SEQ ID NO: 10230. In some cases, the anti-TL1A antibody comprises a heavy chain (HC) variable domain comprising SEQ ID NO: 10231 and a light chain (LC) variable domain comprising SEQ ID NO: 10232.

In some embodiments, the anti-TL1A antibody comprises a HCDR1 comprising SEQ ID NO: 10233, a HCDR2 comprising SEQ ID NO: 10234, a HCDR3 comprising SEQ ID NO: 10235, a LCDR1 comprising SEQ ID NO: 10239, a LCDR2 comprising SEQ ID NO: 10240, and a LCDR3 comprising SEQ ID NO: 10241. In some cases, the anti-TL1A antibody comprises a HCDR1 comprising SEQ ID NO: 102000136, a HCDR2 comprising SEQ ID NO: 10237, a HCDR3 comprising SEQ ID NO: 10238, a LCDR1 comprising SEQ ID NO: 10239, a LCDR2 comprising SEQ ID NO: 10240, and a LCDR3 comprising SEQ ID NO: 10241. In some cases, the anti-TL1A antibody comprises a heavy chain (HC) variable domain comprising SEQ ID NO: 10242 and a light chain (LC) variable domain comprising SEQ ID NO: 10243. In some cases, the anti-TL1A antibody comprises a heavy chain comprising SEQ ID NO: 10244. In some cases, the anti-TL1A antibody comprises a light chain comprising SEQ ID NO: 10245.

In some embodiments, the anti-TL1A antibody comprises a HCDR1 comprising SEQ ID NO: 10246, a HCDR2 comprising SEQ ID NO: 10247, a HCDR3 comprising SEQ ID NO: 10248, a LCDR1 comprising SEQ ID NO: 10249, a LCDR2 comprising SEQ ID NO: 10250, and a LCDR3 comprising SEQ ID NO: 10251. In some cases, the anti-TL1A antibody comprises a heavy chain (HC) variable domain comprising SEQ ID NO: 10252 and a light chain (LC) variable domain comprising SEQ ID NO: 10253.

In some embodiments, the anti-TL1A antibody comprises a HCDR1 comprising SEQ ID NO: 10254, a HCDR2 comprising SEQ ID NO: 10255, a HCDR3 comprising SEQ ID NO: 10256, a LCDR1 comprising SEQ ID NO: 10257, a LCDR2 comprising SEQ ID NO: 10258, and a LCDR3 comprising SEQ ID NO: 10259. In some cases, the anti-TL1A antibody comprises a heavy chain (HC) variable domain comprising SEQ ID NO: 10260 and a light chain (LC) variable domain comprising SEQ ID NO: 10261.

In some embodiments, the anti-TL1A antibody comprises a HCDR1 comprising SEQ ID NO: 10262, a HCDR2 comprising SEQ ID NO: 10264, a HCDR3 comprising SEQ ID NO: 10265, a LCDR1 comprising SEQ ID NO: 10267, a LCDR2 comprising SEQ ID NO: 10269, and a LCDR3 comprising SEQ ID NO: 10270. In some cases, the anti-TL1A antibody comprises a heavy chain (HC) variable domain comprising SEQ ID NO: 10271 and a light chain (LC) variable domain comprising SEQ ID NO: 10275. In some cases, the anti-TL1A antibody comprises a heavy chain (HC) variable domain comprising SEQ ID NO: 10271 and a light chain (LC) variable domain comprising SEQ ID NO: 10276. In some cases, the anti-TL1A antibody comprises a heavy chain (HC) variable domain comprising SEQ ID NO: 10271 and a light chain (LC) variable domain comprising SEQ ID NO: 10277. In some cases, the anti-TL1A antibody comprises a heavy chain (HC) variable domain comprising SEQ ID NO: 10271 and a light chain (LC) variable domain comprising SEQ ID NO: 10278.

In some embodiments, the anti-TL1A antibody comprises a HCDR1 comprising SEQ ID NO: 10262, a HCDR2 comprising SEQ ID NO: 10264, a HCDR3 comprising SEQ ID NO: 10265, a LCDR1 comprising SEQ ID NO: 10268, a LCDR2 comprising SEQ ID NO: 10269, and a LCDR3 comprising SEQ ID NO: 10270. In some cases, the anti-TL1A antibody comprises a heavy chain (HC) variable domain comprising SEQ ID NO: 10271 and a light chain (LC) variable domain comprising SEQ ID NO: 10279. In some cases, the anti-TL1A antibody comprises a heavy chain (HC) variable domain comprising SEQ ID NO: 10271 and a light chain (LC) variable domain comprising SEQ ID NO: 10280. In some cases, the anti-TL1A antibody comprises a heavy chain (HC) variable domain comprising SEQ ID NO: 10271 and a light chain (LC) variable domain comprising SEQ ID NO: 10281. In some cases, the anti-TL1A antibody comprises a heavy chain (HC) variable domain comprising SEQ ID NO: 10271 and a light chain (LC) variable domain comprising SEQ ID NO: 10282.

In some embodiments, the anti-TL1A antibody comprises a HCDR1 comprising SEQ ID NO: 10262, a HCDR2 comprising SEQ ID NO: 10264, a HCDR3 comprising SEQ ID NO: 10265, a LCDR1 comprising SEQ ID NO: 10267, a LCDR2 comprising SEQ ID NO: 10269, and a LCDR3 comprising SEQ ID NO: 10270. In some cases, the anti-TL1A antibody comprises a heavy chain (HC) variable domain comprising SEQ ID NO: 10272 and a light chain (LC) variable domain comprising SEQ ID NO: 10275. In some cases, the anti-TL1A antibody comprises a heavy chain (HC) variable domain comprising SEQ ID NO: 10272 and a light chain (LC) variable domain comprising SEQ ID NO: 10276. In some cases, the anti-TL1A antibody comprises a heavy chain (HC) variable domain comprising SEQ ID NO: 10272 and a light chain (LC) variable domain comprising SEQ ID NO: 10277. In some cases, the anti-TL1A antibody comprises a heavy chain (HC) variable domain comprising SEQ ID NO: 10272 and a light chain (LC) variable domain comprising SEQ ID NO: 10278.

In some embodiments, the anti-TL1A antibody comprises a HCDR1 comprising SEQ ID NO: 10262, a HCDR2 comprising SEQ ID NO: 10264, a HCDR3 comprising SEQ ID NO: 10265, a LCDR1 comprising SEQ ID NO: 10268, a LCDR2 comprising SEQ ID NO: 10269, and a LCDR3comprising SEQ ID NO: 10270. In some cases, the anti-TL1A antibody comprises a heavy chain (HC) variable domain comprising SEQ ID NO: 10272 and a light chain (LC) variable domain comprising SEQ ID NO: 10279. In some cases, the anti-TL1A antibody comprises a heavy chain (HC) variable domain comprising SEQ ID NO: 10272 and a light chain (LC) variable domain comprising SEQ ID NO: 10280. In some cases, the anti-TL1A antibody comprises a heavy chain (HC) variable domain comprising SEQ ID NO: 10272 and a light chain (LC) variable domain comprising SEQ ID NO: 10281. In some cases, the anti-TL1A antibody comprises a heavy chain (HC) variable domain comprising SEQ ID NO: 10272 and a light chain (LC) variable domain comprising SEQ ID NO: 10282.

In some embodiments, the anti-TL1A antibody comprises a HCDR1 comprising SEQ ID NO: 10263, a HCDR2 comprising SEQ ID NO: 10264, a HCDR3 comprising SEQ ID NO: 10266, a LCDR1 comprising SEQ ID NO: 10267, a LCDR2 comprising SEQ ID NO: 10269, and a LCDR3comprising SEQ ID NO: 10270. In some cases, the anti-TL1A antibody comprises a heavy chain (HC) variable domain comprising SEQ ID NO: 10273 and a light chain (LC) variable domain comprising SEQ ID NO: 10275. In some cases, the anti-TL1A antibody comprises a heavy chain (HC) variable domain comprising SEQ ID NO: 10273 and a light chain (LC) variable domain comprising SEQ ID NO: 10276. In some cases, the anti-TL1A antibody comprises a heavy chain (HC) variable domain comprising SEQ ID NO: 10273 and a light chain (LC) variable domain comprising SEQ ID NO: 10277. In some cases, the anti-TL1A antibody comprises a heavy chain (HC) variable domain comprising SEQ ID NO: 10273 and a light chain (LC) variable domain comprising SEQ ID NO: 10278. In some cases, the anti-TL1A antibody comprises a heavy chain (HC) variable domain comprising SEQ ID NO: 10273 and a light chain (LC) variable domain comprising SEQ ID NO: 10279. In some cases, the anti-TL1A antibody comprises a heavy chain (HC) variable domain comprising SEQ ID NO: 10273 and a light chain (LC) variable domain comprising SEQ ID NO: 10280. In some cases, the anti-TL1A antibody comprises a heavy chain (HC) variable domain comprising SEQ ID NO: 10273 and a light chain (LC) variable domain comprising SEQ ID NO: 10281. In some cases, the anti-TL1A antibody comprises a heavy chain (HC) variable domain comprising SEQ ID NO: 10273 and a light chain (LC) variable domain comprising SEQ ID NO: 10282.

In some embodiments, the anti-TL1A antibody comprises a HCDR1 comprising SEQ ID NO: 10263, a HCDR2 comprising SEQ ID NO: 10264, a HCDR3 comprising SEQ ID NO: 10266, a LCDR1 comprising SEQ ID NO: 10268, a LCDR2 comprising SEQ ID NO: 10269, and a LCDR3comprising SEQ ID NO: 10270. In some cases, the anti-TL1A antibody comprises a heavy chain (HC) variable domain comprising SEQ ID NO: 10274 and a light chain (LC) variable domain comprising SEQ ID NO: 10279. In some cases, the anti-TL1A antibody comprises a heavy chain (HC) variable domain comprising SEQ ID NO: 10274 and a light chain (LC) variable domain comprising SEQ ID NO: 10280. In some cases, the anti-TL1A antibody comprises a heavy chain (HC) variable domain comprising SEQ ID NO: 10274 and a light chain (LC) variable domain comprising SEQ ID NO: 10281. In some cases, the anti-TL1A antibody comprises a heavy chain (HC) variable domain comprising SEQ ID NO: 10274 and a light chain (LC) variable domain comprising SEQ ID NO: 10282. In some cases, the anti-TL1A antibody comprises a heavy chain (HC) variable domain comprising SEQ ID NO: 10274 and a light chain (LC) variable domain comprising SEQ ID NO: 10275. In some cases, the anti-TL1A antibody comprises a heavy chain (HC) variable domain comprising SEQ ID NO: 10274 and a light chain (LC) variable domain comprising SEQ ID NO: 10276. In some cases, the anti-TL1A antibody comprises a heavy chain (HC) variable domain comprising SEQ ID NO: 10274 and a light chain (LC) variable domain comprising SEQ ID NO: 10277. In some cases, the anti-TL1A antibody comprises a heavy chain (HC) variable domain comprising SEQ ID NO: 10274 and a light chain (LC) variable domain comprising SEQ ID NO: 10278.

In some embodiments, the anti-TL1A antibody comprises a HCDR1 comprising SEQ ID NO: 10283, a HCDR2 comprising SEQ ID NO: 10284, a HCDR3 comprising SEQ ID NO: 10285, a LCDR1 comprising SEQ ID NO: 10286, a LCDR2 comprising SEQ ID NO: 10287, and a LCDR3comprising SEQ ID NO: 10288. In some cases, the anti-TL1A antibody comprises a heavy chain (HC) variable domain comprising SEQ ID NO: 10289 and a light chain (LC) variable domain comprising SEQ ID NO: 10294. In some cases, the anti-TL1A antibody comprises a heavy chain (HC) variable domain comprising SEQ ID NO: 10289 and a light chain (LC) variable domain comprising SEQ ID NO: 10295. In some cases, the anti-TL1A antibody comprises a heavy chain (HC) variable domain comprising SEQ ID NO: 10289 and a light chain (LC) variable domain comprising SEQ ID NO: 10296. In some cases, the anti-TL1A antibody comprises a heavy chain (HC) variable domain comprising SEQ ID NO: 10289 and a light chain (LC) variable domain comprising SEQ ID NO: 10297. In some cases, the anti-TL1A antibody comprises a heavy chain (HC) variable domain comprising SEQ ID NO: 10290 and a light chain (LC) variable domain comprising SEQ ID NO: 10294. In some cases, the anti-TL1A antibody comprises a heavy chain (HC) variable domain comprising SEQ ID NO: 10290 and a light chain (LC) variable domain comprising SEQ ID NO: 10295. In some cases, the anti-TL1A antibody comprises a heavy chain (HC) variable domain comprising SEQ ID NO: 10290 and a light chain (LC) variable domain comprising SEQ ID NO: 10296. In some cases, the anti-TL1A antibody comprises a heavy chain (HC) variable domain comprising SEQ ID NO: 10290 and a light chain (LC) variable domain comprising SEQ ID NO: 10297. In some cases, the anti-TL1A antibody comprises a heavy chain (HC) variable domain comprising SEQ ID NO: 10291 and a light chain (LC) variable domain comprising SEQ ID NO: 10294. In some cases, the anti-TL1A antibody comprises a heavy chain (HC) variable domain comprising SEQ ID NO: 10291 and a light chain (LC) variable domain comprising SEQ ID NO: 10295. In some cases, the anti-TL1A antibody comprises a heavy chain (HC) variable domain comprising SEQ ID NO: 10291 and a light chain (LC) variable domain comprising SEQ ID NO: 10296. In some cases, the anti-TL1A antibody comprises a heavy chain (HC) variable domain comprising SEQ ID NO: 10291 and a light chain (LC) variable domain comprising SEQ ID NO: 10297. In some cases, the anti-TL1A antibody comprises a heavy chain (HC) variable domain comprising SEQ ID NO: 10292 and a light chain (LC) variable domain comprising SEQ ID NO: 10294. In some cases, the anti-TL1A antibody comprises a heavy chain (HC) variable domain comprising SEQ ID NO: 10292 and a light chain (LC) variable domain comprising SEQ ID NO: 10295. In some cases, the anti-TL1A antibody comprises a heavy chain (HC) variable domain comprising SEQ ID NO: 10292 and a light chain (LC) variable domain comprising SEQ ID NO: 10296. In some cases, the anti-TL1A antibody comprises a heavy chain (HC) variable domain comprising SEQ ID NO: 10292 and a light chain (LC) variable domain comprising SEQ ID NO: 10297. In some cases, the anti-TL1A antibody comprises a heavy chain (HC) variable domain comprising SEQ ID NO: 10293 and a light chain (LC) variable domain comprising SEQ ID NO: 10294. In some cases, the anti-TL1A antibody comprises a heavy chain (HC) variable domain comprising SEQ ID NO: 10293 and a light chain (LC) variable domain comprising SEQ ID NO: 10295. In some cases, the anti-TL1A antibody comprises a heavy chain (HC) variable domain comprising SEQ ID NO: 10293 and a light chain (LC) variable domain comprising SEQ ID NO: 10296. In some cases, the anti-TL1A antibody comprises a heavy chain (HC) variable domain comprising SEQ ID NO: 10293 and a light chain (LC) variable domain comprising SEQ ID NO: 10297.

In some embodiments, the anti-TL1A antibody comprises a HCDR1 comprising SEQ ID NO: 10298, a HCDR2 comprising SEQ ID NO: 10299, a HCDR3 comprising SEQ ID NO: 10300, a LCDR1 comprising SEQ ID NO: 10301, a LCDR2 comprising SEQ ID NO: 10302, and a LCDR3comprising SEQ ID NO: 10303. In some cases, the anti-TL1A antibody comprises a heavy chain (HC) variable domain comprising SEQ ID NO: 10304 and a light chain (LC) variable domain comprising SEQ ID NO: 10305. In some cases, the anti-TL1A antibody comprises a heavy chain (HC) variable domain comprising SEQ ID NO: 10306 and a light chain (LC) variable domain comprising SEQ ID NO: 10307. In some cases, the anti-TL1A antibody comprises a heavy chain (HC) variable domain comprising SEQ ID NO: 10308 and a light chain (LC) variable domain comprising SEQ ID NO: 10309. In some cases, the anti-TL1A antibody comprises a heavy chain (HC) variable domain comprising SEQ ID NO: 10310 and a light chain (LC) variable domain comprising SEQ ID NO: 10311. In some cases, the anti-TL1A antibody comprises a heavy chain (HC) variable domain comprising SEQ ID NO: 10312 and a light chain (LC) variable domain comprising SEQ ID NO: 10313. In some cases, the anti-TL1A antibody comprises a heavy chain (HC) variable domain comprising SEQ ID NO: 10314 and a light chain (LC) variable domain comprising SEQ ID NO: 10315. In some cases, the anti-TL1A antibody comprises a heavy chain (HC) variable domain comprising SEQ ID NO: 10316 and a light chain (LC) variable domain comprising SEQ ID NO: 10317. In some cases, the anti-TL1A antibody comprises a heavy chain (HC) variable domain comprising SEQ ID NO: 10318 and a light chain (LC) variable domain comprising SEQ ID NO: 10319. In some cases, the anti-TL1A antibody comprises a heavy chain (HC) variable domain comprising SEQ ID NO: 10320 and a light chain (LC) variable domain comprising SEQ ID NO: 10321. In some cases, the anti-TL1A antibody comprises a heavy chain (HC) variable domain comprising SEQ ID NO: 10322 and a light chain (LC) variable domain comprising SEQ ID NO: 10323. In some cases, the anti-TL1A antibody comprises a heavy chain (HC) variable domain comprising SEQ ID NO: 10324 and a light chain (LC) variable domain comprising SEQ ID NO: 10325. In some cases, the anti-TL1A antibody comprises a heavy chain (HC) variable domain comprising SEQ ID NO: 10326 and a light chain (LC) variable domain comprising SEQ ID NO: 10327.

In some embodiments, the anti-TL1A antibody comprises a HCDR1 comprising SEQ ID NO: 10328, a HCDR2 comprising SEQ ID NO: 10329, a HCDR3 comprising SEQ ID NO: 10330, a LCDR1 comprising SEQ ID NO: 10331, a LCDR2 comprising SEQ ID NO: 10332, and a LCDR3comprising SEQ ID NO: 10333. In some cases, the anti-TL1A antibody comprises a heavy chain (HC) variable domain comprising SEQ ID NO: 10334 and a light chain (LC) variable domain comprising SEQ ID NO: 10335.

In some embodiments, the anti-TL1A antibody comprises a HCDR1 comprising SEQ ID NO: 10336, a HCDR2 comprising SEQ ID NO: 10337, a HCDR3 comprising SEQ ID NO: 10338, a LCDR1 comprising SEQ ID NO: 10339, a LCDR2 comprising SEQ ID NO: 10340, and a LCDR3comprising SEQ ID NO: 10341. In some cases, the anti-TL1A antibody comprises a heavy chain (HC) variable domain comprising SEQ ID NO: 10342 and a light chain (LC) variable domain comprising SEQ ID NO: 10343.

In some embodiments, the anti-TL1A antibody comprises a HCDR1 comprising SEQ ID NO: 10346, a HCDR2 comprising SEQ ID NO: 10347, a HCDR3 comprising SEQ ID NO: 10348, a LCDR1 comprising SEQ ID NO: 10349, a LCDR2 comprising SEQ ID NO: 10350, and a LCDR3comprising SEQ ID NO: 10351. In some cases, the anti-TL1A antibody comprises a heavy chain (HC) variable domain comprising SEQ ID NO: 10344 and a light chain (LC) variable domain comprising SEQ ID NO: 10345. In some cases, the anti-TL1A antibody comprises a heavy chain (HC) variable domain comprising SEQ ID NO: 10352 and a light chain (LC) variable domain comprising SEQ ID NO: 10353. In some cases, the anti-TL1A antibody comprises a heavy chain (HC) variable domain comprising SEQ ID NO: 10354 and a light chain (LC) variable domain comprising SEQ ID NO: 10355. In some cases, the anti-TL1A antibody comprises a heavy chain (HC) variable domain comprising SEQ ID NO: 10356 and a light chain (LC) variable domain comprising SEQ ID NO: 10357.

In some embodiments, the anti-TL1A antibody comprises a HCDR1 comprising SEQ ID NO: 10376, a HCDR2 comprising SEQ ID NO: 10377, a HCDR3 comprising SEQ ID NO: 10378, a LCDR1 comprising SEQ ID NO: 10379, a LCDR2 comprising SEQ ID NO: 10380, and a LCDR3comprising SEQ ID NO: 10381. In some cases, the anti-TL1A antibody comprises a heavy chain (HC) variable domain comprising SEQ ID NO: 10382 and a light chain (LC) variable domain comprising SEQ ID NO: 10383.

In some embodiments, the anti-TL1A antibody comprises a HCDR1 comprising SEQ ID NO: 10384, a HCDR2 comprising SEQ ID NO: 10385, a HCDR3 comprising SEQ ID NO: 10386, a LCDR1 comprising SEQ ID NO: 10387, a LCDR2 comprising SEQ ID NO: 10388, and a LCDR3comprising SEQ ID NO: 10399. In some cases, the anti-TL1A antibody comprises a heavy chain (HC) variable domain comprising SEQ ID NO: 10390 and a light chain (LC) variable domain comprising SEQ ID NO: 10391.

In some embodiments, the anti-TL1A antibody comprises one or more of A101-A177 of Table 5. In some embodiments, the anti-TL1A antibody is A100. In some embodiments, the anti-TL1A antibody is A101. In some embodiments, the anti-TL1A antibody is A102. In some embodiments, the anti-TL1A antibody is A103. In some embodiments, the anti-TL1A antibody is A104. In some embodiments, the anti-TL1A antibody is A105. In some embodiments, the anti-TL1A antibody is A106. In some embodiments, the anti-TL1A antibody is A107. In some embodiments, the anti-TL1A antibody is A108. In some embodiments, the anti-TL1A antibody is A109. In some embodiments, the anti-TL1A antibody is A110. In some embodiments, the anti-TL1A antibody is A111. In some embodiments, the anti-TL1A antibody is A112. In some embodiments, the anti-TL1A antibody is A113. In some embodiments, the anti-TL1A antibody is A114. In some embodiments, the anti-TL1A antibody is A115. In some embodiments, the anti-TL1A antibody is A116. In some embodiments, the anti-TL1A antibody is A117. In some embodiments, the anti-TL1A antibody is A118. In some embodiments, the anti-TL1A antibody is A119. In some embodiments, the anti-TL1A antibody is A120. In some embodiments, the anti-TL1A antibody is A121. In some embodiments, the anti-TL1A antibody is A122. In some embodiments, the anti-TL1A antibody is A123. In some embodiments, the anti-TL1A antibody is A124. In some embodiments, the anti-TL1A antibody is A125. In some embodiments, the anti-TL1A antibody is A126. In some embodiments, the anti-TL1A antibody is A127. In some embodiments, the anti-TL1A antibody is A128. In some embodiments, the anti-TL1A antibody is A129. In some embodiments, the anti-TL1A antibody is A130. In some embodiments, the anti-TL1A antibody is A131. In some embodiments, the anti-TL1A antibody is A132. In some embodiments, the anti-TL1A antibody is A133. In some embodiments, the anti-TL1A antibody is A134. In some embodiments, the anti-TL1A antibody is A135. In some embodiments, the anti-TL1A antibody is A136. In some embodiments, the anti-TL1A antibody is A137. In some embodiments, the anti-TL1A antibody is A138. In some embodiments, the anti-TL1A antibody is A139. In some embodiments, the anti-TL1A antibody is A140. In some embodiments, the anti-TL1A antibody is A141. In some embodiments, the anti-TL1A antibody is A142. In some embodiments, the anti-TL1A antibody is A143. In some embodiments, the anti-TL1A antibody is A144. In some embodiments, the anti-TL1A antibody is A145. In some embodiments, the anti-TL1A antibody is A146. In some embodiments, the anti-TL1A antibody is A147. In some embodiments, the anti-TL1A antibody is A148. In some embodiments, the anti-TL1A antibody is A149. In some embodiments, the anti-TL1A antibody is A150. In some embodiments, the anti-TL1A antibody is A151. In some embodiments, the anti-TL1A antibody is A152. In some embodiments, the anti-TL1A antibody is A153. In some embodiments, the anti-TL1A antibody is A154. In some embodiments, the anti-TL1A antibody is A155. In some embodiments, the anti-TL1A antibody is A156. In some embodiments, the anti-TL1A antibody is A157. In some embodiments, the anti-TL1A antibody is A158. In some embodiments, the anti-TL1A antibody is A159. In some embodiments, the anti-TL1A antibody is A160. In some embodiments, the anti-TL1A antibody is A161. In some embodiments, the anti-TL1A antibody is A162. In some embodiments, the anti-TL1A antibody is A163. In some embodiments, the anti-TL1A antibody is A164. In some embodiments, the anti-TL1A antibody is A165. In some embodiments, the anti-TL1A antibody is A166. In some embodiments, the anti-TL1A antibody is A167. In some embodiments, the anti-TL1A antibody is A168. In some embodiments, the anti-TL1A antibody is A169. In some embodiments, the anti-TL1A antibody is A170. In some embodiments, the anti-TL1A antibody is A171. In some embodiments, the anti-TL1A antibody is A172. In some embodiments, the anti-TL1A antibody is A173. In some embodiments, the anti-TL1A antibody is A174. In some embodiments, the anti-TL1A antibody is A175. In some embodiments, the anti-TL1A antibody is A176. In some embodiments, the anti-TL1A antibody is A177.

In some embodiments, the anti-DR3 is A178. In some embodiments, the anti-DR3 is A179. In some embodiments, the anti-DR3 is A180. In some embodiments, the anti-DR3 is A181. In some embodiments, the anti-DR3 is A182. In some embodiments, the anti-DR3 is A183. In some embodiments, the anti-DR3 is A184. In some embodiments, the anti-DR3 is A185. In some embodiments, the anti-DR3 is A186. In some embodiments, the anti-DR3 is A187. In some embodiments, the anti-DR3 is A188. In some embodiments, the anti-DR3 is A189. In some embodiments, the anti-DR3 is A190. In some embodiments, the anti-DR3 is A191. In some embodiments, the anti-DR3 is A192. In some embodiments, the anti-DR3 is A193. In some embodiments, the anti-DR3 is A194. In some embodiments, the anti-DR3 is A195. In some embodiments, the anti-DR3 is A196. In some embodiments, the anti-DR3 is A197. In some embodiments, the anti-DR3 is A198. In some embodiments, the anti-DR3 is A199. In some embodiments, the anti-DR3 is A200. In some embodiments, the anti-DR3 is A201. In some embodiments, the anti-DR3 is A202. In some embodiments, the anti-DR3 is A203. In some embodiments, the anti-DR3 is A204. In some embodiments, the anti-DR3 is A205. In some embodiments, the anti-DR3 is A206. In some embodiments, the anti-DR3 is A207. In some embodiments, the anti-DR3 is A208. In some embodiments, the anti-DR3 is A209. In some embodiments, the anti-DR3 is A210. In some embodiments, the anti-DR3 is A211. In some embodiments, the anti-DR3 is A212. In some embodiments, the anti-DR3 is A213. In some embodiments, the anti-DR3 is A214. In some embodiments, the anti-DR3 is A215. In some embodiments, the anti-DR3 is A216. In some embodiments, the anti-DR3 is A217. In some embodiments, the anti-DR3 is A218. In some embodiments, the anti-DR3 is A219. In some embodiments, the anti-DR3 is A220. In some embodiments, the anti-DR3 is A221. In some embodiments, the anti-DR3 is A222. In some embodiments, the anti-DR3 is A223. In some embodiments, the anti-DR3 is A224. In some embodiments, the anti-DR3 is A225. In some embodiments, the anti-DR3 is A226. In some embodiments, the anti-DR3 is A227. In some embodiments, the anti-DR3 is A228. In some embodiments, the anti-DR3 is A229. In some embodiments, the anti-DR3 is A230. In some embodiments, the anti-DR3 is A231. In some embodiments, the anti-DR3 is A232. In some embodiments, the anti-DR3 is A233. In some embodiments, the anti-DR3 is A234. In some embodiments, the anti-DR3 is A235. In some embodiments, the anti-DR3 is A236. In some embodiments, the anti-DR3 is A237. In some embodiments, the anti-DR3 is A238. In some embodiments, the anti-DR3 is A239. In some embodiments, the anti-DR3 is A240. In some embodiments, the anti-DR3 is A241. In some embodiments, the anti-DR3 is A242.

TABLE 5

Non-Limiting Examples of anti-TL1A and anti-DR3 Antibodies

| Antibody Name | HC Variable Domain (SEQ ID NO) | LC Variable Domain (SEQ ID NO) |
|---|---|---|
| A100 | 10215 | 10216 |
| A101 | 10223 | 10224 |

TABLE 5-continued

Non-Limiting Examples of anti-TL1A and anti-DR3 Antibodies

| Antibody Name | HC Variable Domain (SEQ ID NO) | LC Variable Domain (SEQ ID NO) |
|---|---|---|
| A102 | 10231 | 10232 |
| A103 | 10242 | 10243 |
| A104 | 10252 | 10253 |
| A105 | 10260 | 10261 |
| A106 | 10271 | 10275 |
| A107 | 10271 | 10276 |
| A108 | 10271 | 10277 |
| A109 | 10271 | 10278 |
| A110 | 10271 | 10279 |
| A111 | 10271 | 10280 |
| A112 | 10271 | 10281 |
| A113 | 10271 | 10282 |
| A114 | 10272 | 10275 |
| A115 | 10272 | 10276 |
| A116 | 10272 | 10277 |
| A117 | 10272 | 10278 |
| A118 | 10272 | 10279 |
| A119 | 10272 | 10280 |
| A120 | 10272 | 10281 |
| A121 | 10272 | 10282 |
| A122 | 10273 | 10275 |
| A123 | 10273 | 10276 |
| A124 | 10273 | 10277 |

CD30L Modulators

In some embodiments, the therapeutic agent is a modulator of CD30 ligand (CD30L). In some embodiments, the modulator of CD30L is an agonist or an antagonist of CD30L. In some instances, the antagonist of CD30L is an inhibitor of CD30L. In some embodiments, an inhibitor of CD30L specifically binds directly or indirectly to CD30L, CD30, or a molecule that interferes directly or indirectly with binding between CD30L and CD30. In some embodiments, as used herein, an inhibitor of CD30L comprises an agent that modulates at least one functional activity of CD30L, such as binding to CD30. Non-limiting examples of inhibitors of CD30L include agents that specifically bind to CD30L, including a polypeptide such as an anti-CD30L antibody or antigen binding fragment thereof, and a nucleic acid, e.g., an antisense construct, siRNA, and ribozyme. An antisense construct includes an expression plasmid that when transcribed in the cell produces RNA complementary to a portion of mRNA encoding CD30L, and an oligonucleotide that inhibits protein expression by hybridizing with the CD30L mRNA. In some embodiments the inhibitor of CD30L comprises a non-polypeptide or non-nucleic acid portion as an active agent that binds to and inhibits CD30L activity.

In some embodiments, an inhibitor of CD30L is a polypeptide that binds to CD30L and/or CD30. In some cases, the polypeptide is a CD30 polypeptide or a portion thereof, wherein the portion retains the ability to bind to CD30L. A portion of a CD30 polypeptide includes at least about 10, 15, 20, 25, 30, 35, 40, 45, or 50 amino acids that have at least about 85%, 90%, or 95% identity to human CD30 having SEQ ID NOS: 448, or SEQ ID NOS: 449, or a sequence of any CD30 protein-coding isoform (for e.g., P28908). For example, an inhibitor of CD30L comprises a CD30polypeptide that comprises all or part of the extracellular region of human CD30. In some embodiments, the CD30 polypeptide comprises amino acids 19-390 of SEQ ID NOS: 448 or 449, or a binding fragment thereof, having at least about 85%, 90%, or 95% sequence identity to CD30. In some embodiments, the CD30 polypeptide is a homologue of mammalian CD30, e.g., the CD30polypeptide inhibitor of CD30L is a viral CD30 polypeptide or fragment thereof. As a non-limiting example, the viral CD30 polypeptide comprises viral CD30 from a poxvirus, such as ectromelia virus or cowpox virus.

In a non-limiting example, the inhibitor is an anti-CD30L antibody or an anti-CD30antibody. As used herein, an antibody includes an antigen-binding fragment of a full length antibody, e.g., a Fab or scFv. In some embodiments, the antibody binds to the extracellular domain of CD30L. In some embodiments, an anti-CD30L antibody comprises a heavy chain comprising three complementarity-determining regions: HCDR1, HCDR2, and HCDR3; and a light chain comprising three complementarity-determining regions: LCDR1, LCDR2, and LCDR3. In some embodiments, the anti-CD30L antibody comprises a HCDR1 comprising SEQ ID NOS: 11100, a HCDR2comprising SEQ ID NOS: 11101, a HCDR3 comprising SEQ ID NOS: 11102, a LCDR1 comprising SEQ ID NOS: 11103, a LCDR2 comprising SEQ ID NOS: 11104, and a LCDR3 comprising SEQ ID NOS: 11105.

In some embodiments, the anti-CD30L antibody comprises a HCDR1 comprising SEQ ID NOS: 11106, a HCDR2 comprising SEQ ID NOS: 11107, a HCDR3 comprising SEQ ID NOS: 11108, a LCDR1 comprising SEQ ID NOS: 11109, a LCDR2 comprising SEQ ID NOS: 11110, and a LCDR3 comprising SEQ ID NOS: 11111.

In some embodiments, the anti-CD30L antibody comprises a HCDR1 comprising SEQ ID NOS: 11112, a HCDR2 comprising SEQ ID NOS: 11113, a HCDR3 comprising SEQ ID NOS: 11114, a LCDR1 comprising SEQ ID NOS: 11115, a LCDR2 comprising SEQ ID NOS: 11116, and a LCDR3 comprising SEQ ID NOS: 11117.

In some embodiments, the anti-CD30L antibody comprises a HCDR1 comprising SEQ ID NOS: 11118, a HCDR2 comprising SEQ ID NOS: 11119, a HCDR3 comprising SEQ ID NOS: 11120, a LCDR1 comprising SEQ ID NOS: 11121, a LCDR2 comprising SEQ ID NOS: 11122, and a LCDR3 comprising SEQ ID NOS: 11123.

In some embodiments, the anti-CD30L antibody comprises a HCDR1 comprising SEQ ID NOS: 11124, a HCDR2 comprising SEQ ID NOS: 11125, a HCDR3 comprising SEQ ID NOS: 11126, a LCDR1 comprising SEQ ID NOS: 11127, a LCDR2 comprising SEQ ID NOS: 11128, and a LCDR3 comprising SEQ ID NOS: 11129.

In some embodiments, the anti-CD30L antibody comprises a HCDR1 comprising SEQ ID NOS: 11130, a HCDR2 comprising SEQ ID NOS: 11131, a HCDR3 comprising SEQ ID NOS: 11132, a LCDR1 comprising SEQ ID NOS: 11133, a LCDR2 comprising SEQ ID NOS: 11134, and a LCDR3 comprising SEQ ID NOS: 11135.

In some cases, the anti-CD30L antibody comprises a heavy chain (HC) variable domain comprising SEQ ID NOS: 11136 and a light chain (LC) variable domain comprising SEQ ID NOS: 11137. In some cases, the anti-CD30L antibody comprises a heavy chain (HC) variable domain comprising SEQ ID NOS: 11138 and a light chain (LC) variable domain comprising SEQ ID NOS: 11139. In some cases, the anti-CD30L antibody comprises a heavy chain (HC) variable domain comprising SEQ ID NOS: 11140 and a light chain (LC) variable domain comprising SEQ ID NOS: 11141. In some cases, the anti-CD30L antibody comprises a heavy chain (HC) variable domain comprising SEQ ID NOS: 11142 and a light chain (LC) variable domain comprising SEQ ID NOS: 11143. In some cases, the anti-CD30L antibody comprises a heavy chain (HC) variable domain comprising SEQ ID NOS: 11144 and a light chain (LC) variable domain comprising SEQ ID NOS: 11145. In some cases, the anti-CD30L antibody comprises a heavy chain (HC) variable domain comprising SEQ ID NOS: 11146 and a light chain (LC) variable domain comprising SEQ ID NOS: 11154. In some cases, the anti-CD30L antibody comprises a heavy chain (HC) variable domain comprising SEQ ID NOS: 11147 and a light chain (LC) variable domain comprising SEQ ID NOS: 11154. In some cases, the anti-CD30L antibody comprises a heavy chain (HC) variable domain comprising SEQ ID NOS: 11148 and a light chain (LC) variable domain comprising SEQ ID NOS: 11154. In some cases, the anti-CD30L antibody comprises a heavy chain (HC) variable domain comprising SEQ ID NOS: 11149 and a light chain (LC) variable domain comprising SEQ ID NOS: 11154. In some cases, the anti-CD30L antibody comprises a heavy chain (HC) variable domain comprising SEQ ID NOS: 11150 and a light chain (LC) variable domain comprising SEQ ID NOS: 11154. In some cases, the anti-CD30L antibody comprises a heavy chain (HC) variable domain comprising SEQ ID NOS: 11151 and a light chain (LC) variable domain comprising SEQ ID NOS: 11154. In some cases, the anti-CD30L antibody comprises a heavy chain (HC) variable domain comprising SEQ ID NOS: 11152 and a light chain (LC) variable domain comprising SEQ ID NOS: 11154. In some cases, the anti-CD30L antibody comprises a heavy chain (HC) variable domain comprising SEQ ID NOS: 11153 and a light chain (LC) variable domain comprising SEQ ID NOS: 11154.

In some embodiments, the anti-CD30 antibody comprises a heavy chain variable region comprising SEQ ID NOS: 446 and a light chain variable region comprising SEQ ID NOS: 447. Non-limiting examples of anti-CD30 antibodies include MDX-60, Ber-H2, SGN-30 (cAC10), Ki-4.dgA, HRS-3/A9, AFM13, and H22xKi-4.

In some embodiments, the anti-CD30 antibody comprises an antibody drug conjugate. As a non-limiting example, the antibody drug conjugate is brentuximab, an anti-CD30 antibody conjugated to monomethyl auristatin E.

Dosages and Routes of Administration

In general, methods disclosed herein comprise administering a therapeutic agent by oral administration. However, in some instances, methods comprise administering a therapeutic agent by intraperitoneal injection. In some instances, methods comprise administering a therapeutic agent in the form of an anal suppository. In some instances, methods comprise administering a therapeutic agent by intravenous ("i.v.") administration. It is conceivable that one may also administer therapeutic agents disclosed herein by other routes, such as subcutaneous injection, intramuscular injection, intradermal injection, trasndermal injection percutaneous administration, intranasal administration, intralymphatic injection, rectal administration intragastric administration, or any other suitable parenteral administration. In some embodiments, routes for local delivery closer to site of injury or inflammation are preferred over systemic routes. Routes, dosage, time points, and duration of administrating therapeutics may be adjusted. In some embodiments, administration of therapeutics is prior to, or after, onset of either, or both, acute and chronic symptoms of the disease or condition.

An effective dose and dosage of therapeutics to prevent or treat the disease or condition disclosed herein is defined by an observed beneficial response related to the disease or condition, or symptom of the disease or condition. Beneficial response comprises preventing, alleviating, arresting, or curing the disease or condition, or symptom of the disease or condition (e.g., reduced instances of diarrhea, rectal bleeding, weight loss, and size or number of intestinal lesions or strictures, reduced fibrosis or fibrogenesis, reduced fibrostenosis, reduced inflammation). In some embodiments, the beneficial response may be measured by detecting a measurable improvement in the presence, level, or activity, of biomarkers, transcriptomic risk profile, or intestinal microbiome in the subject. An "improvement," as used herein refers to shift in the presence, level, or activity used towards a presence, level, or activity, observed in normal individuals (e.g. individuals who do not suffer from the disease or condition). In instances wherein the therapeutic agent is not therapeutically effective or is not providing a sufficient alleviation of the disease or condition, or symptom of the disease or condition, then the dosage amount and/or route of administration may be changed, or an additional agent may be administered to the subject, along with the therapeutic agent. In some embodiments, as a patient is started on a regimen of a therapeutic agent, the patient is also weaned off (e.g., step-wise decrease in dose) a second treatment regimen.

Suitable dose and dosage administrated to a subject is determined by factors including, but no limited to, the particular therapeutic agent, disease condition and its severity, the identity (e.g., weight, sex, age) of the subject in need of treatment, and can be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day. Non-limiting examples of effective dosages of for oral delivery of a therapeutic agent include between about 0.1 mg/kg and about 100 mg/kg of body weight per day, and preferably between about 0.5 mg/kg and about 50 mg/kg of body weight per day. In other instances, the oral delivery dosage of effective amount is about 1 mg/kg and about 10 mg/kg of body weight per day of active material. Non-limiting examples of effective dosages for intravenous administration of the therapeutic agent include at a rate between about 0.01 to 100 pmol/kg body weight/min. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the therapeutic agent used, the disease or condition to be treated, the mode of administration, the requirements of the individual subject, the severity of the disease or condition being treated, and the judgment of the practitioner.

In some embodiments, the administration of the therapeutic agent is hourly, once every 2hours, 3 hours, 4 hours, 5 hours, 6 hours, 7 hours, 8 hours, 9 hours, 10 hours, 11 hours, 12 hours, 13hours, 14 hours, 15 hours, 16 hours, 17 hours, 18 hours, 19 hours, 20 hours, 21 hours 22 hours, 23hours, 1 day, 2 days, 3 days, 4 days, 5 days, 6 days, 7 days, 8 days, 9 days, 10 days, 11 days, 12 days, 13 days, 14 days, 15 days, 1 month, 2 months, 3 months, 4 months, 5 months, 6 months, 7 months, 8months, 9 months, 10 months, 11 months, 1 year, 2 years, 3 years, 4 years, or 5 years, or 10 years. The effective dosage ranges may be adjusted based on subject's response to the treatment. Some routes of administration will require higher concentrations of effective amount of therapeutics than other routes.

In certain embodiments wherein the patient's condition does not improve, upon the doctor's discretion the administration of therapeutic agent is administered chronically, that is, for an extended period of time, including throughout the duration of the patient's life in order to ameliorate or otherwise control or limit the symptoms of the patient's disease or condition. In certain embodiments wherein a patient's status does improve, the dose of therapeutic agent being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In certain embodiments, the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the therapeutic agent described herein lies within a range of circulating concentrations that include the ED50 with minimal toxicity. In certain embodiments, the daily dosage range and/or the unit dosage amount varies within this range depending upon the dosage form employed and the route of administration utilized.

A therapeutic agent may be used alone or in combination with an additional therapeutic agent. In some cases, an "additional therapeutic agent" as used herein is administered alone. The therapeutic agents may be administered together or sequentially. The combination therapies may be administered within the same day, or may be administered one or more days, weeks, months, or years apart. In some cases, a therapeutic agent provided herein is administered if the subject is determined to be non-responsive to a first line of therapy, e.g., such as TNF inhibitor. Such determination may be made by treatment with the first line therapy and monitoring of disease state and/or diagnostic determination that the subject would be non-responsive to the first line therapy.

In some embodiments, the therapeutic agent or additional therapeutic agent comprises an anti-TNF therapy, e.g., an anti-TNFα therapy. In some embodiments, the additional therapeutic agent or therapeutic agent comprises a second-line treatment to an anti-TNF therapy. In some embodiments, the additional therapeutic agent comprises an immunosuppressant, or a class of drugs that suppress, or reduce, the strength of the immune system. In some embodiments, the immunosuppressant is an antibody. Non-limiting examples of immunosuppressant therapeutic agents include STELARA® (ustekinumab) azathioprine (AZA), 6-mercaptopurine (6-MP), methotrexate, cyclosporin A. (CSA).

In some embodiments, the additional therapeutic agent or therapeutic agent comprises a selective anti-inflammatory drug, or a class of drugs that specifically target pro-inflammatory molecules in the body. In some embodiments, the anti-inflammatory drug comprises an antibody. In some embodiments, the anti-inflammatory drug comprises a small molecule. Non-limiting examples of anti-inflammatory drugs include ENTYVIO (vedolizumab), corticosteroids, aminosalicylates, mesalamine, balsalazide (Colazal) and olsalazine (Dipentum).

In some embodiments, the additional therapeutic agent or therapeutic agent comprises a stem cell therapy. The stem cell therapy may be embryonic or somatic stem cells. The stem cells may be isolated from a donor (allogeneic) or isolated from the subject (autologous). The stem cells may be expanded adipose-derived stem cells (eASCs), hematopoietic stem cells (HSCs), mesenchymal stem (stromal) cells (MSCs), or induced pluripotent stem cells (iPSCs) derived from the cells of the subject. In some embodiments, the therapeutic agent comprises Cx601/Alofisel®, (darvadstrocel).

In some embodiments, the additional therapeutic agent comprises a small molecule. The small molecule may be used to treat inflammatory diseases or conditions, or fibrostenonic or fibrotic disease. Non-limiting examples of small molecules include Otezla® (apremilast), alicaforsen, or ozanimod (RPC-1063).

In some instances, the additional therapeutic agent or therapeutic agent comprises administering to the subject an antimycotic agent. In some instances, the antimycotic agent comprises an active agent that inhibits growth of a fungus. In some instances, the antimycotic agent comprises an active agent that kills a fungus. In some embodiments, the antimycotic agent comprises polyene, an azole, an echinocandin, an flucytosine, an allylamine, a tolnaftate, or griscofulvin, or a combination thereof. In other embodiments, the azole comprises triazole, imidazole, clotrimazole, ketoconazole, itraconazole, terconazole, oxiconazole, miconazole, econazole, tioconazole, voriconazole, fluconazole, isavuconazole, itraconazole, pramiconazole, ravuconazole, or posaconazole. In some other embodiments, the polyene comprises amphotericin B, nystatin, or natamycin. In vet other embodiments, the echinocandin comprises caspofungin, anidulafungin, or micafungin. In various other embodiments, the allylamine comprises naftifine or terbinafine.

Pharmaceutical Composition

A pharmaceutical composition, as used herein, refers to a mixture of a therapeutic agent, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. Optionally, the compositions include two or more therapeutic agent (e.g., one or more therapeutic agents and one or more additional agents) as discussed herein. In practicing the methods of treatment or use provided herein, therapeutically effective amounts of therapeutic agents described herein are administered in a pharmaceutical composition to a mammal having a disease, disorder, or condition to be treated, e.g., an inflammatory disease, fibrostenotic disease, and/or fibrotic disease. In some embodiments, the mammal is a human. A therapeutically effective amount can vary widely depending on the severity of the disease, the age and relative health of the subject, the potency of the therapeutic agent used and other factors. The therapeutic agents can be used singly or in combination with one or more therapeutic agents as components of mixtures.

The pharmaceutical formulations described herein are administered to a subject by appropriate administration routes, including but not limited to, intravenous, intraarterial, oral, parenteral, buccal, topical, transdermal, rectal, intramuscular, subcutaneous, intraosscous, transmucosal, inhalation, or intraperitoneal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a therapeutic agent are manufactured in a conventional manner, such as, by way of example only, by means of conventional mixing, dissolving, granulating, dragee-making, levigating, emulsifying, encapsulating, entrapping or compression processes.

The pharmaceutical compositions may include at least a therapeutic agent as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, therapeutic agents exist in unsolvated form or in solvated forms with pharmaceutically acceptable solvents such as water, ethanol, and the like. The solvated forms of the therapeutic agents are also considered to be disclosed herein.

In some embodiments, a therapeutic agent exists as a tautomer. All tautomers are included within the scope of the agents presented herein. As such, it is to be understood that a therapeutic agent or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound.

In some embodiments, a therapeutic agent exists as an enantiomer, diastereomer, or other steroisomeric form. The agents disclosed herein include all enantiomeric, diasterecomeric, and epimeric forms as well as mixtures thereof.

In some embodiments, therapeutic agents described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a therapeutic agent described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moicty. In certain embodiments, upon in vivo administration, a prodrug is chemically converted to the biologically, pharmaceutically or therapeutically active form of the therapeutic agent. In certain embodiments, a prodrug is enzymatically metabolized by one or more steps or processes to the biologically, pharmaceutically or therapeutically active form of the therapeutic agent.

Prodrug forms of the therapeutic agents, wherein the prodrug is metabolized in vivo to produce an agent as set forth herein are included within the scope of the claims. Prodrug forms of the herein described therapeutic agents, wherein the prodrug is metabolized in vivo to produce an agent as set forth herein are included within the scope of the claims. In some cases, some of the therapeutic agents described herein may be a prodrug for another derivative or active compound. In some embodiments described herein, hydrazones are metabolized in vivo to produce a therapeutic agent.

In certain embodiments, compositions provided herein include one or more preservatives to inhibit microbial activity. Suitable preservatives include mercury-containing substances such as merfen and thiomersal: stabilized chlorine dioxide: and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1mM to about 10 mM EDTA, (c) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc: or (n) combinations thereof.

The pharmaceutical compositions described herein are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In one aspect, a therapeutic agent as discussed herein, e.g., therapeutic agent is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections or drips or infusions, a therapeutic agent described herein is formulated in aqueous solutions, preferably in physiologically compatible buffers such as Hank's solution. Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a therapeutic agent is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the therapeutic agent described herein and a suitable powder base such as lactose or starch.

Representative intranasal formulations are described in, for example, U.S. Pat. Nos. 4,476,116, 5,116,817 and 6,391,452. Formulations that include a therapeutic agent are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Pharmaceutical preparations for oral use are obtained by mixing one or more solid excipient with one or more of the therapeutic agents described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol: cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose: or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active therapeutic agent doses.

In some embodiments, pharmaceutical formulations of a therapeutic agent are in the form of a capsules, including push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active therapeutic agent is dissolved or suspended in suitable liquids, such as fatty oils, liquid paraffin, or liquid polyethylene glycols. In some embodiments, stabilizers are added. A capsule may be prepared, for example, by placing the bulk blend of the formulation of the therapeutic agent inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

All formulations for oral administration are in dosages suitable for such administration. In one aspect, solid oral dosage forms are prepared by mixing a therapeutic agent with one or more of the following: antioxidants, flavoring agents, and carrier materials such as binders, suspending agents, disintegration agents, filling agents, surfactants, solubilizers, stabilizers, lubricants, wetting agents, and diluents. In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. Compressed tablets are solid dosage forms prepared by compacting the bulk blend of the formulations described above. In various embodiments, tablets will include one or more flavoring agents. In other embodiments, the tablets will include a film surrounding the final compressed tablet. In some embodiments, the film coating can provide a delayed release of a therapeutic agent from the formulation. In other embodiments, the film coating aids in patient compliance (e.g., Opadry® coatings or sugar coating). Film coatings including Opadry® typically range from about 1% to about 3% of the tablet weight. In some embodiments, solid dosage forms, e.g., tablets, effervescent tablets, and capsules, are prepared by mixing particles of a therapeutic agent with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents. Exemplary useful microencapsulation materials include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to therapeutic agent the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that include a therapeutic agent are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a therapeutic agent is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In various embodiments, the particles of a therapeutic agents and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a therapeutic agent is formulated to include one or more pharmaceutical excipients and flavors. Such a powder is prepared, for example, by mixing the therapeutic agent and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

In some embodiments, the pharmaceutical dosage forms are formulated to provide a controlled release of a therapeutic agent. Controlled release refers to the release of the therapeutic agent from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a therapeutic agent that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following: Shellac—this coating dissolves in media of pH>7; Acrylic polymers—examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Poly Vinyl Acetate Phthalate (PVAP)-PVAP dissolves in pH>5, and it is much less permeable to water vapor and gastric fluids. Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381,5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of a therapeutic agent upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a therapeutic agent and at least one dispersing agent or suspending agent for oral administration to a subject. The formulations may be a powder and/or granules for suspension, and upon admixture with water, a substantially uniform suspension is obtained.

In some embodiments, particles formulated for controlled release are incorporated in a gel or a patch or a wound dressing.

In one aspect, liquid formulation dosage forms for oral administration and/or for topical administration as a wash are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of a therapeutic agent, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Furthermore, pharmaceutical compositions optionally include one or more pH adjusting agents or buffering agents, including acids such as acetic, boric, citric, lactic, phosphoric and hydrochloric acids: bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopcia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, aspartame, chocolate, cinnamon, citrus, cocoa, cyclamate, dextrose, fructose, ginger, glycyrrhetinate, glycyrrhiza (licorice) syrup, monoammonium glyrrhizinate (MagnaSweet®), malitol, mannitol, menthol, neohesperidine DC, neotame, Prosweet® Powder, saccharin, sorbitol, stevia, sucralose, sucrose, sodium saccharin, saccharin, aspartame, acesulfame potassium, mannitol, sucralose, tagatose, thaumatin, vanilla, xylitol, or any combination thereof.

In some embodiments, a therapeutic agent is prepared as transdermal dosage form. In some embodiments, the transdermal formulations described herein include at least three components: (1) a therapeutic agent; (2) a penetration enhancer; and (3) an optional aqueous adjuvant. In some embodiments the transdermal formulations include additional components such as, but not limited to, gelling agents, creams and ointment bases, and the like. In some embodiments, the transdermal formulation is presented as a patch or a wound dressing. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of a therapeutic agent described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the therapeutic agents described herein can be accomplished by means of iontophoretic patches and the like. In one aspect, transdermal patches provide controlled delivery of a therapeutic agent. In one aspect, transdermal devices are in the form of a bandage comprising a backing member, a reservoir containing the therapeutic agent optionally with carriers, optionally a rate controlling barrier to deliver the therapeutic agent to the skin of the host at a controlled and predetermined rate over a prolonged period of time, and means to secure the device to the skin.

In further embodiments, topical formulations include gel formulations (e.g., gel patches which adhere to the skin). In some of such embodiments, a gel composition includes any polymer that forms a gel upon contact with the body (e.g., gel formulations comprising hyaluronic acid, pluronic polymers, poly(lactic-co-glycolic acid (PLGA)-based polymers or the like). In some forms of the compositions, the formulation comprises a low-melting wax such as, but not limited to, a mixture of fatty acid glycerides, optionally in combination with cocoa butter which is first melted. Optionally, the formulations further comprise a moisturizing agent.

In certain embodiments, delivery systems for pharmaceutical therapeutic agents may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, a therapeutic agent described herein may be administered topically and can be formulated into a variety of topically administrable compositions, such as solutions, suspensions, lotions, gels, pastes, medicated sticks, balms, creams or ointments. Such pharmaceutical therapeutic agents can contain solubilizers, stabilizers, tonicity enhancing agents, buffers and preservatives.

F. Methods of Characterizing an Inflammatory Disease

In an aspect, provided herein, are methods of characterizing an inflammatory disease of a subject, the method comprising: (a) assaying a sample obtained from a subject with an inflammatory disease to identify the presence of a risk genotype or transcriptional risk profile; and (b) characterizing the inflammatory disease as a severe or refractory form of the inflammatory disease, provided the risk genotype or the transcriptional risk profile is detected in (a). In some cases, the inflammatory disease is inflammatory bowel disease (IBD), such as Crohn's disease (CD) or UC. In some instances, the IBD is characterized as refractory. In some instances, the IBD is characterized as "severe," which is relative to a range of disease severity typically observed in IBD patients. In some cases, the IBD is characterized as mild or less severe (e.g., CD1) as compared to the severe forms of disease (e.g., CD3).

A "severe" disease course may include more incidences of surgery (e.g., small bowel resection, colectomy), and more reoccurrence of symptoms following a surgery. In addition, a subject with a "severe" form of IBD (such as those in CD3) experiences more flare-ups as compared to a CD1 subject. A subject with severe IBD is more likely to experience complications associated with the disease, such as stricturing disease, penetrating disease, or stricturing and penetrating disease. Stricturing disease results from long term intestinal inflammation or intestinal fibrosis that leads to the formation of scar tissue in the intestinal wall (fibrostenosis) or swelling. Both outcomes can cause narrowing, or obstruction, and are known as either fibrotic or inflammatory strictures. Severe strictures can lead to blockage of the intestine, leading to abdominal pain, bloating, nausea and the inability to pass stool. Penetrating disease is the formation of fistula or extraluminal abscesses of the intestine. Severe disease may also be associated with a non-response or loss-of-response to a standard IBD therapy, such as an anti-tumor necrosis factor (TNF) therapy.

In some embodiments, the risk genotype comprises a polymorphism from Table 1 (CD1), which is associated with, and therefore predictive of, a less severe form of disease as compared to CD3. In some embodiments, the risk genotype comprises a polymorphism from Table 2 (CD3), which is associated with, and therefore predictive of, a more severe form of disease as compared to CD1. In some embodiments, the risk genotype comprises any one of SEQ ID NOS: 1-439, each of which is associated with, and therefore predictive of, a severe form of disease as compared to CD1. In some embodiments, the risk genotype detected comprises a combination of polymorphisms from Table 1 or Table 2. In some embodiments, a single polymorphism from Table 1 or Table 2 is detected.

In some embodiments, the transcriptomic risk signature comprises one or more genes from Table 3 and 4. In some cases, the transcriptomic risk signature comprises: (a) a high level of expression of at least one of phosphodiesterase 4C (PDE4C), intercellular adhesion molecule 3(ICAM3), interleukin 18 binding protein (IL18BP), and oncostatin-M-specific receptor subunit (OSMR), as compared to a reference level; and (b) a low level of expression of SMAD Family Member 3 (SMAD3), as compared to a reference level.

Provided herein are methods of selecting a subject for treatment with a therapeutic agent disclosed herein (e.g., agonist of ADCY7, inhibitor of PDE4), provided the subject has an inflammatory disease that has been characterized as severe. In some instances, the subject is not administered a standard IBD therapy, such as an anti-TNF inhibitor, provided the inflammatory disease is characterized as severe. In some instances, the subject is administered a therapeutically effective amount of an agonist of ADCY7. In some instances, the subject is administered a therapeutically effective amount of an inhibitor of PDE4.

Provided herein are methods of characterizing and inflammatory bowel disease (IBD), such as Crohn's disease (CD) and ulcerative colitis (UC) in a subject, provided that a presence of a transcriptomic risk signature is detected in the subject. Once the transcriptomic risk signature is detected in the subject, in some cases, the subject is administered a therapeutically effective amount of an agonist of ADCY7 or an inhibitor of PDE4, provided the disease is characterized as a severe form of CD (e.g., CD3). In some cases, the subject is selected for treatment with an agonist of ADCY7 or an inhibitor of PDE4. provided the disease is characterized as a severe form of CD (e.g., CD3). The transcriptomic risk signature may involve one gene. Alternatively, the transcriptomic risk signature involves multiple genes, for e.g., 2, 3, 4, 5, 6, 7, 8, 9, 10, 11, 12, 13, 14, 15, 16, or 17 genes described herein.

Methods disclosed herein comprise characterizing an IBD as a severe form of CD characteristic of CD3, provided that a transcriptomic risk signature is detected in a subject, which in some cases involves detecting a level of protein tyrosine phosphatase. non-receptor type 11(PTPN11). In some cases, the transcriptomic risk signature is a downregulation of PTPN11, as compared to a normal (e.g., non-diseased individual), or an individual with a less severe form of CD, such as CD1. In some cases, the transcriptomic risk signature is detected by detecting a level of gene expression product expressed from PTPN11. In some cases, the transcriptomic risk signature is detected by detecting a presence of a single nucleotide polymorphism (SNP) associated with the downregulation of PTPN11. In some cases, the SNP is at rs2301756 and comprises a "G" allele, which is provided in SEQ ID NO: 339. In some cases, the SNP is rs7958372 and comprises an "A" allele, which is provided in SEQ ID NO: 408. The transcriptomic signature may be detected with a single SNP. Alternatively, the transcriptomic risk signature may be detected with multiple SNPs described herein, for e.g., both rs2301756 and rs7958372. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of ribosomal protein (RL30). In some cases, the transcriptomic risk signature is a downregulation of RPL30, as compared to a normal (e.g., non-diseased individual), or an individual with a less severe form of CD, such as CD1. In some cases, the transcriptomic risk signature is detected by detecting a level of gene expression product expressed from RPL30. In some cases, the transcriptomic risk signature is detected by detecting a presence of a SNP associated with the downregulation of RPL30. In some cases, the SNP is at rs2877453 and comprises a "C" allele, which is provided in SEQ ID NO: 353. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of X-C motif chemokine receptor 1 (XCR1) In some cases, the transcriptomic risk signature is an upregulation of XCR1, as compared to a normal (e.g., non-diseased individual), or an individual with a less severe form of CD, such as CD1. In some cases, the transcriptomic risk signature is detected by detecting a level of gene expression product expressed from XCR1. In some cases, the transcriptomic risk signature is detected by detecting a presence of a SNP associated with the upregulation of XCR1. In some cases, the SNP is selected from the group consisting of a G at rs36040135 (SEQ ID NO: 378), a "G" at rs13074382 (SEQ ID NO: 379), a "G" at rs13097556 (SEQ ID NO: 380), a "G" at rs2230322 (SEQ ID NO: 381), and an "A" at rs71327010(SE ID NO: 382). The transcriptomic signature may be detected with a single SNP. Alternatively, the transcriptomic risk signature may be detected with multiple SNPs described herein, for e.g., two or more of rs36040135, rs13074382, rs13097556, rs2230322, and rs71327010. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of HNF1 homeobox A (HNF1A). In some cases, the transcriptomic risk signature is an upregulation of HNF1, as compared to a normal (e.g., non-diseased individual), or an individual with a less severe form of CD, such as CD1. In some cases, the transcriptomic risk signature is detected by detecting a level of gene expression product expressed from HNF1. In some cases, the transcriptomic risk signature is detected by detecting a presence of a SNP associated with the upregulation of HNF1. In some cases, the SNP is selected from the group consisting of a "G" at rs2244608 (SEQ ID NO: 424), a "C" at rs1169302 (SEQ ID NO: 336), and a "G" at rs1169303 (SEQ ID NO: 337). The transcriptomic signature may be detected with a single SNP. Alternatively, the transcriptomic risk signature may be detected with multiple SNPs described herein, e.g., two or more of rs2244608, rs1169302, and rs1169303. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of ribosomal protein L3 (RPL3). In some cases, the transcriptomic risk signature is adownregulation of RPL3, as compared to a normal (e.g., non-diseased individual), or an individual with a less severe form of CD, such as CD1. In some cases, the transcriptomic risk signature is detected by detecting a level of gene expression product expressed from RPL3 In some cases, the transcriptomic risk signature is detected by detecting a presence of a SNP associated with the downregulation of RPL3. In some cases, the SNP is an "A" at rs6519183, which is provided in SEQ ID NO: 174. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of cholinergic receptor muscarinic 3 (CHRM3). In some cases. the transcriptomic risk signature is a upregulation of CHRM3, as compared to a normal (e.g., non-diseased individual), or an individual with a less severe form of CD, such as CD1. In some cases, the transcriptomic risk signature is detected by detecting a level of gene expression product expressed from CHRM3. In some cases, the transcriptomic risk signature is detected by detecting a presence of a SNP associated with the upregulation of CHRM3. In some cases, the SNP is a "C" at rs685548, which is provided in SEQ ID NO: 423. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of DLC1 Rho GTPase activating protein (DLC1). In some cases, the transcriptomic risk signature is a downregulation of DLC1, as compared to a normal (e.g., non-diseased individual), or an individual with a less severe form of CD, such as CD1.

In some cases, the transcriptomic risk signature is detected by detecting a level of gene expression product expressed from DLC1. In some cases, the transcriptomic risk signature is detected by detecting a presence of a SNP associated with the downregulation of DLC1. In some cases, the SNP is an "A" at rs11998187A, which is provided in SEQ ID NO: 404. In some embodiments, a single SNP is detected, In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of apolipoprotein B (APOB). In some cases, the transcriptomic risk signature is a downregulation of APOB, as compared to a normal (e.g., non-diseased individual), or an individual with a less severe form of CD, such as CD1. In some cases, the transcriptomic risk signature is detected by detecting a level of gene expression product expressed from APOB. In some cases, the transcriptomic risk signature is detected by detecting a presence of a SNP associated with the downregulation of APOB. In some cases, the SNP is selected from the group consisting of an "A" at rs531819 (SEQ ID NO: 258), a "G" at rs1041968 (SEQ ID NO: 354), a "G" at rs693 (SEQ ID NO: 388), an "A" at rs512535 (SEQ ID NO: 400), a "G" at rs550619 (SEQ ID NO: 406), an "A" at rs570877 (SEQ ID NO: 407), and a "G" at rs12713956 (SEQ ID NO: 437). The transcriptomic signature may be detected with a single SNP. Alternatively, the transcriptomic risk signature may be detected with multiple SNPs described herein, e.g., two or more of rs531819, rs1041968, rs693, rs512535, rs550619, rs570877, and rs12713956. In some embodiments, a single SNP is detected, In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of ribosomal protein L6 (RPL6). In some cases, the transcriptomic risk signature is a downregulation of RPL6, as compared to a normal (e.g., non-diseased individual), or an individual with a less severe form of CD, such as CD1. In some cases, the transcriptomic risk signature is detected by detecting a level of gene expression product expressed from RPL6. In some cases, the transcriptomic risk signature is detected by detecting a presence of a SNP associated with the downregulation of RPL6. In some cases, the SNP is an "A" at rs2301723A, which is provided in SEQ ID NO: 340. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of glutamate metabotropic receptor 4 (GRM4). In some cases, the transcriptomic risk signature is an upregulation of GRM4, as compared to a normal (e.g., non-diseased individual), or an individual with a less severe form of CD, such as CD1. In some cases, the transcriptomic risk signature is detected by detecting a level of gene expression product expressed from GRM4. In some cases, the transcriptomic risk signature is detected by detecting a presence of a SNP associated with the upregulation of GRM4. In some cases, the SNP is an "A" at rs2499714A, which is provided in SEQ ID NO: 181. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of p21 (RAC1) activated kinase 2 (PAK2). In some cases, the transcriptomic risk signature is a downregulation of PAK2, as compared to a normal (e.g., non-diseased individual), or an individual with a less severe form of CD, such as CD1. In some cases, the transcriptomic risk signature is detected by detecting a level of gene expression product expressed from PAK2. In some cases, the transcriptomic risk signature is detected by detecting a presence of a SNP associated with the downregulation of PAK2. In some cases, the SNP is an "A" at rs6583176, which is provided in SEQ ID NO: 341. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of ribosomal protein L18 (RPL18). In some cases, the transcriptomic risk signature is a downregulation of RPL18, as compared to a normal (e.g., non-diseased individual), or an individual with a less severe form of CD, such as CD1. In some cases, the transcriptomic risk signature is detected by detecting a level of gene expression product expressed from RPL18. In some cases, the transcriptomic risk signature is detected by detecting a presence of a SNP associated with the downregulation of RPL18. In some cases, the SNP is an "A" at rs369880, which is provided in SEQ ID NO: 395.

Methods disclosed herein comprise characterizing an IBD as a severe form of CD characteristic of CD3, provided that a transcriptomic risk signature is detected in a subject, which in some cases involves detecting a level of phosphodiesterase 4C (PDE4C). In some cases, the transcriptomic risk signature is an upregulation of PDE4C, as compared to a normal (e.g., non-diseased individual), or an individual with a less severe form of CD, such as CD1. In some cases, the transcriptomic risk signature is detected by detecting a level of gene expression product expressed from PDE4C. In some cases, the transcriptomic risk signature is detected by detecting a presence of a SNP associated with the upregulation of PDE4C. In some cases, the SNP is a "G" at rs57884093G, which is provided in SEQ ID NO: 396. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of protein kinase C alpha (PRKCA). In some cases, the transcriptomic risk signature is an upregulation or downregulation of PRKCA, as compared to a normal (e.g., non-diseased individual), or an individual with a less severe form of CD, such as CD1. In some cases, the transcriptomic risk signature is detected by detecting a level of gene expression product expressed from PRKCA. In some cases, the transcriptomic risk signature is detected by detecting a presence of a SNP associated with the upregulation or downregulation of PRKCA. In some cases, the SNP is an "A" at rs9896905, which is provided in SEQ ID NO: 321. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of protein phosphatase 2 catalytic subunit alpha (PPP2CA). In some cases, the transcriptomic risk signature is a downregulation of PPP2CA, as compared to a normal (e.g., non-diseased individual), or an individual with a less severe form of CD, such as CD1. In some cases, the transcriptomic risk signature is detected by detecting a level of gene expression product expressed from PPP2CA. In some cases, the transcriptomic risk signature is detected by detecting a presence of a SNP associated with the downregulation of PPP2CA. In some cases, the SNP is an "A" at rs7704116, which is provided in SEQ ID NO: 348. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of phosphatidylinositol-4-phosphate 5-kinase type 1 gamma (PIP5K1C). In some cases, the transcriptomic risk signature is an upregulation or a downregulation of PIP5K1C, as compared to a normal (e.g., non-diseased individual), or an individual with a less severe form of CD, such as CD1. In some cases, the transcriptomic risk signature is detected by detecting a level of gene expression product expressed from PIP5K1C. In some cases, the transcriptomic risk signature is detected by detecting a presence of a SNP associated with the downregulation of PIP5K1C. In some cases, the SNP is an "A" at rs12984273, which is provided in SEQ ID NO: 405. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of histone cluster 1 H1 family member A (HIST1H1A). In some cases, the transcriptomic risk signature is an upregulation of HIST1H1A, as compared to a normal (e.g., non-diseased individual), or an individual with a less severe form of CD, such as CD1. In some cases, the transcriptomic risk signature is detected by detecting a level of gene expression product expressed from HIST1H1A. In some cases, the transcriptomic risk signature is detected by detecting a presence of a SNP associated with the upregulation of HIST1H1A. In some cases, the SNP is a "G" at rs16891235, which is provided in SEQ ID NO: 236. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of Aldehyde Dehydrogenase 2 Family Member (ALDH2). In some cases, the transcriptomic risk signature is a downregulation of ALDH2, as compared to a normal (e.g., non-diseased individual), or an individual with a less severe form of CD, such as CD1. In some cases, the transcriptomic risk signature is detected by detecting a level of gene expression product expressed from ALDH2. In some cases, the transcriptomic risk signature is detected by detecting a presence of a SNP associated with the downregulation of ALDH2. In some cases, the SNP is a "C" at rs7296651, which is provided in SEQ ID NO: 412. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of BRD2, which is predictive of a risk of developing a severe form of CD characteristic of CD3. In some cases, the transcriptomic risk signature is a downregulation of BRD2, as compared to a normal (e.g., non-diseased individual), or an individual with a less severe form of CD, such as CD1. In some cases, the transcriptomic risk signature is detected by detecting a level of gene expression product expressed from BRD2. In some cases, the transcriptomic risk signature is detected by detecting a presence of a SNP associated with the downregulation of BRD2. In some cases, the SNP is at is rs516535 and comprises an "A" allele, which is provided in SEQ ID NO: 320. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of HLA-DQA2, which is predictive of a risk of developing a severe form of CD characteristic of CD3. In some cases, the transcriptomic risk signature is a downregulation or upregulation of HLA-DQA2, as compared to a normal (e.g., non-diseased individual), or an individual with a less severe form of CD, such as CD1. In some cases, the transcriptomic risk signature is detected by detecting a level of gene expression product expressed from HLA-DQA2. In some cases, the transcriptomic risk signature is detected by detecting a presence of a SNP associated with the downregulation or the upregulation of AHLA-DQA2. In some cases, the SNP is at rs9276427 and comprises an "A" allele, which is provided in SEQ ID NO: 351. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of KIF21B, which is predictive of a risk of developing a severe form of CD characteristic of CD3. In some cases, the transcriptomic risk signature is an upregulation of KIF21B, as compared to a normal (e.g., non-diseased individual), or an individual with a less severe form of CD, such as CD1. In some cases, the transcriptomic risk signature is detected by detecting a level of gene expression product expressed from KIF21B. In some cases, the transcriptomic risk signature is detected by detecting a presence of a SNP associated with the upregulation of KIF21B. In some cases, the SNP is at rs296564 and comprises an "A" allele, which is provided in SEQ ID NO: 323. In some cases, the SNP is at rs296569 and comprises a "A" allele, which is provided in SEQ ID NO: 331. In some cases, the SNP is and comprises an "A" allele, which is provided in SEQ ID NO: 332. In some cases, the SNP is at rs296567 and comprises a "G' allele, which is provided in SEQ ID NO: 333. In some cases, the SNP is at rs296561 and comprises a "G" allele, which is provided in SEQ ID NO: 334. In some cases, the SNP is at rs72749142 and comprises a "G" allele, which is provided in SEQ ID NO: 389. In some embodiments, a single SNP is detected, In some embodiments, more than one SNP is detected, In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of PCDH7, which is predictive of a risk of developing a severe form of CD characteristic of CD3. In some cases, the transcriptomic risk signature is a downregulation of PCDH7, as compared to a normal (e.g., non-diseased individual), or an individual with a less severe form of CD, such as CD1. In some cases, the transcriptomic risk signature is detected by detecting a level of gene expression product expressed from PCDH7. In some cases, the transcriptomic risk signature is detected by detecting a presence of a SNP associated with the downregulation of PCDH7, In some cases, the SNP is at rs9291547 and comprises an "A" allele, which is provided in SEQ ID NO: 255. In some embodiments, a single SNP is detected, In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of ANK3, which is predictive of a risk of developing a severe form of CD characteristic of CD3. In some cases, the transcriptomic risk signature is a downregulation of ANK3, as compared to a normal (e.g., non-diseased individual), or an individual with a less severe form of CD, such as CD1. In some cases, the transcriptomic risk signature is detected by detecting a level of gene expression product expressed from ANK3. In some cases, the transcriptomic risk signature is detected by detecting a presence of a SNP associated with the downregulation of ANK. In some cases, the SNP is at rs10761532 and comprises an "A" allele, which is provided in SEQ ID NO: 194. In some cases, the SNP is at rs10821813 and comprises an "A" allele, which is provided in SEQ ID NO: 195. In some cases, the SNP is at rs1561852 and comprises a "C" allele, which is provided in SEQ ID NO: 196. In some cases, the SNP is at rs10994464 and comprises an "A" allele, which is provided in SEQ ID NO: 204. In some cases, the SNP is at rs993402 and comprises a "G" allele, which is provided in SEQ ID NO: 205. In some cases, the SNP is at rs10994467 and comprises an "A" allele, which is provided in SEQ ID NO: 206. In some cases, the SNP is at rs10821822 and comprises an "A" allele, which is provided in SEQ ID NO: 207. In some cases, the SNP is at rs1837949 and comprises a "G" allele, which is provided in SEQ ID NO: 208. In some cases, the SNP is at rs35597961 and comprises a "C" allele, which is provided in SEQ ID NO: 209. In some cases, the SNP is at rs10821830 and comprises a "G" allele, which is provided in SEQ ID NO: 210. In some cases, the SNP is at rs975262 and comprises an "A" allele, which is provided in SEQ ID NO: 211. In some cases, the SNP is at rs973067 and comprises an "A" allele, which is provided in SEQ ID NO: 212. In some cases, the SNP is at rs10509139 and comprises a "G" allele, which is provided in SEQ ID NO: 213. In some cases, the SNP is at rs1442539 and comprises an "A" allele, which is provided in SEQ ID NO: 214. In some cases, the SNP is at rs2197155 and comprises an "A" allele, which is provided in SEQ ID NO: 215. In some cases, the SNP is at rs7919914 and comprises a "G" allele, which is provided in SEQ ID NO: 216. In some cases, the SNP is at rs10994476 and comprises a "G" allele, which is provided in SEQ ID NO: 275. In some cases, the SNP is at rs35471473 and comprises an "A" allele, which is provided in SEQ ID NO: 243. In some cases, the SNP is at rs12785023 and comprises a "G" allele, which is provided in SEQ ID NO: 244. In some cases, the SNP is at rs12783716 and comprises a "G" allele, which is provided in SEQ ID NO: 245. In some cases, the SNP is at rs10821821 and comprises a "G" allele, which is provided in SEQ ID NO: 246. In some cases, the SNP is at rs10994441 and comprises a "G" allele, which is provided in SEQ ID NO: 284. In some cases, the SNP is at rs10994442 and comprises a "C" allele, which is provided in SEQ ID NO: 285. In some cases, the SNP is at rs10821814 and comprises a "T" allele, which is provided in SEQ ID NO: 286. In some cases, the SNP is at rs10994465 and comprises an "A" allele, which is provided in SEQ ID NO: 287. In some cases, the SNP is at rs12218617 and comprises a "T" allele, which is provided in SEQ ID NO: 288. In some cases, the SNP is at rs10509138 and comprises a "C" allele, which is provided in SEQ ID NO: 289. In some cases, the SNP is at rs61854518 and comprises an "A" allele, which is provided in SEQ ID NO: 290. In some cases, the SNP is at rs10821699 and comprises a "G" allele, which is provided in SEQ ID NO: 345. In some cases, the SNP is at rs7919274 and comprises a "G" allele, which is provided in SEQ ID NO: 352. In some cases, the SNP is at rs10761552 and comprises an "A" allele, which is provided in SEQ ID NO: 368. In some cases, the SNP is at rs17037425 and comprises a "G" allele, which is provided in SEQ ID NO: 369. In some cases, the SNP is at rs2893861 and comprises an "A" allele, which is provided in SEQ ID NO: 370. In some cases, the SNP is at rs1993939 and comprises a "C" allele, which is provided in SEQ ID NO: 371. In some cases, the SNP is at rs10821833 and comprises a "G" allele, which is provided in SEQ ID NO: 372. In some cases, the SNP is at rs1904418 and comprises a "G" allele, which is provided in SEQ ID NO: 373. In some cases, the SNP is at rs16915196 and comprises a "G" allele, which is provided in SEQ ID NO: 432. In some cases, the SNP is at rs61853514 and comprises an "A" allele, which is provided in SEQ ID NO: 433. In some cases, the SNP is at rs10994430 and comprises an "A" allele, which is provided in SEQ ID NO: 434. In some cases, the SNP is at rs16915231 and comprises an "A" allele, which is provided in SEQ ID NO: 435. In some cases, the SNP is at rs2028564 and comprises a "G" allele, which is provided in SEQ ID NO: 436. In some embodiments, a single SNP is detected, In some embodiments, more than one SNP is detected, In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of TRIM38, which is predictive of a risk of developing a severe form of CD characteristic of CD3. In some cases, the transcriptomic risk signature is a downregulation of TRIM38, as compared to a normal (e.g., non-diseased individual), or an individual with a less severe form of CD, such as CD1. In some cases, the transcriptomic risk signature is detected by detecting a level of gene expression product expressed from TRIM38. In some cases, the transcriptomic risk signature is detected by detecting a presence of a SNP associated with the downregulation of TRIM38. In some cases, the SNP is at rs13196552 and comprises a "G" allele, which is provided in SEQ ID NO: 237. In some cases, the SNP is at rs17587597 and comprises an "A" allele, which is provided in SEQ ID NO: 282. In some cases, the SNP is at rs17587226 and comprises an "A" allele, which is provided in SEQ ID NO: 301. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

Methods disclosed herein comprise characterizing an IBD as a severe form of CD characteristic of CD3, provided that a transcriptomic risk signature is detected in a subject, which in some cases involves detecting a level of CYP4V2, which is predictive of a risk of developing a severe form of CD characteristic of CD3. In some cases, the transcriptomic risk signature is a downregulation of CYP4V2, as compared to a normal (e.g., non-diseased individual), or an individual with a less severe form of CD, such as CD1. In some cases, the transcriptomic risk signature is detected by detecting a level of gene expression product expressed from CYP4V2. In some cases, the transcriptomic risk signature is detected by detecting a presence of a SNP associated with the downregulation of CYP4V2. In some cases, the SNP is at rs2276917 and comprises an "A" allele, which is provided in SEQ ID NO: 200. In some cases, the SNP is at rs10013653 and comprises an "A" allele, which is provided in SEQ ID NO: 312.

Methods disclosed herein comprise characterizing an IBD as a severe form of CD characteristic of CD3, provided that a transcriptomic risk signature is detected in a subject, which in some cases involves detecting a level of VAMP3, which is predictive of a risk of developing a severe form of CD characteristic of CD3. In some cases, the transcriptomic risk signature is a downregulation of VAMP3, as compared to a normal (e.g., non-diseased individual), or an individual with a less severe form of CD, such as CD1. In some cases, the transcriptomic risk signature is detected by detecting a level of gene expression product expressed from VAMP3. In some cases, the transcriptomic risk signature is detected by detecting a presence of a SNP associated with the downregulation of VAMP3. In some cases, the SNP is at rs11582799 and comprises an "A" allele, which is provided in SEQ ID NO: 222. In some cases, the SNP is at rs111692854 and comprises an "A" allele, which is provided in SEQ ID NO: 223. In some cases, the SNP is at rs72632053 and comprises an "A" allele, which is provided in SEQ ID NO: 224. In some embodiments, a single SNP is detected. In some embodiments, more than one SNP is detected. In some embodiments, methods further comprise administering to the subject a therapeutically effective amount of a therapeutic agent disclosed herein (e.g., agonist of ADYC, inhibitor of PDE4).

G. Methods of Detection

Disclosed herein, in some embodiments, are methods of detecting a presence, absence, or level, of a genotype or biomarker in a sample obtained from a subject. In some instances, the methods of detection disclosed herein are useful for the diagnosis, prognosis, monitoring of disease progression, selection for treatment, monitoring of treatment, and/or treatment of inflammatory bowel disease (e.g., Crohn's disease, ulcerative colitis, and the like) disclosed herein.

In some embodiments, methods of detecting a presence, absence, or level of a genotype or biomarker in the sample obtained from the subject involve detecting a nucleic acid sequence. In some cases, the nucleic acid sequence comprises deoxyribonucleic acid (DNA). In some instances, the nucleic acid sequence comprises a denatured DNA molecule or fragment thereof. In some instances, the nucleic acid sequence comprises DNA selected from: genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. The circular DNA may be cleaved or fragmented. In some instances, the nucleic acid sequence comprises ribonucleic acid (RNA). In some instances, the nucleic acid sequence comprises fragmented RNA. In some instances, the nucleic acid sequence comprises partially degraded RNA. In some instances, the nucleic acid sequence comprises a microRNA or portion thereof. In some instances, the nucleic acid sequence comprises an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof.

Disclosed herein, in some embodiments, the genotype or biomarker is detected by subjecting a sample obtained from the subject to a nucleic acid-based detection assay. In some instances, the nucleic acid-based detection assay comprises quantitative polymerase chain reaction (qPCR), gel electrophoresis (including for e.g., Northern or Southern blot), immunochemistry, in situ hybridization such as fluorescent in situ hybridization (FISH), cytochemistry, or sequencing. In some embodiments, the sequencing technique comprises next generation sequencing. In some embodiments, the methods involve a hybridization assay such as fluorogenic qPCR (e.g., TaqMan™, SYBR green, SYBR green I, SYBR green II, SYBR gold, ethidium bromide, methylene blue, Pyronin Y, DAPI, acridine orange, Blue View or phycoerythrin), which involves a nucleic acid amplification reaction with a specific primer pair, and hybridization of the amplified nucleic acid probes comprising a detectable moiety or molecule that is specific to a target nucleic acid sequence. In some instances, a number of amplification cycles for detecting a target nucleic acid in a qPCR assay is about 5 to about 30 cycles. In some instances, the number of amplification cycles for detecting a target nucleic acid is at least about 5 cycles. In some instances, the number of amplification cycles for detecting a target nucleic acid is at most about 30 cycles. In some instances, the number of amplification cycles for detecting a target nucleic acid is about 5 to about 10, about 5 to about 15, about 5 to about 20, about 5to about 25, about 5 to about 30, about 10 to about 15, about 10 to about 20, about 10 to about 25,about 10 to about 30, about 15 to about 20, about 15 to about 25, about 15 to about 30, about 20 to about 25, about 20 to about 30, or about 25 to about 30 cycles. For TaqMan™ methods, the probe may be a hydrolysable probe comprising a fluorophore and quencher that is hydrolyzed by DNA polymerase when hybridized to a target nucleic acid. In some cases, the presence of a target nucleic acid is determined when the number of amplification cycles to reach a threshold value is less than 30,29, 28, 27, 26, 25, 24, 23, 22, 21, or 20 cycles. In some instances, hybridization may occur at standard hybridization temperatures, e.g., between about 35° C, and about 65° C, in a standard PCR buffer.

An additional exemplary nucleic acid-based detection assay comprises the use of nucleic acid probes conjugated or otherwise immobilized on a bead, multi-well plate, or other substrate, wherein the nucleic acid probes are configured to hybridize with a target nucleic acid sequence. In some instances, the nucleic acid probe is specific to one or more genetic variants disclosed herein is used. In some instances, the nucleic acid probe specific to a SNP or SNV comprises a nucleic acid probe sequence sufficiently complementary to a risk or protective allele of interest, such that hybridization is specific to the risk or protective allele. In some instances, the nucleic acid probe specific to an indel comprises a nucleic acid probe sequence sufficiently complementary to an insertion of a nucleobase within a polynucleotide sequence flanking the insertion, such that hybridization is specific to the indel. In some instances, the nucleic acid probe specific to an indel comprises a probe sequence sufficiently complementary to a polynucleotide sequence flanking a deletion of a nucleobase within the polynucleotide sequence, such that hybridization is specific to the indel. In some instances, the nucleic acid probe specific to a biomarker comprises a nucleic acid probe sequence sufficiently complementary to the polynucleotide sequence of the biomarker. In some instances, the biomarker comprises a transcribed polynucleotide sequence (e.g., RNA, cDNA). In some embodiments, the nucleic acid probe can be, for example, a full-length cDNA, or a portion thereof, such as an oligonucleotide of at least about 7, 8, 9, 10, 11, 12, 13, 14, 15, 20, 25, 30, 35, 40,45, or 50 nucleotides in length and sufficient to specifically hybridize under standard hybridization conditions to the target nucleic acid sequence. In some embodiments, the target nucleic acid sequence is immobilized on a solid surface and contacted with a probe, for example by running the isolated target nucleic acid sequence on an agarose gel and transferring the target nucleic acid sequence from the gel to a membrane, such as nitrocellulose.

In some embodiments, the probe(s) are immobilized on a solid surface, for example, in an Affymetrix gene chip array, and the probe(s) are contacted with the target nucleic acid sequence.

The present disclosure provides exemplary probes that are hybridizable to a target nucleic acid sequence within SEQ ID NOS: 1-439, including the risk allele at the position indicated with the non-nucleobase letter (e.g., "r". In some embodiments, the nucleic acid probe comprises sequences complementary to the nucleic acid sequence of SEQ ID NOS: 1-439, including the risk allele at the position indicated with the non-nucleobase letter. Alternatively, the nucleic acid probe is specific to a gene, or part of a gene, of Table 3 or Table 4. In some instances, the biomarker is provided in Table 6.

In an aspect, provided herein, are methods comprising: a) providing a sample obtained from a subject with an inflammatory disease; b) assaying to detect in the sample obtained from the subject a presence of a risk genotype a transcriptomic risk signature; and c) detecting the presence of the risk genotype. In some embodiments, the risk genotype comprises one or more polymorphisms provided in Table 2, and assaying comprises contacting a nucleic acid probe to a sample obtained from the subject, the nucleic acid probe capable of hybridizing to at least about 10 contiguous nucleotides of a nucleic acid sequence provided in any one of SEQ ID NOS: 1-439, or reverse complement thereof, the 10 contiguous nucleotides comprising a risk allele (see Table 2) at the [bracketed] position within SEQ ID NOS: 1-439. An exemplary assay to detect a risk genotype is qPCR, and sequencing methodologies. In some instances, the assaying is performed under standard hybridization conditions. The standard hybridization conditions may comprise an annealing temperature between about 30° C and about 65° C.

In an aspect, provided herein, the detection of the polymorphism involves amplification of the subject's nucleic acid by the polymerase chain reaction (PCR). In some embodiments, the PCR assay involves use of a pair of primers capable of amplifying at least about 10 contiguous nucleobases within a nucleic acid sequence provided in SEQ ID NOS: 1-439 comprising a risk allele at the [bracketed] position in any one of SEQ ID NOS: 1-439, thereby amplifying a risk genotype provided in Table 2. In fluorogenic quantitative PCR, quantitation is based on amount of fluorescence signals (TaqMan and SYBR green). In some embodiments, the nucleic acid probe is conjugated to a detectable molecule. The detectable molecule may be a fluorophore. The nucleic acid probe may also be conjugated to a quencher.

In some embodiments, the term "probe" with regards to nucleic acids, refers to any nucleic acid molecule that is capable of selectively binding to a specifically intended target nucleic acid sequence. In some instances, probes are specifically designed to be labeled, for example, with a radioactive label, a fluorescent label, an enzyme, a chemiluminescent tag, a colorimetric tag, or other labels or tags that are known in the art. In some instances, the fluorescent label comprises a fluorophore. In some instances, the fluorophore is an aromatic or heteroaromatic compound. In some instances, the fluorophore is a pyrene, anthracene, naphthalene, acridine, stilbene, benzoxaazole, indole, benzindole, oxazole, thiazole, benzothiazole, canine, carbocyanine, salicylate, anthranilate, xanthenes dye, coumarin. Exemplary xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N, N; N'-tetramethyl-6-carboxyrhodamine (TAMRA), 6-carboxy-X-rhodamine (ROX). Suitable fluorescent probes also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl) aminonaphthalene-1-sulfonic acid (EDANS). Exemplary coumarins include, e.g., 3-phenyl-7-isocyanatocoumarin; acridines, such as 9-isothiocyanatoacridine and acridine orange; N-(p-(2-benzoxazolyl) phenyl) maleimide; cyanines, such as, e.g., indodicarbocyanine 3 (Cy3), indodicarbocyanine 5 (Cy5), indodicarbocyanine 5,5 (Cy5.5), 3-(-carboxy-pentyl)-3'-ethyl-5,5'-dimethyloxacarbocyanine (CyA); 1H, 5H, 11H, 15H-Xantheno[2,3, 4-ij: 5,6, 7-i'j'] diquinolizin-18-ium, 9-[2 (or 4)-[[[6-[2,5-dioxo-1-pyrrolidinyl)oxy]-6-oxohexyl]amino]sulfonyl]-4 (or 2)-sulfophenyl]-2,3, 6,7, 12,13, 16,17-octahydro-inner salt (TR or Texas Red); or BODIPYTM dyes. In some cases, the probe comprises FAM as the dye label.

Disclosed herein, in some embodiments, a genotype or biomarker is detected by subjecting a sample obtained from the subject to a nucleic acid amplification assay. In some instances, the amplification assay comprises polymerase chain reaction (PCR), qPCR, self-sustained sequence replication, transcriptional amplification system, Q-Beta Replicase, rolling circle replication, or any suitable other nucleic acid amplification technique. A suitable nucleic acid amplification technique is configured to amplify a region of a nucleic acid sequence comprising one or more genetic risk variants disclosed herein. In some instances, the amplification assays requires primers. The nucleic acid sequence for the genetic risk variants and/or genes known or provided herein is sufficient to enable one of skill in the art to select primers to amplify any portion of the gene or genetic variants. A DNA sample suitable as a primer may be obtained, e.g., by polymerase chain reaction (PCR) amplification of genomic DNA, fragments of genomic DNA, fragments of genomic DNA ligated to adaptor sequences or cloned sequences. A person of skill in the art would utilize computer programs to design of primers with the desired specificity and optimal amplification properties, such as Oligo version 7.0 (National Biosciences). Controlled robotic systems are useful for isolating and amplifying nucleic acids and can be used.

In some embodiments, detecting the biomarker or genotype of the subject comprises sequencing genetic material obtained from a biological sample from the subject. Sequencing can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. Sequencing methods also include next-generation sequencing, e.g., modern sequencing technologies such as Illumina sequencing (e.g., Solexa), Roche 454 sequencing, Ion torrent sequencing, and SOLiD sequencing. In some cases, next-generation sequencing involves high-throughput sequencing methods. Additional sequencing methods available to one of skill in the art may also be employed.

In some instances, a number of nucleotides that are sequenced are at least 5, 10, 15, 20,25, 30, 35, 40, 45, 50, 100, 150, 200, 300, 400, 500, 2000, 4000, 6000, 8000, 10000, 20000, 50000,100000, or more than 100000 nucleotides. In some instances, the number of nucleotides sequenced is in a range of about 1 to about 100000 nucleotides, about 1 to about 10000 nucleotides, about 1 to about 1000 nucleotides, about 1 to about 500 nucleotides, about 1 to about 300 nucleotides, about 1 to about 200 nucleotides, about 1 to about 100 nucleotides, about 5 to about 100000 nucleotides, about 5to about 10000 nucleotides, about 5 to about 1000 nucleotides, about 5 to about 500 nucleotides, about 5 to about 300 nucleotides, about 5 to about 200 nucleotides, about 5 to about 100 nucleotides, about 10 to about 100000 nucleotides, about 10 to about 10000 nucleotides, about 10 to about 1000nucleotides, about 10 to about 500 nucleotides, about 10 to about 300 nucleotides, about 10 to about 200 nucleotides, about 10 to about 100 nucleotides, about 20 to about 100000 nucleotides, about 20 to about 10000 nucleotides, about 20 to about 1000 nucleotides, about 20 to about 500 nucleotides, about 20 to about 300 nucleotides, about 20 to about 200 nucleotides, about 20 to about 100nucleotides, about 30 to about 100000 nucleotides, about 30 to about 10000 nucleotides, about 30 to about 1000 nucleotides, about 30 to about 500 nucleotides, about 30 to about 300 nucleotides, about 30 to about 200 nucleotides, about 30 to about 100 nucleotides, about 50 to about 100000 nucleotides, about 50 to about 10000 nucleotides, about 50 to about 1000 nucleotides, about 50 to about 500nucleotides, about 50 to about 300 nucleotides, about 50 to about 200 nucleotides, or about 50 to about 100 nucleotides.

Disclosed herein, in some embodiments, are methods for detecting a transcriptomic risk signature or transcriptomic risk profile in a sample obtained from the subject. In some embodiments, the presence, level, or activity of two or more biomarkers in a sample is determined by detecting a transcribed or reverse transcribed polynucleotide, or portion thereof (e.g., mRNA, or cDNA), of a target gene making up the transcriptomic risk signature or transcriptomic risk profile. Any suitable method of detecting a biomarker, such as those disclosed herein, may be utilized to detect a transcriptomic risk signature or transcriptomic risk profile, such as those disclosed herein. A transcriptomic risk signature or transcriptomic risk profile can also be detected at the protein level, using a detection reagent that detects the protein product encoded by the mRNA of the biomarker, directly or indirectly, such the detection reagents disclosed herein.

In an aspect, provided herein, are methods comprising: a) providing a sample obtained from a subject with an inflammatory disease; b) assaying to detect in the sample obtained from the subject a presence of a transcriptomic risk signature; and c) detecting the presence of the transcriptomic risk signature. In some embodiments, the transcriptomic risk signature comprises a level of expression of two or more genes from Table 3 or 4. In some cases, the transcriptomic risk signature comprises a level of expression of one or more of protein tyrosine phosphatase, non-receptor type 11 (PTPN11), ribosomal protein L30 (RPL30), X-C motif chemokine receptor 1 (XCR1), HNF1homeobox A (HNF1), ribosomal protein L3 (RPL3), cholinergic receptor muscarinic 3 (CHRM3), DLC1 Rho GTPase activating protein (DLC1), apolipoprotein B (APOB), ribosomal protein L6(RPL6), glutamate metabotropic receptor 4 (GRM4), p21 (RAC1) activated kinase 2 (PAK2), ribosomal protein L18 (RPL18), phosphodiesterase 4C (PDE4C), protein kinase C alpha (PRKCA), protein phosphatase 2 catalytic subunit alpha (PPP2CA), phosphatidylinositol-4-phosphate 5-kinase type 1 gamma (PIP5K1C), histone cluster 1 H1 family member A (HIST1H1A), Aldehyde Dehydrogenase 2 Family Member (ALDH2), bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2 (CYP4V2), Vesicle Associated Membrane Protein 3 (VAMP3), The mRNA and corresponding protein sequences for the above genes are listed in Table 6.

The mRNA sequence for PTPN11 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 455. The mRNA sequence for RPL30 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 464. The mRNA sequence for XCR1 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 474. The mRNA sequence for HNF1 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 484. The mRNA sequence for RPL3 SEQ ID NO: 506. The mRNA sequence for CHRM3 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 466. The mRNA sequence for DLCI is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 476. The mRNA sequence for APOB is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 486. The mRNA sequence for RPL6 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 458. The mRNA sequence for GRM4 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 468. The mRNA sequence for PAK2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 478. The mRNA sequence for RPL18 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 460. The mRNA sequence for PDE4C is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 470. The mRNA sequence for PRKCA is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 480. The mRNA sequence for PPP2CA is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 480. The mRNA sequence for PIP5K1C is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 472. The mRNA sequence for HIST1H1A is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 482. The mRNA sequence for ALDH2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 488. The mRNA sequence for BRD2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 494. The mRNA sequence for HLA-DQA2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 496. The mRNA sequence for KIF21B is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 498. The mRNA sequence for PCDH7 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 500. The mRNA sequence for ANK3 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 502. The mRNA sequence for TRIM38 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 504. The mRNA sequence for CYP4V2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 492. The mRNA sequence for VAMP3 in at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 489.

In some embodiments, a complementary DNA (cDNA) library is prepared. In some embodiments, the cDNA library is sequenced using suitable sequence methodologies disclosed herein. In some embodiments, the cDNA library is labeled, a plurality of nucleic acid probes are generated, and fixed to an immobile surface (such as a microarray). In some embodiments, the plurality of nucleic acid probes are capable of hybridizing to at least about 10 contiguous nucleotides of the two or more genes in a sample obtained from the subject. In some embodiments, detecting the presence of the transcriptomic risk signature includes detecting a high or a low level of expression of the two or more genes from Table 3, as compared to a reference level.

Disclosed herein, in some embodiments, genetic material is extracted from a sample obtained from a subject, e.g., a sample of blood or serum. In certain embodiments where nucleic acids are extracted, the nucleic acids are extracted using any technique that does not interfere with subsequent analysis. In certain embodiments, this technique uses alcohol precipitation using ethanol, methanol or isopropyl alcohol. In certain embodiments, this technique uses phenol, chloroform, or any combination thereof. In certain embodiments, this technique uses cesium chloride. In certain embodiments, this technique uses sodium, potassium or ammonium acetate or any other salt commonly used to precipitate DNA. In certain embodiments, this technique utilizes a column or resin based nucleic acid purification scheme such as those commonly sold commercially, one non-limiting example would be the GenElute Bacterial Genomic DNA Kit available from Sigma Aldrich. In certain embodiments, after extraction the nucleic acid is stored in water, Tris buffer, or Tris-EDTA buffer before subsequent analysis. In an exemplary embodiment, the nucleic acid material is extracted in water. In some cases, extraction does not comprise nucleic acid purification. In certain embodiments, RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland).

In some embodiments, methods of detecting a presence, absence, or level of a target protein (e.g., biomarker) in the sample obtained from the subject involve detecting protein activity or expression. A target protein may be detected by use of an antibody-based assay, where an antibody specific to the target protein is utilized. In some embodiments, antibody-based detection methods utilize an antibody that binds to any region of target protein. An exemplary method of analysis comprises performing an enzyme-linked immunosorbent assay (ELISA). The ELISA assay may be a sandwich ELISA or a direct ELISA. Another exemplary method of analysis comprises a single molecule array, e.g., Simoa. Other exemplary methods of detection include immunohistochemistry and lateral flow assay. Additional exemplary methods for detecting target protein include, but are not limited to, gel electrophoresis, capillary electrophoresis, high performance liquid chromatography (HPLC), thin layer chromatography (TLC), hyperdiffusion chromatography, and the like, or various immunological methods such as fluid or gel precipitation reactions, immunodiffusion (single or double), immunoelectrophoresis, radioimmunoassay (RIA), immunofluorescent assays, and Western blotting. In some embodiments, antibodies, or antibody fragments, are used in methods such as Western blots or immunofluorescence techniques to detect the expressed proteins. The antibody or protein can be immobilized on a solid support for Western blots and immunofluorescence techniques. Suitable solid phase supports or carriers include any support capable of binding an antigen or an antibody. Exemplary supports or carriers include glass, polystyrene, polypropylene, polyethylene, dextran, nylon, amylases, natural and modified celluloses, polyacrylamides, gabbros, and magnetite.

In some cases, a target protein may be detected by detecting binding between the target protein and a binding partner of the target protein. In some cases, the target protein comprises phosphodiesterase 4C (PDE4C), adenylate cyclase 7 (ADCY7), intercellular adhesion molecule 3(ICAM3), interleukin 18 binding protein (IL18BP), and oncostatin-M-specific receptor subunit (OSMR), or SMAD Family Member 3 (SMAD3). In some cases, the target protein is one or more of tyrosine phosphatase, non-receptor type 11 (PTPN11), ribosomal protein (RL30), X-C motif chemokine receptor 1 (XCR1), HNF1 homeobox A (HNF1A), ribosomal protein L3 (RPL3), cholinergic receptor muscarinic 3 (CHRM3), DLC1 Rho GTPasc activating protein (DLC1), apolipoprotein B (APOB), ribosomal protein L6 (RPL6), glutamate metabotropic receptor 4 (GRM4), p21 (RAC1) activated kinase 2 (PAK2), ribosomal protein L18 (RPL18), phosphodiesterase 4C (PDE4C), protein kinase C alpha (PRKCA), protein phosphatase 2 catalytic subunit alpha (PPP2CA), phosphatidylinositol-4-phosphate 5-kinase type 1 gamma (PIP5K1C), histone cluster 1 H1 family member A (HIST1H1A), Aldehyde Dehydrogenase 2 Family Member (ALDH2), bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2 (CYP4V2), Vesicle Associated Membrane Protein 3 (VAMP3). In some instances, the target protein is listed in Table 6.

The protein sequence for PTPN11 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 454. The protein sequence for RPL30 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 463. The protein sequence for XCR1 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 473. The protein sequence for HNF1A is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 483. The protein sequence for RPL3 SEQ ID NO: 456. The protein sequence for CHRM3 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 465. The protein sequence for DLC1 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 475. The protein sequence for APOB is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 485. The protein sequence for RPL6 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 457. The protein sequence for GRM4 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 467. The protein sequence for PAK2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 477. The protein sequence for RPL18 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 459. The protein sequence for PDE4C is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 469. The protein sequence for PRKCA is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 479. The protein sequence for PPP2CA is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 461. The protein sequence for PIP5K1C is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 471. The protein sequence for HIST1H1A is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 481. The protein sequence for ALDH2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 487. The protein sequence for BRD2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 495. The protein sequence for HLA-DQA2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 497. The protein sequence for KIF21B is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 499. The protein sequence for PCDH7 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 501. The protein sequence for ANK3 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 503. The protein sequence for TRIM38 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 505. The protein sequence for CYP4V2 is at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 493. The protein sequence for VAMP3 in at least or about 70%, 75%, 80%, 85%, 86%, 87%, 88%, 89%, 90%, 91%, 92%, 93%, 94%, 95%, 96%, 97%, 98%, 99%, or 100% identical to SEQ ID NO: 491.

Exemplary methods of analysis of protein-protein binding comprise performing an assay in vivo or in vitro, or ex vivo. In some instances, the method of analysis comprises an assay such as a co-immunoprecipitation (co-IP), pull-down, crosslinking protein interaction analysis, labeled transfer protein interaction analysis, or Far-western blot analysis, FRET based assay, including, for example FRET-FLIM, a yeast two-hybrid assay, BiFC, or split luciferase assay.

The identifiers for the relevant biomarkers (RNA, protein, DNA) are provided in Table 6.

TABLE 6

Biomarkers Identifiers

| Name | Transcript ID | bp | CCDS | UniProt | RefSeq |
|---|---|---|---|---|---|
| PTPN11-001 | ENST00000351677.2 | 6101 | CCDS9163 | B3GUD3 B3GUD4 Q06124 | NM_002834 NP_002825 |
| PTPN11-002 | ENST00000392597.1 | 1876 | CCDS58280 | B3GUD3 B3GUD4 Q06124 | NM_080601 NP_542168 |
| PTPN11-004 | ENST00000530818.1 | 486 | — | — | — |
| PTPN11-003 | ENST00000531326.1 | 573 | — | — | — |
| RPL3-001 | ENST00000216146.4 | 1442 | CCDS13988 | B4DN06 B5MCW2 G5E9G0 P39023 Q49AJ9 Q8TBW1 Q9BT63 Q9NY85 | NM_000967 NM_001033853 NP_000958 NP_001029025 |
| RPL3-003 | ENST00000401609.1 | 1289 | — | B5MCW2 G5E9G0 Q49AJ9 Q9BT63 Q9NY85 | — |
| RPL3-009 | ENST00000402527.1 | 1205 | — | B5MCW2 | — |
| RPL3-012 | ENST00000453303.1 | 916 | — | H7C422 | — |
| RPL3-011 | ENST00000427905.1 | 782 | — | — | — |
| RPL3-014 | ENST00000420536.1 | 711 | — | F8WCR1 | — |
| RPL3-002 | ENST00000465618.1 | 2108 | — | — | NR_000026 |
| RPL3-016 | ENST00000471290.1 | 481 | — | — | — |
| RPL3-008 | ENST00000459859.1 | 447 | — | — | — |
| RPL3-004 | ENST00000467105.1 | 1396 | — | — | NR_000028 |
| RPL3-013 | ENST00000484615.1 | 827 | — | — | — |
| RPL3-006 | ENST00000461967.1 | 767 | — | — | — |
| RPL3-007 | ENST00000498462.1 | 669 | — | — | — |
| RPL3-010 | ENST00000460589.1 | 630 | — | — | — |
| RPL3-019 | ENST00000464182.1 | 616 | — | — | — |
| RPL3-015 | ENST00000484358.1 | 557 | — | — | NR_000026 |
| RPL3-017 | ENST00000481985.1 | 557 | — | — | — |
| RPL3-018 | ENST00000473638.1 | 523 | — | — | — |
| RPL6-002 | ENST00000424576.2 | 1074 | CCDS9162 | F8VR69 F8VU16 F8VWR1 F8VZ45 F8VZA3 Q02878 U3KQR5 | NM_001024662 NP_001019833 |
| RPL6-001 | ENST00000202773.9 | 947 | CCDS9162 | F8VR69 F8VU16 F8VWR1 F8VZ45 F8VZA3 Q02878 U3KQR5 | NM_000970 NP_000961 |
| RPL6-017 | ENST00000550566.2 | 1014 | — | F8VU16 F8VWR1 F8VZ45 F8VZA3 U3KQR5 | — |
| RPL6-012 | ENST00000551291.2 | 700 | — | F8VU16 F8VWR1 F8VZA3 | — |
| RPL6-009 | ENST00000548343.1 | 612 | — | F8VZA3 | — |
| RPL6-008 | ENST00000549847.1 | 588 | — | F8VU16 F8VWR1 F8VZ45 F8VZA3 | — |
| RPL6-016 | ENST00000553213.2 | 438 | — | F8VWR1 F8VZA3 | — |
| RPL6-011 | ENST00000550238.1 | 338 | — | F8VR69 | — |
| RPL6-006 | ENST00000546368.2 | 2008 | — | — | — |
| RPL6-003 | ENST00000551041.2 | 1082 | — | — | — |
| RPL6-014 | ENST00000553205.1 | 899 | — | — | — |
| RPL6-015 | ENST00000552455.1 | 781 | — | — | — |
| RPL6-010 | ENST00000549562.1 | 583 | — | — | — |
| RPL18-013 | ENST00000550973.1 | 1111 | — | F8VUA6 | — |
| RPL18-014 | ENST00000549273.1 | 1036 | — | G3V203 | — |
| RPL18-006 | ENST00000084795.5 | 612 | — | F8VUA6 Q0QEW2 | — |
| RPL18-015 | ENST00000546623.1 | 541 | — | — | — |
| RPL18-012 | ENST00000550645.1 | 463 | — | F8VYV2 | — |
| RPL18-010 | ENST00000547897.1 | 440 | — | — | — |
| RPL18-009 | ENST00000549370.1 | 628 | — | F8VXR6 | — |
| RPL18-003 | ENST00000547892.1 | 3844 | — | — | — |
| RPL18-004 | ENST00000551749.1 | 2091 | — | — | — |
| RPL18-005 | ENST00000552347.1 | 1645 | — | — | — |

TABLE 6-continued

Biomarkers Identifiers

| Name | Transcript ID | bp | CCDS | UniProt | RefSeq |
|---|---|---|---|---|---|
| RPL18-002 | ENST00000552705.1 | 1081 | — | — | — |
| RPL18-007 | ENST00000550671.1 | 764 | — | — | — |
| RPL18-011 | ENST00000552851.1 | 691 | — | — | — |
| RPL18-016 | ENST00000549533.1 | 666 | — | — | — |
| PPP2CA-001 | ENST00000481195.1 | 4649 | CCDS4173 | B3KQ51 B3KUN1 E5RHP4 P67775 | NM_002715 NP_002706 |
| PPP2CA-005 | ENST00000522385.1 | 585 | — | E5RHP4 | — |
| PPP2CA-006 | ENST00000523082.1 | 510 | — | E7ESG8 | — |
| PPP2CA-007 | ENST00000231504.5 | 564 | — | — | — |
| PPP2CA-003 | ENST00000495833.1 | 739 | — | — | — |
| RPL30-007 | ENST00000521291.1 | 575 | CCDS34928 | E5RI99 E5RJH3 P62888 | — |
| RPL30-001 | ENST00000287038.3 | 543 | CCDS34928 | E5RI99 E5RJH3 P62888 | NM_000989 NP_000980 |
| RPL30-003 | ENST00000521726.1 | 1129 | — | E5RI99 E5RJH3 | — |
| RPL30-009 | ENST00000396070.2 | 440 | — | — | — |
| RPL30-008 | ENST00000523172.1 | 274 | — | — | — |
| RPL30-010 | ENST00000518850.1 | 614 | — | E5RJH3 | — |
| RPL30-002 | ENST00000518164.1 | 1128 | — | — | — |
| RPL30-011 | ENST00000522156.1 | 531 | — | — | — |
| RPL30-012 | ENST00000517805.1 | 433 | — | — | — |
| RPL30-006 | ENST00000520998.1 | 747 | — | — | — |
| RPL30-004 | ENST00000517489.1 | 631 | — | — | — |
| RPL30-005 | ENST00000521112.1 | 573 | — | — | — |
| RPL30-013 | ENST00000521534.1 | 573 | — | — | — |
| CHRM3-001 | ENST00000255380.4 | 8778 | CCDS1616 | B1AN12 P20309 Q8NG01 | NM_000740 NP_000731 |
| CHRM3-002 | ENST00000448020.1 | 587 | — | B1AN12 Q8NG01 | — |
| CHRM3-004 | ENST00000468573.1 | 2005 | — | — | — |
| CHRM3-005 | ENST00000481779.1 | 1101 | — | — | — |
| CHRM3-006 | ENST00000492335.1 | 719 | — | — | — |
| CHRM3-003 | ENST00000487470.1 | 581 | — | — | — |
| GRM4-001 | ENST00000538487.2 | 4153 | CCDS4787 | A1L4F9 A8K0J8 Q14833 | NM_000841 NM_001256811 NP_000832 NP_001243740 |
| GRM4-201 | ENST00000374181.4 | 3878 | CCDS4787 | A1L4F9 A8K0J8 Q14833 | — |
| GRM4-002 | ENST00000374177.3 | 3590 | CCDS59012 | Q14833 | NM_001256809 NP_001243738 |
| GRM4-004 | ENST00000609222.1 | 3176 | CCDS59010 | A8K0J8 | NM_001256813 NP_001243742 |
| GRM4-202 | ENST00000535756.1 | 3137 | CCDS59010 | A8K0J8 Q14833 | — |
| GRM4-003 | ENST00000544773.2 | 2983 | CCDS59011 | A8K0J8 Q14833 | NM_001256812 NP_001243741 |
| GRM4-005 | ENST00000455714.2 | 2574 | — | A8K0J8 Q14833 | NM_001256814 NP_001243743 |
| GRM4-011 | ENST00000609443.1 | 570 | — | — | — |
| GRM4-010 | ENST00000609278.1 | 2978 | — | — | NM_001282847 NP_001269776 |
| GRM4-009 | ENST00000545715.1 | 3471 | — | — | — |
| GRM4-012 | ENST00000609915.1 | 555 | — | — | — |
| GRM4-007 | ENST00000609973.1 | 5822 | — | — | — |
| GRM4-008 | ENST00000609860.1 | 3850 | — | — | — |
| GRM4-006 | ENST00000607916.1 | 1004 | — | — | — |
| PDE4C-001 | ENST00000355502.3 | 5979 | CCDS12373 | B7Z2S3 M0R1P5 O76105 Q08493 Q32MM7 Q9P1U3 Q9UPJ5 | — |
| PDE4C-002 | ENST00000594617.3 | 4655 | CCDS12373 | B7Z2S3 M0R1P5 O76105 Q08493 Q32MM7 Q9P1U3 Q9UPJ5 | NM_000923 NP_000914 |
| PDE4C-003 | ENST00000594465.3 | 2988 | CCDS12373 | B7Z2S3 M0R1P5 O76105 Q08493 Q32MM7 Q9P1U3 Q9UPJ5 | — |
| PDE4C-005 | ENST00000447275.3 | 2542 | CCDS46016 | Q08493 Q32MM7 Q9P1U3 Q9UPJ5 | NM_001098819 NP_001092289 |
| PDE4C-004 | ENST00000262805.12 | 2472 | CCDS42523 | Q08493 Q32MM7 Q9P1U3 Q9UPJ5 | NM_001098818 NP_001092288 |
| PDE4C-201 | ENST00000539010.1 | 1699 | — | Q32MM7 Q9P1U3 Q9UPJ5 | — |
| PDE4C-007 | ENST00000597297.1 | 1559 | — | O43850 Q9P1U3 Q9UPJ5 | — |
| PDE4C-008 | ENST00000598111.2 | 1284 | — | O76104 Q9P1U3 | — |

TABLE 6-continued

Biomarkers Identifiers

| Name | Transcript ID | bp | CCDS | UniProt | RefSeq |
|---|---|---|---|---|---|
| PDE4C-016 | ENST00000610023.1 | 583 | — | — | — |
| PDE4C-010 | ENST00000599754.1 | 528 | — | M0R1P5 | — |
| PDE4C-009 | ENST00000599188.1 | 2101 | — | B7Z6T1 | — |
| PDE4C-012 | ENST00000593594.1 | 481 | — | — | — |
| PDE4C-013 | ENST00000595343.1 | 420 | — | — | — |
| PDE4C-015 | ENST00000596647.1 | 619 | — | — | NR_036575 |
| PDE4C-006 | ENST00000597360.1 | 3511 | — | — | — |
| PDE4C-014 | ENST00000600667.2 | 702 | — | — | — |
| PDE4C-011 | ENST00000597573.1 | 603 | — | — | — |
| PIP5K1C-001 | ENST00000335312.3 | 5080 | CCDS32872 | O60331 Q7LE22 | NM_001195733 NM_012398 NP_001182662 NP_036530 |
| PIP5K1C-002 | ENST00000539785.1 | 2289 | CCDS56074 | O60331 Q7LE22 | — |
| PIP5K1C-005 | ENST00000537021.1 | 3326 | — | O60331 Q7LE22 | — |
| PIP5K1C-003 | ENST00000589578.1 | 2933 | — | O60331 Q7LE22 | — |
| PIP5K1C-004 | ENST00000587482.1 | 1311 | — | — | — |
| PIP5K1C-006 | ENST00000592530.1 | 456 | — | — | — |
| XCR1-001 | ENST00000309285.3 | 5281 | CCDS2736 | P46094 Q689E2 | NM_001024644 NP_001019815 |
| XCR1-201 | ENST00000542109.1 | 1373 | CCDS2736 | P46094 Q689E2 | NM_005283 NP_005274 |
| XCR1-002 | ENST00000395946.2 | 332 | — | Q689E2 | — |
| DLC1-001 | ENST00000276297.4 | 7447 | CCDS5989 | Q96QB1 | NM_182643 NP_872584 |
| DLC1-002 | ENST00000358919.2 | 4392 | CCDS5990 | Q45XF9 Q96QB1 | NM_006094 NP_006085 |
| DLC1-008 | ENST00000520226.1 | 3556 | CCDS55201 | Q96QB1 | NM_001164271 NP_001157743 |
| DLC1-004 | ENST00000511869.1 | 2451 | CCDS5991 | Q96QB1 | NM_024767 NP_079043 |
| DLC1-005 | ENST00000512044.2 | 3758 | — | E9PDZ8 | — |
| DLC1-003 | ENST00000316609.5 | 1837 | — | Q96QB1 | — |
| DLC1-016 | ENST00000503161.2 | 562 | — | E5RI70 | — |
| DLC1-019 | ENST00000517868.1 | 383 | — | — | — |
| DLC1-006 | ENST00000510318.1 | 2028 | — | — | — |
| DLC1-007 | ENST00000513883.1 | 920 | — | — | — |
| DLC1-012 | ENST00000515225.1 | 582 | — | — | — |
| DLC1-013 | ENST00000517333.1 | 575 | — | — | — |
| DLC1-010 | ENST00000506171.1 | 560 | — | — | — |
| DLC1-009 | ENST00000509922.1 | 455 | — | — | — |
| DLC1-017 | ENST00000510250.2 | 1925 | — | — | — |
| DLC1-018 | ENST00000521730.1 | 485 | — | — | — |
| PAK2-001 | ENST00000327134.3 | 6139 | CCDS3321 | H9XFB4 Q13177 | NM_002577 NP_002568 |
| PAK2-004 | ENST00000426668.1 | 689 | — | — | — |
| PAK2-003 | ENST00000481344.1 | 371 | — | — | — |
| PRKCA-002 | ENST00000413366.3 | 8751 | CCDS11664 | L7RSM7 P17252 | NM_002737 NP_002728 |
| PRKCA-003 | ENST00000284384.6 | 2718 | — | — | — |
| PRKCA-001 | ENST00000578063.1 | 1733 | — | J3KRN5 Q7Z727 | — |
| PRKCA-005 | ENST00000583361.1 | 519 | — | — | — |
| PRKCA-004 | ENST00000583775.1 | 321 | — | — | — |
| HIST1H1A-002 | ENST00000244573.3 | 781 | CCDS4569 | Q02539 | NM_005325 NP_005316 |
| HNF1A-001 | ENST00000257555.6 | 3442 | — | B8YNU9 B8YNW1 E0YMJ1 E0YMJ2 | — |
| HNF1A-023 | ENST00000541395.1 | 3332 | — | B8YNU9 B8YNW1 F5H5U3 | NM_000545 NP_000536 |
| HNF1A-003 | ENST00000402929.1 | 3002 | — | B8YNU9 B8YNW1 U3KPW5 | — |
| HNF1A-002 | ENST00000400024.2 | 2337 | — | B8YNU9 B8YNW1 E0YMK2 U3KQS6 | — |
| HNF1A-025 | ENST00000544413.1 | 2014 | — | B8YNU9 B8YNW1 F5H0K0 | — |
| HNF1A-201 | ENST00000543427.1 | 1493 | — | B8YNW1 P20823 | — |
| HNF1A-017 | ENST00000538626.1 | 582 | — | E0YMK3 | — |
| HNF1A-020 | ENST00000535955.1 | 434 | — | U3KQ02 | — |
| HNF1A-024 | ENST00000540108.1 | 3039 | — | B8YNU9 E2I9R5 | — |
| HNF1A-027 | ENST00000560968.1 | 3030 | — | B8YNU9 E0YMI8 | — |
| HNF1A-015 | ENST00000538646.1 | 1649 | — | B8YNU9 P20823 | — |
| HNF1A-014 | ENST00000541924.1 | 1594 | — | B8YNU9 P20823 | — |
| HNF1A-016 | ENST00000544574.1 | 725 | — | F5H3Z5 | — |
| HNF1A-026 | ENST00000543255.1 | 762 | — | — | — |

TABLE 6-continued

Biomarkers Identifiers

| Name | Transcript ID | bp | CCDS | UniProt | RefSeq |
|---|---|---|---|---|---|
| APOB-001 | ENST00000233242.1 | 14121 | — | P04114 Q13828 Q9UE52 Q9UE53 S5FVK9 | NM_000384 NP_000375 |
| APOB-002 | ENST00000399256.4 | 3128 | — | A8MUN2 | — |
| ALDH2-001 | ENST00000261733.2 | 2018 | CCDS9155 | B0LUF9 B4YAH7 P05091 Q9UN17 | NM_000690 NP_000681 |
| ALDH2-003 | ENST00000416293.3 | 1572 | CCDS55885 | B0LUF9 B4YAH7 P05091 Q9UN17 | NM_001204889 NP_001191818 |
| ALDH2-005 | ENST00000548536.1 | 1760 | — | F8VSB0 | — |
| ALDH2-007 | ENST00000549106.1 | 580 | — | — | — |
| VAMP3-201 | ENST00000054666.11 | 2178 | — | Q15836 Q6FGG2 | — |
| VAMP3-202 | ENST00000470357.1 | 954 | — | K7EKX0 | — |
| VAMP3-203 | ENST00000487194.1 | 274 | — | — | — |
| CYP4V2-201 | ENST00000378802.5 | 4657 | CCDS34119 | Q6ZWL3 | — |
| CYP4V2-202 | ENST00000502665.1 | 3628 | — | — | — |
| CYP4V2-204 | ENST00000513354.5 | 1062 | — | — | — |
| CYP4V2-203 | ENST00000507209.5 | 8646 | — | — | — |
| BRD2-201 | ENST00000374825.9 | 4956 | CCDS4762 | A0A024RCR5 P25440 | NM_005104.4 |
| BRD2-202 | ENST00000374831.8 | 4807 | CCDS4762 | A0A024RCR5 P25440 | — |
| BRD2-203 | ENST00000395287.5 | 3467 | CCDS56420 | P25440 | — |
| BRD2-205 | ENST00000449085.3 | 3210 | CCDS56421 | P25440 X5CF57 | — |
| BRD2-204 | ENST00000449025.5 | 3210 | — | H0Y6K2 | — |
| BRD2-219 | ENST00000607833.5 | 2338 | — | U3KQA6 | — |
| BRD2-206 | ENST00000456339.5 | 887 | — | H0Y799 | — |
| BRD2-214 | ENST00000496118.2 | 735 | — | J3QR72 | — |
| BRD2-218 | ENST00000606059.1 | 565 | — | U3KPW0 | — |
| BRD2-212 | ENST00000482914.5 | 4834 | — | E9PKQ9 | — |
| BRD2-213 | ENST00000495733.1 | 3404 | — | E9PIQ3 | — |
| BRD2-210 | ENST00000481259.1 | 667 | — | H0YDJ7 | — |
| BRD2-215 | ENST00000580234.1 | 718 | — | — | — |
| BRD2-216 | ENST00000581002.1 | 550 | — | — | — |
| BRD2-217 | ENST00000584808.1 | 547 | — | — | — |
| BRD2-209 | ENST00000469132.1 | 1628 | — | — | — |
| BRD2-208 | ENST00000464592.5 | 1590 | — | — | — |
| BRD2-207 | ENST00000463639.1 | 946 | — | — | — |
| BRD2-211 | ENST00000482838.1 | 759 | — | — | — |
| HLA-DQA2-210 | ENST00000374940.3 | 1524 | CCDS4753 | P01906 Q76NI6 | — |
| KIF21B-201 | ENST00000332129.6 | 9897 | CCDS30965 | O75037 | — |
| KIF21B-203 | ENST00000422435.2 | 5519 | CCDS58056 | O75037 | — |
| KIF21B-204 | ENST00000461742.6 | 5428 | CCDS58055 | O75037 | — |
| KIF21B-202 | ENST00000360529.9 | 5389 | CCDS58054 | O75037 | — |
| KIF21B-205 | ENST00000534043.1 | 3065 | — | — | — |
| PCDH7-201 | ENST00000361762.3 | 6403 | — | O60245 | — |
| PCDH7-206 | ENST00000543491.2 | 4457 | — | O60245 | — |
| PCDH7-205 | ENST00000511884.6 | 6769 | — | H0YAH0 | — |
| PCDH7-208 | ENST00000621961.1 | 2029 | — | A0A087X2C4 | — |
| PCDH7-203 | ENST00000509759.2 | 865 | — | A0A087X0C9 | — |
| PCDH7-204 | ENST00000509925.5 | 543 | — | — | — |
| PCDH7-202 | ENST00000507864.1 | 340 | — | — | — |
| PCDH7-207 | ENST00000610830.1 | 287 | — | — | — |
| ANK3-201 | ENST00000280772.7 | 17019 | CCDS7258 | Q12955 | NM_020987.5 |
| ANK3-205 | ENST00000373827.6 | 7202 | CCDS55712 | Q12955 | — |
| ANK3-216 | ENST00000503366.5 | 5792 | CCDS55711 | Q12955 | — |
| ANK3-202 | ENST00000355288.6 | 3811 | CCDS7259 | Q12955 | — |
| ANK3-224 | ENST00000610321.4 | 4930 | — | A0A087WTF3 | — |
| ANK3-228 | ENST00000616444.4 | 2939 | — | A0A087WZ65 | — |
| ANK3-204 | ENST00000373820.5 | 2358 | — | H0Y3A4 | — |
| ANK3-206 | ENST00000459732.2 | 1466 | — | A0A087WWI5 | — |
| ANK3-225 | ENST00000610901.4 | 965 | — | A0A087WVC2 | — |
| ANK3-217 | ENST00000503925.1 | 947 | — | D6RHY3 | — |
| ANK3-211 | ENST00000474360.1 | 761 | — | H0Y8Z4 | — |
| ANK3-227 | ENST00000613207.4 | 724 | — | A0A087WTE8 | — |
| ANK3-226 | ENST00000612776.4 | 681 | — | A0A087WY90 | — |
| ANK3-207 | ENST00000460468.5 | 677 | — | D6RF31 | — |
| ANK3-203 | ENST00000373815.5 | 660 | — | B1AQT1 | — |
| ANK3-215 | ENST00000502769.5 | 657 | — | H0Y951 | — |
| ANK3-223 | ENST00000514197.5 | 651 | — | H0YAH5 | — |
| ANK3-230 | ENST00000618080.4 | 604 | — | A0A087WZ26 | — |
| ANK3-209 | ENST00000467420.6 | 587 | — | H0Y9E9 | — |
| ANK3-218 | ENST00000506635.5 | 569 | — | D6RBY7 | — |
| ANK3-221 | ENST00000511043.5 | 562 | — | H0YA66 | — |
| ANK3-229 | ENST00000617800.4 | 545 | — | A0A087WX55 | — |
| ANK3-222 | ENST00000513049.5 | 544 | — | D6RFK6 | — |

TABLE 6-continued

Biomarkers Identifiers

| Name | Transcript ID | bp | CCDS | UniProt | RefSeq |
|---|---|---|---|---|---|
| ANK3-213 | ENST00000486349.2 | 493 | — | A0A087X0L3 | — |
| ANK3-232 | ENST00000622427.4 | 5071 | — | A0A087X0B4 | — |
| ANK3-231 | ENST00000621739.1 | 3166 | — | A0A087WTP5 | — |
| ANK3-220 | ENST00000510382.1 | 1226 | — | — | — |
| ANK3-212 | ENST00000480699.5 | 489 | — | — | — |
| ANK3-214 | ENST00000489505.2 | 2268 | — | — | — |
| ANK3-210 | ENST00000469721.3 | 738 | — | — | — |
| ANK3-208 | ENST00000465749.2 | 554 | — | — | — |
| ANK3-219 | ENST00000508449.1 | 470 | — | — | — |
| TRIM38-201 | ENST00000357085.5 | 418 | CCDS4568 | A0A024QZY4 O00635 | NM_006355.5 |

II. COMPOSITIONS

Aspects disclosed herein provide compositions comprising a nucleic acid sequence with at least 10 but less than 50 contiguous nucleobases of any one of SEQ ID NOS: 1-439, wherein the contiguous nucleobases comprise a risk allele (see Table 1 and 2), and wherein the nucleic acid sequence comprises a detectable molecule or moiety. In some embodiments, the risk allele is a risk allele listed in Table 1 and/or Table 2. The detectable molecule may be any molecule suitable for nucleic acid detection. In some embodiments, the detectable molecule is a fluorophore. In some embodiments, the composition is complementary to at least about 10 and less than 50 contiguous nucleobases within the sequence of a polymorphism of Table 1 or Table 2 and/or gene from Table 3 and/or Table 4. Additional compositions include those having a sequence that is a reverse complement to those described herein. In some embodiments the contiguous nucleobase residues are connected to a quencher.

Primers capable of amplifying at least 10 but less than 50 contiguous nucleobases of any one of SEQ ID NOS: 1-439 are provided herein, wherein the contiguous nucleobases comprise a risk allele (see Table 1 and 2). In addition, primers capable of amplifying at least 10 but less than 50contiguous nucleobases of a nucleic acid sequence of phosphodiesterase 4C (PDE4C), adenylate cyclase 7 (ADCY7), intercellular adhesion molecule 3 (ICAM3), interleukin 18 binding protein (IL18BP), and oncostatin-M-specific receptor subunit (OSMR), or SMAD Family Member 3(SMAD3), are also provided herein.

Also provided are primers capable of amplifying at least 10 but less than 50 contiguous nucleobases of a nucleic acid sequence of one or more of protein tyrosine phosphatase, non-receptor type 11 (PTPN11), ribosomal protein (RL30), X-C motif chemokine receptor 1 (XCR1), HNF1homeobox A (HNF1), ribosomal protein L3 (RPL3), cholinergic receptor muscarinic 3 (CHRM3), DLC1 Rho GTPase activating protein (DLC1), apolipoprotein B (APOB), ribosomal protein L6(RPL6), glutamate metabotropic receptor 4 (GRM4), p21 (RAC1) activated kinase 2 (PAK2), ribosomal protein L18 (RPL18), phosphodiesterase 4C (PDE4C), protein kinase C alpha (PRKCA), protein phosphatase 2 catalytic subunit alpha (PPP2CA), phosphatidylinositol-4-phosphate 5-kinase type 1 gamma (PIP5K1C), histone cluster 1 H1 family member A (HIST1H1A), Aldehyde Dehydrogenase 2 Family Member (ALDH2), bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2 (CYP4V2), Vesicle Associated Membrane Protein 3 (VAMP3).

Also provided herein are compositions comprising an antibody or antigen-binding fragment that specifically binds to ALDH2, BRD2, HLA-DQA2, KIF21B, PCDH7, ANK3, TRIM38,CYP4V2, VAMP3, PTPN11, RPL30, XCR1, HNF1A, RPL3, CHRM3, DLC1, APOB, RPL6, GRM4, PAK2, RPL18, PDE4C, PRKCA, PPP2CA, PIP5K1C, HIST1H1A PDE4C, ADCY7, ICAM3,IL18BP, OSMR, or SMAD3, wherein the antibody or antigen-binding fragment comprises a detectable molecule. In various embodiments, the antibody comprises a monoclonal antibody, a chimeric antibody, a CDR-grafted antibody, a a Fab, a Fab', a F(ab')2, a Fv, a disulfide linked Fv, a scFv, a single domain antibody, a diabody, a multispecific antibody, a dual specific antibody, an anti-idiotypic antibody, or a bispecific antibody. In some embodiments, the antibody or antigen-binding fragment comprises an IgG antibody, an IgM antibody, and/or an IgE antibody. In some embodiments, the detectable molecule comprises a fluorophore. In some embodiments, the antibody or antigen-binding fragment is conjugated to a paramagnetic particle (e.g., bead).

III. KITS

Disclosed herein, in some embodiments, are kits useful for to detect the genotypes and/or biomarkers disclosed herein. In some embodiments, the kits disclosed herein may be used to diagnose and/or treat a disease or condition in a subject; or select a patient for treatment and/or monitor a treatment disclosed herein. In some embodiments, the kit comprises the compositions described herein, which can be used to perform the methods described herein. Kits comprise an assemblage of materials or components, including at least one of the compositions. Thus, in some embodiments the kit contains a composition including of the pharmaceutical composition, for the treatment of IBD. In other embodiments, the kits contains all of the components necessary and/or sufficient to perform an assay for detecting and measuring IBD markers, including all controls, directions for performing assays, and any necessary software for analysis and presentation of results.

In some instances, the kits described herein comprise components for detecting the presence, absence, and/or quantity of a target nucleic acid and/or protein described herein. In some embodiments, the kit comprises the compositions (e.g., primers, probes, antibodies) described herein. The disclosure provides kits suitable for assays such as enzyme-linked immunosorbent assay (ELISA), single-molecular array (Simoa), PCR, and qPCR. The exact nature of the components configured in the kit depends on its intended purpose. For example, some embodiments are configured for the purpose of treating a disease or condition disclosed herein (e.g., IBD, CD, UC) in a subject. In some embodiments, the kit is configured particularly for the purpose of treating mammalian subjects. In some embodiments, the kit is configured particularly for the purpose of treating human subjects. In further embodiments, the kit is configured for veterinary applications, treating subjects such as, but not limited to, farm animals, domestic animals, and laboratory animals. In some embodiments, the kit is configured to select a subject for a therapeutic agent, such as those disclosed herein. In some embodiments, the kit is configured to select a subject for treatment with an agonist of ADCY7 or an inhibitor of PDE4.

Instructions for use may be included in the kit. Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of the pharmaceutical composition. The packaging material has an external label which indicates the contents and/or purpose of the kit and its components.

Disclosed herein are methods of contacting DNA from a subject with the composition described herein, or using the kit described herein under conditions configured to hybridize the composition to the DNA if the DNA comprises a sequence complementary to the composition. In further embodiments, provided herein are methods of treating the subject with an inhibitor of PDE4activity or expression or an agonist of ADCY7, such as those disclosed herein, provided that the DNA from the subject comprises the sequence complementary to the composition. In some embodiments, the PDE4 inhibitor comprises Apremilast.

IV. SYSTEMS

Provided herein are systems of analyzing gene or gene products (e.g., transcriptomic risk signature) in a sample obtained from a subject to diagnose, prognose, or treat an inflammatory bowel disease (IBD), such as Crohn's disease (CD) and ulcerative colitis (UC). In some cases, a sample obtained from a subject (directly or indirectly) is analyzed for a presence of a transcriptomic risk signature. Once the transcriptomic risk signature is detected in the subject, in some cases, the subject is administered a therapeutically effective amount of an agonist of ADCY7 or an inhibitor of PDE4. In some cases, the subject is selected for treatment with an agonist of ADCY7 or an inhibitor of PDE4, provided the transcriptomic risk signature is detected using the systems disclosed herein. The transcriptomic risk signature may involve one gene. Alternatively, the transcriptomic risk signature involves multiple genes, for e.g., 2, 3, 4, 5, 6, 7, 8, 9, 10, 11, 12, 13, 14, 15, 16, or 17 genes described herein.

Systems disclosed herein comprise analyzing a sample obtained from a subject to detect a presence of a transcriptomic risk signature that is predictive of a severe form of CD characteristic of CD3, which in some cases involves detecting a level of protein tyrosine phosphatase, non-receptor type 11 (PTPN11). In some cases, the transcriptomic risk signature is a downregulation of PTPN11,as compared to a normal (e.g., non-diseased individual), or an individual with a less severe form of CD, such as CD1. In some cases, the transcriptomic risk signature is detected by detecting a level of gene expression product expressed from PTPN11. In some cases, the transcriptomic risk signature is detected by detecting a presence of a single nucleotide polymorphism (SNP) associated with the downregulation of PTPN11. In some cases, the SNP is at rs2301756 and comprises a "G" allele, which is provided in SEQ ID NO: 339. In some cases, the SNP is rs7958372 and comprises an "A" allele, which is provided in SEQ ID NO: 408. The transcriptomic signature may be detected with a single SNP. Alternatively, the transcriptomic risk signature may be detected with multiple SNPs described herein, for e.g., both rs2301756 and rs7958372.

Systems disclosed herein comprise analyzing a sample obtained from a subject to detect a presence of a transcriptomic risk signature that is predictive of a severe form of CD characteristic of CD3, which in some cases involves detecting a level of ribosomal protein (RL30). In some cases, the transcriptomic risk signature is a downregulation of RPL30, as compared to a normal (e.g., non-diseased individual), or an individual with a less severe form of CD, such as CD1. In some cases, the transcriptomic risk signature is detected by detecting a level of gene expression product expressed from RPL30. In some cases, the transcriptomic risk signature is detected by detecting a presence of a SNP associated with the downregulation of RPL30. In some cases, the SNP is at rs2877453 and comprises a "C" allele, which is provided in SEQ ID NO: 353.

Systems disclosed herein comprise analyzing a sample obtained from a subject to detect a presence of a transcriptomic risk signature that is predictive of a severe form of CD characteristic of CD3, which in some cases involves detecting a level of X-C motif chemokine receptor 1 (XCR1). In some cases, the transcriptomic risk signature is an upregulation of XCR1, as compared to a normal (e.g., non-diseased individual), or an individual with a less severe form of CD, such as CD1. In some cases, the transcriptomic risk signature is detected by detecting a level of gene expression product expressed from XCR1. In some cases, the transcriptomic risk signature is detected by detecting a presence of a SNP associated with the upregulation of XCR1. In some cases, the SNP is selected from the group consisting of a G at rs36040135 (SEQ ID NO: 378), a "G" at rs13074382 (SEQ ID NO: 379), a "G" at rs13097556 (SEQ ID NO: 380), a "G" at rs2230322 (SEQ ID NO: 381), and an "A" at rs71327010 (SE ID NO: 382). The transcriptomic signature may be detected with a single SNP. Alternatively, the transcriptomic risk signature may be detected with multiple SNPs described herein, for e.g., two or more of rs36040135, rs13074382, rs13097556, rs2230322, and rs71327010.

Systems disclosed herein comprise analyzing a sample obtained from a subject to detect a presence of a transcriptomic risk signature that is predictive of a severe form of CD characteristic of CD3, which in some cases involves detecting a level of HNF1 homeobox A (HNF1). In some cases, the transcriptomic risk signature is an upregulation of HNF1, as compared to a normal (e.g., non-diseased individual), or an individual with a less severe form of CD, such as CD1. In some cases, the transcriptomic risk signature is detected by detecting a level of gene expression product expressed from HNF1. In some cases, the transcriptomic risk signature is detected by detecting a presence of a SNP associated with the upregulation of HNF1. In some cases, the SNP is selected from the group consisting of a "G" at rs2244608 (SEQ ID NO: 424), a "C" at rs1169302 (SEQ ID NO: 336), and a "G" at rs1169303 (SEQ ID NO: 337). The transcriptomic signature may be detected with a single SNP. Alternatively, the transcriptomic risk signature may be detected with multiple SNPs described herein, e.g., two or more of rs2244608, rs1169302, and rs1169303.

Systems disclosed herein comprise analyzing a sample obtained from a subject to detect a presence of a transcriptomic risk signature that is predictive of a severe form of CD characteristic of CD3, which in some cases involves detecting a level of ribosomal protein L3 (RPL3). In some cases, the transcriptomic risk signature is a downregulation of RPL3, as compared to a normal (e.g., non-diseased individual), or an individual with a less severe form of CD, such as CD1. In some cases, the transcriptomic risk signature is detected by detecting a level of gene expression product expressed from RPL3 In some cases, the transcriptomic risk signature is detected by detecting a presence of a SNP associated with the downregulation of RPL3. In some cases, the SNP is an "A" at rs6519183, which is provided in SEQ ID NO: 174.

Systems disclosed herein comprise analyzing a sample obtained from a subject to detect a presence of a transcriptomic risk signature that is predictive of a severe form of CD characteristic of CD3, which in some cases involves detecting a level of cholinergic receptor muscarinic 3 (CHRM3). In some cases, the transcriptomic risk signature is a upregulation of CHRM3, as compared to a normal (e.g., non-diseased individual), or an individual with a less severe form of CD, such as CD1. In some cases, the transcriptomic risk signature is detected by detecting a level of gene expression product expressed from CHRM3. In some cases, the transcriptomic risk signature is detected by detecting a presence of a SNP associated with the upregulation of CHRM3. In some cases, the SNP is a "C" at rs685548, which is provided in SEQ ID NO: 423.

Systems disclosed herein comprise analyzing a sample obtained from a subject to detect a presence of a transcriptomic risk signature that is predictive of a severe form of CD characteristic of CD3, which in some cases involves detecting a level of DLC1 Rho GTPase activating protein (DLC1). In some cases, the transcriptomic risk signature is a downregulation of DLC1, as compared to a normal (e.g., non-diseased individual), or an individual with a less severe form of CD, such as CD1. In some cases, the transcriptomic risk signature is detected by detecting a level of gene expression product expressed from DLC1. In some cases, the transcriptomic risk signature is detected by detecting a presence of a SNP associated with the downregulation of DLC1. In some cases, the SNP is an "A" at rs11998187A, which is provided in SEQ ID NO: 404.

Systems disclosed herein comprise analyzing a sample obtained from a subject to detect a presence of a transcriptomic risk signature that is predictive of a severe form of CD characteristic of CD3, which in some cases involves detecting a level of apolipoprotein B (APOB). In some cases, the transcriptomic risk signature is a downregulation of APOB, as compared to a normal (e.g., non-diseased individual), or an individual with a less severe form of CD, such as CD1. In some cases, the transcriptomic risk signature is detected by detecting a level of gene expression product expressed from APOB. In some cases, the transcriptomic risk signature is detected by detecting a presence of a SNP associated with the downregulation of APOB. In some cases, the SNP is selected from the group consisting of an "A" at rs531819 (SEQ ID NO: 258), a "G" at rs1041968 (SEQ ID NO: 354), a "G" at rs693 (SEQ ID NO: 388), an "A" at rs512535 (SEQ ID NO: 400), a "G" at rs550619 (SEQ ID NO: 406), an "A" at rs570877 (SEQ ID NO: 407), and a "G" at rs12713956 (SEQ ID NO: 437). The transcriptomic signature may be detected with a single SNP. Alternatively, the transcriptomic risk signature may be detected with multiple SNPs described herein, e.g., two or more of rs531819, rs1041968, rs693, rs512535, rs550619, rs570877, and rs12713956.

Systems disclosed herein comprise analyzing a sample obtained from a subject to detect a presence of a transcriptomic risk signature that is predictive of a severe form of CD characteristic of CD3, which in some cases involves detecting a level of ribosomal protein L6 (RPL6). In some cases, the transcriptomic risk signature is a downregulation of RPL6, as compared to a normal (e.g., non-diseased individual), or an individual with a less severe form of CD, such as CD1. In some cases, the transcriptomic risk signature is detected by detecting a level of gene expression product expressed from RPL6. In some cases, the transcriptomic risk signature is detected by detecting a presence of a SNP associated with the downregulation of RPL6. In some cases, the SNP is an "A" at rs2301723A, which is provided in SEQ ID NO: 340.

Systems disclosed herein comprise analyzing a sample obtained from a subject to detect a presence of a transcriptomic risk signature that is predictive of a severe form of CD characteristic of CD3, which in some cases involves detecting a level of glutamate metabotropic receptor 4 (GRM4). In some cases, the transcriptomic risk signature is an upregulation of GRM4, as compared to a normal (e.g., non-diseased individual), or an individual with a less severe form of CD, such as CD1. In some cases, the transcriptomic risk signature is detected by detecting a level of gene expression product expressed from GRM4. In some cases, the transcriptomic risk signature is detected by detecting a presence of a SNP associated with the upregulation of GRM4. In some cases, the SNP is an "A" at rs2499714A, which is provided in SEQ ID NO: 181.

Systems disclosed herein comprise analyzing a sample obtained from a subject to detect a presence of a transcriptomic risk signature that is predictive of a severe form of CD characteristic of CD3, which in some cases involves detecting a level of p21 (RAC1) activated kinase 2 (PAK2). In some cases, the transcriptomic risk signature is a downregulation of PAK2, as compared to a normal (e.g., non-diseased individual), or an individual with a less severe form of CD, such as CD1. In some cases, the transcriptomic risk signature is detected by detecting a level of gene expression product expressed from PAK2. In some cases, the transcriptomic risk signature is detected by detecting a presence of a SNP associated with the downregulation of PAK2. In some cases, the SNP is an "A" at rs6583176, which is provided in SEQ ID NO: 341.

Systems disclosed herein comprise analyzing a sample obtained from a subject to detect a presence of a transcriptomic risk signature that is predictive of a severe form of CD characteristic of CD3, which in some cases involves detecting a level of ribosomal protein L18 (RPL18). In some cases, the transcriptomic risk signature is a downregulation of RPL18, as compared to a normal (e.g., non-diseased individual), or an individual with a less severe form of CD, such as CD1. In some cases, the transcriptomic risk signature is detected by detecting a level of gene expression product expressed from RPL18. In some cases, the transcriptomic risk signature is detected by detecting a presence of a SNP associated with the downregulation of RPL18. In some cases, the SNP is an "A" at rs369880, which is provided in SEQ ID NO: 395.

Systems disclosed herein comprise analyzing a sample obtained from a subject to detect a presence of a transcriptomic risk signature that is predictive of a severe form of CD characteristic of CD3, which in some cases involves detecting a level of phosphodiesterase 4C (PDE4C). In some cases, the transcriptomic risk signature is an upregulation of PDE4C, as compared to a normal (e.g., non-diseased individual), or an individual with a less severe form of CD, such as CD1. In some cases, the transcriptomic risk signature is detected by detecting a level of gene expression product expressed from PDE4C. In some cases, the transcriptomic risk signature is detected by detecting a presence of a SNP associated with the upregulation of PDE4C. In some cases, the SNP is a "G" at rs57884093G, which is provided in SEQ ID NO: 396.

Systems disclosed herein comprise analyzing a sample obtained from a subject to detect a presence of a transcriptomic risk signature that is predictive of a severe form of CD characteristic of CD3, which in some cases involves detecting a level of protein kinase C alpha (PRKCA). In some cases, the transcriptomic risk signature is an upregulation or downregulation of PRKCA, as compared to a normal (e.g., non-diseased individual), or an individual with a less severe form of CD, such as CD1. In some cases, the transcriptomic risk signature is detected by detecting a level of gene expression product expressed from PRKCA. In some cases, the transcriptomic risk signature is detected by detecting a presence of a SNP associated with the upregulation or downregulation of PRKCA. In some cases, the SNP is an "A" at rs9896905, which is provided in SEQ ID NO: 321.

Systems disclosed herein comprise analyzing a sample obtained from a subject to detect a presence of a transcriptomic risk signature that is predictive of a severe form of CD characteristic of CD3, which in some cases involves detecting a level of protein phosphatase 2 catalytic subunit alpha (PPP2CA). In some cases, the transcriptomic risk signature is a downregulation of PPP2CA, as compared to a normal (e.g., non-diseased individual), or an individual with a less severe form of CD, such as CD1. In some cases, the transcriptomic risk signature is detected by detecting a level of gene expression product expressed from PPP2CA. In some cases, the transcriptomic risk signature is detected by detecting a presence of a SNP associated with the downregulation of PPP2CA. In some cases, the SNP is an "A" at rs7704116, which is provided in SEQ ID NO: 348.

Systems disclosed herein comprise analyzing a sample obtained from a subject to detect a presence of a transcriptomic risk signature that is predictive of a severe form of CD characteristic of CD3, which in some cases involves detecting a level of phosphatidylinositol-4-phosphate 5-kinase type 1 gamma (PIP5K1C). In some cases, the transcriptomic risk signature is an upregulation or a downregulation of PIP5K1C, as compared to a normal (e.g., non-diseased individual), or an individual with a less severe form of CD, such as CD1. In some cases, the transcriptomic risk signature is detected by detecting a level of gene expression product expressed from PIP5K1C. In some cases, the transcriptomic risk signature is detected by detecting a presence of a SNP associated with the downregulation of PIP5K1C. In some cases, the SNP is an "A" at rs12984273, which is provided in SEQ ID NO: 405.

Systems disclosed herein comprise analyzing a sample obtained from a subject to detect a presence of a transcriptomic risk signature that is predictive of a severe form of CD characteristic of CD3, which in some cases involves detecting a level of histone cluster 1 H1 family member A (HIST1H1A). In some cases, the transcriptomic risk signature is a downregulation of HIST1H1A, as compared to a normal (e.g., non-diseased individual), or an individual with a less severe form of CD, such as CD1. In some cases, the transcriptomic risk signature is detected by detecting a level of gene expression product expressed from HIST1H1A. In some cases, the transcriptomic risk signature is detected by detecting a presence of a SNP associated with the downregulation of XCR10. In some cases, the SNP is a "G" at rs16891235, which is provided in SEQ ID NO: 236.

Systems disclosed herein comprise analyzing a sample obtained from a subject to detect a presence of a transcriptomic risk signature that is predictive of a severe form of CD characteristic of CD3, which in some cases involves detecting a level of Aldehyde Dehydrogenase 2 Family Member (ALDH2). In some cases, the transcriptomic risk signature is a downregulation of ALDH2, as compared to a normal (e.g., non-diseased individual), or an individual with a less severe form of CD, such as CD1. In some cases, the transcriptomic risk signature is detected by detecting a level of gene expression product expressed from ALDH2, In some cases, the transcriptomic risk signature is detected by detecting a presence of a SNP associated with the downregulation of ALDH2. In some cases, the SNP is at rs7296651 and comprises a "C" allele, which is provided in SEQ ID NO: 412.

Systems disclosed herein comprise analyzing a sample obtained from a subject to detect a presence of a transcriptomic risk signature that is predictive of a severe form of CD characteristic of CD3, which in some cases involves detecting a level of BRD2. In some cases, the transcriptomic risk signature is a downregulation of BRD2, as compared to a normal (e.g., non-diseased individual), or an individual with a less severe form of CD, such as CD1. In some cases, the transcriptomic risk signature is detected by detecting a level of gene expression product expressed from BRD2. In some cases, the transcriptomic risk signature is detected by detecting a presence of a SNP associated with the downregulation of BRD2. In some cases, the SNP is at is rs516535 and comprises an "A" allele, which is provided in SEQ ID NO: 320.

Systems disclosed herein comprise analyzing a sample obtained from a subject to detect a presence of a transcriptomic risk signature that is predictive of a severe form of CD characteristic of CD3, which in some cases involves detecting a level of HLA-DQA2. In some cases, the transcriptomic risk signature is a downregulation or upregulation of HLA-DQA2, as compared to a normal (e.g., non-diseased individual), or an individual with a less severe form of CD, such as CD1. In some cases, the transcriptomic risk signature is detected by detecting a level of gene expression product expressed from HLA-DQA2. In some cases, the transcriptomic risk signature is detected by detecting a presence of a SNP associated with the downregulation or the upregulation of AHLA-DQA2. In some cases, the SNP is at rs9276427 and comprises an "A' allele, which is provided in SEQ ID NO: 351.

Systems disclosed herein comprise analyzing a sample obtained from a subject to detect a presence of a transcriptomic risk signature that is predictive of a severe form of CD characteristic of CD3, which in some cases involves detecting a level of KIF21B. In some cases, the transcriptomic risk signature is an upregulation of KIF21B, as compared to a normal (e.g., non-diseased individual), or an individual with a less severe form of CD, such as CD1. In some cases, the transcriptomic risk signature is detected by detecting a level of gene expression product expressed from KIF21B. In some cases, the transcriptomic risk signature is detected by detecting a presence of a SNP associated with the upregulation of KIF21B. In some cases, the SNP is at rs296564 and comprises an "A" allele, which is provided in SEQ ID NO: 323. In some cases, the SNP is at rs296569 and comprises a "A" allele, which is provided in SEQ ID NO: 331. In some cases, the SNP is and comprises an "A" allele, which is provided in SEQ ID NO: 332. In some cases, the SNP is at rs296567 and comprises a "G" allele, which is provided in SEQ ID NO: 333. In some cases, the SNP is at rs296561 and comprises a "G" allele, which is provided in SEQ ID NO: 334. In some cases, the SNP is at rs72749142 and comprises a "G" allele, which is provided in SEQ ID NO: 389.

Systems disclosed herein comprise analyzing a sample obtained from a subject to detect a presence of a transcriptomic risk signature that is predictive of a severe form of CD characteristic of CD3, which in some cases involves detecting a level of PCDH7. In some cases, the transcriptomic risk signature is a downregulation of PCDH7, as compared to a normal (e.g., non-diseased individual), or an individual with a less severe form of CD, such as CD1. In some cases, the transcriptomic risk signature is detected by detecting a level of gene expression product expressed from PCDH7. In some cases, the transcriptomic risk signature is detected by detecting a presence of a SNP associated with the downregulation of PCDH7. In some cases, the SNP is at rs9291547 and comprises an "A" allele, which is provided in SEQ ID NO: 255.

Systems disclosed herein comprise analyzing a sample obtained from a subject to detect a presence of a transcriptomic risk signature that is predictive of a severe form of CD characteristic of CD3, which in some cases involves detecting a level of ANK3. In some cases, the transcriptomic risk signature is a downregulation of ANK3, as compared to a normal (e.g., non-diseased individual), or an individual with a less severe form of CD, such as CD1. In some cases, the transcriptomic risk signature is detected by detecting a level of gene expression product expressed from ANK3. In some cases, the transcriptomic risk signature is detected by detecting a presence of a SNP associated with the downregulation of ANK. In some cases, the SNP is at rs10761532 and comprises an "A" allele, which is provided in SEQ ID NO: 194. In some cases, the SNP is at rs10821813 and comprises an "A" allele, which is provided in SEQ ID NO: 195. In some cases, the SNP is at rs1561852 and comprises a "C" allele, which is provided in SEQ ID NO: 196. In some cases, the SNP is at rs10994464 and comprises an "A" allele, which is provided in SEQ ID NO: 204. In some cases, the SNP is at rs993402 and comprises a "G" allele, which is provided in SEQ ID NO: 205. In some cases, the SNP is at rs10994467 and comprises an "A" allele, which is provided in SEQ ID NO: 206. In some cases, the SNP is at rs10821822 and comprises an "A" allele, which is provided in SEQ ID NO: 207. In some cases, the SNP is at rs1837949 and comprises a "G" allele, which is provided in SEQ ID NO: 208. In some cases, the SNP is at rs35597961 and comprises a "C" allele, which is provided in SEQ ID NO: 209. In some cases, the SNP is at rs10821830 and comprises a "G" allele, which is provided in SEQ ID NO: 210. In some cases, the SNP is at rs975262 and comprises an "A" allele, which is provided in SEQ ID NO: 211. In some cases, the SNP is at rs973067 and comprises an "A" allele, which is provided in SEQ ID NO: 212. In some cases, the SNP is at rs10509139 and comprises a "G" allele, which is provided in SEQ ID NO: 213. In some cases, the SNP is at rs1442539 and comprises an "A" allele, which is provided in SEQ ID NO: 214. In some cases, the SNP is at rs2197155 and comprises an "A" allele, which is provided in SEQ ID NO: 215. In some cases, the SNP is at rs7919914 and comprises a "G" allele, which is provided in SEQ ID NO: 216. In some cases, the SNP is at rs10994476 and comprises a "G" allele, which is provided in SEQ ID NO: 275. In some cases, the SNP is at rs35471473 and comprises an "A" allele, which is provided in SEQ ID NO: 243. In some cases, the SNP is at rs12785023 and comprises a "G" allele, which is provided in SEQ ID NO: 244. In some cases, the SNP is at rs12783716 and comprises a "G" allele, which is provided in SEQ ID NO: 245. In some cases, the SNP is at rs10821821 and comprises a "G" allele, which is provided in SEQ ID NO: 246. In some cases, the SNP is at rs10994441 and comprises a "G" allele, which is provided in SEQ ID NO: 284. In some cases, the SNP is at rs10994442 and comprises a "C" allele, which is provided in SEQ ID NO: 285. In some cases, the SNP is at rs10821814 and comprises a "T" allele, which is provided in SEQ ID NO: 286. In some cases, the SNP is at rs10994465 and comprises an "A" allele, which is provided in SEQ ID NO: 287. In some cases, the SNP is at rs12218617 and comprises a "T" allele, which is provided in SEQ ID NO: 288. In some cases, the SNP is at rs10509138 and comprises a "C" allele, which is provided in SEQ ID NO: 289. In some cases, the SNP is at rs61854518 and comprises an "A" allele, which is provided in SEQ ID NO: 290. In some cases, the SNP is at rs10821699 and comprises a "G" allele, which is provided in SEQ ID NO: 345. In some cases, the SNP is at rs7919274 and comprises a "G" allele, which is provided in SEQ ID NO: 352. In some cases, the SNP is at rs10761552 and comprises an "A" allele, which is provided in SEQ ID NO: 368. In some cases, the SNP is at rs17037425 and comprises a "G" allele, which is provided in SEQ ID NO: 369. In some cases, the SNP is at rs2893861 and comprises an "A" allele, which is provided in SEQ ID NO: 370. In some cases, the SNP is at rs1993939 and comprises a "C" allele, which is provided in SEQ ID NO: 371. In some cases, the SNP is at rs10821833 and comprises a "G" allele, which is provided in SEQ ID NO: 372. In some cases, the SNP is at rs1904418 and comprises a "G" allele, which is provided in SEQ ID NO: 373. In some cases, the SNP is at rs16915196 and comprises a "G" allele, which is provided in SEQ ID NO: 432. In some cases, the SNP is at rs61853514 and comprises an "A" allele, which is provided in SEQ ID NO: 433. In some cases, the SNP is at rs10994430 and comprises an "A" allele, which is provided in SEQ ID NO: 434. In some cases, the SNP is at rs16915231 and comprises an "A" allele, which is provided in SEQ ID NO: 435. In some cases, the SNP is at rs2028564 and comprises a "G" allele, which is provided in SEQ ID NO: 436.

Systems disclosed herein comprise analyzing a sample obtained from a subject to detect a presence of a transcriptomic risk signature that is predictive of a severe form of CD characteristic of CD3, which in some cases involves detecting a level of TRIM38. In some cases, the transcriptomic risk signature is a downregulation of TRIM38, as compared to a normal (e.g., non-diseased individual), or an individual with a less severe form of CD, such as CD1. In some cases, the transcriptomic risk signature is detected by detecting a level of gene expression product expressed from TRIM38. In some cases, the transcriptomic risk signature is detected by detecting a presence of a SNP associated with the downregulation of TRIM38. In some cases, the SNP is at rs13196552 and comprises a "G" allele, which is provided in SEQ ID NO: 237. In some cases, the SNP is at rs17587597 and comprises an "A" allele, which is provided in SEQ ID NO: 282. In some cases, the SNP is at rs17587226 and comprises an "A" allele, which is provided in SEQ ID NO: 301.

Systems disclosed herein comprise analyzing a sample obtained from a subject to detect a presence of a transcriptomic risk signature that is predictive of a severe form of CD characteristic of CD3, which in some cases involves detecting a level of CYP4V2. In some cases, the transcriptomic risk signature is a downregulation of CYP4V2, as compared to a normal (e.g., non-diseased individual), or an individual with a less severe form of CD, such as CD1. In some cases, the transcriptomic risk signature is detected by detecting a level of gene expression product expressed from CYP4V2, In some cases, the transcriptomic risk signature is detected by detecting a presence of a SNP associated with the downregulation of CYP4V2, In some cases, the SNP is at rs2276917 and comprises an "A" allele, which is provided in SEQ ID NO: 200. In some cases, the SNP is at rs10013653 and comprises an "A" allele, which is provided in SEQ ID NO: 312.

Systems disclosed herein comprise analyzing a sample obtained from a subject to detect a presence of a transcriptomic risk signature that is predictive of a severe form of CD characteristic of CD3, which in some cases involves detecting a level of VAMP3. In some cases, the transcriptomic risk signature is a downregulation of VAMP3, as compared to a normal (e.g., non-diseased individual), or an individual with a less severe form of CD, such as CD1. In some cases, the transcriptomic risk signature is detected by detecting a level of gene expression product expressed from VAMP3. In some cases, the transcriptomic risk signature is detected by detecting a presence of a SNP associated with the downregulation of VAMP3. In some cases, the SNP is at rs11582799 and comprises an "A" allele, which is provided in SEQ ID NO: 222. In some cases, the SNP is at rs111692854 and comprises an "A" allele, which is provided in SEQ ID NO: 223. In some cases, the SNP is at rs72632053 and comprises an "A" allele, which is provided in SEQ ID NO: 224.

In some embodiments, disclosed herein is a system for treating an inflammatory disease in a subject, comprising: (a) a computer processing device, optionally connected to a computer network; and (b) a software module executed by the computer processing device to analyze genes or gene products described above, and provided in Table 1, Table 2, and/or Table 3 and/or Table 4, in a sample obtained from a subject, In some embodiments, a risk genotype comprising one or more polymorphisms in Tables 1 and/or Table 2 is analyzed. In some embodiments, any group of polymorphisms from Tables 1 and/or Table 2 are analyzed. In some instances, the system comprises a central processing unit (CPU), memory (e.g., random access memory, flash memory), electronic storage unit, computer program, communication interface to communicate with one or more other systems, and any combination thereof. In some instances, the system is coupled to a computer network, for example, the Internet, intranet, and/or extranet that is in communication with the Internet, a telecommunication, or data network. In some embodiments, the system comprises a storage unit to store data and information regarding any aspect of the methods described in this disclosure. Various aspects of the system are a product or article or manufacture.

One feature of a computer program includes a sequence of instructions, executable in the digital processing device's CPU, written to perform a specified task. In some embodiments, ccomputer readable instructions are implemented as program modules, such as functions, features, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions are combined or distributed as desired in various environments. In some instances, a computer program comprises one sequence of instructions or a plurality of sequences of instructions. A computer program may be provided from one location, A computer program may be provided from a plurality of locations. In some embodiment, a computer program includes one or more software modules. In some embodiments, a computer program includes, in part or in whole, one or more web applications, one or more mobile applications, one or more standalone applications, one or more web browser plug-ins, extensions, add-ins, or add-ons, or combinations thereof.

Web application

In some embodiments, a computer program includes a web application. In light of the disclosure provided herein, those of skill in the art will recognize that a web application may utilize one or more software frameworks and one or more database systems. A web application, for example, is created upon a software framework such as Microsoft® .NET or Ruby on Rails (RoR). A web application, in some instances, utilizes one or more database systems including, by way of non-limiting examples, relational, non-relational, feature oriented, associative, and XML database systems. Suitable relational database systems include, by way of non-limiting examples, Microsoft® SQL Server, mySQL™, and Oracle®. Those of skill in the art will also recognize that a web application may be written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML). Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash®, Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). A web application may integrate enterprise server products such as IBM® Lotus Domino®. A web application may include a media player element. A media player element may utilize one or more of many suitable multimedia technologies including, by way of non-limiting examples, Adobe® Flash®, HTML 5, Apple® QuickTime®, Microsoft® Silverlight®, Java™, and Unity®.

Mobile application

In some instances, a computer program includes a mobile application provided to a mobile digital processing device. The mobile application may be provided to a mobile digital processing device at the time it is manufactured. The mobile application may be provided to a mobile digital processing device via the computer network described herein.

A mobile application is created by techniques known to those of skill in the art using hardware, languages, and development environments known to the art. Those of skill in the art will recognize that mobile applications may be written in several languages. Suitable programming languages include, by way of non-limiting examples, C, C++, C#, Featureive-C, Java™, Javascript, Pascal, Feature Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone application

In some embodiments, a computer program includes a standalone application, which is a program that may be run as an independent computer process, not an add-on to an existing process, e.g., not a plug-in. Those of skill in the art will recognize that standalone applications are sometimes compiled. In some instances, a compiler is a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Python™, Visual Basic, and VB .NET, or combinations thereof. Compilation may be often performed, at least in part, to create an executable program. In some instances, a computer program includes one or more executable complied applications.

Web browser plug-in

A computer program, in some aspects, includes a web browser plug-in. In computing, a plug-in, in some instances, is one or more software components that add specific functionality to a larger software application. Makers of software applications may support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. The toolbar may comprise one or more web browser extensions, add-ins, or add-ons. The toolbar may comprise one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

In some embodiments, Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. The web browser, in some instances, is a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software modules

The medium, method, and system disclosed herein comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. In some embodiments, a software module comprises a file, a section of code, a programming feature, a programming structure, or combinations thereof. A software module may comprise a plurality of files, a plurality of sections of code, a plurality of programming features, a plurality of programming structures, or combinations thereof. By way of non-limiting examples, the one or more software modules comprises a web application, a mobile application, and/or a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The medium, method, and system disclosed herein comprise one or more databases, or use of the same. In view of the disclosure provided herein, those of skill in the art will recognize that many databases are suitable for storage and retrieval of geologic profile, operator activities, division of interest, and/or contact information of royalty owners. Suitable databases include, by way of non-limiting examples, relational databases, non-relational databases, feature oriented databases, feature databases, entity-relationship model databases, associative databases, and XML databases. In some embodiments, a database is internet-based. In some embodiments, a database is web-based. In some embodiments, a database is cloud computing-based. A database may be based on one or more local computer storage devices.

Data transmission

The subject matter described herein, are configured to be performed in one or more facilities at one or more locations. Facility locations are not limited by country and include any country or territory. In some instances, one or more steps of a method herein are performed in a different country than another step of the method. In some instances, one or more steps for obtaining a sample are performed in a different country than one or more steps for analyzing a genotype of a sample. In some embodiments, one or more method steps involving a computer system are performed in a different country than another step of the methods provided herein. In some embodiments, data processing and analyses are performed in a different country or location than one or more steps of the methods described herein. In some embodiments, one or more articles, products, or data are transferred from one or more of the facilities to one or more different facilities for analysis or further analysis. An article includes, but is not limited to, one or more components obtained from a sample of a subject and any article or product disclosed herein as an article or product. Data includes, but is not limited to, information regarding genotype and any data produced by the methods disclosed herein. In some embodiments of the methods and systems described herein, the analysis is performed and a subsequent data transmission step will convey or transmit the results of the analysis.

In some embodiments, any step of any method described herein is performed by a software program or module on a computer. In additional or further embodiments, data from any step of any method described herein is transferred to and from facilities located within the same or different countries, including analysis performed in one facility in a particular location and the data shipped to another location or directly to an individual in the same or a different country. In additional or further embodiments, data from any step of any method described herein is transferred to and/or received from a facility located within the same or different countries, including analysis of a data input, such as cellular material, performed in one facility in a particular location and corresponding data transmitted to another location, or directly to an individual, such as data related to the diagnosis, prognosis, responsiveness to therapy, or the like, in the same or different location or country.

V. EXEMPLARY EMBODIMENTS (1) A method of inhibiting or reducing phosphodiesterase 4C (PDE4C) activity or expression in a subject having or suspected of having an inflammatory disease, the method comprising: (a) identifying the subject as being a carrier of a risk genotype and/or transcriptomic risk signature by: (i) obtaining, or having obtained, a sample from the subject; and (ii) assaying, or having assayed, to detect in the sample a presence of a risk genotype or transcriptomic risk signature; and (b) administering to the subject a therapeutically effective amount of an inhibitor of PDE4C activity or expression, thereby inhibiting or reducing PDE4C activity or expression in the subject. (2) A method of treating an inflammatory disease in a subject comprising administering a therapeutically effective amount of an inhibitor of PDE4C activity or expression to the subject, provided a risk genotype and/or transcriptomic risk signature was detected in a sample obtained from the subject. (3) A method of increasing adenylate cyclase 7 (ADCY7) activity or expression in a subject having or suspected of having an inflammatory disease, the method comprising: (a) identifying the subject as being a carrier of a risk genotype and/or transcriptomic risk signature by: (i) obtaining, or having obtained, a sample from the subject; and assaying, or having assayed, to detect in the sample a presence of a risk genotype or transcriptomic risk signature; and (ii) administering to the subject a therapeutically effective amount of an agonist of ADCY7, thereby increasing ADCY7 activity or expression in the subject. (4) The embodiment of 1-2, wherein the inhibitor of PDE4C activity or expression comprises a PDE4 antibody, or PDE4-binding antibody fragment. (5) The embodiment of 1-2, wherein inhibitor of PDE4C activity or expression comprises apremilast. (6) The embodiment of 1-2, wherein the inhibitor of PDE4C activity or expression comprises a blocking anti-PDE4C antibody. (7) The embodiment of 1-2, wherein the inhibitor of PDE4C activity or expression comprises a small molecule that binds to PDE4C. (8) The embodiment of 1-2, wherein the inhibitor of PDE4C activity or expression comprises an allosteric modulator of PDE4C. (9) The embodiment of 3-4, wherein the agonist of ADCY7 comprises a partial agonist, or a full agonist. (10) The embodiment of 3-4, wherein the agonist of ADCY7 comprises forskolin or colforsin daropate, or an analog thereof. (11) The embodiment of 3-4, wherein the agonist of ADCY7 increases ADCY7 activity or expression in the subject directly or indirectly. (12) The embodiment of 3-4, wherein the agonist of ADCY7 comprises an ADCY7 antibody, or ADCY7-binding antibody fragment. (13) The embodiment of 3-4, wherein the agonist of ADCY7 comprises a small molecule. (14) The embodiment of 3-4, wherein the agonist of ADCY7 comprises a polypeptide. (15) The embodiment of 3-4, wherein the agonist of ADCY7 comprises an allosteric modulator of ADCY7. (16) The method in any previous embodiment, the risk genotype comprises a polymorphism from Table 2. (17) The method in any previous embodiment, the transcriptomic risk signature comprises one or more genes from Table 3. (18) The method in any previous embodiment, the inflammatory disease comprises Inflammatory Bowel Disease (IBD), Crohn's disease (CD), ulcerative colitis (UC), rheumatoid arthritis (RA), multiple sclerosis (MS), psoriasis, chronic colitis, pancreatitis, leukopenia, chronic asthma, or a combination thereof. (19) The method in any previous embodiment, the risk genotype and/or transcriptomic risk is associated with perianal Crohn's disease (pCD). (20) The method in any previous embodiment, the risk genotype and/or transcriptomic risk signature is associated with a refractory CD. (21) The method in any previous embodiment, the subject is, or is suspected to be, non-responsive to anti-TNF alpha therapy, anti-a4-b7 therapy (vedolizumab), anti-IL12p40 therapy (ustekinumab), Thalidomide, or Cytoxin, or a combination thereof. (22) The method in any previous embodiment, the risk genotype is associated with an increase or a decrease in gene expression of a gene in the adenosine monophosphate (cAMP) pathway. (23) The method in any previous embodiment, the risk genotype is associated with an increase or decrease in gene expression of a gene comprising PDE4C, ADCY7, intercellular adhesion molecule 3 (ICAM3), SMAD Family Member 3 (SMAD3), or Interleukin 18 Binding Protein (IL18BP), or a combination thereof. (24) The method in any previous embodiment, the increase or decrease in gene expression comprises a 1-fold, 1,2-fold, 1,3-fold, 1,4-fold, 1,5 fold, 1,6-fold, 1,7-fold fold, 1,8-fold, 1,9-fold, 2,0-fold, 2,1-fold, 2,2-fold, 2,3-fold, 2,4-fold, 2,5-fold, 2,6-fold, 2,7-fold, 2,8-fold, 2,0-fold, 3,0-fold, 3,1-fold, 3,2-fold, 3,3-fold, 3,4-fold, 3,5-fold, 4-fold, 5-fold, 10-fold, 20-fold, 30-fold, 40-fold, 50-fold, or more, increase or decrease between the sample obtained from the subject and a gene expression in an individual who does not express the risk genotype. (25) The method in any previous embodiment, the risk genotype is associated with and increase or decrease in gene expression of a gene from any one of Tables 1-3. (26) The method in any previous embodiment, the polymorphism is detected by using an assay comprising DNA sequencing, a genotyping array, allelic discrimination, restriction fragment length polymorphism analysis, allele-specific oligonucleotide hybridization, heteroduplex mobility assay, single strand conformational polymorphism, or denaturing gradient gel electrophoresis, or any combination thereof. (27) The method in any previous embodiment, the subject has been determined to be a carrier of the risk genotype by a process comprising contacting the sample obtained from the subject comprising genetic material from the subject with a nucleic acid sequence capable of hybridizing to at least 10 contiguous nucleobases of a sequence corresponding to a polymorphism from Table 2 under standard hybridization conditions, wherein the at least 10 contiguous nucleobases comprises a risk allele. (28) The method in any previous embodiment, the subject has been determined to be a carrier of the transcriptomic risk signature by a process comprising contacting the sample obtained from the subject comprising genetic material from the subject with a nucleic acid sequence capable of hybridizing to at least 10 contiguous nucleobases of a sequence corresponding to a gene from Table 3 under standard hybridization conditions. (29) The method in any previous embodiment, the standard hybridization conditions comprise an annealing temperature between about 35° C, and about 65° C. (30) The method in any previous embodiment, the standard hybridization conditions are performed with a TaqMan master mix solution. (31) The method in any previous embodiment, the nucleic acid sequence is conjugated to a detectable molecule. (32) The method in any previous embodiment, the detectable molecule comprises a fluorophore. (33) The method in any previous embodiment, the nucleic acid sequence is conjugated to a quencher. (34) The method in any previous embodiment, the sample obtained from the subject comprises genetic material from the subject that is amplified using a nucleic acid amplification assay. (35) The method in any previous embodiment, the nucleic acid amplification assay comprises amplification of DNA from the subject with a pair of primers capable of amplifying at least 15 contiguous nucleobases of the sequence corresponding to the polymorphism from Table 2, wherein one of the nucleobases within the sequence that is amplified comprises the risk allele. (36) In any previous embodiment, the nucleic acid amplification assay comprises amplification of DNA from the subject with a pair of primers capable of amplifying at least 15 contiguous nucleobases of the sequence corresponding to the gene from Table 3. (37) The method in any previous embodiment, the sample obtained from the subject comprises whole blood, blood plasma, blood serum, check swab, urine, saliva, or tissue. (38) The method in any previous embodiment, the subject is a mammal. (39) The method in any previous embodiment, the subject is a human. (40) The method in any previous embodiment, the subject is susceptible to, or is inflicted with, thiopurine toxicity, or a disease caused by thiopurine toxicity. In any previous embodiment, the subject is non-responsive to a therapy comprising anti-TNF alpha therapy, anti-a4-b7 therapy (vedolizumab), anti-IL12p40 therapy (ustekinumab), Thalidomide, or Cytoxin. (41) A method of characterizing an inflammatory bowel disease of a subject, the method comprising: (a) assaying a sample comprising genetic material obtained from a subject with an inflammatory disease to detect a presence or an absence of a risk genotype and/or a transcriptomic risk signature; and (b) characterizing the inflammatory disease as severe and/or refractory, provided the presence of the risk genotype and/or transcriptomic risk signature is detected in (a). (42) The method of embodiment 41, further comprising administering a therapeutically effective amount of an active agent to the subject, provided the inflammatory disease is characterized as severe and/or refractory in step (b). (43) The method of embodiment 42, wherein the subject is selected for treatment at least in part because the subject suffers, or is suspected to suffer, from non-response to anti-TNF alpha therapy, anti-a4-b7 therapy (vedolizumab), anti-IL12p40therapy (ustekinumab), Thalidomide, or Cytoxin, or a combination thereof. (44) The method of embodiments 42-43, wherein the active agent comprises an inhibitor of PDE4C activity or expression, and/or agonist of ADCY7, or combination thereof. (45) The method of embodiment 44, wherein the agonist of ADCY7 comprises a partial agonist, or a full agonist. (46) The method of embodiment 44, wherein the agonist of ADCY7 increases ADCY7 activity or expression in the subject directly or indirectly. (47) The method of embodiment 44, wherein the agonist of ADCY7 comprises an ADCY7 antibody, or ADCY7-binding antibody fragment. (48) The method of embodiment 44, wherein the agonist of ADCY7 comprises a small molecule. (49) The method of embodiment 44, wherein the agonist of ADCY7 comprises a polypeptide. (50) The method of embodiment 44, wherein the agonist of ADCY7 comprises an allosteric modulator of ADCY7. (51) The method of embodiment 44, wherein the inhibitor of PDE4C activity or expression comprises a PDE4C antibody, or PDE4C-binding antibody fragment. (52) The method of embodiment 44, wherein the inhibitor of PDE4C activity or expression comprises apremilast. (53) The method of embodiment 44, wherein the inhibitor of PDE4C activity or expression comprises a blocking anti-PDE4C antibody. (54) The method of embodiment 44, wherein the inhibitor of PDE4C activity or expression comprises a small molecule that binds to PDE4C. (55) The method of embodiment 44, wherein the inhibitor of PDE4C activity or expression comprises an allosteric modulator of PDE4C. (56) In any previous embodiment, the sample obtained from the subject comprises whole blood, blood plasma, blood serum, check swab, urine, saliva, or tissue. (57) In any previous embodiment, the subject is a mammal. (58) The method in any previous embodiment, the subject is a human. (59) The method in any previous embodiment, the subject is susceptible to, or is inflicted with, thiopurine toxicity, or a disease caused by thiopurine toxicity, In any previous embodiment, the subject is, or is suspected to be, non-responsive to a therapy comprising anti-TNF alpha therapy, anti-a4-b7 therapy (vedolizumab), anti-IL12p40 therapy (ustekinumab), Thalidomide, or Cytoxin. (60) The method in any previous embodiment, the risk genotype comprises a polymorphism from Table 2. (61) The method in any previous embodiment, the transcriptomic risk signature comprises one or more genes from Table 1. (62) The method in any previous embodiment, the inflammatory disease is selected from the group consisting of Inflammatory Bowel Disease (IBD), Crohn's disease (CD), ulcerative colitis (UC), rheumatoid arthritis (RA), multiple sclerosis (MS), psoriasis, chronic colitis, pancreatitis, leukopenia, chronic asthma, and a combination thereof. (63) The method in any previous embodiment, the risk genotype and/or the transcriptomic risk signature is associated with perianal Crohn's disease (pCD). (64) The method in any previous embodiment, the risk genotype and/or transcriptomic risk signature is associated with refractory CD. (65) The method in any previous embodiment, the risk genotype is associated with an increase or a decrease in gene expression of a gene in the adenosine monophosphate (cAMP) pathway. (66) The method of embodiment 65, wherein the gene comprises PDE4C, ADCY7, or a combination thereof. (67) The method of embodiment 65, wherein the increase or decrease in gene expression comprises a 1-fold, 1,2-fold, 1,3-fold, 1,4-fold, 1,5 fold, 1,6-fold, 1,7-fold, 1,8-fold, 1,9-fold, 2,0-fold, 2,1-fold, 2,2-fold, 2,3-fold, 2,4-fold, 2,5-fold, 2,6-fold, 2,7-fold, 2,8-fold, 2,0-fold, 3,0-fold, 3,1-fold, 3,2-fold, 3,3-fold, 3,4-fold, 3,5-fold, 4-fold, 5-fold, 10-fold, 20-fold, 30-fold, 40-fold, 50-fold, or more, increase or decrease between the sample obtained from the subject and a gene expression in an individual who does not express the risk genotype. (68) A composition comprising: (a) a nucleic acid sequence comprising at least 10 but less than 50 contiguous nucleobases of any one of SEQ ID NOS: 1-439 that comprises a nucleobase provided in the [bracketed] position within any one of SEQ ID NOS: 1-439; and (ii) a detectable moiety conjugated to the nucleic acid sequence. (69) The composition of embodiment 68, wherein the detectable molecule is a fluorophore, (70) The composition of embodiment 68, wherein the contiguous nucleobase residues are connected to a quencher. (71) A kit comprising the composition of embodiment 68 and a primer pair capable of amplifying the nucleic acid sequence, or reverse complement sequence thereof. (72) A method comprising contacting DNA from a subject with the composition of embodiment 68 using the kit of embodiment 71 under conditions suitable to hybridize the composition to the DNA if the DNA comprises a sequence complementary to the composition. (73) The method of embodiment 72, further comprising administering a therapeutically effective amount of an active agent to the subject. (74) The method of embodiment 42, wherein the subject is selected for treatment at least in part because the subject suffers, or is suspected to suffer, from non-response to anti-TNF alpha therapy, anti-a4-b7 therapy (vedolizumab), anti-IL12p40 therapy (ustekinumab), Thalidomide, or Cytoxin, or a combination thereof. (75) The method of embodiments 72-74, wherein the active agent comprises an inhibitor of PDE4C activity or expression, and/or agonist of ADCY7, or combination thereof. (76) The method of embodiment 72-75, wherein the agonist of ADCY7 comprises a partial agonist, or a full agonist. (77) The method of embodiment 75, wherein the agonist of ADCY7 increases ADCY7 activity or expression in the subject directly or indirectly. (78) The method of embodiment 75, wherein the agonist of ADCY7 comprises an ADCY7 antibody, or ADCY7-binding antibody fragment. (79)

The method of embodiment 75, wherein the agonist of ADCY7 comprises a small molecule. (80) The method of embodiment 75, wherein the agonist of ADCY7 comprises a polypeptide. (81) The method of embodiment 75, wherein the agonist of ADCY7 comprises an allosteric modulator of ADCY7. (82) The method of embodiment 75, wherein the inhibitor of PDE4C activity or expression comprises a PDE4C antibody, or PDE4C-binding antibody fragment. (83) The method of embodiment 75, wherein the inhibitor of PDE4C activity or expression comprises apremilast. (84) The method of embodiment 75, wherein the inhibitor of PDE4C activity or expression comprises a blocking anti-PDE4C antibody. (85) The method of embodiment 75, wherein the inhibitor of PDE4C activity or expression comprises a small molecule that binds to PDE4C. (86) The method of embodiment 75, wherein the inhibitor of PDE4C activity or expression comprises an allosteric modulator of PDE4C. (87) The method of any previous embodiment, the sample obtained from the subject comprises whole blood, blood plasma, blood serum, check swab, urine, saliva, or tissue. (88) In any previous embodiment, the subject is a mammal. (89) The method in any previous embodiment, the subject is a human. (90) The method in any previous embodiment, the subject is susceptible to, or is inflicted with, thiopurine toxicity, or a disease caused by thiopurine toxicity. (91) The method of any previous embodiment, the subject is, or is suspected to be, non-responsive to a therapy comprising anti-TNF alpha therapy, anti-a4-b7 therapy (vedolizumab), anti-IL12p40 therapy (ustekinumab), Thalidomide, or Cytoxin. The method of any previous embodiment, wherein the risk genotype comprises one or more of an "A" at rs7958372, a "C" at rs2877453, an "A" at rs71327010, a "C" at rs1169302C, a "G" at rs1169303, an "A" at rs6519183, a "C" at rs685548, an "A" at rs11998187, an "A" at rs531819A, a "G" at rs1041968, a "G" at rs693, an "A" at rs512535, a "G" at rs550619G, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547,an "A" at rs10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs 10821830, an "A" at rs975262, an "A" at rs973067, a "G" at rs10509139, an "A" at rs1442539, an "A" at rs2197155, a "G" at rs7919914, a "G" at rs10994476, an "A" at rs35471473, a "G" at rs12785023, a "G" at rs12783716, a "G" at rs10821821, a "G" at rs 10994441, a "C" at rs10994442, a "T" at rs10821814, an "A" at rs10994465, a "T" at rs12218617, a "C" at rs10509138, an "A" at rs61854518, a "G" at rs 10821699, a "G" at rs7919274, an "A" at rs10761552, a "G" at rs17037425, an "A" at rs2893861, a "C" at rs1993939, a "G" at rs10821833, a "G" at rs 1904418, a "G" rs16915196, an "A" at rs61853514, an "A" at rs 10994430, an "A" at rs16915231, a "G" at rs2028564, a "G" at rs13196552, an "A" at rs17587597, an "A" at rs17587226, an "A" at rs2276917, an "A" at rs10013653, an "A" at rs11582799, an "A" at rs111692854, and an "A" at rs72632053. (92) The method of embodiment 92, wherein the risk genotype is associated with an upregulation or a downregulation of a gene selected from the group consisting of tyrosine phosphatase, non-receptor type 11 (PTPN11), ribosomal protein (RPL30), X-C motif chemokine receptor 1 (XCR1), HNF1 homeobox A (HNF1), ribosomal protein L3 (RPL3), cholinergic receptor muscarinic 3 (CHRM3), DLC1 Rho GTPase activating protein (DLC1), apolipoprotein B (APOB), ribosomal protein L6 (RPL6), glutamate metabotropic receptor 4 (GRM4), p21 (RAC1) activated kinase 2 (PAK2), ribosomal protein L18 (RPL18), phosphodiesterase 4C (PDE4C), protein kinase C alpha (PRKCA), protein phosphatase 2 catalytic subunit alpha (PPP2CA), phosphatidylinositol-4-phosphate 5-kinase type 1 gamma (PIP5K1C), histone cluster 1 H1 family member A (HIST1H1A), Aldehyde Dehydrogenase 2 Family Member (ALDH2), bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2 (CYP4V2), Vesicle Associated Membrane Protein 3 (VAMP3), which is associated with a severe form of CD characteristic of CD3.

VI. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87:2264-2268, 1990, modified as in Proc. Natl. Acad. Sci. USA 90:5873-5877, 1993). Such a formula is incorporated into the basic local alignment search tool (BLAST) programs of Altschul et al. (J Mol Biol. 1990 Oct 5;215(3): 403-10; Nucleic Acids Res. 1997 Sep 1;25(17):3389-402). Percent homology of sequences can be determined using the most recent version of BLAST, as of the filing date of this application. Percent identity of sequences can be determined using the most recent version of BLAST, as of the filing date of this application.

The terms "increased" or "increase" are used herein to generally mean an increase by a statically significant amount. In some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control, Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased" or "decrease" are used herein generally to mean a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The terms "subject" encompass mammals. Non-limiting examples of mammal include, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In some instances, a human subject is a "patient," which as used herein, refers to a subject who may be diagnosed with a disease or condition disclosed herein.

The term "gene," as used herein, refers to a segment of nucleic acid that encodes an individual protein or RNA (also referred to as a "coding sequence" or "coding region"), optionally together with associated regulatory region such as promoter, operator, terminator and the like, which may be located upstream or downstream of the coding sequence. A "genetic locus" referred to herein, is a particular location within a gene.

The term, "genotype" as disclosed herein, refers to the chemical composition of polynucleotide sequences within the genome of an individual. In some embodiments, the genotype comprises a single nucleotide polymorphism (SNP) or and indel (insertion or deletion, of a nucleobase within a polynucleotide sequence). In some embodiments, a genotype for a particular SNP, or indel is heterozygous. In some embodiments, a genotype for a particular SNP, or indel is homozygous.

A "polymorphism" as used herein refers to an aberration in (e.g., a mutation), or of (e.g., insertion/deletion), a nucleic acid sequence, as compared to the nucleic acid sequence in a reference population. In some embodiments, the polymorphism is common in the reference population. In some embodiments, the polymorphism is rare in the reference population.

The term, "single nucleotide polymorphism" or SNP as disclosed herein, refers to a variation in a single nucleotide within a polynucleotide sequence. The term should not be interpreted as placing a restriction on a frequency of the SNP in a given population. The variation of an SNP may have multiple different forms. A single form of an SNP is referred to as an "allele," An SNP can be mono-, bi-, tri, or tetra-allelic. A SNP may include a "risk allele," a "protective allele," or neither. By way of example, a reference polynucleotide sequence reading 5' to 3' is TTACG. A SNP at allele position 3 (of 5'-TTACG-3') comprise a substitution of the reference allele, "A" to a non-reference allele, "C." If the "C" allele of the SNP is associated with an increased probability of developing a phenotypic trait, the allele is considered a "risk" allele. However, the same SNP may also comprise a substitution of the "A" allele to a "T" allele at position 3. If the T allele of the SNP is associated with a decreased probability of developing a phenotypic trait, the allele is considered a "protective" allele. The SNP may be observed in at least 1% of a given population. In some embodiments, the SNP is represented by an "rs" number, which refers to the accession of reference cluster of one more submitted SNPs in the dbSNP bioinformatics database as of the filing date of this patent application, and which is included within a sequence that comprises the total number of nucleobases from 5' to 3'. In some embodiments, a SNP may be further defined by the position of the SNP (nucleobase) within the dbSNP sequence, the position of which is always with reference to 5' length of the sequence plus 1. In some embodiments, a SNP is defined as the genomic position in a reference genome and the allele change (e.g., chromosome 7 at position 234,123,567 from G allele to A allele in the reference human genome build 37). In some embodiments, the SNV is defined as the genomic position identified with [brackets] or an "N" in a sequence disclosed herein.

The term, "indel," as disclosed herein, refers to an insertion, or a deletion, of a nucleobase within a polynucleotide sequence. An indel can be mono-, bi-, tri, or tetra-allelic. An indel may be "risk," a "protective," or neither, for a phenotypic trait. In some embodiments, the indel is represented by an "rs" number, which refers to the accession of reference cluster of one more submitted indels in the dbSNP bioinformatics database as of the filing date of this patent application, and which is included in a sequence that comprises the total number of nucleobases from 5' to 3'. In some embodiments, an indel may be further defined by the position of the insertion/deletion within the dbSNP sequence, the position of which is always with reference to the 5' length of the sequence plus 1. In some embodiments, an indel is defined as the genomic position in a reference genome and the allele change. In some embodiments, the indel is defined as the genomic position identified with [brackets] or an "N" in a sequence disclosed herein.

"Haplotype" as used herein, encompasses a group of one or more genotypes, which tend to be inherited together in a reference population. In some embodiments, a haplotype comprises particular polymorphism or another polymophism in linkage disequilibrium (LD) therewith.

"Linkage disequilibrium," or "LD," as used herein refers to the non-random association of alleles or indels in different gene loci in a given population. LD may be defined by a D' value corresponding to the difference between an observed and expected allele or indel frequencies in the population (D=Pab-PaPb), which is scaled by the theoretical maximum value of D. LD may be defined by an $r^2$ value corresponding to the difference between an observed and expected unit of risk frequencies in the population (D=Pab-PaPb), which is scaled by the individual frequencies of the different loci. In some embodiments, D' comprises at least 0.20. In some embodiments, $r^2$ comprises at least 0.70.

The term "medically refractory," or "refractory," as used herein, refers to the failure of a standard treatment to induce remission of a disease, In some embodiments, the disease comprises an inflammatory disease disclosed herein. A non-limiting example of refractory inflammatory disease includes refractory Crohn's disease, and refractory ulcerative colitis (e.g., mrUC). Non-limiting examples of standard treatment include glucocorticosteriods, anti-TNF therapy, anti-a4-b7 therapy (vedolizumab), anti-IL 12p40 therapy (ustekinumab), Thalidomide, and Cytoxin.

The terms "treat," "treating," and "treatment" as used herein refers to alleviating or abrogating a disorder, disease, or condition; or one or more of the symptoms associated with the disorder, disease, or condition; or alleviating or eradicating a cause of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" refers to the amount of a compound or therapy that, when administered, is sufficient to prevent development of, or alleviate to some extent, one or more of the symptoms of a disorder, disease, or condition of the disease; or the amount of a compound that is sufficient to elicit biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition; Lippincott Williams & Wilkins: Philadelphia, PA, 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, FL, 2004).

The term "pharmaceutical composition" refers to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration.

The term "inflammatory bowel disease" or "IBD" as used herein refers to gastrointestinal disorders of the gastrointestinal tract. Non-limiting examples of IBD include, Crohn's disease (CD), ulcerative colitis (UC), indeterminate colitis (IC), microscopic colitis, diversion colitis, Behcet's disease, and other inconclusive forms of IBD. In some instances, IBD comprises fibrosis, fibrostenosis, stricturing and/or penetrating disease, obstructive disease, or a disease that is refractory (e.g., mrUC, refractory CD), perianal CD, or other complicated forms of IBD.

Non-limiting examples of "sample" include any material from which nucleic acids and/or proteins can be obtained. As non-limiting examples, this includes whole blood, peripheral blood, plasma, serum, saliva, mucus, urine, semen, lymph, fecal extract, check swab, cells or other bodily fluid or tissue, including but not limited to tissue obtained through surgical biopsy or surgical resection. In various embodiments, the sample comprises tissue from the large and/or small intestine. In various embodiments, the large intestine sample comprises the cecum, colon (the ascending colon, the transverse colon, the descending colon, and the sigmoid colon), rectum and/or the anal canal. In some embodiments, the small intestine sample comprises the duodenum, jejunum, and/or the ileum. Alternatively, a sample can be obtained through primary patient derived cell lines, or archived patient samples in the form of preserved samples, or fresh frozen samples.

The term "biomarker" comprises a measurable substance in a subject whose presence, level, or activity, is indicative of a phenomenon (e.g., phenotypic expression or activity; disease, condition, subclinical phenotype of a disease or condition, infection; or environmental stimuli). In some embodiments, a biomarker comprises a gene, gene expression product (e.g., RNA or protein), or a cell-type (e.g., immune cell).

The term "serological marker," as used herein refers to a type of biomarker representing an antigenic response in a subject that may be detected in the serum of the subject. In some embodiments, a serological comprises an antibody against various fungal antigens. Non-limiting examples of a serological marker comprise anti-Saccharomyces cerevisiae antibody (ASCA), an anti-neutrophil cytoplasmic antibody (ANCA), E.coli outer membrane porin protein C (OmpC), anti-Malassezia restricta antibody, anti-Malassezia pachydermatis antibody, anti-Malassezia furfur antibody, anti-Malassezia globasa antibody, anti-Cladosporium albicans antibody, anti-laminaribiose antibody (ALCA), anti-chitobioside antibody (ACCA), anti-laminarin antibody, anti-chitin antibody, PANCA antibody, anit-I2 antibody, and anti-Cbirl flagellin antibody.

The term "microbiome" and its variation used herein describe the populations and interactions of the bacteria, fungi, protists, and virus that align the gastrointestinal tract of a subject. A subject afflicted with IBD may possess presence, absence, excess, diminished, or a combination thereof of a microbiome s compared to a healthy subject.

The terms "response," or "responsive," as used herein, refers to phenomena in which a subject or a patient responds to the induction of a therapy, or a "successful induction" of the therapy, which may in some cases, be an initial therapeutic response or benefit provided by the therapy.

The terms "non-response," or "loss-of-response," as used herein, refer to phenomena in which a subject or a patient does not respond to the induction of a standard treatment (e.g., anti-TNF therapy), or experiences a loss of response to the standard treatment after a successful induction of the therapy. The induction of the standard treatment may include 1, 2, 3, 4, or 5, doses of the therapy. A "successful induction" of the therapy may be an initial therapeutic response or benefit provided by the therapy. The loss of response may be characterized by a reappearance of symptoms consistent with a flare after a successful induction of the therapy.

The term, "transcriptomic risk signature," or "transcriptomic signature," as disclosed herein, refers to two or more biomarkers comprising transcribed polynucleotides (e.g., RNA, cDNA) whose presence, level, or activity, is indicative of a phenomenon (e.g., phenotypic expression or activity; disease, condition, subclinical phenotype of a disease or condition, infection; or environmental stimuli). In some embodiments, the biomarkers comprise non-protein coding oligonucleotide sequence. In some embodiments, the biomarkers comprise protein coding oligonucleotide sequence, such as mRNA or cDNA.

The term, "transcriptomic risk profile," or "transcriptomic profile," as disclosed herein, refers to the particular level of expression or activity of a transcriptomic risk signature or transcriptomic signature in a subject at a point in time.

Where substituent groups are specified by their conventional chemical formulae, written from left to right, they equally encompass the chemically identical substituents that result from writing the structure from right to left, e.g., —CH$_2$O— is equivalent to —OCH$_2$-.

The term "alkyl," by itself or as part of another substituent, means, unless otherwise stated, a straight (i.e., unbranched) or branched carbon chain (or carbon), or combination thereof, which may be fully saturated, mono- or polyunsaturated and includes mono-, di- and multivalent radicals, having the number of carbon atoms designated (i.e., $C_1$-$C_{10}$ means one to ten carbons). Alkyl is an uncylized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic) carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$-], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxvalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic) alkyl, or haloalkyl. An alkoxy is an alkyl attached to the remainder of the molecule via an oxygen linker (—O—).

As used herein, an "alkenyl" group refers to an aliphatic carbon group that contains 2-8 (e.g., 2-8, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$-, cycloaliphatic-$SO_2$-, or aryl-$SO_2$-], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-8, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$-, aliphaticamino-$SO_2$-, or cycloaliphatic-$SO_2$-], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

The term "alkylene," by itself or as part of another substituent, means, unless otherwise stated, a divalent radical derived from an alkyl, as exemplified, but not limited by, —$CH_2CH_2CH_2CH_2$—, Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

As used herein, an "amido" encompasses both "aminocarbonyl" and "carbonylamino". These terms when used alone or in connection with another group refer to an amido group such as —$N(R^X)$—$C(O)$—$R^Y$ or —$C(O)$—$N(R^X)2$, when used terminally, and —$C(O)$—$N(R^X)$— or —$N(R^X)$—$C(O)$— when used internally, wherein RX and RY are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O) —$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$, and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$- and $CH_2$—S—$CH_2$—$CH_2$—NH—$CH_2$-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$-. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[8 2.2.2] octane, etc.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaralphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogens. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —S(O)$_3$— when used internally.

As used herein, a "sulfamide" group refers to the structure —NR$^X$—S(O)$_2$-NR$^Y$R$^Z$ when used terminally and —NR$^X$—S(O)$_2$-NR$^Y$— when used internally, wherein R$^X$, R$^Y$, and R$^Z$ have been defined above.

As used herein, a "sulfonamide" group refers to the structure —S(O)$_2$-NR$^X$R$^Y$ or —NR$^X$-S(O)$_2$-R$^Z$ when used terminally; or —S(O)$_2$-NR$^X$— or —NR$^X$—S(O)$_2$- when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$- when used internally, wherein R$^X$ has been defined above. Exemplary sulfonyl groups include aliphatic-S(O)$_2$-, aryl-S(O)$_2$-, (cycloaliphatic (aliphatic))-S(O)$_2$-, cycloaliphatic-S(O)$_2$-, heterocycloaliphatic-S(O)$_2$-, heteroaryl-S(O)$_2$-, (cycloaliphatic(amido(aliphatic)))-S(O)$_2$- or the like.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, the term "phospho" refers to phosphinates and phosphonates. Examples of phosphinates and phosphonates include —P(O)($R^P$)$_2$, wherein $R^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure ($R^X$)$_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein Rx, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl -C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$-, where v is 1-12. A branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, and $R_3$, and other variables contained in formulae described herein encompass specific groups, such as alkyl and aryl. Unless otherwise noted, each of the specific groups for the variables $R_1$, $R_2$, and $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this disclosure are those combinations that result in the formation of stable or chemically feasible compounds.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇⌇⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

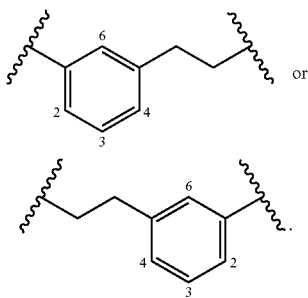

An alkylarylene moiety may be substituted (e.g., with a substituent group) on the alkylene moiety or the arylene linker (e.g. at carbons 2, 3, 4, or 6) with halogen, oxo, —N₃, —CF₃, —CCl₃, —CBr₃, —Cl₃, —CN, —CHO, —OH, —NH₂, —COOH, —CONH₂, —NO₂, —SH, —SO₂CH₃, —SO₃H, —OSO₃H, —SO₂NH₂, ⁻NHNH₂, ⁻ONH₂, ⁻NHC(O)NHNH₂, substituted or unsubstituted C₁-C₅ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO₂R', —CONR'R", —OC(O)NR'R", —NR"C(O)R', —NR'—C(O)NR"R", —NR"C(O)₂R', —NR—C(NR'R"R''')=NR'''', —NR—C(NR'R")=NR''', —S(O)R', —S(O)₂R', —S(O)₂NR'R", —NRSO₂R', ⌐NR'NR"R''', ⌐ONR'R", ⌐NR'C(O)NR"NR'''R'''', —CN, —NO₂, —NR'SO₂R", —NR'C(O)R", —NR'C(O)—OR", —NR'OR", in a number ranging from zero to (2m'+1), where m' is the total number of carbon atoms in such radical, R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —C(O)₂R', —CONR'R", —NR"C(O)R', —NR'—C(O)NR"R''', —NR"C(O)₂R', —NR—C(NR'R"R''')=NR'''', —NR—C(NR'R")=NR''', —S(O)R', —S(O)₂R', —S(O)₂NR'R", —NRSO₂R', ⊓NR'NR"R''', ⁻ONR'R", ⁻NR'C(O)NR"NR'''R'''', —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency, Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms, Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$-B—, wherein A and B are independently —CRR'—, —O—, —NR—, —S—, —S(O)—, —S(O)$_2$-, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$-X'(C"R"R''')$_d$-, where s and d are independently integers of from 0 to 3, and X' is —O—, —NR'—, —S—, —S(O)—, —S(O)$_2$-, —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, _NHNH$_2$, ⊔ONH$_2$, _NHC=(O)NHNH$_2$, ⊔NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and alkyl, heteroalkyl, cycloalkyl, heterocycloalkyl, aryl, heteroaryl, substituted with at least one substituent selected from:

oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, _NHNH$_2$, ׀׀ONH$_2$, _NHC=(O)NHNH$_2$, ׀׀NHC=(O) NH$_2$, —NHSO$_2$H, —NHC= (O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and alkyl, heteroalkyl, cycloalkyl, heterocycloalkyl, aryl, heteroaryl, substituted with at least one substituent selected from:

oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, ⁻NHNH$_2$, ⊓ONH$_2$, ⁻NHC=(O)NHNH$_2$, ⊓NHC=(O) NH$_2$, —NHSO$_2$H, —NHC= (O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and alkyl, heteroalkyl, cycloalkyl, heterocycloalkyl, aryl, heteroaryl, substituted with at least one substituent selected from:

oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, ⊓NHNH$_2$, ⁻ONH$_2$, ⊓NHC=(O)NHNH$_2$, ⁻NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)— or (S)— or, as (D)— or (L)— for amino acids, and individual isomers are encompassed within the scope of the present disclosure. The present disclosure is meant to include compounds in racemic and optically pure forms. Optically active (R)— and (S)—, or (D)— and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure: i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68,and Copper-64. Exemplary magnetic contrast agents include gadolinium, iron oxide and iron platinum, and manganese.

VII. EXAMPLES

Example 1

Presence of Three Subgroups in Small Bowel Resection Expression Data

A total of 139 Caucasian CD patients were included in this study. Transcriptomic data was generated using uninvolved ileal tissue from CD patients who underwent SB resection using methods described in VanDussen, K. L., et al., *Genetic variants synthesize to produce paneth cell phenotypes that define subtypes of Crohn's disease*. Gastroenterology, 2014. 146 (1): p. 200-9. The data was generated in two batches (n=100, n=57) and analyzed separately or as a merged dataset.

Clinical Phenotyping and Genotyping

Figure 8A:
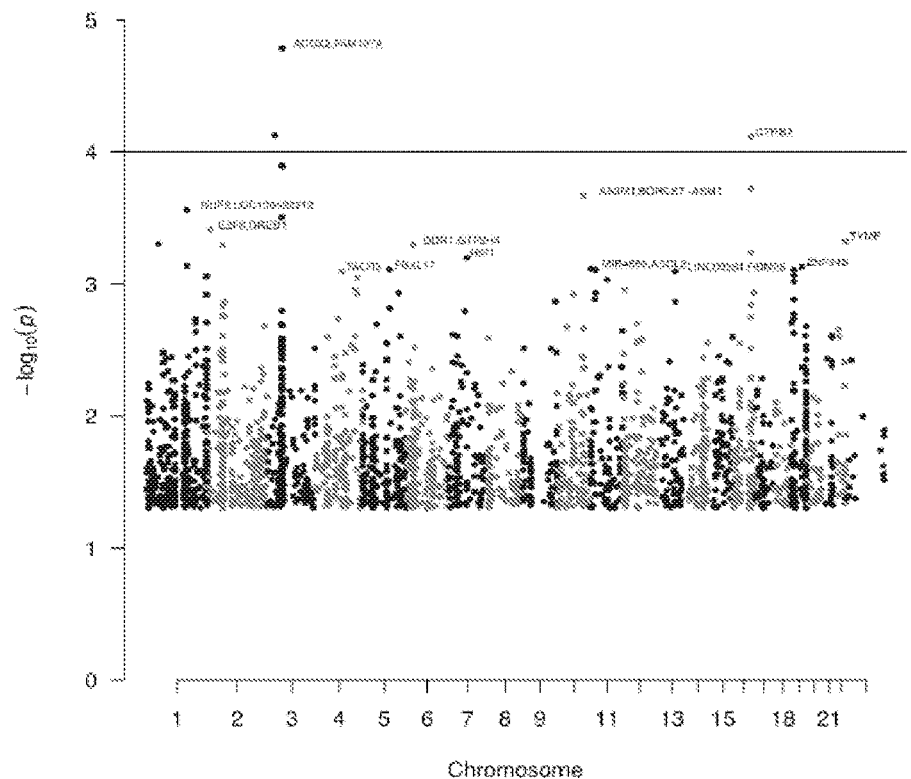
FIGS. 8A-8C shows a genotype association with the three sub-groups. A logistic regression was performed using genotype of the patients in the merged cohort (SB139) and the presence or absence of either CD1, CD2 and CD3 sub-groups.
Figure 8B:
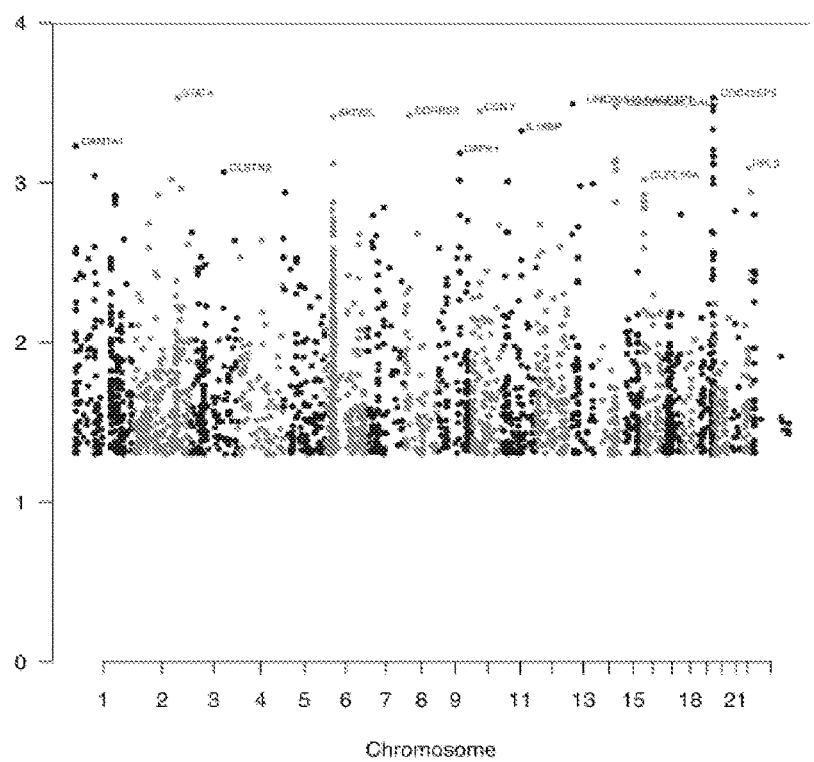

Clinical data, including patients' gender, age at diagnosis, disease location and behavior (according to the Montreal Classification) and surgical history were collected as described. Genotyping was performed at Cedars-Sinai Medical Center using the Illumina Immuno-BeadChip array. Markers were excluded from analysis based on: Hardy-Weinberg Equilibrium p≤0.001; genotyping rate<98%; minor allele frequency<5%. Related individuals (Pi-hat scores>0.25) were identified using identity-by-descent and excluded from analysis using PLINK. Admixture was used to generate ethnicity proportion estimations for all individuals. Only subjects identified by admixture as Caucasian (proportion≥0.75) were included in the analysis; thus, a total 139 independent Caucasian samples were retained in analysis. Principal component analysis was performed using Eigenstrat and top two principal components were included as covariates in the analysis to adjust for potential population sub-structure. We performed genetic associations (logistic regression with PC adjustment) for the presence or absence of a given sub-group (CD1/CD2/CD3) using genotype data for the 139 subjects in the combined cohort. Results indicate that the CD3 sub-group which was associated with pCD had significant genetic associations with SNPs (intronic rs888338, OR=3.5, P=6.5 ×10-4) in DAPK1, a pCD risk gene locus. FIGS. 8A-8B show Manhattan plot for associations with p<0.05 for CD1 and CD3 phenotypes, respectively. Interestingly, some of the top SNPs associated with CD3 sub-group belong to genes also associated with very-early onset-IBD (VEO-IBD), including genes (SKIV2L and DAPK1) (FIG. 8B).

Sample Cohorts

Uninflamed tissue from formalin-fixed paraffin-embedded (FFPE) small bowel resection margins of subjects requiring surgery at Cedars-Sinai Medical Center for Crohn's disease was identified. Whole-thickness ileal tissue was scraped from the FFPE tissue sections followed by RNA extraction using the RNeasy FFPE kit (Qiagen) according to the manufacturer's instructions. The Transplex Whole Transcriptome Amplification kit (WTA2; Sigma) was used for cDNA synthesis and amplification. Subsequent purification of the cDNA product was performed with the PCR Purification kit (Qiagen). Sample quality was confirmed using the Agilent Bioanalyzer. For samples passing quality control, Cy5 labeling with the ULST Fluorescent Labeling kit (Kreatech) and hybridization (performed in duplicate for each sample) to Whole Human Genome 4×44k Microarrays (Agilent) was performed.

Expression Data Processing and Clustering

Single channel microarray expression data extracted using Agilent feature extraction software was received from Genome Technology Access Center at Washington University in St. Louis. Raw expression data available in technical duplicates was normalized using LIMMA package implemented in R version 3.2.1. All the gene expression data including the sample meta data, Agilent raw data along with the processed data for all the 157 samples can be accessed at Gene Expression Omnibus using accession number GSE120782. The expression data preprocessing included background correction of the expression data, followed by log2-transformation and quantile-normalization. Unsupervised hierarchical clustering of expression data was used to remove outlier subjects.

Differential gene expression analysis was done by class comparison in BRB array tools using expression corresponding to each of the three sub-groups. Sometimes, a gene filter cut-off was applied during class comparison where a gene was excluded if <20% of expression data had at least a 1.5-fold change in either direction from gene's median value. Multiple probes per gene were used to verify expression analysis. The "removebatcheffect" function in LIMMA R package was used to remove the batch effects between the SB85 and SB54 datasets.

Figure 7A:
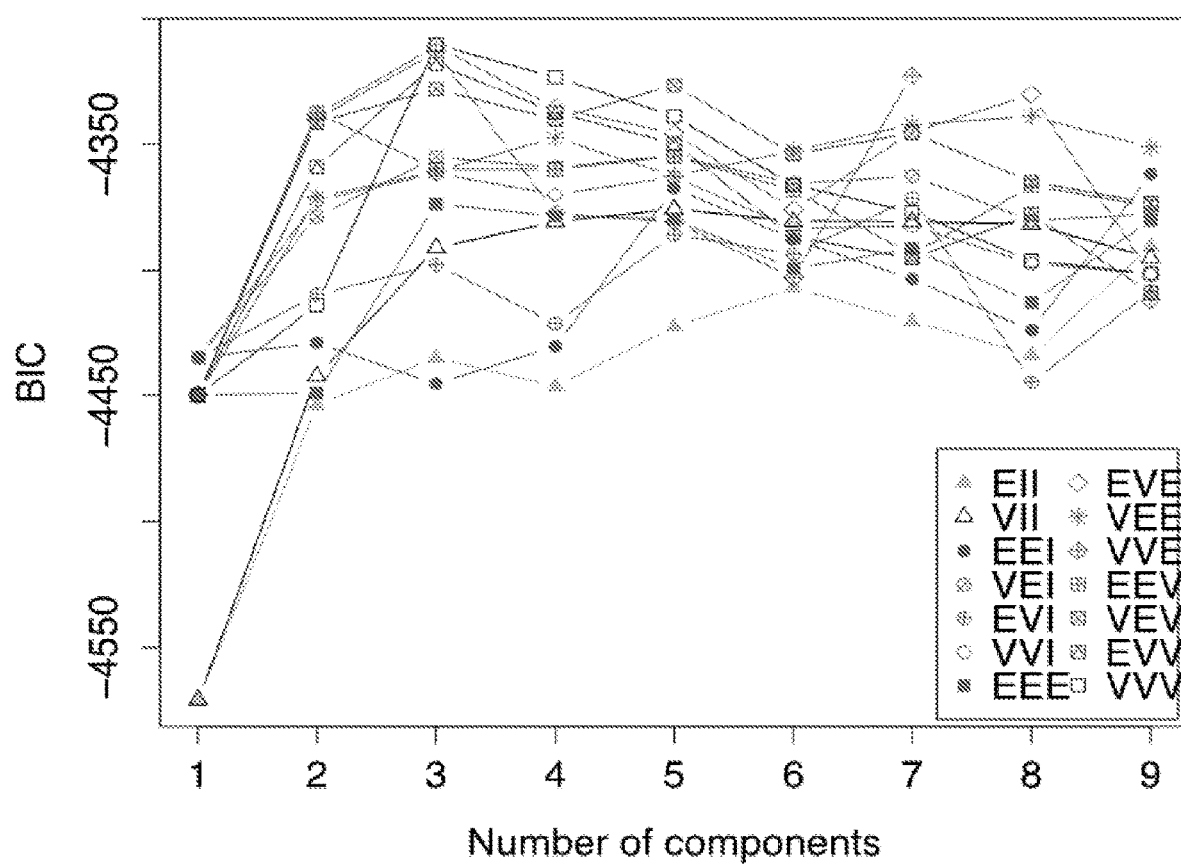
FIGS. 7A-7B shows validation of the presence of three subgroups in SB139 expression data using model-based clustering method implemented in "mclust" R-package.
Figure 7B:
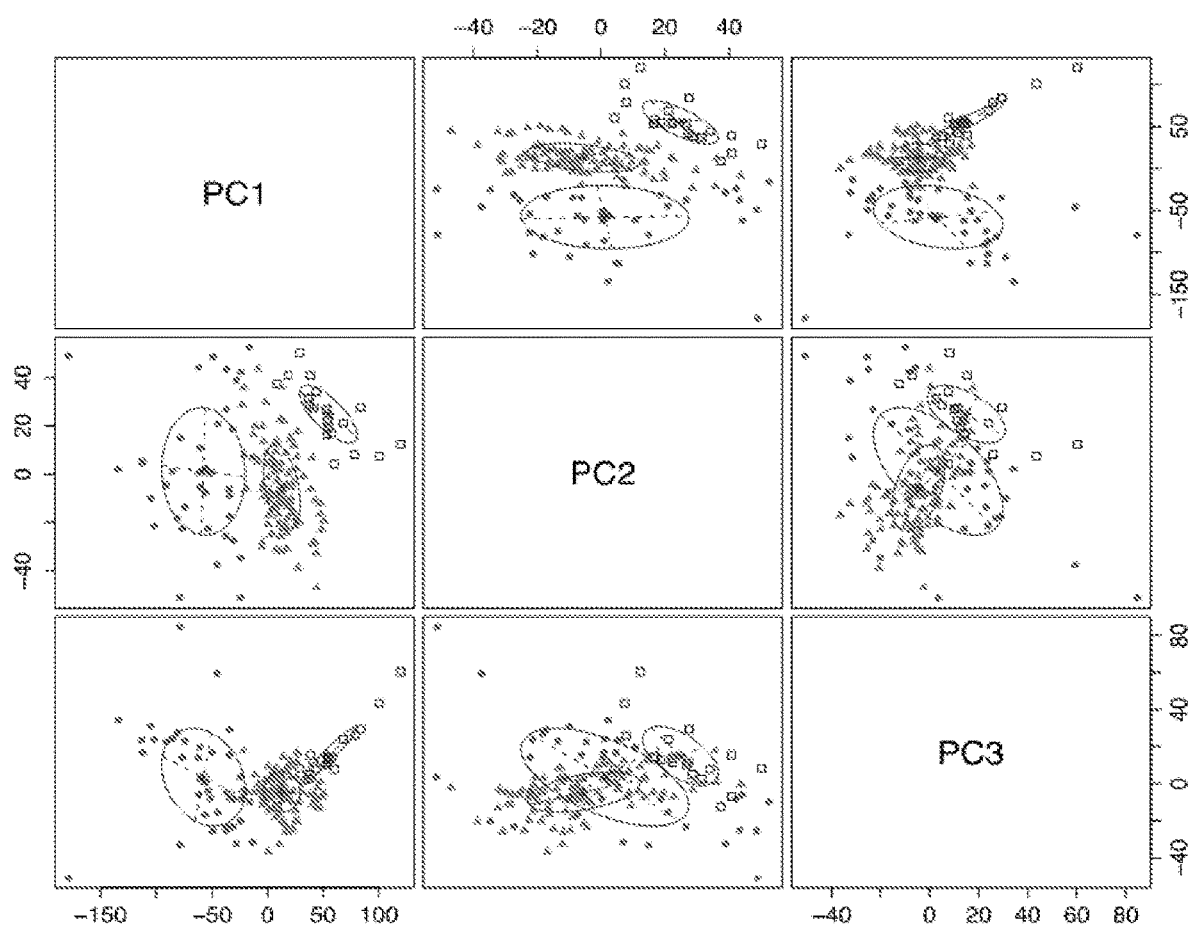

The presence of three patient subgroups in our combined expression data was validated using a non-heuristic, model-based clustering method. This was implemented using "mclust" R package which is based on using Gaussian finite mixture models. In this method, the data is assumed to be part of a distribution that is a mixture of two or more subgroups where each group is modeled by a Gaussian distribution with a specific mean vector, covariance matrix and associated probability in the mixture. The advantage of using model-based clustering is the recommendation of number of clusters/subgroups present and the best model to fit the data. Using the Bayesian information criterion score, an optimal number of three subgroups were recommended by application of mclust package on the merged dataset (FIG. 7A, B).

Results

Figure 1A:
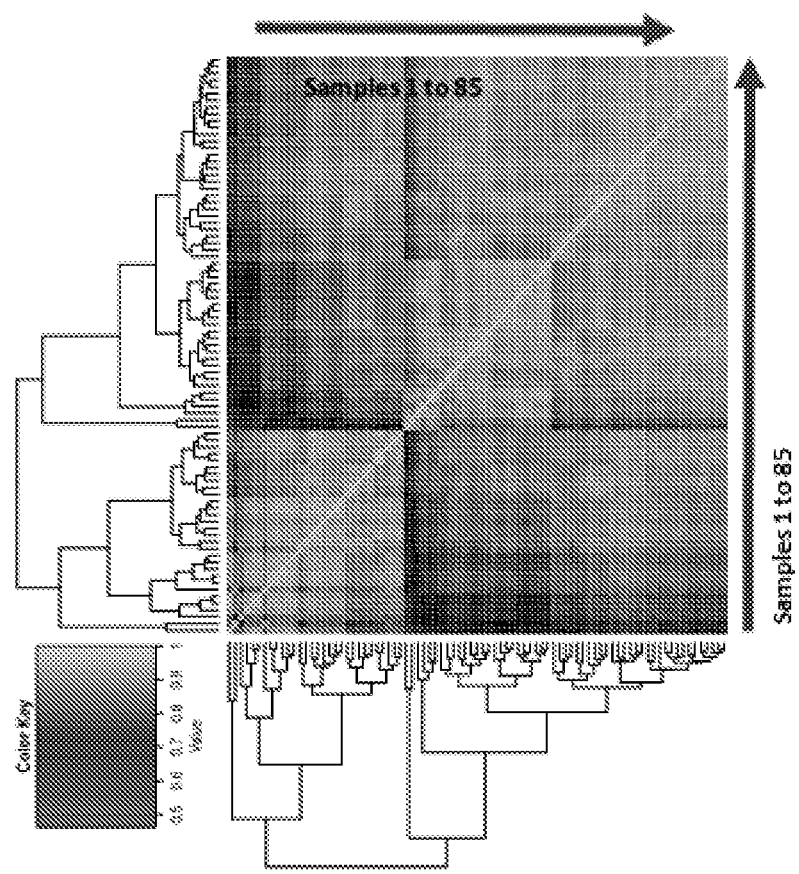

Sample correlation was analyzed of normalized, background corrected expression data after removing outliers and non-Caucasian samples from the larger cohort of 100 samples. This cohort is herein referred to as SB85 (post quality control, n=85). FIG. 1A shows the heat map of Pearson correlation coefficient between the samples using normalized expression probe data in SB85 cohort. The heat map revealed the presence of three patient sub-groups. The dimensionality of the expression dataset was reduced using principal component analysis (PCA) and the top three principal components (that explained most of the variance in expression data) also indicated that the samples clustered into three sub-groups. Multiple clustering methods (hierarchical, k-means clustering and model-based clustering) were applied to allocate samples to each sub-group. FIG. 1B shows the PCA plot for the SB85 cohort highlighting the three CD patient sub-groups, CD1, CD2 and CD3. The three subgroups in SB85 were homogenous in terms of Jewish ethnicity and disease behavior.

Figure 1C:
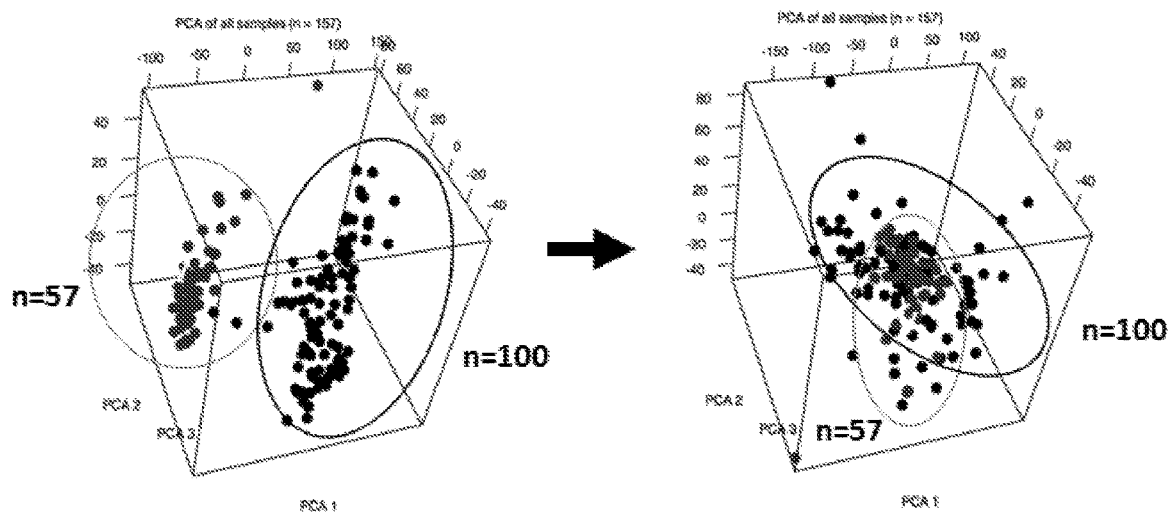
Figure 1D:
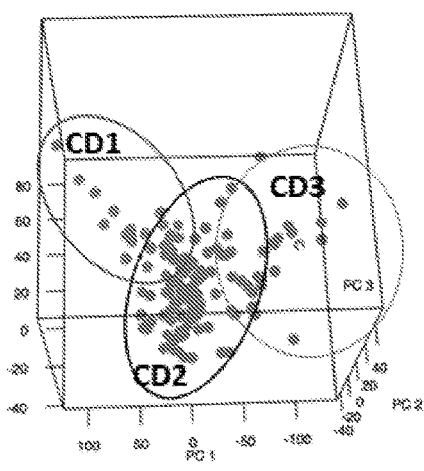
Figure 1E:
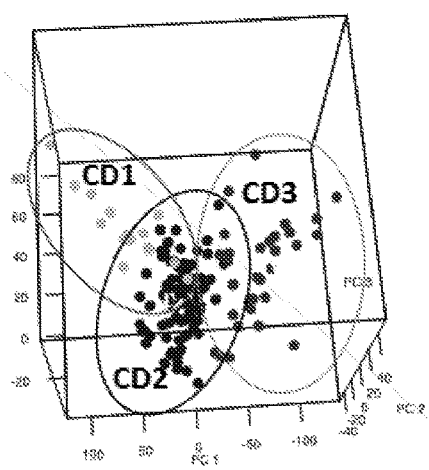

Next, the two expression cohorts were merged into a combined cohort to increase the sample size to perform further associations as we are underpowered to draw conclusive results using only the SB54 dataset. Batch effects were removed, and the two datasets were merged (combined cohort SB139; FIG. 1C). Both SB85 and SB54 cohorts are similar in terms of baseline characteristics. There were no statistically significant differences in average age at diagnosis (24 years for both cohorts), gender, disease location and behavior, pCD occurrence and time to second surgery or follow-up between the two cohorts. The PCA plot of our combined cohort SB139 confirmed the presence of three distinct patient subgroups (FIG. 1D) using k-means/hierarchical clustering. CD1 and CD3 subgroups were found to be the most distant as seen in the 3-D PCA plot (FIGS. 1B, C, D). The presence of three patient subgroups was validated in Cedars-Sinai Medical Center combined expression data using a non-heuristic, model-based clustering method. A comparison of the three subgroups from model-based clustering and k-means/hierarchical clustering indicated mostly similar sorting of samples into the three-subgroups (FIGS. 1D and 1E).

Example 2

Clinical Variables Associated with the Patient Subgroups Indicate CD3 Cluster to be More Severe Clinical data, including the current age, gender, age at diagnosis, disease location and behavior (according to the Montreal Classification) and surgical history of the subjects were collected. Phenotypic differences in the transcriptomic-based patient subgroups and clinical variables associated with the subjects were investigated. Table 7 shows baseline clinical characteristics of each of the three patient subgroups in the combined cohort (Total, n=139; CD1, n=26; CD2, n=88 and CD3, n=25). Clinical differences between the most distant subgroups (CD1 and CD3) of SB139 were observed. CD3 was associated with higher occurrence of second surgery (OR=5.07, P=0.016) and presence of pCD (OR=3.61, P=0.036) (Table 8). No significant differences were found when comparing the three subgroups simultaneously for differences in various clinical phenotypes, including disease location, CD disease behavior information based on Montreal classification (described as B1, nonstricturing, nonpenetrating; B2, stricturing: and B3, penetrating diseases) and occurrence of second surgery.

Gender was also a predictor of clustering (Table 9), with the more severe CD3 subgroup consisting of a higher percentage of females Without being bound by any particular theory, women may be at higher risk of inflammation associated diseases due to enhanced immune activation in the gut. Given these gender differences, enrichment of females in CD3 group may indicate exacerbation of severe CD in females. Table 9 provides phenotype data, therapy and smoking habit prior to first surgery labeled by sample sub-groups.

Figure 2A:
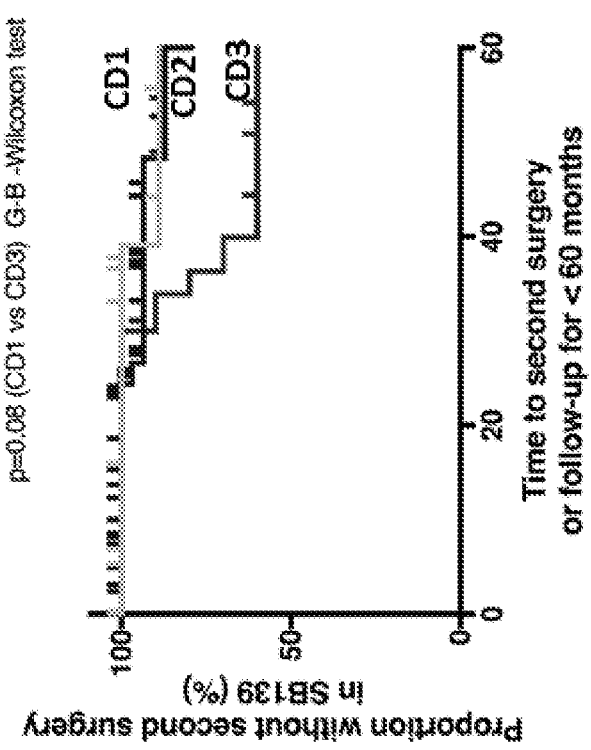
FIGS. 2A-2B shows the CD3 patient sub-group has faster disease recurrence and trending towards shorter time to second surgery compared to CD1.
Figure 2B:
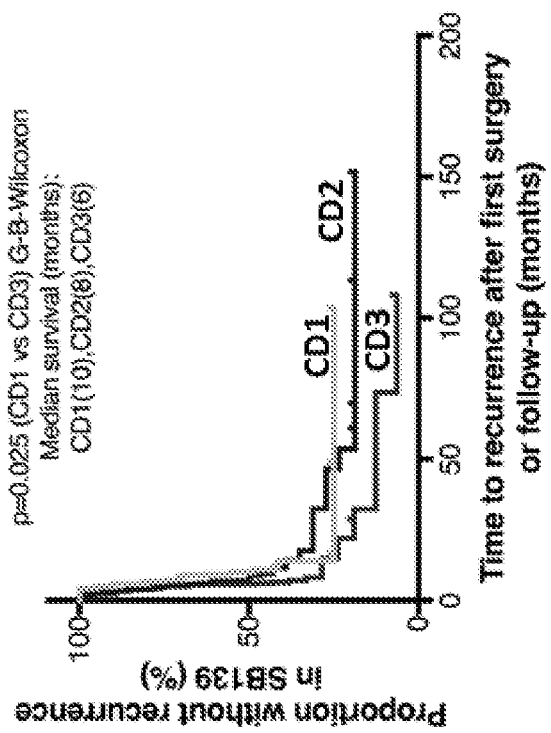

Survival analysis using time from first surgery to recurrence or last follow-up indicated the time to recurrence in CD3 was shorter than in CD1 (p=0.02) (FIG. 2A). The median time to recurrence from first surgery in months for CD1 was 10, CD2 was 8 and CD3 was shortest at 6 months (FIG. 2A). Compared to CD1, CD3 was enriched for subjects with increased disease recurrence after first surgery (OR=6.78, P=0.04). Using time from first to second surgery or last follow-up within 5 years suggested a greater proportion without second surgery in CD1 compared to CD3 (p=0.08) (FIG. 2B). These data suggest that the CD3 cluster contains individuals with a more severe disease course. Given our small sample size, in separate multivariate models with gender as covariate, significance of association of clustering (CD1 and CD3) with pCD dropped (OR=2.82, P=0.1) while occurrence of second surgery remained significant (OR=4.62, P=0.03).

TABLE 7

Baseline characteristics of patients in three subgroups of SB139 cohort

|  | CD1 (n = 26) | CD2 (n = 88) | CD3 (n = 25) |
| --- | --- | --- | --- |
| Age at diagnosis, yr ± SD | 21.89 ± 12.99 | 25.38 ± 13.61 | 22.94 ± 11.02 |
| Gender (Female), n (%) | 12 (46.1) | 38 (43.1) | 20 (80) |
| Disease location, n (%) | | | |
| L1, ileum | 14 (53.1) | 39 (44.3) | 9(36) |
| L2, colon | 0 (0) | 2 (2.3) | 0(0) |
| L3, ileocolon | 12 (46.1) | 44 (50) | 16(64) |
| L4, upper GI | 4 (15.3) | 7 (7.9) | 3(12) |
| Disease behavior, n (%) | | | |
| B1, nonstricturing nonpenetrating | 1 (3.8) | 2 (2.2) | 2(8) |
| B2, stricturing | 11 (42.3) | 38 (43.1) | 13(52) |
| B3, penetrating | 14 (53.8) | 48 (54.5) | 10(40) |
| Perianal disease, n (%) | 6 (27.7) | 24 (27.2) | 13 (52) |
| Second surgery, n (%) | 4 (15.4) | 24 (27.2) | 12 (48) |
| Recurrence, n (%) | 12 (46) | 23 (26) | 19 (76) |

TABLE 8

The most distant sub-groups, CD1 and CD3 in merged SB139 are clinically different.

| Phenotype | (CD1, n = 26) | | | (CD3, n = 25) | | | OR(95% C1) | P |
|---|---|---|---|---|---|---|---|---|
| | No | Yes | % Yes | No | Yes | % Yes | | |
| Second Surgery | 22 | 4 | 15.38 | 13 | 12 | 48.00 | 5.07(1.44-21.31) | 0.016 |
| Perianal Disease | 20 | 6 | 27.27 | 12 | 13 | 52.00 | 3.61(1.12-12.75) | 0.036 |

| | Male | Female | % Female | Male | Female | % Female | OR(95% C1) | P |
|---|---|---|---|---|---|---|---|---|
| Gender | 14 | 12 | 46.15 | 5 | 20 | 80.00 | 4.66(1.41-17.59) | 0.015 |

TABLE 9

Phenotype data, therapy and smoking habit prior to first surgery labeled by sample sub-groups

| | CD1 (n = 21) | CD2 (n = 69) | CD3 (n = 20) |
|---|---|---|---|
| Disease location, n (%) | | | |
| L1, ileum | 2(9.5) | 13(18.8) | 2(10) |
| L2, colon | 0 | 0 | 0 |
| L3, ileocolon | 17(81) | 53(76.8) | 17(85) |
| L4, upper GI | 2(9.5) | 3(4.3) | 1(5) |
| Disease behavior, n (%) | | | |
| B1, nonstricturing nonpenetrating | 0 | 1(1.4) | 2(10) |
| B2, stricturing | 6(28.5) | 28(40.6) | 6(30) |
| B3, penetrating | 15(71.4) | 40(58) | 12(60) |
| Smoking history, never smoked, n (%) | 19(90.4) | 53(77) | 15(75) |
| Positive family History of IBD, n (%) | 8(38) | 21(30.4) | 5(25) |
| Therapy, n (%) | | | |
| Pre-op 5-aminosalicylic acid (ASA) treatment | 17(81) | 45(65.2) | 16(80) |
| Pre-op Immunomodulator treatment (Methotrexate/AZA/6-MP/Cyclosporine) | 13(62) | 30(43.5) | 10(50) |
| Pre-op Anti-TNF treatment (Infliximab/Adalimumab/Certolizumab) | 9(43) | 37(53.6) | 12(60) |

Example 3

Figure 3:
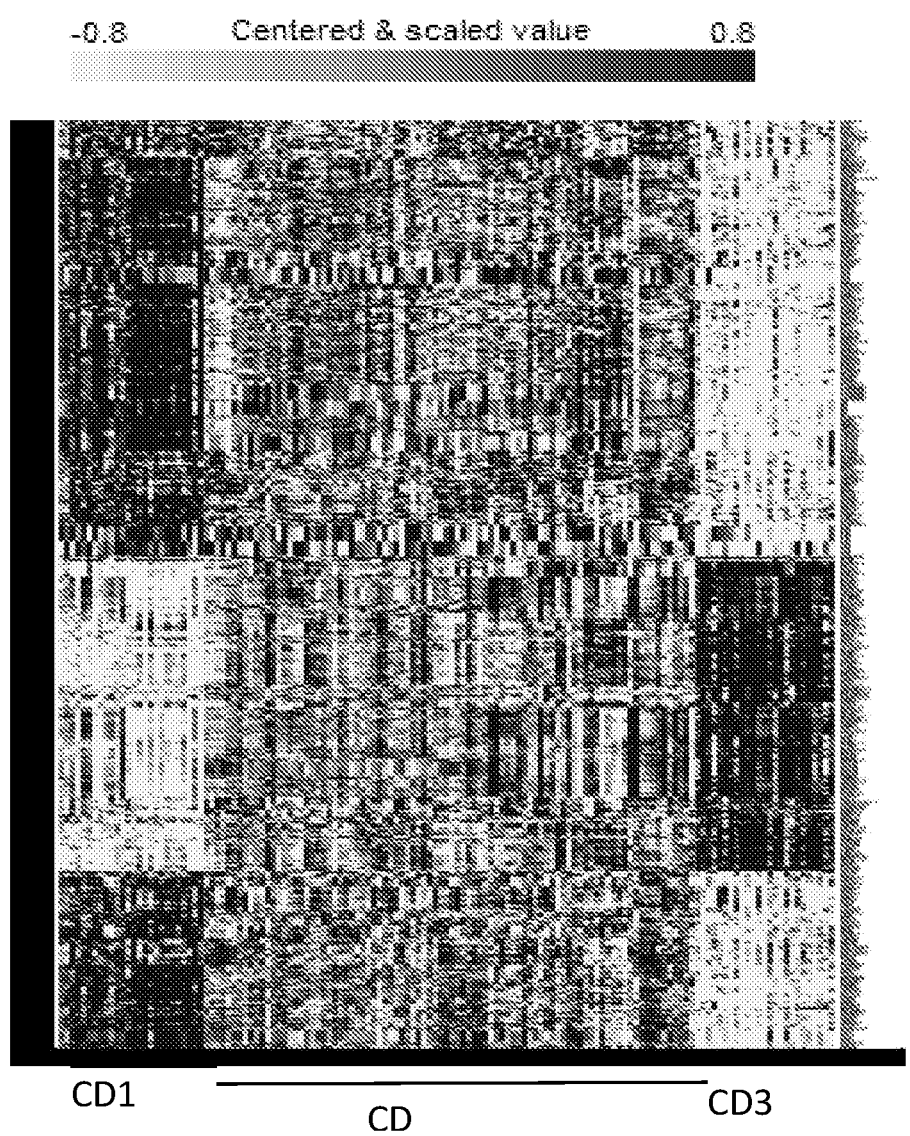
FIG. 3 shows a class comparison of the three groups using probe-expression data of SB139 performed in BrB array tools indicated 4380 gene expression probes to be significantly DE (FDR<0.001). A gene was excluded if <20% of expression data had at least a 1.5 fold change in either direction from gene's median value. The black shade shows higher expression.

Differential Gene Expression Across the Subgroups Reveal Specific Expression Signatures Associated with CD3 Compared to the Less Severe CD1 Sub-Group A class comparison using gene expression corresponding to the three subgroups was performed. This gave a list of 4380 gene expression probes to be significantly different (FDR<0.001) between each of the pairs from the three subgroups. FIG. 3 shows the heat map of the differentially expressed (DE) genes in the three subgroups.

Table 10 provides the results of a pathway analysis performed, Pathway analysis identified eukaryotic initiation factor 2 (EIF2) signaling, actin cytoskeleton and integrin signaling to be down-regulated in CD3 versus CD1 as indicated by negative activation z-scores, while organismal death was activated in CD3 versus CD1 subgroups. Pathway analyses using an expanded list of >18,000 DE genes also indicated that EIF2 signaling was down-regulated in CD3 versus CD1 sub-groups, while RhoGD1 signaling was activated in CD3 compared to CD1.

TABLE 10

Pathway Analysis Results-Signaling Pathways

| Pathway | CD3 v. CD1 | CD2 vs. CD3 | CD2 vs. CD1 |
|---|---|---|---|
| EIF2 Signaling | − | + | − |
| Integrin Signaling | − | + | − |
| NRF2-mediated Oxidative stress | − | + | − |
| Fc γ Receptor-mediated phagocytosis in Macrophages | − | + | − |
| Ephrin Receptor Signaling | − | + | − |
| Actin Cytoskeleton | − | + | − |
| ERK5 Signaling | − | + | − |
| Wnt/β-catenin Signaling | − | + | − |
| Remodeling of Epethial Adherens Junctions | − | + | − |
| Regulation of Actin-based Motility by Rho | − | + | − |
| Leukocyte Extravasation SIgnaling | − | + | − |
| Regulation of eIF4 and p70S6K Signaling | + | + | − |
| RhoGDI Signaling | + | − | + |
| RhoA Signaling | − | + | − |
| Cdc42 Signaling | − | + | − |
| Signaling by Rho Family GPTases | − | + | − |

Next, a pathway analysis was performed for cellular processes, which are provided in Table 11. Organismal death, morbidity, and cell death of osteosarcoma are upregulated in the CD3 cohort as compared to the CD1 cohort. In contrast, Infection and cell viability appear to be down regulated.

TABLE 11

Pathway Analysis-Cellular Processes

| Pathway | CD3 v. CD1 | CD2 vs. CD3 | CD2 vs. CD1 |
|---|---|---|---|
| Organismal Death | + | + | − |
| Morbidity or mortality | + | + | − |
| Cell death or osteosarcoma cells | + | + | − |
| Infection by RNA virus | − | − | + |
| Infection by Retroviridae | − | − | + |
| HIV infection | − | − | + |
| Infection by HIV-1 | − | − | + |
| Viral Infection | − | − | + |
| Infection of cells | − | − | + |
| Invasion of cells | − | − | + |
| Infection of kidney cell lines | − | − | + |
| Infection of epithelial cell lines | − | − | + |
| Infection of embryotic cell lines | − | − | + |
| Cell viability of tumor cell lines | − | − | + |
| Cell viability | − | − | + |

Example 4

Figure 8C:
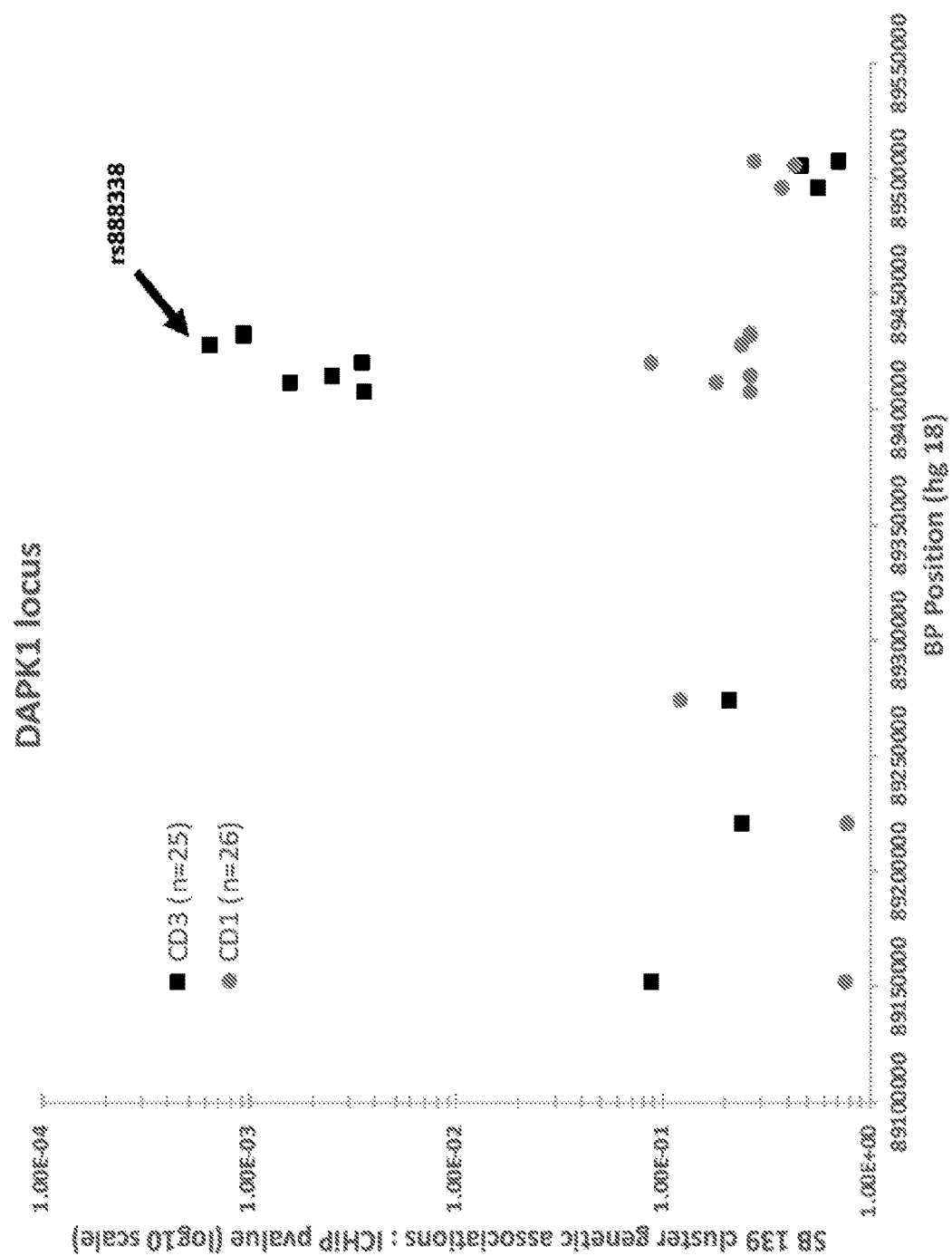

Overlap of Genetic and Gene Expression Signatures Defining the CD3 Sub-Group Reveal Specific Pathways Driving the CD3 Phenotype Differences were identified in genetic loci underlying susceptibility and associated disease severity for the three CD subgroups that were identified via transcriptomics (FIGS. 8A-8C). Results indicate that the CD3 sub-group which was associated with pCD had significant genetic associations with SNPs (intronic rs888338, OR=3.5, P=6.5× 10-4) in DAPK1, a pCD risk gene locus. FIGS. 8A-8B show Manhattan plot for associations with p<0.05 for CD1 and CD3 phenotypes, respectively. Interestingly, some of the top SNPs associated with CD3 sub-group belong to genes also associated with very-early onset-IBD (VEO-IBD), including genes (SKIV2L and DAPK1) (FIG 8B). FIG. 8C shows that the CD3 sub-group is associated with SNPs in DAPK1 gene, a previously reported pCD phenotype locus.

Candidate genes that appeared in the genetic associations as well as DE gene list were analyzed. A total of 174 genes associated specifically with either CD1 or CD3, and were also differentially expressed between the two subgroups (Table 4). Pathway analyses using these genes and the associated expression fold-changes between CD3 versus CD1 subgroups indicated EIF2 signaling was down-regulated in CD3 compared to CD1 and cAMP-mediated signaling was activated in CD3 compared to CD1 (See Table 12).

TABLE 12

Pathway Analysis of 174 Gene Signature Defining CD3 Sub-group

| Pathway | CD3 v. CD1 |
| --- | --- |
| EIF2 Signaling | − |
| cAMP-mediate signaling | + |
| ERK/MAPK Signaling | − |
| RhoGDI Signaling | + |
| Protein Kinase A Signaling | + |
| Production of Nitric Oxide and Reactive Oxygen Species | − |

Key genes, including apolipoprotein B (APOB), phosphodiesterase 4C (PDE4C), protein kinase C alpha (PRKCA) and SMAD family member 3 (SMAD3), that are involved in pathways differentially regulated between CD3 and CD1 subgroups. Oncostatin-M receptor (OSMR) was upregulated in CD3 and high expression of oncostatin-M (OSM) and its receptor, OSMR has been reported to be associated with disease severity and non-response to anti-TNF therapy. SMAD3 was down-regulated in the CD3 sub-group and knock-out mice for SMAD3 have impaired intestinal mucosal healing. SMAD3 variants have been shown to be associated with risk for recurring surgery in CD patients. SH3 and multiple ankyrin repeat domains 3 (SHANK3) was downregulated in CD3, which is consistent with a reported role of SHANK3 in regulation of intestinal barrier function, with SHANK3 knock-out mice showing impaired epithelial barrier. Thus, key genes were identified based on genotype and/or differential expression that differentiate the clinically distinct CD1 and CD3patient subgroups (Table 13).

Polymorphism associated with an up-or down-regulation of the 174 genes are provided in Table 2 in the CD3 population. A negative fold change value in Table 2 indicates that the polymorphism is associated with a downregulation of the gene, whereas a positive fold change value in Table 2 indicates that the polymorphism is associated with an upregulation of the gene. Without being bound by any particular theory, it would be expected that a transcriptomic risk signature (TRSig) may be detected either by detecting a level of expression of one or more genes from Table 4 directly, or by detecting a presence of one or more polymorphisms associated with that expression.

TABLE 13

Keys genes differentiating the clinically distinct CD3 and CD1 patient subgroups based on genotype and expression

| Gene | CD3 vs CD1 fold change | Genetic association (p < 0.05) | Reference |
| --- | --- | --- | --- |
| PDE4C | 2.12 (11 probes) | Associations with CD3 | PDE4 Inhibition and IBD: A Novel Therapeutic Avenue |
| ICAM3 | 2.41 | Associations with CD3 | Increased Cell Adhesion Molecules, PECAM-1, ICAM-3, or VCAM-1, Predict Increased Risk for Flare in Patients With Quiescent IBD |
| SMAD3 | −2.41 (10 probes) | Association with CD1 | Smad3 knockout mice exhibit impaired intestinal mucosal healing; SMAD3 gene variant is a risk factor for recurrent surgery in patients with Crohn's disease |
| IL18BP | 1.476 | Association with CD3 | Interleukin-18 and its Binding Protein in Patients with IBD during Remission and Exacerbation |
| DAPK1 | NA | Associations with CD3 | Perianal Crohn's Disease is Associated with Distal Colonic Disease, Stricturing Disease Behavior, IBD-Associated Serologies and Genetic Variation in the JAK-S |
| SHANK3 | −2.59 | NA | SHANK3 Regulates Intestinal Barrier Function Through Modulating ZO-1 Expression Through the PKCε-dependent Pathway |
| OSMR | 1.95 | NA | Oncostatin M drives intestinal inflammation and predicts response to tumor necrosis factor—neutralizing therapy in patients with IBD |

Example 5 eQTL Analyses Reveal Differences in CD1 and CD3 Sub-Groups

Using the genetic and transcriptomic data for SB139 cohort, expression quantitative trait loci (eQTL) analyses were performed to determine genetic loci that directly regulate local gene expression in the CD subgroups of varying severity with CD1 being less severe and CD3 being more severe using the available expression and genotype data for n=26 (CD1 ) and n=26 (CD3) independent Caucasian samples, Cis-eQTL analysis revealed that CD1 and CD3 subgroups have mostly distinct signatures. All the cis-eQTLs with FDR<0.001 were unique to either CD1 or CD3 subgroup with no overlap.

eQTL Mapping eQTL mapping was implemented in Matrix eQTL R package using the available expression and genotype data for n=26 (CD1) and n=26 (CD3) independent Caucasian samples. eQTLs were also performed considering all the 139 samples together as part of determining eGenes to calculate TRS. Associations between genotype and probe expression level were performed using a linear regression model with additive genotype effects. All associations were adjusted for gender, age and population sub-structure using the first two principal components of genetic data. Gene bounds were defined using a 1 Mb window around the transcription start position of given gene as obtained from UCSC Genome Browser. For cis-eQTL mapping, a 1 Mb cis distance from gene bounds was used, Cis-eQTLs were defined as association signals from SNPs located within 1 Mb from each of the gene bounds. False discovery rates (FDR) were estimated to correct for multiple testing using Matrix eQTL according to the Benjamini and Hochberg method.

Pathway Analysis

Pathway analysis was accomplished through the use of Qiagen's Ingenuity® Pathway Analysis (IPA®, Qiagen, Redwood City, www.qiagen.com/ingenuity). Pathway analysis using the set of DE genes between the subgroups was performed in Ingenuity pathway (IPA) along with a diseases and Biological function analysis. Class comparison analysis in BRB array tools with the gene-filter criterion turned on gave a list of 4380 DE gene expression probes while with the filter turned off gave a much larger (>18000) list of DE expression probes between the sub-groups.

Comparison pathway analyses in IPA using eGenes (genes from unique cis-eQTL pairs to either CD1 or CD3 with p<1e-08, FDR<0.001) demonstrated CD3 subgroup was enriched in Wnt/beta-catenin signaling and regulation of epithelial-mesenchymal transition while CD1 subgroups was enriched in pathways related to inflammation such as antigen presentation and OX40 signaling (FIG. 4A).

The genes identified by overlapping eQTL and pathway analyses are provided in Table 3, which are the genes used to calculate the transcriptional risk score (TRS).

Example 6

Transcriptional Risk Scores

Transcriptional risk score (TRS) was calculated for the SB139 cohort using the methods described in the work by Marigorta, U. M., et al., *Transcriptional risk scores link GWAS to eQTLs and predict complications in Crohn's disease.*, in Nature Genetics. 2017. p. 1517-1521. 122 among 232known IBD loci are either cis-eQTLs or in strong LD (r2>0.8) with at least one cis-eQTL in peripheral blood. This corresponds to a total of 163 (157 unique) corresponding eGenes, that is, ~1.3 candidate gene per SNP. We determined 139/157 eGenes to be present with a nominal pvalue<0.05 in cis-eQTL dataset of all the 139 samples. All 139 eGenes had cis-eQTLs in Jostins-Liu known region in SB139 cis-eQTL dataset. Transcript abundance in SB139 cohort for the short-listed 139 eGenes was standardized and polarized according to direction of risk. Transcript abundance where low expression was associated with risk were flipped. Summation over all eGenes gave TRS which was further standardized.

TRS calculated using expression data of eGenes (eQTL associated genes) in the SB139 cohort (see methods) was found to be associated with the three CD subgroups (p<0.0001, Kruskal-Wallis test). CD3 subgroup was associated with significantly higher score compared to CD1 (p=0.0002, Mann-Whitney test). CD2 subgroup was intermediate with a heterogeneous mix of subjects with both high and low TRS scores (FIG. 4B). Consistent with the conclusions from the Marigorta et al., study, the calculated TRS scores in our study are associated with the sub-population with more severe clinical disease.

Example 7

Cell-Type Specific Signatures Associated With Subgroups

Enrichment of specific cell-types associated gene signatures were performed in the SB resection tissue samples which could possibly lead to the subgroups that identified using the ileal tissue expression. xCell was used to generate cell-type specific signatures associated with the three subgroups. The most pronounced cell-type differences, represented by the gene signature, were in the eosinophil and NKT enrichment score as highlighted in the left and right figure insets in FIG. 5A-5B (eosinophil). CD3 had significantly higher eosinophil enrichment scores compared to the two other subgroups (p<0.0001) (FIG. 5A-5B). The national killer T (NKT) cell type enrichment scores were associated with the subgroups in a similar way (FIG. 5C).

Figure 5B:
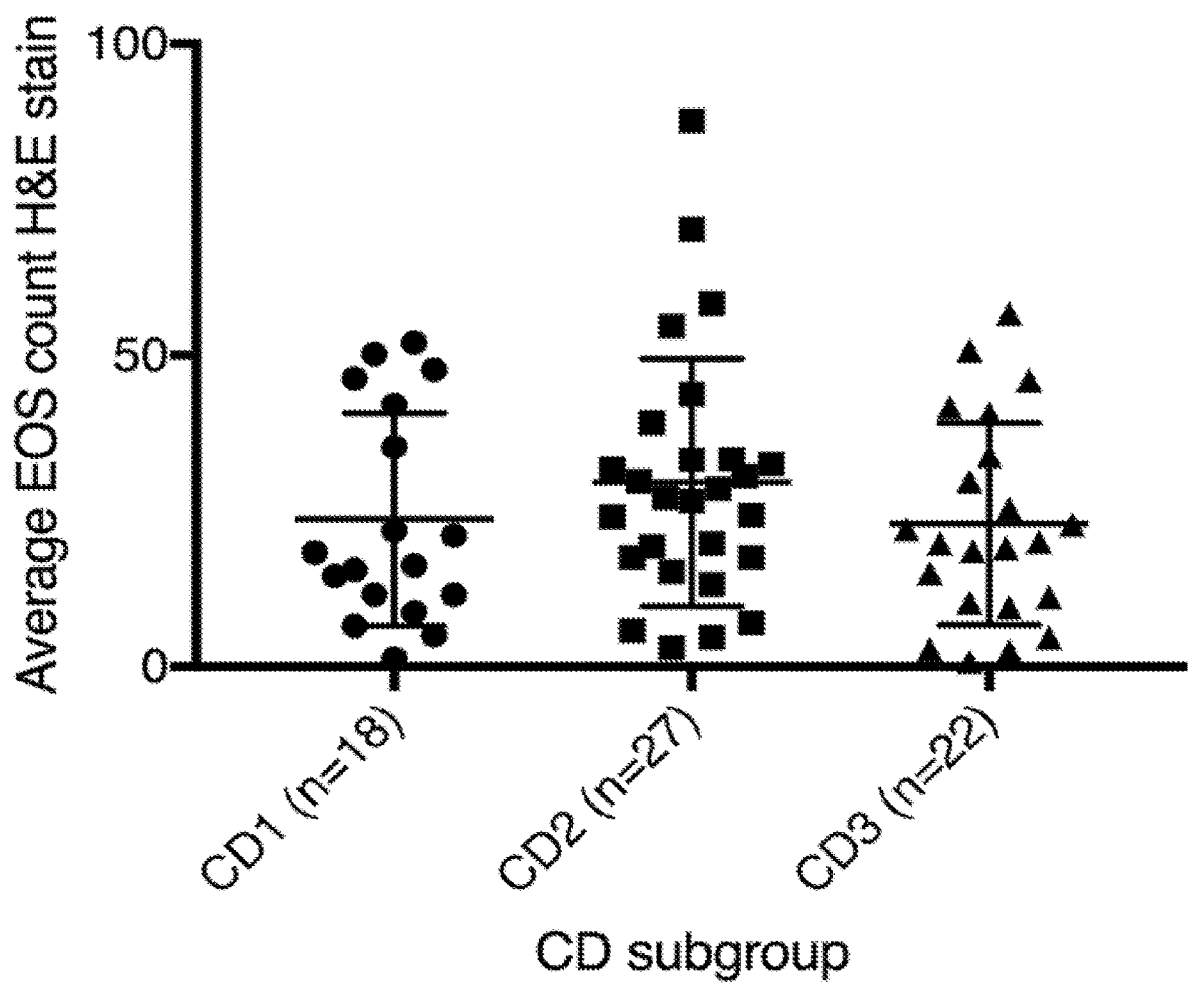

To validate the presence of eosinophils (EOS) in the SB resected tissue, EOS were manually counted using H&E staining of FFPE slides for 67 out of the 139 patients (CD1=18, CD2=27 and CD3=22) (FIG. 5B). Slides were scanned at 20x and eosinophils were manually counted by a trained Pathologist in 6 (300×300 micron) random fields of the lamina propria with areas with outliers or artifacts excluded. Results indicate that all the samples had EOS present, however, a statistically significant difference in the EOS counts across the three subgroups was not observed. These results indicate that other cellular mechanisms such as EOS activation, rather than differential cell count, may be involved in pathogenesis in CD3 patients.

Example 8

Phase 1A Clinical Trial

A phase 1 clinical trial is performed to evaluate the safety, tolerability, pharmacokinetics and pharmacodynamics of an inhibitor of PDE4 and/or agonist of ADCY7 in subjects positive for the risk genotype and/transcriptomic risk profile.

Single ascending dose (SAD) arms: Subjects in each group (subjects are grouped based on the presence or absence of risk genotype or transcriptomic risk profile) receive either a single dose of the antibody or a placebo. Exemplary doses are 1, 3, 10, 30, 100, 300, 600 and 800 mg of antibody. Safety monitoring and PK assessments are performed for a predetermined time. Based on evaluation of the PK data, and if the antibody is deemed to be well tolerated, dose escalation occurs, either within the same groups or a further group of healthy subjects. Dose escalation continues until the maximum dose has been attained unless predefined maximum exposure is reached or intolerable side effects become apparent.

Multiple ascending dose (MAD) arms: Subjects in each group (subjects are grouped based on the presence or absence of rs911605A genotype) receive multiple doses of the antibody or a placebo. The dose levels and dosing intervals are selected as those that are predicted to be safe from the SAD data. Dose levels and dosing frequency are chosen to achieve therapeutic drug levels within the systemic circulation that are maintained at steady state for several days to allow appropriate safety parameters to be monitored. Samples are collected and analyzed to determination PK profiles.

Inclusion Criteria: Subjects of non-childbearing potential between the ages of 18 and 55 years having obstructive Crohn's disease. Female subjects of non-childbearing potential must meet at least one of the following criteria: (1) achieved postmenopausal status, defined as: cessation of regular menses for at least 12 consecutive months with no alternative pathological or physiological cause; and have a serum follicle stimulating hormone (FSH) level within the laboratory's reference range for postmenopausal females; (2) have undergone a documented hysterectomy and/or bilateral oophorectomy; (3) have medically confirmed ovarian failure, All other female subjects (including females with tubal ligations and females that do not have a documented hysterectomy, bilateral oophorectomy and/or ovarian failure) will be considered to be of childbearing potential. Body Mass Index (BMI) of 17.5 to 30.5 kg/m2; and a total body weight >50 kg (110 lbs). Evidence of a personally signed and dated informed consent document indicating that the subject (or a legal representative) has been informed of all pertinent aspects of the study.

Two groups of subjects are selected: subjects having rs911605A genotype, and subjects lacking the genotype.

Exclusion Criteria: Evidence or history of clinically significant hematological, renal, endocrine, pulmonary, gastrointestinal, cardiovascular, hepatic, psychiatric, neurologic, or allergic disease (including drug allergies, but excluding untreated, asymptomatic, seasonal allergies at time of dosing) or than Crohn's disease. Subjects with a history of or current positive results for any of the following serological tests: Hepatitis B surface antigen (HBsAg), Hepatitis B core antibody (HBcAb), anti-Hepatitis C antibody (HCV Ab) or human immunodeficiency virus (HIV). Subjects with a history of allergic or anaphylactic reaction to a therapeutic drug. Treatment with an investigational drug within 30 days (or as determined by the local requirement, whichever is longer) or 5 half-lives or 180 days for biologics preceding the first dose of study medication. Pregnant females; breast-feeding females; and females of childbearing potential.

Primary Outcome Measures: Incidence of dose limiting or intolerability treatment related adverse events (AEs) [Time Frame: 12 weeks]. Incidence, severity and causal relationship of treatment emergent AEs (TEAEs) and withdrawals due to treatment emergent adverse events [Time Frame: 12 weeks]. Incidence and magnitude of abnormal laboratory findings [Time Frame: 12 weeks]. Abnormal and clinically relevant changes in vital signs, blood pressure (BP) and electrocardiogram (ECG) parameters [Time Frame: 12 weeks].

Secondary Outcome Measures:

Single Ascending Dose: Maximum Observed Plasma Concentration (Cmax) [Time Frame: 12 weeks]. Single Ascending Dose: Time to Reach Maximum Observed Plasma Concentration (Tmax) [Time Frame: 12 weeks]. Single Ascending Dose: Area under the plasma concentration-time profile from time zero to 14 days (AUC14 days) [Time Frame: 12 weeks]. Single Ascending Dose: Area under the plasma concentration-time profile from time zero extrapolated to infinite time (AUCinf) [Time Frame: 12 weeks]. Single Ascending Dose: Area under the plasma concentration-time profile from time zero to the time of last quantifiable concentration (AUClast) [Time Frame: 12 weeks]. Single Ascending Dose: Dose normalized maximum plasma concentration (Cmax[dn]) [Time Frame: 12 weeks]. Single Ascending Dose: Dose normalized area under the plasma concentration-time profile from time zero extrapolated to infinite time (AUCinf[dn]) [Time Frame: 12 weeks]. Single Ascending Dose: Dose normalized area under the plasma concentration-time profile from time zero to the time of last quantifiable concentration (AUClast[dn]) [Time Frame: 12 weeks]. Single Ascending Dose: Plasma Decay Half-Life (t½) [Time Frame: 12 weeks]. Plasma decay half-life is the time measured for the plasma concentration to decrease by one half. Single Ascending Dose: Mean residence time (MRT) [Time Frame: 12 weeks]. Single Ascending Dose:

Volume of Distribution at Steady State (Vss) [Time Frame: 6 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Single Ascending Dose: Systemic Clearance (CL) [Time Frame: 6]. CL is a quantitative measure of the rate at which a drug substance is removed from the body.

Multiple Ascending Dose First Dose: Maximum Observed Plasma Concentration (Cmax) [Time Frame: 12 weeks]. Multiple Ascending Dose First Dose: Time to Reach Maximum Observed Plasma Concentration (Tmax) [Time Frame: 12 weeks]. Multiple Ascending Dose First Dose: Area under the plasma concentration-time profile from time zero to time τ, the dosing interval where τ=2 weeks (AUCτ) [Time Frame: 12 weeks]. Multiple Ascending Dose First Dose: Dose normalized maximum plasma concentration (Cmax[dn]) [Time Frame: 12 weeks]. Multiple Ascending Dose First Dose: Dose normalized Area under the plasma concentration-time profile from time zero to time τ, the dosing interval where τ=2 weeks (AUCτ [dn]) [Time Frame: 12 weeks]. Plasma Decay Half-Life (t½) [Time Frame: 12 weeks]. Plasma decay half-life is the time measured for the plasma concentration to decrease by one half. Multiple Ascending Dose First Dose: Mean residence time (MRT) [Time Frame: 12 weeks], Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose First Dose: Volume of Distribution at Steady State (Vss) [Time Frame: 12 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Multiple Ascending Dose First Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance is estimated from population pharmacokinetic (PK) modeling. Drug clearance is a quantitative measure of the rate at which a drug substance is removed from the blood. Multiple Ascending Dose First Dose: Systemic Clearance (CL) [Time Frame: 12 weeks]. CL is a quantitative measure of the rate at which a drug substance is removed from the body.

Multiple Ascending Dose Multiple Dose: Maximum Observed Plasma Concentration (Cmax) [Time Frame: 12 weeks]. Multiple Ascending Dose Multiple Dose: Time to Reach Maximum Observed Plasma Concentration (Tmax) [Time Frame: 12 weeks]. Multiple Ascending Dose Multiple Dose: Area under the plasma concentration-time profile from time zero to time τ, the dosing interval where τ=2 weeks (AUCτ) [Time Frame: 12 weeks]. Multiple Ascending Dose Multiple Dose: Dose normalized maximum plasma concentration (Cmax[dn]) [Time Frame: 12 weeks]. Multiple Ascending Dose Multiple Dose: Dose normalized Area under the plasma concentration-time profile from time zero to time τ, the dosing interval where τ=2 weeks (AUCτ [dn]) [Time Frame: 12 weeks]. Multiple Ascending Dose Multiple Dose: Plasma Decay Half-Life (t½) [Time Frame: 12 weeks]. Plasma decay half-life is the time measured for the plasma concentration to decrease by one half. Multiple Ascending Dose Multiple Dose: Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose Multiple Dose: Volume of Distribution at Steady State (Vss) [ Time Frame: 12 weeks ]. Volume of distribution is defined as the theoretical volume in which the total amount of drug would need to be uniformly distributed to produce the desired blood concentration of a drug. Steady state volume of distribution (Vss) is the apparent volume of distribution at steady-state.

Multiple Ascending Dose Multiple Dose: Apparent Oral Clearance (CL/F) [Time Frame: 12 weeks ]. Clearance of a drug is a measure of the rate at which a drug is metabolized or eliminated by normal biological processes. Clearance obtained after oral dose (apparent oral clearance) is influenced by the fraction of the dose absorbed. Clearance was estimated from population pharmacokinetic (PK) modeling. Drug clearance is a quantitative measure of the rate at which a drug substance is removed from the blood. Multiple Ascending Dose Multiple Dose: Systemic Clearance (CL) [Time Frame: 12 weeks]. CL is a quantitative measure of the rate at which a drug substance is removed from the body. Multiple Ascending Dose Multiple Dose: Minimum Observed Plasma Trough Concentration (Cmin) [Time Frame: 12 weeks]. Multiple Ascending Dose Multiple Dose: Average concentration at steady state (Cav) [Time Frame: 12 weeks]. Multiple Ascending Dose Multiple Dose: Observed accumulation ratio (Rac) [Time Frame: 12 weeks]. Multiple Ascending Dose Multiple Dose: Peak to trough fluctuation (PTF) [Time Frame: 12 weeks]. Multiple Ascending Dose Additional Parameter: estimate of bioavailability (F) for subcutaneous administration at the corresponding intravenous dose [Time Frame: 12 weeks]. Immunogenicity for both Single Ascending Dose and Multiple Ascending Dose: Development of anti-drug antibodies (ADA) [Time Frame: 12 weeks].

Example 9

Phase 1B Clinical Trial

A phase 1B clinical trial is performed to evaluate the safety and efficacy of a compound described herein comprising an ADCY7 agonist and/or PDE4 inhibitor in participants with moderately to severely active Crohn's disease that are positive for the risk genotype and/or transcriptomic risk profile.

Inclusion Criteria: Eligible subjects are men and women 18 years and older. Two groups of subjects are selected: (i) subjects having a risk genotype comprising one or more polymorphisms from Table 2 and/or a transcriptomic risk signature comprising one or more genes from Table 3, and (ii) subjects lacking the risk genotype and the transcriptomic risk signature. Subjects are patients with Crohn's disease or fistulizing Crohn's disease of at least 3 months' duration, with colitis, ileitis, or ilcocolitis, confirmed at any time in the past by radiography, histology, and/or endoscopy. Female patient of childbearing potential must have a negative highly sensitive serum (beta-human chorionic gonadotropin [b-hCG]) pregnancy test result at screening and a negative urine pregnancy test result at Week 0. Subjects must adhere to the following requirements for concomitant medication for the treatment of Crohn's disease, which are permitted provided that doses meeting these requirements are stable, or have been discontinued, for at least 3 weeks before baseline (Week 0), unless otherwise specified: a) Oral 5-aminosalicylic acid (5-ASA) compounds, b) Oral corticosteroids at a prednisone-equivalent dose at or below 40 milligram per day (mg/day), or 9 mg/day of budesonide, or 5 mg/day beclomethasone dipropionate, c) Antibiotics being used as a primary treatment of Crohn's disease, d) Conventional immunomodulators (that is, azathioprine (AZA), 6-mercaptopurine (6-MP), or Methotrexate (MTX)): participants must have been taking them for at least 12 weeks and at a stable dose for at least 4 weeks before baseline. Subjects who has or had extensive colitis for greater than or equal to (>=) 8 years, or disease limited to the left side of the colon for >=12 years, must either have had a colonoscopy to assess for the presence of dysplasia within 1 year before the first administration of study agent or a colonoscopy to assess for the presence of malignancy at the screening visit, with no evidence of malignancy. Subjects must have active Crohn's disease, defined as a baseline Crohn's Disease Activity Index (CDAI) score of >=220 but <=450.

Experimental (Part I): Placebo. Subjects will receive placebo at Weeks 0, 2, 4, 6, 8, and 10. From Week 12 Placebo-treated subjects who are in clinical response at Week 12 (>=100-point reduction from baseline in Crohn's Disease Activity Index (CDAI) or CDAI<150) will continue to receive placebo every 2 weeks from Week 12 through Week 22. Placebo-treated subjects who are not in clinical response at Week 12 will receive test compound (a compound described herein) 400 mg at Week 12 and then test compound every two weeks from Week 14 through Week 22.

Experimental (Part I): Placebo, Test Compound. Subjects will receive test compound 400milligram (mg) at Week 0 then 200 mg every two weeks through Week 22.

Experimental (Part II): Placebo. Placebo at Weeks 0, 2, 4, and 8. From Week 12, placebo-treated subjects who are in clinical response at Week 12 (>=100-point reduction from baseline in CDAI or CDAI <150) will continue to receive placebo at Weeks 12, 14, 16, and 20. Placebo-treated subjects who are not in clinical response at Week 12 will receive test compound 150 mg at Week 12and then test compound 75 mg at Weeks 14, 16, and 20.

Experimental (Part II): Test Compound High Dose. Test compound 400 mg at Week 0and 200 mg at Weeks 2, 4, 8, 12, 16, and 20.

Experimental (Part II) Test Compound Middle Dose. Test compound 150 mg at Week 0and 75 mg at Weeks 2, 4, 8, 12, 16, and 20.

Experimental (Part II) Test compound Low Dose. Test compound 50 mg at Week 0 and 25 mg at Weeks 2, 4, 8, 12, 16, and 20.

Primary Outcome Measures: Part I: Change From Baseline in the Crohn's Disease Activity Index (CDAI) Score at Week 8 [Time Frame: Baseline through Week 8]-CDAI will be assessed by collecting information on 8 different Crohn's disease-related variables: extra-intestinal manifestations, abdominal mass, weight, hematocrit, total number of liquid stools, abdominal pain/cramping, use of antidiarrheal drug(s) and/or opiates, and general well-being. The last 4 variables are scored over 7 days by the participant on a diary card. Part II: Change From Baseline in the Crohn's Disease Activity Index (CDAI) Score at Week 8 [Time Frame: Baseline through Week 8]—CDAI are assessed by collecting information on 8 different Crohn's disease-related variables: extra-intestinal manifestations, abdominal mass, weight, hematocrit, total number of liquid stools, abdominal pain/cramping, use of antidiarrheal drug(s) and/or opiates, and general well-being. The last 4 variables are scored over 7 days by the participant on a diary card.

Secondary Outcome Measures: Part II: Clinical Remission at Week 8 as Measured by Crohn's Disease Activity Index (CDAI<150) [Time Frame: Week 8]. Part II: Clinical Response at Week 8 as Measured by CDAI (>=100-point reduction from baseline in CDAI or CDAI<150) [Time Frame: Week 8 ]. Part II: Change in Patient-Reported Outcome (PRO)-2 from baseline at Week 8 [Time Frame: Baseline through Week 8 ]—The PRO-2 score is the sum of the abdominal pain and stool frequency subscores of the CDAI score. Part II: Clinical remission at Week 8 as measured by PRO-2 (PRO-2 <75) [Time Frame: Week 8]. Part II: Clinical response at Week 8 as measured by PRO-2 (>=50-point reduction from baseline in PRO-2 or PRO-2 <75) [Time Frame: Week 8]. Part II: Change in Simple Endoscopic Score for Crohn's Disease (SES-CD) from baseline at Week 12 [Time Frame: Baseline through Week 12]—The SES-CD score is based on the evaluation of 4 endoscopic components (presence/size of ulcers, proportion of mucosal surface covered by ulcers, proportion of mucosal surface affected by any other lesions, and presence/type of narrowing/strictures) across 5 ileocolonic segments. Each endoscopic component is scored from 0 to 3 for each segment, and a total score is derived from the sum of all the component scores (range, 0 to 56).

Example 10

Calculating a Polygenic Risk Score (PRS)

Genetic patient selection criteria for treatment with an ADCY7 agonist or inhibitor of PDE4 is determined by calculating a polygenic risk score (PRS) for all patients within the Precision IBD database (n~12,000), based on a defined set of polymorphisms (SNPs) within the genes representing the CD3 risk signature. The PRS is based on polymorphisms within the multiple genes associated with the CD3 risk signature (n=174 genes) and their associated weights (e.g., the strength of their association with disease phenotype). Thus, PRS is calculated as a normalized weighted sum of the number of risk alleles carried by each individual (0, 1, or 2) at each CD3 risk loci, with weights proportional to the odds ratio of disease association. The PRS is binomially distributed within the population and gives an individual risk assessment for variants within this signature.

Defining the SNPs to Calculate the PRS

The defined set of SNPs is either selected from Table 2 or Table 14, Table 2 represents the CD3 associated independent signals among 266 unique SNPs belonging to the 174 genes comprising the transcriptomic risk signature. Conditional analysis is performed to determine independent signals. The weights (odds ratio) for building the PRS in Cedars cohort is obtained by genetic associations of Table 2 SNPs using the international (IIBDGC) case-control cohort. Association of PRS with CD3 associated phenotypes are done in Cedars cohort to assess utility of a genetic kit with Table 2 SNPs in identifying CD3 patients. Alternatively, only specific SNPs are selected from Table 2 that are located at gene loci of 17 genes listed in Table 14 that have been determined to drive specific gene pathways (e.g., cAMP, or RhoGDI) based on the overlap observed of genetics and expression between CD1 and CD3 subgroups. The weights (odds ratio) for building the PRS in Cedars cohort are obtained by genetic associations of SNPs at gene loci listed in Table 14using the international (IIBDGC) case-control cohort. Association of PRS with CD3 associated phenotypes is done to assess utility of a genetic kit with SNPs within genes listed in Table 14 in identifying CD3 patients.

TABLE 14

| 17 genes determined to drive specific gene pathways | | | |
|---|---|---|---|
| PTPN11 | RPL30 | XCR1 | HNF1A |
| RPL3 | CHRM3 | DLC1 | APOB |
| RPL6 | GRM4 | PAK2 | |
| RPL18 | PDE4C | PRKCA | |
| PPP2CA | PIP5K1C | HIST1H1A | |

Example 11

Figure 6:
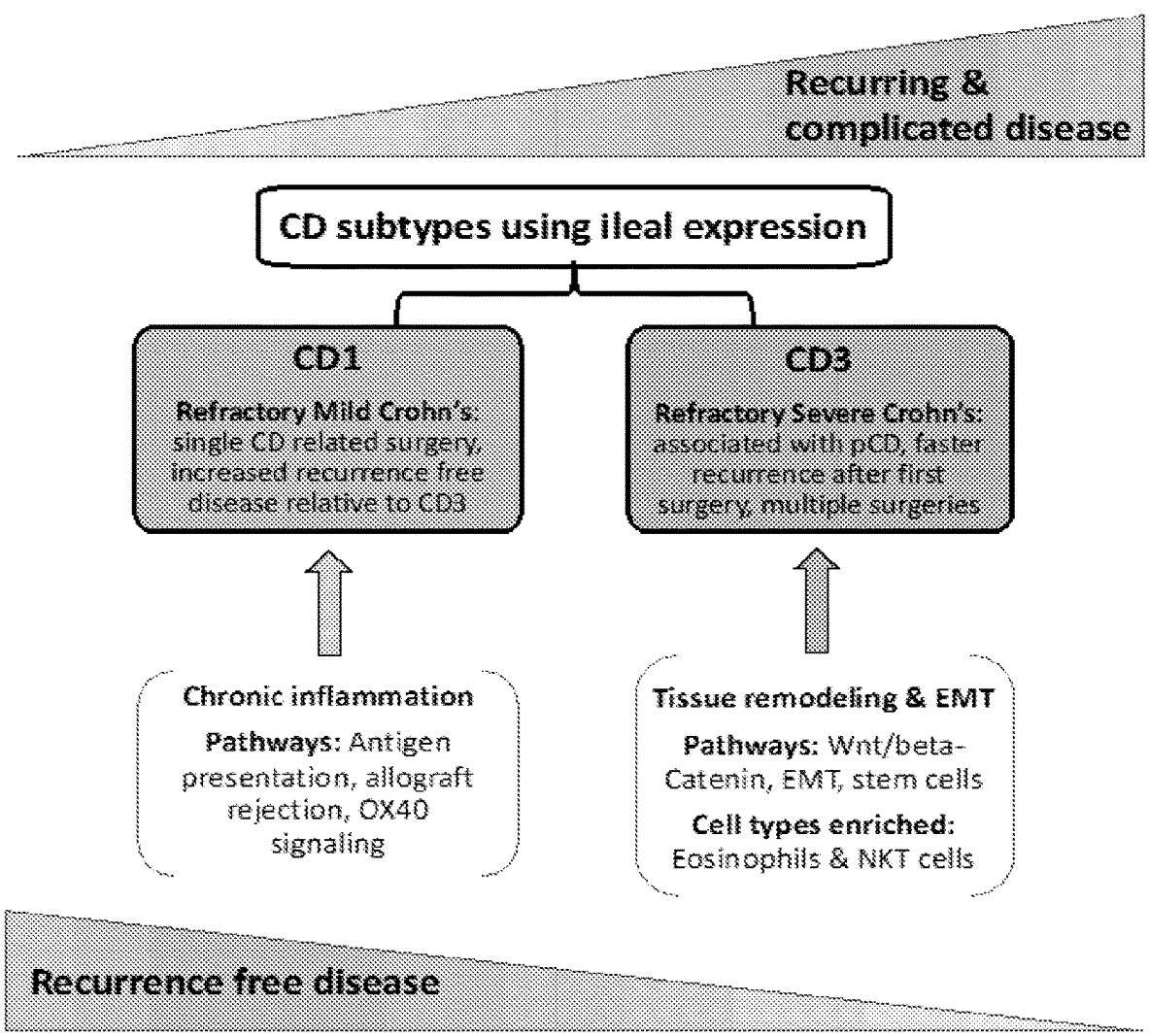
FIG. 6 shows ileal expression from CD patients who underwent a single small bowel resection shows CD subtypes associated with varying extent of recurrence free and complicated disease. Without being bound by a particular theory. this suggests that the CD1 and CD3 subgroups are located on the opposite ends of refractory disease spectrum. Pathway analysis indicated that the more severe CD3 subtype involved epithelial architecture changes driven by EMT (epithelial-mesenchymal transition) while CD1 was associated with chronic inflammation related pathways.

Transcriptional Risk Signature (TRSig) for Enriching a Population of Severe Crohn's Disease Subjects In a population of refractory CD patients that underwent SB resection, CD3 is identified as a more severe refractory, distinct clinical sub-group (FIG. 6). The genetic and transcriptomic analyses described herein identify genetic burden, gene expression signature and mechanistic pathways that could potentially underlie the pathogenesis of this severe patient sub-group. Pathways and genetic signatures described herein might reflect an abnormality in wound healing as indicated by the differential regulation of signatures for epithelial to mesenchymal transition (EMT) and the WNT/B-catenin pathway. Signatures for infiltrating cell types implicated in intestinal remodeling were also identified, and described herein. Lastly, potential pathways identified in the work described herein may provide clues as to the most appropriate therapeutic options for these patients that are faced with a poor quality of life and recurring, severe disease.

A number of genes were identified that may be used in a transcriptional risk signature (TRSig) to identify Crohn's disease (CD) patients at risk for progressing to a severe form of the disease characterized by the CD3 phenotype. Table 14 provides a narrowed list 17 of genes determined to drive specific gene pathways (e.g., cAMP, or RhoGDI) with a polymorphism (see Table 2) associated with the up or down regulation of that gene in CD3 patients. In addition to the 17genes identified, 8 polymorphisms from Table 2 that were also cis eQTL in the small bowel expression data (p<0.01) were identified. Lastly, the I gene that were used in the TRS calculation from Example 6 and the TRSig associated with CD3 were identified. Thus, a total of 26 genes were identified that are powerful indicators of the CD3 subtype.

The 26 genes making up the final TRSig provided herein are protein tyrosine phosphatase, non-receptor type 11 (PTPN11), ribosomal protein (RL30), X-C motif chemokine receptor 1 (XCR1), HNF1 homeobox A (HNF1A), ribosomal protein L3 (RPL3), cholinergic receptor muscarinic 3 (CHRM3), DLC1 Rho GTPase activating protein (DLC1), apolipoprotein B (APOB), ribosomal protein L6 (RPL6), glutamate metabotropic receptor 4 (GRM4), p21 (RAC1) activated kinase 2 (PAK2), ribosomal protein L18 (RPL18), phosphodiesterase 4C (PDE4C), protein kinase C alpha (PRKCA), protein phosphatase 2 catalytic subunit alpha (PPP2CA), phosphatidylinositol-4-phosphate 5-kinase type 1 gamma (PIP5K1C), histone cluster 1 H1 family member A (HIST1H1A), Aldehyde Dehydrogenase 2 Family Member (ALDH2), bromodomain containing 2 (BRD2), major histocompatibility complex, class II, DQ alpha 2 (HLA-DQA2), kinesin family member 21B (KIF21B), Protocadherin 7 (PCDH7), Ankyrin 3 (ANK3), Tripartite Motif Containing 38 (TRIM38), Cytochrome P450 Family 4 Subfamily V Member 2 (CYP4V2), Vesicle Associated Membrane Protein 3 (VAMP3). Each gene is a predictor of the CD3 phenotype, either alone or in combination.

Example 12

Treating an Inflammatory Disease

An inflammatory disease (e.g., Crohn's disease) is treated in a subject, by first, determining the genotype and/or transcriptomic signature of the subject. Optionally, the subject is, or is susceptible to be, non-responsive to certain therapies such as anti-TNF, steroids, or immunomodulators, such as those disclosed herein. A sample of whole blood is obtained from the subject. An assay is performed on the sample obtained from the subject to detect a presence of a risk genotype comprising one or more polymorphisms from Table 2, by Illumina ImmunoArray or polymerase chain reaction (PCR) under standard hybridization conditions. In addition, or alternatively, a sample of intestinal tissue is obtained from the subject. As assay is performed on the sample obtained from the subject to detect a presence of a transcriptomic risk signature comprising one or more genes from Table 3 or Table 4, by Illumina ImmunoArray or polymerase chain reaction (PCR) under standard hybridization conditions.

The subject is determined to be at risk for developing a severe form of inflammatory disease if the risk genotype and/or the transcriptomic risk signature is detected in the sample obtained from the subject. A therapeutically effective amount of an ADCY7 agonist and/or an inhibitor of PDE4 is administered to the subject, provided the subject is determined to have the risk genotype and/or the transcriptomic risk signature.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention claimed is:

1. A method of treating an inflammatory bowel disease, the method comprising:
   a) identifying a presence of a risk genotype predictive of inflammatory bowel disease (IBD) in a subject by assaying a sample obtained from the subject to detect the presence of the risk genotype, the risk genotype comprising a single nucleotide polymorphism (SNP) selected from the group consisting of an "A" at rs7958372, a "C" at rs2877453, an "A" at rs71327010, a "C" at rs1169302, a "G" at rs1169303, an "A" at rs6519183, a "C" at rs685548, an "A" at rs11998187, an "A" at rs531819, a "G" at rs1041968, a "G" at rs693, an "A" at rs512535, a "G" at rs550619, an "A" at rs570877, a "G" at rs12713956, an "A" at rs2301723, an "A" at rs2499714, an "A" at rs6583176, an "A" at rs369880, a "G" at rs57884093, an "A" at rs989690, an "A" at rs7704116, an "A" at rs12984273, a "G" at rs16891235, a "C" at rs7296651, an "A" at is rs516535, an "A" at rs9276427, an "A" at rs296564, an "A" at rs296569, an "A" at rs296568, a "G" at rs296567, a "G" at rs296561, a "G" at rs72749142, an "A" at rs9291547, an "A" at rs10761532, an "A" at rs10821813, a "C" at rs1561852, an "A" at rs10994464, a "G" at rs993402, an "A" at rs10994467, an "A" at rs10821822, a "G" at rs1837949, a "C" at rs35597961, a "G" at rs10821830, an "A" at rs975262, an "A" at rs973067, a "G" at rs10509139, an "A" at rs1442539, an "A" at rs2197155, a "G" at rs7919914, a "G" at rs10994476, an "A" at rs35471473, a "G" at rs12785023, a "G" at rs12783716, a "G" at rs10821821, a "G" at rs10994441, a "C" at rs10994442, a "T" at rs10821814, an "A" at rs10994465, a "T" at rs12218617, a "C" at rs10509138, an "A" at rs61854518, a "G" at rs10821699, a "G" at rs7919274, an "A" at rs 10761552, a "G" at rs17037425, an "A" at rs2893861, a "C" at rs1993939, a "G" at rs10821833, a "G" at rs1904418, a "G" rs16915196, an "A" at rs61853514, an "A" at rs10994430, an "A" at rs16915231, a "G" at rs2028564, a "G" at rs13196552, an "A" at rs17587597, an "A" at rs17587226, an "A" at rs2276917, an "A" at rs10013653, an "A" at rs11582799, an "A" at rs111692854, and an "A" at rs72632053; and
   b) administering to the subject a therapeutically effective amount of a therapeutic agent, the therapeutic agent comprising at least one of an inhibitor of phosphodiesterase 4C (PDE4C) activity or expression and an inhibitor or agonist of adenylate cyclase 7 (ADCY7), provided the risk genotype is present in (a).

2. The method of claim 1, wherein the IBD is Crohn's disease (CD).

3. The method of claim 2, wherein the CD is ileal CD.

4. The method of claim 2, wherein the subject is, or is suspected to be, non-responsive to a standard therapy selected from the group consisting of anti-tumor necrosis factor (TNF) alpha therapy, anti-a4-b7 therapy, anti-IL12p40 therapy, Thalidomide, Cytoxan, and a combination thereof.

5. The method of claim 1, wherein the risk genotype comprises at least two SNPs selected from the group consisting of the "A" at rs7958372, the "C" at rs2877453, the "A" at rs71327010, the "C" at rs1169302, the "G" at rs1169303, the "A" at rs6519183, the "C" at rs685548, the "A" at rs11998187, the "A" at rs531819, the "G" at rs1041968, the "G" at rs693, the "A" at rs512535, the "G" at rs550619, the "A" at rs570877, the "G" at rs12713956, the "A" at rs2301723, the "A" at rs2499714, the "A" at rs6583176, the "A" at rs369880, the "G" at rs57884093, the "A" at rs989690, the "A" at rs7704116, the "A" at rs12984273, the "G" at rs16891235, the "C" at rs7296651, the "A" at is rs516535, the "A" at rs9276427, the "A" at rs296564, the "A" at rs296569, the "A" at rs296568, the "G" at rs296567, the "G" at rs296561, the "G" at rs72749142, the "A" at rs9291547, the "A" at rs10761532, the "A" at rs10821813, the "C" at rs1561852, the "A" at rs10994464, the "G" at rs993402, the "A" at rs10994467, the "A" at rs10821822, the "G" at rs1837949, the "C" at rs35597961, the "G" at rs10821830, the "A" at rs975262, the "A" at rs973067, the "G" at rs10509139, the "A" at rs1442539, the "A" at rs2197155, the "G" at rs7919914, the "G" at rs10994476, the "A" at rs35471473, the "G" at rs12785023, the "G" at rs12783716, the "G" at rs10821821, the "G" at rs10994441, the "C" at rs10994442, the "T" at rs10821814, the "A" at rs10994465, the "T" at rs12218617, the "C" at rs10509138, the "A" at rs61854518, the "G" at rs10821699, the "G" at rs7919274, the "A" at rs10761552, the "G" at rs17037425, the "A" at rs2893861, the "C" at rs1993939, the "G" at rs10821833, the "G" at rs1904418, the "G" rs16915196, the "A" at rs61853514, the "A" at rs10994430, the "A" at rs16915231, the "G" at rs2028564, the "G" at rs13196552, the "A" at rs17587597, the "A" at rs17587226, the "A" at rs2276917, the "A" at rs10013653, the "A" at rs11582799, the "A" at rs111692854, and the "A" at rs72632053.

6. The method of claim 1, further comprising assaying the sample obtained from the subject to detect a transcriptomic risk signature, the transcriptomic risk signature comprising:
   a) a high level of expression of at least one of X-C motif chemokine receptor 1 (XCR1), HNF 1 homeobox A (HNF1A), metabotropic receptor 4 (GRM4), cholinergic receptor muscarinic 3 (CHRM3), phosphodiesterase 4C (PDE4C), protein kinase C alpha (PRKCA), phosphatidylinositol-4-phosphate 5-kinase type 1 gamma (PIP5K1C), histone cluster 1 H1 family member A (HIST1H1A), and kinesin family member 21B (KIF21B), as compared to a reference level; and
   b) a low level of expression of at least one of ribosomal protein L3 (RPL3), protein tyrosine phosphatase, non-receptor type 11 (PTPN11), ribosomal protein L30 (RPL30), DLC1 Rho GTPase activating protein (DLC1), apolipoprotein B (APOB), ribosomal protein L6 (RPL6), p21 (RAC1) activated kinase 2 (PAK2), ribosomal protein L18 (RPL18), protein phosphatase 2 catalytic subunit alpha (PPP2CA), Aldehyde Dehydrogenase 2 Family Member (ALDH2), bromodomain containing 2 (BRD2), major histocompatibility complex, class II, DQ alpha 2(HLA-DQA2), Protocadherin 7 (PCDH7), Ankyrin 3 (ANK3), Tripartite Motif Containing 38 (TRIM38), and Cytochrome P450 Family 4 Subfamily V Member 2 (CYP4V2), Vesicle Associated Membrane Protein 3 (VAMP3), as compared to a reference level.

7. The method of claim 6, wherein the reference level is a level of expression in a non-diseased individual.

8. The method of claim 1, wherein the presence of the risk genotype is indicative of:

a) a high level of expression of at least one of XCR1, HNF1A, GRM4, CHRM3, PDE4C, PRKCA, PIP5K1C, HIST1H1A, and KIF21B, as compared to a reference level; and b) a low level of expression of at least one of RPL3, PTPN11, RPL30, DLC1, APOB, RPL6, PAK2, RPL18, PPP2CA, ALDH2, BRD2, HLA-DQA2, PCDH7, ANK3, TRIM38, CYP4V2, and VAMP3, as compared to a reference level.

9. The method of claim 1, wherein the therapeutic agent comprises the inhibitor of phosphodiesterase 4C (PDE4C) activity or expression.

10. The method of claim 1, wherein the therapeutic agent comprises the inhibitor or agonist of adenylate cyclase 7 (ADCY7).

* * * * *

SEQUENCE LISTING

```
<160> NUMBER OF SEQ ID NOS: 445

<210> SEQ ID NO 1
<211> LENGTH: 121
<212> TYPE: DNA
<213> ORGANISM: Homo sapiens

<400> SEQUENCE: 1
tcctggattc aatgtcatcc agagcccaga gcaggtacgg ggcgccacgg atcagtcatt      60
ratccaggtt gatgatggag accctggcca gaatcactaa aagatcactg gtggatcatt     120
a                                                                    121

<210> SEQ ID NO 2
<211> LENGTH: 121
<212> TYPE: DNA
<213> ORGANISM: Homo sapiens

<400> SEQUENCE: 2
ccggtgtctc tgcctccatc agacgtcagt ctggagattg tgccgtgaat ccactgttgc      60
rgaggacagc agcctctgga tctcatggga catcctgacc cgagctccca acctgagtat     120
t                                                                    121

<210> SEQ ID NO 3
<211> LENGTH: 121
<212> TYPE: DNA
<213> ORGANISM: Homo sapiens

<400> SEQUENCE: 3
agagtaaaag aatatactga cattacttca tggtttagaa caaacacctt gagaataaaa      60
mgtcatgttt aacatgactt gcactgaact agatacacac catatttatg gctttatgtc     120
```

```
a                                                                    121

<210> SEQ ID NO 4
<211> LENGTH: 121
<212> TYPE: DNA
<213> ORGANISM: Homo sapiens

<400> SEQUENCE: 4
gtggacaaaa gacaaacgcg cctgttggct cattgttctt ccccagccct ggcatcggac    60
rgcacttgcc tttacggttt cattacaacg ggcagattta gaaatacaag gaaattggcc   120
c                                                                    121

<210> SEQ ID NO 5
<211> LENGTH: 121
<212> TYPE: DNA
<213> ORGANISM: Homo sapiens

<400> SEQUENCE: 5
cacttactag ttcaatccat ccccaaatcc acgccaccct ttcaactttg caattaagag    60
rgagaaggag aaatcccggt caactcgcct tgggggttg gtctgagggt agaggactca    120
a                                                                    121

<210> SEQ ID NO 6
<211> LENGTH: 121
<212> TYPE: DNA
<213> ORGANISM: Homo sapiens

<400> SEQUENCE: 6
aaggccaaac gtgccccatg ggaaagggtc gacatggcag tgctggcccg ggggctgtcc    60
rggcagtgtg gggacaggcc ctgcgagagc ttcaggcatc agaggccctt gcacaggcaa   120
a                                                                    121

<210> SEQ ID NO 7
<211> LENGTH: 121
<212> TYPE: DNA
<213> ORGANISM: Homo sapiens

<400> SEQUENCE: 7
tggtctcctt tgagcctacc atagcatttg gatttaccat cattatgttt acttatgtgc    60
rttgagaaac ttatgtgata taaggtttgc tttaaactat gaggtcttaa atatttccca   120
t                                                                    121

<210> SEQ ID NO 8
<211> LENGTH: 121
<212> TYPE: DNA
<213> ORGANISM: Homo sapiens

<400> SEQUENCE: 8
tcccaaaaca ctgggattac ggatgagtca ccatgcctgc cataaaagag taagttttct    60
rtcccagatt agataggaaa agaagaaata ggttgtataa aatgtcagtc aagacaaaaa   120
a                                                                    121

<210> SEQ ID NO 9
<211> LENGTH: 121
<212> TYPE: DNA
<213> ORGANISM: Homo sapiens

<400> SEQUENCE: 9
```

```
taatttgtct agaaaaatac ttgaaagatg gttttgcagg agttaccttc caggtcagga      60
rctggtaaac caaagcccat gggtgcctgc actctgcttc tggtgacctg caagctaaga     120
g                                                                    121
```

<210> SEQ ID NO 10
<211> LENGTH: 121
<212> TYPE: DNA
<213> ORGANISM: Homo sapiens

<400> SEQUENCE: 10

```
tttacaacta agatttggga ttttgtatat tcattgagag gcacagttag tacagatatc      60
rcaaggtaaa gtttctgttt attgatgttc gctgtctggg gaaaaccgac aataatcagt     120
t                                                                    121
```

<210> SEQ ID NO 11
<211> LENGTH: 121
<212> TYPE: DNA
<213> ORGANISM: Homo sapiens

<400> SEQUENCE: 11

```
atacatgtct ttgggtgaac gtgtgtgtcc atttctgctg ggtgcgcacc tgggactggc      60
rctacgtgtc agagggtgtg cctctggatt cagtctgat gtacctgctt actcccaacc     120
t                                                                    121
```

<210> SEQ ID NO 12
<211> LENGTH: 121
<212> TYPE: DNA
<213> ORGANISM: Homo sapiens

<400> SEQUENCE: 12

```
tgttgctagg aaacggtgca tggccaggag gagctgtggt gatatttaa ccttcatctc      60 rctgtctgtc tgcttaaagg cagaaaaatc ttgctttcgt tcccggtgag ccactttctt    120
t                                                                    121
```

<210> SEQ ID NO 13
<211> LENGTH: 121
<212> TYPE: DNA
<213> ORGANISM: Homo sapiens

<400> SEQUENCE: 13

```
gcccagccac agttggtttt taaacagtca tttgtgagga aggatgaaaa gaacgtaaac      60
rtacaaataa tattctctga gacctctgac gaccctccaa gtgaggaaag gataaaacag    120
a                                                                    121
```

<210> SEQ ID NO 14
<211> LENGTH: 121
<212> TYPE: DNA
<213> ORGANISM: Homo sapiens

<400> SEQUENCE: 14

```
agaaacaaga tctagcccca tctagattcc cacgccccca agccccccgc ttcccccaag      60
rctagaatca gctattctcc atggagccag ttgcttttgt ggtagaatag tattaggtac    120
t                                                                    121
```

<210> SEQ ID NO 15

```
<211> LENGTH: 121
<212> TYPE: DNA
<213> ORGANISM: Homo sapiens

<400> SEQUENCE: 15
ggctctccca gtagcaaggc atccccgaga gactgtgtgt ggagaagcag acgtgagccc      60
rgataggttg acagggcaga gttcctgagg ccagagaagc tgggctaggc aggcttggct     120
c                                                                    121

<210> SEQ ID NO 16
<211> LENGTH: 121
<212> TYPE: DNA
<213> ORGANISM: Homo sapiens

<400> SEQUENCE: 16
caaggagcaa aacagacaat tgccaggga agttgacaac taactgccag gtccagccac       60
rctgcactca cgtctctcac cttaacaaac tgcagatccg aaagggctcg caccgagtaa     120
t                                                                    121

<210> SEQ ID NO 17
<211> LENGTH: 121
<212> TYPE: DNA
<213> ORGANISM: Homo sapiens

<400> SEQUENCE: 17
ttcatatcaa ctgatttgtt gtaaatttag agaaagcaaa ttaccctaga aactccagaa      60
rgaattccta cttagtaaca taaatcaacc gcagctctca tatattgcag gtgggaatgc     120
a                                                                    121

<210> SEQ ID NO 18
<211> LENGTH: 121
<212> TYPE: DNA
<213> ORGANISM: Homo sapiens

<400> SEQUENCE: 18
ttattacttc ttctacctca tgagatctat agcagtaagg gaagcctcca tgaaagtggt      60
ragattagcc taatgccaga ctggctccct ggctcaagga aggggatccc taaaaaataa     120
t                                                                    121

<210> SEQ ID NO 19
<211> LENGTH: 121
<212> TYPE: DNA
<213> ORGANISM: Homo sapiens

<400> SEQUENCE: 19
gtatgacttc ggggttcaga gctaccttca ccgctacact gacagtctag ctgagaaaaa      60
rtccaaccca gaagaaaaga gaaccaaata ataattctaa tgaccaacac ttgagaacag     120
a                                                                    121

<210> SEQ ID NO 20
<211> LENGTH: 121
<212> TYPE: DNA
<213> ORGANISM: Homo sapiens

<400> SEQUENCE: 20
ataactgtag cagaaccccca agacgtaagg gaggggagt tcctgaaagg gtgggatgcc      60
raggaatcaa tactacagga aatgatctct tttaaaacat ttaatctctc ttacttggag     120
```

```
g                                                                      121

<210> SEQ ID NO 21
<211> LENGTH: 121
<212> TYPE: DNA
<213> ORGANISM: Homo sapiens

<400> SEQUENCE: 21
tttaatcatt atatgccatg gattttcagg gcattttaag cctttataat ggtgtaactt      60
rtgattaaga tttacacagt caaaattgtt agctggtata atagctgaat agttaagtat     120
t                                                                      121

<210> SEQ ID NO 22
<211> LENGTH: 121
<212> TYPE: DNA
<213> ORGANISM: Homo sapiens

<400> SEQUENCE: 22
taaaagacta aaattggcag catgcataca aaaagatga acaaactata ggctgtctac       60
magaacttgg tccaaattca acattaagta agctaaaagt aaaaggataa aaaaaattat    120
a                                                                      121

<210> SEQ ID NO 23
<211> LENGTH: 121
<212> TYPE: DNA
<213> ORGANISM: Homo sapiens

<400> SEQUENCE: 23
ttcacttaaa tgtgcggaac gaaactaaaa ttttcaatat aagggcattt gtttatgacc      60
rtaggatagg gaagggttgt ttttaaattt ttgttatttt ttttttaaat aattgggtct    120
t                                                                      121

<210> SEQ ID NO 24
<211> LENGTH: 121
<212> TYPE: DNA
<213> ORGANISM: Homo sapiens

<400> SEQUENCE: 24
tctagtttac catttaacta atgttgacaa gtgtcttaat cgctataaat ctctgtttcc      60 mcccttttaaa aaatgtggtt gttatcatta tttactttag aggattattg tgagaattaa    120
a                                                                      121

<210> SEQ ID NO 25
<211> LENGTH: 121
<212> TYPE: DNA
<213> ORGANISM: Homo sapiens

<400> SEQUENCE: 25
tggcttagca aaaaaacttt taaatggctt cacataataa aaagtttgga gatagtcttc      60
ratgacttaa gtttctttct ttctttctca tagtcttagg atatctgtga agttgcaggt    120
g                                                                      121

<210> SEQ ID NO 26
<211> LENGTH: 121
<212> TYPE: DNA
<213> ORGANISM: Homo sapiens
```

```
<400> SEQUENCE: 26
gattatgtta gcttgaagaa tggactgata aactttctat aaggcttatt acaggcttta      60
rcctgtaaaa ttgatctcat cgtaaacagc tttgagagta tacagatagt tgactatttt     120
t                                                                    121

<210> SEQ ID NO 27
<211> LENGTH: 121
<212> TYPE: DNA
<213> ORGANISM: Homo sapiens

<400> SEQUENCE: 27
ttctttgggc ttcatggatt tggatgttca ttttttttctt ccagatttgg ggtggttttc     60
rtcattattt ctttaaataa actttatgcc ccttctcttt ctcttttatt tctgtaatac    120
a                                                                    121

<210> SEQ ID NO 28
<211> LENGTH: 121
<212> TYPE: DNA
<213> ORGANISM: Homo sapiens
<220> FEATURE:
<221> NAME/KEY: modified_base
<222> LOCATION: (23)..(23)
<223> OTHER INFORMATION: a, c, t, g, unknown or other

<400> SEQUENCE: 28
agcctggggc catgagagct gangtggcag tggaatggcc ctggaatctg ggtccacagg     60
rgttgacctg gatgttagct ctgtaggagt ggacctggag cctggggcta tagacattga    120
c                                                                    121

<210> SEQ ID NO 29
<211> LENGTH: 121
<212> TYPE: DNA
<213> ORGANISM: Homo sapiens

<400> SEQUENCE: 29
gggtatagat aagacaagat tggccatgag tttatagttg tcgaagttgg tgaaaggaac     60
rtggaggctc gttatactat tcttcctgcc ttttatatgc ttaacatttt ttacaataaa    120
t                                                                    121

<210> SEQ ID NO 30
<211> LENGTH: 121
<212> TYPE: DNA
<213> ORGANISM: Homo sapiens

<400> SEQUENCE: 30
gattgggatc aaaatataaa tatttaattt tacacaacct acttagaatc aatattttat     60
macttcaagg gggatataga aatgttataa tcatttagat cctattacct tccctcttta    120
t                                                                    121

<210> SEQ ID NO 31
<211> LENGTH: 121
<212> TYPE: DNA
<213> ORGANISM: Homo sapiens

<400> SEQUENCE: 31
ctgcaacaaa gaccatctcc ccaaacacct cctgcaacgc caccacagcc agcgccttta     60
mcttaagcac caggtatgtt cacagtacaa ccactggcat aggataccat catactaaac    120
```

```
a                                                                            121

<210> SEQ ID NO 32
<211> LENGTH: 121
<212> TYPE: DNA
<213> ORGANISM: Homo sapiens

<400> SEQUENCE: 32
cacatgattc aaagcaccaa atatctgttt ggtcttttca ataattcttc ctgggtagct             60
rtcccttctg ctaataactt catctttcat caagactaaa ataaactttt tgagatatcg           120
c                                                                           121

<210> SEQ ID NO 33
<211> LENGTH: 121
<212> TYPE: DNA
<213> ORGANISM: Homo sapiens

<400> SEQUENCE: 33
ggggacccag gacctaggtg tcctaggtcc aagtcctgct ggcacagaaa agggaggcgg             60
rgccccagtt tagggtgggt ctgtgattcc tctgtggcaa cccaggccgg acaaggaacc           120
a                                                                           121

<210> SEQ ID NO 34
<211> LENGTH: 121
<212> TYPE: DNA
<213> ORGANISM: Homo sapiens

<400> SEQUENCE: 34
aatggggctc tgggaggggt gcaaactgaa agtgaaacag ctgacatcca ggaaacactc             60
rccctgatga ggggtcacag caggttgggg ctgcggtcag gaccaggcaa agaggaaaat           120
t                                                                           121

<210> SEQ ID NO 35
<211> LENGTH: 121
<212> TYPE: DNA
<213> ORGANISM: Homo sapiens
<220> FEATURE:
<221> NAME/KEY: modified_base
<222> LOCATION: (121)..(121)
<223> OTHER INFORMATION: a, c, t, g, unknown or other

<400> SEQUENCE: 35
ctcactggcc aaactcattg gccattttc ttctgtacaa ggttcttaac tgggaggtgt              60
ratgtcagta ggcaaaccta cttcaaagct gcagacgaca gtaacttgag agtggaatag           120 n                                                                           121

<210> SEQ ID NO 36
<211> LENGTH: 121
<212> TYPE: DNA
<213> ORGANISM: Homo sapiens

<400> SEQUENCE: 36
aaagcagaac attaccagga cctcaaaaac cttcttgtgt gtctctgatg ataaacctct             60
scctccctcc atcctcaaaa gtgactacca tcttgacatc tgtgatgatt tcctttcctt           120
t                                                                           121

<210> SEQ ID NO 37
```

```
<211> LENGTH: 121
<212> TYPE: DNA
<213> ORGANISM: Homo sapiens

<400> SEQUENCE: 37
cctctgtact tgccattgtt ttaatttgta ttttctggtt cctgatgagc gtgggcattt      60
mtaaatacac tcagccattt gggcttcctt ttctgggaat cacctgtttt cctctttctc     120
a                                                                    121

<210> SEQ ID NO 38
<211> LENGTH: 121
<212> TYPE: DNA
<213> ORGANISM: Homo sapiens

<400> SEQUENCE: 38
acattatgga agattgccgt tgtattactg gttatctttt tgctgctggc tctcataaat      60
rtcgtgaggg ctcctggagg gcaggagctg tgtctcctgc ttctttgaca gccatcccca    120
t                                                                    121

<210> SEQ ID NO 39
<211> LENGTH: 121
<212> TYPE: DNA
<213> ORGANISM: Homo sapiens

<400> SEQUENCE: 39
atggaaccac cattgtatat atggtctgtc tttcaccaaa acgttacgtg gggcctgaca      60
rtaattgcaa atgaagaacc atttggccga ggtgctgctg catctgctta aatgaatcaa    120
c                                                                    121

<210> SEQ ID NO 40
<211> LENGTH: 121
<212> TYPE: DNA
<213> ORGANISM: Homo sapiens

<400> SEQUENCE: 40
acagagagaa agcaagaaat agaggatcct gctttgctgc agtgttttaa agatgtgtga      60
mtgcaaaggc gtttcccatt ttagacattt cacatctgcc cctgggcctg cgaaagaccc    120
a                                                                    121

<210> SEQ ID NO 41
<211> LENGTH: 121
<212> TYPE: DNA
<213> ORGANISM: Homo sapiens

<400> SEQUENCE: 41
aaaatctaaa ggatgaatac tttgaggaaa tcatggaaga atatgaagat attagacagg      60
rccattatga gtctctcaag gtaagtggta gaaacagatt tttgcttgtt tttaatgtga    120
c                                                                    121

<210> SEQ ID NO 42
<211> LENGTH: 121
<212> TYPE: DNA
<213> ORGANISM: Homo sapiens
<220> FEATURE:
<221> NAME/KEY: modified_base
<222> LOCATION: (27)..(27)
<223> OTHER INFORMATION: a, c, t, g, unknown or other

<400> SEQUENCE: 42
```

```
caagcgttta tttagcacta tgctagntat tttggaggat acagagacac acaaaacata    60
rtttctgact tcacacatgc ttaagatcca gtgagggaag cagacacgta cccactgttc   120
t                                                                  121
```

<210> SEQ ID NO 43
<211> LENGTH: 121
<212> TYPE: DNA
<213> ORGANISM: Homo sapiens

<400> SEQUENCE: 43

```
taccaactaa ataatgcatt tttaagcaac atagcttagt tttgccactt ttgcaacctc    60
rtatgaatgg aatcacataa catgcattct cttctgtcca caccaatact tgtcatgagg   120
c                                                                  121
```

<210> SEQ ID NO 44
<211> LENGTH: 121
<212> TYPE: DNA
<213> ORGANISM: Homo sapiens

<400> SEQUENCE: 44

```
ggctgagtga acggtggccc ggatgggaag ccaggctgcc gggcccaggt ctacgctgtg    60
rttcggccat gggctctcag gcctggtgtc actgatgtgc tcaattttag agctctgatc   120
c                                                                  121
```

<210> SEQ ID NO 45
<211> LENGTH: 121
<212> TYPE: DNA
<213> ORGANISM: Homo sapiens

<400> SEQUENCE: 45

```
gtattttgat gattttataa atcagtccta tctcccctca accatagggt gggtatgagt    60
mcaaagaaga ggggcagctc aatgtagtct gtgcatttgt gagttaggag ataagatttg   120
g                                                                  121
```

<210> SEQ ID NO 46
<211> LENGTH: 121
<212> TYPE: DNA
<213> ORGANISM: Homo sapiens

<400> SEQUENCE: 46

```
gctagtcaga gaagcccagg gcttctggtc tgaaacagac tagggagcgg ggaagaattc    60
rtgtgaatgc aggacgtggg tgagtctgga aatatttcac tgttcagtgg agtacttta   120 a                                                                  121
```

<210> SEQ ID NO 47
<211> LENGTH: 121
<212> TYPE: DNA
<213> ORGANISM: Homo sapiens

<400> SEQUENCE: 47

```
aggttttcct gaagaattga aatttaagct gatacccaat agaaaataga gaagagctgg    60
rtgaacttga gcaggggagg gtgaggtaag caaaaaagtg gaatgaaact tgttgcaagg   120
g                                                                  121
```

<210> SEQ ID NO 48

<211> LENGTH: 121
<212> TYPE: DNA
<213> ORGANISM: Homo sapiens

<400> SEQUENCE: 48
cagtgaccgg ctcctggagc agggctgcct ccctgcccct gccgccccc gccccactgc        60 rctgcaccac cctgggcaac accatttact gcctcaaccc ccaggtcact gccaccttca     120
c                                                                    121

<210> SEQ ID NO 49
<211> LENGTH: 121
<212> TYPE: DNA
<213> ORGANISM: Homo sapiens
<220> FEATURE:
<221> NAME/KEY: modified_base
<222> LOCATION: (96)..(96)
<223> OTHER INFORMATION: a, c, t, g, unknown or other

<400> SEQUENCE: 49
tacaaatctg tctctgtaat ttccacccac aaattctaat tctatccctt tggactgcac        60
rgtatcatca caaagatcct tctaagaggg tagtangagg gtcaaagtga gagaaggaga     120
t                                                                    121

<210> SEQ ID NO 50
<211> LENGTH: 121
<212> TYPE: DNA
<213> ORGANISM: Homo sapiens

<400> SEQUENCE: 50
taacaccttc atagactcca ctctgataaa ataagaagaa aaaagaaat gtatttattc         60 mcttttttc cccttacttc tatattatat gttaaaatcc taccctgtgg tttgcatttg      120
t                                                                    121

<210> SEQ ID NO 51
<211> LENGTH: 121
<212> TYPE: DNA
<213> ORGANISM: Homo sapiens

<400> SEQUENCE: 51
agactaaaat tctgcaatga agcagctttc ggatcaaaac tccaaaaata aatgaatgcc        60
maatgacttc actgaacctt aatcctaaac agaagacctt atggctacta catccttga      120 c                                                                    121

<210> SEQ ID NO 52
<211> LENGTH: 121
<212> TYPE: DNA
<213> ORGANISM: Homo sapiens

<400> SEQUENCE: 52
gggaagggtg gcatatgggg aggaagggat cattgagaat acagggtgaa aaagaacgac        60
rttactgaag gtagacattg ctagtgcaag gtacggaatc catgtgcaaa aggtggctgg     120
a                                                                    121

<210> SEQ ID NO 53
<211> LENGTH: 121
<212> TYPE: DNA
<213> ORGANISM: Homo sapiens

<400> SEQUENCE: 53 actttgttttt ccctgaggaa ctagtaagca ttgcccatcc accaaccaga gccatagacc    60
rtgtcatgtt cccttttgt cttgtctact aggaagctca gagccaaact ggatgctttt    120
g    121

<210> SEQ ID NO 54
<211> LENGTH: 121
<212> TYPE: DNA
<213> ORGANISM: Homo sapiens

<400> SEQUENCE: 54
ttggacattt tattggcatc aatctgacta agaaacagt taggtttcta aaatatcat    60 ragattgatt cggcacctag gagtagggg caattggaaa ccagctaaag atgctacagg    120
a    121

<210> SEQ ID NO 55
<211> LENGTH: 121
<212> TYPE: DNA
<213> ORGANISM: Homo sapiens

<400> SEQUENCE: 55
ccccacgtgg cctcctcgag gcctgaaccc tgggttgaat ggcaaagact tgtgaaggat    60
raggctgcat ttcagtaaaa cctccccagc gaggggcacc agagcccaca ggcagatgcg    120
g    121

<210> SEQ ID NO 56
<211> LENGTH: 121
<212> TYPE: DNA
<213> ORGANISM: Homo sapiens

<400> SEQUENCE: 56
aacactggca gtatctagat atctccatgt gcagagtcag aaatttcaga gagcatttgt    60
raagagtaat tgctgttttg tttttaaaag attggcagat caagggaata ttctggctgt    120
t    121

<210> SEQ ID NO 57
<211> LENGTH: 121
<212> TYPE: DNA
<213> ORGANISM: Homo sapiens

<400> SEQUENCE: 57
tccagaacga tttgagaata agaggcaggg cacaaggatg gtacttaaca aacttctgtc    60
rcctaagcat ggcaagaata agctgcagag aaaatgggag tgcagaagaa atggtggag    120 a    121

<210> SEQ ID NO 58
<211> LENGTH: 121
<212> TYPE: DNA
<213> ORGANISM: Homo sapiens

<400> SEQUENCE: 58
gtatagttaa aattttcatt caattagtca tacatacttc actttgaact tcctgtgtat    60
mttattctgt gctcaattaa actattcctt cccccaaatt ccattcccag acttcttatt    120
c    121

<210> SEQ ID NO 59

```
<211> LENGTH: 121
<212> TYPE: DNA
<213> ORGANISM: Homo sapiens

<400> SEQUENCE: 59
tgtcaggcac tggtctgtgt gcttaacatg gagcactctt caaaatgacc ctatgtggta      60
mgggctatta gtgtctacat tttacagatg aagttcatgg ggcaaagaga tgagaaacat     120
t                                                                     121

<210> SEQ ID NO 60
<211> LENGTH: 121
<212> TYPE: DNA
<213> ORGANISM: Homo sapiens

<400> SEQUENCE: 60
agagccccag taaagatcgg ggcgctgggg ctgagaaggg ctgggcacgt ctttcttcct      60
rtgctccgct cttctctgta cttccagagc actccactca aaggccagct ttgacctcgc     120
a                                                                     121

<210> SEQ ID NO 61
<211> LENGTH: 121
<212> TYPE: DNA
<213> ORGANISM: Homo sapiens

<400> SEQUENCE: 61
tttctggctt atttttataaa ctactgtagc acacatttt ccctgaatgg ggatataaag      60
mctcattatt tccaaaagcc aatggcagaa taaggtttcc atcctgagcc cttccagggt     120
a                                                                     121

<210> SEQ ID NO 62
<211> LENGTH: 121
<212> TYPE: DNA
<213> ORGANISM: Homo sapiens

<400> SEQUENCE: 62
tttaaattaa gtgtttatac aaatatttgc gttcatacaa agacctaagg tacattcact      60
raggtgggac cccagatgag agtcactacc agcctcagag tgtagctcag tgacatcccc     120
c                                                                     121

<210> SEQ ID NO 63
<211> LENGTH: 121
<212> TYPE: DNA
<213> ORGANISM: Homo sapiens

<400> SEQUENCE: 63
gtcaaccagt gctcctgcct cagtcgtgtt ttgcttttaa ccatgtcttc ctggaatgac      60
rcttgaaagg gcagtcatca tgtgttagcc cagaatgaac tcaccggaat cccacattta     120
c                                                                     121

<210> SEQ ID NO 64
<211> LENGTH: 121
<212> TYPE: DNA
<213> ORGANISM: Homo sapiens

<400> SEQUENCE: 64
ctttattttg atgaactgtt caaatgtcat ggtaaatcat taatcactga aaattttgtt      60
rtttcttgta gtttggcaaa tgctctcaca ctgtatcttt tgagttcaca atttcatctt     120
```

<210> SEQ ID NO 65
<211> LENGTH: 121
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, c, t, g, unknown or other

<400> SEQUENCE: 65
ggtgnacttg ggaggggggct ggcactgctg ctggctctgc tggcaggaca tcttggtggc    60
rgattcagga gctgaaagag agtcaaacag caagtcagac ctaggcagag gccaccctg    120 c                                                                  121

<210> SEQ ID NO 66
<211> LENGTH: 121
<212> TYPE: DNA
<213> ORGANISM: Homo sapiens

<400> SEQUENCE: 66
ggttgctgat cagacacgtc aacacatgcc tctgtgttga cagcactgcc tgcagctctc    60
maagcatcct gcatctccgg caagcaccag actagcctga gttcccaaca caagcactcc   120
a                                                                  121

<210> SEQ ID NO 67
<211> LENGTH: 121
<212> TYPE: DNA
<213> ORGANISM: Homo sapiens

<400> SEQUENCE: 67
aaatatatat tccttctaaa atcttgaaaa ataactacaa aacaaattac ccttagtcat    60
rcttctcagg gataagcaca tttggtgtaa tttcagtcct agacacacag atacagttaa   120
t                                                                  121

<210> SEQ ID NO 68
<211> LENGTH: 121
<212> TYPE: DNA
<213> ORGANISM: Homo sapiens

<400> SEQUENCE: 68
ggacaggtgc agccggggtg tgctctgcct cactcctggg agtcacgtcc acacccatcc    60
rcacatactt ggaaaatatg ggtcaaaaat gccaaggagc aagttacttc aaaaagtgca   120
g                                                                  121

<210> SEQ ID NO 69
<211> LENGTH: 121
<212> TYPE: DNA
<213> ORGANISM: Homo sapiens

<400> SEQUENCE: 69
gaaaatgttc ttttttttact tcctaataca gagcctttaa ttgatcactg cagttctttt    60
rgcggtaaac ttgtttgtaa tctctatagt tgatgcttca tgtaagtcac ttgttaaact   120
g                                                                  121

<210> SEQ ID NO 70

```
<211> LENGTH: 121
<212> TYPE: DNA
<213> ORGANISM: Homo sapiens

<400> SEQUENCE: 70
cgaccccgtg ctggcccgca ctctcggcct ccttatctgg tttaggaatg cgcggtatcc    60
rcgctcgctc gcgcgggagc cacgcctcct ctcccccccg ccccgagac cgccacacgc    120 g                                                                    121

<210> SEQ ID NO 71
<211> LENGTH: 121
<212> TYPE: DNA
<213> ORGANISM: Homo sapiens

<400> SEQUENCE: 71
aattaatata gtaatattag aaaacaaaaa ccaattaatt ttttcaatag atgcagaaaa    60
rttatttggc aaaattcaac tcccatttat gacagaatct gtcagaaaac tagtctgcca    120
t                                                                    121

<210> SEQ ID NO 72
<211> LENGTH: 121
<212> TYPE: DNA
<213> ORGANISM: Homo sapiens

<400> SEQUENCE: 72
caatcctatg tgttctacct taccgccatc tcacaaatct caccttctg ggttccagct     60 rtcattgcct ctgctcatgc cctcattagc aatcaagtgg atttgtgtat taggctcctg    120
g                                                                    121

<210> SEQ ID NO 73
<211> LENGTH: 121
<212> TYPE: DNA
<213> ORGANISM: Homo sapiens

<400> SEQUENCE: 73
gaactcacca ggaaactata agtcagctgg tgcactgctg gtactcatga aatcacctat    60
sagggtgttg ctgaacttgc tgtaaggaag tctcctgcag gtgtgccact gaacttgtca    120
c                                                                    121

<210> SEQ ID NO 74
<211> LENGTH: 121
<212> TYPE: DNA
<213> ORGANISM: Homo sapiens

<400> SEQUENCE: 74
caggggttgg gggagctccc tgagaattgg aatgaagaaa tgggaagcag gagacctcct    60
rccctgaaga cctctccagc tgtggtaact gagaggatgt gtgggatgga ggctgggcgg    120
c                                                                    121

<210> SEQ ID NO 75
<211> LENGTH: 121
<212> TYPE: DNA
<213> ORGANISM: Homo sapiens

<400> SEQUENCE: 75
agaactttat tttaaaataa ttttaaaatc tttcccttcc ccaacaagaa aaaaaaaaa     60 raagaagaag aaaaaggaaa gggactctct cttacttgga ataatttctt ttttcccctcc   120
``` c                                                                        121

<210> SEQ ID NO 76
<211> LENGTH: 121
<212> TYPE: DNA
<213> ORGANISM: Homo sapiens

<400> SEQUENCE: 76
gaagcgcatc atggaagtgg tgggcacacc cagccctgag gttctggcaa aaatctcctc    60
rgaacacgtg agttggtgcc cgccagccag cagctccctc tcctggctga gccccaggc    120 t                                                                        121

<210> SEQ ID NO 77
<211> LENGTH: 121
<212> TYPE: DNA
<213> ORGANISM: Homo sapiens

<400> SEQUENCE: 77
atgcatttta taagaatgta tacaagcaaa gggcttcatg ttaaacaaac tgaaatagtt    60
rggatgggga acgggattgt ggatgaagaa aacaaactca ggggcaaaca tgaatgaact    120
t                                                                        121

<210> SEQ ID NO 78
<211> LENGTH: 121
<212> TYPE: DNA
<213> ORGANISM: Homo sapiens

<400> SEQUENCE: 78
gctggattca ttttctcctg gattttgat agctgctccc gccagcgctg tggtcacttg      60
rcctgggcct gcagatttgg ttgttgctat gctcatagca cctgttgcag gactcattgc    120
t                                                                        121

<210> SEQ ID NO 79
<211> LENGTH: 121
<212> TYPE: DNA
<213> ORGANISM: Homo sapiens

<400> SEQUENCE: 79
caggctgggg gaaactctgt agaaaaagat tatgagaacc tagatacttt ccacagtcca    60
matgaaccct gggttttcta gactatgtga gtcccattaa atgctgagga cactgggtg    120 g                                                                        121

<210> SEQ ID NO 80
<211> LENGTH: 121
<212> TYPE: DNA
<213> ORGANISM: Homo sapiens

<400> SEQUENCE: 80
agaaaaggga agatgcttga gctgatcccc taggtatagc ttctgaaggt ctggcttctt    60
rctagatttg ctgacctaga ctccatgctg ctcatcctac ccccttgccc atgtcctccc    120
t                                                                        121

<210> SEQ ID NO 81
<211> LENGTH: 121
<212> TYPE: DNA
<213> ORGANISM: Homo sapiens

```
<400> SEQUENCE: 81
aagccctaac ccaaagcctt tcacagctca gactagacag ctacaaaaca gaagactact    60
mttttgccta gtagagcagc aaaaataaaa atcttgaaaa cattttttaa agttttgatg   120
a                                                                  121

<210> SEQ ID NO 82
<211> LENGTH: 121
<212> TYPE: DNA
<213> ORGANISM: Homo sapiens

<400> SEQUENCE: 82
tcagctaaaa ccttgaaaag cagtaatgtg ttttctcata taccatattt cccccattac    60
rtttattgaa tatgacttca catttatgtt tgtgcagtgg ttacagtgtt gtatgttttt   120
c                                                                  121

<210> SEQ ID NO 83
<211> LENGTH: 121
<212> TYPE: DNA
<213> ORGANISM: Homo sapiens
<220> FEATURE:
<221> NAME/KEY: modified_base
<222> LOCATION: (38)..(38)
<223> OTHER INFORMATION: a, c, t, g, unknown or other

<400> SEQUENCE: 83
ggccacaagg gtgtgagctt ccccggctgc ctccacancc acagtgcccc caagcccccc    60
magagccatc ttaccccagg aggccatgca gtgtgagagt cccaacagcc ccccacaggc   120
c                                                                  121

<210> SEQ ID NO 84
<211> LENGTH: 121
<212> TYPE: DNA
<213> ORGANISM: Homo sapiens
<220> FEATURE:
<221> NAME/KEY: modified_base
<222> LOCATION: (88)..(88)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other

<400> SEQUENCE: 84
atggaatctg ctagagattt gggcagtgtt tatatataga agttgggact ctcactctct    60
rgtgctctgg tttctctccc ttgttttntg gcagctattn ttaccccaaa ctgttctcta   120
g                                                                  121

<210> SEQ ID NO 85
<211> LENGTH: 121
<212> TYPE: DNA
<213> ORGANISM: Homo sapiens

<400> SEQUENCE: 85
ctttggagca gtgataacct ttacttttct ccttttctt gcaaacatta ttgctagtca    60
ratcttgtac taggcactag aataaaaggg gaacaagaca aagtcctact tcttaaggag   120
t                                                                  121

<210> SEQ ID NO 86
<211> LENGTH: 121
```

```
<212> TYPE: DNA
<213> ORGANISM: Homo sapiens

<400> SEQUENCE: 86
cccatcatct gacttgaagt aatatctttt tattcctacg aaatataagg taatcagtaa    60
rtgtatccca cactttgctg tgcttttctc attcttaccc tactttttt gatagttggg    120
c                                                                    121

<210> SEQ ID NO 87
<211> LENGTH: 121
<212> TYPE: DNA
<213> ORGANISM: Homo sapiens

<400> SEQUENCE: 87
cttgttaaaa caagataata aaaatatgta cttgtacttt ctaagatagg tctttttttt    60
mtactgccct ctgccacttt cacttaagtt tttcttttaa ttttattgtt ccagttttgc    120
a                                                                    121

<210> SEQ ID NO 88
<211> LENGTH: 121
<212> TYPE: DNA
<213> ORGANISM: Homo sapiens

<400> SEQUENCE: 88
gttggtcctg gaaagaaag aaaccaagag attatgggga ctcaatgggc ttcttaagag    60
rgaataagtt gaaatcaatg accagaagac cctgatggaa gtggaggaga atcatctcag    120
g                                                                    121

<210> SEQ ID NO 89
<211> LENGTH: 121
<212> TYPE: DNA
<213> ORGANISM: Homo sapiens
<220> FEATURE:
<221> NAME/KEY: modified_base
<222> LOCATION: (81)..(81)
<223> OTHER INFORMATION: a, c, t, g, unknown or other

<400> SEQUENCE: 89
tgtgccctcg gcagctttcc ctgggctgca cctggtgggt gatgctggac ggcagggact    60
mcagggaggg gtgagaaggc nccaaggaac cacgtgctgg gtgaggcggc cccaacccgg    120
g                                                                    121

<210> SEQ ID NO 90
<211> LENGTH: 121
<212> TYPE: DNA
<213> ORGANISM: Homo sapiens

<400> SEQUENCE: 90
tcacacacca cttggagcca cggaaagact gctgattgcc acagtagggg ccctgattgc    60
rgtaacagat gcagatgagc ctagctccta tagctccact tattctttt aatgttatct    120
t                                                                    121

<210> SEQ ID NO 91
<211> LENGTH: 121
<212> TYPE: DNA
<213> ORGANISM: Homo sapiens

<400> SEQUENCE: 91
```

```
cagcctcccc cctgggctct ggactagcag gatactgaac acagctaata ggttctaagt    60
rctgtgctaa gtgtgttcag cgaattggcc aagtttatgt tcacaccaac tgagatagaa   120
a                                                                   121

<210> SEQ ID NO 92
<211> LENGTH: 121
<212> TYPE: DNA
<213> ORGANISM: Homo sapiens

<400> SEQUENCE: 92
ttgtatagtt atgtatataa ttgtatcatc tctcctgttg aaactgaaaa ctgcatgaga    60
rtgagattca ttgttttgtg tcttttagc caccagataa atgagcacag ttgctggcat   120
a                                                                   121

<210> SEQ ID NO 93
<211> LENGTH: 121
<212> TYPE: DNA
<213> ORGANISM: Homo sapiens

<400> SEQUENCE: 93
tcatttatct ggtggctaaa aagacacaaa acaatgaatc tcattctcat gcagttttca    60
rtttcaacag gagagatgat acaattatat acataactat acaacatggc agaaggcaaa   120
g                                                                   121

<210> SEQ ID NO 94
<211> LENGTH: 121
<212> TYPE: DNA
<213> ORGANISM: Homo sapiens

<400> SEQUENCE: 94
ataaaagcac tagatttcct tttaactcca aaaaggata atttattcat agaacttccc     60
rtgttctcat caaggccatc tacagaggtg ttcagaacaa taattcagaa ataggacaca   120
a                                                                   121

<210> SEQ ID NO 95
<211> LENGTH: 120
<212> TYPE: DNA
<213> ORGANISM: Homo sapiens

<400> SEQUENCE: 95
actcctttcc tccttaggtt tggcattgga tgtgtaaatt ctggaaaaaa aaaaaaaaam    60
ctttgcgttt cacactccac tttgcagaac accagtggag tctttccggt ctcctgcctc   120

<210> SEQ ID NO 96
<211> LENGTH: 121
<212> TYPE: DNA
<213> ORGANISM: Homo sapiens
<220> FEATURE:
<221> NAME/KEY: modified_base
<222> LOCATION: (95)..(95)
<223> OTHER INFORMATION: a, c, t, g, unknown or other

<400> SEQUENCE: 96
cattatttaa aatgtcattt ttgcacgttt aagacaagcg tttatttagc actatgctag    60
rtattttgga ggatacagag acacacaaaa catantttct gacttcacac atgcttaaga   120
t                                                                   121
```

```
<210> SEQ ID NO 97
<211> LENGTH: 121
<212> TYPE: DNA
<213> ORGANISM: Homo sapiens
<220> FEATURE:
<221> NAME/KEY: modified_base
<222> LOCATION: (108)..(108)
<223> OTHER INFORMATION: a, c, t, g, unknown or other

<400> SEQUENCE: 97
caaaaacact tctttctgtg gaagaggcat aggaatgaga caagaacaag aaatggaaac    60
rctgatgact agggctgtta ttttagaatt attatcatta ttatatanat attaattata   120
t                                                                  121

<210> SEQ ID NO 98
<211> LENGTH: 121
<212> TYPE: DNA
<213> ORGANISM: Homo sapiens
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 98
aacagaaagt ccaacaagtc ctcgcttcgc actgatggtt ctggaaacag ccacgaagca    60
wagcgaccnc cgtggaanga agccgaattc accatccaca caggccgcca atgggagcaa   120
g                                                                  121

<210> SEQ ID NO 99
<211> LENGTH: 121
<212> TYPE: DNA
<213> ORGANISM: Homo sapiens

<400> SEQUENCE: 99
tgacagaggg aggctctgtc tccaaaaaca aacaaacaa caacaataac aaaaagtcat    60
ragagttata gatgttatgt tagtctcatt ctccccatta acccagcctc acctagacat   120
t                                                                  121

<210> SEQ ID NO 100
<211> LENGTH: 121
<212> TYPE: DNA
<213> ORGANISM: Homo sapiens

<400> SEQUENCE: 100
cccagtaaat atacccatag tagatgaaaa ataagctata ctgaaactta agaattgatc    60
rtggatctat gcaatgatca tcaacaaagt tttcccaggt aaatcaagtt gatgtttact   120
a                                                                  121

<210> SEQ ID NO 101
<211> LENGTH: 121
<212> TYPE: DNA
<213> ORGANISM: Homo sapiens

<400> SEQUENCE: 101
gactaattca gagaaagcca caataagttg ctgatgtatt tgggtggtga tgcagagaaa    60
mggaaggggt caggaatgac tgcaggcctg gggctgctcg gtttggggtg ggggtggtg   120
``` t                                                                        121

<210> SEQ ID NO 102
<211> LENGTH: 121
<212> TYPE: DNA
<213> ORGANISM: Homo sapiens

<400> SEQUENCE: 102
ttttgtaagc tactattttg atcctagtgt tttaaccaat agaatggatt gacagcagct        60
rgaagtgcat aagctgaggt ttgttataga tggagtcata tgttggcctg gcatggtggc       120
t                                                                        121

<210> SEQ ID NO 103
<211> LENGTH: 121
<212> TYPE: DNA
<213> ORGANISM: Homo sapiens

<400> SEQUENCE: 103
aaaaaatcct gtgacactga aactgatctt attcttctga aattataatt cattgtcttc        60
rttggggttt tccaacattc tgagtatatc ttacagaatg aggtatttct gttcacttga       120
a                                                                        121

<210> SEQ ID NO 104
<211> LENGTH: 121
<212> TYPE: DNA
<213> ORGANISM: Homo sapiens

<400> SEQUENCE: 104
ttctacaaga ttcctttaag tagggcatac ctttatgttt ctaataatcc ctattctcaa        60
ratataaaag tttaattata ccccatttat ctccaggtag aatttcccat aagctcatta       120
c                                                                        121

<210> SEQ ID NO 105
<211> LENGTH: 121
<212> TYPE: DNA
<213> ORGANISM: Homo sapiens

<400> SEQUENCE: 105
gacaggtagc cccctcaacc ccaaggtact ggtggcagag tagggagctg ggggctaggt        60
rtccactctg gctaactctg gccaactccc ttctctctga gcctcagcca gcgccattcc       120
c                                                                        121

<210> SEQ ID NO 106
<211> LENGTH: 121
<212> TYPE: DNA
<213> ORGANISM: Homo sapiens

<400> SEQUENCE: 106
aggcctgggg aggcaggatg tgctaaaggg cagagcccag gatgggaacc aggggacccc        60
rgaacaaatg tgactgttaa tgaataactt tgggccagtg aagttacctc ttttggcttc       120
a                                                                        121

<210> SEQ ID NO 107
<211> LENGTH: 121
<212> TYPE: DNA
<213> ORGANISM: Homo sapiens

<400> SEQUENCE: 107

```
ttatgaggag attttatcaa gattttcaaa acttacacca accgcagaag tcactgtgat    60
matctctgga ctaagtgttc ttctcaattg agcatcaaga tcctctagag gttgctggga   120
c                                                                  121
```

<210> SEQ ID NO 108
<211> LENGTH: 121
<212> TYPE: DNA
<213> ORGANISM: Homo sapiens

<400> SEQUENCE: 108

```
atgtgaaaac tactccagtg gctgactgaa ttgctgaccc ttcaagctct gtccttatcc    60
rttacctcaa agcagtcatt ccttagtaaa gtttccaaca aatagaaatt aatgacactt   120
t                                                                  121
```

<210> SEQ ID NO 109
<211> LENGTH: 121
<212> TYPE: DNA
<213> ORGANISM: Homo sapiens

<400> SEQUENCE: 109

```
aattgggtgg taaggccaca ccctccctgg caacaggttc tgctgtgacc ccccacccac    60
scgggtcaag cacatgtccc acagtcggga atggcgagtg gactcacgag ggccttcagg   120
c                                                                  121
```

<210> SEQ ID NO 110
<211> LENGTH: 121
<212> TYPE: DNA
<213> ORGANISM: Homo sapiens

<400> SEQUENCE: 110

```
cattatctct tacagaccct ttctgatgcc tcctgggcca gtgggagaac catgggctct    60
ragaggtact gcttactgca gaaccttcag gaagttttta aggcctctga gcttcagttt   120
c                                                                  121
```

<210> SEQ ID NO 111
<211> LENGTH: 121
<212> TYPE: DNA
<213> ORGANISM: Homo sapiens

<400> SEQUENCE: 111

```
gagcatgttg ttttgaggaa taataaaaat ccagaccatc ttaaaaaaaa aaaaaaagcc    60
mtatgaaaat aattatgcaa ataggattc tcctctacta acatgactat attataaatt   120
a                                                                  121
```

<210> SEQ ID NO 112
<211> LENGTH: 121
<212> TYPE: DNA
<213> ORGANISM: Homo sapiens

<400> SEQUENCE: 112

```
ttacccctaa tgctcttcct ccacatttct gcacagcttc ctcccttact gtaatcttta    60
rtgtttactc aaatgtcacc ctatcagtga gccctcccct aaacacccctt actttaaatt  120 t                                                                  121
```

<210> SEQ ID NO 113

```
<211> LENGTH: 121
<212> TYPE: DNA
<213> ORGANISM: Homo sapiens

<400> SEQUENCE: 113
ggagggcgtg gagggcgtgg gagcgtggga ggcgggagtg gagtggaaga agagggagag     60
rtggagcaaa gtgagggccg agtgagagcg tgctccagcc tggctcccac aggcagcttt    120
a                                                                    121

<210> SEQ ID NO 114
<211> LENGTH: 121
<212> TYPE: DNA
<213> ORGANISM: Homo sapiens

<400> SEQUENCE: 114
tgtatatgta ccacatttc ttttattttt ttcttcagag agacacgaaa caagtaatcc     60
rgaggtctat gactaaagct aaaagaaaac catataactt agagctgctg taggcaaata    120
c                                                                    121

<210> SEQ ID NO 115
<211> LENGTH: 121
<212> TYPE: DNA
<213> ORGANISM: Homo sapiens

<400> SEQUENCE: 115
tgatttggac tgtttaaata tcttttcttt ttctttttt ttttttttgg aatcagattc     60
mccgtcccca tagctaaaga atttaaattt gtctttatga tgctgttgtt tttaccttt    120 t                                                                    121

<210> SEQ ID NO 116
<211> LENGTH: 121
<212> TYPE: DNA
<213> ORGANISM: Homo sapiens
<220> FEATURE:
<221> NAME/KEY: modified_base
<222> LOCATION: (104)..(104)
<223> OTHER INFORMATION: a, c, t, g, unknown or other

<400> SEQUENCE: 116
ggcagtgggg gaaatgttgg tagaggaaac aagacatgcg acagcactta cttgagctgg     60
rgaagaacac agtggttaga ggaactgaga gaaatccagt gttnctggct cttagaaagt    120
g                                                                    121

<210> SEQ ID NO 117
<211> LENGTH: 121
<212> TYPE: DNA
<213> ORGANISM: Homo sapiens

<400> SEQUENCE: 117
atctgttttt aatttacata tgtaaccttg acttataaat tacttagaag ccaaggcgta     60
rtattagcat ttagagcaaa gtctggctat gttaagaatg ctaacgttat gaagaatctt    120
t                                                                    121

<210> SEQ ID NO 118
<211> LENGTH: 121
<212> TYPE: DNA
<213> ORGANISM: Homo sapiens

<400> SEQUENCE: 118
```

-continued gccaaaatat cacacttaca aaattgtccc tcacactttt ctttacaact gttcgtctcg    60
rtgttacatc cagaatccca gtagaaatga acggtgaaaa acagagtgca attccagcct   120
t                                                                  121

<210> SEQ ID NO 119
<211> LENGTH: 121
<212> TYPE: DNA
<213> ORGANISM: Homo sapiens

<400> SEQUENCE: 119
ttgagtgcct ctctaggcca agcagtttac atatatgctc tcattttaaa tcctagtaac    60
wgctatatga ggtaagtctt gttattctaa ttctatatag agagtttctg aggatcagga   120
a                                                                  121

<210> SEQ ID NO 120
<211> LENGTH: 121
<212> TYPE: DNA
<213> ORGANISM: Homo sapiens

<400> SEQUENCE: 120
tgaggctaaa gatattgatc acatcaataa aaatttaaga agtttcacac tggctactga    60
rtaaagtcta gaactatttg taaaacagag attcagagac tttaagaata acaagatgga   120
c                                                                  121

<210> SEQ ID NO 121
<211> LENGTH: 121
<212> TYPE: DNA
<213> ORGANISM: Homo sapiens

<400> SEQUENCE: 121
atgagaggtg ggatgctgat aattcatgag aagccatggc atcacaattt aattacagta    60
wcacttatgg ttgattgtga agaaatgaca aatgaaccca gtaccttgag agcccaaatg   120
a                                                                  121

<210> SEQ ID NO 122
<211> LENGTH: 121
<212> TYPE: DNA
<213> ORGANISM: Homo sapiens

<400> SEQUENCE: 122
gatagtattc aaataaccta acatttagat ttctgagcat ggttaacagc attacacaga    60
rttgtgtgtt gaaactgcca atttaaggac ttacttagcc tccaaacttg ttatttcttg   120
g                                                                  121

<210> SEQ ID NO 123
<211> LENGTH: 121
<212> TYPE: DNA
<213> ORGANISM: Homo sapiens
<220> FEATURE:
<221> NAME/KEY: modified_base
<222> LOCATION: (70)..(70)
<223> OTHER INFORMATION: a, c, t, g, unknown or other

<400> SEQUENCE: 123
ccttcaggcc tcagctaggt ggtctcctcc cctaggaagc tattcttgac actataccct    60
ragcttccan aggatggtaa gttcacccat gctgtgctgc agttacctga ctggttttct   120
g                                                                      121

<210> SEQ ID NO 124
<211> LENGTH: 121
<212> TYPE: DNA
<213> ORGANISM: Homo sapiens

<400> SEQUENCE: 124
tccgtcctgg actaggctga cccctgtgtc gttaccccca gaaccagcct gtgaggatgc      60
rgatgaggat gaggacgact atcacaaccc aggctacctg tgagtggcca ggtgggaggt     120
g                                                                      121

<210> SEQ ID NO 125
<211> LENGTH: 121
<212> TYPE: DNA
<213> ORGANISM: Homo sapiens

<400> SEQUENCE: 125 gcccttttcca ccgcaccccg gtgcttccag cctcaaccgc tggagaccaa gcctcctgag    60
rtggggtaaa gcgtacaggc acagctaggg gcacagaaag gcctggaggc cctaagacgt    120
t                                                                      121

<210> SEQ ID NO 126
<211> LENGTH: 121
<212> TYPE: DNA
<213> ORGANISM: Homo sapiens

<400> SEQUENCE: 126
aatacatgta tgtacactga gagggcagga ggaactttat gccaaggtct tcataagccc      60
raattaacaa attgccaagt atgtcaaaac ttgtgtctgt gttggcagga cctgtgaagc     120
a                                                                      121

<210> SEQ ID NO 127
<211> LENGTH: 121
<212> TYPE: DNA
<213> ORGANISM: Homo sapiens

<400> SEQUENCE: 127
gggaccaggt cagcagattc ttccagatca ccaaggtagc cctccacagt cagatggacc      60
rgacccatgg gtctgaagga gatgctgatt gtttctgctc catgttgttt gggactgcct     120
g                                                                      121

<210> SEQ ID NO 128
<211> LENGTH: 121
<212> TYPE: DNA
<213> ORGANISM: Homo sapiens

<400> SEQUENCE: 128
ctggggccgt cctcaggtac cgtcgttcgc ggcagggctg cggccgggtc gggacgagag      60
rgagggaggg atccgcccca gccgggaagc cccgccccgc ttctccgagg tcgccctagc     120
c                                                                      121

<210> SEQ ID NO 129
<211> LENGTH: 121
<212> TYPE: DNA
<213> ORGANISM: Homo sapiens
<220> FEATURE:
<221> NAME/KEY: modified_base

```
<222> LOCATION: (117)..(117)
<223> OTHER INFORMATION: a, c, t, g, unknown or other

<400> SEQUENCE: 129
tagtagtcag tactttgccc gcttatagaa gaatctttgg tttcacctat tgcttggctc    60
rattagttac ttgtttctta attatgaccc tgttgtttat ttttctgcaa agagaanagt   120
t                                                                   121

<210> SEQ ID NO 130
<211> LENGTH: 121
<212> TYPE: DNA
<213> ORGANISM: Homo sapiens

<400> SEQUENCE: 130
ttacattttt catactaaat tgtctcagtc tttggggctt tattattatt attattttat    60
wggcagtgtt agatcttgta gccaaaaaaa gattttttt tcctcttttg gttccaaata   120
g                                                                   121

<210> SEQ ID NO 131
<211> LENGTH: 121
<212> TYPE: DNA
<213> ORGANISM: Homo sapiens

<400> SEQUENCE: 131
tcccaatcaa aatacagatt tcaaaaatcc cccataaaat tccctggttc ctccctgtag    60
rttggtgatc ttttgagaat gcaatttcac cttataatgt atttcaacga aataaaagtt   120
t                                                                   121

<210> SEQ ID NO 132
<211> LENGTH: 121
<212> TYPE: DNA
<213> ORGANISM: Homo sapiens

<400> SEQUENCE: 132
tattagactc tttaaagcct cttcctaaaa gaaagaaaac ctaattacca agttttatca    60
rtttttcttt ctttataata ttttttatat cctcatccat tcatttttat tttcatattc   120
a                                                                   121

<210> SEQ ID NO 133
<211> LENGTH: 121
<212> TYPE: DNA
<213> ORGANISM: Homo sapiens

<400> SEQUENCE: 133
gaaataactg attcagtcat caataaatgc taagccattt agtatgaaat tattcccacc    60
ratttcctgc taatctcaaa ggagaaaagt attttattac acagaaaaga tcaaacttat   120
t                                                                   121

<210> SEQ ID NO 134
<211> LENGTH: 121
<212> TYPE: DNA
<213> ORGANISM: Homo sapiens

<400> SEQUENCE: 134
tagaggcaca gggctgccca catgagaagc agctcagtga cagactagca cctgagatta    60
raaggtctgc tcttccagtt tgcagcagga tttgaaacca cttttttttct ttctgccct   120
```

```
g                                                                121

<210> SEQ ID NO 135
<211> LENGTH: 121
<212> TYPE: DNA
<213> ORGANISM: Homo sapiens

<400> SEQUENCE: 135
actgtttagg actcagcaga cccagcaaga ggcatctgcc ctttccccag ccacctcccc    60
rgcaagcaac ctgaaatctc agcagatgcc caccatttct ctagatcgcc tagtctcaac   120
c                                                                  121

<210> SEQ ID NO 136
<211> LENGTH: 121
<212> TYPE: DNA
<213> ORGANISM: Homo sapiens

<400> SEQUENCE: 136
atggagttag gtgttcagta agggctactt ccactctccc aaatcatttt taaggtcttc    60
rtgtaataga tattgagaga ctaaccaagt cagcctgact tgagttcaag ttgtacttaa   120
a                                                                  121

<210> SEQ ID NO 137
<211> LENGTH: 121
<212> TYPE: DNA
<213> ORGANISM: Homo sapiens

<400> SEQUENCE: 137
gatactgtct taaactgaaa tgtctgaaat caaatgtaac atcttttct cattatatcc    60 rttgtttatt tcggtatagg tagtcacaaa aagtgtactg cctagttgtc taagcaaata   120
c                                                                  121

<210> SEQ ID NO 138
<211> LENGTH: 121
<212> TYPE: DNA
<213> ORGANISM: Homo sapiens

<400> SEQUENCE: 138
catatcacct aataaaaccc ttcattctga tgaggaaatt gaggcccaga gatgataaac    60
rgctaagagt ttcaaacagc tagtttgtga ggaagccaag acaaactaag tctgtttagt   120
t                                                                  121

<210> SEQ ID NO 139
<211> LENGTH: 121
<212> TYPE: DNA
<213> ORGANISM: Homo sapiens

<400> SEQUENCE: 139
ctcttctagc tattttttaa aaaccaagaa aatacagtat ctggttttat atctgcctga    60
rgggaaatga tactctacat ttattataaa tgaaaagttt gccctaagta cattaccttu   120
a                                                                  121

<210> SEQ ID NO 140
<211> LENGTH: 121
<212> TYPE: DNA
<213> ORGANISM: Homo sapiens

<400> SEQUENCE: 140
```

```
gctgtccacc cccacccccca actccaagcc tgggcggtct ggatccggct gtacagtttg    60
rccacctggc ccctgtccc atcccaggtg cctccggact ccttcctctg gccgcctctt    120
c                                                                    121
```

<210> SEQ ID NO 141
<211> LENGTH: 121
<212> TYPE: DNA
<213> ORGANISM: Homo sapiens

<400> SEQUENCE: 141

```
ggttccctga ttggcccact gggtttccca agggagcaaa ggacacttgg gggctgtccc    60
rttctcagag ctgacggcca cccactgctg acggctgcct cactcccgca gaggtggaca    120
t                                                                    121
```

<210> SEQ ID NO 142
<211> LENGTH: 121
<212> TYPE: DNA
<213> ORGANISM: Homo sapiens

<400> SEQUENCE: 142

```
aagaaaacca tataacttag agctgctgta ggcaaatact aatactacgt tatttagcta    60
stgtgatgaa aaataaaca ggtgtcacat gagaaaaaac aaggcacaca ggtaacgaga    120
c                                                                    121
```

<210> SEQ ID NO 143
<211> LENGTH: 121
<212> TYPE: DNA
<213> ORGANISM: Homo sapiens

<400> SEQUENCE: 143

```
agaatcagcg cagcagaaaa ttgtattggt gaaataggag gcagagtcaa gaaacatact    60
raacataaga aattagctga gacgtgaagt gaatgaatgc tcacagatgt gcaggggaag    120
t                                                                    121
```

<210> SEQ ID NO 144
<211> LENGTH: 121
<212> TYPE: DNA
<213> ORGANISM: Homo sapiens
<220> FEATURE:
<221> NAME/KEY: modified_base
<222> LOCATION: (48)..(48)
<223> OTHER INFORMATION: a, c, t, g, unknown or other

<400> SEQUENCE: 144

```
gaaataagca cattttagaa tatgttttgc atacacatat aagaaacntg taccaatttt    60
rtaaatattg tatactaaat gctattctgc accttcctct ttttttttaac tcaatatatt    120 t                                                                    121
```

<210> SEQ ID NO 145
<211> LENGTH: 121
<212> TYPE: DNA
<213> ORGANISM: Homo sapiens
<220> FEATURE:
<221> NAME/KEY: modified_base
<222> LOCATION: (121)..(121)
<223> OTHER INFORMATION: a, c, t, g, unknown or other

<400> SEQUENCE: 145

```
gggtgaactc atggtgaatt agaaggtact ctgccacagc tcatacactt tttgtcatgt    60
rctattccac tctcaagtta ctgtcgtctg cagctttgaa gtaggtttgc ctactgacat   120 n                                                                   121

<210> SEQ ID NO 146
<211> LENGTH: 121
<212> TYPE: DNA
<213> ORGANISM: Homo sapiens

<400> SEQUENCE: 146
ttttagaagt gttatcctga ggctatttac aattttttct ttgtgacgct cacatcagga    60
rtcattagca aacctgtcgt aatgccagat aaccaatgcc tggctggcac accaataact   120
g                                                                   121

<210> SEQ ID NO 147
<211> LENGTH: 121
<212> TYPE: DNA
<213> ORGANISM: Homo sapiens

<400> SEQUENCE: 147
atttttaaaa taatttatat aattaaattc ctctccagtc ccaagtgtga aaagcattaa    60
wtactctgga gtctcttgag ccatttccat ttttaaaact agtcagtttt tcaagttaca   120
g                                                                   121

<210> SEQ ID NO 148
<211> LENGTH: 121
<212> TYPE: DNA
<213> ORGANISM: Homo sapiens

<400> SEQUENCE: 148
ttttaaatct cactctggct tctaagtggt gggcagcagg aaggagacaa gaatgatgcc    60
rattagaagg ctgggacaga attccagatg aggaatcagt ggtggcttag attagggtgg   120
t                                                                   121

<210> SEQ ID NO 149
<211> LENGTH: 121
<212> TYPE: DNA
<213> ORGANISM: Homo sapiens
<220> FEATURE:
<221> NAME/KEY: modified_base
<222> LOCATION: (98)..(98)
<223> OTHER INFORMATION: a, c, t, g, unknown or other

<400> SEQUENCE: 149
ttatttatag gtactataat taaaatatgt acctgcaata taatgtggga ataattttac    60
rtggtaaggg agggagaagg tacaggtcag agaaggtnac aaaaatattc agagtaattt   120
c                                                                   121

<210> SEQ ID NO 150
<211> LENGTH: 121
<212> TYPE: DNA
<213> ORGANISM: Homo sapiens

<400> SEQUENCE: 150
atggggaggg gagagatttc tacttctgca atgaagtacc agtaccataa ctagtactag    60 rtttacccctt tgtaataaa gaactggaaa ttggacgagg aatatgtaac agctgttttc   120
a                                                                   121
```

<210> SEQ ID NO 151
<211> LENGTH: 121
<212> TYPE: DNA
<213> ORGANISM: Homo sapiens

<400> SEQUENCE: 151
atacttgtga ttgcattgag aagttcttgt agtgtgtttt cagctataac aggggggttat    60 rttcctctct aaaatggctt tggctgtcag ctcctgtact gttctatgat aattcttagc   120
t                                                                  121

<210> SEQ ID NO 152
<211> LENGTH: 121
<212> TYPE: DNA
<213> ORGANISM: Homo sapiens

<400> SEQUENCE: 152
ttaataattt gatgaatgtc agtgcaaaat gaaatacatt tttttctggc atatttatca    60
mcaaacaaag atcaagacca tcagataaaa caattgatac tttgtgcttt aaaatttcat   120
t                                                                  121

<210> SEQ ID NO 153
<211> LENGTH: 121
<212> TYPE: DNA
<213> ORGANISM: Homo sapiens

<400> SEQUENCE: 153
aacacccaag cttatataga catttccatg aaagaagtgc tgtggctgat cagaagggaa    60
rttaatgact tttaataaat tattttgagt agtcatttgg aaaaaaagga aattagactg   120
g                                                                  121

<210> SEQ ID NO 154
<211> LENGTH: 121
<212> TYPE: DNA
<213> ORGANISM: Homo sapiens

<400> SEQUENCE: 154
tccctggcag gaagtccttc tgcctgtctg acctgggtct ctcctgcttt gattttagta    60
maagtggact ctgccattct ctgcctttcc ttttctgact ggtgctccct ctcttccatc   120
t                                                                  121

<210> SEQ ID NO 155
<211> LENGTH: 121
<212> TYPE: DNA
<213> ORGANISM: Homo sapiens

<400> SEQUENCE: 155
ctgtttatct gctgttccat cattcattca ttcattcgcc aaacatctga gcatatctta    60
ratatatata gcatatagat gctaatctag gcactgaaaa gatgaataat aagccccctt   120
c                                                                  121

<210> SEQ ID NO 156
<211> LENGTH: 121
<212> TYPE: DNA
<213> ORGANISM: Homo sapiens

<400> SEQUENCE: 156

```
tgttctcaaa gaggtcccag cttcatggga gtgggacctg caaacaatca accaccacca    60
sgataattac tctaagttgc acatgcaaga gaacagaact tgcctgaggg agttgaggct   120
g                                                                  121

<210> SEQ ID NO 157
<211> LENGTH: 121
<212> TYPE: DNA
<213> ORGANISM: Homo sapiens

<400> SEQUENCE: 157
tcactgcgtc tgactgcaga cccggctgga agcccctgg aaccaggccc aagcctcccc    60
rccatgaatt ttgttcacac aagtaaggcc tcggggtgag gtgatggggg tggctgaggt   120
g                                                                  121

<210> SEQ ID NO 158
<211> LENGTH: 121
<212> TYPE: DNA
<213> ORGANISM: Homo sapiens

<400> SEQUENCE: 158
ccagggagat gcagggtcac caaggagagg cctggccttg gcacctcctc aggaggaaga    60
mgcagaagcc caggagaccc cccaccctgg ctggggcgaa actgccatcc gataccagag   120
g                                                                  121

<210> SEQ ID NO 159
<211> LENGTH: 121
<212> TYPE: DNA
<213> ORGANISM: Homo sapiens

<400> SEQUENCE: 159
atgtgtgggg caaaatgcta gggatagtgt agtaatccag tggagctgtt actactccta    60
raccagaaga gaagaaagga agggccaatt accagaacct agaaggagag aggcagatag   120
a                                                                  121

<210> SEQ ID NO 160
<211> LENGTH: 121
<212> TYPE: DNA
<213> ORGANISM: Homo sapiens

<400> SEQUENCE: 160
tccctcactc tacccacccc ccaggaggtg agaatggtaa gtcacttttta ttaatttggg    60 rcaacacata aagccgggat agttgctacc tggatcacag aatccctagg tgagaaatag   120
c                                                                  121

<210> SEQ ID NO 161
<211> LENGTH: 121
<212> TYPE: DNA
<213> ORGANISM: Homo sapiens

<400> SEQUENCE: 161
ttaccttttt cttgggacac ggtgaatatt aatattctca tttcaatgta atttcttttt    60
ratttttgag ttttcttcaa ctgtgcttct tgtttattaa acatttagtt cattctcttt   120
t                                                                  121

<210> SEQ ID NO 162
<211> LENGTH: 121
```

```
<212> TYPE: DNA
<213> ORGANISM: Homo sapiens

<400> SEQUENCE: 162
acagcatgtt ttgtggggac agaattgaag aaaggtgcca tccttaaagg aaaggtcagg      60
rtaagaatgt gggagagcca gatgatacag ctcttaaggc attaaattta agccactacc     120
t                                                                    121

<210> SEQ ID NO 163
<211> LENGTH: 121
<212> TYPE: DNA
<213> ORGANISM: Homo sapiens
<220> FEATURE:
<221> NAME/KEY: modified_base
<222> LOCATION: (63)..(63)
<223> OTHER INFORMATION: a, c, t, g, unknown or other

<400> SEQUENCE: 163
ttggctgggg attaggaggt tcgagggtct ctattttcc tgaattatgc ccattaatca      60
santatcaag gaaactggat ataccatgac agaaataaaa agtccacttt ttctaagtaa    120
g                                                                    121

<210> SEQ ID NO 164
<211> LENGTH: 121
<212> TYPE: DNA
<213> ORGANISM: Homo sapiens

<400> SEQUENCE: 164
aacaaaatag aagcaagcag aagaaaactt ccacaaactc ccaccatcac atctacacag      60
maactgtgcc cattgactcc accatctgtt actatggaag aactgtttgt actcctagct    120
a                                                                    121

<210> SEQ ID NO 165
<211> LENGTH: 121
<212> TYPE: DNA
<213> ORGANISM: Homo sapiens

<400> SEQUENCE: 165
taatgaatga atctgaggaa tacaaatgga gcctgttgga gattaatgtt caaacatcat      60
rtcttttagt cacttttaat ctttactttt gaaataattt tctcctcctt tattttactg    120
t                                                                    121

<210> SEQ ID NO 166
<211> LENGTH: 121
<212> TYPE: DNA
<213> ORGANISM: Homo sapiens

<400> SEQUENCE: 166
ttacaagtgt gagccaccat gcccagccca agaataatt tttaaaataa tttttatacc      60
rtagttgttt ataaagcttt ccatagtaag ttccttctta tggtgaaatc agccattcta    120
a                                                                    121

<210> SEQ ID NO 167
<211> LENGTH: 121
<212> TYPE: DNA
<213> ORGANISM: Homo sapiens
<220> FEATURE:
<221> NAME/KEY: modified_base
<222> LOCATION: (102)..(102)
```

<223> OTHER INFORMATION: a, c, t, g, unknown or other

<400> SEQUENCE: 167
gtccctgctg cccatttctc taccaccact cttaatgttt acaaatggca aagctccagc    60
rtggacaaca tagtaagacc ccatctctac aaaaaaaaaa antttttttt aattagctgg   120
g                                                                  121

<210> SEQ ID NO 168
<211> LENGTH: 121
<212> TYPE: DNA
<213> ORGANISM: Homo sapiens

<400> SEQUENCE: 168
ctgaccaggt acctacttgg ctaaggcttg gagcccggct gtgaagggct gagaatcacc    60
raggttgagc tctgcaagcc tgaacccgga tgcttccgca cagaaagggc cttggatgct   120
g                                                                  121

<210> SEQ ID NO 169
<211> LENGTH: 121
<212> TYPE: DNA
<213> ORGANISM: Homo sapiens

<400> SEQUENCE: 169 catctttgg gaacagggtg tggacaggta caacacatgc ccccaggaac tcatcaccac     60
rgggattcca agagggctga ggccagccct gcctgtggtc ttcagccttc tttccaggct   120
c                                                                  121

<210> SEQ ID NO 170
<211> LENGTH: 121
<212> TYPE: DNA
<213> ORGANISM: Homo sapiens

<400> SEQUENCE: 170
ggggcacgtt ctccccatgc accccgacga cccacctggg tgcctgtccc ttccacaagc    60
rtgcactgcc ttcccggggt gtgccaggca ccgccaggtg ccgaggggca gcagggccca   120
g                                                                  121

<210> SEQ ID NO 171
<211> LENGTH: 121
<212> TYPE: DNA
<213> ORGANISM: Homo sapiens

<400> SEQUENCE: 171
gttctaagac atgagtgctg ggctccagga gaaggggcag gcatgggcta aaaaggatac    60
maggtcctgg atggggtgg gagcccaaca taaaagagga gcaaccatga gagaagggca   120
a                                                                  121

<210> SEQ ID NO 172
<211> LENGTH: 121
<212> TYPE: DNA
<213> ORGANISM: Homo sapiens

<400> SEQUENCE: 172
accaaaaaac actccaaaga aatgaccagg tcagtctacg atggaagaat agatacaagc    60
rtaaaaagca aagaaactgg atcactcaaa attagagggg gtgacatcag atgatccttc   120
t                                                                  121

<210> SEQ ID NO 173
<211> LENGTH: 121
<212> TYPE: DNA
<213> ORGANISM: Homo sapiens

<400> SEQUENCE: 173
gctttaaggg tggaattcca gcaggcactg cattttccca gcttttgtac tcagttactc    60
mgagctcatt cctttgcagc tctaaagctc ttttgtgttt catcatcttg ctcgaaacct   120
t                                                                   121

<210> SEQ ID NO 174
<211> LENGTH: 121
<212> TYPE: DNA
<213> ORGANISM: Homo sapiens
<220> FEATURE:
<221> NAME/KEY: modified_base
<222> LOCATION: (115)..(115)
<223> OTHER INFORMATION: a, c, t, g, unknown or other

<400> SEQUENCE: 174
cccatgcccg aggggctgg ggtacagggg ccatctccag tgggaacagg gactgcacca     60
rccaagtccc agaaggtaga ccccagccca gagggacac agccctctgc cacangttcc    120
a                                                                   121

<210> SEQ ID NO 175
<211> LENGTH: 121
<212> TYPE: DNA
<213> ORGANISM: Homo sapiens

<400> SEQUENCE: 175
tccctattaa tagtttctgg tgtacctttg cagatatttg caatgttata caagttttac    60
mtgcctgtgg gggttgggaa gattgtaatc cttttaaaa attacaggtt aaaattatag   120
a                                                                   121

<210> SEQ ID NO 176
<211> LENGTH: 121
<212> TYPE: DNA
<213> ORGANISM: Homo sapiens

<400> SEQUENCE: 176
ggcagatggt cgtttggctg aataccttcc ctgggggagg ccagtcaaaa gagaagcaaa    60
rtgagggagc acgcagggcc cttgtgaccc tgagatccaa gcttaccacc tcttcccaga   120
g                                                                   121

<210> SEQ ID NO 177
<211> LENGTH: 121
<212> TYPE: DNA
<213> ORGANISM: Homo sapiens

<400> SEQUENCE: 177
aaaaaaacca gtgtagggga acacaataga aaggggggtg aggagcaggg taaataaatg    60
rtatcagaga ggtagagaac agacttgccc agggagggta tcctttaggg ttgggcggaa   120
t                                                                   121

<210> SEQ ID NO 178
<211> LENGTH: 121
<212> TYPE: DNA

<213> ORGANISM: Homo sapiens

<400> SEQUENCE: 178

| ctctctgtta ccaggtgttc caactgtgtg ggaccaatgc ttgctggaga tgctgcagag | 60 |
| rcctcagtgc ccagtgtcaa gcaggctaag aaagccttta cagcagcttc aggtacccag | 120 |
| c | 121 |

<210> SEQ ID NO 179
<211> LENGTH: 121
<212> TYPE: DNA
<213> ORGANISM: Homo sapiens

<400> SEQUENCE: 179

| ccaaagttgt cgtagactct tgataaactt accagccaga aagctgcttc acaccatgat | 60 |
| rgactctgaa gttgtctgga tagcagacct tgttttctgc ccactatgca tagacgtggc | 120 |
| a | 121 |

<210> SEQ ID NO 180
<211> LENGTH: 121
<212> TYPE: DNA
<213> ORGANISM: Homo sapiens

<400> SEQUENCE: 180

| gcatgaatcc aaggccttaa ttttgatcac tttgtcttga tgagcctggt aggtcacttt | 60 |
| rcaatttcca gagatatcta cctaaaaaga aaggcaaggg cataatgctt gggattcctt | 120 |
| g | 121 |

<210> SEQ ID NO 181
<211> LENGTH: 121
<212> TYPE: DNA
<213> ORGANISM: Homo sapiens

<400> SEQUENCE: 181

| atctgaaaaa tgaaggtaat aagtagtgtt cacttcatgg gattattgtg tgagggagaa | 60 |
| rtgaataatc cacacgaagt gcttggcaca gagtaggtgc tcgttagcca acagccacca | 120 |
| g | 121 |

<210> SEQ ID NO 182
<211> LENGTH: 121
<212> TYPE: DNA
<213> ORGANISM: Homo sapiens

<400> SEQUENCE: 182

| ggaaaaacct cgcattccac ctgtttacgg ttacatgagt tcttcttcct ctttaaaagt | 60 |
| mtcttttttg agacaaggtc tcgctgtcac caggctgaaa gtgtaggggt gcaatcacag | 120 |
| c | 121 |

<210> SEQ ID NO 183
<211> LENGTH: 121
<212> TYPE: DNA
<213> ORGANISM: Homo sapiens

<400> SEQUENCE: 183

| gtctctggac ctttgctggg gtctccgtat ctaacactct tccttaactt tgcttcttaa | 60 |
| mctcttactc actcgtcaag gactaactcc ttgtcttcag cacactttgc ccagattgac | 120 |
| a | 121 |

<210> SEQ ID NO 184
<211> LENGTH: 121
<212> TYPE: DNA
<213> ORGANISM: Homo sapiens

<400> SEQUENCE: 184
ggcagcacag tgtagttcag ggaagggctg actactaatg ccacggaaga gctccagtgg      60
rtcccgagat aaagaagaaa accaggattc tgtcatcctc agaaggtcat cagtctgctg     120
c                                                                    121

<210> SEQ ID NO 185
<211> LENGTH: 121
<212> TYPE: DNA
<213> ORGANISM: Homo sapiens

<400> SEQUENCE: 185
aggaaaacag gttttacaga aaacaggttg gtatgacttg gccctgttca gggatatctt      60
matctttgac aggggttcaa tatgtaagtt catttgctgg tgggttaact acattgtaga     120
a                                                                    121

<210> SEQ ID NO 186
<211> LENGTH: 121
<212> TYPE: DNA
<213> ORGANISM: Homo sapiens

<400> SEQUENCE: 186
actgcactcc agcctggcca acagagcaag acccttttta tatatatata tatatttaca      60
rtgcaatata attactatga tagagaagat attgaaacca gacttgaaaa aatttgtagt     120
a                                                                    121

<210> SEQ ID NO 187
<211> LENGTH: 121
<212> TYPE: DNA
<213> ORGANISM: Homo sapiens

<400> SEQUENCE: 187
gccaggggct ggggcaaggg gagaatggga gttcgtgtct agtgggtagg aagtttcagt      60
stgggaagag gagttctgga agtggagggt gacagtccac agcaatgtga gtggacttca     120
t                                                                    121

<210> SEQ ID NO 188
<211> LENGTH: 121
<212> TYPE: DNA
<213> ORGANISM: Homo sapiens

<400> SEQUENCE: 188
tggaataaat gggggcaatc tctcatttct ggcttgtttc caagttggga attacctcct      60
mcttcttgaa agttacccat aatttaattt cagtagcttt ggcttgatac cttctaagat     120
t                                                                    121

<210> SEQ ID NO 189
<211> LENGTH: 121
<212> TYPE: DNA
<213> ORGANISM: Homo sapiens

<400> SEQUENCE: 189

```
gattcatgag ttcggtgtgt gagagccttt aaccttggga actggacctt tgtctttccc    60
rttttaagtc ctgcaagtgt ctaaatgttt tctttcagag tgtgacaaag gcagcattca   120
c                                                                   121

<210> SEQ ID NO 190
<211> LENGTH: 121
<212> TYPE: DNA
<213> ORGANISM: Homo sapiens

<400> SEQUENCE: 190
acaggcagcc cacgctcctt caccaggccc agtgggagcc ttagttctcc cgggccagcc    60
rgtgcagaat aagaaaggga acggagaagg gtgagaacta cctgtgtcgt aacatcctgc   120
c                                                                   121

<210> SEQ ID NO 191
<211> LENGTH: 121
<212> TYPE: DNA
<213> ORGANISM: Homo sapiens

<400> SEQUENCE: 191
gtcgaggctg gggccatttc ttcatccttt cctggggctg catcagaaaa tagaatgggt    60
rggcatgcct ggtgggcctc cttttaacca agggactctg ggattctctt agacacacca   120
a                                                                   121

<210> SEQ ID NO 192
<211> LENGTH: 121
<212> TYPE: DNA
<213> ORGANISM: Homo sapiens

<400> SEQUENCE: 192
aggaagcaag gttttgctct ttattagacg ctgtcaggaa gaagggataa ccctattacc    60
rggcgtctca ctaagtctta tctttgggga ggtcaactag agcaaggcca aagctgccat   120
t                                                                   121

<210> SEQ ID NO 193
<211> LENGTH: 121
<212> TYPE: DNA
<213> ORGANISM: Homo sapiens

<400> SEQUENCE: 193
gccccagctg tcttgaattc aggtcagaag gtgggcccag tctggcccta acttaagatc    60
ratttctgat tataatcata atcagatttt gtggcttcct tatggtccct caaccatgcc   120
a                                                                   121

<210> SEQ ID NO 194
<211> LENGTH: 121
<212> TYPE: DNA
<213> ORGANISM: Homo sapiens

<400> SEQUENCE: 194
ttctcaggct aatttagccc tactactaag gcatgacctt cttgaggtct acccaatatc    60
rcatgtatta caaagtctct ccactctggc tgatggcaac atgaattatt tgtaaacctg   120
t                                                                   121

<210> SEQ ID NO 195
<211> LENGTH: 121
```

```
<212> TYPE: DNA
<213> ORGANISM: Homo sapiens
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other

<400> SEQUENCE: 195
gagtaaaact gtattttaaa ggctgaaata attagtggaa tctaccttgt atatttattg      60
rtttnggcan atgctatgtt ctccttattt tctctgggca cttctatcaa gagattgacc     120
a                                                                    121

<210> SEQ ID NO 196
<211> LENGTH: 121
<212> TYPE: DNA
<213> ORGANISM: Homo sapiens

<400> SEQUENCE: 196 ggacccagg aggctgtttg cagcaattgt atctcatcac aactttgtta ttctccactc      60
mgcttcaaag ttttcaaata aactgtcatg aaaggtcaaa aatattatgt atctgggccc    120
a                                                                    121

<210> SEQ ID NO 197
<211> LENGTH: 121
<212> TYPE: DNA
<213> ORGANISM: Homo sapiens

<400> SEQUENCE: 197
cctgacgacc aggccagaac tagcattcag ccctcttggg caggcccatg gggtggaaat      60
rgtgccacct gcagaagtca tcgcccctgt gctgggctgg cctctgtgcc ctccatgtct    120
c                                                                    121

<210> SEQ ID NO 198
<211> LENGTH: 121
<212> TYPE: DNA
<213> ORGANISM: Homo sapiens

<400> SEQUENCE: 198
tcactgtgcg gcccggttcc taacaggccg cagaccagtc tgtggcctgg ggtttgggga      60
mccctgctat atgccaaacc tgaaatgtca tgttctgcca ctgcagcagt gcttgtgcta    120
t                                                                    121

<210> SEQ ID NO 199
<211> LENGTH: 121
<212> TYPE: DNA
<213> ORGANISM: Homo sapiens
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other

<400> SEQUENCE: 199
atagcaactg gagtccaacc ttggcaatgt agcaagatgt aagagtgaga gagagagaga      60
```

```
rnagagagaa gacangaagg aggagaagag aagaaggaga aggagaagag gagaggagaa    120
g                                                                    121

<210> SEQ ID NO 200
<211> LENGTH: 121
<212> TYPE: DNA
<213> ORGANISM: Homo sapiens

<400> SEQUENCE: 200
cttgatccac ctgttctttt tagatgtctg caccccagc ccccactgct ctttcaggtc      60
rtcttatcta cttgctttca tcagggaagt ctgaccgtcc cgctacagta gaagacctga   120
a                                                                    121

<210> SEQ ID NO 201
<211> LENGTH: 121
<212> TYPE: DNA
<213> ORGANISM: Homo sapiens

<400> SEQUENCE: 201 tttttattt tgtttctcta gtgttatggc agtggaggtg ggaatttagt ccccaggtgg      60
racaagggaa gttttttcat tttggagcta gttactggga gtaagggagg gtggggtggg   120
g                                                                    121

<210> SEQ ID NO 202
<211> LENGTH: 121
<212> TYPE: DNA
<213> ORGANISM: Homo sapiens

<400> SEQUENCE: 202
tttaggtaca aaatagccac ctgtactagt gggctagtgg ccactgaatt gaacagtgta    60
saggacaacc caccatcgca gaagttcatt tggacaatgc tgatctagaa cgttccagtg   120
a                                                                    121

<210> SEQ ID NO 203
<211> LENGTH: 121
<212> TYPE: DNA
<213> ORGANISM: Homo sapiens

<400> SEQUENCE: 203 ggaaccccctt cattatttca atctcaattg acttcttgtt aaaatggttt ttatctacca    60
ragaaacttc agatttatta ggtaataatt tacatgtttg tttattttgg aattcagtga   120
g                                                                    121

<210> SEQ ID NO 204
<211> LENGTH: 121
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other

<400> SEQUENCE: 204
tgcncctgtt gtcatttccc ttctacctga aaattttttc ctgaatatag gtcaaaagtt    60
mttgtttctt tgcatgtcta gtgggataat atagcaactc tgggttgtgc tgggttcctc   120
t                                                                    121
```

```
<210> SEQ ID NO 205
<211> LENGTH: 121
<212> TYPE: DNA
<213> ORGANISM: Homo sapiens

<400> SEQUENCE: 205
atctagagcc aggtctagca tgtcgttggt gctcaaaaga tatctgttga atggatgaat      60
rtattaagag tacagtctgc tattaaactg gcctttaaga taaacaatta aactatccca     120
g                                                                     121

<210> SEQ ID NO 206
<211> LENGTH: 121
<212> TYPE: DNA
<213> ORGANISM: Homo sapiens
<220> FEATURE:
<221> NAME/KEY: modified_base
<222> LOCATION: (29)..(29)
<223> OTHER INFORMATION: a, c, t, g, unknown or other

<400> SEQUENCE: 206
tactacaagc attttgtggg gaaagggcna ctgattttta tacagtggtc ataggagaa      60 rgcagaggca gattccactg agaaggctcc ttgttgaagc tactggctaa tagaaagggt    120
c                                                                     121

<210> SEQ ID NO 207
<211> LENGTH: 121
<212> TYPE: DNA
<213> ORGANISM: Homo sapiens

<400> SEQUENCE: 207
ttgagtaaac aattggatgt acatttcagt tgtttgggg gaggtcagag tatattcatt      60
rtatttgcag ccatgggata tttaaaatca attagggctg ggcacagtgg ttcatgcctg    120
t                                                                     121

<210> SEQ ID NO 208
<211> LENGTH: 121
<212> TYPE: DNA
<213> ORGANISM: Homo sapiens

<400> SEQUENCE: 208
agaccagaga aaacctcctc cacacagata taataggtat tgatattcat ctttctttta    60
rtgatcatat catgcagttt ctcaagtcct tcctttaggc catctcctat gattgcgcag    120
g                                                                     121

<210> SEQ ID NO 209
<211> LENGTH: 121
<212> TYPE: DNA
<213> ORGANISM: Homo sapiens

<400> SEQUENCE: 209
gcataagtta ccagaagtgg aatgtgagca aagggtgtgg atattttgac agttttatgc    60
mccctttatt ttttgagtac cactacttct tccttctaat aggttatacc aatttacatc   120
t                                                                     121

<210> SEQ ID NO 210
<211> LENGTH: 121
<212> TYPE: DNA
<213> ORGANISM: Homo sapiens
```

```
<400> SEQUENCE: 210
tgaaaactat tgtaatgaa aggtttgaaa gttaccaaga gactgagaga ttgacaccaa      60
rttggtgaga tttgcatcat ttaaagaaaa atttcagtca aattaaattt agtagagttt     120
a                                                                    121

<210> SEQ ID NO 211
<211> LENGTH: 121
<212> TYPE: DNA
<213> ORGANISM: Homo sapiens

<400> SEQUENCE: 211
ttaaaatggg aggagtcgac gaagcaagga atgtattcac ctgagcaata atttgaaatg      60
rgaggagtca atgatacaga gaatttactc acctgaaatt aaaaaggatg aggacagggc     120
t                                                                    121

<210> SEQ ID NO 212
<211> LENGTH: 121
<212> TYPE: DNA
<213> ORGANISM: Homo sapiens

<400> SEQUENCE: 212
ctttaaagaa aaatgttgaa cgaattccca tcattttatt acaagaggat gagagaagag      60
raggaagttt aagcaaaaga atctgatgtc cttttgcaac agagaatttg tgagaaatgt     120
c                                                                    121

<210> SEQ ID NO 213
<211> LENGTH: 121
<212> TYPE: DNA
<213> ORGANISM: Homo sapiens

<400> SEQUENCE: 213
atgaggaaat gggtctttga gaaatgaatt cagttaccct tgtcacacag ctactatgaa      60
rtctactata ctatgttatt tagcagaaaa ttgttgcagg atcaaagctt ccaaaaatac     120
a                                                                    121

<210> SEQ ID NO 214
<211> LENGTH: 121
<212> TYPE: DNA
<213> ORGANISM: Homo sapiens

<400> SEQUENCE: 214
cccaagttag atatcggtgt cattaataag acctttctcc ctgtctcatg gaatgaagta      60
maaatcattt taatactact ccacaaatgt ccattgaatc caatctttgt tttatatgta     120
c                                                                    121

<210> SEQ ID NO 215
<211> LENGTH: 121
<212> TYPE: DNA
<213> ORGANISM: Homo sapiens

<400> SEQUENCE: 215
ttgcggccct atccttcatt ttgcagagtc ttggtggatt gaaaagctgc tgtggggtgc      60
raggggtatg aaatggcata gtttaggttg gtgcggatgt ccacttaagt ctccatggag     120
a                                                                    121
```

```
<210> SEQ ID NO 216
<211> LENGTH: 121
<212> TYPE: DNA
<213> ORGANISM: Homo sapiens
<220> FEATURE:
<221> NAME/KEY: modified_base
<222> LOCATION: (40)..(40)
<223> OTHER INFORMATION: a, c, t, g, unknown or other

<400> SEQUENCE: 216
catagtacta agcaatttga attaattacc taatcatacn atttgatcct tatgacttga      60
saggaagtag gaattattat tcccaggctg cagataagga aatcatctct tgaatctaat    120
c                                                                    121

<210> SEQ ID NO 217
<211> LENGTH: 121
<212> TYPE: DNA
<213> ORGANISM: Homo sapiens

<400> SEQUENCE: 217
atgccccaca taggctttta taggagagga ggtcctggaa gtgaagacag agtccctgtc     60
sccttcagga tgcctcctgt gggatgtccc agcccctca cttggagctg tccagatcag    120
c                                                                    121

<210> SEQ ID NO 218
<211> LENGTH: 121
<212> TYPE: DNA
<213> ORGANISM: Homo sapiens

<400> SEQUENCE: 218
gaacaagccc atgattgaat gggccctggg gggcttccag ccttctggcc ctaagggcct     60
rgagccacca gaaggtaaat gagggcaccc agctttctgg daccctgcc cgccaggcag    120 a                                                                    121

<210> SEQ ID NO 219
<211> LENGTH: 121
<212> TYPE: DNA
<213> ORGANISM: Homo sapiens

<400> SEQUENCE: 219
aagtagaata acaaaattac tatgacataa aaagctaatg ttggcttatc taggaacatt     60
macatttaag tcagttagcc taaattaaaa gatctgttca taaaggaaat agattatatc    120
t                                                                    121

<210> SEQ ID NO 220
<211> LENGTH: 121
<212> TYPE: DNA
<213> ORGANISM: Homo sapiens

<400> SEQUENCE: 220
tatgtgtctg aaatgcttct taggttcaag tccttccgtt tatttcccta tacatagttc     60
rggcttttct caccagttta cctgaagtat aaaaaccttc ctacgtatag ttcttctcct    120
c                                                                    121

<210> SEQ ID NO 221
<211> LENGTH: 121
<212> TYPE: DNA
<213> ORGANISM: Homo sapiens
```

<400> SEQUENCE: 221
aggttgagtt gaatatcgca tactcaattg ctaacacggt tagaggaaca tcaccagtgt    60
raagtaccag tgttaagtcc ctgggtctgt tcctcatgga ggcccttctc cttttttcag   120
g                                                                   121

<210> SEQ ID NO 222
<211> LENGTH: 121
<212> TYPE: DNA
<213> ORGANISM: Homo sapiens

<400> SEQUENCE: 222
cagctcctgg aagaaacccg gggcttcctc cgacggtgag caatgagcag aatggaggtg    60
raagagggag tccttgtgat tcttaaccat tagcattctc tgagtcttac cactggaagc   120
a                                                                   121

<210> SEQ ID NO 223
<211> LENGTH: 121
<212> TYPE: DNA
<213> ORGANISM: Homo sapiens

<400> SEQUENCE: 223
tcctgcctgg aaattctgtt tacttacaaa atcaaattgg atttttttttt ttagccaaag    60 raattttaag gagagttgtt tttttattga ggcaaaatta ccataacata caactaaaca   120
t                                                                   121

<210> SEQ ID NO 224
<211> LENGTH: 121
<212> TYPE: DNA
<213> ORGANISM: Homo sapiens
<220> FEATURE:
<221> NAME/KEY: modified_base
<222> LOCATION: (6)..(6)
<223> OTHER INFORMATION: a, c, t, g, unknown or other

<400> SEQUENCE: 224
ataccnagga gtagcattgc taggtcatag tagctgtatg tttaattta cgaggaactg    60 mcaaattgtt ttccacaata gctgcaccat tttattttcc caccagcaat gtccaagagt   120
t                                                                   121

<210> SEQ ID NO 225
<211> LENGTH: 121
<212> TYPE: DNA
<213> ORGANISM: Homo sapiens

<400> SEQUENCE: 225
ctgaggccag ggttaggttg tgattgattc aggatgtttc ttaaggatag gatgtaggac    60
rtgaaagaaa ctgaggatga ctgggtttgg ccttgagcaa ctgggtgatc agggtggagc   120
a                                                                   121

<210> SEQ ID NO 226
<211> LENGTH: 121
<212> TYPE: DNA
<213> ORGANISM: Homo sapiens

<400> SEQUENCE: 226
aggtggtcag aagggatacg acagacacag gccacctggc tagtgagagc tagggccaaa    60
mtttgagagc tttgtgctcc ttaacagaag agttgcctcc agtttaaaaa aaacccatgt   120

```
t                                                                   121

<210> SEQ ID NO 227
<211> LENGTH: 121
<212> TYPE: DNA
<213> ORGANISM: Homo sapiens

<400> SEQUENCE: 227
cagtacagcc ttttgcctca agctaggggc tagaggccca gagcagcatg gatggccaga    60
rgcagctccc ctgcggcctc tctcccttcc tgtctctggc tgggtctgtc tggccatctc   120
t                                                                   121

<210> SEQ ID NO 228
<211> LENGTH: 121
<212> TYPE: DNA
<213> ORGANISM: Homo sapiens

<400> SEQUENCE: 228
gatttgaact aagaatgtgt cattccagaa ccagggctca ttgccttgac aacatacagc    60
rcaaatcctg tactcaggat gtcaccctct tcagaatgtt gctgctgtca ctcaagctgg   120
c                                                                   121

<210> SEQ ID NO 229
<211> LENGTH: 121
<212> TYPE: DNA
<213> ORGANISM: Homo sapiens
<220> FEATURE:
<221> NAME/KEY: modified_base
<222> LOCATION: (69)..(69)
<223> OTHER INFORMATION: a, c, t, g, unknown or other

<400> SEQUENCE: 229
tcacctgtca aatgaggtaa taaggatact catctcctag ggccagttcg ggtctagagg    60
rgatagtgng tattgagggt tggtacagca cctagaagta ctccatcaag ttaagatgtt   120
a                                                                   121

<210> SEQ ID NO 230
<211> LENGTH: 121
<212> TYPE: DNA
<213> ORGANISM: Homo sapiens
<220> FEATURE:
<221> NAME/KEY: modified_base
<222> LOCATION: (101)..(101)
<223> OTHER INFORMATION: a, c, t, g, unknown or other

<400> SEQUENCE: 230
atggcagccg ctgtcattac acagacatca cgtttgtgaa ctgtacatac attcgtgggc    60
rcacacacaa cctaagcgat attcctccac tcctcacaca ncctcccaca cttgcatgca   120
t                                                                   121

<210> SEQ ID NO 231
<211> LENGTH: 121
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (101)..(101)
```

-continued

<223> OTHER INFORMATION: a, c, t, g, unknown or other

<400> SEQUENCE: 231
aactggaacn tgaatgaacg ccttcgtgac tgcagtgtgc atgcatgcaa gtgtgggagg    60
rtgtgtgagg agtggaggaa tatcgcttag gttgtgtgtg ngcccacgaa tgtatgtaca   120
g                                                                   121

<210> SEQ ID NO 232
<211> LENGTH: 121
<212> TYPE: DNA
<213> ORGANISM: Homo sapiens

<400> SEQUENCE: 232
agggtctggt agcagatggt cctgtgctgg ctttggcaga ggtgggcaca catggtgtgt    60
sgtgggagcc tgaggagggg cctcacccgg cctgaggaaa ctcactgaga agtggaggcc   120
g                                                                   121

<210> SEQ ID NO 233
<211> LENGTH: 121
<212> TYPE: DNA
<213> ORGANISM: Homo sapiens

<400> SEQUENCE: 233
gcacttggct gtggccaggc tgggcggagg tgatggtggg aggcccagca gccttgatag    60
sgtaggggtg ggggtgggcc cccaaagggt ccttggcaca agaggccaac tgcatggaca   120
g                                                                   121

<210> SEQ ID NO 234
<211> LENGTH: 121
<212> TYPE: DNA
<213> ORGANISM: Homo sapiens

<400> SEQUENCE: 234
ccctctgcca ctgggacatg cccaaccaag tccccagcct gccaggccag atatctcgcc    60
rcgccagtcc ccgagggccc cgcctctatc aggacagccc caggtgggct cacctgtgtg   120
t                                                                   121

<210> SEQ ID NO 235
<211> LENGTH: 121
<212> TYPE: DNA
<213> ORGANISM: Homo sapiens

<400> SEQUENCE: 235
tcaggagtgc acagccccac accatggtca acagcatcag cccagagcac tgtcatcgcc    60
rcagccgagc ccctgggcag gtgcttccca ggcatgactc cctgacccct cgtgtcgacc   120
c                                                                   121

<210> SEQ ID NO 236
<211> LENGTH: 121
<212> TYPE: DNA
<213> ORGANISM: Homo sapiens

<400> SEQUENCE: 236
agcccggcgc ctcaaaggtg gctacaaaaa ctaaggcaac gggtgcatct aaaaagctca    60
raaaggccac gggggctagc aaaaagagcg tcaagactcc gaaaaaggct aaaaagcctg   120
c                                                                   121

<210> SEQ ID NO 237
<211> LENGTH: 121
<212> TYPE: DNA
<213> ORGANISM: Homo sapiens

<400> SEQUENCE: 237
acaaaatcaa aaaacccct gaaaatggaa agttttatca tgattcattt ggctacaaaa      60
rtctggccta acctgaaatg atttggtggt tatattagtt atctattagt acaaacaaat    120
t                                                                    121

<210> SEQ ID NO 238
<211> LENGTH: 121
<212> TYPE: DNA
<213> ORGANISM: Homo sapiens

<400> SEQUENCE: 238
tggaaggaga aagctgtggt gtctctcggc tcttcctgag gcccagctgt atcctcttct      60
rctcctccag ggatttggct attcagccct tccttggatg ccctcagtaa aatattaccc    120
t                                                                    121

<210> SEQ ID NO 239
<211> LENGTH: 121
<212> TYPE: DNA
<213> ORGANISM: Homo sapiens

<400> SEQUENCE: 239
agtgatccta ccacctcggt ctcccaaagg gctaggatta caggtgtgag ccatcgcgtc      60
rgccaggaaa tttcaaaagc aagatgcaac aaacagttaa aagaaggaat ttctttcaac    120
c                                                                    121

<210> SEQ ID NO 240
<211> LENGTH: 121
<212> TYPE: DNA
<213> ORGANISM: Homo sapiens

<400> SEQUENCE: 240
ggtggaagct tacacatctc cctcagcctc tggtttttca gcacttggga ttggggttaa      60
rcctttaaaa acggctgtca ggtttgatct cagtgtaacg acatggccag tgcctgttcc    120
c                                                                    121

<210> SEQ ID NO 241
<211> LENGTH: 121
<212> TYPE: DNA
<213> ORGANISM: Homo sapiens

<400> SEQUENCE: 241
ccatcaagaa gtggctgcaa gaatattcta cattcaaaga catctcaaaa gtaactatct      60
rttcacataa acagtttaat acaactcaat ccaattcttg ccaattctaa acaagaaaag    120
a                                                                    121

<210> SEQ ID NO 242
<211> LENGTH: 121
<212> TYPE: DNA
<213> ORGANISM: Homo sapiens

<400> SEQUENCE: 242
ggacagccag tggaagatca gaggacaaca gagtaaagtt ataatgcaga acctagagca    60
magcgccaaa cctgtcttcc cacctggatg ataggaggag agtttgggct ctgctgggaa   120
a                                                                  121

<210> SEQ ID NO 243
<211> LENGTH: 121
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, c, t, g, unknown or other

<400> SEQUENCE: 243
aaagtgtngc agagcagata gaaactagaa aagaaactgg aaaagagcaa atggaactgg    60
raaaaagaac tatgactgaa gggggtcaac atgatgagtt gtgtcattct ggcccaatag   120
t                                                                  121

<210> SEQ ID NO 244
<211> LENGTH: 121
<212> TYPE: DNA
<213> ORGANISM: Homo sapiens
<220> FEATURE:
<221> NAME/KEY: modified_base
<222> LOCATION: (115)..(115)
<223> OTHER INFORMATION: a, c, t, g, unknown or other

<400> SEQUENCE: 244
tttaaagttg tacaactgcc gactacttcc agcataagca gagaggtgat aaggtcacac    60
raactctctt gcagataaca atgataaaaa tagaataaag taataattaa aaatnagaaa   120
c                                                                  121

<210> SEQ ID NO 245
<211> LENGTH: 121
<212> TYPE: DNA
<213> ORGANISM: Homo sapiens
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other

<400> SEQUENCE: 245
tatttggcct ttctgaaaca ccataatcac tgtacatata aacatttttta ataaaagagt    60 rtatccttag tttatcataa attttttata agatanaata atcattaaag tgactaaggn   120
a                                                                  121

<210> SEQ ID NO 246
<211> LENGTH: 121
<212> TYPE: DNA
<213> ORGANISM: Homo sapiens
<220> FEATURE:
<221> NAME/KEY: modified_base
<222> LOCATION: (73)..(73)
<223> OTHER INFORMATION: a, c, t, g, unknown or other

<400> SEQUENCE: 246
tttatcttat ttgtttcaaa gtctcataga aacaaaggat gcccattatc agattccttt    60
rtataccttg tcncattttt taagctttct agatcttaat ttgcctttgt gtagaaggca   120
g 121

<210> SEQ ID NO 247
<211> LENGTH: 121
<212> TYPE: DNA
<213> ORGANISM: Homo sapiens

<400> SEQUENCE: 247
ggttgcccag gcttacttaa cactcttgaa cgtcaaaacc cacgctcagt acccgcttca    60
mgtggaagtc ggtgttgaga tacaagcata ggaacgaact caaggctaac agctgttctg   120
t                                                                   121

<210> SEQ ID NO 248
<211> LENGTH: 121
<212> TYPE: DNA
<213> ORGANISM: Homo sapiens

<400> SEQUENCE: 248 tgtgttctttt tctgtaatca gtcatgaata aagaaatcta tcttctagca ctggatgcca   60
rtagatttga atgtgagttc agacctatga gtattataga caaagactag attgagagct   120
g                                                                   121

<210> SEQ ID NO 249
<211> LENGTH: 121
<212> TYPE: DNA
<213> ORGANISM: Homo sapiens

<400> SEQUENCE: 249
agtggaactt ttcctgcata ggaggtttag ggaaagcttc tggagttgaa caccagagtt    60
magttttact tatttttttta tttttctcag agacaggatt tcgctctgtt gcccaggctg   120
g                                                                   121

<210> SEQ ID NO 250
<211> LENGTH: 121
<212> TYPE: DNA
<213> ORGANISM: Homo sapiens
<220> FEATURE:
<221> NAME/KEY: modified_base
<222> LOCATION: (60)..(60)
<223> OTHER INFORMATION: a, c, t, g, unknown or other

<400> SEQUENCE: 250
gttcttgagt tacagaaatt acagcagata tttaattatt taaatcattc ttactaagan   60
rttgaaattc ctttagattc tagaaagagt ctaaagcagg gatgatagtc tgaccacact   120
a                                                                   121

<210> SEQ ID NO 251
<211> LENGTH: 121
<212> TYPE: DNA
<213> ORGANISM: Homo sapiens

<400> SEQUENCE: 251
gagaaaacac tgtagaaaaa gcgcatgagt ggattaccta atgatatact gctttaccct   60 rtaactatttt tctacaaagg aaaatcacta ttccatgtat tcattagctt aagagagtat   120
g                                                                   121

<210> SEQ ID NO 252

<211> LENGTH: 121
<212> TYPE: DNA
<213> ORGANISM: Homo sapiens

<400> SEQUENCE: 252
ggtagataga gcagaggttg aaggactgag ccctggggca tgccatatga ggctgccggc    60
rgacagaggt gcacagctag tgagaaaaaa acaaggcctt tttgtagttc tgaagcctca   120
a                                                                   121

<210> SEQ ID NO 253
<211> LENGTH: 121
<212> TYPE: DNA
<213> ORGANISM: Homo sapiens

<400> SEQUENCE: 253
actcagccct agaaactgtt gggggaatgt gcttccccac agccccagat ggatcacagg    60
rgtatgggag ggtctaagca ttttgttgag aaggcattta agcacctact gggtggcagg   120
c                                                                   121

<210> SEQ ID NO 254
<211> LENGTH: 121
<212> TYPE: DNA
<213> ORGANISM: Homo sapiens
<220> FEATURE:
<221> NAME/KEY: modified_base
<222> LOCATION: (107)..(107)
<223> OTHER INFORMATION: a, c, t, g, unknown or other

<400> SEQUENCE: 254
gctccagggc caggaaggag ggtccaggaa ctccaagccc tccttaggtt ggagggagaa    60
scaagtcagc tggaccagca tcccagattt cagtccaggc tgagtgncct tggatgggtt   120
a                                                                   121

<210> SEQ ID NO 255
<211> LENGTH: 121
<212> TYPE: DNA
<213> ORGANISM: Homo sapiens

<400> SEQUENCE: 255
tttccctcag ataaatttat tagtgtttta aacaaattca gagatagcaa aagtttaagc    60
ratcagttat ttttctgtaa aatgaaaggt ttattctcat atacaaggct gtcaaatatt   120
t                                                                   121

<210> SEQ ID NO 256
<211> LENGTH: 121
<212> TYPE: DNA
<213> ORGANISM: Homo sapiens

<400> SEQUENCE: 256
caattatggt agcacacatt aaatgaaata ggaggataat ataagagcag gcccatagtt    60
rtatatatta gtggactaaa tgagtgatat ctttattgtg atcatcatgg tcacatttat   120
t                                                                   121

<210> SEQ ID NO 257
<211> LENGTH: 121
<212> TYPE: DNA
<213> ORGANISM: Homo sapiens

<400> SEQUENCE: 257

```
ttgtgctcct taacagaaga gttgcctcca gtttaaaaaa aacccatgtt caggccaggc    60
rtggtggctc atgcctgtac tcccagcact ttgggaggcc gaggcaggtg gatcacttga   120
g                                                                   121

<210> SEQ ID NO 258
<211> LENGTH: 121
<212> TYPE: DNA
<213> ORGANISM: Homo sapiens

<400> SEQUENCE: 258
atcgtggatc agggaattac tgagttttca caatcatcaa aaagagagaa gcattagtta    60
mccttcccta gttaggttcc tttaattatc attttcatgt gtttctaaaa atctcatgct   120
t                                                                   121

<210> SEQ ID NO 259
<211> LENGTH: 121
<212> TYPE: DNA
<213> ORGANISM: Homo sapiens

<400> SEQUENCE: 259
atttggatgc ccaaagaagc accctctggc acctcctgga gcctggagcc cccagagcct    60
rggctcagct gctctagccc gacatttggg attccgcaag cactttcctt ccaaggttca   120
g                                                                   121

<210> SEQ ID NO 260
<211> LENGTH: 121
<212> TYPE: DNA
<213> ORGANISM: Homo sapiens

<400> SEQUENCE: 260
agagcgagac tcgtctgaaa acaaacaaac aaacaaaaca aaacaaaaca aaacacagag    60
mtctttccat gtccacatac atatatatac atctacctca ataacttaaa taactgcaca   120
g                                                                   121

<210> SEQ ID NO 261
<211> LENGTH: 121
<212> TYPE: DNA
<213> ORGANISM: Homo sapiens

<400> SEQUENCE: 261
acccacggca cctgccctgg ggactctgcc ccagcctggg gctggcctct gggctttccc    60
rtagcctcca atctgattgt ccctaggccc ctgaaaaggc cagcatccac cggctgatgg   120
a                                                                   121

<210> SEQ ID NO 262
<211> LENGTH: 121
<212> TYPE: DNA
<213> ORGANISM: Homo sapiens

<400> SEQUENCE: 262
gggaaaaaag gaaagtgcac ttggaagaga tccaagtggg caacttgaag aacaagtgcc    60
raatagcact tctgtcatgc tggatgtcag ggctctttgt ccactttgta tagccgctgg   120
c                                                                   121

<210> SEQ ID NO 263
```

```
<211> LENGTH: 121
<212> TYPE: DNA
<213> ORGANISM: Homo sapiens

<400> SEQUENCE: 263
tttaatctta gaatttatag ctactaaaga gaaagcaaca attgaagaac atatttcaag      60
rcaatcagaa tgctgcacag agaaaaagag attacgagct gtgaaggcta gaatcagaag    120
g                                                                    121

<210> SEQ ID NO 264
<211> LENGTH: 121
<212> TYPE: DNA
<213> ORGANISM: Homo sapiens

<400> SEQUENCE: 264
tccagacttc tgctgggtgt gctggatctc tctgtcacat ccttcacagg ttttctgata    60
rgtgccgagt ggctgggagg gcttttgttg acagcctttg ttttaaaccc ccaagcatct   120
t                                                                   121

<210> SEQ ID NO 265
<211> LENGTH: 121
<212> TYPE: DNA
<213> ORGANISM: Homo sapiens
<220> FEATURE:
<221> NAME/KEY: modified_base
<222> LOCATION: (69)..(69)
<223> OTHER INFORMATION: a, c, t, g, unknown or other

<400> SEQUENCE: 265
ctcagcaata acatcttaac ttgatggagt acttctaggt gctgtaccaa ccctcaatac    60
rcactatcnc ctctagaccc gaactggccc taggagatga gtatccttat tacctcattt   120
g                                                                   121

<210> SEQ ID NO 266
<211> LENGTH: 121
<212> TYPE: DNA
<213> ORGANISM: Homo sapiens
<220> FEATURE:
<221> NAME/KEY: modified_base
<222> LOCATION: (118)..(118)
<223> OTHER INFORMATION: a, c, t, g, unknown or other

<400> SEQUENCE: 266
aatgttgagt ctatagcaaa gtagggcact ttagaactga tttgcatttt cgaaaactgg    60
rctaaattta aaacaccaaa aatggtgtta tataatgcag aatgcaaaaa gaaactcnga   120
c                                                                   121

<210> SEQ ID NO 267
<211> LENGTH: 121
<212> TYPE: DNA
<213> ORGANISM: Homo sapiens

<400> SEQUENCE: 267
attcactgtt ccaaacagcc cgtccaacct actctacaga tgggactccc aagacactac    60
rgggatcccc tgtgtgccaa gtcccggggg aagctgctag agaaggctgg gacgtccttg   120
c                                                                   121

<210> SEQ ID NO 268
<211> LENGTH: 121
```

```
<212> TYPE: DNA
<213> ORGANISM: Homo sapiens

<400> SEQUENCE: 268
tgctcacctc tggcagggac agatcagagt cctctgtgtg acactctgtg tccccagttg      60
rggaaggcgg aaggagctgc gggctccttt ggtattctag gctggagagc cacctggcta     120
g                                                                    121

<210> SEQ ID NO 269
<211> LENGTH: 121
<212> TYPE: DNA
<213> ORGANISM: Homo sapiens

<400> SEQUENCE: 269
cggggaaagc tctgccccgt tcctccggag cccagtgcgc ccctggccaa gttctcccag      60
mgtccactct agggcctgct agcaccctct cgggcggcgc gccctctgcg tacctaagga     120
g                                                                    121

<210> SEQ ID NO 270
<211> LENGTH: 121
<212> TYPE: DNA
<213> ORGANISM: Homo sapiens

<400> SEQUENCE: 270
accatttaag tgtgacatct ataccccag aaaagaacaa ctcgtagtac acagctcagt      60
raatttaggc aacgggagcg cagccctgtg acaaacacat agctccccgg aagcccctct     120
a                                                                    121

<210> SEQ ID NO 271
<211> LENGTH: 121
<212> TYPE: DNA
<213> ORGANISM: Homo sapiens

<400> SEQUENCE: 271
attcacaggc acaatacagc ctcaaactcc tgccctcaag cgatcctcct gcctcagctt      60
mccgagaagc tggatcttca gatgtgcatc accacacaca gctccccaat tactttcagt     120
t                                                                    121

<210> SEQ ID NO 272
<211> LENGTH: 121
<212> TYPE: DNA
<213> ORGANISM: Homo sapiens

<400> SEQUENCE: 272
tttgtccatt ttgtttgagg cgagattctc cgcacgcagg agagtgatat tcaatataca      60
mttagtagca ctcatggctg ctgctacttg ttgataattc tgccaagaaa agattcgttg     120
a                                                                    121

<210> SEQ ID NO 273
<211> LENGTH: 121
<212> TYPE: DNA
<213> ORGANISM: Homo sapiens

<400> SEQUENCE: 273
ctctctactc tggctacacc accctcctca cttatctgtt aacatgtcag acaggccctc      60
rctgccaggc tgttgcactt gccattccct ccacctggga agcttcttcc ccgttaattc     120
```

```
t                                                                      121

<210> SEQ ID NO 274
<211> LENGTH: 121
<212> TYPE: DNA
<213> ORGANISM: Homo sapiens

<400> SEQUENCE: 274
atgtgtgtgt gtgtatatat atatatatat acacacacac acatatacat acgtacacac      60
rttttggaac aactaaatcc agctatttaa catatgcatt agctcacata cttatctttt     120
t                                                                      121

<210> SEQ ID NO 275
<211> LENGTH: 121
<212> TYPE: DNA
<213> ORGANISM: Homo sapiens

<400> SEQUENCE: 275
catctcataa aacttactgt aataagcagg aaaattgaga attattgctt tataaattgt      60
rtttatctgt attggaatta tttaggtcat tgatatctag tttatctttt gtagtttatt     120
t                                                                      121

<210> SEQ ID NO 276
<211> LENGTH: 121
<212> TYPE: DNA
<213> ORGANISM: Homo sapiens

<400> SEQUENCE: 276
gtgccaggca ccgtgtgttg gttggagtgg ggacatgagg gggcatggca gaggttgtgt      60
rtaggactgc cagagctggg cagaaaaacc ccgctgccaa aggcctccta gcgggcagct     120
g                                                                      121

<210> SEQ ID NO 277
<211> LENGTH: 121
<212> TYPE: DNA
<213> ORGANISM: Homo sapiens

<400> SEQUENCE: 277
gagtcctaga gaggttacca gccactcagg tgatgggcct gggatttgaa tccagccccc      60
rcagggtttt cctcttggct cagtttccca gaatggggc actggctgtg atctgaagtt     120
g                                                                      121

<210> SEQ ID NO 278
<211> LENGTH: 121
<212> TYPE: DNA
<213> ORGANISM: Homo sapiens

<400> SEQUENCE: 278
tggacacaag gttttgactc acccaagaaa aggggacctg gctgccccg ggcctgagca      60 rtgggtcatg aggtcacaac ttcagatcac agccagtgcc cccattctgg gaaactgagc    120
c                                                                      121

<210> SEQ ID NO 279
<211> LENGTH: 121
<212> TYPE: DNA
<213> ORGANISM: Homo sapiens

<400> SEQUENCE: 279
```

```
cgggcagagg gcagagccag gctgtatcga ggggcggcgc tgggaccctc ctcgcccaga      60
rttcctactc atccccagca cagaagtgct ctgtagggcc agctgaggac accccggttc     120
a                                                                     121
```

<210> SEQ ID NO 280
<211> LENGTH: 121
<212> TYPE: DNA
<213> ORGANISM: Homo sapiens

<400> SEQUENCE: 280

```
tgagaccacg tgaggctaaa atcagactaa agaatgatct tggcgtctgt ggtgaataat      60
saaattgagt atcatttctt tacttttgct ggaaatgtgt agttactaaa atagtaggca     120
t                                                                     121
```

<210> SEQ ID NO 281
<211> LENGTH: 121
<212> TYPE: DNA
<213> ORGANISM: Homo sapiens

<400> SEQUENCE: 281

```
ggcactctga caaactgtca cagcattttc cccaagatta ttatgtggga actccagaga      60
sggagtccat ctgttctcct tctcctcccc taccccaaaa cagcccctgg ctcaccttgg     120
c                                                                     121
```

<210> SEQ ID NO 282
<211> LENGTH: 121
<212> TYPE: DNA
<213> ORGANISM: Homo sapiens

<400> SEQUENCE: 282

```
caatggccta actgacccaa gaagggaaag aaaatctaaa cagactgata aatacaaaat      60
raaattcaga cacttacaga gcagccaggc atggtggctc acacctgtaa tcctgtcact     120
t                                                                     121
```

<210> SEQ ID NO 283
<211> LENGTH: 121
<212> TYPE: DNA
<213> ORGANISM: Homo sapiens

<400> SEQUENCE: 283

```
ccttagtctc tcaaagtact aggattacat gtgtgagcca cagcacctgg cctatttaat      60
rtattataga tatataaggg ccagggcagg ctgcctccag tgttgggggg aggagtcttc     120
t                                                                     121
```

<210> SEQ ID NO 284
<211> LENGTH: 121
<212> TYPE: DNA
<213> ORGANISM: Homo sapiens

<400> SEQUENCE: 284

```
ggttacacct aaattctttt tacctatctg tagagagtgg tctttctgag acttcttcag      60
rtttaatatc tactgattta tctgtaattt gaataaactc atgtaattag agtcccagcc     120
c                                                                     121
```

<210> SEQ ID NO 285

```
<211> LENGTH: 121
<212> TYPE: DNA
<213> ORGANISM: Homo sapiens
<220> FEATURE:
<221> NAME/KEY: modified_base
<222> LOCATION: (120)..(120)
<223> OTHER INFORMATION: a, c, t, g, unknown or other

<400> SEQUENCE: 285
attcaggact taaaatgttc gtagtcattt taaaaaataa attattatag cttaaaccct      60
sgatattaca aaaaaaaaaa agctcattgc agccaaaaat acctgaagaa tcagattaan     120
a                                                                    121

<210> SEQ ID NO 286
<211> LENGTH: 121
<212> TYPE: DNA
<213> ORGANISM: Homo sapiens
<220> FEATURE:
<221> NAME/KEY: modified_base
<222> LOCATION: (77)..(77)
<223> OTHER INFORMATION: a, c, t, g, unknown or other

<400> SEQUENCE: 286
tgtaagatac gtgatctctt ccattatcta atctaggaga agaggaaggg gaggttgaag      60
wggatcagtg tgtggcngga ggagaattat ttgccaagaa tagtgtaatc aatcccataa     120
a                                                                    121

<210> SEQ ID NO 287
<211> LENGTH: 121
<212> TYPE: DNA
<213> ORGANISM: Homo sapiens

<400> SEQUENCE: 287
tgggataata tagcaactct gggttgtgct gggttcctct gaggattatg gcagaaatgc      60
ratggaatag ggaaaaatat taatagttct ctggggtaga ggctggaagg attcctggaa     120
g                                                                    121

<210> SEQ ID NO 288
<211> LENGTH: 121
<212> TYPE: DNA
<213> ORGANISM: Homo sapiens

<400> SEQUENCE: 288
gattacaggc atgaaccacc acgcccagcc atcagacaag ttttttaaata aggtctcaca     60 wgtgttcacg gtaaaaataa agattttcag gacacaagta tctactaaac tctaaccttc    120
t                                                                    121

<210> SEQ ID NO 289
<211> LENGTH: 121
<212> TYPE: DNA
<213> ORGANISM: Homo sapiens

<400> SEQUENCE: 289
cggtaactta gaataatttt cttacattcc aggtacacaa aggcaatgat aaaagctcta      60
mgagttagct tgaatatttc aaaaccataa cagaaattga attttaaaat ttattaaggt     120
t                                                                    121

<210> SEQ ID NO 290
<211> LENGTH: 121
```

```
<212> TYPE: DNA
<213> ORGANISM: Homo sapiens
<220> FEATURE:
<221> NAME/KEY: modified_base
<222> LOCATION: (120)..(120)
<223> OTHER INFORMATION: a, c, t, g, unknown or other

<400> SEQUENCE: 290
gctcggagaa gttgtttctt gttttaaatc aacaggtatc aagtggcaga atcaggatta       60
ragcccagga tgtccgattt ggtgttgcac gtgccttcca ctggaaaaca gcatggattn      120
g                                                                     121

<210> SEQ ID NO 291
<211> LENGTH: 121
<212> TYPE: DNA
<213> ORGANISM: Homo sapiens
<220> FEATURE:
<221> NAME/KEY: modified_base
<222> LOCATION: (112)..(112)
<223> OTHER INFORMATION: a, c, t, g, unknown or other

<400> SEQUENCE: 291
tgacctcaag tgaataggga agtgtggtct taccctgctt ctcccagaga gaactggaac       60
rtgaatgaac gccttcgtga ctgcagtgtg catgcatgca agtgtgggag gntgtgtgag      120
g                                                                     121

<210> SEQ ID NO 292
<211> LENGTH: 121
<212> TYPE: DNA
<213> ORGANISM: Homo sapiens
<220> FEATURE:
<221> NAME/KEY: modified_base
<222> LOCATION: (17)..(17)
<223> OTHER INFORMATION: a, c, t, g, unknown or other

<400> SEQUENCE: 292
gccatcgcaa ccggaangat gctgtccttg gtaagaaatc agccacaggc gaccccctgc       60
rgaggacacc ccatcctgat gtgggccagg cctgggcctt tggtttccct ggagcattgg      120
c                                                                     121

<210> SEQ ID NO 293
<211> LENGTH: 121
<212> TYPE: DNA
<213> ORGANISM: Homo sapiens

<400> SEQUENCE: 293
acagcttaga aacccaaccc ataacaagag tctgacattt gggcactctg gggtcccacc       60
rtttttattt ttatttatt tatttattta tttatttatt tattttttct ttttttgaga      120
t                                                                     121

<210> SEQ ID NO 294
<211> LENGTH: 121
<212> TYPE: DNA
<213> ORGANISM: Homo sapiens

<400> SEQUENCE: 294
gctatgagac ctggccatgt gaggtgacca ccctgtaca acagagacca ttttgccatc       60
rcccagggca gtggtgggtt atatctgtgg cagacccagc acacactgga tcctgtcgaa      120
g                                                                     121
```

<210> SEQ ID NO 295
<211> LENGTH: 121
<212> TYPE: DNA
<213> ORGANISM: Homo sapiens

<400> SEQUENCE: 295
ccaccctgtg tgtgtgatgc ccttatgtct gaatgtgaag ggagcaagga cgggtacatc    60
magagctacg aataaccttg agttttggag actgggcact gacagctaca acttgggact   120
t                                                                   121

<210> SEQ ID NO 296
<211> LENGTH: 121
<212> TYPE: DNA
<213> ORGANISM: Homo sapiens

<400> SEQUENCE: 296
aaagccagaa aataatgtat taagaccaca aatggcccta tctgttccct atggtttcaa    60
wctaactaaa accttatcaa tttaacattc tccagtcaat gctccttctt ttgagacagg   120
g                                                                   121

<210> SEQ ID NO 297
<211> LENGTH: 121
<212> TYPE: DNA
<213> ORGANISM: Homo sapiens

<400> SEQUENCE: 297
ctttttattt tctaaaacag cactcggctg caacaacaac aacaaaaaag caagtaagct    60
ratactacca taacaattac ttccaactaa acacatagaa cacattaatt tccagaaatt   120
t                                                                   121

<210> SEQ ID NO 298
<211> LENGTH: 121
<212> TYPE: DNA
<213> ORGANISM: Homo sapiens

<400> SEQUENCE: 298
gcatcacact tattacattt tattttccca ctccttcaaa gcaaattgta gctgtattat    60
rtttaaaata tttggcagtt taaaagtggt agtttaaaga atgtgatcat agcatttcta   120
t                                                                   121

<210> SEQ ID NO 299
<211> LENGTH: 121
<212> TYPE: DNA
<213> ORGANISM: Homo sapiens

<400> SEQUENCE: 299
gtgttatgtt ttcatgtaat agtgtcttgg agaatgagga cttttgagga aacccaaata    60
rtagttgcag atcctgtttt ttactaagct gtcatggaga taaatccaaa atagttttta   120
c                                                                   121

<210> SEQ ID NO 300
<211> LENGTH: 121
<212> TYPE: DNA
<213> ORGANISM: Homo sapiens

<400> SEQUENCE: 300
gcctggggcc cagacgggct gcacaggccc ctggaactca gcgagaaaga aatcaattcc    60

```
rtttttaaaa aacttatcga gcacctgtgt gatgtgatgg ctactttact agagcctgga    120
g                                                                    121

<210> SEQ ID NO 301
<211> LENGTH: 121
<212> TYPE: DNA
<213> ORGANISM: Homo sapiens

<400> SEQUENCE: 301
ttaatgactt agctccagct tctccacttc aaaatgaaag gaaaagtact atcaccaccc    60
rttagaatta ttatttcatg gggaaaaaag atggattact atctcacaat aagagcttgt    120
c                                                                    121

<210> SEQ ID NO 302
<211> LENGTH: 121
<212> TYPE: DNA
<213> ORGANISM: Homo sapiens

<400> SEQUENCE: 302
tcatatacaa tagagaaaaa aatttaaaat aaaaatgtct aatactagaa gaaatctgag    60
rtatctttta cacgaaagta taaaagtgac aggaggggtt caagtctccg aattctgagc    120
t                                                                    121

<210> SEQ ID NO 303
<211> LENGTH: 121
<212> TYPE: DNA
<213> ORGANISM: Homo sapiens

<400> SEQUENCE: 303
ggcatctgcc cttcccagca gggactgcct ccctcactgg cctcatgtga cctgttaatc    60
raatcctgca ccagccccat ggagttttcc catcactcat tggggaggaa gcagatgccc    120
a                                                                    121

<210> SEQ ID NO 304
<211> LENGTH: 121
<212> TYPE: DNA
<213> ORGANISM: Homo sapiens
<220> FEATURE:
<221> NAME/KEY: modified_base
<222> LOCATION: (67)..(67)
<223> OTHER INFORMATION: a, c, t, g, unknown or other

<400> SEQUENCE: 304
cgcaatggat ttatattttc atgagtgaat attgtttggt tgagaaaagg ttcagcatta    60
wttctgntct tattttgtt tcttataggt caaagggctg ggaaaccctg ctcaaataag    120
c                                                                    121

<210> SEQ ID NO 305
<211> LENGTH: 121
<212> TYPE: DNA
<213> ORGANISM: Homo sapiens
<220> FEATURE:
<221> NAME/KEY: modified_base
<222> LOCATION: (67)..(67)
<223> OTHER INFORMATION: a, c, t, g, unknown or other

<400> SEQUENCE: 305
ccagctgctt atttgagcag ggtttcccag cccttttgacc tataagaaac aaaaataaga    60
```

```
scagaantaa tgctgaacct tttctcaacc aaacaatatt cactcatgaa aatataaatc    120
c                                                                   121

<210> SEQ ID NO 306
<211> LENGTH: 121
<212> TYPE: DNA
<213> ORGANISM: Homo sapiens

<400> SEQUENCE: 306
cttggcctac caaagtgctg ggatcacagg cgtgagcccc cacgcctggc ctcactcaac    60
rttattttta agacctcatc agttgatatc cccatgaagt cctctcctct tcaattcagt   120
t                                                                   121

<210> SEQ ID NO 307
<211> LENGTH: 121
<212> TYPE: DNA
<213> ORGANISM: Homo sapiens

<400> SEQUENCE: 307 ctatttagg gtaaggcacg gttcaccagc agattattct ggcccagaa taatctctcc     60 rgaggcaaac tggtagtcaa ttgtcctaaa ctcaaaccct gcctccaact cttgtcctga   120
g                                                                   121

<210> SEQ ID NO 308
<211> LENGTH: 121
<212> TYPE: DNA
<213> ORGANISM: Homo sapiens

<400> SEQUENCE: 308
agtcacttag ccatttggcc ctgcaccttc gggagtaggg gaatgattgc agagaggccc    60
rtattgacta agtcccagat ccatgagagg tgccatttcc cagcttctgc agcagctgtg   120
a                                                                   121

<210> SEQ ID NO 309
<211> LENGTH: 121
<212> TYPE: DNA
<213> ORGANISM: Homo sapiens

<400> SEQUENCE: 309
gctacaggct cagctggaga gccaagagaa cccttctgat gcattctaga cttttacaac    60
rtaaagtgga gaccctccaa aggccagagg agggaaagca ggactaacaa ggcacagagg   120
a                                                                   121

<210> SEQ ID NO 310
<211> LENGTH: 121
<212> TYPE: DNA
<213> ORGANISM: Homo sapiens
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 310
cctaattttt ttttntttt nacagagaag tttcacttca agtcatggat gtctaaggtc    60
rgtgcccaac ttcttctttt tgaagttttt catttcacaa agtttcctgt tatcaaacca   120
``` a                                                                        121

<210> SEQ ID NO 311
<211> LENGTH: 121
<212> TYPE: DNA
<213> ORGANISM: Homo sapiens

<400> SEQUENCE: 311
cagtaagtcg ccgtctggca gtaagttagc tctgcaggtg tggaccccaa gaccacacac        60
rgcctttctc aggtgcaggt cctgccaagc ctcacttcgc agtggtgaca ggcaaccccg       120
t                                                                        121

<210> SEQ ID NO 312
<211> LENGTH: 121
<212> TYPE: DNA
<213> ORGANISM: Homo sapiens

<400> SEQUENCE: 312
aaatgagaaa acaaaccttt gtccaatact ggtcacaact ttctcatctt gattgaattt        60
maaatttgat gttttccccc agaattttttt cagcagatca ttgagtacac agaggaatac      120
c                                                                        121

<210> SEQ ID NO 313
<211> LENGTH: 121
<212> TYPE: DNA
<213> ORGANISM: Homo sapiens

<400> SEQUENCE: 313
ggtacccaaa cccatgtggt ggatccccca cagcatccat cacagcatct tgtccatggt        60
ragacccact gccaaatgaa gtgtgaggga ttaacagtgt tttgttccct cacaggcttg       120
g                                                                        121

<210> SEQ ID NO 314
<211> LENGTH: 121
<212> TYPE: DNA
<213> ORGANISM: Homo sapiens

<400> SEQUENCE: 314
agtctgaggt ggttggtgag tcagctatga gtagattggg attttctgcc tgttctgaag        60
maaacttctg tctcgccttg gggttccctt tcttaccgcc ctggcccacc ctccctggcc       120
a                                                                        121

<210> SEQ ID NO 315
<211> LENGTH: 121
<212> TYPE: DNA
<213> ORGANISM: Homo sapiens

<400> SEQUENCE: 315
ctttatgatg aatgtttaat aagactgctt tcttctggat atctagttga gatcagctga        60
rcaacgagag ttttatggct aaatggatat gaagacacga ggcaatttag ggtcacggag       120
a                                                                        121

<210> SEQ ID NO 316
<211> LENGTH: 121
<212> TYPE: DNA
<213> ORGANISM: Homo sapiens
<220> FEATURE:

```
<221> NAME/KEY: modified_base
<222> LOCATION: (4)..(4)
<223> OTHER INFORMATION: a, c, t, g, unknown or other

<400> SEQUENCE: 316
tgtngataat tttgtgttgt tcagtatttg cataatcact gtgagggcaa ggaccttgta    60
wgttcttctg ttcatcactg tattttcagt acccactagt gcctggcaca tggtagataa   120
t                                                                   121

<210> SEQ ID NO 317
<211> LENGTH: 121
<212> TYPE: DNA
<213> ORGANISM: Homo sapiens

<400> SEQUENCE: 317
ttggtaacag aaaagttttg catgcggaga gcatcctaga cagggaaaac aagtgaaaat    60
rtaattagca aaatcagaaa actaaaattc agtatgatga gagcagaagg aacaggctac   120
a                                                                   121

<210> SEQ ID NO 318
<211> LENGTH: 121
<212> TYPE: DNA
<213> ORGANISM: Homo sapiens

<400> SEQUENCE: 318
gctgggctga gactacatgt agcaagggta ttctttgaca ttgttgctca gggattgtcc    60
rtcttttcct ggtggggagg tactttgat agccttgtag tctgatcatt gtggaactga    120
g                                                                   121

<210> SEQ ID NO 319
<211> LENGTH: 121
<212> TYPE: DNA
<213> ORGANISM: Homo sapiens

<400> SEQUENCE: 319
ctccctgcat cacacatgat gacgatactg tctgctgggc gggggaagc ctgggtggct    60 rtcagcatca gagcactcga aactgcctgg aatgaggctt tatgggttga cgttgtttct   120
g                                                                   121

<210> SEQ ID NO 320
<211> LENGTH: 121
<212> TYPE: DNA
<213> ORGANISM: Homo sapiens

<400> SEQUENCE: 320
ccctggggaa gggaatgcag ggttgctggg gctgggccca gaagcagcag caccagggaa    60
raggattcga aaccctctc tcttgtatga gggctttgag agcccacaa tggcttcggt    120 g                                                                   121

<210> SEQ ID NO 321
<211> LENGTH: 121
<212> TYPE: DNA
<213> ORGANISM: Homo sapiens

<400> SEQUENCE: 321
ttaagtctct ctaggctcaa gtctccctgg agcatctgac aggtaatcac tcgctctcag    60
rccctggcgt tgaaggcaag ggaacggtga aaagttacta attctattcc ttttcctttc   120
``` t    121

<210> SEQ ID NO 322
<211> LENGTH: 121
<212> TYPE: DNA
<213> ORGANISM: Homo sapiens

<400> SEQUENCE: 322
tttcaaggct caaattgcat ccaataataa gctgtcttaa ccggtcactt tttatcacca    60
rtggttaatt aaatccttga gtctcctagg ataatttctt cttttcttgt ttgaaatgga    120
g    121

<210> SEQ ID NO 323
<211> LENGTH: 121
<212> TYPE: DNA
<213> ORGANISM: Homo sapiens

<400> SEQUENCE: 323
ccctaaagcc cacagcacag gccaccccag catggctcct ggaaccagtg tcacccgccc    60
rtgtggcagc tctagaggcc aggggagcct ggaagtagct ccactactag caagaggggc    120
c    121

<210> SEQ ID NO 324
<211> LENGTH: 121
<212> TYPE: DNA
<213> ORGANISM: Homo sapiens

<400> SEQUENCE: 324
gagattaagt aatttgtcta cagtcatgtg gcaaagccaa catggagccc agctgtgcta    60
rtctctgaag cccatgttct taaactaccc aggtctacta cactggttgt cctctaccct    120
g    121

<210> SEQ ID NO 325
<211> LENGTH: 121
<212> TYPE: DNA
<213> ORGANISM: Homo sapiens

<400> SEQUENCE: 325
attcaaagat tggaatacta tacagcaatg aaaaagcaaa gtactagtac atttaataac    60
rtagataaat ctcacaaaac agtaaaagga cccagacaga gtgagtacac actgtaagat    120
t    121

<210> SEQ ID NO 326
<211> LENGTH: 121
<212> TYPE: DNA
<213> ORGANISM: Homo sapiens

<400> SEQUENCE: 326
aaagagttaa aacacataca acactaagaa gcctacccga accagagtaa gtgctcagtg    60
mgtgttagac agtgtcattg tcattattgc cacctcttca gtcctgccca cacactctca    120
a    121

<210> SEQ ID NO 327
<211> LENGTH: 121
<212> TYPE: DNA
<213> ORGANISM: Homo sapiens

```
<400> SEQUENCE: 327
atgaagtcct ctcctcttca attcagtttc cttgaggaat tgagaatgcc agatatgaac    60
ratttattac cgttttgtct ttttgtttgc tgtccctatt gttttatac ccatgggttc    120 a                                                                    121

<210> SEQ ID NO 328
<211> LENGTH: 121
<212> TYPE: DNA
<213> ORGANISM: Homo sapiens

<400> SEQUENCE: 328
gcaaatctag gtatttctga aagaaagaa gattaatata ggggactgga agattccaca    60
racgttggaa ggctagggaa gcaaaagtca ggttggttac tttcagaaaa tccaggacat   120
g                                                                    121

<210> SEQ ID NO 329
<211> LENGTH: 121
<212> TYPE: DNA
<213> ORGANISM: Homo sapiens

<400> SEQUENCE: 329
cttacacagt atacatacta tatgatttca tttatattta gttctggaac agattaatct    60
rttgtgggaa aaaatcaggg tactaactgc ctctggaagg tgatagagga gcaggattg    120 a                                                                    121

<210> SEQ ID NO 330
<211> LENGTH: 121
<212> TYPE: DNA
<213> ORGANISM: Homo sapiens

<400> SEQUENCE: 330
actcctatca tgatacagaa cattcctaaa accccagaaa attagcaata ccctttccta    60
rtcaatccct gctcctctat caccttccag aggcagttag taccctgatt ttttcccaca   120
a                                                                    121

<210> SEQ ID NO 331
<211> LENGTH: 121
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 331
gtaaggctgc ccggcacggg tnccaggccc cggaacggag gaaggcactg agcgtcaggc    60
rgcctagagg ccaggggtag ctagaagact ccctgggggc tgtgtcgggg acaggcctga   120
g                                                                    121

<210> SEQ ID NO 332
<211> LENGTH: 121
<212> TYPE: DNA
<213> ORGANISM: Homo sapiens

<400> SEQUENCE: 332
ccaggggtag ctagaagact ccctgggggc tgtgtcgggg acaggcctga gctgcagagt    60
mgaaggagca gttccctcct ctgcaaagca aacagaggag gcggccctgg agggccgggg   120
```

```
c                                                                  121

<210> SEQ ID NO 333
<211> LENGTH: 121
<212> TYPE: DNA
<213> ORGANISM: Homo sapiens

<400> SEQUENCE: 333
ttgttatttt tattttttgc tgttgcctcc tggaaacgga cttgaagttt cttcccctat    60
rttctttccc tcagctcttg ggggccagaa atcccaaagg gagtccgctg ccccggccct   120
c                                                                  121

<210> SEQ ID NO 334
<211> LENGTH: 121
<212> TYPE: DNA
<213> ORGANISM: Homo sapiens
<220> FEATURE:
<221> NAME/KEY: modified_base
<222> LOCATION: (82)..(82)
<223> OTHER INFORMATION: a, c, t, g, unknown or other

<400> SEQUENCE: 334
gccctgggag tacccatgaa aaattataag acttctgggg atgtctgctg aagaaatcac    60
sccaaagaag gcaagaattt angtgcagaa agttatagat tgcagcatta ttttgtaact   120
g                                                                  121

<210> SEQ ID NO 335
<211> LENGTH: 121
<212> TYPE: DNA
<213> ORGANISM: Homo sapiens
<220> FEATURE:
<221> NAME/KEY: modified_base
<222> LOCATION: (75)..(75)
<223> OTHER INFORMATION: a, c, t, g, unknown or other

<400> SEQUENCE: 335
ggctcctgtc cctggaagtc ccaccagccc aagcctaact ctgtgttttt gttctaaacc    60
rgcagggtcc tcctnccgca ggagtatctt gcagtccaac tcccacgatt gtcctgactg   120
g                                                                  121

<210> SEQ ID NO 336
<211> LENGTH: 121
<212> TYPE: DNA
<213> ORGANISM: Homo sapiens

<400> SEQUENCE: 336
gaatgaacag agtgaagtag agtgataagg agtggcatga atggaatgga accaaactga    60
mgtgcaaaga ggtttaggtg actgctgtca ctgggacagt cctccccaac cctcccacct   120
t                                                                  121

<210> SEQ ID NO 337
<211> LENGTH: 121
<212> TYPE: DNA
<213> ORGANISM: Homo sapiens

<400> SEQUENCE: 337
ctttctgtga ggtctcaagg cttagtattt aatctctaat tgcttacact tgtcgccttg    60
raggactgga agatacatct ttaatagtcc tcagcagggc tggatgcctt caatcccgca   120
```

```
g                                                                      121

<210> SEQ ID NO 338
<211> LENGTH: 121
<212> TYPE: DNA
<213> ORGANISM: Homo sapiens

<400> SEQUENCE: 338
aagacttgga atgggtctaa tgtattcaac tggtcctcag atatttatag cctgctgtgt      60
rctgggttat gggagatcca tcacaaactg ccttcctaag gctgcagggg gtggggatt     120 g                                                                      121

<210> SEQ ID NO 339
<211> LENGTH: 121
<212> TYPE: DNA
<213> ORGANISM: Homo sapiens

<400> SEQUENCE: 339
agaggaggga tttaaaaaaa aacaggaaag attggggcat ttgtctctaa aggactgtgg      60
rctcatttaa gaagtttagt ggtcattctt accatctttg tggttttcc tgcctgcatg     120 g                                                                      121

<210> SEQ ID NO 340
<211> LENGTH: 121
<212> TYPE: DNA
<213> ORGANISM: Homo sapiens
<220> FEATURE:
<221> NAME/KEY: modified_base
<222> LOCATION: (91)..(91)
<223> OTHER INFORMATION: a, c, t, g, unknown or other

<400> SEQUENCE: 340
ttttgacaat cctttccttg gaatgctgtg aaacacaacc cattttttaa tgtaataaaa      60
rtagctctta agcttttgta tactttagga nacatcaagg ataagtaagg gcacattccc    120
a                                                                      121

<210> SEQ ID NO 341
<211> LENGTH: 121
<212> TYPE: DNA
<213> ORGANISM: Homo sapiens

<400> SEQUENCE: 341
gttaaattct tagcaagatt ttagcagttg gaatccagca gtgtataaaa agggtaatac      60
rtcatgacca agtggatttc gttggtttaa gtttgaaaat cgatggatgt tatttactgt    120
a                                                                      121

<210> SEQ ID NO 342
<211> LENGTH: 121
<212> TYPE: DNA
<213> ORGANISM: Homo sapiens

<400> SEQUENCE: 342
acctttttgg aatttgggac tgggttaaga gatttggggc ctgtgtatgt ctgtgtgtac      60
mtggttgaga gtgtatgcgt gtgtgtgtgt tacatttta tctgagtcac tgtgagaata     120
t                                                                      121

<210> SEQ ID NO 343
<211> LENGTH: 121
```

```
<212> TYPE: DNA
<213> ORGANISM: Homo sapiens

<400> SEQUENCE: 343
tttcattttt ccatcaacag agcataaaaa acttgagtaa tgtgggcaca agggaactgg      60
rgggataaca gctctgaggg aagagagaga ccctcccgta tcgctttata ttgttttata     120
c                                                                    121

<210> SEQ ID NO 344
<211> LENGTH: 121
<212> TYPE: DNA
<213> ORGANISM: Homo sapiens

<400> SEQUENCE: 344
gagggagaaa ttagctatgg ccagagtata gagaataagg gaagtatgat ttgtgaggag      60
rctgtagaag aattaaggtc aggagcacac aggatgatgt aggcccagtg aagtgcgttg     120
g                                                                    121

<210> SEQ ID NO 345
<211> LENGTH: 121
<212> TYPE: DNA
<213> ORGANISM: Homo sapiens

<400> SEQUENCE: 345
tgtatcaacc agccaatcag cacactgttg tgggggtccc aatcatgagt cagggattac      60
rgggtcatca gcacatttga cctcatgaga ctacagcaaa ctaaaaggaa tgtgcagctg     120
g                                                                    121

<210> SEQ ID NO 346
<211> LENGTH: 121
<212> TYPE: DNA
<213> ORGANISM: Homo sapiens

<400> SEQUENCE: 346
aactaaccaa tattaccgaa ttggtgggca ttctaaaaac ctgatgcgac atatagttga      60
raagattgta aatggttctg gctagtgaaa gcacatttga acatgtaat tgtctggcat      120
a                                                                    121

<210> SEQ ID NO 347
<211> LENGTH: 121
<212> TYPE: DNA
<213> ORGANISM: Homo sapiens

<400> SEQUENCE: 347
accatctgaa tggcaatcta tgtagatttt tgcagtgtgt ctgtgtagtg tgctgggagc      60
rggtatttgt atttatctct gtgtacttat gtctaggcca gtaggataga gtatctatct     120
g                                                                    121

<210> SEQ ID NO 348
<211> LENGTH: 121
<212> TYPE: DNA
<213> ORGANISM: Homo sapiens

<400> SEQUENCE: 348
gatacagaaa cttgatttct gtctaggcat ggtggctcat acctacaatc ctggtgcttt      60
rggaggcgga ggctggaagc tcactcgaga ctaggagttt gagaccagct tgggcaatgt     120
``` a                                                                         121

<210> SEQ ID NO 349
<211> LENGTH: 121
<212> TYPE: DNA
<213> ORGANISM: Homo sapiens
<220> FEATURE:
<221> NAME/KEY: modified_base
<222> LOCATION: (94)..(94)
<223> OTHER INFORMATION: a, c, t, g, unknown or other

<400> SEQUENCE: 349
atgatattca ctttaaccaa tattgaacga gaagctacca atgcatttaa atgccctag     60 rcagtcttct ggaaattgta aagcatgatc tttnatgcta agtgaaatgc ctgcttcttt    120
t                                                                    121

<210> SEQ ID NO 350
<211> LENGTH: 121
<212> TYPE: DNA
<213> ORGANISM: Homo sapiens

<400> SEQUENCE: 350
ccctgctgga gctcatgagg cccccgtggg gacccttttct tccccagcac ctatggtccg    60
rctcctttgt gggttcctct tcctgctcct ggcccttgcc tctccatggc ggcttcacag    120
a                                                                    121

<210> SEQ ID NO 351
<211> LENGTH: 121
<212> TYPE: DNA
<213> ORGANISM: Homo sapiens

<400> SEQUENCE: 351
atgaactgaa tagtgggaga atcaggtcgg taagggagca aatacaatgt actttgggga    60
rttctgtgag gaggatatcg acagccttac agtccgacat tcttcacaac tatctgccaa    120
t                                                                    121

<210> SEQ ID NO 352
<211> LENGTH: 121
<212> TYPE: DNA
<213> ORGANISM: Homo sapiens

<400> SEQUENCE: 352
agcgctcaat tcagtgaatt ttgtttattt acagagttgt acaaccacca ccacaaacta    60
rttttagaaa atttctatca ctctcaaata ggaagtaccc atttacagca aagaagaaaa    120
a                                                                    121

<210> SEQ ID NO 353
<211> LENGTH: 121
<212> TYPE: DNA
<213> ORGANISM: Homo sapiens

<400> SEQUENCE: 353
aaaccaacat ttgtatgtat cccttgcaag tgaaggggca accagcaaat atctaatcaa    60
mccctactat gtttaagaca gtatcaatac tcacggaaga gggtaagatg caaataaaag    120
a                                                                    121

<210> SEQ ID NO 354
<211> LENGTH: 121

<212> TYPE: DNA
<213> ORGANISM: Homo sapiens

<400> SEQUENCE: 354
ctcagctact tcaaaatccc caataagatt tataacaaag tgtttgacat gctcaagaac      60
rtcatttatt ctttcaaatg aaattgtagt tcccaattga tctaaaagca ctctaacatc     120
a                                                                    121

<210> SEQ ID NO 355
<211> LENGTH: 121
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other

<400> SEQUENCE: 355
accccacagg tcaancagga ggtctgaggg agttcagggg agtccatctc ttcttgaagc      60
rtgtggggct ggagatgagc tctgactgtt gctgatgcaa aaagacattg agccagaagt    120
c                                                                    121

<210> SEQ ID NO 356
<211> LENGTH: 121
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other

<400> SEQUENCE: 356
tctccagccc cacangcttc aagaagagat ggactcccct gaactccctc agacctcctg      60
mttgacctgt ggggttattt tgttgtaatg caacatttca ataacaccct ttgctaatgg    120
t                                                                    121

<210> SEQ ID NO 357
<211> LENGTH: 121
<212> TYPE: DNA
<213> ORGANISM: Homo sapiens

<400> SEQUENCE: 357
aatcaccagc ccctcacata tttgccacaa ggaagagtca caggagacac tatggctcag      60
ragccacagc ccctcccacc attgagtctt gaccacttcc acctgtgcca tctcctgtct    120
c                                                                    121

<210> SEQ ID NO 358
<211> LENGTH: 121
<212> TYPE: DNA
<213> ORGANISM: Homo sapiens
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (119)..(119)
<223> OTHER INFORMATION: a, c, t, g, unknown or other

<400> SEQUENCE: 358
ttctcctact gaatattttt atggtctttg aacccacaga gaaaatgtcc atcaagaaac    60
magtcaggct gggtanggtg gttcacacct gtaatcccag cactttggga ggcnaaggna   120
g                                                                  121

<210> SEQ ID NO 359
<211> LENGTH: 121
<212> TYPE: DNA
<213> ORGANISM: Homo sapiens
<220> FEATURE:
<221> NAME/KEY: modified_base
<222> LOCATION: (40)..(40)
<223> OTHER INFORMATION: a, c, t, g, unknown or other

<400> SEQUENCE: 359
attttactga acactgactc tgcagcaggc tctcaccccn tcatctcatt catcttccca    60
rcagcactgg agggaggtat ttgcatgcat tcttgctttc acagaggctg agaaggagcc   120
t                                                                  121

<210> SEQ ID NO 360
<211> LENGTH: 121
<212> TYPE: DNA
<213> ORGANISM: Homo sapiens
<220> FEATURE:
<221> NAME/KEY: modified_base
<222> LOCATION: (108)..(108)
<223> OTHER INFORMATION: a, c, t, g, unknown or other

<400> SEQUENCE: 360
atcacagact tcctcacatg ggtaaaaagc aacataaagt gttctgggag gcagcatggc    60
rctgcggggg agaagggtgg actctggatc cagagaactc ggcttgcntc ttatctccaa   120
g                                                                  121

<210> SEQ ID NO 361
<211> LENGTH: 121
<212> TYPE: DNA
<213> ORGANISM: Homo sapiens
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other

<400> SEQUENCE: 361
gaggcagcat ggcnctgcgg gggagaaggg tggactctgg atccagagaa ctcggcttgc    60
rtcttatctc caaggcttat tagctgggtg accttaggta accgaggaag ctcaggtaan   120
c                                                                  121

<210> SEQ ID NO 362
<211> LENGTH: 121
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, c, t, g, unknown or other

<400> SEQUENCE: 362
cntcttatct ccaaggctta ttagctgggt gaccttaggt aaccgaggaa gctcaggtaa    60

```
mctctatggc aatatgatg cactcccatc cctcggatgg agagatggga gagactgtgc    120
t                                                                   121

<210> SEQ ID NO 363
<211> LENGTH: 121
<212> TYPE: DNA
<213> ORGANISM: Homo sapiens
<220> FEATURE:
<221> NAME/KEY: modified_base
<222> LOCATION: (86)..(86)
<223> OTHER INFORMATION: a, c, t, g, unknown or other

<400> SEQUENCE: 363
tattttttag accaatgaga gagtgcctat ttaaacaaga acacccgggt ttacataaaa    60
rtagtggtac aagtgtaaga cagtcncaag tgtgtgtgcg tatgtgtgtg tgtggtgccc   120
t                                                                   121

<210> SEQ ID NO 364
<211> LENGTH: 121
<212> TYPE: DNA
<213> ORGANISM: Homo sapiens

<400> SEQUENCE: 364
attccctgtt taataaacaa tgctctgtca aagtagattc ttggccaaca attatccgtg    60
raaaggagcc atagagaagt ttgtcttggt tttcagtttt cctcccatgg aaagatgcta   120
c                                                                   121

<210> SEQ ID NO 365
<211> LENGTH: 121
<212> TYPE: DNA
<213> ORGANISM: Homo sapiens
<220> FEATURE:
<221> NAME/KEY: modified_base
<222> LOCATION: (13)..(13)
<223> OTHER INFORMATION: a, c, t, g, unknown or other

<400> SEQUENCE: 365
ttgtctttgg aanttgctca agttatgaat ttttccagcc agcattaact aaggtcacag    60
matggttaca gagatatgag tggaagtagc atctttccat gggaggaaaa ctgaaaacca   120
a                                                                   121

<210> SEQ ID NO 366
<211> LENGTH: 121
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other

<400> SEQUENCE: 366
cagagcgaga ctctgtctcc naaaaaaaaa anaaaagaaa tgttctgatg ttttgtgttt    60
rtctggtgct tgttggcatt tctggaggaa gacattcagg gagcccagag gcacctcgtg   120
g                                                                   121

<210> SEQ ID NO 367
```

```
<211> LENGTH: 121
<212> TYPE: DNA
<213> ORGANISM: Homo sapiens

<400> SEQUENCE: 367
ggggctgtgg agtgggatgg agacaagctc tgaaaggaca catgggagat ctagatgtag    60
raggtacaca agtagtagga taactcacag gatggatcca ctggaggtta agacatgtgg   120
t                                                                  121

<210> SEQ ID NO 368
<211> LENGTH: 121
<212> TYPE: DNA
<213> ORGANISM: Homo sapiens

<400> SEQUENCE: 368
ttccctcatt tggctttgct attatacttc ttagctccct aagaaccagg aataagtcta    60
mctcagaacc ttgcttttct tttcttttca ataaaatgag actctctact tcaactacct   120
g                                                                  121

<210> SEQ ID NO 369
<211> LENGTH: 121
<212> TYPE: DNA
<213> ORGANISM: Homo sapiens

<400> SEQUENCE: 369
gacatccatt ctcattatag gtggtttgaa aaatggtaac tttctgtgag atgtgccatt    60
rcaaacagga atgttttcat gcaggtcaca cagtctattt atattgtacc tttgaattag   120
a                                                                  121

<210> SEQ ID NO 370
<211> LENGTH: 121
<212> TYPE: DNA
<213> ORGANISM: Homo sapiens
<220> FEATURE:
<221> NAME/KEY: modified_base
<222> LOCATION: (62)..(62)
<223> OTHER INFORMATION: a, c, t, g, unknown or other

<400> SEQUENCE: 370
atggtagggt agaggaaaat ccattgggga aattgttcct ttggtattta cttaatctga    60 rnattttta aatgcaattg taactattga tgaaatgtga atattgattg aaaaaagacg    120
t                                                                  121

<210> SEQ ID NO 371
<211> LENGTH: 121
<212> TYPE: DNA
<213> ORGANISM: Homo sapiens
<220> FEATURE:
<221> NAME/KEY: modified_base
<222> LOCATION: (115)..(115)
<223> OTHER INFORMATION: a, c, t, g, unknown or other

<400> SEQUENCE: 371
tcacagtcaa aagttgaaaa caactcaaat gtctggtgaa tggacaaact gtggcatgtt    60
matgcaatga aatactactt agcaataaaa aggaataatc tactaatacc taaancaaca   120
t                                                                  121

<210> SEQ ID NO 372
<211> LENGTH: 121
```

```
<212> TYPE: DNA
<213> ORGANISM: Homo sapiens

<400> SEQUENCE: 372
tagacaacaa acatttgtta gttccaacag gaagtggtaa gatgacatgt cagtgagttt     60
sggctggtaa ttgaacactc accaaaaaac aaggacttgg gtgtagaaga acggaaacat    120
t                                                                    121

<210> SEQ ID NO 373
<211> LENGTH: 121
<212> TYPE: DNA
<213> ORGANISM: Homo sapiens

<400> SEQUENCE: 373
tttcagcatt taaattttt taaatcgtag actgttatag ttggaataaa ccttagaaat      60
rcttttttcc aaccctctcc ttcgtctagt gaagaaatgg aagctcagga agtgatacat    120
t                                                                    121

<210> SEQ ID NO 374
<211> LENGTH: 121
<212> TYPE: DNA
<213> ORGANISM: Homo sapiens

<400> SEQUENCE: 374
cctggaatca actgaaagga gtgtctgggc tggagataag gggaggccaa ggttgttatg     60
ragattaggt cttataggtg gccgcactta gagatgacag atggcaagtg tttcctattc    120
c                                                                    121

<210> SEQ ID NO 375
<211> LENGTH: 121
<212> TYPE: DNA
<213> ORGANISM: Homo sapiens

<400> SEQUENCE: 375
tacacctgag agctggaaat gttggtttgg gttccggggc gtcctgcgcc aagaggaggg     60
racgggccgc cctatcgcag tgcgggaacc ctacagatcc cccggagacg ggaggcctgg    120
a                                                                    121

<210> SEQ ID NO 376
<211> LENGTH: 121
<212> TYPE: DNA
<213> ORGANISM: Homo sapiens
<220> FEATURE:
<221> NAME/KEY: modified_base
<222> LOCATION: (48)..(48)
<223> OTHER INFORMATION: a, c, t, g, unknown or other

<400> SEQUENCE: 376
cctgttgtca gaccaagctg cattattctg cgttatttga agttgganaa cctcaaaacc     60
rtggcttaaa tcactgaaga tttatttttgc tcacgaatat gcaggttgac tgggggctct    120
g                                                                    121

<210> SEQ ID NO 377
<211> LENGTH: 121
<212> TYPE: DNA
<213> ORGANISM: Homo sapiens
<220> FEATURE:
<221> NAME/KEY: modified_base
<222> LOCATION: (13)..(13)
```

```
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other

<400> SEQUENCE: 377
tgagaaaggc cangaaccag aggaggagac agaaacacag gccacagngg cgcgaggatg    60
maaggtcagg gtgagctggt cctcaggtta tttttaatat tattgtcata ttttcccttc   120
a                                                                   121

<210> SEQ ID NO 378
<211> LENGTH: 121
<212> TYPE: DNA
<213> ORGANISM: Homo sapiens

<400> SEQUENCE: 378
ttcatttgta agtaatgagg agccactaag ggttttgaag cacctggtgt aagggcagag    60
racagcctgg tggggaaaga gaggagcagt ggggagatgc caaggaagtg aggccctgtt   120
t                                                                   121

<210> SEQ ID NO 379
<211> LENGTH: 121
<212> TYPE: DNA
<213> ORGANISM: Homo sapiens

<400> SEQUENCE: 379
tccttcaatc aaatatttat gagctaaatt tttaagggcc agttcgtggg ctaggacttg    60
ratccaggat acagaacatt tctccagtct agttgtggat ttttagaatc cagatatcaa   120
c                                                                   121

<210> SEQ ID NO 380
<211> LENGTH: 121
<212> TYPE: DNA
<213> ORGANISM: Homo sapiens

<400> SEQUENCE: 380
gcacgatgct gacaagacaa tgcctccctt ccctgactgt aaggttgtcc ctactggttt    60
rttcactttg gaggcgcctg gctccgtatt cctcaggtac tgctggatga ggctgtctgg   120
a                                                                   121

<210> SEQ ID NO 381
<211> LENGTH: 121
<212> TYPE: DNA
<213> ORGANISM: Homo sapiens

<400> SEQUENCE: 381
tcagagccag ccgtgtgaga accaggcctg ggtctttgct accctcgcca ccactgtcct    60
rtactgcctg gtgtttctcc tcagcctagt gggcaacagc ctggtcctgt gggtcctggt   120
g                                                                   121

<210> SEQ ID NO 382
<211> LENGTH: 121
<212> TYPE: DNA
<213> ORGANISM: Homo sapiens
<220> FEATURE:
<221> NAME/KEY: modified_base
<222> LOCATION: (53)..(53)
<223> OTHER INFORMATION: a, c, t, g, unknown or other
```

<400> SEQUENCE: 382

```
caaacattttt aaacttatgt tttcctctaa ttgtaacagc ctatatcagg agntcttaag    60
mtttgctgca catcagaacc acctggaggg ctagtaaata tgctgattcc tgagctacct   120
c                                                                   121
```

<210> SEQ ID NO 383
<211> LENGTH: 121
<212> TYPE: DNA
<213> ORGANISM: Homo sapiens

<400> SEQUENCE: 383

```
aagaaaagga cttagtgccc ctgaattgta tacttaaaaa cagagagaga ggtgggagga    60
rgggagaaga gtattctagg aggaagagac tatgtgcaaa aagtattgga agcaggaatg   120
a                                                                   121
```

<210> SEQ ID NO 384
<211> LENGTH: 121
<212> TYPE: DNA
<213> ORGANISM: Homo sapiens

<400> SEQUENCE: 384

```
catcctgaga cctaactact tctaggcata ttagtaaatg gaatgagtct tggaccagtt    60
rctccctatc cctgttaatc aataataagt atatagatga tcatcctgga agctatctct   120
g                                                                   121
```

<210> SEQ ID NO 385
<211> LENGTH: 121
<212> TYPE: DNA
<213> ORGANISM: Homo sapiens

<400> SEQUENCE: 385

```
aaccactgca acccatctcc tttaagtttt tgtatttaat ataattcagt agataattca    60
rtcagcccct acagtgctgc caaaatacct ggggagcttt tcaatggta tagatgtccg    120
g                                                                   121
```

<210> SEQ ID NO 386
<211> LENGTH: 121
<212> TYPE: DNA
<213> ORGANISM: Homo sapiens

<400> SEQUENCE: 386

```
tgtccgggcc gtactccaga gatgctaatg cagttggtct ggggtggggc ctgggcactt    60
rcttttttag atactcccct cgtgagtctg atggatagct aggtaaagaa ccactccact   120
g                                                                   121
```

<210> SEQ ID NO 387
<211> LENGTH: 121
<212> TYPE: DNA
<213> ORGANISM: Homo sapiens

<400> SEQUENCE: 387

```
ttttaaaaat tttacttcat gcccattttt gtggctgggc tgggggagg aggcaaattc    60
ratttgaaca tatacttgta attctaatgc aaaattatac aattttttcct gtaaacaata  120
c                                                                   121
```

<210> SEQ ID NO 388
<211> LENGTH: 121
<212> TYPE: DNA
<213> ORGANISM: Homo sapiens

<400> SEQUENCE: 388
gtatcgttga agttcctgct gaatgtccat ttgatacatt cggtctcgtg tatcttctag    60
rgtctctcgg aatttggcct tcatgtgagc caaagatgct gaacttaaag cctcctgtaa   120
c                                                                    121

<210> SEQ ID NO 389
<211> LENGTH: 121
<212> TYPE: DNA
<213> ORGANISM: Homo sapiens

<400> SEQUENCE: 389
ccagctgcca gccaggtgcc acacatgcac aaatagctcc ccaagctgct ccagcaccct    60
rcttctgaca atggtttggc ttcactgcat ggccacagaa ctatgtcaaa gggatcatgc   120
t                                                                    121

<210> SEQ ID NO 390
<211> LENGTH: 121
<212> TYPE: DNA
<213> ORGANISM: Homo sapiens
<220> FEATURE:
<221> NAME/KEY: modified_base
<222> LOCATION: (88)..(88)
<223> OTHER INFORMATION: a, c, t, g, unknown or other

<400> SEQUENCE: 390
cagctggaaa agacaaaacc tggatttgaa tcccagtttg tctgcctgac tttgcagtcc    60
rtgtacgtaa gcacaatgtt atatgctnaa atacctagca tggctctgtg gagtgacaca   120
c                                                                    121

<210> SEQ ID NO 391
<211> LENGTH: 121
<212> TYPE: DNA
<213> ORGANISM: Homo sapiens

<400> SEQUENCE: 391
agggcaaaga attcacatgt ctttcctgac aatctgttcc ttggcctgag tgaactgtcc    60
raggagaact gcacaggtgc tgtcctggga agataacgaa aggtggcagc acatgaccac   120
t                                                                    121

<210> SEQ ID NO 392
<211> LENGTH: 121
<212> TYPE: DNA
<213> ORGANISM: Homo sapiens

<400> SEQUENCE: 392
tgtcctgtgc ttttctgatc tctgtacgct gcagccctct tccctccaac aagaaaggca    60
scatgcccag aagtacctgc ctggatatcc cctgacacag ctcctgtgtt ctctctcagc   120
a                                                                    121

<210> SEQ ID NO 393
<211> LENGTH: 121
<212> TYPE: DNA
<213> ORGANISM: Homo sapiens

<400> SEQUENCE: 393
tgagctcgac tgtcccaaag tgaacttgga aaatgttccc cagggatggg gacaaacatg    60
raacttagca gggtaggaga aagggagag atctgagtgc tggaggagcc caggccacag   120
g                                                                   121

<210> SEQ ID NO 394
<211> LENGTH: 121
<212> TYPE: DNA
<213> ORGANISM: Homo sapiens

<400> SEQUENCE: 394
cccttcaaat gtagaggata tttcacaggt gtgtccccac cccaggcttc tcttccttaa    60
rctaaacacc cacgtcacct tctaagctgg ttttcagacc ccacaagatc ctttaatctg   120
t                                                                   121

<210> SEQ ID NO 395
<211> LENGTH: 121
<212> TYPE: DNA
<213> ORGANISM: Homo sapiens

<400> SEQUENCE: 395
agctctggga gcaaccaggg catcaagggt ttgtctcagc cagtcgcgag cgtagagctt    60
rgactgttgg ttggaactga gtgtccatgg gcagtgggca agtctcctgg tcctcctctc   120
c                                                                   121

<210> SEQ ID NO 396
<211> LENGTH: 121
<212> TYPE: DNA
<213> ORGANISM: Homo sapiens

<400> SEQUENCE: 396
ttaccaccac tgcggagtcc tgcctgggtc ccatgacctg ctggctagtg agggaaggag    60
rggagaaaat gacctgacca agagggaggc ccagggctcc ctcaacaccc actcagcgga   120
g                                                                   121

<210> SEQ ID NO 397
<211> LENGTH: 121
<212> TYPE: DNA
<213> ORGANISM: Homo sapiens

<400> SEQUENCE: 397
tacgatcaag gccacttgaa ttgtcttccc cagtttcctg gagtgaggga tggggactgc    60
rttcatggaa gacaccatca ggctggtcgg gtacagaagg gctgcatgtg ctccgggagt   120
g                                                                   121

<210> SEQ ID NO 398
<211> LENGTH: 121
<212> TYPE: DNA
<213> ORGANISM: Homo sapiens

<400> SEQUENCE: 398
ctgaattaat gatgtgaact tgaagtttca ggtcttcaag taatccctgg gtgatgcatc    60
rggattaggc ctttgtagta gaaattatgg acatgcgtgc tgagcttttt gtgtcttgct   120
a                                                                   121

```
<210> SEQ ID NO 399
<211> LENGTH: 121
<212> TYPE: DNA
<213> ORGANISM: Homo sapiens

<400> SEQUENCE: 399
gaaagtctct cattaattat aaaaatgatt taatctgctg gaaatattta tttccagaga      60
rggaagtgtg gtgtcccagc tctgtaatgc tatcaacgtt atgtatgtgc agtaagtaga     120
a                                                                    121

<210> SEQ ID NO 400
<211> LENGTH: 121
<212> TYPE: DNA
<213> ORGANISM: Homo sapiens

<400> SEQUENCE: 400
tgggcagagg cagcgagcgc tggctgaagt ttccggtggg aaatgggcag tgcctagaag      60
rgaaggaaac gatgcatgag aaggttccag atgtctatga ggaacatgac gtgtcctgtc     120
c                                                                    121

<210> SEQ ID NO 401
<211> LENGTH: 121
<212> TYPE: DNA
<213> ORGANISM: Homo sapiens

<400> SEQUENCE: 401
ccatccacag ccccgaccca cattctggag ggatggtcgt acctctgtga ccagccctcc      60
rcaccgtcac ataggccagc aggggcaat gccaggtgcc atccagagcc accccccatg     120
t                                                                    121

<210> SEQ ID NO 402
<211> LENGTH: 121
<212> TYPE: DNA
<213> ORGANISM: Homo sapiens

<400> SEQUENCE: 402
ccaggtgtgg ctcctgtctc acgtgcctgt gctggctgcc ccaacactgc gaggcgggga      60 mtggccttttt acacgacgaa atgagagcac tgtgacaaaa ggtgttatac atggcaccac    120
c                                                                    121

<210> SEQ ID NO 403
<211> LENGTH: 121
<212> TYPE: DNA
<213> ORGANISM: Homo sapiens

<400> SEQUENCE: 403
gcggcctcat ggctgtgaat ctgagtgcag aagaacagag tataagattc ccaggcaaga      60
maactgtaca cgtatgatga ggtcaacaca gaggtcacgt caaacacaat tctgccagaa     120
t                                                                    121

<210> SEQ ID NO 404
<211> LENGTH: 121
<212> TYPE: DNA
<213> ORGANISM: Homo sapiens

<400> SEQUENCE: 404
aacaaatata tgaagagaga aggaatcaga attatctcag tagtctccag tgatgggtaa      60
```

```
rgagaggagt atgtaaaatg agcagcatta gatataactg cgacaaaggg ccactcacgt    120
t                                                                   121

<210> SEQ ID NO 405
<211> LENGTH: 121
<212> TYPE: DNA
<213> ORGANISM: Homo sapiens

<400> SEQUENCE: 405
tttcatttgt ttgttttaag acaaagtctc gctctgtcac tcaggccgaa gagcattggt    60
rcgatcttgg ctcactgcaa cctctgcctt ctgagtcgac cctattctcc tgccccagcc   120
t                                                                   121

<210> SEQ ID NO 406
<211> LENGTH: 121
<212> TYPE: DNA
<213> ORGANISM: Homo sapiens

<400> SEQUENCE: 406
cagcaaacac aggtgaagca tcaaacaaaa gcaggggtgg ggtggccagg actcctcaat    60
ractgtttta aaattagacc caacctgata agcctgcttg ggatgatctg tcagtgagcc   120
t                                                                   121

<210> SEQ ID NO 407
<211> LENGTH: 121
<212> TYPE: DNA
<213> ORGANISM: Homo sapiens

<400> SEQUENCE: 407
acaaacactt gtgcaaatgt gtagcagatc tagacccaaa gacttagggt caatgaaatc    60
magacatttt ggtagtgatt ggaaatccat atttacttgg ggtgcaagag tcaaaggata   120
a                                                                   121

<210> SEQ ID NO 408
<211> LENGTH: 121
<212> TYPE: DNA
<213> ORGANISM: Homo sapiens

<400> SEQUENCE: 408
ctccaaataa agtctacaat ctgtaatatg gcctacaagg cccacctctc cctccaaact    60
raaaaatctg gtctcagctt acttttccaa tctccccatc acactccaca ttgcccccca   120
g                                                                   121

<210> SEQ ID NO 409
<211> LENGTH: 121
<212> TYPE: DNA
<213> ORGANISM: Homo sapiens

<400> SEQUENCE: 409
tctgatgtga gggtttaccc atcttgtcct ctccagcccc aagcctcatt actctcaccc    60
rcattatatc atccacccca cctgacctcc cagcttccag cctcccgtcc tctgcagaac   120
t                                                                   121

<210> SEQ ID NO 410
<211> LENGTH: 121
<212> TYPE: DNA
```

```
<213> ORGANISM: Homo sapiens

<400> SEQUENCE: 410
tgtgttatct ctaagaattc tctgtctacc gcaaggtctt taagatattt tctcttagga    60
sggggtggat ttttgagcta gggtttggat aagctgcttt tgagaagcca gcagattggt   120
g                                                                  121

<210> SEQ ID NO 411
<211> LENGTH: 121
<212> TYPE: DNA
<213> ORGANISM: Homo sapiens
<220> FEATURE:
<221> NAME/KEY: modified_base
<222> LOCATION: (64)..(64)
<223> OTHER INFORMATION: a, c, t, g, unknown or other

<400> SEQUENCE: 411
agacagggcc tgtaggctcg gacacgaccc ggtcctgatt ttaacagtag acttgagaag    60
scangctcag cagacaggct gctggaggat ccacccgctg tctcccgcag cggcccact    120 g                                                                  121

<210> SEQ ID NO 412
<211> LENGTH: 121
<212> TYPE: DNA
<213> ORGANISM: Homo sapiens

<400> SEQUENCE: 412
aagtgctaag attacaggcg tgagccatgg cacgtggcct gtaactatga ttttgatgaa    60
sagttatagg ccaatgatgt cagaatttct atttcaaatc tgggtcttgc ccctggagct   120
c                                                                  121

<210> SEQ ID NO 413
<211> LENGTH: 121
<212> TYPE: DNA
<213> ORGANISM: Homo sapiens

<400> SEQUENCE: 413
agtcagacag tctcaaatta aaaacacaag tgagtggtgg aacagggcta tatgtataag    60
rcctactcca gcacagtcat aatttagcga tataaagcat gcactgcacc tagcacagtg   120
c                                                                  121

<210> SEQ ID NO 414
<211> LENGTH: 121
<212> TYPE: DNA
<213> ORGANISM: Homo sapiens
<220> FEATURE:
<221> NAME/KEY: modified_base
<222> LOCATION: (92)..(92)
<223> OTHER INFORMATION: a, c, t, g, unknown or other

<400> SEQUENCE: 414
accatctttt tcctgaacaa ctgcaacagc tcctgactgg catccctgct tccttgcacc    60 rccctaacc cccagccacc accttcttc tnctggggc tttagagatc tttaaaacat    120
g                                                                  121

<210> SEQ ID NO 415
<211> LENGTH: 121
<212> TYPE: DNA
<213> ORGANISM: Homo sapiens
```

<400> SEQUENCE: 415
agacgagatt acgccgctgc actccagcct gggtgacgag agactctgcc tcaaaaaaat    60
waaaaaatga aacagccagt gaggaggaag gctccccgcc ttcccccgc cggaacatag    120 c                                                                    121

<210> SEQ ID NO 416
<211> LENGTH: 121
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other

<400> SEQUENCE: 416
taatagaaac tcccgtctct gagcctgcat ncagggttcn ttctncttta tngtcctggg    60
rtttgctgct ttaggcatga ggggaggctc aaaagcaaat catccatttt tcataaccaa    120
t                                                                    121

<210> SEQ ID NO 417
<211> LENGTH: 121
<212> TYPE: DNA
<213> ORGANISM: Homo sapiens
<220> FEATURE:
<221> NAME/KEY: modified_base
<222> LOCATION: (83)..(83)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other

<400> SEQUENCE: 417
gtaagggagc ttgttaaaca aacataacat caatagcagc atctggcaat gattcacaga    60
raccactgca aatgaaacaa cancactcaa cagagtgcat gcagnaagca ctcagtaaga    120
a                                                                    121

<210> SEQ ID NO 418
<211> LENGTH: 121
<212> TYPE: DNA
<213> ORGANISM: Homo sapiens
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (47)..(47)
<223> OTHER INFORMATION: a, c, t, g, unknown or other

<400> SEQUENCE: 418
taacttaaat ttaaangtca acagccacat gtggctacta gctaccntat cagatggtgc    60

```
rgtaatagaa actaaaaagg tgggccattc cctcattttc attcatgaca atcatctggt    120
t                                                                    121
```

```
<210> SEQ ID NO 419
<211> LENGTH: 121
<212> TYPE: DNA
<213> ORGANISM: Homo sapiens

<400> SEQUENCE: 419
attctgcacc acccaatatg gcagccacca gtccgcatgt ggctactgag tgcttgaaac    60
rtggctcatc tgttgaagaa ctaaagttta atttcctta gttttaatta acttaaattt     120
a                                                                    121
```

```
<210> SEQ ID NO 420
<211> LENGTH: 121
<212> TYPE: DNA
<213> ORGANISM: Homo sapiens
<220> FEATURE:
<221> NAME/KEY: modified_base
<222> LOCATION: (43)..(43)
<223> OTHER INFORMATION: a, c, t, g, unknown or other

<400> SEQUENCE: 420
aagcttctaa ctgggccagt tctttactcg tccataagga agnagattca cggagaagca    60
rataggaact tgcactaatt agacaccgta tctgaattct tctactgaaa gcctccagtt    120
t                                                                    121
```

```
<210> SEQ ID NO 421
<211> LENGTH: 121
<212> TYPE: DNA
<213> ORGANISM: Homo sapiens
<220> FEATURE:
<221> NAME/KEY: modified_base
<222> LOCATION: (43)..(43)
<223> OTHER INFORMATION: a, c, t, g, unknown or other

<400> SEQUENCE: 421
agaagaattc agatacggtg tctaattagt gcaagttcct atntgcttct ccgtgaatct    60
rcttccttat ggacgagtaa agaactggcc cagttagaag cttccttgca caattcttta    120
c                                                                    121
```

```
<210> SEQ ID NO 422
<211> LENGTH: 121
<212> TYPE: DNA
<213> ORGANISM: Homo sapiens

<400> SEQUENCE: 422
tactattgtc caactataca agcccattat cattttctta aagaaaactg tcatttatac    60
mtgtgggtct ttttaatgtc ctcatttctt tctaccatgg aatgaaacat tttcttggtg    120
a                                                                    121
```

```
<210> SEQ ID NO 423
<211> LENGTH: 121
<212> TYPE: DNA
<213> ORGANISM: Homo sapiens

<400> SEQUENCE: 423
cagatatttg ccaggctatg cttgaaatga taaactatct ctttgtttaa gattctcaac    60
mgttccatca gtctgtttga tattctttct ataaccacag acaaaattag aggatgagtt    120
``` c                                                                             121

<210> SEQ ID NO 424
<211> LENGTH: 121
<212> TYPE: DNA
<213> ORGANISM: Homo sapiens

<400> SEQUENCE: 424
ggagagccta gagggcccc cctcagctcc taacgagccc cccttctgag ttgagtcccc    60
rtgaccttca gcctttagcc tagttgctgg aaggggac agggcccatg agagcccagg    120
g                                                                             121

<210> SEQ ID NO 425
<211> LENGTH: 121
<212> TYPE: DNA
<213> ORGANISM: Homo sapiens

<400> SEQUENCE: 425
actccatggc tatttagcag tcactcccca ttcccacatt ccacagtttt ggcaaccaac    60
rgttggtgat ttctttctgt ctttgtagat ttacctatgc tggatatttc atttcagtgg    120
a                                                                             121

<210> SEQ ID NO 426
<211> LENGTH: 121
<212> TYPE: DNA
<213> ORGANISM: Homo sapiens

<400> SEQUENCE: 426
tctagagcag agatccccat ggaactggga cagaggcagc ggccttccag gcagcagaac    60
rtgccatgag tgcagggct gcagggcggg gacctggcag gtggtacaag tgaggggatc    120
c                                                                             121

<210> SEQ ID NO 427
<211> LENGTH: 121
<212> TYPE: DNA
<213> ORGANISM: Homo sapiens

<400> SEQUENCE: 427
tccctgacca gggctctttc tcatgggtgc attgccaggg gcaagaaagt gggagtctgt    60
rttcctcagg acagaggagt ttcagctcaa gaagtgcctg gctgtccagc ttgacactgt    120
c                                                                             121

<210> SEQ ID NO 428
<211> LENGTH: 121
<212> TYPE: DNA
<213> ORGANISM: Homo sapiens

<400> SEQUENCE: 428
aagagggaaa agagaaagaa tggcaagtga gccctccaat gacgcacacc caaatgctcc    60
mgcctggggt ctcacaggag ctgagaaccg aagaagtgat tgtccttggt aaggggaaga    120
g                                                                             121

<210> SEQ ID NO 429
<211> LENGTH: 121
<212> TYPE: DNA
<213> ORGANISM: Homo sapiens

<400> SEQUENCE: 429
cttggaaaat ttagagtgag tgctatgcct gctctgggtt acttctggag aatggcagta    60
rtcatgcatt ctatttttat tcaaatgctc acatagaata cactgagtca ggtaaaagca   120
c                                                                  121

<210> SEQ ID NO 430
<211> LENGTH: 121
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other

<400> SEQUENCE: 430
tgcngcccct gtgacaccca caccaggctg ctgcacagac ctgcnggggcc tggagctcag    60 rgtgcagagg aatgctgagg agctgggcca tgaggccttc tgggagcaag agctgcgccg   120
g                                                                  121

<210> SEQ ID NO 431
<211> LENGTH: 121
<212> TYPE: DNA
<213> ORGANISM: Homo sapiens

<400> SEQUENCE: 431
gccataccac ctagctacct ctccctaatt ttccttcctt tattttggta gcactgggta    60
rgaaatcaca gcctagaatg aaggtttcta tgaacttggc tcccaaaaat ttggtatata   120
t                                                                  121

<210> SEQ ID NO 432
<211> LENGTH: 121
<212> TYPE: DNA
<213> ORGANISM: Homo sapiens
<220> FEATURE:
<221> NAME/KEY: modified_base
<222> LOCATION: (93)..(93)
<223> OTHER INFORMATION: a, c, t, g, unknown or other

<400> SEQUENCE: 432
tttaaataac cccagtttgt acactcagaa aaatggctta aatgacttgc ctaaaattat    60
rtaggtagca aacaatattt gactcaaaag ctnctacttt taactggatt ttagtcttag   120
t                                                                  121

<210> SEQ ID NO 433
<211> LENGTH: 121
<212> TYPE: DNA
<213> ORGANISM: Homo sapiens

<400> SEQUENCE: 433
atttacgaag catgaaaaaa tattctatcc attagtaatc aaagaaaggc aaggagggcc    60
mcttttgtag aaagattgct tcctgcctgt aatcccagca ctttgggagg ctgaggtgag   120
c                                                                  121

<210> SEQ ID NO 434
<211> LENGTH: 121

```
<212> TYPE: DNA
<213> ORGANISM: Homo sapiens

<400> SEQUENCE: 434
tgtccatttc agatgtgaga gctctgaact cgacagagat aacttgctgc ttggcaccca    60
mtcagcccct gcagctcctg tcacttaatg gtccaaccct ctttgccagc aaaatgtctg   120
g                                                                  121

<210> SEQ ID NO 435
<211> LENGTH: 121
<212> TYPE: DNA
<213> ORGANISM: Homo sapiens
<220> FEATURE:
<221> NAME/KEY: modified_base
<222> LOCATION: (48)..(48)
<223> OTHER INFORMATION: a, c, t, g, unknown or other

<400> SEQUENCE: 435
aaaaagtaaa gaaacaaaca tttagcaaac atgaaagaat tccatatntt taccatgacg    60
rtgatttaca catgcacatt attaattgac ttataaacat agtaagttcc ttaaaagggg   120
a                                                                  121

<210> SEQ ID NO 436
<211> LENGTH: 121
<212> TYPE: DNA
<213> ORGANISM: Homo sapiens

<400> SEQUENCE: 436
tcagagtgct aggaatcttt ctagcaagtt attaaacctg agggtcgcct taggaactca    60
raaacttaca gttggtgtca gaatgaaca tggtcttggg atcttcctaa ctttacacca   120
a                                                                  121

<210> SEQ ID NO 437
<211> LENGTH: 121
<212> TYPE: DNA
<213> ORGANISM: Homo sapiens

<400> SEQUENCE: 437
ttatttctgt taggtctcct tatgctcact ttaccaggga gactttccct tattattcca    60
ratgcactgc tttccctgcc cttcttcctc cctcctactc ctagccctcc atagaccagt   120
c                                                                  121

<210> SEQ ID NO 438
<211> LENGTH: 121
<212> TYPE: DNA
<213> ORGANISM: Homo sapiens

<400> SEQUENCE: 438
caaggagact gctgcctgcc tcatgcaggg agacctttcc caaagcttgg cacctgccct    60
rtgctggccc agtggaggcc aaatgggggga gcagaaagga agacattgct aaagttctct   120
t                                                                  121

<210> SEQ ID NO 439
<211> LENGTH: 115
<212> TYPE: DNA
<213> ORGANISM: Homo sapiens

<400> SEQUENCE: 439
```

```
ggctcctgag aaatagaaaa gtttaatgaa gcaactctca ggagctgctt tcatratata         60
acttgaagat actggaactc aggtctgcta aataccagtt cagtgttctt gccct            115
```

<210> SEQ ID NO 440
<211> LENGTH: 712
<212> TYPE: PRT
<213> ORGANISM: Homo sapiens

<400> SEQUENCE: 440

```
Met Glu Asn Leu Gly Val Gly Glu Gly Ala Glu Ala Cys Ser Arg Leu
1               5                   10                  15

Ser Arg Ser Arg Gly Arg His Ser Met Thr Arg Ala Pro Lys His Leu
            20                  25                  30

Trp Arg Gln Pro Arg Arg Pro Ile Arg Ile Gln Gln Arg Phe Tyr Ser
        35                  40                  45

Asp Pro Asp Lys Ser Ala Gly Cys Arg Glu Arg Asp Leu Ser Pro Arg
    50                  55                  60

Pro Glu Leu Arg Lys Ser Arg Leu Ser Trp Pro Val Ser Ser Cys Arg
65                  70                  75                  80

Arg Phe Asp Leu Glu Asn Gly Leu Ser Cys Gly Arg Arg Ala Leu Asp
                85                  90                  95

Pro Gln Ser Ser Pro Gly Leu Gly Arg Ile Met Gln Ala Pro Val Pro
            100                 105                 110

His Ser Gln Arg Arg Glu Ser Phe Leu Tyr Arg Ser Asp Ser Asp Tyr
        115                 120                 125

Glu Leu Ser Pro Lys Ala Met Ser Arg Asn Ser Ser Val Ala Ser Asp
    130                 135                 140

Leu His Gly Glu Asp Met Ile Val Thr Pro Phe Ala Gln Val Leu Ala
145                 150                 155                 160

Ser Leu Arg Thr Val Arg Ser Asn Val Ala Ala Leu Ala Arg Gln Gln
                165                 170                 175

Cys Leu Gly Ala Ala Lys Gln Gly Pro Val Gly Asn Pro Ser Ser Ser
            180                 185                 190

Asn Gln Leu Pro Pro Ala Glu Asp Thr Gly Gln Lys Leu Ala Leu Glu
        195                 200                 205

Thr Leu Asp Glu Leu Asp Trp Cys Leu Asp Gln Leu Glu Thr Leu Gln
    210                 215                 220

Thr Arg His Ser Val Gly Glu Met Ala Ser Asn Lys Phe Lys Arg Ile
225                 230                 235                 240

Leu Asn Arg Glu Leu Thr His Leu Ser Glu Thr Ser Arg Ser Gly Asn
                245                 250                 255

Gln Val Ser Glu Tyr Ile Ser Arg Thr Phe Leu Asp Gln Gln Thr Glu
            260                 265                 270

Val Glu Leu Pro Lys Val Thr Ala Glu Glu Ala Pro Gln Pro Met Ser
        275                 280                 285

Arg Ile Ser Gly Leu His Gly Leu Cys His Ser Ala Ser Leu Ser Ser
    290                 295                 300

Ala Thr Val Pro Arg Phe Gly Val Gln Thr Asp Gln Glu Glu Gln Leu
305                 310                 315                 320

Ala Lys Glu Leu Glu Asp Thr Asn Lys Trp Gly Leu Asp Val Phe Lys
                325                 330                 335

Val Ala Glu Leu Ser Gly Asn Arg Pro Leu Thr Ala Ile Ile Phe Ser
            340                 345                 350

Ile Phe Gln Glu Arg Asp Leu Leu Lys Thr Phe Gln Ile Pro Ala Asp
```

```
                355                 360                 365
Thr Leu Ala Thr Tyr Leu Leu Met Leu Glu Gly His Tyr His Ala Asn
            370                 375                 380

Val Ala Tyr His Asn Ser Leu His Ala Ala Asp Val Ala Gln Ser Thr
385                 390                 395                 400

His Val Leu Leu Ala Thr Pro Ala Leu Glu Ala Val Phe Thr Asp Leu
                405                 410                 415

Glu Ile Leu Ala Ala Leu Phe Ala Ser Ala Ile His Asp Val Asp His
            420                 425                 430

Pro Gly Val Ser Asn Gln Phe Leu Ile Asn Thr Asn Ser Glu Leu Ala
                435                 440                 445

Leu Met Tyr Asn Asp Ala Ser Val Leu Glu Asn His His Leu Ala Val
            450                 455                 460

Gly Phe Lys Leu Leu Gln Ala Glu Asn Cys Asp Ile Phe Gln Asn Leu
465                 470                 475                 480

Ser Ala Lys Gln Arg Leu Ser Leu Arg Arg Met Val Ile Asp Met Val
                485                 490                 495

Leu Ala Thr Asp Met Ser Lys His Met Asn Leu Leu Ala Asp Leu Lys
            500                 505                 510

Thr Met Val Glu Thr Lys Lys Val Thr Ser Leu Gly Val Leu Leu Leu
                515                 520                 525

Asp Asn Tyr Ser Asp Arg Ile Gln Val Leu Gln Asn Leu Val His Cys
            530                 535                 540

Ala Asp Leu Ser Asn Pro Thr Lys Pro Leu Pro Leu Tyr Arg Gln Trp
545                 550                 555                 560

Thr Asp Arg Ile Met Ala Glu Phe Phe Gln Gln Gly Asp Arg Glu Arg
                565                 570                 575

Glu Ser Gly Leu Asp Ile Ser Pro Met Cys Asp Lys His Thr Ala Ser
            580                 585                 590

Val Glu Lys Ser Gln Val Gly Phe Ile Asp Tyr Ile Ala His Pro Leu
                595                 600                 605

Trp Glu Thr Trp Ala Asp Leu Val His Pro Asp Ala Gln Asp Leu Leu
            610                 615                 620

Asp Thr Leu Glu Asp Asn Arg Glu Trp Tyr Gln Ser Lys Ile Pro Arg
625                 630                 635                 640

Ser Pro Ser Asp Leu Thr Asn Pro Glu Arg Asp Gly Pro Asp Arg Phe
                645                 650                 655

Gln Phe Glu Leu Thr Leu Glu Glu Ala Glu Glu Asp Glu Glu Glu
            660                 665                 670

Glu Glu Glu Gly Glu Glu Thr Ala Leu Ala Lys Glu Ala Leu Glu Leu
                675                 680                 685

Pro Asp Thr Glu Leu Leu Ser Pro Glu Ala Gly Pro Asp Pro Gly Asp
            690                 695                 700

Leu Pro Leu Asp Asn Gln Arg Thr
705                 710

<210> SEQ ID NO 441
<211> LENGTH: 712
<212> TYPE: PRT
<213> ORGANISM: Homo sapiens

<400> SEQUENCE: 441

Met Glu Asn Leu Gly Val Gly Glu Gly Ala Glu Ala Cys Ser Arg Leu
1               5                   10                  15
```

```
Ser Arg Ser Arg Gly Arg His Ser Met Thr Arg Ala Pro Lys His Leu
            20                  25                  30

Trp Arg Gln Pro Arg Arg Pro Ile Arg Ile Gln Gln Arg Phe Tyr Ser
        35                  40                  45

Asp Pro Asp Lys Ser Ala Gly Cys Arg Glu Arg Asp Leu Ser Pro Arg
    50                  55                  60

Pro Glu Leu Arg Lys Ser Arg Leu Ser Trp Pro Val Ser Ser Cys Arg
65                  70                  75                  80

Arg Phe Asp Leu Glu Asn Gly Leu Ser Cys Gly Arg Arg Ala Leu Asp
                85                  90                  95

Pro Gln Ser Ser Pro Gly Leu Gly Arg Ile Met Gln Ala Pro Val Pro
            100                 105                 110

His Ser Gln Arg Arg Glu Ser Phe Leu Tyr Arg Ser Asp Ser Asp Tyr
        115                 120                 125

Glu Leu Ser Pro Lys Ala Met Ser Arg Asn Ser Ser Val Ala Ser Asp
    130                 135                 140

Leu His Gly Glu Asp Met Ile Val Thr Pro Phe Ala Gln Val Leu Ala
145                 150                 155                 160

Ser Leu Arg Thr Val Arg Ser Asn Val Ala Ala Leu Ala Arg Gln Gln
                165                 170                 175

Cys Leu Gly Ala Ala Lys Gln Gly Pro Val Gly Asn Pro Ser Ser Ser
            180                 185                 190

Asn Gln Leu Pro Pro Ala Glu Asp Thr Gly Gln Lys Leu Ala Leu Glu
        195                 200                 205

Thr Leu Asp Glu Leu Asp Trp Cys Leu Asp Gln Leu Glu Thr Leu Gln
    210                 215                 220

Thr Arg His Ser Val Gly Glu Met Ala Ser Asn Lys Phe Lys Arg Ile
225                 230                 235                 240

Leu Asn Arg Glu Leu Thr His Leu Ser Glu Thr Ser Arg Ser Gly Asn
                245                 250                 255

Gln Val Ser Glu Tyr Ile Ser Arg Thr Phe Leu Asp Gln Gln Thr Glu
            260                 265                 270

Val Glu Leu Pro Lys Val Thr Ala Glu Glu Ala Pro Gln Pro Met Ser
        275                 280                 285

Arg Ile Ser Gly Leu His Gly Leu Cys His Ser Ala Ser Leu Ser Ser
    290                 295                 300

Ala Thr Val Pro Arg Phe Gly Val Gln Thr Asp Gln Glu Glu Gln Leu
305                 310                 315                 320

Ala Lys Glu Leu Glu Asp Thr Asn Lys Trp Gly Leu Asp Val Phe Lys
                325                 330                 335

Val Ala Glu Leu Ser Gly Asn Arg Pro Leu Thr Ala Ile Ile Phe Ser
            340                 345                 350

Ile Phe Gln Glu Arg Asp Leu Leu Lys Thr Phe Gln Ile Pro Ala Asp
        355                 360                 365

Thr Leu Ala Thr Tyr Leu Leu Met Leu Glu Gly His Tyr His Ala Asn
    370                 375                 380

Val Ala Tyr His Asn Ser Leu His Ala Ala Asp Val Ala Gln Ser Thr
385                 390                 395                 400

His Val Leu Leu Ala Thr Pro Ala Leu Glu Ala Val Phe Thr Asp Leu
                405                 410                 415

Glu Ile Leu Ala Ala Leu Phe Ser Ala Ile His Asp Val Asp His
            420                 425                 430

Pro Gly Val Ser Asn Gln Phe Leu Ile Asn Thr Asn Ser Glu Leu Ala
```

```
                        435                 440                 445
Leu Met Tyr Asn Asp Ala Ser Val Leu Glu Asn His His Leu Ala Val
    450                 455                 460

Gly Phe Lys Leu Leu Gln Ala Glu Asn Cys Asp Ile Phe Gln Asn Leu
465                 470                 475                 480

Ser Ala Lys Gln Arg Leu Ser Leu Arg Arg Met Val Ile Asp Met Val
                485                 490                 495

Leu Ala Thr Asp Met Ser Lys His Met Asn Leu Leu Ala Asp Leu Lys
            500                 505                 510

Thr Met Val Glu Thr Lys Lys Val Thr Ser Leu Gly Val Leu Leu Leu
        515                 520                 525

Asp Asn Tyr Ser Asp Arg Ile Gln Val Leu Gln Asn Leu Val His Cys
    530                 535                 540

Ala Asp Leu Ser Asn Pro Thr Lys Pro Leu Pro Leu Tyr Arg Gln Trp
545                 550                 555                 560

Thr Asp Arg Ile Met Ala Glu Phe Phe Gln Gln Gly Asp Arg Glu Arg
                565                 570                 575

Glu Ser Gly Leu Asp Ile Ser Pro Met Cys Asp Lys His Thr Ala Ser
            580                 585                 590

Val Glu Lys Ser Gln Val Gly Phe Ile Asp Tyr Ile Ala His Pro Leu
        595                 600                 605

Trp Glu Thr Trp Ala Asp Leu Val His Pro Asp Ala Gln Asp Leu Leu
    610                 615                 620

Asp Thr Leu Glu Asp Asn Arg Glu Trp Tyr Gln Ser Lys Ile Pro Arg
625                 630                 635                 640

Ser Pro Ser Asp Leu Thr Asn Pro Glu Arg Asp Gly Pro Asp Arg Phe
                645                 650                 655

Gln Phe Glu Leu Thr Leu Glu Glu Ala Glu Glu Asp Glu Glu Glu
            660                 665                 670

Glu Glu Glu Gly Glu Glu Thr Ala Leu Ala Lys Glu Ala Leu Glu Leu
        675                 680                 685

Pro Asp Thr Glu Leu Leu Ser Pro Glu Ala Gly Pro Asp Pro Gly Asp
    690                 695                 700

Leu Pro Leu Asp Asn Gln Arg Thr
705                 710

<210> SEQ ID NO 442
<211> LENGTH: 1080
<212> TYPE: PRT
<213> ORGANISM: Homo sapiens

<400> SEQUENCE: 442

Met Pro Ala Lys Gly Arg Tyr Phe Leu Asn Glu Gly Glu Gly Pro
1               5                   10                  15

Asp Gln Asp Ala Leu Tyr Glu Lys Tyr Gln Leu Thr Ser Gln His Gly
            20                  25                  30

Pro Leu Leu Leu Thr Leu Leu Val Ala Ala Thr Ala Cys Val Ala
        35                  40                  45

Leu Ile Ile Ile Ala Phe Ser Gln Gly Asp Pro Ser Arg His Gln Ala
    50                  55                  60

Ile Leu Gly Met Ala Phe Leu Val Ala Val Phe Ala Ala Leu Ser
65                  70                  75                  80

Val Leu Met Tyr Val Glu Cys Leu Leu Arg Arg Trp Leu Arg Ala Leu
                85                  90                  95
```

-continued

```
Ala Leu Leu Thr Trp Ala Cys Leu Val Ala Leu Gly Tyr Val Leu Val
                100                 105                 110
Phe Asp Ala Trp Thr Lys Ala Ala Cys Ala Trp Glu Gln Val Pro Phe
            115                 120                 125
Phe Leu Phe Ile Val Phe Val Val Tyr Thr Leu Leu Pro Phe Ser Met
        130                 135                 140
Arg Gly Ala Val Ala Val Gly Ala Val Ser Thr Ala Ser His Leu Leu
145                 150                 155                 160
Val Leu Gly Ser Leu Met Gly Gly Phe Thr Thr Pro Ser Val Arg Val
                165                 170                 175
Gly Leu Gln Leu Leu Ala Asn Ala Val Ile Phe Leu Cys Gly Asn Leu
            180                 185                 190
Thr Gly Ala Phe His Lys His Gln Met Gln Asp Ala Ser Arg Asp Leu
        195                 200                 205
Phe Thr Tyr Thr Val Lys Cys Ile Gln Ile Arg Arg Lys Leu Arg Ile
210                 215                 220
Glu Lys Arg Gln Gln Glu Asn Leu Leu Leu Ser Val Leu Pro Ala His
225                 230                 235                 240
Ile Ser Met Gly Met Lys Leu Ala Ile Ile Glu Arg Leu Lys Glu His
                245                 250                 255
Gly Asp Arg Arg Cys Met Pro Asp Asn Asn Phe His Ser Leu Tyr Val
            260                 265                 270
Lys Arg His Gln Asn Val Ser Ile Leu Tyr Ala Asp Ile Val Gly Phe
        275                 280                 285
Thr Gln Leu Ala Ser Asp Cys Ser Pro Lys Glu Leu Val Val Val Leu
290                 295                 300
Asn Glu Leu Phe Gly Lys Phe Asp Gln Ile Ala Lys Ala Asn Glu Cys
305                 310                 315                 320
Met Arg Ile Lys Ile Leu Gly Asp Cys Tyr Tyr Cys Val Ser Gly Leu
                325                 330                 335
Pro Val Ser Leu Pro Thr His Ala Arg Asn Cys Val Lys Met Gly Leu
            340                 345                 350
Asp Met Cys Gln Ala Ile Lys Gln Val Arg Glu Ala Thr Gly Val Asp
        355                 360                 365
Ile Asn Met Arg Val Gly Ile His Ser Gly Asn Val Leu Cys Gly Val
370                 375                 380
Ile Gly Leu Arg Lys Trp Gln Tyr Asp Val Trp Ser His Asp Val Ser
385                 390                 395                 400
Leu Ala Asn Arg Met Glu Ala Ala Gly Val Pro Gly Arg Val His Ile
                405                 410                 415
Thr Glu Ala Thr Leu Lys His Leu Asp Lys Ala Tyr Glu Val Glu Asp
            420                 425                 430
Gly His Gly Gln Gln Arg Asp Pro Tyr Leu Lys Glu Met Asn Ile Arg
        435                 440                 445
Thr Tyr Leu Val Ile Asp Pro Arg Ser Gln Pro Pro Pro Pro Pro Ser
450                 455                 460
Gln His Leu Pro Arg Pro Lys Gly Asp Ala Ala Leu Lys Met Arg Ala
465                 470                 475                 480
Ser Val Arg Met Thr Arg Tyr Leu Glu Ser Trp Gly Ala Ala Arg Pro
                485                 490                 495
Phe Ala His Leu Asn His Arg Glu Ser Val Ser Ser Gly Glu Thr His
            500                 505                 510
Val Pro Asn Gly Arg Arg Pro Lys Ser Val Pro Gln Arg His Arg Arg
```

```
                515                 520                 525
Thr Pro Asp Arg Ser Met Ser Pro Lys Gly Arg Ser Glu Asp Asp Ser
    530                 535                 540
Tyr Asp Asp Glu Met Leu Ser Ala Ile Glu Gly Leu Ser Ser Thr Arg
545                 550                 555                 560
Pro Cys Cys Ser Lys Ser Asp Asp Phe Tyr Thr Phe Gly Ser Ile Phe
                565                 570                 575
Leu Glu Lys Gly Phe Glu Arg Glu Tyr Arg Leu Ala Pro Ile Pro Arg
                580                 585                 590
Ala Arg His Asp Phe Ala Cys Ala Ser Leu Ile Phe Val Cys Ile Leu
                595                 600                 605
Leu Val His Val Leu Leu Met Pro Arg Thr Ala Ala Leu Gly Val Ser
        610                 615                 620
Phe Gly Leu Val Ala Cys Val Leu Gly Leu Val Leu Gly Leu Cys Phe
625                 630                 635                 640
Ala Thr Lys Phe Ser Arg Cys Cys Pro Ala Arg Gly Thr Leu Cys Thr
                645                 650                 655
Ile Ser Glu Arg Val Glu Thr Gln Pro Leu Leu Arg Leu Thr Leu Ala
                660                 665                 670
Val Leu Thr Ile Gly Ser Leu Leu Thr Val Ala Ile Ile Asn Leu Pro
            675                 680                 685
Leu Met Pro Phe Gln Val Pro Glu Leu Pro Val Gly Asn Glu Thr Gly
        690                 695                 700
Leu Leu Ala Ala Ser Ser Lys Thr Arg Ala Leu Cys Glu Pro Leu Pro
705                 710                 715                 720
Tyr Tyr Thr Cys Ser Cys Val Leu Gly Phe Ile Ala Cys Ser Val Phe
                725                 730                 735
Leu Arg Met Ser Leu Glu Pro Lys Val Leu Leu Thr Val Ala Leu
                740                 745                 750
Val Ala Tyr Leu Val Leu Phe Asn Leu Ser Pro Cys Trp Gln Trp Asp
            755                 760                 765
Cys Cys Gly Gln Gly Leu Gly Asn Leu Thr Lys Pro Asn Gly Thr Thr
    770                 775                 780
Ser Gly Thr Pro Ser Cys Ser Trp Lys Asp Leu Lys Thr Met Thr Asn
785                 790                 795                 800
Phe Tyr Leu Val Leu Phe Tyr Ile Thr Leu Leu Thr Leu Ser Arg Gln
                805                 810                 815
Ile Asp Tyr Tyr Cys Arg Leu Asp Cys Leu Trp Lys Lys Lys Phe Lys
                820                 825                 830
Lys Glu His Glu Glu Phe Glu Thr Met Glu Asn Val Asn Arg Leu Leu
            835                 840                 845
Leu Glu Asn Val Leu Pro Ala His Val Ala Ala His Phe Ile Gly Asp
        850                 855                 860
Lys Leu Asn Glu Asp Trp Tyr His Gln Ser Tyr Asp Cys Val Cys Val
865                 870                 875                 880
Met Phe Ala Ser Val Pro Asp Phe Lys Val Phe Tyr Thr Glu Cys Asp
                885                 890                 895
Val Asn Lys Glu Gly Leu Glu Cys Leu Arg Leu Leu Asn Glu Ile Ile
            900                 905                 910
Ala Asp Phe Asp Glu Leu Leu Leu Lys Pro Lys Phe Ser Gly Val Glu
        915                 920                 925
Lys Ile Lys Thr Ile Gly Ser Thr Tyr Met Ala Ala Gly Leu Ser
            930                 935                 940
```

Val Ala Ser Gly His Glu Asn Gln Glu Leu Glu Arg Gln His Ala His
945                 950                 955                 960

Ile Gly Val Met Val Glu Phe Ser Ile Ala Leu Met Ser Lys Leu Asp
            965                 970                 975

Gly Ile Asn Arg His Ser Phe Asn Ser Phe Arg Leu Arg Val Gly Ile
        980                 985                 990

Asn His Gly Pro Val Ile Ala Gly Val Ile Gly Ala Arg Lys Pro Gln
    995                 1000                1005

Tyr Asp Ile Trp Gly Asn Thr Val Asn Val Ala Ser Arg Met Glu
1010            1015                1020

Ser Thr Gly Glu Leu Gly Lys Ile Gln Val Thr Glu Glu Thr Cys
1025                1030                1035

Thr Ile Leu Gln Gly Leu Gly Tyr Ser Cys Glu Cys Arg Gly Leu
1040                1045                1050

Ile Asn Val Lys Gly Lys Gly Glu Leu Arg Thr Tyr Phe Val Cys
1055                1060                1065

Thr Asp Thr Ala Lys Phe Gln Gly Leu Gly Leu Asn
1070                1075                1080

<210> SEQ ID NO 443
<211> LENGTH: 6154
<212> TYPE: DNA
<213> ORGANISM: Homo sapiens

<400> SEQUENCE: 443

| | | | | | |
|---|---|---|---|---|---|
| agctgaggaa | ctgcgtgtgg | agtcagccca | gtctggatgc | acaggaggat | gctggcggca | 60 |
| cagtgagtga | ggcctggtgc | agagctgtg  | cggacccctt | gttggccatg | agcagcagg  | 120 |
| cccagaggcc | ctctccccag | ccctgcttgc | ctgcctcgga | gaggacagag | gcctaggccc | 180 |
| acggggagg  | gtgttggcag | acagatgccc | tccaggccct | ggggcctcct | aacggcccc  | 240 |
| ttaacgacac | gcgtgccaag | ggtggaggat | gccagccaag | gggcgctact | tcctcaacga | 300 |
| gggcgaggag | ggccctgacc | aagatgcgct | ctacgagaag | taccagctca | ccagccagca | 360 |
| tgggccgctg | ctgctcacgc | tcctgctggt | ggccgccact | gctgcgtgg  | ccctcatcat | 420 |
| cattgcctc  | agccaggggg | acccctccag | acaccaggcc | attctgggca | tggcgttcct | 480 |
| ggtgctggcg | tgtttgcgg  | ccctctctgt | gctgatgtac | gtcgagtgtc | tcctgcggcg | 540 |
| ctggctcagg | gccttggcgc | tgctcacctg | gcctgcttg  | gtggcgctgg | gctatgtgct | 600 |
| ggtgttcgac | gcatggacaa | aggcggcctg | tgcgtgggag | caggtgccct | tcttcctgtt | 660 |
| cattgtcttc | gtggtgtaca | cactactgcc | cttcagcatg | cggggcgctg | tcgccgttgg | 720 |
| ggccgtctcc | actgcctccc | acctcctggt | gtcggttct  | tgatgggag  | gcttcacgac | 780 |
| acccagtgtc | cgggtggggc | tgcagctgct | ggccaacgca | gtcatcttcc | tgtgtgggaa | 840 |
| cctgacaggc | gccttccaca | gcaccaaat  | gcaggatgcg | tcccgggacc | tcttcaccta | 900 |
| cactgtgaag | tgcatccaga | tccgccggaa | gctgcgcatc | gagaagcgcc | agcaggagaa | 960 |
| cctgctgctg | tcagtgcttc | cggcccacat | ctccatgggc | atgaagctgg | ccatcatcga | 1020 |
| acggctcaag | gagcatggtg | accgtcgctg | catgcctgac | aacaacttcc | acagcctcta | 1080 |
| cgtcaagagg | caccagaatg | tcagcatcct | ctatgcggac | atcgtgggct | tcacgcagct | 1140 |
| ggccagcgac | tgttctccca | aggagctggt | ggtggtgctg | aatgagctct | ttggcaagtt | 1200 |
| cgaccagatc | gccaaggcca | acgagtgcat | gcgaatcaag | atcctcggcg | actgctacta | 1260 |
| ctgtgtatcg | ggcctgcccg | tgtcgctgcc | tacccacgcc | cggaactgcg | tgaagatggg | 1320 |

```
gctggacatg tgccaggcca tcaagcaggt gcgggaggcc acgggcgtgg acatcaacat   1380
gcgtgtgggc atacactcgg ggaatgtgct gtgcggggtc atcgggctgc gcaagtggca   1440
gtatgacgtg tggtcccacg acgtgtccct ggccaaccgg atggaggcag ccggagtacc   1500
cggccgggtg cacatcacgg aggccacgct aaagcacctg acaaggcgt acgaggtgga   1560
ggatgggcac gggcagcagc gggaccccta cctcaaggag atgaacatcc gcacctacct   1620
ggtcatcgac ccccggagcc agcagccacc cccgcccagc caacacctcc caggcccaa    1680
gggggacgcg gccctgaaga tgcgggcgtc agtgcgcatg acccggtacc tcgagtcctg   1740
gggggcggca cggcccttg cacatctcaa ccaccgtgag agcgtgagca gtggtgagac    1800
ccacgtcccc aacgggcgga ggcctaagag cgttccccag cgccaccgcc ggaccccaga   1860
cagaagcatg tcccccaagg ggcggtcgga ggatgactcg tacgatgacg agatgctgtc   1920
agccattgag gggctcagct ccacgaggcc ctgctgctcc aagtccgatg acttctacac   1980
ctttgggtcc atcttcctgg agaagggctt tgagcgcgag taccgcctgg cacccatccc   2040
ccgggcccgc cacgactttg cctgcgccag cctgatcttc gtctgcatcc tgctcgtcca   2100
tgtcctgctc atgcccagga cggcggcact gggtgtgtcc ttcgggctgg tggcctgtgt   2160
actggggctg gtgctgggcc tgtgcttgc caccaagttc tcgaggtgct gcccagctcg   2220
ggggacgctc tgcactatct ctgagagggt ggagacacag cccctgctga ggctgaccct   2280
ggccgtcctg accatcggca gcctgctcac tgtggccatc atcaacctgc ccctgatgcc   2340
tttccaagtt ccagagctgc ctgttggcaa tgagacaggc ctactggccg cgagcagcaa   2400
gacaagagcc ctgtgtgagc ccctcccgta ctacacctgc agctgtgtcc tgggcttcat   2460
cgcctgctcg gtcttcctga ggatgagcct ggagccaaag gttgtgctgc tgacagtggc   2520
cctggtggcc tacctggtgc tcttcaacct ctccccatgc tggcagtggg actgctgcgg   2580
ccaaggcctg gcaacctca ccaagcccaa cggcaccacc agtggcaccc ctagctgttc    2640
ctggaaggac ctgaagacca tgaccaattt ctacctggtc ctgttctaca tcaccctgct   2700
tacactctcc agacagattg actattactg ccgcttggac tgcctatgga agaagaagtt   2760
caagaaggag cacgaggagt ttgagaccat ggagaacgtg aaccgccttc ttctggagaa   2820
cgtcctgcca gcccacgtgg ctgcccactt tatcggtgac aagttaaacg aggactggta   2880
ccatcagtcc tatgactgcg tctgtgtcat gtttgcctcc gtgccggact tcaaagtgtt   2940
ctacacagag tgcgatgtca acaaagaagg gctggagtgc ctacgcctgc tcaatgagat   3000
cattgccgac ttcgacagc tcctactgaa gcccaagttc agcggcgtgg agaagatcaa    3060
gaccatcggc agcacgtaca tggcagctgc agggctcagc gtcgcctcag gcacgagaa    3120
ccaggagctg gagcggcagc atgcccacat tggtgtcatg gtggagttca gcatcgccct   3180
gatgagtaag ctggacggca tcaacaggca ctccttcaac tccttccgcc tccgcgtcgg   3240
cataaaccat gggcctgtga ttgctggagt gattggggcc cgaaaacctc agtatgacat   3300
ctggggaaac actgtcaatg tggccagccg aatggaaagc actggagaac ttgggaaaat   3360
ccaggttacc gaggagacct gcaccatcct ccagggcctc gggtactctt gtgaatgccg   3420
tggcctgatc aacgtcaaag gcaaaggcga gctgaggact tactttgtct gtacggacac   3480
tgccaagttt caggggctgg ggctgaactg agggctcctg ctggattccg aaaaggccgg   3540
gaagccagtc tccttccctg aagcaagccc aggagaagac tctccgcccc acgccaatcc   3600
caaaggcatg cagatggctg tgcatgttgg cttctttgga cctgcactgg aggatttctc   3660
```

```
agacacatgc accagattct ggctcgaagc agccactgag ccataatgcg caggggaggc    3720
cagaagctct gtgcctggtc tgtaacagtt tccaggccag ctggagaatg ttcactggtt    3780
cggggctgac tttgagatct ttgttccctg aggtgccagg caggcaactt tagcacatga    3840
tgaaaacaga cttccacctc agtggcctgt gggcacgcac aagtgaggtc tgttttttcta   3900 gacaccaagg gggagtaagc tgagctgtct agcacggatt ggagactccc tctccctggt    3960
gggcctggca atgacagcat ttctcacaga ggcattctgg taaatgaagc tgaaaggggt    4020
gttttacatc tgtaaacggt ttcaaacagg tagagagaaa aacaccacaa ttaacactgt    4080 tacttttttgc cttgtctggc atgtttgttt taaatgaata cattaatggg gttttttatcc  4140 ttttgaatga cttttcagac actagacata aatctcttcc ctccagtgta tgctctgcct    4200
ttttaaccac tgacatgtaa ggaggactac tgtctagcat cagcttatgg ggtcagctgg    4260
ctgtggggat agagtcctga ggaatgtggt cacagcaaga aggcggggag cagcagagcc    4320
ttgcctttga atgaggcagc ttgtgaggca agcattctgg agagaggtgc tttgaaagta    4380
aggtgcggcc tttcacctct tccttgatta ctcacacatc tttgcgttct cccctgccgt    4440
ccttcaactg tatcttactt ttcttaccag aaaggaatgg agtctgttta gagacaactt    4500
ggacaacctg tgagtgcatc tcttcttttcc tttagtcttc acagctaact ctggagagct   4560
tcaaaactag aaggatctac tccgcatggg tgcatgcaga ggctcctgga tctgggaagc    4620 ccgcccccctc acaaatgctg agccgttctt gctctgaaac tgcgtgagtc aaggcaaatg   4680
caaaaagcca ggttttgggg atgtgtctta ctgtgcttca acttcccaag gaattgaaag    4740
tcaacctaac tgtaacaaca gggtgagaaa tgaccaaact gcccgtgact ttttctgaat    4800
ggacttcata accggaagac ttaaccggtg gcctcatcac cagagcatcg ccaggatttc    4860
taatgcactc agtttcccta catagcaggg attcttagct aggtgtcccc atgaaccccg    4920
taaagttcta cacaaagtct tgcatacagg agcctttaca agatgattat acagggttgc    4980
agattgggtg actgaccaga cttgttgggg tcctgggatg agttgccccg ggctgcaaat    5040
taagagtaca gctaagtgcg ggggtggcgg tggagggaac gaaaattgaa cctgtctgcc    5100
tgtgctgtgt cgtgtggctt tatcagcccg aggaagggca ggtgtattct aatttgcaca    5160
aaggtgctgg gtagactagt ggcagctctc atgtgctgca cataagtgga atcagtatga    5220
atagaagaac ttgctgtata aaggaatttc atggcaacaa tgctggtaag ggcaattagc    5280
ctcgcttaag ttgccttttt tacacaccaa aacttttttac atgaagggct ggtttcacat   5340
gaatactata ctgaaatctg tgctctcaag atctagcagt gaccagggct gcccggcggg    5400
ggctctcctg gcaagtcagg aaggtttctg ttgctaatat aacatagaaa cacattagtg    5460
cactgggcct ctctgaggtc agcatatttg tactcttgga atatttgttt ttttcttcag    5520
taacaacaga aaccccagtt gggagtttaa caaataactg actaccactc actcatgcat    5580
ttttatttcc aattaaagca aagcactgtg ctgtgctcag ataataatag tttgtaagta    5640
aaagttttta gttttcagtg ttcaggttat agaatataac tgaccataaa aattacctgc    5700
aggtattttc ttttttatgaa cttgttttta aattaccaag taattactgg tgtcattttg    5760
ttttatgaca gacacacgta tctaacaaac aaacaaacag tgaccttctc catgggtcaa    5820
ggacttcctt acaatttctc ctgagttaac ttttgtgaaa ataataccta aggttttctg    5880
gcttattgag gaaatttcct aacaaacaaa caaacaaaca aacagaagag aagatcatta    5940
accactgtat actttgtgta tataataggt cagtgtaaag aaatatgatt tgaggtggtg    6000
catgcaagta actagggttt attctatata atgaatattt atagatctgt aacatttgtt    6060
```

```
tcaaaatgct gtttcatttt tataaagtac cagtgtttag ctgcttttta tacattaaat      6120
tagcaatttg aaaaactcaa aaaaaaaaaa aaaa                                  6154
```

<210> SEQ ID NO 444
<211> LENGTH: 734
<212> TYPE: PRT
<213> ORGANISM: Homo sapiens

<400> SEQUENCE: 444

| | | | | | | | | | | | | | | |
|---|---|---|---|---|---|---|---|---|---|---|---|---|---|---|
| Met | Pro | Ala | Lys | Gly | Arg | Tyr | Phe | Leu | Asn | Glu | Gly | Glu | Glu | Pro |
| 1 | | | | 5 | | | | | 10 | | | | | 15 |
| Asp | Gln | Asp | Ala | Leu | Tyr | Glu | Lys | Tyr | Gln | Leu | Thr | Ser | Gln | His | Gly |
| | | | | 20 | | | | | 25 | | | | | 30 | |
| Pro | Leu | Leu | Leu | Thr | Leu | Leu | Leu | Val | Ala | Ala | Thr | Ala | Cys | Val | Ala |
| | | | | 35 | | | | | 40 | | | | | 45 | |
| Leu | Ile | Ile | Ile | Ala | Phe | Ser | Gln | Gly | Asp | Pro | Ser | Arg | His | Gln | Ala |
| | | 50 | | | | | 55 | | | | | 60 | | | |
| Ile | Leu | Gly | Met | Ala | Phe | Leu | Val | Leu | Ala | Val | Phe | Ala | Ala | Leu | Ser |
| 65 | | | | | 70 | | | | | 75 | | | | | 80 |
| Val | Leu | Met | Tyr | Val | Glu | Cys | Leu | Leu | Arg | Arg | Trp | Leu | Arg | Ala | Leu |
| | | | | 85 | | | | | 90 | | | | | 95 | |
| Ala | Leu | Leu | Thr | Trp | Ala | Cys | Leu | Val | Ala | Leu | Gly | Tyr | Val | Leu | Val |
| | | | | 100 | | | | | 105 | | | | | 110 | |
| Phe | Asp | Ala | Trp | Thr | Lys | Ala | Ala | Cys | Ala | Trp | Glu | Gln | Val | Pro | Phe |
| | | | 115 | | | | | 120 | | | | | 125 | | |
| Phe | Leu | Phe | Ile | Val | Phe | Val | Val | Tyr | Thr | Leu | Leu | Pro | Phe | Ser | Met |
| 130 | | | | | 135 | | | | | 140 | | | | | |
| Arg | Gly | Ala | Val | Ala | Val | Gly | Ala | Val | Ser | Thr | Ala | Ser | His | Leu | Leu |
| 145 | | | | | 150 | | | | | 155 | | | | | 160 |
| Val | Leu | Gly | Ser | Leu | Met | Gly | Gly | Phe | Thr | Thr | Pro | Ser | Val | Arg | Val |
| | | | | 165 | | | | | 170 | | | | | 175 | |
| Gly | Leu | Gln | Leu | Leu | Ala | Asn | Ala | Val | Ile | Phe | Leu | Cys | Gly | Asn | Leu |
| | | | 180 | | | | | 185 | | | | | 190 | | |
| Thr | Gly | Ala | Phe | His | Lys | His | Gln | Met | Gln | Asp | Ala | Ser | Arg | Asp | Leu |
| | | | 195 | | | | | 200 | | | | | 205 | | |
| Phe | Thr | Tyr | Thr | Val | Lys | Cys | Ile | Gln | Ile | Arg | Arg | Lys | Leu | Arg | Ile |
| | | 210 | | | | | 215 | | | | | 220 | | | |
| Glu | Lys | Arg | Gln | Gln | Glu | Asn | Leu | Leu | Leu | Ser | Val | Leu | Pro | Ala | His |
| 225 | | | | | 230 | | | | | 235 | | | | | 240 |
| Ile | Ser | Met | Gly | Met | Lys | Leu | Ala | Ile | Ile | Glu | Arg | Leu | Lys | Glu | His |
| | | | | 245 | | | | | 250 | | | | | 255 | |
| Gly | Asp | Arg | Arg | Cys | Met | Pro | Asp | Asn | Asn | Phe | His | Ser | Leu | Tyr | Val |
| | | | 260 | | | | | 265 | | | | | 270 | | |
| Lys | Arg | His | Gln | Asn | Val | Ser | Ile | Leu | Tyr | Ala | Asp | Ile | Val | Gly | Phe |
| | | | 275 | | | | | 280 | | | | | 285 | | |
| Thr | Gln | Leu | Ala | Ser | Asp | Cys | Ser | Pro | Lys | Glu | Leu | Val | Val | Val | Leu |
| | | 290 | | | | | 295 | | | | | 300 | | | |
| Asn | Glu | Leu | Phe | Gly | Lys | Phe | Asp | Gln | Ile | Ala | Lys | Ala | Asn | Glu | Cys |
| 305 | | | | | 310 | | | | | 315 | | | | | 320 |
| Met | Arg | Ile | Lys | Ile | Leu | Gly | Asp | Cys | Tyr | Tyr | Cys | Val | Ser | Gly | Leu |
| | | | | 325 | | | | | 330 | | | | | 335 | |
| Pro | Val | Ser | Leu | Pro | Thr | His | Ala | Arg | Asn | Cys | Val | Lys | Met | Gly | Leu |
| | | | | 340 | | | | | 345 | | | | | 350 | |

```
Asp Met Cys Gln Ala Ile Lys Gln Val Arg Glu Ala Thr Gly Val Asp
        355                 360                 365

Ile Asn Met Arg Val Gly Ile His Ser Gly Asn Val Leu Cys Gly Val
370                 375                 380

Ile Gly Leu Arg Lys Trp Gln Tyr Asp Val Trp Ser His Asp Val Ser
385                 390                 395                 400

Leu Ala Asn Arg Met Glu Ala Ala Gly Val Pro Gly Arg Val His Ile
                405                 410                 415

Thr Glu Ala Thr Leu Lys His Leu Asp Lys Ala Tyr Glu Val Glu Asp
            420                 425                 430

Gly His Gly Gln Gln Arg Asp Pro Tyr Leu Lys Glu Met Asn Ile Arg
        435                 440                 445

Thr Tyr Leu Val Ile Asp Pro Arg Ser Gln Gln Pro Pro Pro Pro Ser
    450                 455                 460

Gln His Leu Pro Arg Pro Lys Gly Asp Ala Ala Leu Lys Met Arg Ala
465                 470                 475                 480

Ser Val Arg Met Thr Arg Tyr Leu Glu Ser Trp Gly Ala Ala Arg Pro
                485                 490                 495

Phe Ala His Leu Asn His Arg Glu Ser Val Ser Ser Gly Glu Thr His
            500                 505                 510

Val Pro Asn Gly Arg Arg Pro Lys Ser Val Pro Gln Arg His Arg Arg
        515                 520                 525

Thr Pro Asp Arg Ser Met Ser Pro Lys Gly Arg Ser Glu Asp Asp Ser
    530                 535                 540

Tyr Asp Asp Glu Met Leu Ser Ala Ile Glu Gly Leu Ser Ser Thr Arg
545                 550                 555                 560

Pro Cys Cys Ser Lys Ser Asp Asp Phe Tyr Thr Phe Gly Ser Ile Phe
                565                 570                 575

Leu Glu Lys Gly Phe Glu Arg Glu Tyr Arg Leu Ala Pro Ile Pro Arg
            580                 585                 590

Ala Arg His Asp Phe Ala Cys Ala Ser Leu Ile Phe Val Cys Ile Leu
        595                 600                 605

Leu Val His Val Leu Leu Met Pro Arg Thr Ala Ala Leu Gly Val Ser
    610                 615                 620

Phe Gly Leu Val Ala Cys Val Leu Gly Leu Val Leu Gly Leu Cys Phe
625                 630                 635                 640

Ala Thr Lys Phe Ser Arg Cys Cys Pro Ala Arg Gly Thr Leu Cys Thr
                645                 650                 655

Ile Ser Glu Arg Val Glu Thr Gln Pro Leu Leu Arg Leu Thr Leu Ala
            660                 665                 670

Val Leu Thr Ile Gly Ser Leu Leu Thr Val Ala Ile Ile Asn Leu Pro
        675                 680                 685

Leu Met Pro Phe Gln Val Pro Glu Leu Pro Val Gly Asn Glu Thr Gly
    690                 695                 700

Leu Leu Ala Ala Ser Ser Lys Thr Arg Ala Leu Cys Glu Pro Leu Pro
705                 710                 715                 720

His Leu His Thr Val Phe Ser Arg Leu Asn Glu Leu Thr Ser
                725                 730
```

<210> SEQ ID NO 445
<211> LENGTH: 2582
<212> TYPE: DNA
<213> ORGANISM: Homo sapiens

<400> SEQUENCE: 445

-continued

| | |
|---|---|
| agatgtgact cactctcatt aggtagcgtg gaaggagcct tcggatggag ctgaggaact | 60 |
| gcgtgtggag tcagcccagt ctggatgcac aggaggatgc tggcggcaca gtgagtgagg | 120 |
| cctggtgcca gagctgtgcg gacccottgt tggccatgga gcagcaggcc cagaggccct | 180 |
| ctccccagcc ctgcttgcct gcctcggaga ggacagaggc ctaggcccac gggggagggt | 240 |
| gttggcagac agatgccctc caggccctgg ggcctcctta acggcccctt aacgacacgc | 300 |
| gtgccaaggg tggaggatgc cagccaaggg gcgctacttc ctcaacgagg gcgaggaggg | 360 |
| ccctgaccaa gatgcgctct acgagaagta ccagctcacc agccagcatg gccgctgct | 420 |
| gctcacgctc ctgctggtgg ccgccactgc ctgcgtggcc ctcatcatca ttgccttcag | 480 |
| ccagggggac ccctccagac accaggccat tctgggcatg gcgttcctgg tgctggcggt | 540 |
| gtttgcggcc ctctctgtgc tgatgtacgt cgagtgtctc ctgcggcgct ggctcagggc | 600 |
| cttggcgctg ctcacctggg cctgcttggt ggcgctgggc tatgtgctgg tgttcgacgc | 660 |
| atggacaaag gcggcctgtg cgtgggagca ggtgcccttc ttcctgttca ttgtcttcgt | 720 |
| ggtgtacaca ctactgccct tcagcatgcg gggcgctgtc gccgttgggg ccgtctccac | 780 |
| tgcctcccac ctcctggtgc tcggttcttt gatgggaggc ttcacgacac ccagtgtccg | 840 |
| ggtggggctg cagctgctgg ccaacgcagt catcttcctg tgtgggaacc tgacaggcgc | 900 |
| cttccacaag caccaaatgc aggatgcgtc ccgggacctc ttcacctaca ctgtgaagtg | 960 |
| catccagatc cgccggaagc tgcgcatcga gaagcgccag caggagaacc tgctgctgtc | 1020 |
| agtgcttccg gcccacatct ccatgggcat gaagctggcc atcatcgaac ggctcaagga | 1080 |
| gcatggtgac cgtcgctgca tgcctgacaa caacttccac agcctctacg tcaagaggca | 1140 |
| ccagaatgtc agcatcctct atgcggacat cgtgggcttc acgcagctgg ccagcgactg | 1200 |
| ttctcccaag gagctggtgg tggtgctgaa tgagctcttt ggcaagttcg accagatcgc | 1260 |
| caaggccaac gagtgcatgc gaatcaagat cctcggcgac tgctactact gtgtatcggg | 1320 |
| cctgcccgtg tcgctgccta cccacgcccg gaactgcgtg aagatggggc tggacatgtg | 1380 |
| ccaggccatc aagcaggtgc gggaggccac gggcgtggac atcaacatgc gtgtgggcat | 1440 |
| acactcgggg aatgtgctgt gcgggtcat cgggctgcgc aagtggcagt atgacgtgtg | 1500 |
| gtcccacgac gtgtccctgg ccaaccggat ggaggcagcc ggagtacccg gccgggtgca | 1560 |
| catcacggag gccacgctaa agcacctgga caaggcgtac gaggtggagg atgggcacgg | 1620 |
| gcagcagcgg gacccctacc tcaaggagat gaacatccgc acctacctgg tcatcgaccc | 1680 |
| ccggagccag cagccacccc cgcccagcca acacctcccc aggcccaagg gggacgcggc | 1740 |
| cctgaagatg cgggcgtcag tgcgcatgac ccggtacctc gagtcctggg gggcggcacg | 1800 |
| gccctttgca catctcaacc accgtgagag cgtgagcagt ggtgagaccc acgtccccaa | 1860 |
| cggggcggagg cctaagagcg ttccccagcg ccaccgccgg accccagaca gaagcatgtc | 1920 |
| ccccaagggg cggtcggagg atgactcgta cgatgacgag atgctgtcag ccattgaggg | 1980 |
| gctcagctcc acgaggccct gctgctccaa gtccgatgac ttctacacct ttgggtccat | 2040 |
| cttcctggag aagggcttg agcgcgagta ccgcctggca cccatccccc gggcccgcca | 2100 |
| cgactttgcc tgcgccagcc tgatcttcgt ctgcatcctg ctcgtccatg tcctgctcat | 2160 |
| gcccaggacg gcggcactgg gtgtgtcctt cgggctggtg gcctgtgtac tggggctggt | 2220 |
| gctgggcctg tgctttgcca ccaagttctc gaggtgctgc ccagctcggg ggacgctctg | 2280 |
| cactatctct gagagggtgg agacacagcc cctgctgagg ctgaccctgg ccgtcctgac | 2340 |

```
catcggcagc ctgctcactg tggccatcat caacctgccc ctgatgcctt tccaagttcc    2400
agagctgcct gttggcaatg agacaggcct actggccgcg agcagcaaga caagagccct    2460
gtgtgagccc ctcccgcacc tgcatactgt tttttcccgt ttaaatgagc tcacttcata    2520
agaaataaaa ctacagtgaa aacaacactg gaaaaaaaaa aaaaaaaaaa aaaaaaaaa    2580 aa                                                                   2582
```